United States Patent
Cogan et al.

(10) Patent No.: US 10,577,616 B2
(45) Date of Patent: Mar. 3, 2020

(54) FAD2 PERFORMANCE LOCI AND CORRESPONDING TARGET SITE SPECIFIC BINDING PROTEINS CAPABLE OF INDUCING TARGETED BREAKS

(71) Applicants: Dow AgroSciences LLC, Indianapolis, IN (US); Sangamo Therapeutics, Inc., Richmond, CA (US)

(72) Inventors: Noel Cogan, Macleod (AU); John Forster, Diamond Creek (AU); Matthew Hayden, Templestowe (AU); Tim Sawbridge, Coburg (AU); German Spangenberg, Bundoora (AU); Steven R. Webb, Westfield, IN (US); Manju Gupta, Carmel, IN (US); W. Michael Ainley, Carmel, IN (US); Matthew J. Henry, Indianapolis, IN (US); Jeffrey C. Miller, Richmond, CA (US); Dmitry Y. Guschin, Richmond, CA (US)

(73) Assignees: Dow AgroSciences LLC, Indianapolis, IN (US); Sangamo Therapeutics, Inc., Richmond, CA (US)

( * ) Notice: Subject to any disclaimer, the term of this patent is extended or adjusted under 35 U.S.C. 154(b) by 54 days.

(21) Appl. No.: 15/943,106

(22) Filed: Apr. 2, 2018

(65) Prior Publication Data
US 2018/0223297 A1 Aug. 9, 2018

Related U.S. Application Data

(62) Division of application No. 14/019,244, filed on Sep. 5, 2013, now Pat. No. 9,963,711.

(60) Provisional application No. 61/697,886, filed on Sep. 7, 2012.

(51) Int. Cl.
*C12N 15/82* (2006.01)
*C12N 15/90* (2006.01)

(52) U.S. Cl.
CPC ..... *C12N 15/8216* (2013.01); *C12N 15/8247* (2013.01); *C12N 15/902* (2013.01)

(58) Field of Classification Search
None
See application file for complete search history.

(56) References Cited

U.S. PATENT DOCUMENTS

| | | |
|---|---|---|
| 4,769,061 A | 9/1988 | Comai |
| 4,810,648 A | 3/1989 | Stalker |
| 4,940,835 A | 7/1990 | Fraley et al. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,200,759 B1 | 3/2001 | Dove et al. |
| 6,242,568 B1 | 6/2001 | Barbas et al. |
| 6,453,242 B1 | 9/2002 | Eisenberg et al. |
| 6,479,626 B1 | 11/2002 | Kim et al. |
| 6,534,261 B1 | 3/2003 | Cox et al. |
| 6,599,692 B1 | 6/2003 | Case et al. |
| 6,689,558 B2 | 2/2004 | Case |
| 6,794,136 B1 | 9/2004 | Eisenberg et al. |
| 6,903,185 B2 | 6/2005 | Kim et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,253,273 B2 | 8/2007 | Collingwood |
| 7,262,054 B2 | 8/2007 | Jamieson et al. |
| 7,361,635 B2 | 4/2008 | Miller et al. |
| 8,420,782 B2 | 4/2013 | Bonas et al. |
| 8,440,431 B2 | 5/2013 | Voytas et al. |
| 2003/0232410 A1 | 12/2003 | Liljedahl et al. |
| 2005/0026157 A1 | 2/2005 | Baltimore et al. |
| 2005/0064474 A1 | 3/2005 | Holmes et al. |
| 2005/0208489 A1 | 9/2005 | Carroll et al. |
| 2005/0267061 A1 | 12/2005 | Martin |
| 2006/0188987 A1 | 8/2006 | Guschin et al. |
| 2006/0246440 A1 | 11/2006 | Joung |
| 2007/0059795 A1 | 3/2007 | Moore et al. |
| 2007/0134796 A1 | 6/2007 | Holmes et al. |
| 2007/0218528 A1 | 9/2007 | Miller |
| 2008/0131962 A1 | 6/2008 | Miller |
| 2008/0168586 A1 | 7/2008 | Laga et al. |
| 2008/0182332 A1 | 7/2008 | Cai |
| 2009/0111119 A1 | 4/2009 | Doyon et al. |
| 2009/0117617 A1 | 5/2009 | Holmes et al. |
| 2009/0205083 A1 | 8/2009 | Gupta et al. |

(Continued)

FOREIGN PATENT DOCUMENTS

| | | |
|---|---|---|
| EP | 0 242 246 | 11/1992 |
| EP | 1 806 398 | 7/2007 |

(Continued)

OTHER PUBLICATIONS

FAD2-1A (NCBI Gene ID: 547814, updated Jul. 19, 2019).*
Ainley et al., "Trait Stacking via Targeted Genome Editing," *Plant Biotechnol. J.* 11(9):1126-1134 (2013).
Alt, et al., "Phenotypic and Molecular Analysis of Oleate Content in the Mutant Soybean Line M23," *Crop Science: A Journal Serving the International Community of Crop Scientists, Crop Science Society of America* 45(5):1997-2000 (2005).
ATCC 39256.
ATCC 53435.
ATCC 67441.
ATCC 67442.

(Continued)

*Primary Examiner* — Matthew R Keogh
(74) *Attorney, Agent, or Firm* — Pasternak Patent Law

(57) ABSTRACT

A method of gene editing or gene stacking within a FAD2 loci by cleaving, in a site directed manner, a location in a FAD2 gene in a cell, to generate a break in the FAD2 gene and then ligating into the break a nucleic acid molecule associated with one or more traits of interest is disclosed.

15 Claims, 28 Drawing Sheets

Specification includes a Sequence Listing.

(56) References Cited

U.S. PATENT DOCUMENTS

| | | |
|---|---|---|
| 2009/0263900 A1 | 10/2009 | DeKelver et al. |
| 2010/0047805 A1 | 2/2010 | Wang |
| 2010/0199389 A1 | 8/2010 | Butler et al. |
| 2011/0041195 A1 | 2/2011 | Doyon |
| 2011/0123509 A1 | 5/2011 | Jantz et al. |
| 2011/0145940 A1 | 6/2011 | Voytas et al. |
| 2011/0159541 A1 | 6/2011 | Collingwood et al. |
| 2011/0167521 A1* | 7/2011 | DeKelver .......... C12N 15/8216 800/298 |
| 2011/0189775 A1 | 8/2011 | Ainley et al. |
| 2011/0201055 A1 | 8/2011 | Doyon et al. |
| 2011/0207221 A1 | 8/2011 | Cost et al. |
| 2011/0239315 A1 | 9/2011 | Bonas et al. |
| 2011/0281361 A1 | 11/2011 | DeKelver et al. |
| 2011/0293785 A1 | 12/2011 | Franklin et al. |
| 2011/0301073 A1 | 12/2011 | Gregory et al. |
| 2012/0102587 A1 | 4/2012 | Anai et al. |
| 2013/0326645 A1 | 12/2013 | Cost et al. |

FOREIGN PATENT DOCUMENTS

| | | |
|---|---|---|
| EP | 1 862 551 | 12/2007 |
| GB | 2338237 | 8/1998 |
| WO | WO 93/19181 | 9/1993 |
| WO | WO 95/19431 | 7/1995 |
| WO | WO 96/06166 | 7/1995 |
| WO | WO 96/30517 | 2/1996 |
| WO | WO 98/53057 | 8/1998 |
| WO | WO 98/53058 | 11/1998 |
| WO | WO 98/53059 | 11/1998 |
| WO | WO 98/53060 | 11/1998 |
| WO | WO 98/54311 | 11/1998 |
| WO | WO 98/56239 | 12/1998 |
| WO | WO 00/27878 | 12/2000 |
| WO | WO 01/60970 | 8/2001 |
| WO | WO 01/88197 | 11/2001 |
| WO | WO 02/016536 | 2/2002 |
| WO | WO 02/077227 | 10/2002 |
| WO | WO 02/099084 | 12/2002 |
| WO | WO 03/016496 | 2/2003 |
| WO | WO 04/072259 | 8/2004 |
| WO | WO 05/012515 | 2/2005 |
| WO | WO 05/028620 | 3/2005 |
| WO | WO 05/107437 | 11/2005 |
| WO | WO 06/079567 | 8/2006 |
| WO | WO 07/014275 | 2/2007 |
| WO | WO 07/053482 | 5/2007 |
| WO | WO 2008/084107 | 7/2008 |
| WO | WO 2011/005998 | 1/2011 |
| WO | WO 2011/049627 | 4/2011 |
| WO | WO 2011/146121 | 11/2011 |
| WO | WO 2014/039702 | 3/2013 |
| WO | WO 03/080802 | 10/2013 |
| WO | WO 2014/141147 | 9/2014 |

OTHER PUBLICATIONS

Barkley, et al., "A Real-Time PCR Genotyping Assay to Detect FAD2A SNPs in Peanuts (*Arachis hypogaea* L.)", *Electronic Journal of Biotechnology* 14(1) ISSN:0717-3458 (2001).

Beerli et al., Toward Controlling Gene Expression at Will: Specific Regulation of the ERBB-2/HER-2 Promoter by Using Polydactyl Zinc Finger Proteins Constructed From Modular Building Blocks, *PNAS USA* 95(25): 14628-14633 (1998).

Beerli et al., "Engineering Polydactyl Zinc-Finger Transcription Factors," *Nature Biotechnol.* 20:135-141(2002).

Bibikova et al., "Stimulation of Gomologous Recombination Through Targeted Cleavage by Chimeric Nucleases," *Mol. Cell. Biol.* 21(1):289-297 (2001).

Bibikova et al., "Enhancing Gene Targeting With Designed Zinc Finger Nucleases," *Science* 300(5620):764 (2003).

Bitinate et al., "FOKI Dimerization Is Required for DNA Cleavage," *PNAS USA* 95:10570-10575 (1998).

Bonas et al., "Genetic and Structural Characterization of the Avirulence Gene AVRBS3 From Xanthomonas Campestris PV. Vesicatori," *Mol. Gen. Genet.* 218:127-136 (1989).

Buhr, et al., "Ribozyme Termination of RNA Transcripts Down-Regulate Seed Fatty Acid Genes in Transgenic Soybean," *The Plant Journal* 30(2):155-163 (2002).

Cai et al., Targeted Transgene Integration in Plant Cells Using Designed Zinc Finger Nucleases, *Plant Mol. Biol.* 69(6):699-709 (2009).

Choo et al., Advances in Zinc Finger Engineering, *Curr. Opin. Struct. Biol.* 10:411-416 (2000).

Curtin, et al., "Text S1 Supplemental Methods Hairy Root Transformation of Soybean Cotyledons," *Plant Physiology* (2011) http://plantphysiol.org/content/suppl/2011/04.04/pp.111.172981.dc2/172981supplemental_methods.pdf.

Curtin et al.,"Targeted Mutagenesis of Duplicated Genes in Soybean With Zinc-Finger Nucleases," *Plant Physiology* 156:466-473 (2011).

D'Halluin et al., "Homologous Recombination: A Basis for Targeted Genome Optimization in Crop Species Such as Maize," *Plant Biotechnology Journal* 6(1):93-102 (2008).

DeGreef et al., "Evaluation of Herbicide Resistance in Transgenic Crops Under Field Conditions," *Nat Biotechnology* 7:61-64 (1989).

Dierking, et al., "New Sources of Soybean Seed Meal and Oil Composition Traits Identified Through Tilling," *BMC Plant Biology* 9:89 (2009).

Doyon et al., "Heritable Targeted Gene Disruption in Zebrafish Using Designed Zinc-Finger Nucleases," *Nat. Biotechnol.* 26:702-708 (2008).

Elliott et al., "Isolation and Characterization of Fruit Vacuolar Invertase Genes From Two Tomato Species and Temporal Differences in MRNA Levels During Fruit Ripening," *Plant Molec. Biol.* 21:515-524 (1993).

Fisher et al., Starch Branching Enzyme II From Maize Endosperm , *Plant Physiol.* 102:1045-1046 (1993).

Geiser et al., "The Hypervariable Region in the Genes Coding for Entomopathogenic Crystal Proteins of Bacillus Thuringiensis: Nucleotide Sequence of the KURHD1 Gene of Subsp. *kurstaki* HD1," *Gene* 48:109-118 (1986).

Guerts et al., Knockout Rats via Embryo Microinjection of Zinc-Finger Nucleases, *Science* 325(5939):433 (2009).

Haft et al., "A Guild of 45 CRISPR-Associated (CAS) Protein Families and Multiple CRISPR/CAS Subtypes Exist in Prokaryotic Genomes," *PLoS Comput. Biol.* 1:e60 (2005) <http://www.jcvi.org/cms/nc/publications/listing/browse/3/article//Haft/#sthash.bXXP6pOi.dpuf>.

Hayes et al., "Molecular Cloning and Heterologous Expression of a CDNA Encoding a Mouse Glutathione S-Transferase YC Subunit Possessing High Catalytic Activity for Aflatoxin B1-8,9-Epoxide," *Biochem. J.* 285:173-180 (1992).

Heppard, et al., "Developmental and Growth Temperature Regulation of Two Different Microsomal Omega-6 Desaturase Genes in Soybeans," *Plant Physiol.* 110:311-319 (1996).

Heuer et al., "Repeat Domain Diversity of AVRBS3-Like Genes in *Ralstonia solanacearum* Strains and Association With Host Preferences in the Field," *Appl. and Envir. Micro.* 73(13):4379-4384 (2007).

Isalan et al., "A Rapid, Generally Applicable Method to Engineer Zinc Fingers Illustrated by Targeting the HIV-1 Promoter," *Nature Biotechnol.* 19:656-660 (2001).

Jansen et al., "Identification of Genes That Are Associated With DNA Repeats in Prokaryotes," *Mol. Microbiol.* 43:1565-1575 (2002).

Jinek, et al., "A Programmable Dual-RNA-Guided DNA Endonuclease in Adaptive Bacterial Immunity," *Science* 337:816-821 (2012).

Jones et al., "Isolation of the Tomato CF-9 Gene for Resistance to Cladosporium Fulvum by Transposon Tagging," *Science* 266:789-793 (1994).

Kay et al., "A Bacterial Effector Acts as a Plant Transcription Factor and Induces a Cell Size Regulator," *Science* 318:648-651 (2007).

Kim et al., "Chimeric Restriction Enzyme:GAL4 Fusion to FOKL Cleavage Domain," *J. Biol. Chem.* 379:489-495 (1998).

Kim et al., "Getting a Handhold on DNA: Design of Poly-Zinc Finger Proteins With Femtomolar Dissociation Constants," *PNAS USA* 95:2812-2817 (1998).

(56) References Cited

OTHER PUBLICATIONS

Kim et al., "Design of TATA Box-Binding Proteinyzinc Finger Fusions for Targeted Regulation of Gene Expression," *PNAS* 94:3616-3620 (1997).
Kim et al., "Site-Specific Cleavage of DNA-RNA Hybrids by Zinc Finger/FOKI Cleavage Domain Fusions," *Gene* 203:43-49 (1997).
Kim et al., "Construction of a Z-DNA-Specific Restriction Endonuclease," *PNAS* 94:12875-12879 (1997).
Kim et al., "Hybrid Restriction Enzymes: Zinc Finger Fusions to FOK I Cleavage Domain," *PNAS* 93:1156-1160 (1996).
Kim et al., "Chimeric Restriction Endonuclease," *PNAS* 91:883-887 (1994).
Knutson et al., "Modification of *Brassica* Seed Oil by Antisense Expression of a Stearoyl-Acyl Carrier Protein Desaturase Gene," *Proc. Natl. Acad. Sci. U.S.A.*, 89:2624-2628 (1992).
Kumar et al., "Controlling Transgene Integration in Plants," *Trends Plant Sci.* 6:155-159 (2001).
Le et al., "Simultaneous Generation and Germline Transmission of Multiple Gene Mutations in Rat Using CRISPR-CAS Systems," *Nature Biotechnology* 31:684-686 (2013).
Lee et al., "The Molecular Basis of Sulfonylurea Herbicide Resistance in Tobacco," *Embo J.* 7(5):1241 (1988).
Liu et al., "Design of Polydactyl Zinc-Finger Proteins for Unique Addressing Within Complex Genomes," *PNAS USA* 94:5525-5530 (1997).
Makarova et al., "A Putative RNA-Interference-Based Immune System Inprokaryotes: Computational Analysis of the Predicted Enzymatic Machinery, Functional Analogies With Eukaryotic RNAI, and Hypothetical Mechanisms of Action," *Biol. Direct.* 1:7 (2006).
Makarova et al., "A DNA Repair System Specific for the Thermophilic Archaea and Bacteria Predicted by Genomic Context Analysis," *Nucleic Acids Res.* 30:482-496 (2002).
Mani et al., "Binding of Two Zinc Finger Nuclease Monomers to Two Specific Sites Is Required for Effective Double-Strand DNA Cleavage," *Biochem. Biophys. Res. Commun.* 334:1191-1197 (2005).
Marshall et al., "Allelic Mutations in Acetyl-Coenzyme A Carboxylase Confer Herbicide Tolerance in Maize," *Theor. Appl. Genet.* 83:435-442 (1992).
Martin et al., "Map-Based Cloning of a Protein Kinase Gene Conferring Disease Resistance to Tomato," *Science* 262:1432-1436 (1993).
Miki et al., "Transformation of *Brassica napus* Canola Cultivars With *Arabidopsis thaliana* Acetohydroxyacid Synthase Genes and Analysis of Herbicide Resistance," *Theor. Appl. Genet.* 80:449 (1990).
Mindrinos et al., "The *A. thaliana* Disease Resistance Gene RPS2 Encodes a Protein Containing a Nucleotide-Binding Site and Leucine-Rich Repeats," *Cell* 78:1089 (1994).
Moehle et al., "Targeted Gene Addition Into a Specified Location in the Human Genome Using Designed Zinc Finger Nucleases," *Proc. Natl. Acad. Sci. USA* 104(9):3055-3060 (2007).
Nekrasov et al., "Targeted Mutagenesis in the Model Plant Nicotiana Benthamiana Using CAS9 RNA-Guided Endonuclease," *Nature Biotechnology* 31:691-693 (2013).
Okuley, et al., "*Arabidopsis* FAD2 Gene Encodes the Enzyme That Is Essential for Polyunsaturated Lipid Synthesis," *Plant Cell* 6:147-158 (1994).
Pabo et al., "Design and Selection of Novel CYS2HIS2 Zincfinger Proteins," *Ann. Rev. Biochem* 70:313-340 (2001).
Paszkowski et al., "Gene Targeting in Plants," *EMBO J.* 7:4021-4026 (1988).
Pen et al., "Production of Active Bacillus Licheniformis Alpha-Amylase in Tobacco and Its Application in Starch Liquefaction," *BioTechnology* 10:292 (1992).
Pham, et al., Mutant Alleles of FAD2-1A and FAD2-1B Combine to Produce Soybeans With the High Oleic Acid Seed Oil Trait, *BMC Plant Biology* 10:195 (2010).
Przibilla et al., "Site-Specific Mutagenesis of the D1 Subunit of Photosystem II in Wild-Type Chlamydomona," *Plant Cell* 3:169-174 (1991).

Puchta et al., "Homologous Recombination in Plant Cells Is Enhanced by In Vivo Induction of Double Strand Breaks Into DNA by a Site-Specific Endonuclease," *Nucleic Acid Research* 21:5034-5040 (1993).
Raboy et al., "A Survey of Maize Kernel Mutants for Variation in Phytic Acid," *Maydica* 35:383-390 (1990).
Roberts et al., "Rebase: Restriction Enzymes and Methyltransferases," *Nucleic Acids Res.* 31:418-420 (2003).
Sandhu, et al., "Enhanced Oleic Acid Content in the Soybean Mutant M23 Is Associated With the Deletion in the FAD2-LA Gene Encoding a Fatty Acid Desaturase," *Journal of the American Oil Chemists Society* 84(3):229-235 (2007).
Scheffler et al., "Desaturase Multigene Families of Brassica Napus Arose Through Genome Duplication," *TAG* 94(5):583-591 (1997).
Schierholt et al., "Mapping a High Oleic Acid Mutation in Winter Oilseed Rape (*Brassica napus* L.)" *TAG* 101(5-6):897-901 (2000).
Schierholt et al., "Inheritance of High Oleic Acid Mutations in Winter Oilseed Rape (*Brassica napus* L.)" *Crop Sci.* 41:1444-1449 (2001).
Schornack et al., "Gene-For-Gene-Mediated Recognition of Nuclear-Targeted a VRBS3-Like Bacterial Effector Proteins," *J. Plant Physiol.* 163(3):256-272 (2006).
Segal, "Custom DNA-Binding Proteins Come of Age: Polydactyl Zinc-Finger Proteins," *Curr. Opin. Biotechnol.* 12:632-637 (2001).
Shan et al., "Targeted Genome Modification of Crop Plants Using a CRISPR-CAS System," *Nature Biotechnology* 31:686-680 (2013).
Shiroza et al., "Sequence Analysis of the *Streptococcus mutans* Fructosyltransferase Gene and Flanking Regions," *J. Bacteriol.* 170(2):810-816 (1988).
Shukla et al., "Precise Genome Modification in the Crop Species *Zea mays* Using Zinc-Finger Nucleases," *Nature* 459:437-441 (2009).
Siebert et al., "Efficient Repair of Genomic Double-Strand Breaks by Homologous Recombination Between Directly Repeated Sequences in the Plant Genome," *Plant Cell* 14:1121-1131 (2002).
Smith et al., "A Detailed Study of the Substrate Specificity of a Chimeric Restriction Enzyme," *Nucleic Acids Res.* 27:674-681 (1999).
Smith et al., "Requirements for Double-Strand Cleavage by Chimeric Restriction Enzymes With Zinc Finger DNA-Recognition Domains," *Nucleic Acids Res.* 28:3361-3369 (2000).
Sogaard et al., "Site-Directed Mutagenesis of Histidine 93, Aspartic Acid 180, Glutamic Acid 205, Hisitidine 290, and Aspartic Acid 291 at the Active Site and Tryptophan 279 at the Raw Starch Binding Site in Barley A-Amylase 1," *J. Biol. Chem.* 268:22480 (1993).
Steinmetz et al., "The DNA Sequence of the Gene for the Secreted *Bacillus subtilis* Enzyme Levansucrase and Its Genetic Control Sites," *Mol. Gen. Genet.* 20:220 (1985).
Tanhuanpaa et al., "Mapping and Cloning of FAD2 Gene to Develop Allele-Specific PCR for Oleic Acid in Spring Turnip Rape (*Brassica rapa* Ssp. *oleifera*)," *Mol. Breed.* 4:543-550 (1998).
Terada et al., "Efficient Gene Targeting by Homologous Recombination in Rice," *Nat. Biotechnol.* 20(10):1030 (2002).
Terada et al., "Gene Targeting by Homologous Recombination as a Biotechnological Tool for Rice Functional Genomics," *Plant Physiol.* 144(2):846 (2007).
Urnov et al., "Genome Editing With Engineered Zinc Finger Nucleases," *Nature Reviews* 11:636-546(2010).
Urnov et al., "Highly Efficient Endogenous Human Gene Correction Using Designed Zinc-Finger Nucleases," *Nature* 435:646-651 (2005).
Van Hartingsveldt et al., "Cloning, Characterization and Overexpression of the Phytase-Encoding Gene (PHYA) of Aspergillus Niger," *Gene* 127:87-94 (1993).
Wah et al., "Structure of FOKI Has Implications for DNA Cleavage," *PNAS USA* 95:10564-10569 (1998).
Wang et al., "Application of Zinc Finger Nucleases in Genome Targeting Modification," *Chinese Journal of Biochemistry and Molecular Biology* 25(7):585-589 (English translation of Abstract only).
Wu et al., "Custom-Designed Zinc Finger Nucleases: What Is Next?," *Cell. Mol. Life Sci.* 64:2933-2944 (2007).
Yang et al., "Identification of FAD2 and FAD3 Genes in *Brassica napus* Genome and Development of Allele-Specific Markers for High Oleic and Low Linolenic Acid Contents," *Theory App. Genet.* 125:715-729 (2012).

(56) References Cited

OTHER PUBLICATIONS

Genbank AB188250 "Glycine max GmFAD2-1a gene for mocrosomal omega-6 fatty acid desaturase, complete cds," http://www.ncbi.nlm.nih.gov/nuccore/AB188250 (2011).

* cited by examiner

```
                                         1                                      40
FAD2-3 (SEQ ID NO:8)    (1)  ATGGGTGCAGGTGGAAGAATGCAAGTGTCTCCTCCCTCCA
 FAD2A (SEQ ID NO:5)    (1)  ATGGGTGCAGGTGGAAGAATGCAAGTGTCTCCTCCCTCCA
FAD2-2 (SEQ ID NO:7)    (1)  ATGGGCGCAGGTGGAAGAATGCAAGTCTCTCCTCCCTCCA
FAD2-1 (SEQ ID NO:6)    (1)  ATGGGTGCAGGTGGAAGAATGCAAGTCTCTCCTCCCTCCA
                                        41                                      80
FAD2-3 (SEQ ID NO:8)   (41)  AGAAGTCTGAAACCGACACCATCAAGCGCGTACCCTGCGA
 FAD2A (SEQ ID NO:5)   (41)  AAAAGTCTGAAACCGACAACATCAAGCGCGTACCCTGCGA
FAD2-2 (SEQ ID NO:7)   (41)  GCTCCCCGAAACCAAAACCCTCAAACGCGTCCCCTGCGA
FAD2-1 (SEQ ID NO:6)   (41)  GCTCCCCCGGAACCAACACCCTCAAACGCGTCCCCTGCGA
                                        81                                     120
FAD2-3 (SEQ ID NO:8)   (81)  GACACCGCCCTTCACTGTCGGAGAACTCAAGAAAGCAATC
 FAD2A (SEQ ID NO:5)   (81)  GACACCGCCCTTCACTGTCGGAGAACTCAAGAAAGCAATC
FAD2-2 (SEQ ID NO:7)   (81)  GACACCACCCTTCACTCTCGGAGACCTCAAGAAAGCAATC
FAD2-1 (SEQ ID NO:6)   (81)  GACACCACCATTCACTCTCGGAGACCTCAAGAAAGCAATC
                                       121                                     160
FAD2-3 (SEQ ID NO:8)  (121)  CCACCGCACTGTTTCAAACGCTCGATCCCTCGCTCTTTCT
 FAD2A (SEQ ID NO:5)  (121)  CCACCGCACTGTTTCAAACGCTCGATCCCTCGCTCTTTCT
FAD2-2 (SEQ ID NO:7)  (121)  CCACCTCACTGCTTCAAACGCTCCATCCCTCGCTCCTTCT
FAD2-1 (SEQ ID NO:6)  (121)  CCACCTCACTGCTTCAAACGCTCCATCCCACGCTCCTTCT
                                       161                                     200
FAD2-3 (SEQ ID NO:8)  (161)  CCTACCTCATCTGGGACAT--CATCATAGCCTCCTGCTTC
 FAD2A (SEQ ID NO:5)  (161)  CCTACCTCATCTGGGACAT--CATCATAGCCTCCTGCTTC
FAD2-2 (SEQ ID NO:7)  (161)  CCTACCTCCTCTTCGACAT--CCTCGTCTCCTCCTCCCTC
FAD2-1 (SEQ ID NO:6)  (161)  CCT-CTTCGACATCATCATCTCCTCCTCGGCTCCTCCCTC
                                       201                                     240
FAD2-3 (SEQ ID NO:8)  (199)  TACTACGTCGCCACCACTTACTTCCCTCTCCTCCCTCACC
 FAD2A (SEQ ID NO:5)  (199)  TACTACGTCGCCACCACTTACTTCCCTCTCCTCCCTCACC
FAD2-2 (SEQ ID NO:7)  (199)  TACCACCTCTCCACAGCCTACTTCCCTCTCCTCCCCCACC
FAD2-1 (SEQ ID NO:6)  (200)  TACCACCTCTCCACAGCCTACTTCCCTCTCC---------
```

FIG. 1A

```
                              241                                        280
FAD2-3 (SEQ ID NO:8)   (239) CTCTCTCCTACTTCGCCTGGCCTCTCTACTGGGCCTGCCA
 FAD2A (SEQ ID NO:5)   (239) CTCTCTCCTACTTCGCCTGGCCTCTCTACTGGGCCTGCCA
FAD2-2 (SEQ ID NO:7)   (239) CTCTCCCTTACCTCGCCTGGCCCCTCTACTGGGCCTGCCA
FAD2-1 (SEQ ID NO:6)   (231) ------CTTACCTCGCCTGACCCCTCTACTGGGCCTGCCA
                              281                                        320
FAD2-3 (SEQ ID NO:8)   (279) AGGGTGCGTCCTAACCGGCGTCTGGGTCATAGCCCACGAG
 FAD2A (SEQ ID NO:5)   (279) GGGCTGCGTCCTAACCGGCGTCTGGGTCATAGCCCACGAG
FAD2-2 (SEQ ID NO:7)   (279) AGGCTGCGTCCTAACGGGCCTCTGGGTCATCGCCCACGAA
FAD2-1 (SEQ ID NO:6)   (265) AGGCTGCGTCCTAACGGGCCTCTGGGTCATAGCCCACGAG
                              321                                        360
FAD2-3 (SEQ ID NO:8)   (319) TGCGGCCACCACGCCTTCAGCGACTACCAGTGGCTTGACG
 FAD2A (SEQ ID NO:5)   (319) TGCGGCCACCACGCCTTCAGCGACTACCAGTGGCTGGACG
FAD2-2 (SEQ ID NO:7)   (319) TGCGGCCACCACGCCTTCAGCGACCACCAGTGGCTGGACG
FAD2-1 (SEQ ID NO:6)   (305) TGCGGCCACCACGCCTTCAGCGACCACCAGTGGCTGGACG
                              361                                        400
FAD2-3 (SEQ ID NO:8)   (359) ACACCGTCGGTCTCATCTTCCACTCCTTCCTCCTCGTCCC
 FAD2A (SEQ ID NO:5)   (359) ACACCGTCGGCCTCATCTTCCACTCCTTCCTCCTCGTCCC
FAD2-2 (SEQ ID NO:7)   (359) ACGCCGTGGGCCTCGTCTTCCACTCCTTCCTCCTCGTCCC
FAD2-1 (SEQ ID NO:6)   (345) ACGCCGCCGGCCTCGTCTTCCACTCCTTCCTCCTCGTCCC
                              401                                        440
FAD2-3 (SEQ ID NO:8)   (399) TTACTTCTCCTGGAAGTACAGTCATCGACGCCACCATTCC
 FAD2A (SEQ ID NO:5)   (399) TTACTTCTCCTGGAAGTACAGTCATCGACGCCACCATTCC
FAD2-2 (SEQ ID NO:7)   (399) TTACTTCTCCTGGAAGTACAGCCATCGACGCCACCATTCC
FAD2-1 (SEQ ID NO:6)   (385) GTACTTCTCCTGGAAGTACATCCAT-GACGCCACCATTCC
                              441                                        480
FAD2-3 (SEQ ID NO:8)   (439) AACACTGGCTCCCTCGAGAGAGACGAAGTGTTTGTCCCCA
 FAD2A (SEQ ID NO:5)   (439) AACACTGGCTCCCTCGAGAGAGACGAAGTGTTTGTCCCCA
FAD2-2 (SEQ ID NO:7)   (439) AACACCGGATCCCTCGAGAGGGATGAAGTGTTCGTCCCCA
FAD2-1 (SEQ ID NO:6)   (424) AACACCGGATCCCTCGATAGGGACGAAGTGTTCGTCCCCA
```

FIG. 1B

```
                          481                                    520
FAD2-3 (SEQ ID NO:8)  (479) AGAAGAAGTCAGACATCAAGTGGTACGGCAAGTACCTCAA
 FAD2A (SEQ ID NO:5)  (479) AGAAGAAGTCAGACATCAAGTGGTACGGCAAGTACCTCAA
 FAD2-2 (SEQ ID NO:7) (479) AGAAGAATCCGACATCAAGTGGTACGGAAAGTACCTCAA
 FAD2-1 (SEQ ID NO:6) (464) AGAAGAATCCGACATCAAGTGGTACGGCAAGTACCTCAA
                          521                                    560
FAD2-3 (SEQ ID NO:8)  (519) CAACCCTTTGGGACGCACCGTGATGTTAACGGTTCAGTTC
 FAD2A (SEQ ID NO:5)  (519) CAACCCTTTGGGACGCACCGTGATGTTAACGGTTCAGTTC
 FAD2-2 (SEQ ID NO:7) (519) CAACCCGCTAGGACGCACGGTGATGCTAACCGTCCAGTTC
 FAD2-1 (SEQ ID NO:6) (504) CAACCCGCTAGGACGCACGGTGATGCTAACCGTCCAGTTC
                          561                                    600
FAD2-3 (SEQ ID NO:8)  (559) ACTCTCGGCTGGCCGTTGTACTTAGCCTTCAACGTCTCGG
 FAD2A (SEQ ID NO:5)  (559) ACTCTCGGCTGGCCTTTGTACTTAGCCTTCAACGTCTCGG
 FAD2-2 (SEQ ID NO:7) (559) ACGCTCGGCTGGCCGTTGTACTTAGCCTTCAACGTCTCTG
 FAD2-1 (SEQ ID NO:6) (544) AAGCTCGGCTGGCCGTTGTACTTAGCCTTCAACGTCTCGG
                          601                                    640
FAD2-3 (SEQ ID NO:8)  (599) GAAGACCTTACGACGGCGGCTTCGCTTGCCATTTCCACCC
 FAD2A (SEQ ID NO:5)  (599) GGAGACCTTACGACGGCGGCTTCGCTTGCCATTTCCACCC
 FAD2-2 (SEQ ID NO:7) (599) GAAGACCTTACAGCGACGGTTTCGCTTGCCATTTCCACCC
 FAD2-1 (SEQ ID NO:6) (584) GAAGACCTTACAGCGACGGTTTCGCTTGCCATTTCCACCC
                          641                                    680
FAD2-3 (SEQ ID NO:8)  (639) CAACGCTCCCATCTACAACGACCGCGAGCGTCTCCAGATA
 FAD2A (SEQ ID NO:5)  (639) CAACGCTCCCATCTACAACGACCGTGAGCGTCTCCAGATA
 FAD2-2 (SEQ ID NO:7) (639) GAACGCTCCCATCTACAACGACCGCGAGCGTCTCCAGATA
 FAD2-1 (SEQ ID NO:6) (624) GAACGCTCCCATCTACAACGACCGCGAGCGTCTCCAGATA
                          681                                    720
FAD2-3 (SEQ ID NO:8)  (679) TACATCTCCGACGCTGGCATCCTCGCCGTCTGCTACGGTC
 FAD2A (SEQ ID NO:5)  (679) TACATCTCCGACGCTGGCATCCTCGCCGTCTGCTACGGTC
 FAD2-2 (SEQ ID NO:7) (679) TACATCTCTGACGCTGGCGTCCTCTCCGTATGTTACGGTC
 FAD2-1 (SEQ ID NO:6) (664) TACATCTCTGACGCTGGCGTCCTCTCCGTATGTTACGGTC
```

FIG. 1C

```
                              481                                      520
FAD2-3 (SEQ ID NO:8)   (479) AGAAGAAGTCAGACATCAAGTGGTACGGCAAGTACCTCAA
 FAD2A (SEQ ID NO:5)   (479) AGAAGAAGTCAGACATCAAGTGGTACGGCAAGTACCTCAA
FAD2-2 (SEQ ID NO:7)   (479) AGAAGAAATCCGACATCAAGTGGTACGGAAAGTACCTCAA
FAD2-1 (SEQ ID NO:6)   (464) AGAAGAAATCCGACATCAAGTGGTACGGCAAGTACCTCAA
                              521                                      560
FAD2-3 (SEQ ID NO:8)   (519) CAACCCTTTGGGACGCACCGTGATGTTAACGGTTCAGTTC
 FAD2A (SEQ ID NO:5)   (519) CAACCCTTTGGGACGCACCGTGATGTTAACGGTTCAGTTC
FAD2-2 (SEQ ID NO:7)   (519) CAACCCGCTAGGACGCACGGTGATGCTAACCGTCCAGTTC
FAD2-1 (SEQ ID NO:6)   (504) CAACCCGCTAGGACGCACGGTGATGCTAACCGTCCAGTTC
                              561                                      600
FAD2-3 (SEQ ID NO:8)   (559) ACTCTCGGCTGGCCGTTGTACTTAGCCTTCAACGTCTCGG
 FAD2A (SEQ ID NO:5)   (559) ACTCTCGGCTGGCCTTTGTACTTAGCCTTCAACGTCTCGG
FAD2-2 (SEQ ID NO:7)   (559) ACGCTCGGCTGGCCGTTGTACTTAGCCTTCAACGTCTCTG
FAD2-1 (SEQ ID NO:6)   (544) AAGCTCGGCTGGCCGTTGTACTTAGCCTTCAACGTCTCGG
                              601                                      640
FAD2-3 (SEQ ID NO:8)   (599) GAAGACCTTACGACGGCGGCTTCGCTTGCCATTTCCACCC
 FAD2A (SEQ ID NO:5)   (599) GGAGACCTTACGACGGCGGCTTCGCTTGCCATTTCCACCC
FAD2-2 (SEQ ID NO:7)   (599) GAAGACCTTACAGCGACGGTTTCGCTTGCCATTTCCACCC
FAD2-1 (SEQ ID NO:6)   (584) GAAGACCTTACAGCGACGGTTTCGCTTGCCATTTCCACCC
                              641                                      680
FAD2-3 (SEQ ID NO:8)   (639) CAACGCTCCCATCTACAACGACCGCGAGCGTCTCCAGATA
 FAD2A (SEQ ID NO:5)   (639) CAACGCTCCCATCTACAACGACCGTGAGCGTCTCCAGATA
FAD2-2 (SEQ ID NO:7)   (639) GAACGCTCCCATCTACAACGACCGCGAGCGTCTCCAGATA
FAD2-1 (SEQ ID NO:6)   (624) GAACGCTCCCATCTACAACGACCGCGAGCGTCTCCAGATA
                              681                                      720
FAD2-3 (SEQ ID NO:8)   (679) TACATCTCCGACGCTGGCATCCTCGCCGTCTGCTACGGTC
 FAD2A (SEQ ID NO:5)   (679) TACATCTCCGACGCTGGCATCCTCGCCGTCTGCTACGGTC
FAD2-2 (SEQ ID NO:7)   (679) TACATCTCTGACGCTGGCGTCCTCTCCGTATGTTACGGTC
FAD2-1 (SEQ ID NO:6)   (664) TACATCTCTGACGCTGGCGTCCTCTCCGTATGTTACGGTC
```

FIG. 1D

```
                              961                                    1000
FAD2-3 (SEQ ID NO:8)   (959)  ATCTGTTCTCCACGATGCCGCATTATCACGCGATGGAAGC
 FAD2A (SEQ ID NO:5)   (959)  ACCTGTTCTCGACCATGCCGCATTATCACGCGATGGAAGC
FAD2-2 (SEQ ID NO:7)   (959)  ATCTGTTCTCGACGATGCCGCATTATAACGCGATGGAAGC
FAD2-1 (SEQ ID NO:6)   (944)  ATCTGTTCTCGACGATGCCGCATTATAACGCGATGGAAGC
                              1001                                   1040
FAD2-3 (SEQ ID NO:8)   (999)  TACCAAGGCGATAAAGCCGATACTG-GGAGAGTATTATCA
 FAD2A (SEQ ID NO:5)   (999)  TACGAAGGCGATAAAGCCGATACTG-GGAGAGTATTATCA
FAD2-2 (SEQ ID NO:7)   (999)  GACCAAGGCGATAAAGCCGATACTT-GGAGAGTATTACCA
FAD2-1 (SEQ ID NO:6)   (984)  GACCAAGGCGATAAAGCCGATACTTTGGAGAGTATTACCA
                              1041                                   1080
FAD2-3 (SEQ ID NO:8)  (1038)  GTTCGATGGGACGCCGGTGGTTAAGGCGATGTGGAGGGAG
 FAD2A (SEQ ID NO:5)  (1038)  GTTCGATGGGACGCCGGTGGTTAAGGCGATGTGGAGGGAG
FAD2-2 (SEQ ID NO:7)  (1038)  GTTTGATGGAACGCCGGTGGTTAAGGCGATGTGGAGGGAG
FAD2-1 (SEQ ID NO:6)  (1024)  GTTTGATGGAACGCCGGCGGTTAAGGCGATGTGGAGGGAG
                              1081                                   1120
FAD2-3 (SEQ ID NO:8)  (1078)  GCGAAGGAGTGTATCTATGTGGAACCGGACAGGCAAGGTG
 FAD2A (SEQ ID NO:5)  (1078)  GCGAAGGAGTGTATCTATGTGGAACCGGACAGGCAAGGTG
FAD2-2 (SEQ ID NO:7)  (1078)  GCGAAGGAGTGTATCTATGTTGAACCGGATAGGCAAGGTG
FAD2-1 (SEQ ID NO:6)  (1064)  GCGAAGGAGTGTATCTATGTTGAACCGGATAGGCAAGGTG
                              1121                                   1160
FAD2-3 (SEQ ID NO:8)  (1118)  AGAAGAAAGGTGTGTTCTGG--------------------
 FAD2A (SEQ ID NO:5)  (1118)  AGAAGAAAGGTGTGTTCTGGTACAACAATAAGTTATCTTG
FAD2-2 (SEQ ID NO:7)  (1118)  AGAAGAAAGGTGTGTTCTGGTACAACAATAAGTTATGAGG
FAD2-1 (SEQ ID NO:6)  (1104)  AGAAGAAAGGTGTGTTCTGGTACAACAATAA---------
                              1161
FAD2-3 (SEQ ID NO:8)  (1138)  ----
 FAD2A (SEQ ID NO:5)  (1158)  CTAA
FAD2-2 (SEQ ID NO:7)  (1158)  ATGA
FAD2-1 (SEQ ID NO:6)  (1135)  ----
```

FAD2A locus with perfect ETIP integration - in-out PCR suite 31000 bp

FAD2A locus with perfect ETIP integration - Southern probe 31000 bp

SEQUENCE LISTING

```
<160> NUMBER OF SEQ ID NOS: 480

<210> SEQ ID NO 1
<211> LENGTH: 47493
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ttcccaaaca acacaataag ttattgtcaa taactaatct tatgtccaaa gaatataaaa      60
cattaggtcc agtcttttta ataacttttt atttatattt tttaaattat ttgatttaaa     120
tccactcaaa taatttatac gaagttgaaa ataactataa ctattttgc gggtttagat      180 actacagaaa agcatttaac ttgaaattaa ttaaattaaa attttatttt gtttgtattt     240
tcagaaataa aaaatcgaat tccttttaac ttaataaata ttagattgtt ctttgtaaat     300 tattttatt aattcataag aacatattat tatatatgct atattatgct tggtttaagt     360
taaaattaaa tagttttata gaaataaaat gttagaatca ataaattaac atcaaataag     420
ttttataatt aaaattttat caaataagca tatattaaaa atttaatcca acaaattaaa     480
gatgttttct taaaacctcg taatgataca ggttgaagta attaaaaaaa aattaagtaa     540
tattttagat aattttcctc tttaataaaa taatttatta tgtatgttta aatacactaa     600
aataaaaatg ttaaaacatt acttatataa taatgttaaa atatattgat attataaatt     660 agatttttt ttaaagatat tttcgcacat ttaatcgtgg gttatagtct agtatatttt     720
```

```
aaaacctaac tattaaatgc tgaattttat gaagttataa cataaagtga ttaatgaaca      780
aacgtcttat caattaatta tgcttccgca aagcatcatg ttcattgccc tataaaatca      840
tctctcgttc actgatacca atcaaacatc aaccaatatc aaaaactaaa gcaaatatgg      900
caaagtctct ttacattgca atgtttgtat ctatagtaat gttcttcatg gcaaattcaa      960
tttcttccaa ggaaattggt caatattcac aagaggcacc aggagatgta aagatatctc     1020
ccacatcgga ttttgatatt tacgtcgaat ctcccgatga atctctattt gaagaagtcg     1080
attcacccgc aatggaatat gagatgaagt ctggacatca ttacacacac aaacaacttg     1140
gttttcttga ggcttgcttt caaaatctaa actcattaga ctgtggagat aatattttca     1200
agaacatgtt agatgaggca gcacaagtat tatcaaatga atgttgtcat gatctattaa     1260
agattagcaa agattgttac ctaggaatga ctcaaagcat tttatcgagt tatgagtata     1320
gatttattgc gtctaaggct attcccaaaa gtaaacagac atggaatgat tgtgttctta     1380
gagttgggaa cctgattggt agcccaatcg cttttgagga actacactaa ttgatgttcc     1440
ggtgtgctga tgttttatat atgtgatttt gtaactcagg cgttatgaga cttaccatta     1500
tataaataaa gctaaagatc ttttacagat cttatattag tatacgagac tcattagagt     1560
aacatgaaag ctgaatcaac tatcaacatt ggtggtattt gtctttaggt ttctttaatg     1620
gatatagatg tttggggaca acgctagcag ctcttagtaa ttccgcatat ttatggacta     1680
tgagctcttc gctctaaatt acacaatccg acccaccatt tcagatatca atactcgcaa     1740
acccagtaga gttacagtct ctattgtact tctccttgca ttccttcagc ctgattctct     1800
tatccacaat ggttatactt gtctctgaca acgatcatgt tcctcaagag caaaaaacca     1860
tctaggtctc cgcagctcag tggcgagcct ctcacacaac cattgaacac atctaccaaa     1920
gcaaatgacg tggcattctt gggaatgaaa cctttgatac agttacatgt cagtatcgtg     1980
ctaatgttat agtaaacatt ttattatcat attttttaata ctaatgaggc atgatttgat     2040
tttaatttgc atattttatc tcttaatcct ggattatata tagttttcag cagacaagaa     2100
aatgttattt ccacattcta tgacttgttt ttagactttc atcaattcat tacaacatat     2160
tattgttatt agtcgataac tttgacttaa ccacgtgaat tttatcccaa aaaaaactta     2220
accacctaaa atctaatttt ttttataaag aaattagttt ttgatccgcg ttttgcagat     2280
ttatttttca tttttatatg tttatatctt tgagaatgcc atgaaattga ccgtgtgttt     2340
ctattgtgtt tagttttttgg tctttctaat ttttgagatt attttttctt taaacgatgc     2400
ccgggttatt attaattta tttgataaat taaacattga aatataatta gaattcgaag     2460
tatactttta ggttttatca gttttaaaga tggtcatttg atttgaaatt tgtataaaaa     2520
ttccaacttt tattttggaa ttttttaaaag aaatatatgt ttactgatgt gtggtatatt     2580
ttaataagat aaatatatta atataatatg gcatagtatt atgtagataa ttaaaattta     2640
tatttacaat tatgtaatat aaaactatag atattattga aaactataat atttgttgta     2700
atatgaatta gtttaaatta tgtacaacta tctgtgcaaa attacgtagt ttgtaaatgt     2760
gtatatgtga taaaactata ataatacata ctatatttta actaatattg gtttatatat     2820
ctaatatatt taattgtgta tttcatatta atcaaaaata taaagatttt aaattagaca     2880
gaaaccgttc aaaaataaat atagtttttc atttgacccg caatttcaaa atgcgagatg     2940
ttttataaat aattaacata atctttaatt ttggaaatga tatatgtttt tgaattattt     3000
tacgtttttt atattaccat taacatttat tttaaatttt aaatgagaaa tgattttgta     3060
```

-continued

```
attgtaacta aaatttatat aaatgtaact tatgaaaatt aaaaaaaatg taaccaggat    3120
aattaccaaa aatagcattt tgaatatacc acttttcact tctactttat tcaactttgc    3180
cattaaactt ttaattggca aatgactatt atatccctaa ttaattgaac ctaaactatt    3240
caattagata ggttatatat tcttcctcca tgtgagatcc ggcgagctcc ggcaaaggac    3300
gatgattgga gattattggg gatactgtga acaagaacga ggaacatatc tggaaatatg    3360
taaatgggaa gagatttcta cacagattag attaatgaac atgatatcag attcattgac    3420
atcttgtact gattccaatt ttgtctcgtg cttgttattc ctggctttta atgttttggt    3480
gttgatgtat ctgatagagc aagtggaaag aggagctgga acaagcggaa agaccgagaa    3540
aataaaagta accaataaac atggacacgt taaggaagaa actgactcca atgattcaga    3600
gttttggatg cttaagtcaa gttttggttc agagtcagag taggagagtg atgaagaaaa    3660
ctgcaaaggt acctcttttt ggtgtttttt gttggttcta ctttcatctt tctatcgaaa    3720
cttaaactag atttgtgtct gatcttggta caggttctca ttgtgatgcc agataatatg    3780
aggagctctc agaaaggtaa aggtaaatgt atacatttac tcttatttct gtgtatttct    3840
tacaaaattg cggattggtt ttgatgttca cctctagttg ttttgtctct tctacagagc    3900
aaagaggatg tcaatagaga ttggaccaag tatgatcatt acggcagcgc cactatgatc    3960
atgaggcagt ctttggaaga gcagatgagt tctgttacgg agaagagtgc taagtatgct    4020
cagattgctg ctgaggaagt gcccaagagt ctttactgcc ttggtgttcg tctcactact    4080
gagtgatttc agaactcgag ttttagggga agctcgcgga gagaatctat gttgtggctt    4140
ctaagctcac cgataacagt cttaccatg tctatgtgtt ttctaataac attgttgcta    4200
cttcggttgt ggttaactcc actgctctca aatccaaggc ccctgagaaa ttcgtccttc    4260
atcttgtcac taatgcgatg aagtcatggt ttgctatgaa tatgaacttc ttaattgatt    4320
ccggcttggt tgattcagta tgtggaaatt gcaggtgacg agtgtgcaat cttcgctgtt    4380
tttagaagca gcatttgcgt caaatgatat gcagcatttg ctgcaatgt  taagggtctt    4440 gtcggaattg attccaggat tcaaagaaac taccgagtat tacacattct aaggtcttct    4500
taatgagacc agttccccag ttgctgtctg agatttaaca tctcttacct tatttatgtt    4560
caataactta gataataaga aatttcgttg ataatatttc aatttatgta tgtttcattc    4620
aaagaaaaca atgattagtt ttctcaaatc agtcttctta tttgtttgag ttaagatctt    4680
ccaaacttat gttttttttgt aattcaggag taacaaaatg aatatagtct aaatctggat    4740
ctaattttga aattttttta actggatttt cttttcaaatt aaatccttat ttactcttta    4800 agaattttt taaaagttta ggtttgacat ctctaaccta tacgttgcga acttggacaa    4860
aaccaaaaca agattaagca ttgttttcag aatatttaat ttttaatttt gttgggtttg    4920
atttggatct ttccagtgta catatgttta aacaccatcc tcttcaaaac ggttgtttaa    4980
gtgttcattt tgggtaggt ccaagacgtg actgggacaa ttcaaagcgc tagttatctc    5040
cgtaacacat catatttccc cttacattaa gataaagtat actcgtgaat ctcaattgga    5100
tgcaataaat aaaaacaaaa tcccttccca tcaaggcatc aaactgccaa agtcaattct    5160
agaaaaatat taaaaactat tcttttttta ttttatttta gagacttctc ttccttttta    5220
ttctgtagga agaaaaaaca aaaaagaag aagaagagga gaatcgtctc tttctttctc    5280
ttagaccatc tacaatgcta cgctaaaatt tactctatat ttcactctaa aatagagtaa    5340
ctctattata gagtgaaata tagagtaaat tttagtgttg cattggagat gcccttaact    5400
gtatccgtga aggcaaaaag atacgtataa acaaatacat ttacacataa atatgtatat    5460
```

```
gtatgtattt atactcttct agctctctct ctctcacctg tacctttaat atggtgtttc    5520
tgtttacgag aaaccaaacc cacaccaatt gaaaacgcga cttgttgtta ttcaatcgca    5580
atcaacgagt aatctgctac ctcgtctcct ctctgagatc tctcttcctc ccattagatt    5640
cgcctgagga ggtactcatt cttattcctt tttttctctgt cttttatgg aattttctaa    5700 aaatgctgta aggtttcaga catatccggt aataactgga ctctgaacta atgacttgtt    5760
caagtgttcc agctcttatt acatagtacc gatttggatt gtgttttttt tttgtttga    5820 ccttcttgca attgtgatgc tctgatttgt tttcacgttc gtagcttatg ctttaatttt    5880
tttttgtcat ttatcttctt ttccccctaa ttttttttg tttaattgca aacctttttg    5940
tgtgtgcttc ggcatgaact tagggccct actactggcg taagtttagg cttctttttt    6000 ggtgctttt tagctttact gcttgttggt ggaattcact tttcttttta agttaatttc    6060
agagacatcc ttattgtaac tgctcacttt tcagtgttgt tagtttaagg aatgatgaaa    6120
gaaagaaagc tttctataac tgcttgattt agcttcagtt gttagtaata tgggttagaa    6180
ctgttagcct tgagtagata tcactgtctt tatttttgg tttattgttg atttattttt    6240
gtggtcttgt tttgattcag tgttctcgag gttttgactt cgacttgtga tgatggcatc    6300
atctaaacaa ggatcaaagt cgagaaaaac agggtttagc aatttcaagg gtgctgattc    6360
tactgcttcc tcaacaacct cttcttcaaa gctttatcaa gagacatcta tcgatgatgg    6420
acatagctct cctgcttctt catctgctca aagcaagcag cacttcttct caccggactc    6480
cgcaccgcaa agtgctcagc gttctaaaga gaacgtcaca gtgacagttc gctttcgtcc    6540
actcaggttc acagtgatgt gcttttttat tagggcttgc aaatattagg ttgcctgttt    6600
gttctgtgaa tttgaaataa ctttttccgtg acagtccaag ggaaatccgc caaggggagg    6660
aggttgcttg gtatgcagat ggcgaaacaa tcgtacggaa tgagtataat ccgacgatag    6720
cttatgcata tggttagtct taatagtttc attaatgtca cagtggttcc ataatcatct    6780
taaatattgt atgtcggcat atcactcgag aataacaaac taaggatgat agtgttgttc    6840
ttatgtggta taatcttcct ttttgatgt ctgggtctct atgtctgtta acgattggtt    6900
ctctttatga cagatcgtgt ctttggacct acaaccacaa cacgcaatgt ctacgatgtt    6960
gctgcacacc atgttgttaa tggggctatg gaggggatta acggtatgaa gtgaccatat    7020
ttaatggcag tctattttgt atttagaact caatttatga tatcaactct tttatcgaaa    7080
agcatacttt cttccaaact ctatcaacaa ggctgactgt tcctaattta tgatgaattc    7140
gtcagaacca atttgactt tcgatgtact taccagttga tttgtatata actttgaatg    7200
ttaatccatc tacagggacc attttgcat atggagtgac aagcagtgga aagactcaca    7260
ctatgcatgt aagatacctt catctggata gcttttggct tgttttgtac gatgtagttc    7320
aatttgtcat aaagatatag tgctttgtca gagaatcatg tatttctttt aatttcaact    7380
ccacaagctt aactaacaca tgtaagaatc tttctgcaat agttatagat aaacaacctt    7440
gcgatagata agttttctac cctaatactg ttaggtttct gtgcacccta ctgttgaaac    7500
catatctgat agatttcgat tgggtttttt tttgggttca aatgtcaggg tgaccagaga    7560
tctcctggta ttataccatt agcagtgaaa gatgctttca gcattatcca agaggtactt    7620
cttaggatat tgattttgtc agattccgtg gcctaagtac tagcaacctc acatatctat    7680
tttcttacag acaccaagcc gagaatttct cctgcgtatt tcctacatgg aaatttataa    7740
tgaggtgcta ttatttatcc actttctttc tctgctccat tacctatatt cagcttcaag    7800
```

```
agtagtggag tgatagaata ctctgccttt aaaatcttcc tttgagatta attcccttaa    7860
gatccaccgt atttcaggtt gtcaatgatt tattgaatcc agcaggacat aatttgagga    7920
tcagagaaga taaacaggta tgtgtttcag cttcagatca tcttttgatt acacgggctg    7980
ctgctctcac ttacttgtaa tatttctttt tattacattg ctcgtctaaa atcccaaaat    8040
gtttacatca tattcttaaa ttagtaggaa cccatgtcta ggcttgtttg gtacctgaaa    8100
actatactgg ttccattttt ttcttgtgaa atttgatctc tctgagaact ctgctgttac    8160
aatgatgata tgtgggtcac attgctttca agcagacttg tagatgatcg ctatgagttc    8220
ttttcttcca tgtgttttaa ttgaacgcat cctttaatt tattctaggg aacctttgtc      8280
gaagggatta aagaagaagt tgttttatca cctgctcatg cgctttctct tatagcagct    8340
ggagaaggta tgtggtgctt ccacttttcc ctttagctaa agaaataggt ttactataca    8400
tcctcataac gccagcaaag actgttgcag tcattgtaca tttgttaaag atattgtcat    8460
caggaaagtg gttctcctct acctgcttgg ggctgtacaa aacgttaaaa attgtgtttg    8520
tttttctttt tatttaatat gagagagtag ttctctctct ctcatgattc cagtatacat    8580
atatcatcct taaaatttgt catgatctag taaatttaca tttaattcaa ttcacattga    8640
ttggagtttt gtccttatga cagagcaacg ccatgttgga tccacgaact ataatctgct    8700
cagcagccgg agccatacaa tatttacgtt ggtatgtaaa tactctcttt gaaatattgg    8760
tagctatatc ctttttcttt ctccgcacgt atatacactt gtattgtgga tggatgcacg    8820
caaaaccaac gttcttttct attactataa ttggttaaaa ggtaaaaatg atagtttttt    8880
gtcttataat cacgatagta tttgaaaata gaataccgaa attctatttc ttattcagaa    8940
taagttgtgg accacgttct tcttttcacg tgttttcttc cgttcaagga atttctgttt    9000
gtcttttatt ctaattctag ttgtttagtc gtgtcaagtg ttccaccggt tatggtacta    9060
ctttcttttc attgtaactc atatagctgt accgtttcta aaagatgata aactcatttg    9120
gatgcagaca atagagagta gtcccttagg caacaagatt aaaggtgaag ctgttcacct    9180
ctctcagctg gtaagcttct cctgtgccag tgatattatg tatggttatg atcaacactt    9240
tcttcaacac taagagcaac tgacattaac tacccataat ctcttccgca cccgcagaac    9300
ctcgttgatc tggcaggttc cgagagttca aaggttgaaa ccagtggttt aagacgcaag    9360
gaaggatcat acataaataa aagtttgctg acattaggca ctgtgagttt ttcttacca     9420 cagttttctc ttagtcaaca ataagttttg gagtcagtta aatcgaagga cttcattttc    9480
ttttaaatcc ggtcaatctg tgcttgtcca aacctaaagt taaatagttg tctattcttg    9540
tttatattct ggtcctgttt gaacattctc ctgttggctc aattcaggta attctgttgt    9600
gatattgtag gtgatatcaa agctcacgga tgtgaaggct tcgcatgtac catacagaga    9660
ctctaagtta accaggatcc ttcagtcctc attgagtggc catgaccgag tatctgtaag    9720
ttattagatc ttttctccat cctcttgcta ctataaatat aaaatccaca acatgatcat    9780
cagcagagtg atgtacttta ctgattagtt gtcccttctg gatatggtag ctcatttgta    9840
cagtgactcc tgcatcaagc agctcggaag aaacacacaa cacattgaaa tttgctcatc    9900
gtgcaaaaca tattgagatt caagccgaac aaaacaaggt ttgcctcata tcttcttcta    9960
tcagacctta ttttattgta ctaaagttct tgcttggttt ctaaatctat attactgcag   10020
atacttgatg agaaatcatt aatcaagaag taccaacacg agattcggca gctgaaggag   10080
gagttggaac agattaaaca ggacattgta ccaattcctc agctgaatga tattggcaca   10140
gatgatatcg ttctcctgaa acagaaggta tgagttatat gctcgattag acaagtggaa   10200
```

```
ggatgttttg tgtctttaca ttgagagaat ctgtagtaac cttgtctttt tttttgtttc   10260
tggctatata acgtgatgat attagctaga agatggtcaa gtgaaactgc aatccagact   10320
cgaagaagag gaagaagcta aagcagctct attgagtcga atccaacggt tgacgaaatt   10380
aattttggtg tcgactaaaa cttcacaaac atctcgatta cctcatcgct ttgagcctcg   10440
gaggagacat tcatttgggg aagaagaggt agaatcactg attatagcct tgatattata   10500
aattgtttcc atggtcgttt ctgagaatat tttgctggag caagtacaca aaattgctag   10560
ttttgtttgg ctaatcttgg ttgataatat gcgtgtgcag cttgcttacc taccatacaa   10620
gaggcgggac atgatggacg atgagcacct tgatctgtat gtctctgcgg agggaaataa   10680
tgagattaga gatattgcgt ttagagaaga aaagaagacc aggaagcatg gattgttaaa   10740
ctggttaaag cctaaggtat gcaaacgatt gaattttctt attagcactg tggtttattc   10800
tggttcgttt cagaactgca cctagcaact ataggtttgt actattgcgc actatagatt   10860
tatagagttc tcatgttctt caaagaacaa tgatataagt aaagagtgct aatcatatga   10920
ccttgtgtgc ttatttgatt atttggtgcc tctcttgtcc ccttttttgt aacaatctta   10980
tttttctcct atcagaaaag agataacagt tcaagtgcca gcgaccagtc gagtgtggta   11040
aaatccaaca gcacaccatc gactcctcaa ggaggaggaa ataatctgca tgcagagtca   11100
agattttcag aaggatcgcc tttgatggaa caattctcag agcctaagga agacagagaa   11160
gctctagagg acacttccca tgaaatggag acgccagagg tacgaagaga cattttcaca   11220
tatgttatgg ttccaaagta actacatctt tatcttttcc acttcctgcc ctgttcccag   11280
actagcaata aagtgatcga tgagttggat cttctgaggg aacagaaaaa gattttatct   11340
gaggaggcgg cgttgcaatc aagttcatta aaacggctat tagatgaagc tgcaaagtct   11400
cctgaaaatg aagagattaa agtaatataa ccacttggtt catgatttgt atctagcttc   11460
cgtttaaatc taccaaacat tcactttcct ggttatctgt gttacttagg aggagatcaa   11520
agtcctcaat gatgacatca aggctaagaa tgacgagatt gcaacgttgg agaaacaaat   11580
cttggacttt gttatcacat cacatgaggc gttggacaaa tccgacatcg tgcaggtaag   11640
ttcattgtta agtattatgc agtgactttt tttttctgtg gttcatttct caagctattt   11700
ctctataaat atcttcaggc acttgctgag ctgagagatc aagttaatga gaagtctttt   11760
gaactcgagg taaagaattg tttctgctac agcacctaga gatgtcttgc tactgcgtgg   11820
atgataatta tttctcttag ctccagtata atatctactc atgcctgcat aaagttgctt   11880
ctctgcaaat aatgatgaaa gctaattgca tctataacgt tttttttttct ttctcattct   11940 tgatcttgtt tacaggttaa agctgcagat aataacatca ttcaggaaca actcaatcaa   12000
aaggttgaga gattttttct tttatcgatt tgtcttaagt ttataatctg taaataattt   12060
aataaccaac gaagtatttt gctgcagaca tgtgaatgtg aagcgtttca agaagaagtt   12120
gcaaacctaa agcaggaact ctctaatgcc ctggaactag cacaggttct caaacttttt   12180
atatgaaaaa agcaacacct aatagctaaa tgattctcaa actaaagtca cttgcctttc   12240
tgacatgaca ggaaaccaag atcgaagagc tgaaacagaa agctaaggag ctaagtgaat   12300
cgaaggagca attagaacat cgtaacagga aactcgcaga agagagttca tatgcaaaag   12360
gtcttgcatc agcagctgca gttgagctca aggcattatc tgaagaagtc gcaaaactca   12420
tgaatcacaa cgaacgacta gcatctgagc tagcaacact caagagctca gtcccacagc   12480
acggtaataa gccaggaaca acaacaacaa ccaatgcaag gaacaatggg agaagagaga   12540
```

```
gtcttgcaaa gagacaacaa gagcaagaga gctcgtcgat cgagctgaag agagaactga   12600
ggatgagcaa agagcgggaa cgatcatacg aagctgcact tgttgataga gaccaaagag   12660
aagccgagct tgtgaggata gtagaagaat cgaagcagag agaagcgtat ttggagaacg   12720
agcttgctag tatgtgggtt cttgtttcta agctgagaag gtctcaagaa ggtggttctg   12780
agatctctga ttctgtatcg gagacgctac agaccgatcg atcgttttga gacgtgaagt   12840
agtaggatat gtttgtgcag tgattccaag agtttgtgtt tgtgtaagta tgataaaaca   12900
taaagtaatg atttatttga aaatcatcag attgtttaaa attcaagaaa aaaaaacact   12960
gtttaaatta agaggtaaga gaagtgaaaa gtgggtaaaa gaagaaaata atgatagttc   13020
tggggagctt agagcatgat gattatcccg gtctcttata actcatgatt ttaatatatt   13080
ttttttacac tttttggtta aaaaacatct cttatatatt ttatttaaaa aatgttctta   13140 gtttttaat taaaaactaa gaaacgatta gctaaaaaac tcagttaaga aaccagggtt    13200
aatcatggtc ttagtaaagt tcttaaaatt ttcactttca cccaatacct ttccactaat   13260
ccacatttgc cccaattgat ttccttcttt gtgtatacaa cccaaattaa taattgttaa   13320
caaaacagta aaacactata caaacaccaa gaagtgtact caatcagatg tctgaaaaca   13380
agaagtgcaa ctgaagagtc ttggattgaa gttagagagg cttaagagtg ttcttaggag   13440
cacttatcca cggagtgtct ccaatggcaa atctccacaa ggcattgaca tgttgaggca   13500
atgcgtaatc tattccaacg cgaggaccaa ctagtacttt ctccacatct tctcctccat   13560
ccagaacctc caatcctcct gtttttcata catcatttat tacaacaaag cttaaactct   13620
cttaaagaat cagaaaaaac cagaaactcc attaactgat tttggtttat ttgtctgact   13680
aacccggaga atagagggga tgatgagacc actctgttga aagtccaagc gcctgcccga   13740
cctgcaagag gcacatatga acagatttca tgcattgtgg atttgcaagg tgcattctgt   13800
ttgatgcaga tcagactaac ctttcctggt ccatttagaa gaacaggttt gtcggttttc   13860
tggccacgac gctcctgtat ggtctccagc cctgcaatac catcacaccc ttttaagcca   13920
acgtaagatc tatgtaatca ttcttaacgc aaaaacagta tcaataaagc aattatttaa   13980
gtagaaacat gcatcgataa gagagagtgt aatgaacagt ctcacagaac tgatgtggag   14040
agattattac cggtaacagg agaacaagat cgtatcaaaa cagcagctcc aactccatcc   14100
ttatcagcaa caatattgag catcatatga agaccgtaac aaagataaac atatgcatgt   14160
cctcctggtc caaactaata aacaaaaaaa acacacattt tagagaatgt tatcatgtgt   14220
atttaactaa atgataacaa agcagaatga agaaactcac aataggtgcg gtccgtgggg   14280
tattcccgaa ccgtccatgg caagctgagt catttggtct ataagcttcc acctgccaaa   14340
ggaggaacaa tgttagagag tattaacttc gttaatccaa aatcaaaaat ttttaccaa    14400 caattatagt cagaatatca aaaatcccaa gaaaacaaca aaaaaaacta aattctttta   14460
atgaggaaac aagaacaaaa ctttgtatct gacctctgtg atccgtagga caacattgtc   14520
tctcctcagg aacttcccga gcaaacgtgg cgctagatca agcgcgtcta tttgaaagaa   14580
ctcaggaggc attatcttca tctcgggggt ggagcgggtc agtgggtact cgggtctgac   14640
ccgaaccgcc cgagccttgg aacagtgctt cttctctcgt gctgcacgta gagccactgg   14700
agttgtaacc ttgggtagtt ccgattcctg atcaactcgt ttggaacgac gaggcggcgt   14760
tttcattgac ggacagaacc aaaagatttt tgacttttc gaatgtgttc gactctttga    14820
cttttcttcg ttttgttatt tggcgggtga ctgttacgct gtccgaaggt taagccttaa   14880
acataaactt tccttattat gaccgtcata tcaatttttt cctccgtttt tcaatatttg   14940
```

```
gcgttttaaa aaaaaatttg agaaaaattg attttttttt gtttatccga tttaaattat    15000
atggttacta ataatccggt taaaacttaa aagtaaaact atagtttata gataattaag    15060
tttgtaattc tcaatttgaa gagaaataaa ataatttatg gagagctagc ctgaaattat    15120
aatcggtgga gatattttga ctttatatga tagtggggaa ataaaacaca aaataaataa    15180
tgttttcaaa taaacattta ttaattttat attaattcct attctgtaat tttgaattat    15240
ttttgaaatt attaatgaat aaatgattaa gaatattttt ttaaaagaaa aattagatat    15300
accactctaa aataatactt cctccatttc agaataaatg atgttttata agttttttgt    15360
tgtttcataa tagattgatg atgttttgat atatttatgt tattttttaat tttattgaaa    15420 aattgtgtaa ctaattagat attagagtaa tttatgtagt tggttgaatg attttttaaat   15480 tatattctta aaactaactt ttagttataa aagtaaaatt tttaaaacat catgtgaaat    15540
agatggagta ggatttaaca taatttgtac gttctagaca cttccaaagc gtttcaaaag    15600
ttaattagtt tttcttttc tggcataagt attattttat attttttccat ttttcagtag    15660 gaaaaaata aataaaaaaa aaacattttc tagaggcttc gtttacatat atctaggttt     15720
acctcctctg cttcttccca cacatctcat cgaattcgac tagctcccca ctcaatcact    15780
cctcgttagt tcaatctcga atccctaatc cactcaccat ggcgaagttc ggcgaaggcg    15840
acaagcgatg gatcgtcgaa gaccgccccg acggcaccaa cgtccacaac tggcactggg    15900
ccgaaaccaa ctgcctcgag tggtcccgca gcttcttcac caaccaattc tccaacgccg    15960
tcatcctctc cggcgaaggc aacctcttca tcaaaatcaa gaaactggag aagctcgaag    16020
gcgaggcgta cgtgaacgtg cgcaaggga agatcatccc cggctacgag ctcagcgtct     16080
ctctctcctg ggaaggcgag gcgaaggatt cggaagggaa gacgatctcg aaggcggagg    16140
gggccgtgga tatgccgtat atctccgatg agaatgcgga tgaggatccg gaggttaggg    16200
tttcggttaa ggacgagggg gcggttggga aggcgttgaa ggaggcgatg gtgaagaagg    16260 ggaaggggt tgttttggag aaggttaggg ttttttgtgga ggctatggcg aaaggagggc     16320
cttgtaggga tgaattggag aataagaagg tggctcctaa gtgggtggcg gcggcggcag    16380
cggctgtgga gaagactagt gttttgcctg ctgtggtggt gaaggagaag aagaaggtga    16440
agacgaagga ggggttcaag acgattagta tgactgagaa gttcagttgt agagctaagg    16500
acttgtatga gatcttgatg gatgagaata ggtggaaggg attcacgcag agcaatgcta    16560
agattagtaa agatgtgaat gggcctatta gtgttttttga tgggtcggtt actggggtga    16620
atgtggagct ggaggaaggg aagttgattg tgcagaagtg gaggtttggg agttggtctg    16680
atggtcttga ttctacggtt agtttagttg ttattttttct ttgtgacctt tggtttctat   16740
gtcattgtgg ctgatgtatt gtgctttgac attttcaggt gaagataact tttgaggaac    16800
ctgaaccagg agtcaccatt gtcaatctta ctcacaccga cgtccctgaa gaagacaggt    16860
tagtgtcact gcttgaaatc tttcttataa tagtatggta gtatgcaatg aatatttatg    16920
gtgtttggag tgcttgatag cttggtctta tatataactt tcatattgat gtactatctt    16980
gagggaattg taaccacctt tagcctgttt tgttctcaat gacagacact aattctgacc    17040
ttagtatctg tgctaatcct tgcgactgtt tagcttgctg tatgtagttg ttggactcat    17100
ccagtctttg ttctagtgaa tgaactcttt tggaatttgg gttttgcttt atttgttaat    17160
atatgataga acatttctat ctctaaatcg ctcaatggcc tacacgtctt taaatcttct    17220
acctatgcta cctttccact aactagcttt aggttatgct gatagagcgc ttctttgttc    17280
```

```
cttgtgaaca cctgttggct tattcctgaa agtatttgtt tgtccacatt ctcttactcg    17340
tcctgttgtg aagtgatttt gtccgttact ggatgtgact tattttttctc tgacgtttct    17400 actggctgat gcaggtatgg gaatgcgact gtggtggaaa acacggagag aggatggaga    17460
gacctgatct tccataggat ccgtgctgtt ttcgggtttg gaatgtgatt tgtgattttg    17520
attatcaagt aatcaaaatc agcattgctt catccataag ttcgattatg atttcaattc    17580
acaaggagac ataaagacga tgcagaaatt tggttttttac ttgtagttta tgcattttcc    17640
atgaactctt tggtcttttg ttaacactat ttggattaat ggcacacaac aaactattca    17700
catgagaata agttgtttta agtgttttat tctaaaagtg gtgtccatag tcaaccacgg    17760
catcaagatt gcctaaggaa cattgtctaa agactgatga aaactaggaa caagaagctt    17820
tggtttggaa ctataagctt tttgctaatc gcaatgccta accacaagt tacacatcaa    17880 ccggtaatta accagttacc agaacctgct ttgaccaaaa tattacacat cacagcaagc    17940
tctttggatc gtttatctaa aagggttttg gtttagcctg gaaccacgtg gatgaaatat    18000
ttattaacca caacatcaac agaaacgttt ttactagctt tgtcaggtat agacgtgggc    18060
acaaacaaga cctacttgaa atcagcacct acaaaataaa accaaaaaac atcttactct    18120
taatgtatgg cggtctttaa gacaacaaaa atttcttcta ccacttttaa tcatcaagaa    18180
gagacttgaa atgttacaga ttaaggtatc aagctcagac tcttaaaatg tcatattgtc    18240
agtgcatatg atttgaacta gattgtaata tttaacatta agaatttagt tatggtatac    18300
agagtataac ggtttgtgga tctgtcattg tgttatcatt aagctttgta agatagtca    18360 ttgttttggt tttgttaaaa tgatgttagg tagaaaatag taataatttc aaatcagcat    18420
ttagtataat tatgaaactt cacaaaatcg tgtggaaaac tattaaagac gagttttaaa    18480
tatggttgac cggatagtta atttcttac atcagatcca agattagtat tccgaagatt    18540
gttgcggtta ctggtatcaa tttcctggaa gatttaaaat atcatcatgt cacgtacttc    18600
attactagta accttcgttg tttaaagcgg aaatgtcgca actcgtttgc ttcatttgt    18660 tttcttttg gatccttcaa atgatccgca acacttccgt tggagttgat gccatagaga    18720
gtgcgtcgag ttatttaacg tataataaat attcttgcgt ccttgtacac atcatacgtt    18780
aattaagcca tcaagatgta gcattactgg cgttgtttca gtaaaaaaaa ttattggtaa    18840
aatattaaat tttaattacg cagaaacaac aaagaagaca ggaaaaaaaa ctacaaccag    18900
agactatgtt acaacgaatt caaagagaaa aagaactgag aagaaaagca cacatcttcg    18960
tcattcaaaa attaaccgt ttattgacaa agaaattaat cgtgactaat aagctccttt    19020
gtcggcccca tgtaacccat cttttacgtg taatctgatg cttgcttcca cggttccacc    19080
ccgacttaac tgccacatat acactttggt cattcaaact taccaaacac aaagcgaatt    19140 cgttttttgtt tcatgctttt aagaatcaca atctcaacat tccaaatata tataaaacac    19200
aatctcaaca ttccaagcat ggggtggcat tctcgtagtt atctccatga caaggggcac    19260
tttacaatag aaaacactcg ggatactttt ttatcgacga ttcctaagca aaatattacc    19320
gaacagacac ctctctgtct gtctctttta tatgtcttct caaaaacgaa aaagtctctt    19380
ctccgtcaac atttcacttt ccctctttcc ctcttgttaa tctctctctc tctctctaca    19440
ctcaaagaaa acacagagac tcttcacgcg ccaaaaaaaa aaactcacca ccttcctctc    19500
tcccttacca tgacttcaga ctctgtcaag catacttcta tccacggcgg aacaaccatc    19560
tccgccgcat ccttcgaatt aaaaagcttt atctccgccg cgaaaccaag aaaagcctcg    19620
acttttgtat acgccttcgt cataagcttc gttgccttca ctgttctctt agtcttcaca    19680
```

```
ccttctccca tcaccgtctc tcattccatt ccttcataca tcctccctaa tgtcactgcc   19740
tccttgactt caccgtccag tttcaccgga aacaccccat tgccggaaaa tctcactccg   19800
gcgccggaaa atctcgctcc ggctactaaa aacgcaacct ttgagtctcc catcgctaat   19860
ggagcaaatt cacttgcttc tcagcccegg accgaccatg cattggacaa catgttgtct   19920
ccggacaaca agactaatga tactgctcca agttccgaca aacttggatc cgcggaagca   19980
cctctgtccg aaaatctaac cgtcaattcc tctgctttaa agaagagaaa acagaggagg   20040
aagtcgtgga tgagacgaga gataaagtct ttaaagaact gcgagtttta cgagggagag   20100
tgggtgaaag acgattcgta tccgctttac aaacccggtt cgtgtaatct catcgatgaa   20160
cagtttactt gtatctccaa cgggagacct gacgctgagt ttcagaaact caagtggaag   20220
ccaaagcaat gcactttacc acggtaaagg ataaaacttt gcttttaat tttgactttt    20280 aaatctattt ctttgtctta tatggttggt tgatgttttt ttttttttga aaaattataa   20340
aaggttgaat ggaggcaaat tgctggagat gattagagga agaagacttg cgtttgttgg   20400
agattcactg aacaggaaca tgtgggagtc tttggtttgt attctcaaag gatcagtgaa   20460
agatgagagt caagtctttg aagctcatgg acggcatcag ttccgttggg aggctgagta   20520
ctctttcgtc ttcaaagtag gtttcttta gtaatctaaa tcagtttcat tagttgttgt    20580
ctctcgggac ttgatttgta tgtggttgat aggattataa ctgcactgtg gagttctttg   20640
catcaccttt cttggttcaa gaatgggaac ttacggacaa gaacgggact aagaaggaga   20700
ctttgaggtt agatgtggtc gggaagtcgt ctgagcagta caaggagct gatattcttg     20760 tgttcaatac aggacattgg tggactcatg acaaaacttc caagggtaa tagagttctg    20820 tcagctactt tgatccttga tttgagggat ctgtctcatt tgttatgttt ggatgctttc   20880
attagggagg attactatca agaaggaagc aatgtacacc cgaaactcga cgtggatgaa   20940
gcttttaaga aagcattaac aacttggggt cgatggggttg ataagaatgt gaatccaaag   21000
aagtctcttg tcttcttccg tggatactca ccttcacatt tcaggtatat acagatctca   21060
ttttgtttca taataggt agttgtaggc ttgtagctaa aagcacaaag attaagaacg     21120
ttattatttt ttttaaagta tcatctaatt ttatagtttta gatatatctt aaaccaatca   21180
taaactagtc tatataattt gactggtcac actatatcca ataattcaat aaatatataaa   21240 gttaagtaga aatgtaaaaa ctacataatc ttgaaaagaa aaaaaatatt cactaaaact   21300
acttataata tgtgaaatag agggagtata aaaagagtgt ttctaaaagt tggtttggtt   21360
tggttgcagt ggagggcaat ggaatgcagg aggggcatgt gatgatgaaa cagaaccgat   21420
caagaacgag acttacctaa cgccttaccc ttctaaaatg ttaatacttg aaacagttct   21480
aaagggaatg aaaacgccgg tcacgtatct caacatcacg aggctaacag attacaggaa   21540
ggacgctcac ccatctgttt ataggaaaca taaactatct gcaaaagaaa ggaaatcacc   21600
attgttgtac caagactgta gtcactggtg cctcccaggt gtgcctgatt cttgaaacga   21660
gattctctat gctgagatgc ttgtaaagct ccaccagctt cgtggcaata gaaggcggaa   21720
acctaaaagt ttataggagt tagaatcctt ttcttaagat gatgaataca gatcttttag   21780
gaaacactta gaatcaattt tcactttca gatttgtgcc actgaaggtg tagagaaagt    21840
aagagatggg agtcacatta gtgtttcatg atgtacgtac gtaagagatg agttaatcac   21900
cttatgttgc tgcatttgta gtcaactaca actagtgact catttttttg tgaaaataaa   21960
agattgagcc aacatttgta taaattccaa tgcataccc ttttacttata ataatgatca    22020
```

```
atcgattggt caaacgaata catttagaat taagaaccct gcaacgactt tggatttaaa   22080
ttgacacaga tcttttgctt caaagtaaca gtttgagcta agaacataaa gaatgcacca   22140
gtcctttaat tacagtatta tgataaaact cactagagcc atctagatac aatctgaatg   22200
ataatgtcac aggtggaaag aaagcatgaa catactcagt cgtccttcat gagactcctc   22260
cggtcctctt ggtgtgcaac caaaaccacc accatccacg tctttcgtat ctcacaatgt   22320
tatcagcagc cttatccaag tcctcctcct tcgcgtcagt tccctctctc tttctttctt   22380
tctttctttc tttctttctt tcttgagatt gcaagtttga aattaagctc ttatagattg   22440
tttattttga tgttgttatg tcggtctctg tgtaaatgtt tagttatttt ttcgattct    22500 ttctcagaaa agtgtctcga ccttaagtat tttcttgtta gagacttaga gctgctactc   22560
tttgattctc gtaagattta gtttcctcag ttattgcttt aagcaagcga gagactactc   22620
tcttgactgt tttggccttc tgatttgttg aatccatggc aatatttgtg gttttgtct   22680 cctgctctct ctctctctct ctatgtggat gggctttgtt tcatgttact attattagct   22740
ccaccttcga gattattatt cttttttttt tttttttga atgaatgtta aattttattc   22800
aatccaaaaa aaccctttgtt acatttacaa tgtttcctac tccaattgtt ttataacatt   22860
atcaccccta tttgaattta tctactcaag aaactggtct tgtggagaac cagtgttgta   22920
aaccctcctg ccatctatca tcccctgctc tttgaataga cagaaatcta ttcctcactc   22980
ctctatcaat cagccttatc atcgtagtag tcggctgggg agcttcacca tgccttctac   23040
cattcctctc caaccacagc ccatgtatag tagcttggaa cacatacttc aatgtgaatg   23100
tcttgatagt attctggttt gtagatatca gagctactat ttctgaccag tcacaagtaa   23160
actcatttcc catcaagcct ctcaccaagt ttccccaaac ttctgccgaa tatccacaat   23220
caaagaataa atggtttctg gtttccaatg gatcaccgca gagagagcat gctgtattta   23280
cacttcctcc ccatccttgc attctctctc ccgttgataa tctgttcttg attgtaaccc   23340
acgcaagaaa agcaaactta ggtgtcgcaa aagtgaacca gattcctta ctccactcac   23400 agcttactcc tctagttcgc aattgactcc atgtttgctt agtagaaaac ttccgcttga   23460
atttgtcttc cttataccte cataatccaa catcatcttc ccttgatgcc atcattttac   23520
atttatctat ctcatcctca atcaagttca aaacagggat tctatgtctt ctccttcgat   23580
gagtgctcat tacttcctct acagtagcgt ctttatggat ccccatatcc atgtatcctc   23640
tttcaccagc tctttctacc agacaaccca aatctgacca agcttcatgc caaaacgaag   23700
tttgcttccc actcttcacc ctcacctat agaaaccttt tgccttgtct caaagagatt   23760
attatctctt ccatatggtt cagtactgtt tagtttgact tgctttgtcc gttgatattg   23820
ttagctagct aggttagagg actaatttat aaccccaca tctttaactg ttttctctac   23880
aaactgttat ataggcctgg ccataatatc cgtaacccga aatccgaacc gaacccgaac   23940
cgaaaaacac gatccgtatc cggtccgaaa tgtaaaaaat atctgaatga gtcttgtaag   24000
gtggcacaaa acatatccga acccgaagtg ttattaaccg aacccgaacg ataacccga   24060 aaaactgaaa aaaccgaaaa ttccgaaaaa tatccaaaaa aaccgatctg aatgtccaaa   24120
ataatataca atataattat ataaaacatg aatatatact tcaaatattc aatttcatat   24180
ttattttgat atgttatcta acaataagta tttaaaattt aaataactac cttaaatact   24240
tgattatata taaataaata tatatttta tatttacctt taaattttag atttttattc   24300
gggtatatcc gaaccgatcc gatataaccc gaatccgaat gatatatgat tacttttatgg   24360 gttgtgatac aaaaccgacc cgaacccgat gtgttatatc agaacccgac cgtacttgca   24420
```

```
aatttactag aatggaacct aagaagtatt ataagagaga accaaaatcc gaaaaacccg    24480
atccgaacgc caacgggtac ccgaacgccc aggcctactg ttatatatca ataatttccg    24540
ctttcaaatt tttgtttgat gcagatgaat ttgaaatttc tttgccttac gactccaaaa    24600
cggtgactgg atttgttgga ttaatcaaca atcaatgtgg tgaaaacgca tatgcgagtg    24660
ctctcattca aatgatgttt cacattccat gcttttgaaa agctatctta gaaattccag    24720
agactatccc tgtcaagagt ctcttccact gtcttgagag cagcaagact actgtttcat    24780
tagagagccc agacataacc agtaataccc tgaaaaaggg tttattttga aacagtgaat    24840
gacaagatga aagtaagtta ttttttgcat aaccttatag ttcacactgt agatgctttg    24900
atgtaaatta ttttgtaatt acaaggctca cattggaaga tttgtaattc tcggtttgag    24960
tgaaatatgt gtattttctg caactaatga ctactccaaa actaatactt tgtgtccaac    25020
ttgtgcacaa tgtaatggta attagtcgtt gaaaactaac atatgtgatt taacaataaa    25080
ttcatatatt aacaattcaa aattaattta agctttcgg atcccaaact atgctgtcaa     25140
taatcatgtc caagtcatca atccatttgc gtaaggttaa tgagatatca agaaaaatca    25200
aattcgtaaa ttttttttaaa atatggttgt tacttctcac acactagagc atcgtccaca   25260
aattccttag aaaaatttag tgttctgatc gtaatttgag tctcattgca atcaggaaca    25320
agctgaaatc tacttatttt ttattgatgc tacctcatgt acttcatttt gtttggcagg    25380
tgaaccagat gtatgagtgt atccttatga aatagatctc gagaagtttc ttctaaccac    25440
tgatgctgat gggacaaatc atttcactta caaattgaaa aggtaaactg tgtgttttgt    25500
ttgatgtggt tgagaaatag tagacacgca ccagattcat tctcaagaca cagcttcatc    25560
ttcagaaaca gcttccctag aaagtctaat gtggtcatcg agagtattca ccattagttc    25620
tcagatgatt gatccatcat cacaaaactca atcaaaactc tcttctttgt ttctggcatg    25680
ttgatataaa ccaaaacaag agactgaaaa ggaaaaaatt caaatgccag ctatagtgaa    25740
catagacaag agcatgagga agttgaatga tatagctttg tagcatatttt tctgccatca   25800 gaatgtaccg gacatgcttg cctgccatca tatcatcagc atttttaattt agacccaact   25860 tgcttcacac cagactctct tccacatgat ttttatatat atcttctaac caaaaaatag   25920
gacagaacaa attaaaaaaa aagtttcatc gggctgttct tgttaaatgc aatgaaaaca    25980
acaaaatcta acagttcccc attgtcactc tttaaggtga cttgtttagc ctttactcac    26040
ctgaaggaaa aaaacaacta ctataacggt gatgaagcaa gttggataaa caaaaaaaag    26100
attggaaaag ggcaaaactt atagtgaaca ttgcacccaa aaaaaaaaag ttatagtgaa    26160
catagacact aaaatgaagt atctagcttt cttacctttt ctaccgttag aatgtacggg    26220
acagcttgtc agctacgagc ttgtctgcca aactttacaa tgtatcgttc tattggttac    26280
ataacatata aaaatgaata gacagagaga catagaaccg agcatatgaa gatgagagaa    26340
acgaactaac ctaaattaaa ccagaatgtt aataaatata atccaggaaa acccgaact    26400 aaactaaatt gaaccggtag agaactcaaa aaccagaaac cccgagttta tggaaactta    26460
accggatgaa tcgaatccgg ttcggtataa taaaacccag aagaagaaga taaacctttt   26520
cgcagtttgc ttctttctct gctcaaacac gaacaatggc gagtctactt gactcactca    26580
caaccagaaa cttcttctct aaacccataa tctctaggat ctcctctcct tcatcttcct    26640
ttgcttcttc ttcttcttcg aatatctcac ccttttctcc tccctccgtt ctctcttact    26700
ctcacaaaag gtcgcattct cgcttccctt accctgtcgc agcaactctc gatggtccct    26760
```

```
ccgttgaaga agacgagcta gagttcgagg aatccgaaga agacagctac cctgatgagt   26820
cggatgaaga agatgacctc tccatagata tctcaattct tgagaaagaa gcgagagata   26880
tcgttagaga ctacgctact actctgtctc gcgagctcaa actcggtaaa agattgtgtc   26940
tttcttttg  cattatgctc cattgactgt tgaataatga tcgtagcttg atgttttaca   27000
gaggatgatg tagttgaagg gaaggagtca cgtagaaagg ggaagaggca agccaaaaat   27060
gttagtcttt tttcagtaaa gtctagtcct ttgagcttga gatcttcttt aagtagataa   27120
agttttgatt ttttttgttt ggttactgac atttactcta aaaaaaaag  aaccagacgc   27180
agataccaga gcatcttctc caaagagttg ctatcgttgg aaggcccaat gtgggcaaat   27240
cagcattgtt caaccgtctt gttggggtaa aagagtttga ctgttttctc cttacccatt   27300
caagttttag agagttgtta acttgtcctt aatataattg caggagaata aagcaatagt   27360
ggtggatgag cctggagtta ctagggatag actgtacggt agatcctact ggggcgacca   27420
agagtttgtg gtggtggaca ctggtggtgt tatgactgtt tctaagtcgc cagctggtgt   27480
tatggaagag cttaacgttt cgaccaccat tggcatggaa ggtataccat taagctccag   27540
ggaggcagct gttgcgagaa tgccttccat gattgagaag caagctacag cggctgttga   27600
agagtcagat gttattgttt cgttgttga  tggccaggtt cggttcttat cttcaatctt   27660
ctctacgttt atgtctttgg cttattaatt attttggctg tcatgcaatg ttgttgatgg   27720
gtggtaatga tttttggta  ctcgatcaat acgcagacag ggcctacagg tgctgatgtg   27780
gagattgcag actggttgcg gaagtattac tcacataaga atatcatcct cgcggtgaac   27840
aaatgtgaat cgccacgtaa aggactcatg caggcttcag agttttggtc tcttgggtaa   27900
tttcactttc atcctaccct cagaatcatg tttgtgcaca ttcatagttt tcattgatat   27960
ttcagttgcc tacaaaaata aaactcatgg ataaacgtca tttggtactt ttttatcaga   28020
tgatttgaat atttgttgct ttgttgtgtt cacatttaac aaaaaatttg ttctaatttt   28080
acggatttag tattgttatt ttgatgagtt tgtagacctg acgatacttg taagcatcat   28140
aaaatacttt cctccgttgc tatacatttc tttgtcaatt ttggagatta tttggcattg   28200
agcttaacaa gcatgtcatg atggaacttc caggttttca cccatcccta tttccgcatt   28260
gtcgggaact ggaacaggag agctacttga tcttgtttgt tctggactaa acaaactcga   28320
ggtttgtatg taacctttta gtatgttcaa ctggcatcag tttaccaatt atatatcaaa   28380
accaatgatt ttttttttct agatcatgga gaccatggaa gaggaggaag aagaaaacta   28440
catacctgcc attgcaatta taggcaggcc aaatgttggg aaaagtagca ttttgaatgc   28500
acttgtccga gaggatagaa caattgttag ccctgttagt ggcactaccc gtgatgctat   28560
cgatgctgag tttaccggac cagatggaga ggttagttca attttttctc gtgtttgttg   28620
agctgcttag ttttcttgcg gcttctatga tacagtgcct gctgtttcgc tatatgctaa   28680
ttggcatcta tttgatgcgc tttccatgtt aactcctacc attttttctc aatttggttt   28740
ggctactatc atcaatgact agcattgtcc aagttgaata ttgctgaact ctgaatgatga   28800
gcagtgttca aggtgcatt  ggatccgtat aacactgaaa atgatttatg aactgtgttg   28860
cagaagttta ggctaataga tacgctgggg atcaggaaaa aggcagctgt ggcgtcatca   28920
gggagcacta cagaggccat gtcagtgaac cgtgcattcc gagcaattcg tcgttctgat   28980
gtggttgctc ttgtcattga agccatggca tgcataacag agcaggtatc tcactagttc   29040
taaacaatgt gggaaacgaa ctcatctttc tctccttcct taatggtttc ttatttggaa   29100
acacaggaca tgaagatcgc agaaagaata gaaagagaag ggaaaggatg tctggtagta   29160
```

```
gtaaacaaat gggatacaat accaaacaaa aaccaacaga ctgcagcaca ctacgaggat   29220
gatgttaggg agaagctccg ttccctcaaa tgggcaccca ttgtttattc tactgctata   29280
actggccata gcgttgacaa gtacgtctcc ttccaaagtt ttataaacta attcaacctt   29340
tacattttta actttattct gttggagaaa aatgtagtat tgtggttgct gctgcgacgg   29400
ttcaaaagga gagatcaaga agacttagta ctgctacatt gaaccaagtg attagagaag   29460
ctgttgcgtt taaatcccct ccaagaaccc gaggaggcaa acgaggccgc gtttattatt   29520
gcactcaggt gaataacgat aagatctccc aatgtttttt tttattagca gtgaaggcaa   29580
atctttggag actaattgat gtgattaatg caggcagcaa taaggccacc gacatttgtg   29640
ttctttgtaa acgatgcaaa gctgttttcg gatacgtaca ggagatatat ggagaagcag   29700
ctacgcactg atgcaggctt tgctgggact cctattcggc ttctttggcg cagccgtaag   29760
agatctgaca aaaatggagg aggtacgtgt tttgctagcg taaacttgtg attcattttg   29820
aaaaatatga caatgttttg tatgtataac tttaaatgaa atttgcaggt ggaggtacaa   29880
tgagaatgtc aagtctttca cgtgagagaa atcttgcaac aaaaaggtca taatgttaag   29940
tcatctactc atctttgtta aattttgtgt attttttgag aaataatgta ttgaaattcg   30000
atattatata aattcatagt ttgttcaaaa aaaaaaataa attcatagtc tctgactctc   30060
cattgatctt ccatgtatgt tccattttgt ttctttctga gaatcaaaac aagatattac   30120
taatcttctt gacagtttat agaaaacaga actacaacgt ttctttatgt ttatgttttc   30180
ttaatctcaa gctgataaaa aaaagataaa cagaccaaag cacaggcgat gagtctctta   30240
gtaaagctgc tctttctttt catgccacca tctccacctg taatagaaca agaaacacg   30300 aaactatctt tgtcaaaaac attagaaata ttcattttg tcagaagaaa aaagtgaaat   30360
gagatgatat atgataatga tataagtcta cgtagtatac gtaccagtaa tagtcccaac   30420
gaggacggac tttcgtcatg cggttatcat cagaaggatg ataaggatga gcggcgtggc   30480
gagtgttgtg gaaggcgcag caaccagctg catagacagc gatgaggagg acaaggacca   30540
gaatattaac gaccgacaac ttttccagt caagacggat ctcctcaaga acaccagctt   30600
tgcaagcatc acactcgtag cataacgttt caataccatt gttccatcta tagcaatctt   30660
ctcctcctac tattactccg gtaacgtacg tgcacgccgt cggtggctta acatcccg   30720 actataaatc aaacacacac atacaaagtt gatgaagatg ctagcttaca ccatagggca   30780
atgaatatga gaaatatta atgaggatca tggcagtctt ttagcatgtg taaatggaaa   30840
gattgaaaat ggtttgattt ttttttttaat gtataaattg gagtaaaatt taaaatttaa   30900
aatatattta taaattaata cttataattt caaaaaaata acatatataa atggagttat   30960
taatacttat aaaaaaaatc tacagttaat aattttattg aacatggttc taggcactga   31020
aaatggtacc tgaacagaag tcatgtctct ttggaagtaa tcaagtgtag tccaagattc   31080
aatctgagca caagtcttgg aactcaagat acagcttctt atagagatcc aatactgagg   31140
atctctaact ctctctctca accatggatg ataatcaccg agcctatact ctttataaac   31200
cctccctggt acttccacac cgcctccttg gctcgtcacc accaggccaa acagagttag   31260
acccataaga gtcgcgatga ggaagatcat gaccactagg taaacccaaa gagcccatgc   31320
cacgttgaaa caggctccta tgaatccggc gagagatact aagagtatga tgaaacctat   31380
aacgagtaga ggagtctgga ggaagttttc gcaagttgtg ctgcttcttg ccttccatag   31440
agcggctcct atgattggta ttgaagctag taagctgagg aggtttaaga ctccaatcac   31500
```

```
tgtgttgctg aatctgtaca tagtagtagt gttatcaaga agaaaccaga gacttagcag    31560
tgccttctct tatatctcgc tcttttgtaa taagcagatt ctcttcttgc aatgtgaact    31620
tcatcagctt tatcttacaa tcttctttgt tttttagtta ttatattggt taactctacc    31680
ttttttttgc ttttgattct ctcttatcaa ttgggaattt tttaagcgaa aaagtttaga    31740
gttaatggtt tgatgattca tgctcatatt ctctggtcgt ctcttgattt gaatcatcca    31800
aacaataaca ttagaaatag tatttttttc aaataaaagt gtcttttggg acaattggtt    31860
cttgtttatt attctatttt atacgtttaa ctaacaataa agcagaccaa aagtagtgcc    31920
ttaattaaaa tatgatatac catattatta gatacatttt tctagcttag agtccaaaaa    31980
atgcaatcat ggattatata gtggatcata tcatatgtgg gtattgtata ctttgaaatt    32040
gttgactcgt tacgggaaat aattgagata cttttatat atactagatc ctttctccgc    32100
gctacgcgcg gataatatat ttaaatttgt tacatttatc atttttattt gtatgtaaat    32160
ttttctatat taaattatat ataactaatt tttaaatttg agttttttta tattttagt    32220 ttgaagtaaa tatttctatt atatgtaaca caattaacta ataaaatatg aagaatcaag    32280
tctgagattt taaagttatg taaaaaatat ataattatgt atagaacaca aattatctta    32340
gtttaaaaga tcggaatctc atctcgaata aatttacgaa aaaaaaagta ctccaataac    32400
ctacttaaaa tataaaaact ccttttaaaa aaaagcgta cttaataata tttttttaca    32460
tgtaatagtt gaaaactaac aattgaatat cgatctagaa tattattta atatatctaa    32520 tgtaaaatat taattgtaat aaacaaattt tgaattttgt aatattacat gaattagaag    32580
tctttaaaat ctaaaatcta ttttattaac atactatatt ttttattcat ttattatttt    32640
gacgttacaa aatattgctt tagttttatt tgtatattat tttttaata atttagtttc    32700 tttttaagta attttaaaat tatcaagaat gtaatatatt taaaattatt tatttaaata    32760
tatccaaata taatgtctca tttttatgtg tgtttgcgtt gagcatattt aatttgtaat    32820
ttgtatattt aataacacct tattgcgtgt cgttctatgg ttttaataaa tgtgttgtca    32880
tctcattttt attactacta acatgatttt ttagtgatca atgataatgt attttaaacg    32940
ttatgtatta tattttattg tatatttttt aactcttcgt gctggcactt tttttagaat    33000
cattttaatt agataatagg ttttaagatg taaataaaac tgtgtatgtt gtaaatttag    33060
acttcttagt gtagctgagc actatcaatt atggaaatta tattatgatt ttattttaca    33120
aaatcttttt ttctgtgtat tttttttgtt ttattttgta tttttaaaat tttattgcat    33180
tattctttaa ctgcagagaa ttgatatttc taattttttgt ttcatatacc ttaaaagtct    33240
tcggttgatt tttgtttgtt ttctttctcc aattataatg tatagttcga ccgtttcttc    33300
tttttttttg gatcaaacta ctaatatcat cagatagaaa agcttaaact ctaagaattg    33360
agtgaatatt tgtgttagag aaaactgatt taaccaataa tatagtgaga tattataata    33420
ttagaaggta tggaaactct tctatgttgt cctacgctgg acataattaa gttgttgtca    33480
attgatttta tatttgtgat aactggaaat gcatctttat gtcttcctta catcatcctt    33540
aattggtttg cggttcgact atttctaata tactgagagt aacataaaat tagatgttga    33600
ttatctcctc ccaattagga atgcacagaa tgagagaaat tcaagatgag accagtttac    33660
aattttgtcc tcatatctat atagagttag tttatagatt actctatttg tttcaaaatg    33720
taatcaattt ttattaaaat atgtaatatt taaaaattat tactttagaa atctgtcatt    33780
taatatataa atttaatcaa ttacacagta atttacataa tttaattggc tacacaatat    33840
ccaataaata taaagttaca ttgaaatata aaataatttt atatagtgaa acaaaaaata    33900
```

```
cttttaaacc attattatat tataaaacaa agagaatatt taaattatat tgaacattag   33960
aatagtaaaa atcagaaaag ctgaaatctc aacgtcgatc atttacgttg gctatgttat   34020
taactttgaa gataacgtga atgatcaaga acaaaaaagt taattttagc ttcagtcatt   34080
tttttataat cattttacca aaaagaaaaa aataacagga agatgactaa taaaaaaaga   34140
tacaaacaga gtactgtaaa aaggtgttga tcataatagc aaacattata gtctcaaaaa   34200
ttgtcaactt tatattaaat attagtcaaa aataataaaa tatataatat taataaattt   34260
tattttaaat ataatttaac ttttaaaaat tttatcatta cacatggtgc agaaaagcac   34320
ctagtattat ttgaatttca aaactatct  gatgcactaa cttttgtga caaatcaaat    34380
ttaaggaact gggcaagaga ttgagaagag ggatgtggag aggtacaaag agtcttcact   34440
tgatgagtta taatggagca ttgaagtgcc attgttgtag tcgtaagagt tacaccggtg   34500
aagttgggta gacgaacaga tttggagtcg ctggagacgt ctgaggcaag taggctaaag   34560
aaaaggaagc tataagttat acaatgggct ggctattttg atggttttag atggttcgag   34620
acccatcatc taaacattcg cgatgacgtg gcagtttgat tggtagagaa tatttatcc    34680
tatgtggcat tcctaagaag cttcaaaatt agtagctttt atatagtagg atcttgtgtt   34740
ttaatttagt taaatccaaa aatttatttt caagttccat taataatgtt catgtgcatg   34800
tagtcaatta gtaaactaag ttacaatttt gtatgcttac taattgacaa tatgtttacc   34860
aattttgtgt aacgtttagt aaactacgtt aaatttacaa tgacccatga agcgaacgag   34920
ggtaagcaaa gaataataga catggacgga tgaatttgct ttttaagatg cttgtgctgt   34980
cccatcccca taactttcag aatattaggt tttgtaggtt gatgagcaca atatgatctt   35040
tgattcctcc acttcgcttt tttgtgtaag caagaagaac aaaaaaatct tgtttcagct   35100
gacaattta  cgtaccaccg ttttgatttt acattttgca gatgattttt tgacaggaaa    35160
aagggttttt ttttaaaaca acatttgagc caaaagacac acaaacttga aaggctaaaa   35220
gagtttacaa agattgtggt ccttgtgtgt gtggttcaaa agacaaacgg gaaaaggaaa   35280
ataaaatgct aaataagagt ataacaagaa aatcgcaagc ttgaaacaaa gtgttatctt   35340
cctatagaac cataatctct actagtatac atccaaaatc ctcagtattt gaagacatag   35400
aagcagatgc tgctcagttg tactcagttt gcaaggtcaa gtcttgtaca cccaagtcat   35460
ggtatacatc atacacatat tgcagtaaag gcctttcatc tatcccgctc ttcacctaaa   35520
cacaaatacc cgaaataacc aactcaacat cagtgccgtt cttattgagt actcatgttt   35580
taaccgataa gaaaacagga aggaagctag tacctggatt ctgagtgagc caacagtgtg   35640
accaggcaca acctcccaaa aacgagcctg taaaacctct atgacatcct ctcgagaagt   35700
aatctgtaaa taaagagagt tgaagagaaa cccagcttga tcgatctata tgtacacgtt   35760
caggaaacac tttatggaac agagcgaacc tgacgcaagc atttacttaa tgcggaagaa   35820
ggaatgtttg gaggtgccat ctgaagcaag acaccaccgg tggctttgaa gagtggcata   35880
acaagcataa acactgtaac agataccaat cccaaacata ggacctcagc attttcaacc   35940
ctgaaaaatc caaagaccgg aggagaaaaa tggaaaatgt aagaggtcag gtactaagac   36000
attttattc  attttgttcc ttttaaagga agcgagcatt acccgagaga gaggagccag    36060
gatgccagta tcagacctgc actgaaaaga cagaagcaaa gaatatgtca tgtgggatgt   36120
atataagttt catgcaaaga gaaacatttt tccagctagc tctccgcggc tctgcttgag   36180
ataaagaaag ccaaagagaa tatcacacct gcggatggaa tctgatatga catgcaagca   36240
```

-continued

| | | | | | |
|---|---|---|---|---|---|
| aacggagtgg | tagttcatat | cttctgcttt | tctgtacact | gcatcatttt | acgaatttaa | 36300 |
| gaaacacatt | caagaaaaat | gcaatatgta | cgaagggaac | aattcttggc | cagatcagtt | 36360 |
| gctttcatgc | tgtctctctg | ttttcactaa | tcctcctact | tattctatct | taattggaaa | 36420 |
| cccttgcttc | tttgtggctt | tacattgaca | ggggtggcca | gttttacaa | tgaaatatag | 36480 |
| caaagccgcc | aaacaaggct | ataccatata | aagcaccagt | atcggtatta | gttaattcaa | 36540 |
| gtctaaccag | aacttaagca | taataataaa | acagagaata | cataccaata | ttcatacgag | 36600 |
| cataattccg | gaagaaccaa | acaccaagta | ggttcaccag | cagatttgtt | accgctgata | 36660 |
| caataagata | atgcctgcat | gaagtcgatt | tcagtacatc | atattaatgc | aaagaactta | 36720 |
| gtgtaaactt | agtaagtgct | agagaaataa | ctacaagctc | ttaggcatgt | cacttgtgga | 36780 |
| aagaaactta | cttgtgctct | gattcatctt | gaacaaatgc | atgaagagct | tccacagcta | 36840 |
| aggagaacga | catgaacata | agaaacagct | gtctacacat | atgtcaatac | tgaacatatc | 36900 |
| aatgtgttaa | cccaaaagat | aaaatgaatg | agacagtgaa | ggcaaaatga | aagataatc | 36960 |
| aacattttaa | acgagctgta | agattattct | attctatcaa | caacagtaaa | ggaaagtgtg | 37020 |
| caaacactat | cgacactatt | ttctgaaaga | tattaagcca | gttttattgc | atggcacatc | 37080 |
| agccattaga | ccctcaaatt | aaaaccggaa | atgacatcca | acaaacttaa | agaacatact | 37140 |
| tacagcatta | gtgaaagcag | aaagaacttc | aagtcttttg | tacctggaag | aaaagccaac | 37200 |
| gattactaag | tcacaactga | ttcagcatta | tgcaatgtca | gtatcagcag | caagaagca | 37260 |
| aacagacaag | gtttcatatt | tagtaattat | aaaaactgga | tcctatgaaa | acaacggcgg | 37320 |
| atctactta | ggaatgctcc | agagaaagaa | aagaaaaagt | aatttaacaa | attgggaaat | 37380 |
| caaccgtaaa | gtaccacaaa | ccatgcattc | caacatatat | ctccagcaaa | tacaagcacc | 37440 |
| aactaatcgg | atcaaatttg | aaaaatttct | caccgtatg | agtaagcatg | atcaggcttc | 37500 |
| ttccttgaag | tcgccattgc | aaataaagaa | aacgtcagga | gaccacatcc | aaatgtcaaa | 37560 |
| tggaatgcat | cagaaaccaa | acctgcaaga | gtcacatcaa | acatcaaaca | tcaaaaaaga | 37620 |
| gagcaagtaa | acaacaacag | taaacatggg | aatctaaaca | aatctcaaac | caattttgat | 37680 |
| atttacaaaa | cctcagctgc | aacagaagac | aatatcttaa | aaattaaaac | tccataacca | 37740 |
| aaaggtctct | acatacgcat | aggatctact | atccatgcgg | tttagttccc | aaatttaaaa | 37800 |
| gattatatta | accaaaaaaa | aatcaacttt | agctgttttg | tttcatctaa | atctctagtc | 37860 |
| actacccgaa | gtaaggatgt | gaagctcaca | tcgacctgga | gtcttattcc | tccaacaaat | 37920 |
| ccaactctct | ccctctaaca | aagttatcaa | gaactaaaac | caagcaacaa | ccaaatcgta | 37980 |
| cctacacgcc | cagtcaatag | cccaatcaac | agctctgtag | tagagtacgc | cacgttaagc | 38040 |
| gaaatcaaca | taaacaatct | cttcatctgc | cgatttccat | ttctcagcac | cccaaaaacc | 38100 |
| accaaaacca | tacgcaaaac | cgacaccttc | ccaatcgccg | ccgccgcttt | ccttccccg | 38160 |
| aagaaaacat | catccccgtc | gacagagtat | atctccggcg | gcatatcgat | ggtggagacc | 38220 |
| gtcctatcga | gaaaaggctt | agccgccggc | gttcgcgggc | cgtgggagtg | gtgaaaggag | 38280 |
| cgggagtaag | cgagcctccg | atcattggcg | gcgtatccga | cgtcgctgct | ccgatcattc | 38340 |
| gggagttcgt | tatcgccgcg | aagatcgaag | gaaacggatc | tctccatact | tagctttctg | 38400 |
| tttgctcctc | aaatgtgtaa | ttcaacgagt | cttaaaagta | cactgcgtct | actagaatga | 38460 |
| ccttaatggg | ccactgatgt | aagcccatat | aagagctcaa | gtcatgaagc | gttgaccgca | 38520 |
| tttaacgcct | tattggactt | gattgcctct | cgagtagggc | ttttaacgcc | ttattggact | 38580 |
| tgattgcctc | tcgagtaggg | ctgggacttt | taaccgaacc | cgaaccggat | ccgactcgaa | 38640 |

```
atagaccagt tcggttcggt tttggacatg gccatattat ccaatagatc attgcttcta   38700
atatcacggg tcggttccgg ttattaccca aaacctgatc aggtatttat ttaaaccaaa   38760
atggatagtg taaaacctag aatattttaa aaagtattat caccacgact caaacccggg   38820
taaaagtggc tatgttacca ccagaccact tcaacttata tgtattcttc tatattgtaa   38880
atatctatag tatttcaata ttattttta taaaattaat attttagaga ttttgaatcc   38940
gggttggcca cactacaaat agagtatgta accactgaac catttcaatt tacacgtaat   39000
tattttattt aaaaaatatg tatatgattt acataataaa tgagtacccg aaactgactt   39060
ggaatcagag atatccgatc cgaaacctga accgaaattt atctagtacc tattggatag   39120
ataattcatt tatctgaaag atccagaccc gaatggatct tacccgacct gatccggata   39180
accgaagtcc cggatctact ctcgagtctt gtgatatgt ttctcccata caacaaaaa    39240 tacagtatag tataatactt cagataaata aactttatta aaattagtag ggttaacata   39300
tcacattcaa gcattttca gcccgttaat atcaataatt aactttttat tcaagcattt    39360
ttcagcccgt taatattaat aactaatttt tggttggatt tgtctcttta aggaggattt   39420
gtctcatgat ttacaaataa caatattcat attttagtc tcgtaagatt ttatactaca    39480
aaatattaac tattataatt tataaataat acattattta ttattataat ataattatct   39540
agactgtttg taaggtaatc acctagagct ttagaacact ttcatagtga tgtggaatca   39600
ttgtttcagg cattgtgttg gattctggag atggtgtgag tcacactgtt ccaatctacg   39660
aaggatatgc tctcccacac gccattctgc gtcttgatct cgcaggtcgt gacctcactg   39720
attacctcat gaagatctta accgaacgtg gttactcatt caccaccaca gcagagcgtg   39780
agatcgtgag agacgtgaaa gagaaactcg cttacatagc acttgactac gagcaagaga   39840
tggagacggc aaacactagc tcatcggtcg acaagagcta cgagttgcct gatggacagg   39900
tgatcaccat cggagggggag aggttcaggt gtcccgaggt tcttttccag ccgtctttgg   39960
tcggaatgga agctgctggt atccacgaga cgacttacaa ttcgatcatg aagtgtgatg   40020
ttgatatcag gaaggatttg tatgaaaaca ttgtgcttag tggtggaacc acgatgttcc   40080
ctggaattgc tgataggatg agtaaagaga ttactgctct tgctccaagt agtatgaaga   40140
ttaaggtggt tgctccaccg gagaggaagt atagtgtctg gatcggagga tccattctag   40200
catcactcag taccttccaa caggtaaatc atctttctg cttgttactc gttttgtaag    40260
ctgactatga tacacaatgt tggtattgca gatgtggata gcaaaggctg agtatgatga   40320
ggcagggcca tcgatagtcc acaggaaatg cttctaagat tacgctcgcc gttggatgaa   40380 agatttttc gtattatttt atatgttcaa cgagttggtt tcagacaatt tttttctt     40440 ggttttcct cactacaatt gtttcttgtt gtcacactct ctttggttgt ttctgccatt    40500
aatgagaaaa aaaagattc atttgtctta ttttctttg ttccctcaca aatctgaaag    40560
caaataaata tgaagaaatg aatttggctt atgttgacag gttctacaa attaaaagag   40620 aagaatagag tttttacaa agagactgaa ccacatgagt agtaaaggtg atctgccaac   40680
caaacaacgc aataactcaa actaacttaa ctgtaacgaa gattagattt atggttcact   40740
tcaggtgagt aaaacatttt tcttaaagca ttggtatgtc ttgaaacgac aagttgcttt   40800
atgtcaagat tcactagaac ataatagtag tttcagagga agctaagcca ttacactgtt   40860
cagggatcca cattaagata gttcgagaac aagagttcac tagtccgaaa gtcacatttc   40920
aacgatccca aacataacag cgatgagaag aagaacaata cagacacaag acattttaga   40980
```

```
cactaacttc caacatcaca taattttagc caaaatgtca gaaaacacaa caaaatggat    41040
aattaaagat tattgaaaca gaaacatagc ttcttaaaac aaagacaatc atagatgaga    41100
aaggttcagt ttcttctttg cttcataact tattgttgta ccagaacaca cctttcttct    41160
caccttgcct gtccggttcc acatagatac actccttcgc ctccctccac atcgccttaa    41220
ccaccggcgt cccatcgaac tgataatact ctcccagtat cggctttatc gccttcgtag    41280
cttccatcgc gtgataatgc ggcatggtcg agaacaggtg atgcgccacg tgcgtgtccg    41340
tgatattgtg gaagaccttg ttcaagattc cgtagtctct gtcaacggtg gccaaagctc    41400
ccctcaacca atcccactca gacgagtcat agtgaggcag ggaaggatgc gtgtgctgca    41460
agtaagtgat caaaactaag aacccgttga caatcagaag aggaactccg tagaagcaga    41520
ccatcgaggc aactccttgg acagcagcgt agcggtagag accgtagcag acggcgagga    41580
tgccagcgtc ggagatgtat atctggagac gctcacggtc gttgtagatg ggagcgttgg    41640
ggtggaaatg gcaagcgaag ccgccgtcgt aaggtctccc cgagacgttg aaggctaagt    41700
acaaaggcca gccgagagtg aactgaaccg ttaacatcac ggtgcgtccc aaagggttgt    41760
tgaggtactt gccgtaccac ttgatgtctg acttcttctt ggggacaaac acttcgtctc    41820
tctcgaggga gccagtgttg gaatggtggc gtcgatgact gtacttccag gagaagtaag    41880
ggacgaggag gaaggagtgg aagatgaggc cgacggtgtc gtccagccac tggtagtcgc    41940
tgaaggcgtg gtggccgcac tcgtgggcta tgacccagac gccggttagg acgcagccct    42000
ggcaggccca gtagagaggc caggcgaagt aggagagagg gtgagggagg agagggaagt    42060
aagtggtggc gacgtagtag aagcaggagg ctatgatgat gtcccagatg aggtaggaga    42120
aagagcgagg gatcgagcgt ttgaaacagt gcggtgggat tgctttcttg agttctccga    42180
cagtgaaggg cggtgtctcg cagggtacgc gcttgatgtt gtcggtttca gacttttttgg    42240 agggaggaga cacttgcatt cttccacctg cacccatgtt tctgcataaa ccaaaagcaa    42300
agactcaaag ttaattaaac caacaaatta atattcagtg ttacgttatt aaagtttcaa    42360
aaaaatggac taccacaaaa aaaatggata gtacgtggga taaagagcag agaagcggca    42420
tatagtggca aaccaaagaa agaaataaac gatagcgttg agaatactac tagttattaa    42480
tgagatttga tacgttacag cttacatctc tttcttgtgg atatcaattt ctttcgtctt    42540
ttattactaa actacgttag agaagacaag tcataatcac aatgtctctt agaataagca    42600
acttgacaaa aacataaacc taaatgaaac agttgatagc aactctattg tcaacatata    42660
gacttttaaa cataaacaaa caaacaaaaa tacaatcttt ttactatcat gaatcctatt    42720
attttcttca tgcaaatcta ttgcatctga atctatgaag gagcatctaa tccaattaat    42780
ttgcaagaaa aagtttataa gcatgaagtg agcataggcc aaatgaaact ttttcatgta    42840
ttaggtaact acagaatcca gagccaatag gaatcggtca aatctctcag caaatttttac    42900 ccagagacat aagttttac ccaaagattc aacaaatatg tacttacatg tctcaggtcc    42960
agatctaaaa caaaagtaaa caaatatata taactttgaa taggaaggat atttctaaga    43020
ccaggacgtg agactgctat ggtgattttt caactccacc aacccatcaa aatatatat    43080 ataatttaa aaacgattga agtcaaaca gtttgtattc ggacaaatga aaatgcaaca    43140
tttcatattc tccacggtat agacaatata atcagattaa tggttaagac agcatcaaga    43200
tttcacacat gaaaacagag aatcaagacc agatctatag tttaatgcaa taaatattaa    43260
cagatctaga aataaatcga ctgaaatgca aaatgatag atagaacaga aaagcgataa    43320
gaaaagaaca gaccaagatt gaaaacaacg taaaaatgag aagaaatgga agaagaaagg    43380
```

```
gaccttgagc tggctgacgt agggggggat gaagatttaa cgttaataac gatgaaccct    43440
acgaagaagc tcctcctcaa actctctctc tgtctcctct ctttctctct ctctctatct    43500
ctttggtaat gaatctctct ggttctggta agatgcgatt gggcagaagg caggccgttt    43560
aaattgacgg gggcccgtgt gagacgattg agtgacatct cttttctttc ttttttaca    43620
agtgggcccc tccattattt cctctcttca tatttctttt tttttttatta tttttctact    43680
ccaaatatct gatatttaca ccacttatat atatttacgg aaaagtgaaa aagatgccgt    43740
gatcatataa ttgcttttat aaagtttatc acgtttcttt ttgtattttg tttttaaaat    43800
gtaaatattg gtttacccaa tcctaatgtt cacaaagact agtttgggtt atgttataga    43860
actcatccgt tacgttaatt agcattaaga ttatggtatt tgatgtcttt actttaatat    43920
gaggaaacgt ccttgccgac tcacaagtag aactgtagaa gttagtggta gccgaaaga    43980
aaagaaaaaa atgctataaa gttgaggatg gaggatcgtg cttggcttct tcttctccca    44040
tgtgagaaga aaacttaaaa aaatatctgc agacattgtg gttgagatca cgtgaatagc    44100
cccgagtgtg tgtgatgtac tttggagatt cgtcatatat tataataaat taatttaggt    44160
ggtacacaag taggcagcga ctgccgacta gtaattaatt taagtacttt attaaagcta    44220
tcgctctctc ttatgttaag atgattagag ttttctatg cattaccgct tataacgaca    44280
cacattattt ttaacattct ttaaagatca tcacctacca tgattccatt tcatttattc    44340
agctgttact atcagcgacg gctattaata acatgaattt ttcgttatat agtctatcaa    44400
acattataag agaactataa catcgacaac gattagttat acagtctagc atactcacaa    44460
aataatctaa gctgataatc acacacacat cagagaaaca catgaacttg ctgaccaaaa    44520
taaagcagag aaaacatgaa gtattaagta gagacagcac acaaatccta tccactgttt    44580
tgccaatcat tcatcaagcc tgccccatct caaattcaaa ctagattcta aaaaaacacc    44640
aaatggggaa aacttacact gacaatgaaa actaaacatt gtagtttcaa aaaacaaaga    44700
caactaaaaa caagtaggag aagatgatat taggaatcac cacaacaaat gaaagagact    44760
tgtttcacca gtaactctag gagcaattca tgacctgcgt agctctgctt ccccgtgagc    44820
aaagtgacat ctatcaccaa atgtacagct tcctttagag aatctctcac acatcttcgt    44880
cttgaagttg cttcctggat gtggtttccc ttcagaacca agcccacccc cgccaccacc    44940
gccaccaggt ggtctcctag atgcggaatt aagcctccca atcagctctc taaccattgc    45000
gctcgcttcg tttatctgct cgaatgttcc ttcaagctca atgttcttca ggttgggatc    45060
tctctcgtga tcttggatcg atagctttgc tcctgtctga cgacatatct gtttcgaaca    45120
gactccacct tttccaatga ttgcgccggc caaggaagca tccacactga tcttggctgt    45180
ggctgaggca ccaaagctag agacatgcc aggcctgac tctcctctcc ccgaaaaccg    45240
acctccacca ccaccaccac cagatccttg catgtttctg gaaacttgag acatgggtga    45300
tcccatgttt gtcatctgtg ccataggatt gtatcctccg ggaacaaagt gcaagaaatg    45360
gcagttctca ccaaaaggac agccagaagt gctgcaacag acgcataata aatatgtcaa    45420
gagagttaaa aaccattggc attgagaaga cacaagagaa caaacagttg aaacacagaa    45480
gaaatggcac atagcaacta tgctaactgc ttgtctatga cggacatgtt caccagtatt    45540
cagtaatgca acaaccttac tagacactat atgaccatga tgagacaacc ccaaaataac    45600
taatatctta ccaccaaaca gagaattaca acacatatct ttactgccac agctcaaaca    45660
aaaggtgtgg attgatttc tacgctataa tcaccagttg aggctaatat atttctaaat    45720
```

```
ttataatcga atatcatatt tgttatattg aaactttttt ttaactggtt cagcatgaat    45780
aataatacat acctgtaata agagctaatc acttacatta gcatacattt tttagttgtc    45840
aatttgaagc tcagactata aataacaatt ttgaatatta atttagttaa gaaaaaggat    45900
tataacctga aaaattttgt gcatggcttc gatttgcttc ctaaaccaga ttccatctct    45960
gttccaaaga ttaagtgttt ttctttagtt aagactttgc tgatgttcaa taataattgc    46020
ttttagaatc atacatatca ttcataaatt ctcatctata tggaacttca cacttaaatc    46080
aaagctgcta ctctagaatt ttcaggatta tttaccaaca actaccacat gaataactaa    46140
cacataaaaa agctaattca atcacagcaa actcaagctt tgggcatggt gataatatgt    46200
tacaagaggg actaaactaa agcaataatt aaaactcaag ataactataa gcttgattta    46260
actttaagat cacttatcaa aagctcatcc atcattaaac tgaaaaatta atggacttta    46320
gatttgcatc agatcaaaga ctgcagcaat ctctctactt agccagagaa gtgagcacga    46380
aagaaagatc caaacttgaa tttactagag aatacgaagc tcgaattgaa gaaatcatcg    46440
ctaccccaaa tcaaattgac aacaaaggaa ctattcatcc atcaattaag atctaaagtt    46500
tcaaccttta acagagcaag tgaagcaaaa cagaaactgt aacagctaaa acactctttc    46560
gagacaataa agtaagagga agagcgaaag agctaaccct gcttcgactt cttgaatccg    46620
ccgccattgg agttgaatga gccagcttca ggccgtcccc tcttacgagc atccatggct    46680
aaaggtgtac agatccgaat tagaaaccct actgtgtgag tgtctagaga gcgaatcgga    46740
gaagacaaat cgaaatcgga attaaaggga gaaggaacga gtagagagaa gagaataata    46800
ataagataaa taaaaccttt ttaaccctaa gggtggtgtt gtcttgtcgt cgagggggtg    46860
agatgagatt ttccttttt tcctaactct tcccgatttt ttttaattc gatttaaacc    46920 ggagtggcgt aacaaataaa caaaaaggta accggaatg tcctgaaaaa aggataaaag    46980
ataaccggat tcgcaagatg aggctgtttc gattcctttg atacggttaa catgtataat    47040
gacgttgatt gttccttatt cgacatctta cgacgtaaga cgaaaaataa attgcgtacc    47100
ggtctagtaa gttcggattc tattatgttt tccataccga ggagacagac acacaaccaa    47160
tgtttatcat ttaccttaag gctgggcgtt tttaacttaa accggtgtcc acaccttaaa    47220
ccgaaccaaa ataatgagtc cggttcggta acgggaccat gcaaataccg aatgggtttt    47280
tagctctaag cacttcggac accgggtcgg tttggttagg taccaaacca aaaaatttta    47340
aaagaggaaa atcatcttac aaaattactg tatatttatg tagaaactaa attattttgt    47400
tgaaaacgaa gcggtgaaag tcagtataaa tattatatat atatatatat atatatatat    47460
atcttacaag aaataataat tgttctaagt aca                                 47493
```

<210> SEQ ID NO 2
<211> LENGTH: 40174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gggggtgggg tatagatttt ggagtttttt ataatttggg tagactttgg aagttgttta      60
aacgattttg gtgaagtttt gaaaatacat ttaaacaaca ccattgttgc ttctgagtta     120
tctctaacat tatgaattct aatgatatta tcacctccta ggatgcttac agtaaaagaa     180
acaacagttt taatttttttt cttactggtc ttaataagcc cattcagaaa tatctcccaa    240
```

```
taatctcttc actgaaggtc cctacaggca cacgagacac tgctatatgc ttctgcatat    300
ctttggcgaa atagagctc atcacataaa aacaaaaaga tgatgaacct aaatcttcaa     360
attgcaatgc gatctctcgc ggaagaatca aaaccttgaa gttgctgtac ttttcttttc    420
tgtatggttc tctgagtggg actaagtatt atttataata ttttttttgta attactacta   480 ttttttatttt ttattttttt tattttaaaa acataatata acttgataat attttgtttc   540 ttttttataaa agatatcaaa tttgaaataa cacaatccta ttggttggtg aacctaaaga   600
ttcaaaataa acccaagaat aagtcaataa agaacaacaa tatttatttg atatatgttt    660
tcataaatta tatgtagata aaatacaaag cacaacggtg cacaccagca tatgcaacgt    720
taaagtttag attttaaaat aataaaaaac cataatacat ttttaaccgt agattttaag    780
ttacataggg ccggcccgct gcggaagcaa cgtaagcgac ggcgtagggc acacaacgtg    840
tttcaatttt tttttacagc taaatttgtt cactaacttt taaaaaaaaa tcatccagct    900
gattaaaatg cacattttaa ttttggatta gggcatctaa tagtaatgga actcgtacga    960
tgaaactttg aattttgtga agaaaactc caataagtta atataatcat gttattggat    1020
aatgtacata aattttaaag gtgactgttt atgaggaaac aaatcagata tgcacgattt    1080
tgtttcctac aaatggctaa ttttaccaat ttatatttaa gttgtttaga ttgttttcct    1140
tcgagtgtgt attaaaaatt tattcaaaag tatgtggttc attgaatatt gatatttaca   1200
atgaacacgt ttcatacata gatgaaatat agatattaac ctaaataac cttaacaaaa    1260 attaaaatac aataactttc aaatcaatat tcatattatt agtatatata ataatactta   1320
gtcccactca catttacaat cggctttcca aaactttgtg ctacattatg tttcatcttt   1380
caatggccaa cactaaacaa aaaccagttt caatcttatt gcttactaca ttttgcttct   1440
tgtcgttata ctttgtgaaa aatcaagcct tctcaaaagt ctcatatcca tctaccttag   1500
gtctaaacca agagaaacta acacatcttc acttttactt ccacgacatg tatggttaca   1560
acccaacatc agtggaagta gcagaagccg cacaaacaaa cacatctaaa acatattttg   1620
gttccatgtt cgtaatggat tgtcctataa ctacacttcc taatataagc tccaatataa   1680
tagggtatgc acagggtatg acagcatctg catctcaaac cgaattggga ttgttgatga   1740
ttctccattt tgtgtttacg gaaagagaat ataatggaag cacgattagc attcttggac   1800
gtaaccttgt gtttgagaat gttagggaga tgcctgttgt tggaggcagt ggcctgtttc   1860
gattcgctag aggatatgct gagggaaaga cgtattcatt agatgtgaaa tctggaaatg   1920
caactcttga atataatgta tttatcttgc atccttgatg tattatacaa taatgttaaa   1980
gctaaactat tttattatcg ttgattccgc taattttttt gataattaca gtgatgatat   2040
ttcataattt ataaatttgt tttacgtaaa ttaatgtcac tatgtcctaa tttggagaac   2100
aatagtcaca ttgagaaaat gtagatcaac ttttttacta cagagttaaa ccgcaatata   2160
agaactacca catgtaatgt gagagactca aagtttagaa tccaaatgtt tttcgattaa   2220
tttgtttgtt ttgatatgga tctttacaat acaatttctt aaacactaat catttacaaa   2280
actggttgtt aacttttcat tttttgttgg tccaagatgt gaccgagaca cttcaaatct   2340
ctacttatat atctctttaa attttgtaa tcaaccaagt tttagctatc tttgtaatac    2400
aattttcact tcatgaatat tcgcattctc gtgaatcttg attggttgca ataaaataaa   2460
aacaaaatcc ttggcatcaa ctgccaaagt cgatgttaga aataattttt tttttttaa    2520 acgctagaat tttatagaag gataacagaa caaaggttct acaaggatca tcttcaatca   2580
aaagagacaa agagaggtag aaatattgac ctaacaaaat aggtaactaa gccaacatgg   2640
```

```
atatcctcta gcaatataag attgaaaaaa atcctcctgg atcacacttt ttgcaataag    2700
tgttgctcct ttaatgttat gataagagtg gaattgagtc ttccaatccg ggaattcatt    2760
cagtaatggt aagacctttg aagagtagaa ccttatagaa ggccatgcag atggtttaga    2820
gatggcgcca atcaggtcat gatcatcact agcaaagatg atggagctga atggagagt     2880
cttcaatatc tcaataggcc atctctagtt ttctagagag gcatcctgtt tgcacgaagt    2940
gtcagagaag gatcttcttc catggaggag aattttacct tcgctgctac gaagaatcct    3000
agagtaacct tgagtcgtca gtaggtatca ctgcttcttt gtgtgttgat tgattttttgt   3060
actcatcttc ttcattcatt gttctggagg tttaacttcg actttgtgat ggcatctaga    3120
aaaggatcaa agctgaggaa agcagggtat accaatttaa agggtgctga ttctactgct    3180
tcctcagcga cctcgtcttc aaagctttat caggagacat ctattgatga tggccatagc    3240
tcccctgctt cttcatctgc tcaaagcaag cagcagttct tctcatcaga ttcgtttcca    3300
caaagctcta agccttctaa agaaaacgtc acagtgacag ttcgctttcg cccactcagg    3360
ttcagagtga aatacttgta tatgcttgca aatataaggt tgatgtttgt tctgtgaatt    3420
tgacatatat ttttccttg acgtagtcca agggaaatcc gcaatgggga ggaggttgca     3480
tggtatgcag atggggaaac aatcgtaaga aatgagaata atccgacaat agcttatgcc    3540
tatggttagt ctttaacaat ttaattagtg tcatggtgaa cacatcactc aaaaacaaca    3600
aaactaagga caaatagtat tgttcttatg tgatattcat tttcacttgt aatcatgtct    3660
taaaatagga ggactaagat taaattggat attctttttt ttttgatatt ttgatttccc    3720
atgttgtttt cttgaagttg tctttcaatc tgttaatgat tgattctctt tctggcagat    3780
cgtgtctttg gacctacgac cacaacacgc aatgtctacg atgttgctgc acaccaagtt    3840
gttaatggag ctatggaggg gattaacggt atgaagtgac cagttttaat gataagtcta    3900
ttttaaaata gaagaaacga gagcagcga cacttgccgg cggcaattct gtaacaacac      3960
tccactgtaa ttcctctctc atgcttgtta ttttttggtc gctgttctct gacgcgcgtt    4020
agagaaacga acagggcttt tgtatttttt tttgtcacag attatttgtt gaaagactgt    4080
tcttagtgtg ttattcttca gaacagttga tttgaatata atgacatcaa tgttaatcca    4140
ctacagggac cattttttgca tatggagtga caagcagtgg aaagactcac acgatgcatg   4200
taagattccc taataccgtt tgatttcaac acaccctact gttgaaaact tgaaaccatg    4260
tttgcattta actttagaat gtccatgact tacgattaat attatctgat agttttggtt    4320
aatttttttgg ttcaaatgtc agggtgacca agatctcct ggtattatac cgttagcagt    4380
gaaagatgct ttcagcatta tccaagaggt acttttgtag gatattggtt cgtccagatt    4440
ccttggctta agtactagca gcctgacata ttaatctttt acagacacca aatcgagagt    4500
ttctcctgcg tatctcctac ttggaacttt ataatgaggt gctattattt acctattgtc    4560
ttgtctgctt tatattcatt ttcaatagta gcagagagtg atagaaataa ttttcctttg    4620
agattactat ctttaaggtc caccttattt caggttgtca atgatttatt gaatccagaa    4680
ggacacaatt tgaggatcag agaagacaaa caggtatgtg actcactttc agatcacctt    4740
ttgatacatg caactacttc tcttgttgac tcgtaatata tttgttgtgt ttacgagtaa    4800
tatattttgc ttatcataga atctttttatt gggaaccatg gttaggctat ttggtacctg   4860
aaaatatata ttggttccat tatgaggact ctgctattag aatgctttca tatgtggccc    4920
tttgtttcat tgcaatgctc tatgtcacaa tgttttcaag cacatttgaa gttgatcctc    4980
```

```
ctaattatca tttgaaatga gaattgtata atgagcttct catggctttt attcaatttt    5040
ttttaattga acccattttt gttgattcca gggaactttt gtagaaggga taaaataact    5100
tcctctttaa gatatttcgt ccttcaactc tgtcatgatt tggtaaattt ccatattatt    5160
caatgcatgc ttagtaaatc tttttcctca tgacagagca acgccatgtt ggatcaacaa    5220
actttaattt gctcagcagc cggagtcata caatattaac gttggtatgt taataatctc    5280
tttgaagcaa gggagaaatt gctatctgtg tgcagttgat atatcatttt tttctcctga    5340
caagattaaa agtgaagctg tacacctctc acagctggta agctactctt ataaccagtg    5400
atatagttag ttatgattag ctcttcgtc tacgctaaag cgaattcaaa taatattaac    5460
tacccataat ttctctcata tttgcagaac ctcgttgatc tggcaggttc cgagagttca    5520
aaggttgaaa ctagtggctt aagacgcaag gaaggatcat atataaataa agtttgctg    5580
actttagaaa ctgtgagttt ttttcttacc acacagtttt ctcttagtca acaataggtt    5640
ttggagtcaa ttcagatagt acttttgtga tgttgtaggt gatacaaagc tcagggatgt    5700
gaaggcttcg catgtaccat acagagactc taagctaact aggatccttc actcctcact    5760
gagtggtcat ggccgagtat ctgtaagtcc ttttagatct gttctcaatc cccttttctta   5820
tgaaatccac aacatgatta aaacatcttt gataacctta agcacatact ttgctagtta    5880
tgtactttac tgattagttg tccctttgtg gatatggtag ctcatttgta cagtaactcc    5940
tgcatcaaga agttcggaag aaacacacaa cacattgaaa tttggtcatc gtgcaaagca    6000
tattgagatt cagcccgaac aaaacaaggt tttactcgca tatcttctac ctgcctttat    6060
tttttggta ctaacactac aaaactgcag ataactgatg agaaatcact aatcaagaag    6120
taccaacatg agattcggcg actgagggag gagttggaac agcttaaaca ggacattgta    6180
ccagttcctc cactgaagga tatgggtgca catgatacta ttctcctgaa ccagaaggta    6240
tgctcgaaag ataccttcca tccccattta acttttgta gtgattaagg gatgtttttt     6300
ttctgaatag agttccaatt ttgaaaactt aaaatcttgt ttttaattgt cattcatgca    6360
ttttcctgtc agtgataaaa gtttaatatg aactgataat agttgaaacc cacttatacg    6420
ttggattaga caagtaggag gacatttgt gtcattgtgt tttagttaca atcacgcatt     6480
tgagagaatc tgtagtaatt ttgttgtttc cttttttgg ctatataacg tgataataga    6540
agctagaaga tggtcaagcc aagctataat caagactaga ggaagaggaa gaagctagag    6600
cagctctctc gagccgaatc caacagttga cgaaactaat attggtgtct actaaaactt    6660
cactgacata tcgcttacct catcgcttta atcctcggag aaaacactca tttgaggaag    6720
aagaggtaga atcactgata tagcttgaat agtataaatt gtttacacgt tcctgtggag    6780
ggaagtcctg agattagaga tgttccatgt agagaagaaa agaagagccg gaagcatggg    6840
ttgttaaatt ggctaaagcc taaggtatac aaatgtctga cttttgttt aaagaataat     6900
gctataagta atagtagaaa tcaccacaca gccttgtctc ctcttaggtg cagtttcttc    6960
ttttaattat tctctggtca actccccttt gttgatccga gcttactttt acctatcaga    7020
aaagggataa cagttcaagt gctagcgacc agtcgagtgt ggtaaaatcc aacagcacgc    7080
catcgactcc tcaaggggga ggaagttatc tttacacaga atcaagactt tcagaaggat    7140
ggcctttgat ggaaggaaca actctcagag tctagagaag acagagaagc tcctgaagac    7200
atggagactc tggaggtaca taagagatac tttcacatct gtaatggcgc caaagtaact    7260
aaatcattca tatgtgctct tgttcccaga ctagcaataa aatcatcgat gagttggatc    7320
ttatgagagt gcagaaaaag attttatctg agggggtggc gcttcaatca agttcattga    7380
```

```
aaaggttgtc agatgaagct gtgctttaaa tctaccaaat attcaccttc ttggttctct    7440
aatgttactt aggaggagat taatgccta catgatggca tcaaggcaaa gagtgaccag    7500
attgccacct tggagaaatt aacaaatctt ggattatgtt atgacaacac atgaggcatt    7560
ggataaatct gacatcctga aggtaggttg ttgacattgc aaagtattat gcagtgagtt    7620
ctttttccgt tgctcatttc acaagcggtg ctctattatc ttcaggcagt tgctgagctg    7680
agggatcaac ttaatgagaa atcttttgaa ttcgaggtga tcgaattgtt tatgtgttta    7740
catacaatac ttcttcatct attgatccag cacctagagc tagctttgct attgattaga    7800
taatatatgt tcacaccta gtaaagttgt ttctctgcaa atattagtgg tcaaatgcca    7860
gactatttaa cgaagaagcc aaatcatatg ctctacgttt cgactcatca ttacatcttg    7920
tttacaggtt aaaagctgca gaaatcgca tcattcgggg aaaactcaat caaaggtca    7980 gaggctttgt ctttggagaa gcttgtaaac taggtttgta atgtgtagtg gaattgaata    8040
actgatgaat tattttccgc agacatgtga acgtgaagta ttgcaagaag aagttagaaa    8100
cctaaagcag cagctctcta attcccgcaa actagcacag gtctatctac atacatttta    8160
ttcacgcctt acaccaatct tctagcttaa tagcttcatg actctcaaca taaaatctct    8220
ctactttctg ttatgaaagg aaacaaagat cgaagagctg aaatggaaaa cttaaggaac    8280
taaacgaatc taaggagcaa ctagaacacc gtaacaagaa actcgcggaa gagagctcat    8340
attcaaaacg ccttgcatca gcagccgcag ttgagctcag ctcaaggcat tagccgaaga    8400
agttgcaaaa ctaatgaatc aaaacgagag actatcagct gagctagcaa cacagaagaa    8460
ctcagtcaca cagcgaagca acaagacagg aacaacaaca acaaatgtaa ggaacggacg    8520
aagagagagt cttgcaaaga gaatgaaca agacaactcg tgggagctaa agaaagaact    8580
aagaatgagc aaagagcgtg aactatcata cgaagccgca ctcgttgata aagatcaaag    8640
agaagctgag cttgaaagaa tcgtaaaaga ctcaaaacat agagaacgag ctcgctagca    8700
tgtggattct tgtttcctgt gttttaaaag gcgatcgcct tttgcgccaa ggcgcaaggc    8760 gcaccgggc gatggcccta atgcctcagt cctctaaggc gagccctagt tactcaaggc    8820
gctcgccatg gtgcgccatt ggcttaaata taagcgcctt tgaacctctt aaggcgcttg    8880
tagtttccgt taaacactac tttgacggaa tccttaaaac atcttggaac tctatcacta    8940
ctttgtcgac catttaaata tcctaaaaac ataatgctta gatcttcaga gttataggtt    9000
ttgttggatt tgagcaattg aatttagctt tttagtttca agttctttgt tttgatttga    9060
tgttttcggg tttatatatg tgtacatagc tgactatatt agtgtgcatg actaactcgt    9120
tgctgactat attagtgtgt ataaataaga cagtttggta tagctgactg tactagtgtt    9180
atatacgagt ctactctata acttatcttc tgtacgtaac catagaaata gttacacgtc    9240
tgtagcttac acatacactt ctaacctaag aacatctatc aatgcatatc taagttcctc    9300
taaagctgta tataactaaa ccacgtttga atgcatccta accataaggc gagcgccttg    9360
gagcgccatg gcgcaaggcg catggctcca acctcctcgc cttagagcgc catgcgccat    9420
ttaaaacaca gcttgtttct aagctgagaa gatcacaaag aagctgattc tgttaccata    9480
tcagagacac cgccacaaaa acttaacaaa gacgaatcca acaaatacaa taatcatcac    9540
aactttaaat tgtttcttat tccgaagaat taaaaataaa acaaaggat agaacaatga    9600 tcaatactaa cggatcagtc agttagtctt gggatcaggc atggggaaca aaccagcacc    9660
agcagcgcca cgtggcggag aaaaccctag aaacttctgc agattcgtcc ttatactaat    9720
```

```
cgaacacagc aaatacaaaa acgccatgga acaatccgtg gcatcatctc ccttcaaccc    9780
cctgtgactc atcttcttca cgatcgcgat cggatggaac gggagcttcg cgacgacctt    9840
accttcgaag agcgagttca acagcccgaa gacgacgaag aggacgaggg ccacgacggc    9900
gccggatttg aacttgaaga gggacagatc tcggctcgac tccttgaggc tcgtctcgac    9960
gcggtccatc ttcttggtct tcgatttctt gacggtgagc ttggaggaag ggttctcggt   10020
cttcatcgtc tccagcttct tggcggcttt gtcgattgag tattttaggg atttgtagga   10080
ggtggtgcgg tagattagga tccacgagat ggcttcgcag actagcgccg tgcagaagga   10140
gatgccgacg acggttaggc tgtcggcgta cttgaaggag gcgaagagtg ggatcgtcgt   10200
cgccattggg atttagtttc ttctgctttc gcttctgttc tctctctctc actgtggaga   10260
tctgattagg aattgggtaa aataaaagtc aatagagggt acaataagta aataaggaaa   10320
agtttggggg acttttagaa atacttttta attttacttg taaccaatac ctttcgaatt   10380
attagaattt accccagctg ttttttttat tccttgctat gcaaaaccca aattacaatt   10440
tttaacatta gcataaacac tgtggtgcac atcaaatagt gtaaacttgt aatcatgcag   10500
atgtatgttt ttactcacag aaaagaagaa gcaagggaaa aaaagattgg taagtttgta   10560
ccaaactcat tagttgtatg ggttttatgt actagattat ttttttctagg tttgatttga   10620 atcagagttt atttgggttt tgattagaaa aatgtggagt aaaagagagt aaataataaa   10680
gtggaaaatg gagaaaactt tggaaattga atgaaaaga gaacaaaaaa ttagaataaa   10740
actcgtttca cttataaatc ccaaaataaa tatgtgagtg tttttttta atttcatccc   10800 tcaacttaat gatgctacat agttaacatc acgaatttat tttcattcat ctaaaaattg   10860
atgtagattt tagaaaccgt ttaaatctta tgttttattt aattaaaata tgatgtacat   10920
ggcggtaatt taactaaata tgaaagttac ataagatatt atttaatttt ggttttcaat   10980
tattttaata tgttttctta ttaactctta ataaaatttt tgtaatttat ttgattaatt   11040
gtgtggaata tacttatttg atcatttttt ttattataaa acttatttca tgtcaaatta   11100
ctgactctaa cattttattt gtttgatata aaattaaata actaatgaat tattttattt   11160
atatattcat aaaaaaaaat tgcatacatt ttaaaatgta tcaaataagt atatatcaga   11220
caattaatca aatgaattac atatttttta ttaaaatttc ataagaaaat ggattaaaat   11280
aatttaaaaa caaaattaca taatatctta tagaattttc atatttaata taaataaaaa   11340
taatataata atatattttc atatacacaa aaataaaaat gttaaaacac tacttataaa   11400
aaaatgttaa aacatattga ttttgtaaaa tcaattatgt taaaaatatt cttcactttt   11460
taaaatgtgg gtcaaaatct catttagtta aattacggcc gggtcggtca tattttaatt   11520
gatgaaacga gatatttaaa cggtttctaa catttcatc aattttttgga tgaacgaaat   11580 taaacttatg atgttaatga gatatgttat catgcataat atataattcg cgtagctagg   11640
tatacattag tttagtttgc atggttaacc atgtgaatga ctaatacttc aggtagttag   11700
caaatatttt tttccttctt ttaatcaatg aacctaaatc cggattgaaa tcctgataat   11760
tgaattcaac ccaatagaac aatagtgtta tcatagttac aactaaaaaa aaacttaaca   11820
gacaaatcta aaatttagaa atggaaatat gagaaggaat ggaaaaactt aacagacaaa   11880
gcgtttcaag aagaaaaaaa aattctagag gcttcgtttt gcgttagttc attataatgc   11940
aagtagagcg aattcgatga tttatttatt ttgaagtacc atctcattag atggtatttg   12000
tttctagtgg attttgtatg taaaatcaac taggtgatta tccactcaca tgtgtggagt   12060
aaaatgtata tattctaata attgttgaat atgaactttg tccgtataac cataattata   12120
```

```
ttattcataa gcctatatat gtattaattt gaatatctat taaatgttag tttactcgta    12180
tggtttttat gatcatttat atttattat aataaaaaat ttaaactata gatcataaaa    12240
ttttcagtgt gagagtttta acaattttca ttatttatag tcgttttaa acattcaaaa    12300 tataatatat acgaaaaatc tattttttat tatatggtta atatgattgt ttaatttatt    12360
ttaatactat aacattaaaa aataatgaag atatgtgaat tgttgtcaag tctttattat    12420
taaaattatt aattgtcaaa tatatatttt agtcacgttt ggtaattccg taaatttat    12480 ttaagaaaaa aaaacaataa ttatatattg ttaattaatt tcatggttat tctaagtaga    12540
agtatataat acatgtttaa tagaccaaaa tatttcttta gagactttaa gaaacattat    12600
agtgatgaca cgtgttatag ttaaaatgtt gtaatgctta tcttttaata tatagaagat    12660
tatctaataa tttccaataa ctcttgataa atactaggaa aagaacccgt gcgatatcgc    12720
acggtaactc atttttgtaaa aaatacaata caaataaaat tacaataatt tttgaagata    12780
atttttttaa attctttata agagtgtata tatatatata tgaaaataaa tgaaaagcca    12840
atttcatata ttttgataaa aaatttaaaa acaaaggcaa tttcatgtag tgatctttga    12900
tgatctaaat aatgaatctc tttcttttt agtttatttg tgattgttgt gattttctaa    12960
ttttatttgg tgtttattgt ggttgttatt tgtcattttc gacaactatt tatatatatg    13020
actaaggatt gcaatagttg acaatcaacc tttgcaaagg tttaactaag ggttacactg    13080
gttaacacca aaagttgcaa cagttcacaa ctaaaaacaa taatcactaa taattgtaat    13140 tttttttatca tcaaagaatg taatggttca acactaacag ttgcatcatc taaccaattg    13200
taactattca ctaagacaac atactccact taaacagtct caaagattca cttaaatctc    13260
taacaattat ttcttattta attattatca gagattcaca aaataaatat cactcgtatc    13320
aaactcatgc acgaataaaa atgtacgtaa catcaattcg aaaaacatca taaatgtcta    13380
tttatttgat agataacaaa atggatcata tattttttata aaaaaatagg atcatatatg    13440
cgttgtacgt atataatttg acatatcatt aaaccttgta tcagatgtga tgtcaaagtt    13500
actaatatgg tagatagatt attctttgaa aaagtatttg taaatggga tgaccgatga    13560 ttaatagtag cttaacagat ctctcttcac aaaaataaat aaattaatag actatttaga    13620
agaaataaaa tatcgatgt aaaagttgga atcttcgatg tataaatgtt ttcaaagagg    13680
tgtctttgga agaggtttaa gccgttttga tttgaaggaa tgcattgatt cgagaaaggc    13740
aaaagcgttc tttggtttaa taaatgatga tgtcatctat ttaaaggaaa tctaattttt    13800
aaccattaga ttattataaa ataaagcaaa tctaacagtt agatatatct tttttccta    13860 taaaaaatga tgatattatc agttaacaaa aaaacaggtt tcctattatg tatagaaaat    13920 ttaaaaaga agtaagaaaa acttgctttg atagtagcaa atgtcattt atttgcataa    13980 cttcttgtat atctgccaag aagaagcaag gttggtttca aggtgactct ttaataaaaa    14040
caaataaaca cgaaccaaaa acaaaaaatc agtttaatac ccagcgagtt gattattgat    14100
catccatggt ctccagttat caataaccga atagttgaga gatcttatcc aagcttgagt    14160
cccaatgtaa ggtactgtca tatcgtgatc accaatgttc acacaaaacc acacaaatat    14220
ttacataaag attttgaatc ttggtgggag aaaaaaactc tgacctgaag atgagagaac    14280
gatagccatt gatgctatta tccatatggt aaggtacatt acttataatg tcgttactgt    14340
aaggaatatc caaattacat cgtatccatc tccctatgct ctactacaat tatagatctt    14400
cttaaaaaac ttgacagcgc ttctttacta aactctttga aatgaacagt cttatatacc    14460
```

```
ttcttgattt gaagagcttt gcgtacgctt tcgctttcgt catttgccca gtaggtagct    14520
agcaaatacc tataaatctg caaaagcaac cttatatatg ctttgtttcc tgaatggttt    14580
aacggtaaag aaagaaggtt aaaaatttat aacagtagtt attttaaaat tatacttata    14640
ataatagtca caacttttca cttttaaaa gatatctata cataatagca aactccacat    14700
tctgtgtttg atgacatcaa catttttat agcaaaataa aattgaaatc ggacggttga    14760
gattattgcg gttatgtaat ctagtggata ttatttaagt ttcatttagt atatgatgtc    14820
atccgttatt atatctaaac gatgtctttt tcttttgaa acgttgcatt tttgaaacat    14880
tgcttctgaa gagacacgac cctctcaaaa taataattct tatatctaac ggtgtcttgt    14940
ttttgaaacg ttgcattttt gaacgttgc attttgaaa agatacgacc ctctcaaaat    15000
aatagttctt aaatcttaac aaatttatat attcattctt tatgacttcc ctacttcccg    15060
tcatcattgt tctttttct ccttcactta ccatggattt cttttgttct ggaaataacc    15120
gtctctctct aagaattttc atgtctgttt tcaccaccac cgccatcctc ttttctgttt    15180
gttatgttaa tctccatcct catttctgt ctccccaacc cactactata ttaatttact    15240
cataaccgtt gaatattag aacatgtgtt gtcctcatga aaccatttga tgatatttta    15300
accgggagat tcaagagact gaaatttata aagggaaat atgatttcat gtttcaagaa    15360
ggaactgaca atcataatca atttaactta caaattagcg agaaaagctt tagcgagaga    15420
attccgatga ttctccctcc actgtttcca ggccttatga gaatataatc catcctagga    15480
aaattaattg taccaaaaat ttaacaaaaa aattcaccga gcatctttcc acaaatcctg    15540
tatatctgaa gaaaataata attgtgttga attctttata attgtgtttt ttcacaattc    15600
tttttgcacc atcaaatcat catatatcac tctcactaat acgcatctct tcgctctcaa    15660
ctggctattt tcagccaatt gttaaacaat ttttttgatt tccggctgac attgatccta    15720
gcactggttg ttttctcttt ttatttactt ttgttttaa tacatttaga tctcggttta    15780
ctaccattaa aatcagtgga agagacttat aattgaaaaa tgcatggcgg agactattta    15840
tagattttta aaatctattt gaatagtcac atcccttcaa tctgaatagt tgcattcttc    15900
taatactcac aacttttcac ttttttaaaaa atacttatga atagtcacaa cttttaaaca    15960
attttttagaa aagacacaac cttacaacat agaacttta gaaaagacac aaccctttac    16020
acatcttttt caaagatac aacctttcaa tataagtgag attcacaacc tttgaattaa    16080
atgaggattg ctattattag tagattatga gtgaaatctt tgttttccag taaggagaga    16140
ttcgaaagag ttttaataaa tgattaattc aataagagtg gatttgatag aactttata    16200
aatactaaga ggagatttga acaaaaacta gaattctctt aaatcataag ccccctttgt    16260
tcctatctgt tttttggtca ccattccatt ccagaaaatg cttttaaaga taacaatcac    16320
aacattccaa atgtagaaaa ggcacaatct caacattcta aacctgcgtc cacctaacaa    16380
aaaacaattg ccttctcgta gtttactcca aatacaaagg gtgtaatata acaacagaaa    16440
cactcaacac tttaccgaac acacgttg ccttctctcc taactcctta aagttcaatc    16500
ttcataatct ctctctgtct ctctctctct ctctctctct ctctgacaac agagagactc    16560
ttcacgtgcc aacaaaaaaa aactgagcac cttcctctcg cccatggcca cggactccgt    16620
caagcacgtg cctacattcg gcggcgcagc catctctgaa atgaaaagct tcttctccgc    16680
catgaaacca agaaaaacga tcataacttt tgtctacgcc ttcgtcataa cctttgttgc    16740
cttcactgtt tacttagcct tcgcccccttc cctcatcact atctctaatt cagtttcttc    16800
ctatatcctc cctaatgtca gtgccgtgac ttcagcgtcc agtaacatca cattacaagc    16860
```

```
aaccacgccg gaaagtctca ctccggctgt tataaacaca accttttgagc ctcccctagg   16920
taatgaaaca aacccacatt ctagaaacaa cgcttcacgg tctcatgcaa gtgtacactt   16980
atgtcctaac aacaacactg ctcgaaattc ggacaaacaa gcacctctgt ccgtgaattc   17040
aagtgcttct tctccgatga gaaaacaaag taggaagtca ggggctaaac gagagatcaa   17100
gtctctgaag gactgcgatt ttttccaagg agaatgggtc aaagacgaat cctacccgct   17160
ttacaaaccc ggcacgtgta atctcatcga cgaacagttt agctgtttaa ccaacggaag   17220
accagacgtt gagttttaca aactgaagtg gaaacctaaa gaatgcactt taccaaggct   17280
gaacggaggc aagttgctgg agatgattag aggaagaagg ctcgtgttcg ttggagactc   17340
gctgaataga aacatgtggg agtctttggt ttgtattctt aaaggatcag ttaaagatga   17400
gagacaagtc tttgaagctc atggaaggca tcagtttcgt cgggaagctg agtacacttt   17460
ggtcttcaaa gtaagtttgc aatctgtttc ggtgaggcct gcgggtttgg ctagtttggg   17520
ctgggtcgtt cggttcgacc aaaatatcgc ccaactgaac cgaacagagt ttggttcggt   17580
ttaggtagtt cggttttttca acttctttta ccgaaactaa tcaaagtttt tggtttcaat   17640
tatatgttgg tttaaaattt ctttaaattc ggggtaattt ggttaattcg gtttgtcggt   17700
tattttgatt cgaattttttg attagtttag ttagcttttt tttggaaaac ccgagctaac   17760
caattactga agtgaaaacc gaagtatttt ataagcttgc cgaattgaac caaactaacc   17820
aaaaattttc gttcggttcg gttatcaacg aggcctagtt tgactaccta gttgttattg   17880
gagacttgat ttgtgtggtt gatatgatag gaatataatt gcactgtgga gttcttttgcg   17940
tctcctttct tggttcgaga atgggaagtt acggacaaga acgggacgaa gaaggaaact   18000
ttgcgtctag atatgatggg aagctcatca aagcagtaca taggagcgga tgtacttgtg   18060
ttcaataccg gagcttggtg gactgatgac ataacatcca aagggtagag ttctgtcagc   18120
tatttttttat ttttttatat ggaggatttg tctcattggc ttttttggtgt ttggatggtt   18180
ttgattagtg aggactattt tcaagaaaga agcactgttc acccgaaact caacgttgat   18240
gaagcttta gaaaagcatt gactacttgg ggtcgatggg ttgataagta tgtgaatcca   18300
aagaagtctc ttgtcttctt ccgcggattc tccctgtcac atttcaggta tgtacagttc   18360
tttcatggta gtcttaagat tctgttttaaa aaaataaata aatgggtttg gtctggttgc   18420
atgcagtggt gggcgatgga atgcgggagg ggcgtgcgat gatgaaacag aaccgatcaa   18480
gaacgaggca tacctaatgc cttacccttc caagatggag attcttgaaa gagttctaag   18540
gggaatgaag acaccggtca cgtatctcaa catcacgagg ttaacagatt acaggaagga   18600
tgctcacccg tctgtttata ggaaacagaa atttactgca gaagaaagca aatcaccgtt   18660
gttgtaccaa gactgcagtc actggtgcct cccaggtgta cctgattctt ggaacgagat   18720
tctctatgcc gagatgctgg taaagctcga ccagctccgt ggcaacagac ggcggaaacc   18780
tgaagggcta ctataggagg agttgaatca tattcttgtt ttagatgaaa tacacaatat   18840
atattttcaa tggatgaaaa gaaagaaac acttagaagc aattatatgt tttcaaaggc   18900
atagagaaag taagagatga gaatcatatt actgccttgc tcatcacttt tcttggttgt   18960
aaactatgtt catgggagag gtttgagatt gtaaatggtt aatttttatt ttactcaatt   19020
taatagtaag gtttgtcaaa tcataactga accggaaatg gaagcaatca tttggttaaa   19080
agaatccggt tgatgacatc gactggcaaa gcataggcag gatcaatttg gtttgactcc   19140
aggatactcc agccctgcac cagttttgga tcattaagtt ctctttagct ttgaagacct   19200
```

```
taacagtatg tactaatgag acgcaaattt tagtcacctg caactccaaa gtaagtgtga   19260
aagatatcaa cagcatcgtc aggtccattc tccatatctt attcaaatta cacctgaaac   19320
tcagggaagg ctctaaagag atgtgagttt tatcaaccaa tgtttgagaa aaacctgaca   19380
gtccaagatg aactttacaa gctttgattt gtcaatccaa tggactctgt tggtcatgat   19440
aaaactcgat aaaacccacc aagagtggca aacctggtga taattaagca agaacaatca   19500
gtgtggtaag tgttaggata atgacgtatc attatagaga taatcatagt ttaagataac   19560
tgttgtattt atcttataga taactatgag catgtgataa gatcaacttg actctatcac   19620
atgatctcga cttgtataaa tagagagctg cagacatcaa taaacttaag ctttccacaa   19680
tacaaatctt atatggtatc agagcaattc tcgatccaaa tcgtttaaat ttttctttttc   19740 tcttcacgca aacacaaaca tcgttaacat gtctgatcaa aacagctctc tcacaactgc   19800
cactgctaca cgcaccgcag tctatgatcc cgcaaaccct gcaaactcgc ttcttgcggt   19860
taacatgtcg aacgttacac gtttgacaaa caccaattac ctcatgtgga gcagaaaaat   19920
tcaagccctc cttgaaggtc atgaactcca cactttcctt gagaaaacag aatccactcc   19980
agaggcggtc ctcatcaaca atggcctcgc agaacctaac ccggcgtatc taccgtggag   20040
acgtcaggac aggctcctat acagtgccat cattggtgct atatcccttc cagttcaacc   20100
actcgttgca agtgctacaa ccactcatga agtctggagc acacccaatc tcatctttgg   20160
cacaccaact cgcggacaca tcaaacaatt gaagttccaa gtcaagagct gcaccaaagg   20220
aacaaaaacc atcagtgagt atctgcgtct tatcaagacc aaagcagatg aactagcact   20280
ccttggcaag cccattgacc ctgaagatct gatagagcag attctagcgg gtctctctga   20340
ggaatacaaa gccgaagttg atgcaatcaa cggccgagat catctgatct ccttctctga   20400
acttacagag aaacttctta accgagaagc catgattgtc tgcgatcaac cagcaacacc   20460
gacgtttcca gttacagcta acaacaccac aagaagcaac accaacaaca ataaccgcaa   20520
taacaacaac aactggcgtc catcctttgt cccacgacaa ggcaacaact cgcctcgccc   20580
atctcgtccc taccttggaa gatgtcaggc ctgcggaatt caaggacata gcgcccaacg   20640
gtgtccatca ttcaaagtca ttgcaaccaa ctcaatgcag caaaacaccc aacacgctca   20700
gtggcgacca catgccaatg caacgtacat gacaaaccaa caccctgatg cttggcttat   20760
ggacagtgca gcctctcacc atgtcacgag tgatctcaac aacatggctg cacacatgcc   20820
atatgcagga ccagatggca tagtgattgg gaatggagcc aatcttccca tcacacacac   20880
cggttcactt tctcttccaa cttcatctaa aagtttcaat cttaatgatg ttctttatgc   20940
tccatctatg caaaagaatt tgatctctgt taaccggttc tgtaaaacta acaatgcctc   21000
tgtggaattc tttccaacta tgtttcaggt gaaggatctt ccaacgggga caccggtgct   21060
gaccgcgcca gttaatggca acctctatga atggcctacc aatgactcac gcactcctct   21120
tgctttctct gctgtatcat catcgtcctt agactggcat cacagactag gacatccggc   21180
ttttccgatt ttacagcata tttcttcttg ttttttctcct ggttttttctt gtcgttctcc   21240 aaactctctt cattgcaatg cttgttctat taataagagt cacaaattgc cattccataa   21300
aacatctatt acttcctctc gtccgttaca aattcttttc tcagatgttt ggtcctctcc   21360
catcttttct tttgatggtt acaaatacta tttactcata gttgaccact atacaagata   21420
tatgtggttc tttcctttga aactaaagtc acaggtcgca gccacattca ccagatttaa   21480
ggagctcgtc gaaacacagt tccaaacaaa gatcacaaca ctctatagcg acactggcgg   21540
tgaatacatt gcactccgac cattccttgc gcagcacggc atctctcacc tcacaacacc   21600
```

```
accacacaca cctgaacaca atggcctatc cgagagacga catcgacaca ttgtagagac   21660
aggtctttcg cttctcactc acgcttccat ccctactgaa tattggacat atgcctttgc   21720
tgcagctgta tacctgatca ataggatgcc aacgaaagta ctttcaatgg acacccctta   21780
caatcggctc tttggaactg ctcccaacta ctccaaactg aagatctttg ggtgtctctg   21840
ctacccgtgg ctgcgaccgt acacatccaa taagttggaa ccacgctcca ctccatgtgt   21900
ctttcttggt tattctctta ctcaaagtgc ttatttctgt tttgatccct ccacttctcg   21960
agtctttgtc tcacgacatg taacttttgt tgaacataag ttttcctttg tttctttaag   22020
tgccaatgtc tcttccactc cagcaacaga ggagctagcg tgggttccta cggtggaacc   22080
tttaggtcag caacaggtac tcgtggagga gccctcaccg gaaactggac ctgcaccaac   22140
aacggcatct ccaacaccaa cagcacctgc ttcaccaaca gcacctgctt caccaacagc   22200
gcttgctcag tccacagctg cccctcctgc tacaagctct cagccaacac aacatgccat   22260
gacaacacga tcacgcaaca acattgtcaa acccaaccca aagtatggct tgacaacagc   22320
acttgccccg tacgttgagc cacatacaat cacacaagct ctggctgatg agcgctggcg   22380
gaagtctgca actgcagagt tcaatgctca ggttgtcaac aacacatggg atctagttcc   22440
agctgaagaa gcgacaaacc tagttggcaa caggtggatc ttccggtaca aatacaaccc   22500
tgatgggact gagaaatcac tgaaatccag actggtagca aagggatatc atcaacgtcc   22560
aggaatagat tatcatgaaa cattcagtcc agttatcaag tctccaacaa tccgacttct   22620
acttgggctc gcagcaaaat atgactggcc tcttaagcaa ctagacatca acaatgcctt   22680
cctccaaggg actctcaatg aagatgtcta catggtccaa ccagcaggct tcatcgacaa   22740
ggacaaacca aatcatgtgt gcaaactcaa caaagccctc tatggcttga acaggcgcc   22800 acgtgcttgg tacacggagt taaaaacata tcttctcagc cttggattca aaaattctgt   22860
tgcagatgca tctctgttct ttttacatga tcgagggatc gtcatcttca tgctaattta   22920
tgtcgatgac attgtggtta ctggtaactc tctttctcgg atccgtgaca tcatcaacaa   22980
cttgtctagg cgattctctc ttaaagacct cgatgacttg ggatacttct taggcattga   23040
ggtcatgcgc tcgtctcagg gtattgatct ctctcagaga aagtacattg ctgacctact   23100
tcatcggacc aacatgacac acgccaagcc agtaccaact cccatgtgcg cctccacgtc   23160
gctctctata cgagatggta ctaccttgga taatccttca gagtacagaa atgttgtcgg   23220
cagcctacaa tatcttcttc tcacgcgacc tgatattgca cttgctgtca acaaactctc   23280
acaattcatg cacaagccct cagatactca ttggatggcg gctaagagag tgctacgtta   23340
cttggctggc acgtatacct ctggcatctt cctctctcgt cagtgttctc tctccctcca   23400
tgcctattct gatgcggatt gggctggcaa caaggatgat tatacctcca ctggtgcgta   23460
tgtcgtcttc tttggtcaac accctatatc atggtctgct aagaaacaaa cgggaatagc   23520
acgatcgtca actgaggctg aatatcgagc tgtctcagct gctgctgctg aggtacgttg   23580
gctctactcg ttactgcgag aactacacat tccaatcatc tccaccccga cgatctactg   23640
cgacaacgtt ggagctacct accttagtgc caaccctgtg tttcattcac gcatgaaaca   23700
tctagcactt gactttcatt tcatacgtga acaagtgcag aatggagaca cgtctcatca   23760
aaggatcagc ttgctgatgg tttaaccaaa ccgctaccaa ggaaccggtt tcaactcctc   23820
tttaccaaga tcgcctcaa taaccgtgct ccgtcttgag gggggatgtt aggataatga   23880
cgtatcatta tagagataat catagtttaa gataactgtt gtgttttcac tctctaactc   23940
```

```
cagttcgccc tagctggttc tctctcaggc acggagtcca aggcagccgc acagcttgca    24000
tctccgccag aatgaaggtc tctttccggt gcagctcctc ctgtcctaat cacgagcctc    24060
tcttccgctg ctgatgacgt ttcgctcacc atcccgaagc tctccctctt ctcctccaat    24120
gggttcctct gcaactgtcc cgtttggttc tcctcccctg ccgcctgaac caccagatcc    24180
ggatcttgtc gtggtgtttc cgataaatcc tccagaccct ccaccggtcc tgctggtttg    24240
tccctttctc cgccagttct cgccgtctta caccgctcct ctcaatcaaa aggaaatcga    24300
atctcttatg ccatgggatc tctgcttttc aaccggttgc ttgctcaagc ctctctgccc    24360
agacgtcgat gtgctatcca cgcagcctgc tctgctgcat ctttcgttgg ctggaatttc    24420
tccctccgga gctctcaact ctggcctgag ttactcctcc tttcgacatt atcccgtttc    24480
aaagccgata attattacct cttgtgtgga acatgttttg ttaaagtcag ccttaagggc    24540
atcaacgatt tatcatcaag agtcgtgtgt ggtttcctta tctgttgcaa gattattggt    24600
atcaatagct gagtgcaagc tgacttccct tcattactca tctcttcaaa gtcttgagga    24660
ctgggcttgg aaggttgaaa tattggtggt gattttctct ctgttggcag ctcttaatac    24720
cgcaatgcag cattttgaag tggagctctc tactgcttta tgcagttctc agtcaaggcc    24780
tatcttctct tgcttcaagc tctcgcaagg tatggtgttt ttaatttgct ggagtgagtc    24840
acgattgttc gatccttgcc tcctagtaga tcttagttat ctcaatacga accccatttt    24900
aattcggaat gaagaggtaa tgctatcctg gattagctct gtacctcttt ttgaggatgt    24960
tacactccct ttgagtttca ggttgaagct ctctttacct cagtatgagg aagttactcg    25020
ttgtgatact actttgttac ctcagtgtga ggattttatt tggactgctg tctctgtgga    25080
catggtttca cttatctcag gcgtgtttag gctatggtgg ttctcctcac agctctcagt    25140
ctcttcaaag aggtgtttgg tcgcctttga gcttgtagct gggtctttcc caattggtta    25200
ctttcagatt tgcccggcaa agggaatgtg gatgcaaggc cgtgtcctcc atcgcttatt    25260
gagtagagtg ggctctggac acgtcgtcaa agccggtgatg attcacaaag cctctcaacc    25320
agcaatatca actggactct caagacttca gattcttccg gactcaatcg tccccttctg    25380
ttccctgcgc ttagggatgg acttgaatga gattacaggt ttcttgagct tcaaaaacct    25440
tgttcctctc ttcactccgt tatcatgtgt ttataatcta cgcacagcat tatgtttagc    25500
tgttgctttt gcaaagggtg ttgtacccag actttgtatt tcaagtactc tgctttgagt    25560
tggatatgaa ataaaattgt tgacaaaaaa aaaaaagata actgttgtat ttatcttata    25620
gataactatg agcatgtgat aagatcaact tgactctatc acatgatctc gacttgtata    25680
aatagagagc tgcagacatc aataaactta agctttccac aatacaaatc ttatagtaag    25740
aacaattgga ataatgtttt gtgtttgtag agagaagctc cgttccctca aatggacacc    25800
tattgtttat tcatctgcga taaactggtc atggcgttga caagtacgtt tccttacctt    25860
tacagttttg ttttaactta ttctatttga tgttatatat gaacatttat acatgtagta    25920
ttgtggttgc tgctgcgact gttcaaaagg agagatcaag aagactttgt acagccatat    25980 taaccaagt gataagagaa ttagctgttg catttaaacc aagtgatatg aaattattct    26040
cttcttctct cttttgttct tcacattctt cagtttccag caagtaaaaa agctcatatt    26100
ctcacactcc tattcgtctt ctttggctca gcccttaaaa gatcgacaag aatggaggag    26160
gtacatagtt ttttagcact aaaactatta ttcttagttt gtattgaaaa aaaaatgttg    26220
ctggtgaagg aacaatgtca agtctttcac gtgagagaaa tcttgcaacc aaggggggg    26280 cataataaac tgagactata aagtttcgt ttagttatgt atttcttgag aaataatgta    26340
```

```
attctttgtt ttttttttg ttaaagggtt ttataattca cgtttgtgtg ttgagcgtaa    26400
ataaaaggga ccgctttata cgattcagtg atgtttttag tttaatttca gcttctttct    26460
tttcatgaaa ttcaagctac ttcacaaatc aaagatgcat gcatatttgc gtggggaact    26520
acatagacac ccattcaaca agaactctat ttataatcac gtcctaatga atcggtcatt    26580
tgaacaaaaa aaaaccactt cctaatgaat cggtcatact tttatttta aaatagatac    26640 aaagacaccc attcaacaag aactctattt ataatcacgt ccttatgaat cggtcatttg    26700
aacaaaaaaa aatcacttcc taatgaatcg gtcatacttt tattttggag attaatgttt    26760
cataaccaag ttgctttggt ctagtggtat aggagctcca gctggagtgc ccgcccctgg    26820
gttcgagcct tggccactgc ggaatttaac atatgggctg cagcatccga gaccgaaaac    26880
cgttacacgg tgagccacat ggtgacgccc tggcagcgtc catgctcact tcggtctcta    26940
gtctggacca cctcggtgga gccaggatac tcggttagca aaaaaaaat gtttcataaa    27000 taaaaacaga tatcagtgta cgtagtatcc tcccttatct ttaggattcg attcccacct    27060
tcaacattcc acttttttct catttcagtt tgttatttaa agggtttcaa aacatacaac    27120
aattatccaa aactagattg tttcaaattt ctcaaaagat atttaattcg aagctaatta    27180
tcacgagaac tacaaattaa ttccaaaaat gaagttaatt tcattgatgt gcatcgcctt    27240
tgtcatactc ttgacatcat tcccggctac ggctattacg ttcaaccctg cttgcattaa    27300
aaatcatgat acctgcggcc ccctagttgc tgtaaagggc cggcggtgga gacccgaatg    27360
ttgtaaaatt tggagcggga atgtacttcc agaaacaaga caatgtgcat gttatgtact    27420
gaaacattct ttatttggca atggtgttct tccccttatt ttagctaagt gtaaattagg    27480
tggtatcgaa caattcaaat gttcggaggt ggaaacataa aatagttaac taaccagaat    27540
cgtgaaaacc aaactggaga taataagata aagtaatcaa ttgggtattt ctttatttct    27600
ttctaatcat tttaataatg ttactgttca ataaggagag agaaatggtt tgttttttgtt    27660 catgctcgtg tgaattacga ttccatgttt ttttgtttcc atgtattttc ttatatattt    27720
agtaaaaaaa tgaaaggta taatctagtc tggattaagt accataaata aatatttgtt    27780
cttaatctta gtgctttgga cttgtaacac caacttatg cgtaataagc atggggagaa    27840
gaagcaaatg aagaattctt cttattcacc aagttttgta atataataat tttcattcta    27900
ccaaaaaagc ctctctctag tattttctct aacttctttc taaaaaagct tccgaccaaa    27960
tagatttgct catgtggcca gtgggctctt tgctgccggt cacccataat cttttttgttt    28020 ttgttttttgc tttgtattat atttcttctc ttcgcggtgg cgataaaccg tggcaaattt    28080
ttgttgtgta ttcaaaatct taattgaagc aaaacttgat gattgtgttg tgttattctt    28140
cgattgagat tgatctttta tgtatgcttc tcctctttca cagttgctct ttaaatcccg    28200
ttcgctttaa tggagttttc ttcttctcta ttggattcgc atgtactctt ttcttaaggg    28260
agtcaatttt cactctttaa aagatgaagc cgatgaatag gctcttaggt ggaggtgatg    28320
ttagagtaat ctcgatgaag atttagatga atcggcatcc tctcggagat ggtccgataa    28380
agatctttaa ttttattgga ttgattgagt aatcccagag ttattaccca atgaagttga    28440
tggtggctct cattgaagcg acagccggat gaaagatagc agatcgcagt ctcatcccat    28500
gtcagatcca gaagtttaaa gactcatgca aaggaggatg agggcgcgtg tcacgtcttt    28560
cccgtgcatg gaactcgaag agcctaatgg accacgaatt aggcctaata aaatttattt    28620
tatgatgatg agtttcaagc ttgttgcttc tcttgtaatg ttcattggta ggcatggaca    28680
```

```
ttcggggtcc caatcgggtt tcgattttat ccattcgggt ttcggttttt cgggtttatc   28740
aaaatcaacc ccattcgggt tatataaaag ttcggttcgt gaccggttcg ggttctatcg   28800
ggttcgggtc ggggttagta aatcttcaaa gaaccggtat aacccattgt actttcgggt   28860
tcgggtccca atcggttctt cagtttaaaa atacatgatt tgtacctatt ttgtaactaa   28920
aacataaata aaatcggttc ttcggattta aaatacatga tttgtacata ttttaatagc   28980
caaaacataa gtaaaatcga ttcaaaaata agaaaaaaca tcaaacgtga tcattcaaaa   29040
tcaaacgaaa gataaacata gttagtgata taaaaaaaac cttataaatg aaatcataaa   29100
acaaaatata agttctcatg aaatgagaaa cattattcaa taaaaacaaa accaaaatct   29160
aaaaactcca ggcatcaacc gccacattcc accatcaacc ttcatgtaac agataattat   29220
tttagaagtt caataatatc ttaaagtatt ttggatacat attaagaatt aagatcatat   29280
ttggtagaag ttcttttttgt gatttaaat gtttcgggtt ctatcggata tccatttagg   29340
tccgggttcg gttcggataa tacccataac ccaaaatacc aaaaaacagg atccattcgg   29400
tatttatgtc gggttcggat cggttcggat tcatttttat cggatcgggt tcggttcgga   29460
ttttcgggtt cggtttattt gcccagccct attcattggg cctttctaaa ggaaagaaac   29520
agttgacaaa aaaaaaagaa aaaaattcta cctacttagg cccttcttaa ttcctcaaat   29580
ccctcttttt ccaatattac aatttcttcc tcttgactat caacaacaga cctcaatggg   29640
ttcatatcct atggcctctt gggagtcttt tttggatagt catccatact gtgaaggagc   29700
attggggtgt gataaggaaa ccaaatccct ttgtaccagt caactgctga atggttagct   29760
tccatgtgag ctaatcatta ctcatcctcg caagttttta gatgactgct tcttttatc    29820 aggtggttga gtataatcta ttttgaatta gcctgttgga ctagtttctc ttattcaaga   29880
aatccacttg ctcagtgaca caagagcagc taagcgggtc cgtaacttg ttggtaatat    29940 aaagggaaaa ctcagatctt ctgttttgat cttgcttgt gcgcgtctca gacatgtatt    30000
gcacatcttt gtttcttaca agcgtcaaat cgtttataca ttttagtga acaaaggtg     30060 agcaggtagc caggtagtac ctttccttgc aactcacgca tgaatataat aaatcaacta   30120
tttcattgtt gatgactgga tgattcacaa tcaagttgct gggtatagta tttacactaa   30180
attttttttt cttttgttta ctcgtgagat catcaaagat gttttagata tatgaaaagc   30240
acatttcata gtctatattc atcttccatg tatgtttctt tgatgattta aaaaaaacag   30300
aagtacatca acacttctta tctttgtgtt ttcttaatct caagttggta aatagaaaaa   30360
aatgatgaaa agaagaagaa aaacaaatta ctacgaggct ctcagtaaag ctgttctttc   30420
ttttcatgcc accatctcca cctgtaaaca caaaattgct agaaacatta gtgaactttt   30480
atataatttt atataatata aaaaatatat aaaaaattat tttaaaaaat gaattttaat   30540
ataattttgt gccaaatctt gcattctgag atcatcaagt caatgtagta tacgtaccag   30600
taatattccc aacgaggacg gactttggtc atgcggttat catcagatgg gtgataagga   30660
tgagcagcgt ggtgagtgtt gtggaaagcg cagcaacctg cagcgtagac ggatgttgac   30720
aaccgataac tttctccagt caagacggat ctcttcaaga acaccagctt tacaagcatc   30780
acactcgtag cataacgttt caataccatt gttccatcta tagcaatctt ctcctccgac   30840
tattactcca gtctcgtacg tgcacgccgt tggtggctta aacatcccg actacaatca    30900 aagacaggtt agttactaaa caaactgatg aagatgctag ttcatatcat aggacacaag   30960
cggagtttat aaccaaaccg gaaaaaaaaa caaaatccga tatgaacagt tatacaaaaa   31020
tacctgaacg gacctaaaat cattagatat ttttggattc cgaaataata tctgaaatta   31080
```

```
gctaaatttg ttaaactttt acatatttaa ggtaatttag atattatcga aagataagga   31140
tgatgatacc tgaacagaag tcatatccct ttggaaataa tcaagtgtgg tccaagattc   31200
aatcttagaa caagtctttg aagtcaagat acagcttcta atggagttcc aatactcttg   31260
atctctaact cttgatctca gccacggatg ataatctcca agtctatact ctttgtaaac   31320
ccacaccacc tccttggcta gtcaccacaa gaccaaagag cgttagaccc atgagagtcg   31380
ctatgaggaa gatcatgaca actaagtaca cccacagagc ccatgccacg ttgaaacaag   31440
ctcctatgaa accagcaagg gatactaaca gtatgatgaa tcctatcacg agaagcggtg   31500
tctggaggaa gttctcgcaa gttttactgc ttcttgcctt ccatagagca gttcctttga   31560
ttggtattga agctagtaag ctgagaaggt ttatgacccc aatcactgtg ttgctgaacc   31620
tgtacatagt aggattgtta tcaagaagaa accagagaac tttgcagtgt ttctcttctc   31680
taatcagatt ctctcttatc aattaggaat cccctggact atatttgcga agtgattttg   31740
ccacaagtca tttctacaat caatttcaca aaacaagtat gacattgcta ctgaaattga   31800
tgatatgtct tatagcttaa tatgacatgg acaattgcat ttaatgttaa tttatatttt   31860
tggtaaactt tttaaaatat ggtaataact catataatac atttaatgtc aatttatatt   31920
ttagaaattt ttttagaata tgaaaataac tcataaatca tcattaaaat aaatatattc   31980
aaatatgaca ttataaattt cgaaatataa tataattata tatttttaaa ttatataatt   32040
ttattactaa aatttttcaaa aatgtatata attttttttag aaaattataa aaatttaatc   32100
gtaaaatcat tattttctta tatatctaca aatttttataa atattgttta atttttaattg   32160 ttggtgatta tgcaactttt acaaatgtat ttaatatatt taattaaaat aaatagatag   32220
aaaaatctat ctaagattat aatttcaaat ataaacatgc atattttttaa atataattttt   32280 tatgtttaat taaatcaaat ttatattaaa atattgatac gaaaaagaaa atttacaata   32340
ttaaaaaaac ttattttaaa atataattta tatttatctg ttaaaaaata ttttaatttt   32400
ttttactgca catggtgcag gaagacacct agttttaatt aagggaaaaa gttaagagtt   32460
aattgtttaa tgattcatgc tcatattctc ttgtcgtttc ttgatttatt tttatttttg   32520
tcaagaggtc gtttcttgat ttgaatcaac taaacaacaa cattaaaatt gtatttttttt   32580 tcaaataaaa gcgtctttttt ggacaattgt ttcttgttta atagtatttt atacgcttat   32640
gtcgtttaaa ccagaccaca agtagtgcct tgaataaaat atgtacataa aattaaacta   32700
tattgtatat agaatcagat aaattcacaa tgatcaatga aaggtaagca aagaataata   32760
tagaggacgg atggtgaatt ttcttttttaa gatgctttta ctggccccat aacttggcat   32820
attaggttct gtaggtagag cacaatatga tgtttgattc ccacattcac tatttttttaa   32880 gcaagaaaaa tgctaaaaca tacttaattt aagccaaaat gtcataaaac aacaaaataa   32940
gacaataata acattactgc aacaaataca tagttttttaa taccgaaagc tagatcgaat   33000
caaaataaaa aaaacatgag tggcaactct aaggttttgg cgaatggtga aataggggtt   33060
caaaagtcgg gagatcagga tgtgaccatg atggatgtgg gggagagagc gagaccaccc   33120
ggagaccctc cggacatagg gctttcatgg gtagccaagg tagcgggtac gagtgaaggg   33180
ggtatgtcgg taccagagag cttgattgat gatgctttcg tgtcggaaag gctccgagtc   33240
gagttcccga atggagagga tggtgaaccg tgtatcacga tcgagacaga ggttttggaa   33300
gcgatgaacg ggatgtggaa gcagtgcatg atcgttaggg tgttgggaag gagtgttgcg   33360
atctctgcct tgagcaagaa gttacgagag ttatgggatc cgaagggagc aatgtatgtg   33420
```

```
atggacctgc ccaggcagtt tttcatggtc tgtttcgaga agaggatga atacttaggg    33480 gcactgacag gaggcccatg gagagtcttt ggcagttacc tcatggtgag ggcttggtcg    33540
tcggagtttg atcctttaag agatgacatt gtcacaacac cggtttggtg ggttagatta    33600
acaaatatac cagtgaatct ctatcatcga tcgatcctta tgggaatcgc caagggattg    33660
gggcagccag ttcgagtaga catgaccaca ctgaagtttg aaagagcgag gtttgcaaga    33720
atctgtgtgg aggttaatct agcaaagccg ttgaaaggga cagtgctaat taatggtgag    33780
agatacttcg tagcttatga agggttatct gaaatctgtt caaggtgtag aatttacggg    33840
catttggttc atggatgccc aaaaacgatt gcggagaagg tggctaactt ggcaatacag    33900
acggagacgc cgacacttac caatccagtg cctaaacaag tcccaccaag gcaggaagat    33960
ggttttactc aagcaaaggg atcaagaaga ggaacgcaag ccccgcgatc ggtgaatgtt    34020
gtgaccggag aatcaaatgg ggtgactaat cggaagctcc aagagattct taattttaaa    34080
gaggctaatg agattgcact atcgaataag tatggaagtc tggagatggc tacgaatgtg    34140
gatggatcaa aggaggatgt ggttgctggt gaagagaata aggagaatca tgatatgaat    34200
atccagaaca gtaagggaaa gggtctcccg caaggaaaag aagctttaat ctttagtggg    34260
aaaacaagta cgtcgactag cttgaaaggg atgactaagg agaagtgggc tgcgaacaag    34320
agaataatgg agggaggtag aggaaagccc aaaagggtaa ataacaggcc cattagggc    34380 ttggtgttta gtccgacgaa gggtgaaatc agtccggtaa aagactgaga gtggataaca    34440
ttgatgcagg gagatccagg ggtgtgttta gtgatggtgt ggaggaagtc agaagtatgt    34500
ctaaacctct gctactacga gatgaagcgt tggacaacct gatggagagt actatcagcg    34560
aggtggatca gagagtggct gatatacaga cgagctcaca aggagatggt aggatcgtgc    34620
cccttgcatg acagcgtgcc ccggtaattc gtatagacct taacagatta attatgatga    34680
attgcttatt ctggaattgc cggggggcaa aaaaactcaa tttcagacgc tctattcgat    34740
acatattgaa gaagtttaat actgatgttc ttgcactttt tgagactcat gcgggtggag    34800
aaaaaacgag aaggatttgc cagaatttgg ggtttgagta ctccttccgg gtagatgccg    34860
ttggtcaaag tggtggaatt tggctcttgt ggagagacca agcgggcgtg attacggttt    34920
tggaatcgtc agagcagttt gttcatgcta gggtggttaa tgggacagag actatccatc    34980
tcatcgccgt atacgcagca cctacagtta gtcgtagaag tagactttgg gggcagctaa    35040
aaaggatatt ggagtatata gatgaaccgg tgctggttgg tggagacttt aatactatct    35100
tgaggttgga tgagaggaca tggggaatg ggaggctttc atcagactct ctggactttg    35160
gggaatggat taatgagatt gccttggtgg atatgggttt taaaggcaat acatttacat    35220
ggaaacgagg aaaagagacg cggaactttg tggcgaagca tttggacagg gtttatgta    35280 atgcacaggc gcgggttaga tggcaggagg cggtggtgtc ccaccttccg ttcctagcgt    35340
ctgatcatgc accactctat atgcaactaa aacctgagca gagaagtaac ccaaggagga    35400
gaccgtttag atttgaggca gcgtggctga agcatgaagg atttaaagag ctgttattgg    35460
cttcctggaa tggtcaaatg cgtactcctg atgcattggt atctctacaa ctgaaactta    35520
aaaaatggaa taaagagatt tttggaaatg tgattcaacg taaagaaaaa cttctcggtg    35580
agatcaaggg tattcaggag cagttggaaa ggaatccgaa tgatgatcta ctgtcgaggg    35640 aggggtgct tcagaaggag cttgatgtgg tcctagaaca agaggaagta ttatggtatc    35700
agaagtctcg ggaaaaatgg atagttcttg gagacaggaa tacgaactat tatcatcga    35760 gtactatagt gaggcggaag agaaatagga ttgagatgct gaaagacgac gatggccgtt    35820
```

```
ggatagatca gtcggaagag ctggagaagc tagcaataaa ctattacaag agactgtatt    35880
caaccgagga cctcaaccta gacacggaaa agctcccccc gcaaggcttt accgagctgg    35940
agattttgaa tgaacctttc tcgaaactag atatcgagac ttctgttcga tctatgtgga    36000
aatataagtc ccctgggcca gatggctttc aacctgtttt ctatcaagat tcatgggatg    36060
tggtggggga gtcggtaact aggttcgggt tggagttctt tgaatcggga gttctaccgg    36120
aaggcacgaa tgatgcaatg ttagtcctca taccgaaggt tcttaaacct gaaagaataa    36180
tgcagttccg gcctataagt ctatgtaatg ttcttttcaa gatcataaca aaggccatgg    36240
tgttgagact gaagaaacta atgctgaagc tcataggccc agcgcaagca agttttatcc    36300
ttggtcgact caattctgat aatattgtta ttgttcaaga agcggttcac tcaatgagaa    36360
ggaagaaagg acgaagagga cggatgctcc ttaaactaga cctcgagaaa gcttatgata    36420
gaatcaggtg ggacttctta gaggatacac tctatgcagc aaagctacca cggagttgga    36480
ttaaatggat tatggaatgt gtcacaaatc cggaatgag tctattggaa tggagagaga    36540
acataggcgt ttacgcctca acgtggactt cgacagggtg atcctctgtc cccgtaccta    36600
tttgtgctat gcatggagag actatgtcac caaattgaat tttcggtggc aaacaaggag    36660
tggaagccga tcagattatc tagaggtgga ccggctctat cacatgtttg tttcatggat    36720
gatctaattt tgtttgttga ggcctcacta tcgcaaattc gtgtaatacg cagggtactt    36780
gagtggtttt gtggagcttc tcggcagaaa gttaatctgg agaaatctgt tatcttcttc    36840
tctgagaatg ttcatcggga cctagtgaac ttaataagca atgagagtgg cattaaagga    36900
actaaggagt tgggaaaata cctgggtatg ccgatcctgc aaaagaggat taataaggag    36960
acttttggag aagtgattga gaaggtttcc tcaaaacttg ctggatggaa gaagagattc    37020
ttgagtttgg cgggaagaat cactctcacc aaatctgttc tctcatctat cccagtccac    37080
acgatgagta ctatagctct gccggcgtca actctaaacc aactggataa gattgctcga    37140
gcttttatct ggggcagtag cgaaggtaac agaaagcagc atttggtttc ttgggataaa    37200
atttgcaaac ctaaaagaga agggggcttt ggtataaggt tggaaaagga atgaatgtt    37260 gctttattag caaaacttag atggagattg ctgaatacat atgatactct atgggtcaag    37320
gtgctgcgga aaaagttccg agtggggagc tatatgaccc aacatggttg atagtccagg    37380
ggacctggtc accgacttgg agaagcctag tggtgggtat cagagaagtt gttattctgg    37440
gaacgtgttg gatcttgggg gacggccgcc gggttcgttt ctggaaagac aattggttgt    37500
tgaacgagcc cctatacgaa tcaagtatgg tgcatatccc agagccgatc ttagaagcaa    37560
gggcccgaga cttatggcag aatggaacca gttggctact tcaagctatt gagccgtata    37620
tgtcagtata gaatcagtta agactagctg aagtagtgat tgatgatgtt actggagtcc    37680
gagatagaat gtcgtgggaa gagagcaaag atggattgtt ttctgttaaa tatgcgtatg    37740
ccttactgac tagagatgaa gtactgagac caaacatgga atccctatac agcctggtgt    37800
ggtgtctagt tgctccagaa cgagtccgag tcttcttatg gttggtaaca catcaggtta    37860
tcatgacgaa catggaacgg aagcgtagac atttgagtga taatgttgtg tgcccgttgt    37920
gtagagatgg agacgaaacc attctccatg ttcttcgaga ctgtcaggca gcagttgaa    37980 tatgggtgaa aatcatgatt ccgagtagac aacagcattt ctttagctta cctctattgc    38040
aatggctcta cgagaatctg ggagggaca agccgggtaa tggagaccaa tggccaacac    38100
tttttgcctt cactgtgtgg tggtgctgga aatggtgatg tggctatgta tttggtgaaa    38160
```

```
caaggacatg tcgagacaga gtgcagtttg ttaaagaaaa gtccagagaa gtgttggaag    38220
caaataagca tttgcgagat cgttcttgtg ctaggggccg ggtggagaag caaatcgcat    38280
ggcagcgacc cgttaatggc tggcttaaat tgaacattga tggagcatct aggggtaacc    38340
ctggactggc cacagcggga ggagctgtgc gagacgaatt tggaatgtgg aaaggaggtt    38400
ttgcgattaa tataggtatt tgtttggctc cgttggcaga actgtggggt gtttactatg    38460
gactgtgcat agcatgagat tgtggtattc ggaggctaga ggtggaagtt gattcagaga    38520
gtgtggcggg ttttcttcag acagggattc atgattctca tcccatatcc ttcctagtac    38580
gtttgtgcta tgacttcatt tcaagagact ggatagtcaa aatttctcac gtgtataggg    38640
aggctaattg tctagcagat ggattagcta actatgcgtt ttctttaccg tttggtttac    38700
attattttga gtcggctcca gagcatgttg cttcagtttt gttagaagat tgtaacggag    38760
tgtccagaac tcgacaaatt tgcctgtagt tgttttgttt ttgatttgaa taaaaagtag    38820
gcctgcagcc taccaaaaaa atacatagtt tctaattaga acaaagacta aaccagacca    38880
agagaaaagt cgacaacatc ttttaactct gtccttccac tatcatcatc atcatcatca    38940
tcctcataac ttattgttgt accagaacac acctttcttc tcaccttgcc tatccggttc    39000
aacatagata cactccttcg cctccctcca catcgcctta accgccggcg ttccatcaaa    39060
ctggtaatac tctccaaagt atcggcttta tcgccttggt cgcttccatc gcgttataat    39120
gcggcatcgt cgagaacaga tgatgcgcca cgtgcgtgtc cgtgatgtta tggaacacct    39180
tgttcaagat tccatagtct ctatccacag tagccaaagc tcctctcaac caatcccact    39240
cggaagaatc atagtgaggc agcgaagggt gcgtgtgctg caagtaagtg atcaagacga    39300
ggaaacagtt gacaattaga agcggaactc cgtagacaca gaccacagag gctactcctc    39360
gcgaagcagc gtaacggtag agaccgtaac atacggagag gacgccagcg tcagagatgt    39420
atatctggag acgctcgcgg tcgttgtaga tgggagcgtt cgggtggaaa tggcaagcga    39480
aaccgtcgct gtaaggtctt cccgagacgt tgaaggctaa gtacaacggc cagccgagct    39540
tgaactggac ggttagcatc accgtgcgtc ctagcgggtt gttgaggtac ttgccgtacc    39600
acttgatgtc ggatttcttc ttggggacga acacttcgtc cctatcgagg atccggtgt    39660 tggaatggtg gcgtcatgga tgtacttcca ggagaagtac gggacgagga ggaaggagtg    39720
gaagacgagg ccggcggcgt cgtccagcca ctggtggtcg ctgaaggcgt ggtggccgca    39780
ctcgtgggct atgacccaga ggcccgttag gacgcagcct tggcaggccc agtagagggg    39840
tcaggcgagg taagggagag ggaagtaggc tgtggagagg tggtagaggg aggagccgag    39900
gaggagatga tgatgtcgaa gaggagaagg agcgtgggat ggagcgtttg aagcagtgag    39960
gtgggattgc tttcttgagg tctccgagag tgaatggtgg tgtctcgcag gggacgcgtt    40020
tgagggtgtt ggttccgggg gagctggagg gaggagagac ttgcattctt ccacctgcgc    40080
ccatgtttgt ttctgtagag aaaaccaaaa aaaagaaaa gaaagtaata agttagttag    40140
taggaagaac ggaaggggta aggttttttt taac                                40174
```

<210> SEQ ID NO 3
<211> LENGTH: 28527
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | |
|---|---|
| acacaagtat ttgaaatatt cgaaatctta gatttatcta gtaaaacatt acatacacaa | 60 |
| ttccaaatta tcttaaagta cttaaaacca aaaaactggt atgaaaataa ttcaaattta | 120 |
| taaaatttat aaaatattca aaatatataa atcatgaaaa ctgaataaaa attgggaaat | 180 |
| tctcctaaat tgatcatttt caagttttgg tcacaaaaat agaccacagg gaggaaaatg | 240 |
| accaaaatgt tttatttaat aggtaaaaag accttaatac actggatata taaaaaataa | 300 |
| aaaaagtaaa aaataaaaaa atcataaaaa aatttatagt tttagattat atgttttcaa | 360 |
| attcgaaatt tttataaaaa attattttttt ttgaattttt tttcgaaatt ttctttttttt | 420 |
| tcaaattttta ttttttgtaat tcgaaaatat tttttgaaac tattttaaaa attttttattt | 480 |
| ttaaattttt aacatttatt ttttattttta taaaattttta aacctcaatc ccaaatctct | 540 |
| atcccttaac tctaaaccct aaagtttgaa ttagttaacc atacgtgtat aaatgtatat | 600 |
| ttacctcttt catgaaacag tttggtcatt ttgatcatta gagtctatat ttgtgacaaa | 660 |
| ataaaattag tgctatcctc tggtatttct cataaaaatt taataaattt atttaattta | 720 |
| atttttttaat attagtttga gtttagaatc ttatccaaaa gccgaattat catattattt | 780 |
| aaatatttcg taaaatcaga tgaatcaact ttttttgtat ggattttggg ttctaaatat | 840 |
| tgtcgcccaa gttgacaaaa aaaaaagtat tgtcgcccaa tccacatgac acaatagtat | 900 |
| tcttttaatc aatgaaccct aaatcccgat tgaaatccta ataattgaat tcaacccaat | 960 |
| agaacaatag taggcctgcg atttcggttt tccgaaaccg aaccgaacca atttttcggt | 1020 |
| tttcggttaa acggtttttt ttggaaaaaa ctccgaagaa aaccgaattt gaattcggtt | 1080 |
| cagtttttgg ttatttccga ttttttgattt tattccaaaa aaatcgaaat caaacatttt | 1140 |
| caataaaaaa atcggatcac acgattaatt tcgggtattt acggttactg ttgggtttcg | 1200 |
| gttacctaag gttgtttcgg ttatgcctct atttttcacct gccaaatcaa ataatcatgc | 1260 |
| aatcaacaac ggaaaaataa tctccaacat caaaaccaat ttataatcga ttcaccaagt | 1320 |
| taaaacattt aaaagagatc actctcaaac atgaaaatcc aaaaaaagat aacaatctga | 1380 |
| atctatattt cttttgcaaa tatcagactt tgaaagatac attcatacat agattcatga | 1440 |
| agttcaaaaa gataagttgt ccaaaagaga gtgataggct aagttggttt tggcttcctc | 1500 |
| gacattccaa cctacaagtt tatgaagtaa gaaaatcagt aaaaacaggg agaagaacaa | 1560 |
| actacaagaa actatacaaa taatagagca acaaattacc tttaatgatc ggattcactc | 1620 |
| ggaatttgca aagactctac ataatgtcaa aggcagttag gaatatatga ctgtggacat | 1680 |
| ataaaaattg aaggaaaata gttaaatgat tacctaatga ctcatgaaaa tcgagttctt | 1740 |
| caaacatctg aaccaagctt gcaaccttct cagcctggat gttgtttcga agccactgtt | 1800 |
| gtaggcagac aagagcttca atcatgtatg gagtcagaca actacgaaac ggatctaaaa | 1860 |
| tcctaccact tgtactgaat gctgactctg aagcaacaaa ggagacttga acagctagca | 1920 |
| catcttctgc tagttcagac aagattggaa acttacaaga gttcttcctc caccaagata | 1980 |
| acacattgta atccaagccg aagttgtttg agcctcgtgg tactggtttt tccatcaagt | 2040 |
| agatgtcaag ttcactgctt ccttcttcat ttgctgcctc tgaaaccatc tttgaataca | 2100 |
| aagaatctct cctctcaaag tcttcatcat cgtcatcaga gatatcaaac atggttccaa | 2160 |
| cttcaccttc cccattatca ataacgttgc tgagactatc accttgagat gaagagccga | 2220 |
| gcttgctcac atactcctca tacaacgatt tcatcagtgc cctgattgat gttctgagat | 2280 |
| gaccactctc cagactatcc ttcccgtaca gcttatcaaa acatatagaa gcaaattgca | 2340 |
| tcttgttcct tggatcgaac acacttgcaa tgatgaccag tgggttcata ttgataagcc | 2400 |

```
catcccagta tttctcaaat tgttcctca tctcctttgc ttgaatctgt agaatcccat    2460
ctttgctatt gctcaatgca atcaagttcc tctcgataat cacaatctca ttctaacaaa    2520
tggtggacgt gactgtcttc gatgctgaga acgctaaagt gcagccaaag aagattttca    2580
gaaacttcac taacctctgc acctcttccc acccttccgt agtaggaggt ccaactctct    2640
tctgtccatt ctcctcttct tccagaaaat aatcattata caacatgtct tcggctttga    2700
gcttctcaaa agcaaccttaa aacttcaaag cggcagacaa catgagatat gtggagttcc    2760
aacgagttat gcagtccaaa gacaagctcc ctctactaac cattcttgtc agcacccttaa    2820 actgaaacga ctgcaatctt gtacccgatg atctaacata cttcacagca tttctaatag    2880
ccattacact atctttgacc tcagataaac catccctaac tatcaagttg agaatatggg    2940
cacagcaacg catatgcaac aatgcaccat ccttaactaa tgcatttggt cctatctccc    3000
tacatgtttc tgtaaacagc cgtagggcct tgtcattcgc cttagcattg tctactgtaa    3060
ccgtaaagac cttctatatt ccccaatcag agagacatag actcaaatgc tcagaaatat    3120
tgtcaccttt atgatccgtg ataggtttga agctgatgat tctcttctgc atattccagt    3180
ttcgatcaat ccaatgagct gtgacgacca tgtagctgta ggatgttgta ggagcaaccc    3240
aaatattggt ggtaagagac actctctgct tctcagaatt aaacaactgc tttaagctag    3300 cttttctccct tagaaacatt ccaaatatgt cttttgttgt tgttctcctg cagtgaactg    3360
tgtacatagg caagacgttg tgacagaacc tcctaaaccc ttcagattcg acaaaagaaa    3420
atggctcctc attcagcact atcatctcat tcactgatct cctaaacaag gcagcatcat    3480
acttaatggt tgtcaatca ccactactat ctccacctag cacctgctgt tttccaaatt    3540
ctttgtagag ctggtacatc ttacatcgag caatgtgatt cttcatcgca ctcgtcccac    3600
tcttcttcga gtcacatcca atcccttggg cacaataatg gcagttgctg atgcttggat    3660
catcttctct ttgaatgaaa tgttgccaaa cttctgctct gtgagcttgc tttttctttg    3720
caacaggagg catatcagtg cttgatctct cagaagcaga tcttttcttt cccccacctt    3780
gatctatata tgcttcaacg tcttctgcga ggaagttacc attatcttca caagctgaca    3840
tctacaaata caatcagaaa ataaacactt aagatcagac aaatatatat acaaaacgaa    3900
ccaaatgaac acaaaatcat acgctatttc agaaaactca ttcgctaaac tctgttcaaa    3960
atcaacagaa atcgttccta accaaagctg ataaattgat aaactataac tgactcatta    4020
agcgacacac acacaaaccc taacaattaa aatcccaatt cgattatcac acaaagtcac    4080
aaaccctaaa ttcgatttac acataaactt agaaagaaga gaagacatat acgaaaacta    4140
accttctacc ttgtgctcca aattatgtaa ggaagaagag aaattggtct ggtctgagaa    4200
tcagacaagg attgatcgga gatcgtattt gagaaagaga gattaagaga ggcgattagg    4260
gtaaaccgtt tacgacttta ggtttgtcgg cacttaggtt aaggatgact taggttaggc    4320
atacatagtt aggttaaaat ttcggttatc cgttcggtta tcacgaaccg aaccgaggaa    4380
aaaaccgata tatttgaaaa cttgtaccga tcgatttctc tgttatttct gaatcataac    4440
cgatatccga cgttttggt tcggttcgga tcggaccgat cggttcggtt cggaatacca    4500
ggcctaaaaa atagtgttat catagttaca actaaaaaga aagttaacag acgccgtaaa    4560
aaaagaaaaa aagaaaaaaa agaaaaaaaa gttaacagac aagtctaaaa catagaaaag    4620
gaaatacgag aaggagacta gacgcttcct ctactaaagc gttttaagag catgtacaac    4680
ggtataaatc aggaaatcct taggaaagat ccttaatgct ttttgattaa agaaatatta    4740
```

```
aaagaggagg gcaaagttaa ggatgatcct taattaagga ttaaaatacc gaagtcctta    4800
tcgtgcttgc acactttgat tggtccgttt tgtgttgtct ctcgttaggg gagagaaaaa    4860
acacgggacc caacctcatt gtatctcgaa cccgaaaaaa aagcagagga gaaggagagg    4920
cgacagagag gcgatttgcg atcccgactt gtgaaggtaa aatccgatct taatcttttt    4980
tttccttctc gagtttatgc atgttgattt catcacgttt tagggttcga ttgaggtgtt    5040
ttataaaatc tagggtttga aatcagattg gggattttta tcgatttagg gttttcgtct    5100
tggtttgatt tttttttgca ttttcgcatc ggttctttgt tgttatcgtc tggattagag    5160
gttctggatt gagttcacaa tcgatttagg gttttggttc ttgatttcaa ttttttttta    5220
ataagaatcg tctcggtttg ttttttttttc attttgctt tggttgtttg ttgttaacgt    5280
ctcgattaga ggtttaatca attgagttca caatcgatta aggttttggt tcttgatttg    5340
aaattttttt ttaataagaa tcgtctcggt tttttttttca ttttttgcttc ggttgtttgt    5400 tgtgatcgtc tcgattagag gtttaatcga ttgagttcac aatcgattaa ggttttggtt    5460
cttgatttga attttttttt ttgcaggttc tgaaatggat gaagaacagc gagatatgaa    5520
agcacacaaa gcatactacc aaagggttga tttcgtatca aattcgctgc aggggattcc    5580
ccaactgtgc ccctgtggat caatcacgaa ggaaattgta gatgaagagg atacacatga    5640
ctacctccct gggaaaacat acttcatctg caaagacttc gaggtatgaa ctttgtttct    5700
atctctttca tttattacgg gttatatgtt tgctatttga caatttttttt cccttttggca    5760 gaatgacggt ctgcattaca ggaaaccatg ggttattggt gtgcaagaag aggttgagag    5820
gctcaaactg aaagttctcc gccatgagaa ccttcttaga gagtgagagg cacttaaggt    5880
gagtttattt tttttcggta tcataaaaat tgtgtttcta ctatctttct aaccaatgtg    5940
ttttggtttg tcttatgtct gttaaggaac atgttaaaat gttggtcaag cgggtttctg    6000
aacttgaggt tagtcttaaa actcaaccgc aatagtttcc tggttagaga acatagctgt    6060
tagaattgaa acgatagga ctgtcggtaa ctgtgtagtt aggaaaaaat tacttcatta    6120
aatagaccct aactgcattt tggatagtaa aacttcatta aattgtttgt agctgttctg    6180
ataagacagt tttctactag gattcaatgt agaatctctt atttaatcct agtagaatac    6240
tagtagagaa tcacacttca tcttaaatgg caagctctag ttttgttaat ctcttagcga    6300
gccaagggtc agttgacctt aactctgcag agactccatt gtttagtacc caaactccta    6360
cccaaactcc gcaagaacca agtgtcaaag agaggagaaa gtggtctgtg aaggaggatt    6420
taatcctggt gggtgtttgg ctcaacacta gcaaagattc aatcgttggt aacgaacaaa    6480
aaggtgttgc cttctggaag aggattgtag agtactacaa ctccagtcct cttctcgttg    6540
ggacagtgcc aagagaacta gggcaatgca agcaaagatg ggctaggatc aatgatttgg    6600
tctgcaagtt tgctggctgc tacgacacga cattgaggga gcacagaagt ggtcaaaatg    6660
acaacgatgt gatgaaggct gccttggata tcttcaacag tgaccagaac atgaagttca    6720
acttggaaca tgcgtggagg gagcttaggc atgatgtgaa atggtgctcc acctatcagg    6780
agaaggacaa ggataagcgc aaaaccgcgg atacttcggt tgcagaacca gaagatagac    6840
caatatgggt taaggctgcg ggtaagagga agaaaacagg aaaagatgaa gaattaacca    6900
agcttgaagg gctggtggac attaaaaagc aaatctcaag gcaaagtttg cttgaaagtt    6960
tgcttgcaaa gcctgagcca ctgtctgata tggaattagc actgaaaaca aaactgttgt    7020
ctgaaatgtt gtcttgatgg tttgttagct ttagattaac ttgttgcttt tattactttg    7080
ctttgtttac tttactgact cgtttggttg ttgctttgtt tcaggatcag taaagacatg    7140
```

```
tgcaagatga agacaaaaga tggtgtccct ccttttttca gtcactggtc atttcgtttg    7200 cttttttctgt atgttggatg tgtcacgggt tgtatgtgtc acgggttgct ttgtttttgt    7260
tgttgctttc tattttgaac ttctatttat aagtcagtgt ctgttgcttt gtaatttgaa    7320
cttcccttgt atcatttcat caatgaaatc tctttcctct tattccaagc tttgaagcaa    7380
acttcccttg tatcatctcc aagcttttct cctcttctac ttccataaat gtcacgaaca    7440
taaaaccaac aagtgaagaa agttaaacca ttctccaatc tttcctcctc ttctacttct    7500
ctaaattcac gacaataaaa ccaacaattc aagacacttc aaccattctc caagctctcc    7560
tctacttcaa gtaattttt tattctaaaa ttagtaattt ttttatattc taaaacgtga    7620
ttagtaattt tttttattct aaaattattc taaaacctga ttagtatttt tttttggca    7680 gtatgggaga tgaagtcgat cgaagattga atgcggcatt ggataaggct gtcgatgaat    7740
attttgaaga cacatacaac aacatcgtca agaaccaaac aaagaaacaa accaaacgtg    7800
catatgtcga acgaaacagc gaagagggcc acagaagtct atggaattac tacttcagtg    7860
aaaatcctac atttctgcct catttattca gacgacgttt ccgcatgaac aaggcggtgt    7920
tcatgcgtat cgtcgatcgc ctctcaaaaa attttccctc ctttcaacaa agaaaagatg    7980
caactgggag gttaggtcta tctccactac aaaagtgtac ggcggctctt cgtatgcttg    8040
cttatggttg tgctgttgac gccgttgacg agtatctccg acttggagaa agcacaacac    8100
tttcatgttt aaccaatttc acagaaggtg taatacagtt atttggagat gagtatctac    8160
gaaggcccac tctagaggat cttcaacgac tactcgatat tggagagata cgcggctttc    8220
ctgggatgat aggaagcatc gactgtatgc attgggagtg gaaaaattgc ccaaccgcct    8280
ggaaaggaca gtacacacgt ggatcaggaa agccaaccat tgtcttggag gctgtagctt    8340
cacaagatct ttggatatga cacgtttttt ttgtcctcca ggtaccttaa acgatattaa    8400
cgtcctcgat cggtctcctg tttttgatga cattttacaa ggtcgagctc caagggtaca    8460
atatgtggtc aacgggcacc agtatgattt ggtgtactac ctcacagacg acatatatcc    8520
aaaatggtaa acatttatcc aatctatctc aaaccctcaa ggtcctgaag cagaattatt    8580
tgctaaagtt caagaagaaa tccgaaaaaa tgtggagcgt gcttttggag ttttgcaaac    8640
tcgatttgca atagtgaaaa acccggctat tttgtgggac aagagacaaa tagggatgat    8700
tatgcgaaca tgtatcatac tgcacaatat gatagtagaa aatgaacgca atggatacac    8760
tcagtatgat acatcagagt ttgaagaagg agagtcgagt agaagttcac aggtggatat    8820
gtcatattat ctgaagcctt caaatctcct tactatgctt gacatacgaa gtcgtgtgcg    8880
tgacccgcac atacatagac aattgaaata tgatttgatt caaaatattt gtaacaagtt    8940
tggtaatgat gaagatgttt aattattgta tgtttacatt ttgttttca ataaatgaaa    9000 attttaaatt tcaaatttta aaattttaaa tttttaagat taaaaaaaaa aaaatcaaag    9060
tactccttgt tggataacac aattggacct atggttatgt taaagtcct taactattga    9120 agaaaaaaga aattataata taactaagga ttccataccc accattggag ttgctataag    9180
aagaagaaaa aaaattgtct agaggcttcg ttttgcgtta cttcatcata taggtaagta    9240
gagaaccaca tcttatcgaa ttcgacctct ctgcttcgct ctcagtactt gaaagctcaa    9300
tcaaccctct cttgtagtag gcaatttcaa atccacggac atggcaaagt cgtcgaagg    9360 cgacaagcga tggatcgtgg aagacagacc cgacggcacc aacgtccaca actggcactg    9420
ggccgaaaca aactgcctcg aatggtctcg caacttcttc aacaaccaat tctccgacgc    9480
```

```
cgtgatcctc tccggcgagt ccaacctctt cctcaaaatc aacaaggtgg agaagctcga   9540
aggcgaggcc tacgtgaacg tgcgcaaggg gaagatcatc cccggctacg agctcaacgt   9600
ctctctatcg tggcaaggcg aggcgaagga ctctgaagga agacgatctc gaaggcggaa   9660
gggttggtgg agatgccgta catctccgat gagaatgccg atgagaatcc agagattagg   9720
tattagacgg tacttatagg tgtaattcgg tttagtatat accggtagtt atggtggttt   9780
aagtttactt tagtatatta cggtacatat aggtttaatc cggtttatta tatacagatg   9840
gttatggtgg ttaagattcc tttagtatat ttcggcatag gtttaatccg gtttagtata   9900
tacaggtagt tatggtggtt aagtttactt tagtatatta cggtacatat aggtttaatc   9960
cggtttagta tgtaccggta gttatggtgg ttaagtttcc tttagtatat tacggtacat  10020
ataggtttaa tccggtttag tatatacagg tggttatggt ggttaagttt cctttagctt  10080
tccacttgta tttaaacttt gatgtgtaca tttgagaaat atatacattt caatgttagg  10140
gtttcggtta aggacgacgg ggagattggg aagacgttga aggaagcgat ggtgacaaaa  10200
gggaaggtgg ttgttcagga aaggttaggg tttacgtgg aggcgatggc tagaggtggg  10260
ccgtgtaggg atgagttgga gtttaagaag gttgcgccaa aggcaaagga gaagtctagt  10320
ggtttaccgg ttgtatctga tgcgaaggag agtaaggtag tgaaagagaa gaaggggaag  10380
acgaaggaag ggtttaagat gattagtatg accgagaagt ttagttgtag agtgaaagat  10440
ttgtatgaga ttctgatgga tgagaatcgt tggaaggggg ttactcaaga gtaatgccaa  10500
gattagtaga gatgtgagtg gtgcgattag tttgtttgat gggtcggtta ctgggatgaa  10560
tttggagttg gaagaaggga agttgattgt tcagaagtgg aggtttggga gcaggcctga  10620
tggtcttgat ttaacggttg gtttactgat tgttttttgtt gtggttcaga acatggtgc  10680 tttgatttgg atctggttgc gattgatgtg ttggctttct ttgctttgac attttaggtg  10740
agaatcactt tcgaggaacc tgaaccagga gtcaccattg ttaatcttac ccagtgacat  10800
tcctgaagaa gataggttag tctcacttac cgaattgatg tatgtagttg ttcgactcat  10860
taagtctttg ctttagtgaa tggattcttt ggaatttggg tgtgctgtat tggttagtag  10920
tatatgatat agaatactca acgcacaggc cgagaaccat tggactatta gagattagag  10980
aggatcttaa atatcttagc cgcccaaacg tctttgacta tctatgttaa tcatttcctc  11040
taattgactc ttagtatttg ctgcgcattt ggagcttatt tgtttgtcca tgcgctcgtt  11100
ttcttctttt ttgttaagca aatatactta agagttattc gctcgatatt ggctcctttg  11160
atgttatctg atgggtttcc attgacatac gggaatgcga ctgtggtgga aaacacggag  11220
agaggatgga gagaccttat attccacatg atccgtgctg ttttttgggtt tggaatatga  11280 tatgtgattc taattttcaa acaaacaaaa ccagcattgc ttttatctat ggttatgatt  11340
tcaattccaa aacaaggggg actagtgaca agcagcgcaa atgtatgatt tctaagtttt  11400
ttgtttatgc attttcatgt aactatttgc tcacttctat attatttag gaatggacaa  11460 ttatccgtaa atttttgattc gatttttgt ttcgatctga aaaatcttga tataatcaag  11520
caaaaaacta aaatattata tccgtaaaaa aatgaaacaa atcacaaata ctatttgtaa  11580
tatatatata tatatatata attatatctt tttctaaatt ttataatatt tttaaagtaa  11640
ctatttagtt attaattttt taaataatag gtaattttt aaaaaatcgt aataaaatat  11700
tattatttat atcagatttt tttattattc tttttttcgga tcaatcggac attcatgtcc  11760
cgtaaaatac agatttttca gatatctgaa aagttacaga ttaaattgaa tctgaaaatc  11820
gattatctgt acggagtaga atggatatct taaaaaaatt atatctgatt tgcgccgacc  11880
```

```
ctactttgt tgagattgtt tagatcaatg gcacacaccg atctatgtta aaactgttgt    11940
tatcagtatt ctatcaatca ttaaattcag atgggacaag aacttccagt gtaataatac    12000
tgcaggtcaa ctacgttgaa ataatctatg ctcaaaagat atagttataa accccacaat    12060
ttgacatgta agagcatatg taagagcatg ttcaacgcag acatggaacc atatgtaact    12120 tttttgttt tagtattatt ttttagttt gaaaaaaaaa ttaatttaaa accgaaccaa    12180
tcgcgggtcg ccacgtgtca gtgaagtccg caaacagtga taaaaacaga gaaagatcga    12240
tctttatttg cttacttttg tgatcggttt taaaagtttt ggtgggactc ttgcattaag    12300
aaacccagtt ataaccatgg ataaacatgg tctaagcata tgagcctgat gccttgctaa    12360
ttattagcat taatttgtta aacctgtagg ttgggcagaa attaagtact ttacaattat    12420
catatttatt gaaactagca ataaattagt taaacatcgt tcaccaaata atttaattt    12480 ctaacatcag atcccaaaat tcaaatttcg aagattataa cctctgtcgg tttcgtgctt    12540
ccgcgccaga ctaaacagcc acatacacaa atactttgtg gagcttgttg gaatagagat    12600
ttggaaaaat gttaaaagat ttcatatatg atagaattta gctgaatcta tttagattta    12660
aggatttaac agagattttg atgagaaatt tggtagattt tggtcatttt ggtctccctc    12720
tataacctag ctaaagggag tgaactatcc ctaatactaa gcattcacgt tacaacttct    12780
cttgatcagg aaatagcaaa tatcaaagtt agaagacgat gtttacagtt tcagattgat    12840
tcttccacaa gctatcgttg gtccgtcagt ttcggcaaga gaagaagcat ttcttcgaga    12900
gaattggtag gaggttcttt cacaagatca catactttaa tcatgtgtaa gaaaaatttg    12960
tgatatttgt ctctgttttg tttcaaccat cgttggagag tgaggaagga agataattgt    13020
tttatttatt ttgaaatacc atctaggtga ttatccgttc acatgcacga aatgaaatgt    13080
atattctaat aattgttgaa tatgaacttt gtccgtataa ccataattat atcattcata    13140
agcctatata tattaatttg aatatctatt aaatgttatt ttactcatat ggttttatt    13200 atcatttata ttttattata acaaaaaatt taaactatag atcataaaat tttcagtgtg    13260
agagttttaa caatttcgt tatttatagt catttttaaa cattcaaaat ataatatata    13320
tatgaaaatc tattttttat tatatggtta atatgattgt ttaatttatt ttaataatat    13380
aacattaaaa aataatgaag atatgtgaat tgttgtcaaa tctttattat taaaatcatt    13440
aattgtcaaa tatatatttt attcacgttt ggtaattccg taaatttat ttaagaaaag    13500 aaagaaaaac aataattgta gattgttaat taatttcatg gttagtccaa gtagaagtat    13560
ataatatatg tttaatggac caacatattt ctttagagac tttaagaaac attttattga    13620
tgacacgtgt caaagttaaa atgttgtaat gcttatcttt taatatatag atgattatct    13680
aataattcca ataactcttg ataaatatta tgagtgaaat ctttgttttc caataaggag    13740
aaatttgaaa gagttttaat aaatgattaa ttcaataata gtggatttga tagaacttt    13800 ataaatacta agaggagatt tgaacaaaaa ctagaatttt cttaaatcat aagcctccta    13860
taagccccct tgttcctat ctcttttgg tcaccattcc attccagaaa atgcttttaa    13920
agataacaat cacaacattc caaatgtaga aaagtcacaa tctcaacatt ctaaacctgc    13980
ttccacctaa caaaaaacaa ttgccttctc gtagtttact ccaaatacaa agggtgtaat    14040
ataacagaaa cactcgacac tttaccgaac acacacattg ccttctcttc taaataagtt    14100
caatcttcct aatctctctc tgtctctctc tgacaacaga gagactcttc acgtgccaaa    14160
caaaaaaaac tgagcaccct cctctcgcca tggccacgga ctccgtcaag cacgtgccta    14220
```

```
cattcggcgg ggcagccatc tccgccgaaa tgaaaagctt cttctccgcc gtgcctactt    14280
ttgtctacgc cttcgtcgta acctttgttg ccttcactgt ttacttagcc ttcgcccctt    14340
ctctcatcac tgtctctaat tcagtttctt cctatatcct ccctaatgtc agtgccgtga    14400
cttcagcgtc cagtaacatc acattacaag caaccacgcc ggaaagtctc actccggctg    14460
ttataaacac aacctttgag cctcccctag gtaatgaaac aaacccactt tctagaaaca    14520
acgcttcacg ggatcatgca agtgtacact tatgtcctaa caacaatact gctcgaaatt    14580
cggacaaaca agcacctctg tccgtgaatt caagtgcttc ttctccgatg agaaaacaaa    14640
gtaggaagtc aggggctaaa cgagagatca agtctctgaa ggactgcaat tttttcgaag    14700
gagaatgggt caaagacgaa tcctacccgc tttacaaacc cggcacgtgt aatctcatcg    14760
acgaacagtt tagctgttta accaacggaa gaccagacgt tgagttttac aaactgaagt    14820
ggaaacctaa agaatgcact ttaccaaggc tgaacggagg caagttgctg agatgattta    14880
gaggaagaag gctcgtgttc gttggagact cgctgaatag aaacatgtgg gagtctttgg    14940
tttgtattct taaaggatca gttaaagatg agagacaagt ctttgaagct catggaaggc    15000
atcagtttcg tcgggaagct gagtacactt tggtcttcaa agtaagtttg caatctgttt    15060
tggtgaggcc tgcgggttcg ggtagtttgg gctgggtcgt tcggttcgac caaatattg    15120 cccaactgaa ccgaacagag tttggttcgg tttaggtagt tcggtttttc aacttctttt    15180
accgaaacta atcaaagttt ttggtttcaa ttatatgttg gttaaaatt tctttaaatt     15240 cagggtaatt ttggttagtt cggtttgtca gttattttga tttgaatttt tgattaattt    15300
agttagcttt tttttgaaaa cccgagctaa ccaattactg aagtgaaaac cgaagtattt    15360
tataaacttg ccgaattgaa ccaaactaac caaaaaaatt tggttcggtt cggttatcaa    15420
cgcaggccta gtttgactac ctagttgtta ttggagactt gatttgtgtg gttgatatga    15480
taggaatata attgcactgt ggagttcttt gcgtctcctt tcttggttcg agaatgggaa    15540
gttacggata agagcgggac gaagaaggaa actttgcgtc tagatatgat gggaagctca    15600
tcaaagcagt acataggagc ggatgtactt tgttcaata ccggagcttg gtggactgat     15660
gacataacat ccaaagggta gagttctgtc agctattttt tgttttttt atatggagga    15720 tttgtctcat tggcttttg gtgtttaaat ggttttgatt agtgaggatt attttcaaga    15780
aagaagcact gttacccga aactcaacgt tgatgaagct tttagaaaag cattgactac     15840
ttggggtcga tgggttgata agtatgtgaa tccaaagaag tctcttgtct tcttccgcgg    15900
attctccctg tcacatttca ggtatgtaca gttctttcat ggtagtctta agattctgtt    15960
taaaaaaata aataaatggg tttggtctgg ttgcatgcag tggtgggcga tggaatgcgg    16020
gaggggcgtg cgatgatgaa acagaaccga tcaagaacga ggcataccta atgccttacc    16080
cttccaagat ggagattctt gaaagagttc taaggggaat gaagacaccg gtcacgtatc    16140
tcaacatcac gaggttaaca gattacagga aggatgctca cccgtctgtt tataggaaac    16200
agaaatttac tgcagaagaa agcaaatcac cgttgttgca ccaagactgc agtcactggt    16260
gcctcccagg tgtacctgat tcttggaacg agattctcta tgccgagatg ctggtaaagc    16320
tcgaccagct ccgtggcaac agacggcgga aacctaaagg gctactatag gaggagttaa    16380
atcagatttt tgttttagat gaaatacact atatatattt tcaatggatg aaaagaaaag    16440
aaacacttag aagcaattat atgttttcaa aggcatagag aaagtaagag gtgagaatca    16500
tattagtgcc ttgctcatca cttttctagt ttttagattg taaatggtta atttttattt    16560
tactcaattt aatagtaaag gtttgtcaaa tcataactga accggaaatg gaagcaatca    16620
```

```
tttggttaaa agaatccagt tgatgacatc gactggcaaa gcataggcag gatcaatttg    16680
gtttgactcc aggatactcc agccctgcac acagttttgg atcattaagt tctctttagc    16740
tttgaagacc tgaacagtat gaactaatga gaagcaaatt ttagtcacct gcaactccaa    16800
agtaagtgtg aaagatatca acagcatcgt caggtccatt ctccatatct tattcaaatt    16860
acacctgaaa ctcaggaaag actctaaaga gatgtgagct ttataaacca atgtttgaga    16920
aaaacctgac agtccaagat gaactttaca agctttgatt tgtcaatcca atgtactcta    16980
ttggtcatga taaagctcga taaaacccac caagagtggc aaacctggtg ataattaagc    17040
aagaacaatc agtgtggtaa gaacaattgg aataatgttt tgtgtttgta gagagaagct    17100
ccgttccctc aaatggacac ctattgttta ttcaactgcg ataaactggt catggcgttg    17160
acaagtacgt ttccttacct ttacagtttt gttttaactt attctatttg atgttatata    17220
tgaacattta tacatgtagt attgtggttg ctgctgcgac tgttcaaaag gagagatcaa    17280
gaagactttg tacagccata ttaaaccaag tgataagaga actagctgtt gcatttaaac    17340
caagtgatat gaaattattc tctccttctc tcttttgttc ttcacattct tcagtttcca    17400
gcaagtaaaa aagctcatat tctcacactc ctattcgtct tctttggctc agcccttaaa    17460
agatcgacaa gaatggagga ggtacatagt ttttttagcac taaaactatt attcttagtt    17520
tgtattgaaa aaaatgttg ctggtgaagg aacaatgtca agtctttcac gtgagagaaa    17580
tcttgcaacc aaaggggggg gcataataaa ctgagactat ataagtttcg tttagttatg    17640
tatttcttga gaataatgt aattctttga ttttttttt tggttaaagg gttttataat    17700
tcacttttgt gtgttgagcg taaataaaag ggaccgcttt atacgattca gtgatgtttt    17760
tagtttaatt tcagcttctt tcttttcatg aaattcaagc tacttcacaa ataaagatgc    17820
atgcatattt gcgtggggaa ctacatagac acccattcaa caagaactct atttataatc    17880
acgtcctaat gaatcggtca tttgaacaaa aaaaaaacca cttcctaatg aatcggtcat    17940
acttttattt ttaaaataga tacaaagaca cccattcaac aagaactcta tttataatca    18000
cgtccttatg aatcggtcat ttgaacaaaa aaaaatcac ttcctaatga atcggtcata    18060 ctttttatttt ggagattaat gtttcataaa taaaaacaga tatcagtgta cgtagtatcc    18120
tcccttatct ttaggattgg attcccacct tcaacattcc acttttttct catttcagtt    18180
tgttatttaa gggtttcaaa acatacaaca attatccaaa actagattgt ttcaaatttc    18240
tcaaaagata tttaattcga agctaattat cacgagaact acaaattaat tccaaaaatg    18300
aagttaattt cattgatgtg catcgccttt gtcatactct tgcatcatt cccggctacg    18360 gctattacgt tcaatacttc gttcaaccct acagattgcc ttaaaaatca tgatacctgc    18420 ggcccctag ctgctgtaaa gggccggcgg tggagacccg aatgttgtaa atttggagc    18480 gggaatgtac ttccagaaac aagacaatgt gcatgttatg tactgaaata ttctcttggc    18540
gatggttatc ttcccttat tttaggtaag tgtaaattag gtggtatcga acaattcaaa    18600
tgttgggagc tgcgaacata taactaacca gaatcgtgaa aaccaaactg gagataataa    18660
gataaagtaa tcaattgggt attctcttat ttctttctaa tcatttttaat aatgttactg    18720 ttcaataagg agagagaaat ggttttgttt ttgttcatgc tcgtgtgaat tacgattcca    18780
tgtttttttg tttccatata ttttcttata tatttagtaa aaaaaaatgaa aaggtataat    18840 ctactctgga ttaagtacca taaataaata tttgttctta attaatctta gtgctttgga    18900
cttctaacac caactttatg cgtaataagc atggggagaa gaagcaaatg aagaattctt    18960
```

```
cttattcacc aagtttgta atataagaat tttcattcta ccaaaaaagc ctgtctctag   19020
tattttccct aacctctttc taaaaaagct tccgaccaaa tagatttgct catgtggcca   19080
gtgggctctt tacagccggt caccataatc ttttgtttt tgttttgct ttgtattata    19140 tttcttctct tcgcagtggc gattatgtta tgattatgtt attcgcggtg ccgataaacc   19200
gtggcaaatt tttgttgtgt attcaatctt aattgaagca aaacttcatg attgtgttct   19260
gttattcttc gattgagatt gatcttttat gtatgcttct cctctttcac agtttttttt   19320
ttttggtaat ccagggttcc cagtttcgcg ggtcattccc tgggtccggt caggcagcgg   19380
gtcggcttca cccggggaggg tatgtcctga gcccgaaggt ccagtacccg cttcgtgaca   19440
tggatgagca gttcggctcc ggctggcgtc gaacccgcaa gcatgacaat tggccctcaa   19500
ggttctaact agtagaactg actcatcccg tctcctcttt cacagttgct ctttaaatcc   19560
cgttcgcttt aatggagttt tcttcttctc tattggattc gcatgtactc ttttcttaag   19620
ggagtcaatt ttcactcttt aaagatgaa gccgccgatg aataggctct gagtgaagtt    19680
tcctggatag aaaggtggag taatctcgat ttgatttgat gaagatttag atgaatcggc   19740
atcctctcgg agatggtccg ataaagatct ttaattttat tgagtaatcc cagagttatt   19800
acccaatgaa gttgatggtg gctctcattg aagcgacagc cggatgaaag atagcagatc   19860
gagaagttca aagcttgttc ggtgaccatg agcagtctct gccgccggcg aggtgtaccg   19920
acttcctctc atcccatgcg ttggtgcgac agatgcatgt cagatccaga agtttaaaga   19980
ctcatgcaaa ggaggatgag ggcgcgtgtc acgtctttcc cgtgatgaag acacatgcac   20040
tattaggcct aataaaattt attttatgtc gagttgtatg atgagtttca agcctgttgc   20100
ttctcttgta atgttcattg ggcctttcta aaggaaagaa acatttgaca aaaaaagaa    20160 aaaaattcta cctttaggcc cttcttatca acaactttga caacagacct caatgggttc   20220
atatcctatg gcctcttggg actcttttt ggatagtcat ccatactgtg aaggagtatt    20280
cggggtgtga taaggaaacc aaatccctt gtaccagtca actgctgaat ggttagcttc     20340
catgtgagct aatcattact catcctcgca agttttaga tgattgcttc ttttgatca      20400 gatggttgag tataatctat tttgaattag cctgttggac tagtttctct tattcaagaa   20460
atccacttgc tcagtgacac aagagcagct aagcgggtcc gtaactttgt tggtaatata   20520
aagggaaaac tcagatcttc tgttttgatc tttgcttgcg tctcagacat gtattgcaca   20580
tctttgtttc ttacaagcgt caaatcgttt atacattttt agtgaaacaa tggtgagcag   20640
gtagccaggt agtacctttc cttgcaactc acgcatgaat ataataaatc aactatttca   20700
ttgttgatga ctggatgatt cacaatcaag ttgctgggta tagtatttac actaattttt   20760
tttcttttgt ttactcgtga gatcatcaaa gatgttttag atatatgaaa agcatatttc   20820
atagtctata ttcatcttcc atgtatgttt ctttgatgat ttaaaaaaa acagaagtac    20880 atcaacactt cttatctttg tgttttctta atctcaagtt ggtaaataga aaaaatgat    20940 gaaaagaaga agaaaaacaa attactacga ggctctcagt aaagctgttc tttctttca    21000 tgccaccatc tccacctgta aacacaaaat tgctagaaac attagtgaac ttttatataa   21060
ttttatataa tataaaaaac atataaaaaa ttattttaaa aatgaatttt aatataattt   21120
tgtgccaaat cttgcattct gagatcatca agtcaatgta gtatacgtac cagtaatagt   21180
cccaacgagg acggactttg gtcatgcggt tatcatcaga tgggtgataa ggatgagcag   21240
cgtggtgagt gttatggaaa gcgcagcaac ctgcagcgta gactgtgatg aggaggacta   21300
ggactagaat gttgacaacc gataactttc tccagtcaag acggatctct tcaagaacac   21360
```

```
cagctttaca agcatcacac tcgtagcata acgtttcaat accattgttc catctatagc   21420
aatcttctcc tccgactatt actccagtct cgtacgtgca cgccgttggt ggcttacaac   21480
atcccgacta caatcaaaga caggttagtt actaaacaaa ctgatgaaga tgctagttca   21540
tatcatagga cacaagggga gtttataacc aaaccggaaa aaaaaacaaa atccgatatg   21600
aacgggccta aaatcagata tttttggatt ccgaaataat atctgaaatt agctaaattt   21660
gttaaacttt tacatattta aggtaattta gatattatcg aaagataagg atgatgatac   21720
ctgaacagaa gtcatatccc tttggaaata atcaagtgta gtccaagatt caatcttaga   21780
acaagtcttt gaagtcaaga tacagcttct aatggagttc caatactctt gatctctaac   21840
tctctctctc agccacggat gataatctcc aagtctatat tctttgtaaa ccctccctgg   21900
tacttccaca ccacctcctt ggctagtcac cacaagacca aagagcgtta gacccatgag   21960
agtcgctatg aggaagatca tgacaactaa gtacaccccac agagcccatg ccacgttgaa   22020
acaagctcct atgaaaccag caagggatac taacagtatg atgaatccta tcacgagaag   22080
cggtgtctgg aggaagttct cgcaagtttt actgcttctt gccttccata gagcagttcc   22140
tttgattggt attgaagcta gtaagctgag aaggtttatg acccaatca ctgtgttgct   22200 gaacctgtac atactaggat tgttatcaag aagaaaccag agaactttgc agtgtcttct   22260
ctcttctcta agcagattct ctcttatcaa ttaggaatct attggactat atttgcgaag   22320
tgattttgcc acatgttctt tctacaatca atttcacaaa acaaatatga cattgctact   22380
gaaattgatg acatgtatta tagcttaata tgacatggac aattgcattt aatgttaatt   22440 tatattttg gtaaatttt taaaatatgg taataactca tatagtacat ttaatgtcaa   22500
tttatatttt agaaattttt tagaaatatga aaataactca taaatcatca ttagaataaa   22560
tatattcaaa tatggcatta taaatttcga aatataatat aattatatat tttaaaatta   22620
tacaatttta ttactaaaat tttcaaaaat gtatacaatt ttcttagaaa attataaaaa   22680
tttaatcgta aaatcattat tttcttatat atctataaat tttataaata ttgtttaatt   22740
ttaattgttg gtgattatgc aacttttaca aatttattta atatatttaa ttaaaataaa   22800
tagatagaaa aatctatcta agattataat ttcaaatata tacaagcata ttcttaaata   22860 taattttat gtttaattaa attaaattta tattaaaatg ttgatacgaa aaaagaaaat   22920
ttacaatatt aaaaaaaaaa tttaaaatat aatttatatt tatctgttaa aaaatatttt   22980 aatttttta cacacctagt tttaattaag ggaaaaggtt aagagttaat tgtttaatga   23040
ttcatgctca tattctcttg tcgtttcttg atttattttt attttttgtca agaggtcgtt   23100 tcttgatttg aatcaactaa acaacaacat taaaattgta tatttttttt caaataaaag   23160
cgtctttttg gacaattgtt tcttgtttaa tagtatttta tacgcttatg tcgtttaaac   23220
cagaccacaa gtagtgcctt gaataaaata tgtacttaaa attaaactat attgtatata   23280
tagtggaaca tatcatatat agaatcagat aaattcacaa tgatcaatga aaggtaagca   23340
aagaataata tagaggacgg atggtgaatt ttcttttaa gatgctttta ctggccccat   23400
aacttagcat attaggttct gtaggtagag cacaatatga tctttgattc ccccattcac   23460 atttttttg gtttaagcaa gaaaatgct aaaacatact taatttaagc caaaatgtca   23520
taacacaaca aaatgagaca ataataacat tactgtaaca aatacatagt ttctaattag   23580
aacaaagact aaaccagacc aagagaaaag tcgacaacaa cttttaactc tgtccttcca   23640
ccatcatcat catcatcatc atcatcatca tcatcatcat catcctcata acttattgtt   23700
```

```
gtaccagaac acacctttct tctcaccttg cctatccggt tcaacataga tacactcctt   23760
cgcctccctc cacatcgcct taaccaccgg cgttccatca aactggtaat actctccaag   23820
tatcggcttt atcgccttgg tcgcttccat cgcgttataa tgcggcatcg tcgagaacag   23880
atgatgcgcc acgtgcgtgt ccgtgatgtt atgaaacacc ttgttcaaga ttccatagtc   23940
tctatccaca gtagccaaag ctcctctcaa ccaatcccac tccgaagaat catagtgagg   24000
cagcgaaggg tgcgtgtgct gcaagtaagt gatcaagacg aggaaacagt tgacaatcat   24060
aagcggaact ccgtagacac agaccatcga ggccactcct cgcgaaccag cgtagcggta   24120
gagaccgtaa catacggaga ggacgccagc gtcagagatg tatatctgga gacgctcgcg   24180
gtcgttgtag atgggagcgt tcgggtggaa atggcaagcg aaaccgtcgc tgtaaggtct   24240
tccagagacg ttgaaggcta agtacaacgg ccagccgagc gtgaactgga cggttagcat   24300
caccgtgcgt cctagcgggt tgttgaggta cttccgtac cacttgatgt cggatttctt   24360 cttgggacg aacacttcat ccctctcgag ggatccggtg ttggaatggt ggcgtcgatg   24420
gctgtacttc caggagaagt aagggacgag gaggaaggag tggaagacga ggcccacggc   24480
gtcgtccagc cactggtggt cgctgaaggc gtggtggccg cattcgtggg cgatgaccca   24540
gaggcccgtt aggacgcagc cttggcaggc ccagtagagg ggccaggcga ggtaagggag   24600
agggtggggg aggagaggga gtaggctgt ggagaggtgg tagagggagg aggagacgag   24660
gatgtcgaag aggaggtagg agaaggagcg agggatggag cgtttgaagc agtgaggtgg   24720
gattgctttc ttgaggtctc cgagagtgaa gggtggtgtc tcgcagggga cgcgtttgag   24780
ggttttggtt tcgggggagc tggagggagg agagacttgc attcttccac ctgcgcccat   24840
gtttgtttct gtagagaaaa ccaaaaaata ataataatgt tatggaggac ggagactttt   24900
tatcctttaa tcaaagttgt atatgcaact cttcatgcat ttgaatctat aaagaacat   24960 ctaaaccctg aagtacctac ctactttaaa tcatccgttt tatttgtaca aagttgatga   25020
gcttataagt caatgaaacg ttcttccatt tattaagaaa taacagtagc aagaaccagt   25080
aggaatcggt caaatctatc aaaggttcaa caataagtga ttttatatt gaaaaaaaac   25140 aaaaatagca ctaaaccaag ttttttgttcc caaactagca ctcaaggtca aaagtcacaa   25200
aaatatcact taatatttta tcaaaagtca caaacttatg gtttagagtt aaagggtggg   25260 gtttaggggtt tagggtttag ggtttagagt ttagggttta gggtttatgg ttcagagttt   25320
agggtttaga gttgagaaat gaggttttgg ggataagatt tcaaattttg aaaaataaaa   25380
aattaaaatt ttcaaaagat aaaataatat tttggtcatt ttaattttttg agtgctattt   25440 ttgtgatata aacttagaaa gttgctattt tggagatttg acctttctta tttcaccaac   25500
ctattgaata aaaagatttc tgaatagata gaaagttgca acatttcata tgctagcca   25560 tagacagtaa tcattattta acggtgagat gaaagaaaca tgacacaaga tttgtcaaat   25620
ggaaacagag gaacagatct ttagttgaat gcaataaaga ctggcagatc tatcgattta   25680
aatgccaaat gctagactgc tagagagatg gacgagatga acacagacca ggaattcata   25740
aaaataagag gaaatgaga agaagaagaa gaagaagggg accctgaaag ctgctgacgt   25800
agggtggggg gagagagatt ttacgttaat aacgatgaac cctacaatga agctcctcca   25860
aagaatctat ctctctctct tctctttctc tctctctctc tcttgtctcg gcacttctct   25920
caatctgttg tggtttgtct ggtcagatgc gagtggcaat aggcagggcc gttttttaaat  25980 tgatgagaga caggaaggca tttgaatgac atctcttatt cttacaactg gcccctcttt   26040
tctcttattt ttacaactgg gcccctctgt tcaaaatatc tgatatttaa ctcaaggaac   26100
```

```
gaccattaat ttagaattta ccaaaatgta aaagttagag tgatgaaaag gtgatattac  26160
tacgacgttc tctctttttc tcgtccacgt tatcttggtt atgtatgtaa tgtaataaaa  26220
aaggtcgtat catgttattg acttaatcac tttggaacgc aatgacacat gcggtacttg  26280
tttgaatcag ttttctcta cgtaagtcaa tcatgtatca tttcttaata tgacattaga  26340
aacaacttga taaagaagaa gaagaagaag atggtagttg atgcctgaaa atggagtatc  26400
gtgtttggct tcttctcact tttgcccatg tgaacacaca agaacttaca gaaatatgta  26460
acagacaaat tgtggtgatg ctcacgtgag gatttctctc tcttttcttt ttcttattac  26520
aatttgttat gtatgtgtaa tcatctttga tacttataat aatcaaattt gttggcagac  26580
gaaaagaaac tagtaattga ttagattgag atctcttgta ttatactaga cttagaagat  26640
gattagagtt tgatttgtct aagcattacc tctaacaaca acacacttttt ctttcaaaat  26700 tttttgttta agatcacaca cccaccatta ggaatgttat atttattcag ctgattgtta  26760
ctaccagtga cggggtttat aacatgtttt tttggtatca aagatgatgt gtctgactca  26820
cgcacaacag acaaatcaga gcaagcatga ctgtaagaaa attaaggcag catacaaatc  26880
ctaaccaccg tctgtcaatc catccaccaa gtctctcatc aattcaaact caatttaaca  26940
gcaaaaaaac tatattctaa gaatcaccac acagagagaa agaaaactta caaagacaat  27000
gaaactaaca ttgtattttc ataaaacaaa agcaaaatag atgaagaaga tgatgatat  27060 tagagatcac caccacacac aaaagaaaag acagcaaact ccacaaacag caacttaggc  27120
aattcctgac ctgcgcagct ctgcttcccc gtgcgcaaag tgacacctat ccccaaacgt  27180
acagttccct ttcgcgaacc tctcacacat cttcgtcttg aagttgctcc ctggatgtgg  27240
tttcccttcc gaaccaaccc caccaccaat cccaccacca ccaccaggtg gtctcctact  27300
agctgcagag ttaagcctcc caatcagctc tctaaccatc acactcgctt cgtttatctg  27360
ctcaaacgtc ccttcaagct caatgttctt caggttcggg tccctctcgt gatcttgaat  27420
cgacagcttc gcccccgtct gacgacatat ctgcttcgaa ctgactcctc ctttaccgat  27480
gatggctccg gccaacgaag cgtccacgct gattttcgca gtggctgagg cgccaaagct  27540
agacacatgg ccaggtccag actctcctcc tctccctgag aatctccctc ctccaccacc  27600
accaggtcct tgcatgtttc tggaagcttg aggcatgggt agtgccatgt tgtcagctg  27660 tgctacagca ttgtatcctc cgggtacata gtgcaagaag tggcagttat ctccaaaagg  27720
acagccagaa gtgctgcaat agagcataat aaagacatca gatagttaaa accatttccc  27780
ttaagatgac acaagagaag ttgagaacaa acgttaaaa tacagaggaa gtatcaattg  27840
ctatacacaa ggaaccaatt agtcaccacc agtaatgtaa taaacttacc tgaacctgac  27900
catatatgac catgttataa acacaacatc actaacacct taccaccaaa cagaaaatta  27960
tagcaatttt ctaaacaagt tatagtttga tttcgaacgt tatgatcacc aattgagttg  28020
aacgtttcta tgattataat ccagatgcac ttatctctta ttgaaacttt tttttaactt  28080
gtttaggatc aatgatttat aagtacctgt aataacaatt aaccacttca ttagcataca  28140
gttttacttg ttaatttgac aattaacaat tttcaatatt aatccagtta agaaaaaaaa  28200
ggattataaa tttataacct gaaaaattta gtgcaaggct tggatttgct gcctaaacca  28260
gttgaatatg attccatctc tgttccaaac atttaagtgt gttttattc tttagttaag  28320 agttttctca agttcaataa tatgacacca ttcatacttt tcatccatat gaacttgag  28380 acttaagaat taaagctgca tgataccttc tgtaaatttt caggacacat caatccgaca  28440
```
aaggaaaaga catgggctgt cttactcaac tgaacatggt ttactaaaag caaaattgga    28500
actaaagtaa cttcgaaaaa aaaacat                                        28527

<210> SEQ ID NO 4
<211> LENGTH: 26095
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
acatcttcct cggaatatac cgagggacac ctttccttgg aatataccga gggacatgtt      60
cctcggaata ttttgaggaa gatgtccctc ggtatatttc gaacgttttt ttataaacgg     120
atcgatcgat ggtatatatgt ccaaaaacgc atcgatcgat gaacttccga ggaaatatcc    180
cgacgaagtt ctccctcggt atattccgag gagattttcg acaaactagt gatcctcgga    240
atttcctcgg aaatttgttt cctcggaatt ccgtcggaaa attccgaggg atttccgagg    300
aaagaagaaa ttccgaggaa ttatttccga ggacttgttt cgtcggtatg tcgtcggaat    360
aacgttattc cgacgaaatt ccgacgattt tttccctcag tatccttgct gttttcttgt    420
agtgcaagaa agctaataga tattagcaag taagaagaca taagtacttg atggccaagc    480
aaaagcctag aattggaata tcacgacatt caagcaaaag gagaagacat attccaacag    540
agccagagcc atgttcaaga tgagacaaac aaatgtgggt ctataagggg acataaagca    600
aaaactcaat aaaaagttag gctagtgcct atatcagctg gacacatggg agaaccaggt    660
ccatgctata taacaatatt atcaaaagca gtgttttcat ataagtagga gtaactttct    720
tccctagtcc actctgtggt ctaaataacc accagaggca ctacacagga tacaaacaaa    780
agttgaaaac acacacagaa tctatgtata gagagtgaca agaaaagga taagaaggta    840 cttccattga agtacgagg tgtctgatat atattgaatg tataactatt gtaattatca    900
gtcaacaaag tcctcacaaa gtcaagcctt tccatagagt cttttttcgg tagactcttg    960
ttagcaatgg atgaatcttc caagtgccct ggcgcaatat gtttcgagat cgcttgccaa   1020
acccaacact ccagctgatc caccatgact ctctccatcc tccactctac aaccctacaa   1080
cccgctcgac accgtctccg acgttctcaa cgccgctttc ttccgttaaa tctcccgttc   1140
ccgtctttac ccaaccaaaa gcaatctcaa gtgctgtcca atctcaaacg gaggcgaata   1200
cttcatgagt atctcaatcg gtactcgacc aacagccttc agatcgtcaa ataacataag   1260
agagttagac gacgcttgga ttaagccgct tctatcatgt tctatgcttg gactcagaca   1320
gagtatatga cgactatttc ttatcaatac ataggccc aaacaattta aactcaacaa   1380
ctgagcccaa taaaaaactt cgaataaatg aaacgatgag tttcataata ctgggacacg   1440
tggcacaatg atgtaaagtg actttcctaa ctggaatcct atgtgtcaca atgaggaggg   1500
agtaaaacac ttatttatat aattagataa ctatgtatat aacacataat cggttgaatc   1560
gaatgttttg gttcagatct cagtacataa ccaaaccgac ccggtgtccg aagtgcttag   1620
agctaaaaac ccattcggta tttgcctggt cccgttaccg aaccggaccc attattttgg   1680
ttcggtttaa ggtgtggact ccggtttaag ttaaaacccc cagccctagg gtaaatgata   1740
aaacatttgg ttgtgtatct cctcggtggt atggaaaacg taatagaatc cgaacttact   1800
agaccggtac gcgattttat tttcgtctta cgtcgtaaga tgtcgaataa ggaaaaagca   1860
acgtcattat acatgttaat ccggttatct ttgatccttt tcgaggacat ttcggtttac   1920

```
cttttttgttt gttcaatacg ccactccggt ttaaaaaaaa aatcgggaag agttaggaaa    1980
aaaggaaaat ctcatctcac cccctcgacg acaagacaac caccacccct agggttaaaa    2040
aggtttattt atctgattat tattctctct actcgttcgt tctcccttta attccgattt    2100
cgatttcgat ttgtcttctc cgatttgctc tctagacact cacagtaggg tttctaattc    2160
ggatctgtac acctttttgcc atggatgctc gtaagagagg acggcctgaa gctggctcat    2220
tcaactccaa tggcggtgga ttcaagaagt cgaagcaagg ttagctcttt cgcctcgtcc    2280
tcttactttt ctatctcaaa agagtgttat agttctgttg tgcttcactt gctctgttaa    2340
aggttgaaac tttagatctt tattgcttga tggatagttt ctctgtgtca attggatttg    2400
gggtagcgat gatttcttca attcgagctt cgtaatattt tttgctcaac aaaagttttt    2460
gtttttagtt atgagattct ctaggattca agtttggatc tttctttcgt gctcacttgc    2520
tgcagtcttt gatctgatgc aaatctaaag tcaattaatt tttcagttta attgtggatg    2580
agcttttgat aagtgatgtt aaagttagtt tgagtgctgt tcgtagcaag cttattgtta    2640
tttgactttc tcttgagttt cattattgct ttagtttaat ccctttttgca ttagctagta    2700 acatcttatc accatgccca aagcttgagt ttgctgtgat tgaattagcc tttttatgtg    2760
ttagttattc atgtgtctag ttgttggtaa ataatcctga aaattctaga gaatatatct    2820
tgcagctttg atttatgtgt gaagttacat atagatgaat ttgatatgta tgattctaaa    2880
agcaaatatt attgaacatc agcaaagtct taactaaaga aaaacactta atctttggaa    2940
cagagatgga atctggttta ggaagcaaat cgaagccatg cacaaaattt ttcaggttat    3000 aatcctttttc ttaactaaat taatatttaa aattgttatt tatagtctga gctttaaatt    3060
gacaagtaaa aatgtatgct aatgaagtag ttagttgtta ttacaggtat gcatcatcct    3120
tcatgctaaa caagttaaaa aaaagtttca gtataacaaa tatgatattc actaggaacg    3180
gaaaaacaaa tctggattat aaatttagaa atattaagct caactggtga ttatagctta    3240
gaaaatcaat ccacaccttt tgtttgagct gtggcagtag ttaagatatg tgttgtaatt    3300
ctctgtttgg tggtaagata ttagttattg tgtttgtatc atcatggtca tatagtgtct    3360
agtaaggttg ttgcattact gaatactggt gaacatgtcc gtcatagaca agcagttagc    3420
atagttgcta tgtgccaatt cttctgtgtt tcaactgttt gttctcttgt gtcttctcaa    3480
tgccaatggt ttttaacttt ctgacgtatt tgttatcctt cttttttgcagc acttctggct    3540 gtccttttgg tgagaactgc catttcttgc actttgttcc cggaggatac aatcctatgg    3600
cacagatgac aaacatggga tcacccatgt ctcaagtttc cagaaacatg caaggtggtg    3660
gtggtggtgg gggccgattt tcggggagag gagagtctgg acctggccac gtctctagct    3720
ttggtgcctc agccacagcc aaaatcagtg tggatgcttc cttggcaggc gcaatcattg    3780
gaaaaggtgg agtctgttcg aaacagatat gtcgtcaaac aggagcaaag ctatcgatcc    3840
aagaccacga gagagatccc aacctgaaga acattgagct tgaaggaaca ttcgagcaga    3900
tcaacgaagc gagcgcaatg gttagagagc tgattgggag gcttaattct gcatctagga    3960
gaccacctgg tggtggtggc ggtggacttg gttcagaagg gaaaccgcat ccagggagca    4020
acttcaaaac gaagatgtgt gagagattct cgaaaggaag ctgtacattt ggtgatagat    4080
gtcactttgc acacggggaa gcagagctac gcaggtcatg aattgcgcct agagttgctg    4140
gtggagttag agagtttgct ggcgaaacaa gtctctttca tttgttgtgg tgattcctaa    4200
tatcatcttc tcctacttgt ttttagttgt ctttgttttt tgagactaca atgtttagtt    4260
ttcattgtca gtgtaagttt tccccatttg gtgttttttt agaatctagt ttgaatttga    4320
```

```
gatgggggga tgcttgatga atgattgaca aaacagtggt taggatttgt atgctgtttc    4380
tacttaatat ttcatgtttt ctctgcttta ttttggtcag taagttcatg tgtttctctg    4440
acatgtgtgt gattatcagc tttgattatt ttccgagtat gtagatgtta tagttctctt    4500
atgatagaca atataactaa aaattcatgt taataatagc cgtcgctgat agtaacagct    4560
gaataaatga aatgaaatca tggtaggtga tgatcttaaa aaaaatgttg aaaataatgt    4620
gcgttgttac aatagcatct cctaaccact tttatatatg tctctataat agcatttaga    4680
tttagaagta aaatcactgc aatcctactt tatttcttcc tctaaaataa aaattgttat    4740
tttcacggaa atacattcct ttataataaa aacatacttt tttattcaca aaataatctt    4800
ttaatttttt attttaacaa ttataaccaa aataaatatt ttttaatgaa aatgtactgt    4860
ttatataaat atataatcat acttttttatt tacataatag tttctataaa aatattcagt    4920
ataaataata tcatagtttt atgaatgtta cactaaattg gattggtttt caacttttcac   4980 aaataaaaag tactatttat aaaattagaa aaaaatatat caagactatt cttttttaga    5040
ggaagaaata gaagaataca ttggaaacaa atctatctct attatatagt tttcctattt    5100
tagaaaaaaa aatagagaaa tacattggag atggtttaag cggtagtaac acaaagaaaa    5160
actctaaata tcttaagagc atctctaatg tacacttctg taatttcttc taaaatagag    5220
atctctatta tagaggtgaa aatgctccaa tgtatgcctc tataatagaa ttcatctatt    5280
ttaaaagaaa atatagagaa aaattacttt ttgcttttat atttaaaggt ggaaataaaa    5340
tatctctata taaataaata aactctatta tacatgtata cattggagca ttttcacttt    5400
tataatagag ttttttttatt ttaagaaaaa atatagagat agaaatagaa atagaaatag    5460
agatgagttg gagattagaa atagagatga gtttgagatg ttgttacgta agaaagagct    5520
agagctttaa taaagtactt aaattaatta ctagtcggca gtcgctgcct acttgtttac    5580
cacctaaatt aatttattat aatatatatt acgaatctcc aaagtacaca tcacacacac    5640
tctactcacg tgatctcaac cacaatgtct gcagatattt tttatagttt tttctcacat    5700
gggagagaag aagccaagca cgatcctcca tcctcaactt tatagcattt ttttcttttc    5760
tttccggcta ccacttgtga gtcgagtcgg caagggcgtt tccttatatt aaagtaaaga    5820
catcaaatac catcgtctta atgctaatta acgtaattga tgagttctat aacataatcc    5880
aaactagtct ttgtgaacat taggattggg taaaccaata tttacatttt aaaaacaaaa    5940
tacaaaaaga aacgtgataa actttataaa agcaattata tgatcactgc atcttttcca    6000
cttttccgta aataaataca taaaagtgcc gtaaatatca gatatttgga gtagaaaagt    6060
aataaagaaa agaaatatga ggagagggaa taatggaggg ggcccacttg taaaaaagaa    6120
agaaaagaga tgtcactcaa tcgtctccca cgggcccccg tcaatttaaa cggcctgcct    6180
tctgcccaat cgcatcttat cagaaccaga cagattcatt accaaagaga tagagaagag    6240
agagagagag agagagagag agagtgagtt tgaggaggag cttcttcgta gggttcatcg    6300
ttattaacgt taaatcttca cccctacgt cagccagctc aaggtcccctt tcttcttcca    6360 tttcttttca ttctacgttg ttttcaatct tatgaaactt tctggtctgt gctttttctta   6420 tcgcttttct attctatcta tcattttttgc atttcagtcg atttaattct agatctgtta    6480
atattaaact atagatctgt tcttgattct ctgttttcat gtgtgaaatc tgatgctgta    6540
ttaatctgat tatattgtct ataccgtgga gaatatcaaa tgttgcattt tcatttgtcc    6600
gaatacaaag tgtttgactt tcaatcgttt ttaattatat atatatatat attttttgat    6660
```

-continued

```
gggttggtgg agttgaaaaa tcaccatagc agtctcacgt cctggtttta gaaatatcct      6720
attcaaaatt atatatttgt ttacttgttt tagatctgga cctgagacat ataagtacct      6780
atttgttgaa tctttgggta aaaacttatg tctctgggta aaatttgctg ggagatttga      6840
ccgattccta ttggctcttg attctgtagt tacgtaatac atgaaaaagt ttcatttggc      6900
ctatgctcac ttcatgctta taaacgtttt cttgcaaatt aattggatta gatgttattt      6960
catagattca gtcattcaga tacaatggag ttgcatgaag aaaataatag aattcgtgac      7020
agtaaaaaag attgtatttt tgtttgtttg tttatgttta aaagtctata tgttgacaat      7080
agagttgctc tcaactgttt catttagctt cttttttgt caagttgctt attcttagag       7140
acattgtgat tatgacttgt cttctttaac gtagtttagt aataaaagac gaaagaaatt      7200
gatatccaca agaaagagat gtgagctgta gcgtatcaaa tctcgttcat ttactagtag      7260
tattctcaac gctatcgttt atttatttt ctttcgttgg tttgccacta tatgccactt       7320
ctctcctctt tgtcccacgt actatccatt tttttgtgg tagtccattt tcttgtaact       7380
tataataacg taactctgaa tcttttgtct gtagattaat ttgttggttt aattaacttt      7440
taagtctttg cttttggctt atgcagaaac atgggtgcag gtggaagaat gcaagtgtct      7500
cctcccctcca agaagtctga aaccgacacc atcaagcgcg taccctgcga gacaccgccc    7560
ttcactgtcg gagaactcaa gaaagcaatc ccaccgcact gtttcaaacg ctcgatccct      7620
cgtctttcct cctacctcat ctgggacatc atcatagcct cctgcttcta ctacgtcgcc     7680
accacttact tccctctcct ccctcaccct ctctcctact tcgcctggcc tctctactgg     7740
gcctgccaag ggtgcgtcct aaccggcgtc tgggtcatag cccacgagtg cggccaccac    7800
gccttcagcg actaccagtg gcttgacgac accgtcggtc tcatcttcca ctccttcctc     7860
ctcgtccctt acttctcctg gaagtacagt catcgacgcc accattccaa cactggctcc    7920
ctcgagagag acgaagtgtt tgtccccaag aagaagtcag acatcaagtg gtacggcaag    7980
tacctcaaca ccccttttggg acgcaccgtg atgttaacgg ttcagttcac tctcggctgg   8040
ccgttgtact tagccttcaa cgtctcggga agaccttacg acggcggctt cgcttgccat    8100
ttccacccca acgctcccat ctacaacgac cgcgagcgtc tccagatata catctccgac    8160
gctggcatcc tcgccgtctg ctacggtctc ttccgttacg ccgccgcgca gggagtggcc    8220
tcgatggtct gcttctacgg agtcccgctt ctgattgtca atggtttcct cgtgttgatc    8280
acttacttgc agcacacgca tccttccctg cctcactacg attcgtccga gtgggattgg   8340
ttgaggggag ctttggctac cgttgacaga gactacggaa tcttgaacaa ggtcttccac    8400
aatattaccg acacgcacgt ggcgcatcat ctgttctcca cgatgccgca ttatcacgcg    8460
atggaagcta ccaaggcgat aaagccgata ctgggagagt attatcagtt cgatgggacg    8520
ccggtggtta aggcgatgtg gagggaggcg aaggagtgta tctatgtgga accggacagg   8580
caaggtgaga agaaaggtgt gttctggtac aacaataagt tatgaggata tgatgatggt    8640
gaaagaacaa agaagatatt gtcacgaacc tttctcttgc tgtctctggt cgtctttgtt     8700
ttaagaagct atgttttcgt ttcaataatc ttaactatcc attttgttgt gttttctgac    8760
attttggcta agtatgtga tgtgggacac gttagtgtct aaaatgtctc tgtgtctgta      8820
ttgttcttct catctgtgac tttcggacaa ctaaactctt gttctcgaac tacctcaatg    8880
tggcattaat gaaagtgtta ttgttgattt taatctgaaa ctgctattat ttagtgaatt    8940
tttacatcag ccaacttgtt tgtttaagac ctaccaatgg tataagaagg tttgtgtact   9000
aatgttcacc atgtccatag tgttaagaca taaccatgat cttctgtcca attaatttgc    9060
```

```
gtcgagttat cgtgttattt ggcaccttta ctatgttttt ttgtaaagaa ctccttacag    9120
aatagctttt tgtaaagaac tacgttttat cttttgtaa gaaccttta acaaaagcca    9180 aattcattat tacctggcac aagaaaaaac tctggtttct tcctctttct ctgttttag    9240 atttgaggag gaacatgaag atgaagaaaa agaaacaaat aaataacaaa tctctttttt    9300
tccattaacg gcagaaacac caaaacagag tgacaacaag aaacaaatgt agtgaggaaa    9360
aaccaaagaa aaaagaatat tctgaaacca actcgttgaa catattcaaa tacgaaacaa    9420
tctttcatcc aacggcgagc gtaatctaga agcatttcct gtggactatc gatggccctg    9480
cctcatcata ctcagccttt gctatccaca tctgcaagac caacattgtg tatcatagtc    9540
agcttaaaaa cgagtaacaa gcagaatcga caatttttacc tgttggaagg tactgagtga    9600
tgctagaata gatcctccaa tccaaacact atacttcctc tccggtggag caaccacctt    9660
aatcttcata ctactcggag ccaaagcagt aatctcctta ctcatcctat cagcaatccc    9720
agggaacatc gtggtaccac cactaagcac aatgttttcca tacaaatctt tcctaatatc    9780
cacatcacat ttcatgatcg aattgtaagt cgtctcgtgg ataccagcag cttccattcc    9840
gaccaaagac ggctggaaaa gaacctcagg acacctgaac ctctcccctc cgatggtgat    9900
cacctgtcca tcaggcaact cgtagctctt gtcgacggat gagctagtgt tcgccgtctc    9960
catctcttgc tcgtagtcaa gtgctatgta agcgagtttc tctttcacgt ctctcacgat   10020
ctcacgctct gctgttgttg tgaacgagta gccacgctcg gttaaaatct tcatgaggta   10080
gtcagtgagg tcacgacctg cgagatcaag acgcagaatg gcgtgtggaa gagcatatcc   10140
ttcgtagatt ggaacagtgt gactcacacc atctccagag tccaatacaa tacctgaaac   10200
aatgattcca catcaataaa agtgttctac cttttttta tcaacaaaag tgttcttcta   10260
ccttataaac tctctagata attataacat aataataata aataatttat aattataata   10320
attaatattt tttagtataa aatcttatga gaataaacaa tataaatatt attatttgta   10380
aatatttaaa ctcttatatt attatttttt tccaaccact acactcttat attacatata   10440
ttgttataat tggtaaacaa ctaggtcgaa gataggcatt gagttaccgt ctcagcgcta   10500
aaatgtctac taaaattata ttacattaca ttgagaaagc taagatgaac atcataaacc   10560
aatggtgttt gaagatctta ccagtagtac gaccactggc gtagagggac aaaacagctt   10620
ggatagcgac atacatagcg ggggtgttga acgtttcaaa cataatctga gtcatttttct   10680 cacgattagc tttaggattg agaggagcct ctgtgagaag aacgggatgc tcttcaggtg   10740
caacacgcag ctcgttgtag aaagtgtgat gccaaatctt ctccatgtca tcccagttgc   10800
tgacaatacc atgctcaata gggtacttga gagtcaagat acctctcttt gactgagcct   10860
cgtcaccaac gtaagcatct ttttgcccca taccaaccat cacaccagtg tgacgtggtc   10920
taccaacaat gcttgggaac acagctcttg gtgcatcgtc tcccgcgaat ccagcctttc   10980
atatagagat ttggaggtaa gaaaattaaa agattttcag acagcattat attaaacaaa   11040
gttgttacgt ttatgattga ttaccttaac cattcctgtt ccattgtcac acactagtgg   11100
ctgaatgtcc tctccatctg ccattttcta atgattctga aactatatat atatatatat   11160
atatatatat atgtcaatga ttcaattgat tacaaaaaca caataacatt cttgaaaaaa   11220
atcaaatgaa catgaactca aacaaagatc tctgattcac tcacattgtt acaaaataca   11280
aaaaatcaat ttaacatttt accaagaaaa aacaaaaaat cgagaaaagt ctggtaattt   11340
attttaacct gatagttttgc gaggagagga aaatagtac gaagagaaca aagagaagag   11400
```

```
cgaacgaaga agagaatata taggaagagt ctttctgaga aaagaagttt tattttattt   11460
taatggtgga agaagatccg agccgttgat atttgtaaga tgtgaccgaa gaaggacccc   11520
acgacgagtc atgttgatgg tggatacagc tgtctcataa agagtaacga cactccattt   11580
aattatttta ttaatctttc gaaatttggt aacgtaactg aaagtatcta ctctgtaaag   11640
tattaaatgg gctggaaaat gttccttaag ggacaaatcc aaccaaaaat tagttattaa   11700
tattaacggg ctgaaaaatg cttgaataaa aagttaatta ttaatattaa cgggctgaaa   11760
aatgcttgaa tgtgatatgt taaccctact aattttaata aagtttacta gattctgcca   11820
gtatatttgt ttttattcag aaactagggc tggcccgccc tacggacgga atgaatattt   11880
aaaaataatt taaattgtta aaataagtat ttaatgaaaa ttttattaa ttaaaaatat    11940 aaatattagt tatatttctt tttcttgggg tggcattaca tataataact tatgtggtgc   12000
attattaata ttgtgtaagt tgtgattgag atgtaagagt gaagttgtga tcgagaagtt   12060
attaatattg tgtaagtgag aagttattaa tattgataat ttatattatt tatttaaaat   12120 cttaggggt tttaacttgt ttttgttttt tccatttttg ttatgttttt aactttaaaa    12180
gtgtttataa attataaact gctaaattcc cattgaaatt ttgtgattga aatttaaata   12240
tttataacaa aatacaaata attacaaaaa catacgtaag atatatttgt attgtatttt   12300
ttaataacat ataccatata aaaccaacta attatttaaa tttagatttt aatagctgca   12360
ttgtattttt taataacaat tatgaattac taaaaacata tactatttga attttattta   12420
atatatagtg atttccaaca gaatatgcga atgattattt ttatctgaaa atgagaaaca   12480
ttttgactaa aatattgtgt ctcgatacat gtgaccacgt caatttaata tatcggatca   12540
ttaagtgtcc aaatattttg taatgttatt ttctcagttt cataagataa tttgaatata   12600
taactttatt tctaatgtta ttggttagtg tattttaata gatttagaaa tccaaattaa   12660
atatattatt attagttata taattgtaaa atatatattg aaatcatgtg ttactggtgg   12720
catgatttaa aaattctaat tcaaaacaag tgttattcaa tcatactatt tattaataga   12780
tttgatttca taatggattt gaatagattt gtatatattt cttt gttaaa atataaattc   12840 tcaaatctga aggtaacccg aaagaaaacc atcggatttg taaatactaa ttttttttt    12900 ttttttgaca gcaagaaatt tacagactca tgttgactct gtaaaccata ttggtaactc   12960
cgcatccatg tgaacgacaa aggacagttg cttgcgtgca ctacgtgcta agctatccgc   13020
ccgaaggttc gccgtccgag gtacatggac gatgtctgag ttgaggaagt ttccttt gag   13080 gagtttgata tcttccaagt agcttccaaa tgctggccat tcttctggtt ccgaaaccat   13140
cttcaccaat tgagaacaat ccgttgcaaa cgtaacctgg acctgtctta aattcctcat   13200
acatttcatt gcccaaatca aagcctctat ctccgaatgc aggggagaga ggcatgccct   13260
tacattcctt gcccccagta gaccctcgaa ccccggtaaa gtactatgcc agccttgccc   13320
tgacattaat tctttatcct tccatgatcc atcaataaaa caccatcgac ctgatgtctc   13380
taaaggagga atggtttgta ccgaaagccc cctccttggt tcatttctca cttgtgcgtc   13440
tgcccagagt gatgattcca cttcagccaa tttaagagta tcccgcggat caatatccaa   13500
attactataa actttgttat ttcgggcttt ccatatatac cataaaatcc atgcaaaatg   13560
gtggtcatcc atttgcggtt gtactctcca aaaagatga tccatattaa caaataaaga   13620
gctgataggg aagatattat gcggtgaagg aatcttggat agtgcccaca cttgacgtgc   13680
aggaggacat tcaaaaaata catgattat tgattcttcc ggatctccac aacgagcaca     13740
acatatatct cctctgatcc ctcgtgcctt taaattttc atcaccgata tacatcctga    13800
```

```
taccatttgc cacaagaaat gccgtatctt tggtggacac cgcactttcc agcagaaagc   13860
tttaagtata tccactgtgg ggccattaaa aacaggaggt tttaacctat cagggtaaat   13920
acgttcaacc tgataacctg attggaccga atattttcca ttattagtaa aatgccatcc   13980
atccttatcc tccatctgaa tcctacttaa agggatactt tcaataattc ttacatcctt   14040
cggatccact agagccctga ttgcctgtat attccatgaa cgagattcct gattgatgag   14100
ggaatccact gtgagttccg gataaaagtt gtgaaatttt ttatttgctg gtctcgggcg   14160
agtggctggg atccaaggat cattccatac agagatagat gatcctgttc ccacccttt     14220 aattagtcct ttacaaacca gagatctagc agaagtaata ctcttccagc catatgacgg   14280
ggagtaagat cggatcggtt ccaggggtga agcattcctg taataccgtc ctttgaaaac   14340
tcttgaaaaa agagtatttg gtttctcaat tagcctccat agttgcttac caagcattgc   14400
tgtattaaaa tccataagat ccttaaagcc caaaccacca ttatctttgg tttcacacac   14460
tttatcccat gatttccaat gcatacctct tgcactaccc cctggactcc accaaaattg   14520
tgctacagca cccgtcagct tcttaactgt agcttttggt aacctataca cagacatcac   14580
atggtttggt aaggccgtaa tcaccgattt aataatcacc tcctttccac cttttgtaaa   14640
aaaacgaaag gtccatccat taaccctttt attcaaccgc tcttgaacaa atccaaacac   14700
ttgtaccttt atgtatattt aaatttgata ctaatttaaa tttgtatatt aaattttaac   14760
tttatgaaca aatccaaata ctaatttaaa tttgtatatt aaattttaac atatgtatat   14820
tttactttga tttgtaaata ttatttggat ttctgaatca actaaaatac ataaactaaa   14880
taataatata ttttctttgg aaattttaaa tgtatggact attaaatcat gcaaatacta   14940
tgaaaaacaa attgatctac aattggtata aaactatttc catgtatgag atacaatatt   15000
gttacgaacc taaaattata gtttattata ctatcaccta ttactgttat ttttgtaaaa   15060
caatatttta attttagata gaacttcaag attactcttt tggtaactgt tgccttaata   15120
ttcccggttc tattacatca gccattgaaa taaaatgtta ctaataaagt aagttactgc   15180
tggtaactaa aattcagaaa ccgagatgac ttaactcttc tattataacg tagatttata   15240
catttataaa acagatctta cataatcaac ttcttcacat cagactcact tacgtgacct   15300
ttttctagga tttccttgtg agattgggtt tgttcagttc ctagactcag tttcttcgcc   15360
tttgacccct ctattcttct tccataaatt ctcctttcca ttttctcaac tcttgttcta   15420
cgcctaactc ttcttcttta gctttctcaa tttcttctgc aagtgttttt tgcttcttcc   15480
tctccaagtt accttgtcta tttctctagc ttcctcgatc tcagaacaac tgttgcaacc   15540
attgtattgg cttcttcttc agcatcatga gcacgctagc taagcagacg gcggctaatg   15600
ccaacctctc tgaaccctta gcagccttag tttattccta agttgcaaat aaaatggtct   15660
ccattgtact tgccccagcc tttgcttgct ctgcttcttc ttgagacttt cgaagctctt   15720
cagtgaatga ttttgcactg tgacagtgaa aattttttct tcatcagcct ttgtgttgct   15780
ttctgcggct gcttcggtag ctccgctatt tatcttatgg cttcttttcc ttggactcag   15840
aaatagctat tctcatgtta tacgaccatc actcgccagc aaaacaaacc tggataaaca   15900
taaggcattg tttactaaaa gcatgagaaa tgaaactaaa aatcatcttt cttggctttt   15960
tttcaaaaaa aaatatggta acaaaaccat aaactccgaa ttatcacaat atgcttaatt   16020
ctatggaggg acatcaagag aatctacgaa tgatatcttt tttgaattct ctgtaatccg   16080
taaccataag ctatcagtat tgtgaaacac taacatctaa caacctaaaa tcagacaaca   16140
```

```
accccacaaa gttgtagttt tatgacaata caatgaagca tttctctccc accaaccatc    16200
aaagagtatg caaacctaaa gccaactgaa gcatacacct taagattaaa acttgggaga    16260
actgtaaagt agacctctgg ttttggggtg actttaacag caacctcctg acccttgagc    16320
tctctttctt gaacttaggc tagcagagca agtgcaacca aaatgacctc tcccgagctc    16380
tcccatctga aactgcatac ctctgtattc agaaaacata ctgacaacac gttagtttgt    16440
agtaactaaa ataagagag cccagcaaat aattattatt ttacagaacc agacaacatc     16500
aaaatcagat atatttttt gttaggtaga acttgttgca gttttgaaaa atagtaataa     16560
gaatttgctc actctttatg atgaagatgt actaagacac cgtccctctg caaactgctg    16620
ttgatgtcca taatacttgt attgtatcca tccttcaccg tgaagtttgt ttatgtttgg    16680
cagaatgacg gttagaatgg aaaagtgttt ggttattcaa actctaaggc agctgtatct    16740 tcttttagg cttgttgagc ttttctcct tctttctaca aaaacatgtc acagactcag      16800
agttagccaa gttcggtatt actaaagcaa gaggcctaaa caacacagaa ctgcagataa    16860
gttaattgac ccaccaactt ccactcatct gcctagcact cctcatcctt tactcgtgtg    16920
tagcttcttc agcctatgcc agacagtatg aagaaatttt tattaggaaa acgttgccac    16980
gtactaacgc tacaatctta aactttcaca gttagggcct gtaactgttc gactgatatt    17040
catgtagttt cccatccttg ctacttggtt acatatgtga attagataga acaatcaaca    17100
aacaaataaa taatcaacaa aaaaataaaa aatctgtaaa acttggttaa atgattcaac    17160
acaacgcata agttcaataa cataatcaag gataaaaaaa gttggtaagt ggattcacac    17220
ggcggagtcg ttacaaatat aatcaaattt ttttaatag attgatagga tgctttagat    17280
tgtagggatg ctaaccttat tatagtggaa cctccactga ttgatttcta gattggatca    17340
gtaggaaaaa gatgaataaa ttgctccaaa ctctagattc gctactgcgc agattgattg    17400
atggatcagt gaatggatag aaactttaga atttcttact gcggagaaga gagagcgtga    17460
aacgataaaa taagaaaagc ggcgtttcaa acccatcata ttatgcttta tatcgatatg    17520
ggctttaata aagtaaaata cacatacgaa gccaagccca acggaatccg atgaaaaaac    17580
aaatgaaacg gagcgtttaa taaggtggac acatgttaac gcgagagagc tcgactttcc    17640
tagctggaat ctgacgtgga gccctcagga gtgaggtgac tctactttat atataaagat    17700
ttagaaattt aattttcatg tttgtctttt tctttgtaat catatttgtg ttttctttg     17760 agatcatatt tgtgtataaa ttttaatcaa aatctattta taaaataata tcaatttaaa    17820
agttgatctg acatacgctc gtattttgt aatcatatat gttcgtatgc tcgttttttt     17880
gtaaccatct gtgtctattc tagattttga tctccacttt taaagtgtat atttatttgc    17940
taaacaaatc aaatttattt gatataaatt tgtattttg atttttaatt acatttaaat    18000
gttacaaata aagcattata attgtgcaga ttgtaatatg ttttctaata gaaataattt    18060
tgatgatgaa atatgtaacc aagttttact aaaatcaaga tattttttgca ttttagtat    18120 tttgaattat taacgtaatt tataatattt gtactcgaaa acctatgtag catctacctg    18180
taagtctagc cccgaatccg attaaatacg acctatatac tcaaaaatat tggtttcttg    18240
tattgatcta aattttgcta aatttaattt ataatataat tttcatatat tttctcgcta    18300 ttttatatt tgatcataat ccacgataaa aatggtaaat taagtgatct gcatataatt     18360
tatctcagat tttggattaa attataaaat ttattttaa aaactccata aaattcggtt     18420
aaacccaaaa aaaattattg acatgtgatc cgataatggt tgacccgaaa aaactagat    18480 aaatctaatg gtcacctata tgaaaatatt atcactacaa gaaaacataa cattaacgac    18540
```

```
ggcgaaattc gtagtaaatt cgtcgtaaaa caggttttac gaggaattag cgaggaaaca    18600
agtttcgtcg ttattcgttc gtcgtaacgc atatttcctc gctaattcgt cgtaaaatag    18660
cgagaaacac aattcgtcgt aaagacgaag aacaatattc gtcgtaaaaa ccatgtaacc    18720
tttccacgta aggaggacgc tagatttcct cgtaaatacc tcgaaagtaa ttcctcgtaa    18780
attacacata aacctttcca cgtaatatac tcgttaagct ttcctcgtag tgttgccgta    18840 aaagtttctcc tcgtaacttc ttcgcaaact ttccacgtaa cgtagtcgtg ctttaggcgg    18900
atttgaatgc taccagcaaa tttatagatt ttaagtgttg ttatacatac gtagacatgt    18960
tctctattta ttaaataaat agtaacaatg tcaattaggt atagaccatg gccatatttt    19020
tagctaacag ataaaaaaaa tatttgagaa aaataatata tatgtatttc tggtcatgag    19080
aaaataatat gtgggttaaa tcatttatca tatagtagaa gggagtgggt tccgccggtt    19140
acaaggaaaa tgatcacctc gtttgtttcg agtaaaaaag ttaggtaact gtcataccctt    19200 ttataatgtg gtggttacat tcggaaatta aaaaaaggtt gcagttatca tataaaaatg    19260
tatgtgttgt tgaaataata gtttgacccct acgtttatca attggttaca ctaatagaat    19320
agatttatca agagtagtat actgtatttt tgttgttacg tttgtttccc gacaaactta    19380
aattttatta atacgaaagc ataatatctg aatacaaagt tggagttaac cacttaggtg    19440
gataaacttt acaattttca aaaatagaat ttgttggaca atgtcgaaca attttatgga    19500
cggcttgatt tccattacgt ttgacaaaaa aaatgttgt tgtagaaaac ttattcctca    19560
agctagtaat ttcttcaaga agattttgaa tggttgaatt cgttagttga gcattgatca    19620
ttttaaccaa gatttctgag tctccttcga aaatcatatt gctatatcct cctatccaaa    19680
cattctgcat tgccacaagt aaagccaact aaactggaat tagagaaccc caaattagct    19740
gaaccccaca tataaggatg accataacag ttccaaataa tccatgcacc tcgaacttgg    19800
ttcgaattta aatcatatgc tgcatcgtaa ttacatttta gaaaaccttg atctcgtcgt    19860
gtccatgacg ataaagcagg aaaagaagaa attgtgcttg tattgcttac attaggagat    19920
gataaacata aatgagatat ccattctcta acgtcagcac aagcattgtc cactgtgaca    19980 tttggggggca gtatttgttt cctaaagaga agaaaattcc tcttttttcca tatacgccat    20040 agcaaccaaa aaggtaacaa ccgttgataa agcgaaagag attgtatgct ttgaatatgc    20100
agcagaaacc gattttattg tccatataat catttgttaa taatggagcc gtaaaaggta    20160
gatatgaaaa tctccaaata catattgaat ctgagcacgt acaaaaacaa tggtcaattg    20220
tctcttctgc caaactacat ctctgacaaa tagaatctaa attcattcct cttgaattta    20280
gtcgtgtagt tgttccaata gcctttgata gaatacgcca aaaaaatggt taagtttggg    20340
cattatattt aatttcctaa tcttatcctt tagaatagga tcaccataag gaattggagg    20400
agcttcaatc aaaaactctg gtgcatgcct agcaaccttta tatccagaag acacaggata    20460
gttttcatct cgtgtatgac tccaaatcaa cttatcttct tttttttgttt ggcttaaata    20520 tatctggctt acgagacgtt gatcctcatc gcataaataa gactgtagcg ccaccgtatt    20580
ccaatgtttg taaggtgata ctgtaatcat attactaaca cgtaaatcac aattaattgt    20640
tgtagaagca ggtcgaggtg gaataacagg taaccaatta tctttggaag ctcgtatatt    20700
tttgccattt cccacaatat agctacatcc tttctttaaa acctcaatac cagcgagcag    20760
agttgcctat ccatatgact gcttgcgaca tgttttttcct tctagaaatt gttttccttt    20820
aagatatcga gctttataaa gtttggaaaa gaggcaattt ggttttgagt agattcacca    20880
```

```
tgcttgtttg gcaagcaaag catcattaaa ttttggtaaa tctttgaatc caaatcttcc   20940 ttctttttc gtatactgta gttttttca agtcatccat ggtaaacctt taagatcatt    21000
tttaccccac cagaatccca ttaagatggc atctatcttt tgtgttgttg caacagggag   21060
tttaaaatgt gacatagaat agatagggt tgatacagca accgatttga tcgtaacttc   21120
tttaccagct gatgaaaaca tacataatta caagactcga gagccaatca agtccaataa   21180
ggcgtttaat gcggtcaacg cttcttgact tgaggctctt atatgggctt acatcagtgg   21240
cccattaagg tgattcttgt gtacttttaa gacttgttga atttacacat ttgaggatca   21300
aacagaaagc taagtatgga gagatccgtt tccttcgatc ttagcggcga taacgaactc   21360
ccgaatgatc ggagcagcga cgtcggatac accgccaatg atcggaggct cgcttactcc   21420
cgctcctttc accactccca ctcccacggc ccgcgaacgc ccgcagctaa gccttttctc   21480
gataggacgg tctccaccat cgatatgccg ccggagatat actctgtcga cggggatgat   21540
gttttcttcg gggaagggaa agcggcggcg attgggaaag cgtcggcttt gcgtatggtt   21600
ttggtggttt tgggggtgct gagaaatgga aatcggcaga tgaagagatt gtttctgctg   21660
atttcgctta acgtggcgta ttctaccaca gagctgttga ttgggttatt gactgggcgt   21720
gtaggtacga tttggttcca gcttttaaca ttttgttaca cttagttttt agttcgtggt   21780
aactttgtgt gtgtgggaga cttttgga tttgttgaag aactaaggtt ttagtagtgg   21840
ctagagatat agatgaaag tgaaatgaat cagctaaagc cccaagattt tgattccaag   21900
tcttaatttg atataatctg aatcatgaaa ctaaaccacc acatggatag tagatcttgt   21960
gcgtgtatcc agggaacttg gctatgcagc tgtaatttct gattatttat taaccttact   22020
ctcttttttt ggctgttta tttgactctt acaggtttgg tttccgatgc attccatttg   22080
acatttggat gtggtctctt gacgttttct ttgtttgcaa tggcgacttc aaggaagaag   22140
cctgatcatg cttactcgta cgggtaagaa atatgtaaaa tttgatccgc ttagtttgtt   22200
ttgtattagg gatataggtt ggaatgcatg ctttgtggta gttaacggtt gatttctcaa   22260
tttgtcaaat tattttttct tttctttctc tctggagcaa ttcctaaagt agattcgcta   22320
atgttttcgt aggatatagt atttatagtt gctgaatatg aaaccttttc tgtttgattt   22380
ttttgctgct aatactgtaa ttgcataatg ctgaattggt tggaacttag aaatcgttgc   22440 ctttttggt taccaggtac aaaagacttg aagttctatc tgctttcact aatgctgtaa   22500
gtatgttctt aaagtttgtt ggatcatgga tgtcatttcc agttttaatt tgaaggtcta   22560
atggctgatg tgccatgcaa taaaactggt ttaatatcgt atagaaatta gtgtcctgag   22620
cttatctcag tgtttgcaca cttttccttta ctgttgttgg tagaatagaa taatcttaca   22680
gctcgttaaa aatgttgatt atcttttcat tttgccttca tcactgtctc attcatttta   22740
tcttttgggt taacacattg atatgttcag tattgacata tgtgtagaca gctgtttctt   22800
atgttcatgt cgttctcctt agctgtggaa gctcttcatg catttgttca agatgaatca   22860
gagcacaagt aagtttcttt ccccaagtga catgcctaag agagctcgta gttatttctc   22920
tagcacttac taagtttaca ctaagttctt tgcattaata tgatgtattg aaattgactt   22980
catgcaggca ttatcttatt gtatcagcgg taacaaatct gctggtgaac ctacttggtg   23040
tttggttctt ccggaattat gctcgtatga atattggtat gtattctctg ttttataatt   23100
atgcttaagt tctggttaga cttgaatgaa ctgatgccaa tactggtgat ttatatcata   23160
tagccctgtt tggcggcttt ggtatatttc gtttgtaaaa actggccacc cctgtcaatg   23220
taaagcaaca aagaagcaaa gggtttctaa ttaagataga ataagtagga ggattagtta   23280
```

-continued

```
aaatagagag acagaagcat gatgactgaa tctggccttc tgtacatatt caaaactcac   23340
atttttcttg aatgtgtttc ttaaattcat aaaatgatgc agtgtacaga aaagcagaag   23400
atatgaacta ccactccgtt tgcttgcatg tcatatcaga ttccatccgc aggtgtgata   23460 ttcttttttgg ctttctttat ctcaagcaga gccgcagata gctagataga aaatgtttc   23520 tctttgcatg gaatttacat acatcccaca tgacatattc gctgcttctg tcttttcagt   23580
gcaggtctga tactggcatc ctggctcctc tctctggggt aatgctcact tcctttaaaa   23640
ggaacaaaat gaataaaaat gtcttattac ctgacctctt acattttcca ttttttctcct  23700 ccggtctttg gattttcag ggttgaaaat gcagaggtcc tatgtttggg attggtatca    23760
gttacagtgt ttatgcttgt tatgccactc ttcaaagcca ctggtggcgt tttgcttcag   23820
atggcacctc caaacattcc ttcttccgca ttaagtaaat gcttgcgtca ggttcgctct   23880
gttccataaa gtgtttcctg aacgtgtaca tatagatcga tcaacctggg tttctcttca   23940
actatcttta tttacagatt acttctcgag aggatgtcat agaggtttta caggcacgtt   24000
tctgggaggt tgtgcccggt cacactgttg gctcactcag aatccaggta ctagcttcct   24060
tactgttttc atatcggtta aaacacgaat ccataataag aattgtactg attttgagct   24120
ggttatttgt gtttaggtga agagcgggat agatgaaagg cctttactgc aatatgtgta   24180
tgatgtatac catgatttgg gtgtacaaga cttgacgctg caaacagact acagctgagc   24240
tgcatctact tctatgtttt caaatactga ggactttgga tgtatactag tagagattat   24300
ggttctataa aagatagca cttggtttca agcttgcgag tttcttgtta catttgttta   24360
gttttatttt ttttaattcc ttttcccatt cgtcttttga accacacaca caaggaccac   24420 aatcttgta aactcttta gtcttttcaag tttgtgcgtc ttttttggctc aaattctcct   24480 ttttaatcct ttttcatgta aaaaaatcat ctgcaaaatg taaaatcaaa acggtagcac   24540
gtaaaattgt cagctgaaac aagatttat tgttcttctt gtttacacag aaaaaactaa     24600
gtggaggaat caaagatcat attgtgctcc tcaacctaca cagcctaata ttctgcaagt   24660 tatgggaca gtacaagcat cttaaaaagc aaattcatcc gtccatgtct atgttattct    24720
ttgcttaccc ccgtttgctt cgttgatcat tgtaaattta acatagtttta ctaaacgata  24780 caaaaatttg taaacataaa aaaaatgata caaaaattta atatagttta ctaattgact   24840
acgtgcacat gacaaaggaa ttttttattaa tggaacttga aaatatattt tggatttaac  24900
tgaactacaa aaacgcaaga tatatatgaa aagtatctca attatttccc gtaacgagtc   24960
aacaatttca aagtatacaa tacccacata tgatacgatc cattatataa tccatgattg   25020
cgttttttgg actctaagct agaaaaatgt atattaataa tatggtatat catatttaat   25080
taaggcacta cttgtgtggt ctgctttatt gttagttaaa cgtataaaat agaataataa   25140
acaagaacca attgtccaaa aagacacttt tatttgaaaa aatactatttt ttaatgttat  25200 tgtttggatt attcaaatca agagacgacc agagaatatg agcatgaatc atcaaaccat   25260
taactcttaa ccttccccct taaaaaaaat tcccagttga taagatagaa tcaaaagcag   25320
aaaaaaggta gagttaaaca atataataac taaaaaacaa agaagattgt aagataaagc   25380
tgatgaagtt cacattacaa gaagagaatc tgcttattac aaaagagaga gatataagag   25440
aatacactgc taagtctctg gtttcttctt gataacactt tcactatgta cagattcagc   25500
aacacagtga ttggagtctt aaacctcctc agcttactag cttcaatacc aatcataggga  25560 gccgctctat ggaaggcaag aagcagcaca acttgcgaaa acttcctcca gactcctcta  25620
```

-continued

```
ctcgttatag gtttcatcat actcttagta tctctcgccg gattcatagg agcctgtttc    25680
aacgtggcat gggctctttg ggtttactta gtggtcatga tcttcctcat cgcgactctt    25740
atgggtctaa ctctgtttgg tctggtggtg acgagccaag gaggcggtgt ggaagtacca    25800
gggagggttt ataaagagta taggcttggt gattatcatc catggttgag agagagagtt    25860
agagatcctc agtattggat ctctataaga agctgtatct tgagttccaa gacttgtgct    25920
aagattgaat cttggactac acttgattat ttccaaagag acatgacttc tgttcaggta    25980
tcatcctcag tgcctagagc catgttaaaa aaaattaacc gtagattttt atatatgtct    26040
aaagttttta ttgatttata agtattaata actccagtta tatatgtttt tttt         26095

<210> SEQ ID NO 5
<211> LENGTH: 1161
<212> TYPE: DNA
<213> ORGANISM: Brassica napus

<400> SEQUENCE: 5
atgggtgcag gtggaagaat gcaagtgtct cctccctcca aaaagtctga aaccgacaac      60
atcaagcgcg taccctgcga gacaccgccc ttcactgtcg agaactcaa gaaagcaatc     120 ccaccgcact gtttcaaacg ctcgatccct cgctcttttct cctacctcat ctgggacatc    180
atcatagcct cctgcttcta ctacgtcgcc accacttact tccctctcct ccctcaccct    240
ctctcctact tcgcctggcc tctctactgg gcctgccagg gctgcgtcct aaccggcgtc    300
tgggtcatag cccacgagtg cggccaccac gccttcagcg actaccagtg gctggacgac    360
accgtcggcc tcatcttcca ctccttcctc ctcgtccctt acttctcctg gaagtacagt    420
catcgacgcc accattccaa cactggctcc ctcgagagag acgaagtgtt tgtccccaag    480
aagaagtcag acatcaagtg gtacggcaag tacctcaaca ccctttggg acgcaccgtg    540 atgttaacgg ttcagttcac tctcggctgg cctttgtact tagccttcaa cgtctcgggg    600
agaccttacg acgcggctt cgcttgccat ttccacccca acgctcccat ctacaacgac    660
cgtgagcgtc tccagatata catctccgac gctggcatcc tcgccgtctg ctacggtctc    720
taccgctacg ctgctgtcca aggagttgcc tcgatggtct gcttctacgg agttcctctt    780
ctgattgtca acgggttctt agttttgatc acttacttgc agcacacgca tccttccctg    840
cctcactatg actcgtctga gtgggattgg ttgaggggag cttttggccac cgttgacaga    900 gactacggaa tcttgaacaa ggtcttccac aatatcacgg acacgcacgt ggcgcatcac    960
ctgttctcga ccatgccgca ttatcacgcg atggaagcta cgaaggcgat aaagccgata   1020
ctgggagagt attatcagtt cgatgggacg ccggtggtta aggcgatgtg gagggaggcg   1080
aaggagtgta tctatgtgga accggacagg caaggtgaga agaaaggtgt gttctggtac   1140
aacaataagt tatcttgcta a                                             1161

<210> SEQ ID NO 6
<211> LENGTH: 1134
<212> TYPE: DNA
<213> ORGANISM: Brassica napus

<400> SEQUENCE: 6
atgggtgcag gtggaagaat gcaagtctct cctccctcca gctccccgg aaccaacacc       60 ctcaaacgcg tccctgcga gacaccacca ttcactctcg agacctcaa gaaagcaatc       120 ccacctcact gcttcaaacg ctccatccca cgctccttct cctcttcgac atcatcatct     180
cctcctcggc tcctccctct accacctctc cacagcctac ttccctctcc cttacctcgc     240
```

```
ctgacccctc tactgggcct gccaaggctg cgtcctaacg ggcctctggg tcatagccca    300
cgagtgcggc caccacgcct tcagcgacca ccagtggctg gacgacgccg ccggcctcgt    360
cttccactcc ttcctcctcg tcccgtactt ctcctggaag tacatccatg acgccaccat    420
tccaacaccg gatccctcga tagggacgaa gtgttcgtcc ccaagaagaa atccgacatc    480
aagtggtacg gcaagtacct caacaacccg ctaggacgca cggtgatgct aaccgtccag    540
ttcaagctcg gctggccgtt gtacttagcc ttcaacgtct cgggaagacc ttacagcgac    600
ggtttcgctt gccatttcca cccgaacgct cccatctaca acgaccgcga cgtctccag    660 atatacatct ctgacgctgg cgtcctctcc gtatgttacg gtctctaccg ttacgctgct    720
tcgcgaggag tagcctctgt ggtctgtgtc tacggagttc cgcttctaat tgtcaactgt    780
ttcctcgtct tgatcactta cttgcagcac acgcacccdtt cgctgcctca ctatgattct    840
tccgagtggg attggttgag aggagctttg gctactgtgg atagagacta tggaatcttg    900
aacaaggtgt tccataacat cacggacacg cacgtggcgc atcatctgtt ctcgacgatg    960
ccgcattata acgcgatgga agcgaccaag gcgataaagc cgatactttg gagagtatta   1020
ccagtttgat ggaacgccgg cggttaaggc gatgtggagg gaggcgaagg agtgtatcta   1080
tgttgaaccg gataggcaag gtgagaagaa aggtgtgttc tggtacaaca ataa         1134
```

<210> SEQ ID NO 7
<211> LENGTH: 1161
<212> TYPE: DNA
<213> ORGANISM: Brassica napus

<400> SEQUENCE: 7

```
atgggcgcag gtggaagaat gcaagtctct cctccctcca gctccccga aaccaaaacc     60 ctcaaacgcg tccctgcga gacaccaccc ttcactctcg gagacctcaa gaaagcaatc    120
ccacctcact gcttcaaacg ctccatccct cgctccttct cctacctcct cttcgacatc    180
ctcgtctcct cctccctcta ccacctctcc acagcctact ccctctcct ccccacccct    240 ctcccttacc tcgcctggcc cctctactgg gcctgccaag gctgcgtcct aacgggcctc    300
tgggtcatcg cccacgaatg cggccaccac gccttcagcg accaccagtg gctggacgac    360
gccgtgggcc tcgtcttcca ctccttcctc ctcgtccctt acttctcctg gaagtacagc    420
catcgacgcc accattccaa caccggatcc ctcgagaggg atgaagtgtt cgtcccaag    480 aagaaatccg acatcaagtg gtacggaaag tacctcaaca cccgctagg acgcacggtg    540 atgctaaccg tccagttcac gctcggctgg ccgttgtact tagccttcaa cgtctctgga    600
agaccttaca gcgacggttt cgcttgccat ttccacccga acgctcccat ctacaacgac    660
cgcgagcgtc tccagatata catctctgac gctggcgtcc tctccgtatg ttacggtctc    720
taccgctacg ctggttcgcg aggagtggcc tcgatggtct gtgtctacgg agttccgctt    780
atgattgtca actgtttcct cgtcttgatc acttacttgc agcacacgca cccttcgctg    840
cctcactatg attcttcgga gtgggattgg ttgagaggag ctttggctac tgtggataga    900
gactatggaa tcttgaacaa ggtgtttcat aacatcacgg acacgcacgt ggcgcatcat    960
ctgttctcga cgatgccgca ttataacgcg atggaagcga ccaaggcgat aaagccgata   1020
cttggagagt attaccagtt tgatggaacg ccggtggtta aggcgatgtg gagggaggcg   1080
aaggagtgta tctatgttga accggatagg caaggtgaga agaaaggtgt gttctggtac   1140
aacaataagt tatgaggatg a                                             1161
```

<210> SEQ ID NO 8
<211> LENGTH: 1137
<212> TYPE: DNA
<213> ORGANISM: Brassica napus

<400> SEQUENCE: 8

| | | | | | |
|---|---|---|---|---|---|
| atgggtgcag | gtggaagaat | gcaagtgtct | cctccctcca | agaagtctga | aaccgacacc | 60 |
| atcaagcgcg | taccctgcga | gacaccgccc | ttcactgtcg | gagaactcaa | gaaagcaatc | 120 |
| ccaccgcact | gtttcaaacg | ctcgatccct | cgctctttct | cctacctcat | ctgggacatc | 180 |
| atcatagcct | cctgcttcta | ctacgtcgcc | accacttact | tccctctcct | ccctcaccct | 240 |
| ctctcctact | tcgcctggcc | tctctactgg | gcctgccaag | ggtgcgtcct | aaccggcgtc | 300 |
| tgggtcatag | cccacgagtg | cggccaccac | gccttcagcg | actaccagtg | gcttgacgac | 360 |
| accgtcggtc | tcatcttcca | ctccttcctc | ctcgtccctt | acttctcctg | gaagtacagt | 420 |
| catcgacgcc | accattccaa | cactggctcc | ctcgagagag | acgaagtgtt | tgtccccaag | 480 |
| aagaagtcag | acatcaagtg | gtacggcaag | tacctcaaca | accctttggg | acgcaccgtg | 540 |
| atgttaacgg | ttcagttcac | tctcggctgg | ccgttgtact | tagccttcaa | cgtctcggga | 600 |
| agaccttacg | acggcggctt | cgcttgccat | tccacccca | acgctcccat | ctacaacgac | 660 |
| cgcgagcgtc | tccagatata | catctccgac | gctggcatcc | tcgccgtctg | ctacggtctc | 720 |
| ttccgttacg | ccgccgcgca | gggagtggcc | tcgatggtct | gcttctacgg | agtcccgctt | 780 |
| ctgattgtca | atggtttcct | cgtgttgatc | acttacttgc | agcacacgca | tccttccctg | 840 |
| cctcactacg | attcgtccga | gtgggattgg | ttgaggggag | ctttggctac | cgttgacaga | 900 |
| gactacggaa | tcttgaacaa | ggtcttccac | aatattaccg | acacgcacgt | ggcgcatcat | 960 |
| ctgttctcca | cgatgccgca | ttatcacgcg | atggaagcta | ccaaggcgat | aaagccgata | 1020 |
| ctgggagagt | attatcagtt | cgatgggacg | ccggtggtta | aggcgatgtg | gagggaggcg | 1080 |
| aaggagtgta | tctatgtgga | accggacagg | caaggtgaga | agaaaggtgt | gttctgg | 1137 |

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgggtgcag gtggaagaat g                                                21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agcgtctcca gatatacatc                                                  20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
atgtatatct ggagacgctc                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tagatacact ccttcgcctc                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tctttctcct acctcatctg                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttcgtagctt ccatcgcgtg                                               20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gacgccacca ttccaacac                                                19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acttgccgta ccacttgatg                                               20

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cccaaagggt tgttgaggta cttgccgt                                              28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgcaccgtga tgttaacggt tcagttca                                              28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
taagggacga ggaggaagga gtggaaga                                              28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttctcctgga agtacagtca tcgacgcc                                              28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtcgctgaag gcgtggtggc cgcactcg                                              28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cagtggctgg acgacaccgt cggcctca                                              28

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 23
gagaagtaag ggacgaggag gaaggagt                                              28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gaagtacagt catcgacgcc accattcc                                              28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tcccaaaggg ttgttgaggt acttgccg                                              28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
accgtgatgt taacggttca gttcactc                                              28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gagaagtaag ggacgaggag gaaggagt                                              28

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tggaagtaca gtcatcgacg ccaccatt                                              28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
```

-continued gtagagaccg tagcagacgg cgaggatg        28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gctacgctgc tgtccaagga gttgcctc        28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gaggccaggc gaagtaggag agagggtg        28

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
actgggcctg ccagggctgc gtcctaac        28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gagaggccag gcgaagtagg agagaggg        28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
actgggcctg ccagggctgc gtcctaac        28

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aggcccagta gagaggccag gcgaagta                                         28

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ccagggctgc gtcctaaccg gcgtctgg                                         28

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tagtcgctga aggcgtggtg gccgcact                                         28

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agtggctgga cgacaccgtc ggcctcat                                         28

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acactctttc cctacacgac gctcttccga tctacgtacc ctctcycyta cytcgcc        57

<210> SEQ ID NO 40
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acactctttc cctacacgac gctcttccga tctcgtaccc ctctcycyta cytcgcc        57

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acactctttc cctacacgac gctcttccga tctgtacgcc ctctcycyta cytcgcc        57

<210> SEQ ID NO 42
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acactctttc cctacacgac gctcttccga tcttacgtgt catagcccac gagtgcggc     59

<210> SEQ ID NO 43
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acactctttc cctacacgac gctcttccga tctctgacgt catagcccac gagtgcggc     59

<210> SEQ ID NO 44
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acactctttc cctacacgac gctcttccga tcttgactgt cggcctcatc ttccactcc     59

<210> SEQ ID NO 45
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acactctttc cctacacgac gctcttccga tctgactggt cggcctcatc ttccactcc     59

<210> SEQ ID NO 46
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acactctttc cctacacgac gctcttccga tctactgagt cggcctcatc ttccactcc     59

<210> SEQ ID NO 47
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acactctttc cctacacgac gctcttccga tctgctagca gacatcaagt ggtacggc      58

<210> SEQ ID NO 48
<211> LENGTH: 58
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 48
acactctttc cctacacgac gctcttccga tctctagcca gacatcaagt ggtacggc        58

<210> SEQ ID NO 49
<211> LENGTH: 59
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 49
acactctttc cctacacgac gctcttccga tcttagctat ctccgacgct ggcatcctc       59

<210> SEQ ID NO 50
<211> LENGTH: 62
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 50
cggtctcggc attcctgctg aaccgctctt ccgatctacg tactggtagt cgctgaaggc      60
gt                                                                    62

<210> SEQ ID NO 51
<211> LENGTH: 62
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 51
cggtctcggc attcctgctg aaccgctctt ccgatctcgt acctggtagt cgctgaaggc      60
gt                                                                    62

<210> SEQ ID NO 52
<211> LENGTH: 62
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 52
cggtctcggc attcctgctg aaccgctctt ccgatctgta cgctggtagt cgctgaaggc      60
gt                                                                    62

<210> SEQ ID NO 53
<211> LENGTH: 63
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 53
cggtctcggc attcctgctg aaccgctctt ccgatcttac gtggacgagg aggaaggagt    60
gga    63

<210> SEQ ID NO 54
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cggtctcggc attcctgctg aaccgctctt ccgatctctg acggacgagg aggaaggagt    60
gga    63

<210> SEQ ID NO 55
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cggtctcggc attcctgctg aaccgctctt ccgatcttga ctagtgttgg aatggtggcg    60
tcg    63

<210> SEQ ID NO 56
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cggtctcggc attcctgctg aaccgctctt ccgatctgac tgagtgttgg aatggtggcg    60
tcg    63

<210> SEQ ID NO 57
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cggtctcggc attcctgctg aaccgctctt ccgatctact gaagtgttgg aatggtggcg    60
tcg    63

<210> SEQ ID NO 58
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cggtctcggc attcctgctg aaccgctctt ccgatctgct agcccgagac gttgaaggct    60

```
<210> SEQ ID NO 59
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cggtctcggc attcctgctg aaccgctctt ccgatctcta gccccgagac gttgaaggct    60
aag                                                                  63

<210> SEQ ID NO 60
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cggtctcggc attcctgctg aaccgctctt ccgatcttag ctgaaggatg cgtgtgctgc    60
aag                                                                  63

<210> SEQ ID NO 61
<211> LENGTH: 13472
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gaaatatcct tcctattcaa agttatatat atttgtttac ttttgtttta gatctggacc    60
tgagacatgt aagtacatat tgttgaatc tttgggtaaa aacttatgtc tctgggtaaa   120
atttgctgag agatttgacc gattcctatt ggctctggat tctgtagtta cctaatacat   180
gaaaaagttt catttggcct atgctcactt catgcttata aactttttct tgcaaattaa   240
ttggattaga tgctccttca tagattcaga tgcaatagat ttgcatgaag aaaataatag   300
gattcatgat agtaaaaaga ttgtattttt gtttgtttgt ttatgtttaa aagtctatat   360
gttgacaata gagttgctat caactgtttc atttaggttt atgttttgt caagttgctt   420 attctaagag acattgtgat tatgacttgt cttctctaac gtagtttagt aataaaagac   480
gaaagaaatt gatatccaca agaaagagat gtaagctgta acgtatcaaa tctcattaat   540
aactagtagt attctcaacg ctatcgttta tttctttctt tggtttgcca ctatatgccg   600
cttctctgct ctttatccca cgtactatcc atttttttg tggtagtcca ttttttgaa   660 actttaataa cgtaacactg aatattaatt tgttggttta attaactttg agtctttgct   720
tttggtttat gcagaaacat gggtgcaggt ggaagaatgc aagtgtctcc tccctccaaa   780
aagtctgaaa ccgacaacat caagcgcgta ccctgcgaga caccgccctt cactgtcgga   840
gaactcaaga aagcaatccc accgcactgt ttcaaacgct cgatccctcg ctctttctcc   900
tacctcatct gggacatcat catagcctcc tgcttctact acgtcgccac cacttacttc   960
cctctcctcc ctcaccctct ctcctacttc gcctggcctc tctactgggc cggtaccgcc  1020
ttttgcagtt tatctctatg cccgggacaa gtggagtcca tgctcaacac cgtgcaggat  1080
```

```
gaggatgacc accgcggtag cgacttcgtg ggcgaggaaa gcctttcgtc caaggtggtc   1140
cctcctcgca atcttgttgg atggtgaata ttataaaagc ctgcccttct cgcgggtgtt   1200
taaacgtcga cctgcaggtc aacggatcag gatattcttg tttaagatgt tgaactctat   1260
ggaggtttgt atgaactgat gatctaggac cggataagtt cccttcttca tagcgaactt   1320
attcaaagaa tgttttgtgt atcattcttg ttacattgtt attaatgaaa aatatattatt  1380 ggtcattgga ctgaacacga gtgttaaata tggaccaggc cccaaataag atccattgat   1440
atatgaatta ataacaaga ataaatcgag tcaccaaacc acttgccttt tttaacgaga    1500
cttgttcacc aacttgatac aaaagtcatt atcctatgca aatcaataat catacaaaaa   1560
tatccaataa cactaaaaaa ttaaagaaa tggataattt cacaatatgt tatacgataa    1620
agaagttact tttccaagaa attcactgat tttataagcc cacttgcatt agataaatgg   1680
caaaaaaaaa caaaaggaa aagaaataaa gcacgaagaa ttctagaaaa tacgaaatac    1740
gcttcaatgc agtgggaccc acggttcaat tattgccaat tttcagctcc accgtatatt   1800
taaaaaataa aacgataatg ctaaaaaaat ataaatcgta acgatcgtta aatctcaacg   1860
gctggatctt atgacgaccg ttagaaattg tggttgtcga cgagtcagta ataaacggcg   1920
tcaaagtggt tgcagccggc acacacgagt cgtgtttatc aactcaaagc acaaatactt   1980
ttcctcaacc taaaataag gcaattagcc aaaaacaact ttgcgtgtaa caacgctca    2040 atacacgtgt cattttatta ttagctattg cttcaccgcc ttagctttct cgtgacctag   2100
tcgtcctcgt cttttcttct tcttcttcta taaaacaata cccaaagagc tcttcttctt   2160
cacaattcag atttcaattt ctcaaaatct taaaaacttt ctctcaattc tctctaccgt   2220
gatcaaggta aatttctgtg ttccttattc tctcaaaatc ttcgattttg ttttcgttcg   2280
atcccaattt cgtatatgtt ctttggttta gattctgtta atcttagatc gaagacgatt   2340
ttctgggttt gatcgttaga tatcatctta attctcgatt agggtttcat agatatcatc   2400
cgatttgttc aaataatttg agttttgtcg aataattact cttcgatttg tgatttctat   2460
ctagatctgg tgttagtttc tagtttgtgc gatcgaattt gtcgattaat ctgagttttt   2520
ctgattaaca gatggcttca tctgagaacg ttatcactga gttcatgagg ttcaaggtga   2580
ggatggaagg tactgttaac ggacatgagt tcgagatcga gggtgagggt gaaggtagac   2640
cttacgaggg acataacacc gttaagctta aggttacaaa gggtggacct cttccttccg   2700
cttgggatat cctttctcct caattccaat acggaagcaa ggtaagtttg tggattcttc   2760
gtccatgtga tctttgagtt tctttagagc ttgtgaggga ttagtaagta acaatgcttg   2820
agttttttgc tgctgggctt cgaaaagttt gtcacttgtt ggtttgatcc acaaggtctt   2880
cttctccata gctactagac atgttttagc ttaagattca agtttatata tgccttgtgg   2940
attaatcatt gcctgattct tccgtgtcat ctctgagttt atttagagct tggaagtggt   3000
gtagtaataa ctaacaatac tcttgataag ttgtagcaat gctcttgatt agtggatgta   3060
atatgatgtt gataagatat atgaggcaca gaaccaaaag tggtgcttcc actagacccg   3120
tttttagcct aaggttcaag tttatacctt gtagatgttt ctgtattgtc tgattcttcc   3180
ctgtgatatt tgaatttctt agagcttggg aagtgatata ggaacaatgc tcttgtgtgt   3240
ttgtctctat gaagattatc gctgtcgtgt ttcatccgag tgtgcgggat ttttttgctgc  3300 tgggtttagc ctttcttcaa aaagttatta cttgttagtt ttattgtttt ggtcttgata   3360
agagatgtta ggacagacat ggtgcttctt gtctatagcc actagaccta ttttagcata   3420
```

```
aggttaacga aattctctct acataccttg tggatttgtt tacattgcct gatctttcct   3480
gtgatcgctg tcatgtttct ttggaatgat tgatgtttat aaatggaaaa atctttgtgc   3540
agaagactcc cgcccatctc tctatgcccg ggacaagtgc caccccacag tggggcagga   3600
tgaggatgac caccatgggg tcgcagcgtg tgcgtgtccg tcgtacgttc tggccggccg   3660
ggccttgggc gcgcgatcag aagcgttgcg ttggcgtgtg tgtgcttctg gtttgcttta   3720
attttaccaa gtttgtttca aggtggatcg cgtggtcaag gcccgtgtgc tttaaagacc   3780
caccggcact ggcagtgagt gttgctgctt gtgtaggctt tggtacgtat gggctttatt   3840
tgcttctgga tgttgtgtac tacttgggtt tgttgaatta ttatgagcag ttgcgtattg   3900
taattcagct gggctacctg acattgtta tgtattaata aatgctttgc tttcttctaa   3960
agatctttaa gtgctgttta acaaccgac aaccactttg cggacttcct ttcaagagaa   4020
ttcaataagg ttaattccta attgaaatcc gaagataaga ttcccacaca cttgtggctg   4080
atatcaaaag gctactgcct atttaaacac atctctggag actgagaaaa tcagacctcc   4140
aagcatgaag aagcctgagc ttactgctac ttctgttgag aagttcctca tcgagaagtt   4200
cgattctgtg tctgatctta tgcagctctc tgagggtgag gaatcaagag ctttctcttt   4260
cgatgttggt ggaagaggat acgttctcag agttaactct tgcgctgacg gattctacaa   4320
ggatagatac gtgtacagac acttcgcttc agctgctctc cctatccctg aagttcttga   4380
tatcggagag ttctctgagt ctcttaccta ctgtatctca agaagggctc agggtgttac   4440
tcttcaagat cttcctgaga ctgagcttcc tgctgttctt caacctgttg ctgaggctat   4500
ggatgctatc gctgctgctg atctttctca aacttctgga ttcggaccttt tcggtcctca   4560
gggaatcgga cagtacacta cttggagaga tttcatctgc gctatcgctg atcctcatgt   4620
ttaccattgg cagaccgtta tggatgatac cgtttctgct tctgttgctc aagctcttga   4680
tgagcttatg ctttgggctg aggattgtcc tgaggttaga catcttgttc acgctgattt   4740
cggatctaac aacgttctca ccgataacgg aagaatcacc gctgttatcg attggtctga   4800
ggctatgttc ggagattctc aatacgaggt ggccaacata ttcttttgga ggccttggct   4860
tgcttgtatg gaacaacaga ctagatactt cgagagaagg catcctgagc ttgctggatc   4920
tcctagactt agagcttaca tgcttaggat cggacttgat cagctttacc agtctctcgt   4980
tgatggaaac ttcgatgatg ctgcttgggc tcagggaaga tgtgatgcta tcgttagatc   5040
tggtgctgga actgttggaa gaactcaaat cgctagaaga tctgctgctg tttggactga   5100
tggatgtgtt gaagttctcg ctgattctgg aaacagaagg ccttctacta gacctagagc   5160
caagaagtga agatcggcgg caatagcttc ttagcgccat cccgggttga tcctatctgt   5220
gttgaaatag ttgcggtggg caaggctctc tttcagaaag acaggcggcc aaaggaaccc   5280
aaggtgaggt gggctatggc tctcagttcc ttgtggaagc gcttggtcta aggtgcagag   5340
gtgttagcgg gatgaagcaa aagtgtccga ttgtaacaag atatgttgat cctacgtaag   5400
gatattaaag tatgtattca tcactaatat aatcagtgta ttccaatatg tactacgatt   5460
tccaatgtct ttattgtcgc cgtatgtaat cggcgtcaca aaataatccc cggtgacttt   5520
cttttaatcc aggatgaaat aatatgttat tataatttt gcgatttggt ccgttatagg   5580
aattgaagtg tgcttgcggt cgccaccact cccatttcat aatttacat gtatttgaaa   5640
aataaaaatt tatggtattc aatttaaaca cgtatacttg taagaatga tatcttgaaa   5700
gaaatatagt ttaaatattt attgataaaa taacaagtca ggtattatag tccaagcaaa   5760
aacataaatt tattgatgca agtttaaatt cagaaatatt tcaataactg attatatcag   5820
```

```
ctggtacatt gccgtagatg aaagactgag tgcgatatta tggtgtaata catagtttaa      5880
acgggcccaa gactcccgcc catctctcta tgcccgggac aagtgccacc ccacagtggg      5940
gcaggatgag gatgaccagt cagttttact tcccttaatt ttctatgtac tttcataatt      6000
acttatgtta ttttcttcat gagttttaat gcaaattact atatggactc tagtgaaaac      6060
gttcagaatc ctataaacat gactactgag acgaacttga gagtagtttt gatcatacac      6120
acgtttcatg tggtacttga gagttactaa tttttgtcat cttcgtataa gtagtaaaag      6180
atactacaag aatagtttag tagaaaatac tagcggtagg tgaagatttg tcgctatgta      6240
ctattattgt ctagtaactt gagtaacaat ttcgtggtct aaatatcaaa taaaaatgga      6300
tgagtggttc accaaatcta ggcatcaaaa ctattaatgt cattgtctag atcttaggtg      6360
acaccacatt tcgaatattt attggtaatt gagatgttaa agtaccaata tttgacttaa      6420
taaactaaaa gattttggct ttatcaaatg tagacattga tgacatatcg ttgtcattat      6480
cttgagtata tacaagtcga tcaattaggt gaaagtttag tgtctcgtgg ttggtaaacg      6540
attaatacag tagtatattt tatccaaaga caaaatccaa atcatttcac cagtatgaat      6600
agtattattt tatcttaaaa gctaaaatct taaaaaccaa ggtagcaccc acgttgagct      6660
agacgatcaa atcgatttct gctttgtcca atttaccaag ctatttaaag ccaaataatt      6720
gaaatatagg taggtcgtta tattaggcta agatttatct caaatgctta actaaaggaa      6780
taacaaggga ttctagttgt gtggttttat aagattggtc caatttcact taagtttgtt      6840
tattgtagaa ttttatatgt gaataaattg aattccaatt gaaagatat tatagtaaaa       6900 gaaaaaatag tgcgaacaaa aaactttaat cccataaaaa gaaaagaaa aatgaaaagt      6960 tcttctaaca tccatatttt gcatcatatc ataaagataa gaaagataca tatcatagac      7020
gtacagataa acaaacatat catcatttgt gaaatacata gtacaataat ttgcttttaa      7080
atagagttta agtcacacac actgacacac acgataaaac gataatgtct gcaaaaacac      7140
tttaatccca ttgcctagag gacagcttct ccactttgtc tttaaggttg gttttgccgt      7200
gttgttttta tctttatata atgatctatt ttttggatta tgaaatgaat tcacacattt      7260
taattattta agaagatcca tatacaggtt tataacagta ctaagtgatg attatttttt      7320 gttttttgcat agtttagttt attgggtaaa cattcattac gtgtctcttt atacgaatca      7380
cccatccaaa atttcaagta gtcttttagt tcatttatta tttcataact atttgactta      7440
ttgatttgac aagaaacaac aaaagtgttg acttattgat agattgtggg atcataaaag      7500
taattaagcg tcaaccacga cccacaacaa caaagcacat gttatacatt aatatctcgt      7560
ttacttaatt acagttttca gaatgccgtt tcatgtcttg tcactggcga tgttattatc      7620
atgttggaca atattcgact gttgtcgttt ttacattttc gtattgacta aaactaaaaa      7680
aacaaaactc tgtttcaggt tgggcctagg atccacattg tacacacatt tgcttaagtc      7740
tatggaggcg caaggtttta agtctgtggt tgctgttata ggccttccaa acgatccatc      7800
tgttaggttg catgaggctt tgggatacac agcccggggt acattgcgcg cagctggata      7860
caagcatggt ggatggcatg atgttggttt ttggcaaagg gattttgagt tgccagctcc      7920
tccaaggcca gttaggccag ttacccagat ctaatatcaa aatctattta gaaatacaca      7980
atattttgtt gcaggcttgc tggagaatcg atctgctatc ataaaaatta caaaaaaatt      8040
ttatttgcct caattatttt aggattggta ttaaggacgc ttaaattatt tgtcgggtca      8100
ctacgcatca ttgtgattga aagatcagc gatacgaaat attcgtagta ctatcgataa      8160
```

```
tttatttgaa aattcataag aaaagcaaac gttacatgaa ttgatgaaac aatacaaaga    8220
cagataaagc cacgcacatt taggatattg gccgagatta ctgaatattg agtaagatca    8280
cggaatttct gacaggagca tgtcttcaat tcagcccaaa tggcagttga aatactcaaa    8340 ccgcccata tgcaggagcg gatcattcat tgtttgtttg gttgcctttg ccaacatggg     8400
agtccaaggt tgtttaaaca tttaaatacc ctgccaagct tgaggtagcc tccaatttga    8460
cggtgccgcc agcgacgccg tctggaactg tccttttga ggaccactcc gtttgtggag     8520
atcatgagag tccatgctca acaccgtgca ctagggacag gattgaagac tcccgcccat    8580
ctcactaggg acaggattgc caccccacag tggggcctag aaagactgga gttgcagagt    8640
ttgtgtcttc tagattaatc ctccaaactt ttgattaacc aaaaaaatta tcaaactaac    8700
atgttctcct ttttcttta gaaattctaa cgaatttatc tttatactga tttgaatata    8760
cttaatttgg tcatttggat gcccttaca acctccttac caaactattg atcacagttt     8820
ctattgctaa aatcaccaac aaaacgcatg tcgccattca taattatggt ttcacaccta    8880
caactaggct aataagtaaa taagtagaca actagactca ggtttgaaaa aaccataaaa    8940
gccatatagc gttttctcat tgaaactgcg aacacgatcg tgtgaatgtt gcagtttcta    9000
gttttgatac aaacaaacaa aaacacaatt taatcttaga ttaaaaagaa aaagagaac     9060 ggagcccact agccactcct tcaaacgtgt cttaccaact ctcttctaga aacaaattag    9120
gcttcacctt cctcttccaa cctctctctc tctctctctc tcttttctc aaaccatctc     9180 tccataaagc cctaatttct tcatcacaag aatcagaaga agaaagatgg acctgcatct    9240
aattttcggt ccaacttgca caggaaagac gacgaccgcg atagctcttg cccagcagac    9300
agggcttcca gtccttttcgc ttgatcgggt ccaatgctgt cctcaactat caaccggaag    9360
cggacgacca acagtggaag aactgaaagg aacgacgcgc tctaccttg atgatcggcc     9420 tctggtggag ggtatcatcg cagccaagca agctcatcat aggctgatcg aggaggtgta    9480
taatcatgag gccaacggcg ggcttattct tgagggagga tccacctcgt tgctcaactg    9540
catggcgcga aacagctatt ggagtgcaga ttttcgttgg catattattc gccacaagtt    9600
acccgaccaa gagaccttca tgaaagcggc caaggccaga gttaagcaga tgttgcaccc    9660
cgctgcaggc cattctatta ttcaagagtt ggtttatctt tggaatgaac ctcggctgag    9720
gcccattctg aaagagatcg atggatatcg atatgccatg ttgtttgcta gccagaacca    9780
gatcacggca gatatgctat tgcagcttga cgcaaatatg gaaggtaagt tgattaatgg    9840
gatcgctcag gagtatttca tccatgcgcg ccaacaggaa cagaaattcc cccaagttaa    9900
cgcagccgct ttcgacggat tcgaaggtca tccgttcgga atgtattaga aatcaccagt    9960
ctctctctac aaatctatct ctctctattt ttctccagaa taatgtgtga gtagttccca   10020
gataagggaa ttagggttct tatagggttt cgctcatgtg ttgagcatat aagaaaccct   10080
tagtatgtat ttgtatttgt aaaatacttc tatcaataaa atttctaatt cctaaaacca   10140
aaatccagtg tttaaacgag tccatgctca acaccgtgca ctagggacag gattgaagac   10200
tcccgcccat ctcactaggg acaggattgc caccccacag tggggcctag aaagactgga   10260
gttgcagaca ttaaggatga ccagttcgta aaggtcctgc ggtgtctatt gcttttcata   10320
ggttaataag tgtttgctag actgtggtga aaggcctatc cgaagtaagg ccggccggat   10380
ccttcatctt tggacaaggg aataaagact ccccacttgc tactaagaac aatacctaag   10440
ttgcccagac atgactgtac ccattcagag acctaccacc cattagggct atgacactaa   10500
cactagcccc tggaggttga ccatgctagg cagtgggggt ctcacctatg acccactcag   10560
```

```
ataggggttt aaaccagtgg gtgggatctc agcctcatat aggtgtttgt ggtgagcttt   10620
ctcctagaca agagaaccct gaagaacagc aagaaccagc taatatgata tgtagacata   10680
gtgggttgct caaattttgt gtttagtcat attagaattg acctcagtga ccactcagaa   10740
agtgcccaag cccatctata gggccaaag tgctattgac tggtgtgtct gtgaattgtt   10800
cctccctaca gagttggtgc tgatatatcc tagcattctt tggaaaacct agctagggac   10860
tgtcaagtgt aagatacctc ctgaattgga gggaacacta gctgccctgt accttctggc   10920
tagtacctta caccctgaat gggttagggg gtctattatt tgctggaaat ataccagttt   10980
cagtagggct gctgccttag gtcccacaag gtgtaacatg tgctcaatag ttgcactacc   11040
acatgcacgt gaacttaatg atgttatagc cacaacacca accttggttt gcagtttgac   11100
atccctctgg aatgggtgta gtcatcttgc tctggatctg cctgaatcat tggggctgta   11160
tgcagcctgg gcttaaagtg aagaatggga tgtcccagaa atattttggg tgagaagaat   11220
cctggagtag atggtgacct gactatccct gtcctatggg cacaatctat catcagatat   11280
tgcattcaaa gggctatcat gggatcaagt cctaagtcaa ctgttgttta cctggcagac   11340
attcatctag gagttctctt ttatgccacc ccacagtgat ccgccttttg cagtttatcc   11400
actagggaca ggattgccac cccacagtgg ggcctctatg cccgggacaa gtgtaaaata   11460
tagagtatag gggttatcat cacagagaag ctattgctgg agggcctctg ttatttcctc   11520
tccatgccac tcccattttt aacctaccaa ctgaaatccc aagggagact ccaccctgta   11580
actagagtcc tcagaggtga gccatcccat attaacaaat gggcattagg gctaggatgc   11640
caagggatac ctgaaatggg aagttgtggg gctgagtcct cctgggaatc agagataata   11700
tgtaaacagt ttgttgagag attgatgaga gctgactttg agaggtggcc atgctccctg   11760
gtcctcaata gggaaggcac tacacaagaa acctgggttt gatcaactgc actgtgtcct   11820
actcacacat tgtgtgcctg gaaaaatgtt acttagtatt tggagggcct ccagaaccccc   11880 cctgggtgca agactgggtg ctagtgactg ggtgaatgag tcttggacac agtggccttg   11940
tctaggttgt gtgaggtggc taggcatcat ggcaatacct cataattgat gagtgaggaa   12000
acaagactaa gtccttgact cctcttatta catgacctgg tggatattat gtttaaactc   12060
tgcaagctgg aatgagtact gggtgcagat cccctgggat tctggctaca aaggtgaatg   12120
atagctagtc tgtttattag tagccaaaaa agtcagtgag gggtgagtgc cctgggatgt   12180
tgttaagttc acattgcaca cttggagacc ctctccatcc agtaacatac cagagaaaac   12240
tgaccaagcc ctcatgggtg tatgggaaca acaaacctcc tggctacttc aagggcacat   12300
aacaccagca aggagcctgt cataaccacc atctcaaaca atagaacttc ctaagtgaag   12360
caatgacttc aaatctactt gaaggcatgg agtataagcc atgttccttt cagagggac   12420 tgtacttctg tagattactt tccctcatta accagatctg gccggccgca tgccagggct   12480
gcgtcctaac cggcgtctgg gtcatagccc acgagtgcgg ccaccacgcc ttcagcgact   12540
accagtggct ggacgacacc gtcggcctca tcttccactc cttcctcctc gtcccttact   12600
tctcctggaa gtacagtcat cgacgccacc attccaacac tggctccctc gagagagacg   12660
aagtgtttgt ccccaagaag aagtcagaca tcaagtggta cggcaagtac ctcaacaacc   12720
ctttgggacg caccgtgatg ttaacggttc agttcactct cggctggcct ttgtacttag   12780
ccttcaacgt ctcggggaga ccttacgacg gcggcttcgc ttgccatttc cacccaacg   12840 ctcccatcta caacgaccgt gagcgtctcc agatatacat ctccgacgct ggcatcctcg   12900
```

| | |
|---|---|
| ccgtctgcta cggtctctac cgctacgctg ctgtccaagg agttgcctcg atggtctgct | 12960 |
| tctacggagt tcctcttctg attgtcaacg ggttcttagt tttgatcact tacttgcagc | 13020 |
| acacgcatcc ttccctgcct cactatgact cgtctgagtg ggattggttg aggggagctt | 13080 |
| tggccaccgt tgacagagac tacggaatct tgaacaaggt cttccacaat atcacggaca | 13140 |
| cgcacgtggc gcatcacctg ttctcgacca tgccgcatta tcacgcgatg gaagctacga | 13200 |
| aggcgataaa gccgatactg ggagagtatt atcagttcga tgggacgccg gtggttaagg | 13260 |
| cgatgtggag ggaggcgaag gagtgtatct atgtggaacc ggacaggcaa ggtgagaaga | 13320 |
| aaggtgtgtt ctggtacaac aataagttat gaagcaaaga agaaactgaa cctttctcat | 13380 |
| ctatgattgt ctttgtttta agaagctatg tttctgtttc ataatctttt aattatccat | 13440 |
| tttgttgtgt tttctgacat tttggctaaa at | 13472 |

<210> SEQ ID NO 62
<211> LENGTH: 5521
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

| | |
|---|---|
| tggcaggata tattgtggtg taaacaaatt gacgcttaga caacttaata acacattgcg | 60 |
| gacgttttta atgtactgaa ttaacgccga attgaattcg agctcggtac cggggacaac | 120 |
| tttgtataga aaagttgggt ggtttaaact atgtattaca ccataatatc gcactcagtc | 180 |
| tttcatctac ggcaatgtac cagctgatat aatcagttat tgaaatattt ctgaatttaa | 240 |
| acttgcatca ataaatttat gttttttgctt ggactataat acctgacttg ttattttatc | 300 |
| aataaatatt taaactatat ttcttttcaag atatcattct ttacaagtat acgtgtttaa | 360 |
| attgaatacc ataaattttt attttttcaaa tacatgtaaa attatgaaat gggagtggtg | 420 |
| gcgaccgcaa gcacacttca attcctataa cggaccaaat cgcaaaaatt ataataacat | 480 |
| attatttcat cctggattaa agaaagtcaa ccggggatta ttttgtgacg ccgattacat | 540 |
| acggcgacaa taaagacatt ggaaatcgta gtacatattg gaatacactg attatattag | 600 |
| tgatgaatac atactttaat atccttacgt aggatcaaca tatcttgtta caatcggaca | 660 |
| cttttgcttc atcccgctaa cacctctgca ccttagacca agcgcttcca caaggaactg | 720 |
| agagccatag cccacctcac cttgggttcc tttggccgcc tgtctttctg aaagagagcc | 780 |
| ttgcccaccg caactatttc aacacagata ggatcaaccc gggatggcgc taagaagcta | 840 |
| ttgccgccga tcttcacttc ttggctctag gtctagtaga aggccttctg tttccagaat | 900 |
| cagcgagaac ttcaacacat ccatcagtcc aaacagcagc agatcttcta gcgatttgag | 960 |
| ttcttccaac agttccagca ccagatctaa cgatagcatc acatcttccc tgagcccaag | 1020 |
| cagcatcatc gaagtttcca tcaacgagag actggtaaag ctgatcaagt ccgatcctaa | 1080 |
| gcatgtaagc tctaagtcta ggagatccag caagctcagg atgccttctc tcgaagtatc | 1140 |
| tagtctgttg ttccatacaa gcaagccaag gcctccaaaa gaatatgttg gccacctcgt | 1200 |
| attgagaatc tccgaacata gcctcagacc aatcgataac agcggtgatt cttccgttat | 1260 |
| cggtgagaac gttgttagat ccgaaatcag cgtgaacaag atgtctaacc tcaggacaat | 1320 |
| cctcagccca agcataagc tcatcaagag cttgagcaac agaagcagaa acggtatcat | 1380 |
| ccataacggt ctgccaatgg taaacatgag gatcagcgat agcgcagatg aaatctctcc | 1440 |

-continued

| | |
|---|---|
| aagtagtgta ctgtccgatt ccctgaggac cgaaaggtcc gaatccagaa gtttgagaaa | 1500 |
| gatcagcagc agcgatagca tccatagcct cagcaacagg ttgaagaaca gcaggaagct | 1560 |
| cagtctcagg aagatcttga agagtaacac cctgagccct tcttgagata cagtaggtaa | 1620 |
| gagactcaga gaactctccg atatcaagaa cttcagggat agggagagca gctgaagcga | 1680 |
| agtgtctgta cacgtatcta tccttgtaga atccgtcagc gcaagagtta actctgagaa | 1740 |
| cgtatcctct tccaccaaca tcgaaagaga agctcttga ttcctcaccc tcagagagct | 1800 |
| gcataagatc agacacagaa tcgaacttct cgatgaggaa cttctcaaca gaagtagcag | 1860 |
| taagctcagg cttcttcatg cttggaggtc tgattttctc agtctccaga gatgtgttta | 1920 |
| aataggcagt agccttttga tatcagccac aagtgtgtgg gaatcttatc ttcggatttc | 1980 |
| aattaggaat taaccttatt gaattctctt gaaaggaagt ccgcaaagtg gttgtcggtt | 2040 |
| gtttaaacca acttttgtat acaaagttgt cccctctaga gtcgacctgc aggcatgcaa | 2100 |
| gcttagcttg agcttggatc agattgtcgt ttcccgcctt cagtttatca caagtttgta | 2160 |
| caaaaagca ggctgtcgac ctgcaggtca acgatcagg atattcttgt ttaagatgtt | 2220 |
| gaactctatg gaggtttgta tgaactgatg atctaggacc ggataagttc ccttcttcat | 2280 |
| agcgaactta ttcaaagaat gttttgtgta tcattcttgt tacattgtta ttaatgaaaa | 2340 |
| aatattattg gtcattggac tgaacacgag tgttaaatat ggaccaggcc ccaaataaga | 2400 |
| tccattgata tatgaattaa ataacaagaa taaatcgagt caccaaacca cttgcctttt | 2460 |
| ttaacgagac ttgttcacca acttgataca aaagtcatta tcctatgcaa atcaataatc | 2520 |
| atacaaaaat atccaataac actaaaaaat taaagaaat ggataatttc acaatatgtt | 2580 |
| atacgataaa gaagttactt ttccaagaaa ttcactgatt ttataagccc acttgcatta | 2640 |
| gataaatggc aaaaaaaac aaaaaggaaa agaaataaag cacgaagaat tctagaaaat | 2700 |
| acgaaatacg cttcaatgca gtgggaccca cggttcaatt attgccaatt ttcagctcca | 2760 |
| ccgtatattt aaaaaataaa acgataatgc taaaaaaata taaatcgtaa cgatcgttaa | 2820 |
| atctcaacgg ctggatctta tgacgaccgt tagaaattgt ggttgtcgac gagtcagtaa | 2880 |
| taaacggcgt caaagtggtt gcagccggca cacgagtc gtgtttatca actcaaagca | 2940 |
| caaatacttt tcctcaacct aaaaataagg caattagcca aaaacaactt tgcgtgtaaa | 3000 |
| caacgctcaa tacacgtgtc atttttattat tagctattgc ttcaccgcct tagctttctc | 3060 |
| gtgacctagt cgtcctcgtc ttttcttctt cttcttctat aaaacaatac ccaaagagct | 3120 |
| cttcttcttc acaattcaga tttcaatttc tcaaatctt aaaaactttc tctcaattct | 3180 |
| ctctaccgtg atcaaggtaa atttctgtgt tccttattct ctcaaaatct tcgattttgt | 3240 |
| tttcgttcga tcccaatttc gtatatgttc tttggtttag attctgttaa tcttagatcg | 3300 |
| aagacgattt tctgggtttg atcgttagat atcatcttaa ttctcgatta gggtttcata | 3360 |
| gatatcatcc gatttgttca aataatttga gttttgtcga ataattactc ttcgatttgt | 3420 |
| gatttctatc tagatctggt gttagttct agttgtgcg atcgaatttg tcgattaatc | 3480 |
| tgagttttc tgattaacag atggcttcat ctgagaacgt tatcactgag ttcatgaggt | 3540 |
| tcaaggtgag gatggaaggt actgttaacg gacatgagtt cgagatcgag ggtgagggtg | 3600 |
| aaggtagacc ttacgaggga cataacaccg ttaagcttaa ggttacaaag ggtggacctc | 3660 |
| ttccttttcgc ttgggatatc ctttctcctc aattccaata cggaagcaag gtaagtttgt | 3720 |
| ggattcttcg tccatgtgat ctttgagttt ctttagagct tgtgagggat tagtaagtaa | 3780 |
| caatgcttga gttttttgct gctgggcttc gaaaagtttg tcacttgttg gtttgatcca | 3840 |

```
caaggtcttc ttctccatag ctactagaca tgttttagct taagattcaa gtttatatat    3900
gccttgtgga ttaatcattg cctgattctt ccgtgtcatc tctgagttta tttagagctt    3960
ggaagtggtg tagtaataac taacaatact cttgataagt tgtagcaatg ctcttgatta    4020
gtggatgtaa tatgatgttg ataagatata tgaggcacag aaccaaaagt ggtgcttcca    4080
ctagacccgt ttttagccta aggttcaagt ttataccttg tagatgtttc tgtattgtct    4140
gattcttccc tgtgatattt gaatttctta gagctttgga agtgatatag gaacaatgct    4200
cttgtgtgtt tgtctctatg aagattatcg ctgtcgtgtt tcatccgagt gtgcgggatt    4260
ttttgctgct gggtttagcc tttcttcaaa aagttattac ttgttagttt tattgttttg    4320
gtcttgataa gagatgttag gacagacatg gtgcttcttg tctatagcca ctagacctat    4380
tttagcataa ggttaacgaa attctctcta catccttgt ggatttgttt acattgcctg    4440
atctttcctg tgatcgctgt catgtttctt tggaatgatt gatgtttata aatggaaaaa    4500
tctttgtgca ggtttacgtt aagcaccctg ctgatatccc tgattacaag aagctttcat    4560
tccctgaggg attcaagtgg gagagagtta tgaacttcga ggatggtggt gttgctactg    4620
ttactcagga ttcttcactt caggacggat gcttcatcta caaggttaag ttcatcggag    4680
tgaacttccc ttctgatgga cctgttatgc agaaaaagac tatgggatgg gaggcttcta    4740
ccgagagact ttaccctaga gatggtgttc ttagggtga gactcacaag gctcttaagc    4800
ttaaagatgg tggacactac ctcgtcgagt tcaagtctat ctacatggct aagaagcctg    4860
ttcagcttcc tggttactac tacgttgacg ctaagcttga tatcacctct cacaacgagg    4920
actacactat cgttgagcaa tacgagagaa ctgagggtag acatcacttg ttcctctgat    4980
atcaaaatct atttagaaat acacaatatt ttgttgcagg cttgctggag aatcgatctg    5040
ctatcataaa aattacaaaa aaattttatt tgcctcaatt attttaggat tggtattaag    5100
gacgcttaaa ttatttgtcg ggtcactacg catcattgtg attgagaaga tcagcgatac    5160
gaaatattcg tagtactatc gataatttat ttgaaaattc ataagaaaag caaacgttac    5220
atgaattgat gaaacaatac aaagacagat aaagccacgc acatttagga tattggccga    5280
gattactgaa tattgagtaa gatcacggaa tttctgacag gagcatgtct tcaattcagc    5340
ccaaatggca gttgaaatac tcaaaccgcc ccatatgcag gagcggatca ttcattgttt    5400
gtttggttgc ctttgccaac atgggagtcc aaggtttacc cagctttctt gtacaaagtg    5460
gtgataaact atcagtgttt gacaggatat attggcgggt aaacctaaga gaaaagagcg    5520
t                                                                    5521
```

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cttacatgct taggatcgga cttg                                             24

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
agttccagca ccagatctaa cg                                              22

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccctgagccc aagcagcatc atcg                                            24

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cggagagggc gtggaagg                                                   18

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ttcgatttgc tacagcgtca ac                                              22

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
aggcaccatc gcaggcttcg ct                                              22

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cttccactcc ttcctcctcg tc                                              22

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gcgtcccaaa gggttgttga g                                     21

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tctctactgg gcctgccagg gc                                    22

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ccccgagacg ttgaaggcta agtacaaa                              28

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ttgcgctgac ggattctaca agga                                  24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tccatcagtc caaacagcag caga                                  24

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
catagcagtc tcacgtcctg gtc                                   23

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggaagctaag ccattacact gttcag                                          26

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
catagcagtc tcacgtcctg gtc                                             23

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cctgatccgt tgacctgcag                                                 20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gtgtgaggtg gctaggcatc                                                 20

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggaagctaag ccattacact gttcag                                          26

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
agagaggaga cagagagaga gt                                              22

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
agacagcatc aagatttcac aca                                         23

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
caacggcgag cgtaatctta g                                           21

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gttccctgga attgctgata gg                                          22

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tgttggtgga agaggatacg                                             20

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
atcagcagca gcgatagc                                               18

<210> SEQ ID NO 87
<211> LENGTH: 6342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
agcttcaggg ctgcgtccta accggcgtct gggtcatagc ccacgagtgc ggccaccacg      60
ccttcagcga ctaccagtgg ctggacgaca ccgtcggcct catcttccac tccttcctcc     120
tcgtccctta cttctcctgg aagtacagtc atcgacgcca ccattccaac actggctccc     180
tcgagagaga cgaagtgttt gtccccaaga agaagtcaga catcaagtgg tacggcaagt     240
acctcaacaa ccctttggga cgcaccgtga tgttaacggt tcagttcact ctcggctggc     300
ctttgtactt agccttcaac gtctcgggga gaccttacga cggcggcttc gcttgccatt     360
tccaccccaa cgctcccatc tacaacgacc gtgagcgtct ccagatatac atctccgacg     420

```
ctggcatcct cgccgtctgc tacggtctct accgctacgc tgctgtccaa ggagttgcct    480
cgatggtctg cttctacgga gttcctcttc tgattgtcaa cgggttctta gttttgatca    540
cttacttgca gcacacgcat ccttccctgc ctcactatga ctcgtctgag tgggattggt    600 tgagggagc tttggccacc gttgacagag actacggaat cttgaacaag gtcttccaca    660
atatcacgga cacgcacgtg gcgcatcacc tgttctcgac catgccgcat tatcacgcga    720
tggaagctac gaaggcgata aagccgatac tgggagagta ttatcagttc gatgggacgc    780
cggtggttaa ggcgatgtgg agggaggcga aggagtgtat ctatgtggaa ccggacaggc    840
aaggtgagaa gaaaggtgtg ttctggtaca acaataagtt atgaagcaaa gaagaaactg    900
aacctttctc atctatgatt gtctttgttt taagaagcta tgtttctgtt tcaataatct    960
ttaattatcc attttgttgt gttttctgac attttggcta aaatggcgcc acccagctt t   1020 cttgtacaaa gtggtcccct taattaactg ggcctcatgg gccttccgct cactgcccgc    1080
tttccagtcg ggaaacctgt cgtgccagct gcattaacat ggtcatagct gtttccttgc    1140
gtattgggcg ctctccgctt cctcgctcac tgactcgctg cgctcggtcg ttcgggtaaa    1200
gcctggggtg cctaatgagc aaaaggccag caaaaggcca ggaaccgtaa aaaggccgcg    1260
ttgctggcgt ttttccatag gctccgcccc cctgacgagc atcacaaaaa tcgacgctca    1320
agtcagaggt ggcgaaaccc gacaggacta taaagatacc aggcgtttcc ccctggaagc    1380
tccctcgtgc gctctcctgt tccgaccctg ccgcttaccg gatacctgtc cgcctttctc    1440
ccttcgggaa gcgtggcgct ttctcatagc tcacgctgta ggtatctcag ttcggtgtag    1500
gtcgttcgct ccaagctggg ctgtgtgcac gaaccccccg ttcagcccga ccgctgcgcc    1560
ttatccggta actatcgtct tgagtccaac ccggtaagac acgacttatc gccactggca    1620
gcagccactg gtaacaggat tagcagagcg aggtatgtag gcggtgctac agagttcttg    1680
aagtggtggc ctaactacgg ctacactaga agaacagtat ttggtatctg cgctctgctg    1740
aagccagtta ccttcggaaa aagagttggt agctcttgat ccggcaaaca accaccgct    1800 ggtagcggtg ttttttttgt ttgcaagcag cagattacgc gcagaaaaaa aggatctcaa    1860
gaagatcctt tgatcttttc tacggggtct gacgctcagt ggaacgaaaa ctcacgttaa    1920
gggattttgg tcatgagatt atcaaaaagg atcttcacct agatcctttt aaattaaaaa    1980
tgaagtttta aatcaatcta agtatatat gagtaaactt ggtctgacag ttaccaatgc    2040
ttaatcagtg aggcacctat ctcagcgatc tgtctatttc gttcatccat agttgcctga    2100
ctccccgtcg tgtagataac tacgatacgg gagggcttac catctggccc cagtgctgca    2160
atgataccgc gagaaccacg ctcaccggct ccagatttat cagcaataaa ccagccagcc    2220
ggaagggccg agcgcagaag tggtcctgca actttatccg cctccatcca gtctattaat    2280
tgttgccggg aagctagagt aagtagttcg ccagttaata gtttgcgcaa cgttgttgcc    2340
attgctacag gcatcgtggt gtcacgctcg tcgtttggta tggcttcatt cagctccggt    2400
tcccaacgat caaggcgagt tacatgatcc cccatgttgt gcaaaaaagc ggttagctcc    2460
ttcggtcctc cgatcgttgt cagaagtaag ttggccgcag tgttatcact catggttatg    2520
gcagcactgc ataattctct tactgtcatg ccatccgtaa gatgcttttc tgtgactggt    2580
gagtactcaa ccaagtcatt ctgagaatag tgtatgcggc gaccgagttg ctcttgcccg    2640
gcgtcaatac gggataatac cgcgccacat agcagaactt taaaagtgct catcattgga    2700
aaacgttctt cggggcgaaa actctcaagg atcttaccgc tgttgagatc cagttcgatg    2760
```

```
taacccactc gtgcacccaa ctgatcttca gcatctttta ctttcaccag cgtttctggg    2820
tgagcaaaaa caggaaggca aaatgccgca aaaagggaa taagggcgac acggaaatgt     2880
tgaatactca tactcttcct ttttcaatat tattgaagca tttatcaggg ttattgtctc    2940
atgagcggat acatatttga atgtatttag aaaaataaac aaatagggt tccgcgcaca     3000
tttccccgaa aagtgccacc taaattgtaa gcgttaatat tttgttaaaa ttcgcgttaa    3060
attttttgtta aatcagctca ttttttaacc aataggccga atcggcaaa atcccttata   3120
aatcaaaaga atagaccgag atagggttga gtggccgcta cagggcgctc ccattcgcca    3180
ttcaggctgc gcaactgttg ggaagggcgt tcggtgcgg gcctcttcgc tattacgcca    3240
gctggcgaaa gggggatgtg ctgcaaggcg attaagttgg gtaacgccag gttttccca    3300
gtcacgacgt tgtaaaacga cggccagtga gcgcgacgta atacgactca ctataggcg    3360
aattggcgga aggccgtcaa ggccgcatgg cgcgccgggg acaagtttgt acaaaaaagc    3420
aggctgcggc cgcgaaatat ccttcctatt caaagttata tatatttgtt acttttgtt    3480
ttagatctgg acctgagaca tgtaagtaca tatttgttga atctttgggt aaaaacttat    3540
gtctctgggt aaaatttgct gagagatttg accgattcct attggctctg gattctgtag    3600
ttacctaata catgaaaaag tttcatttgg cctatgctca cttcatgctt ataaactttt    3660
tcttgcaaat taattggatt agatgctcct tcatagattc agatgcaata gatttgcatg    3720
aagaaaataa taggattcat gatagtaaaa agattgtatt tttgtttgtt tgtttatgtt    3780
taaaagtcta tatgttgaca atagagttgc tatcaactgt ttcatttagg tttatgtttt    3840
tgtcaagttg cttattctaa gagacattgt gattatgact tgtcttctct aacgtagttt    3900
agtaataaaa gacgaaagaa attgatatcc acaagaaga gatgtaagct gtaacgtatc     3960
aaatctcatt aataactagt agtattctca acgctatcgt ttatttcttt ctttggtttg    4020
ccactatatg ccgcttctct gctctttatc ccacgtacta tccattttt ttgtggtagt     4080
ccatttttt gaaactttaa taacgtaaca ctgaatatta atttgttggt ttaattaact    4140
ttgagtcttt gcttttggtt tatgcagaaa catgggtgca ggtggaagaa tgcaagtgtc    4200
tcctccctcc aaaagtctg aaaccgacaa catcaagcgc gtaccctgcg agacaccgcc    4260
cttcactgtc ggagaactca agaaagcaat cccaccgcac tgtttcaaac gctcgatccc    4320
tcgctcttc tcctacctca tctgggacat catcatagcc tcctgcttct actacgtcgc    4380
caccacttac ttccctctcc tccctcaccc tctctcctac ttcgcctggc ctctctactg    4440
ggccaagctt aaccgacaac cactttgcgg acttcctttc aagagaattc aataaggtta    4500
attcctaatt gaaatccgaa gataagattc ccacacactt gtggctgata tcaaaaggct    4560
actgcctatt taaacacatc tctggagact gagaaaatca gacctccaag catgaagaag    4620
cctgagctta ctgctacttc tgttgagaag ttcctcatcg agaagttcga ttctgtgtct    4680
gatcttatgc agctctctga gggtgaggaa tcaagagctt tctctttcga tgttggtgga    4740
agaggatacg ttctcagagt taactcttgc gctgacggat tctacaagga tagatacgtg    4800
tacagacact tcgcttcagc tgctctccct atccctgaag ttcttgatat cggagagttc    4860
tctgagtctc ttacctactg tatctcaaga agggctcagg tgttactct tcaagatctt    4920
cctgagactg agcttcctgc tgttcttcaa cctgttgctg aggctatgga tgctatcgct    4980
gctgctgatc tttctcaaac ttctggattc ggaccttcg gtcctcaggg aatcggacag    5040
tacactactt ggagagattt catctgcgct atcgctgatc ctcatgttta ccattggcag    5100
accgttatgg atgataccgt ttctgcttct gttgctcaag ctcttgatga gcttatgctt    5160
```

```
tgggctgagg attgtcctga ggttagacat cttgttcacg ctgatttcgg atctaacaac    5220
gttctcaccg ataacggaag aatcaccgct gttatcgatt ggtctgaggc tatgttcgga    5280
gattctcaat acgaggtggc caacatattc ttttggaggc cttggcttgc ttgtatggaa    5340
caacagacta gatacttcga gagaaggcat cctgagcttg ctggatctcc tagacttaga    5400
gcttacatgc ttaggatcgg acttgatcag ctttaccagt ctctcgttga tggaaacttc    5460
gatgatgctg cttgggctca gggaagatgt gatgctatcg ttagatctgg tgctggaact    5520
gttggaagaa ctcaaatcgc tagaagatct gctgctgttt ggactgatgg atgtgttgaa    5580
gttctcgctg attctggaaa cagaaggcct tctactagac ctagagccaa gaagtgaaga    5640
tcggcggcaa tagcttctta gcgccatccc gggttgatcc tatctgtgtt gaaatagttg    5700
cggtgggcaa ggctctcttt cagaaagaca ggcggccaaa ggaacccaag gtgaggtggg    5760
ctatggctct cagttccttg tggaagcgct tggtctaagg tgcagaggtg ttagcgggat    5820
gaagcaaaag tgtccgattg taacaagata tgttgatcct acgtaaggat attaaagtat    5880
gtattcatca ctaatataat cagtgtattc caatatgtac tacgatttcc aatgtcttta    5940
ttgtcgccgt atgtaatcgg cgtcacaaaa taatccccgg tgactttctt ttaatccagg    6000
atgaaataat atgttattat aatttttgcg atttggtccg ttataggaat tgaagtgtgc    6060
ttgcggtcgc caccactccc atttcataat tttacatgta tttgaaaaat aaaaatttat    6120
ggtattcaat ttaaacacgt atacttgtaa agaatgatat cttgaaagaa atatagttta    6180
aatatttatt gataaaataa caagtcaggt attatagtcc aagcaaaaac ataaatttat    6240
tgatgcaagt ttaaattcag aaatatttca ataactgatt atatcagctg gtacattgcc    6300
gtagatgaaa gactgagtgc gatattatgg tgtaatacat aa                      6342
```

<210> SEQ ID NO 88
<211> LENGTH: 5103
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

```
tatgtattac acataatatc gcactcagtc tttcatctac ggcaatgtac cagctgatat      60
aatcagttat tgaaatattt ctgaatttaa acttgcatca ataaatttat gttttttgctt    120 ggactataat acctgacttg ttattttatc aataaatatt taaactatat ttcttttcaag   180 atatcattct ttacaagtat acgtgtttaa attgaatacc ataaattttt attttttcaaa   240 tacatgtaaa attatgaaat gggagtggtg gcgaccgagc tcaagcacac ttcaattcct    300
ataacggacc aaatcgcaaa aattataata acatattatt tcatcctgga ttaaaagaaa    360
gtcaccgggg attattttgt gacgccgatt acatacggcg acaataaaga cattggaaat    420
cgtagtacat attggaatac actgattata ttaatgatga atacatactt taatatcctt    480
acgtaggatc aacatatctt gttacaatcg gacacttttg cttcatcccc gctaacacct    540
ctgcacctta gaccaagcgc ttccacaagg aactgagagc catagcccac ctcaccttgg    600
gttcctttgg ccgcctgtct ttctgaaaga gagccttgcc caccgcaact atttcaacac    660
agataggatc aacccgggat ggcgctaaga agctattgcc gccgatcttc agatctgggt    720
aactggccta actggccttg gaggagctgg caactcaaaa tcccttttgcc aaaaaccaac    780 atcatgccat ccaccatgct tgtatccagc tgcgcgcaat gtaccccggg ctgtgtatcc    840
```

```
caaagcctca tgcaacctaa cagatggatc gtttggaagg cctataacag caaccacaga    900
cttaaaacct tgcgcctcca tagacttaag caaatgtgtg tacaatgtgg atcctaggcc    960
caacctttga tgcctatgtg acacgtaaac agtactctca actgtccaat cgtaagcgtt   1020
cctagccttc cagggcccag cgtaagcaat accagccaca acaccctcaa cctcagcaac   1080
caaccaaggg tatctatctt gcaacctctc gagatcatca atccactctt gtggtgtttg   1140
tggctctgtc ctaaagttca ctgtagacgt ctcaatgtaa tggttaacga tatcacaaac   1200
cgcggccata tcagctgctg tagctggcct aatctcaact ggtctcctct ccggagacat   1260
tacaaactta caaatttctc tgaagttgta tcctcagtac ttcaaagaaa atagcttaca   1320
ccaaattttt tcttgttttc acaaatgccg aacttggttc cttatatagg aaaactcaag   1380
ggcaaaaatg acacggaaaa atataaaagg ataagtagtg ggggataaga ttcctttgtg   1440
ataaggttac tttccgccct tacattttcc accttacatg tgtcctctat gtctctttca   1500
caatcaccga cctatctttc ttcttttcat tgttgtcgtc agtgcttacg tcttcaagat   1560
tcttttcttc gcctggttct tcttttttcaa tttctacgta ttcttcttcg tattctggca   1620
gtataggatc ttgtatctgt acattcttca tttttgaaca taggttgcat atgtgccgca   1680
tattgatctg cttcttgctg agcttacata atacttccat agttttttccc gtaaacattg   1740
gattcttgat gctacatctt ggataattac cttctggtct agagtcgaat cacaagtttg   1800
tacaaaaaag caggctgtcg acctgcaggt caacggatca ggatattctt gtttaagatg   1860
ttgaactcta tggaggtttg tatgaactga tgatctagga ccggataagt tcccttcttc   1920
atagcgaact tattcaaaga atgttttgtg tatcattctt gttacattgt tattaatgaa   1980
aaatatttat tggtcattgg actgaacacg agtgttaaat atggaccagg ccccaaataa   2040
gatccattga tatatgaatt aaataacaag aataaatcga gtcaccaaac cacttgcctt   2100
ttttaacgag acttgttcac caacttgata caaaagtcat tatcctatgc aaatcaataa   2160
tcatacaaaa atatccaata acactaaaaa attaaaagaa atggataatt tcacaatatg   2220
ttatacgata aagaagttac ttttccaaga aattcactga tttttataagc ccacttgcat   2280
tagataaatg gcaaaaaaaa acaaaaagga aagaaataa agcacgaaga attctagaaa   2340
atacgaaata cgcttcaatg cagtgggacc cacggttcaa ttattgccaa ttttcagctc   2400
caccgtatat ttaaaaaata aaacgataat gctaaaaaaa tataaatcgt aacgatcgtt   2460
aaatctcaac ggctggatct tatgacgacc gttagaaatt gtggttgtcg acgagtcagt   2520
aataaacggc gtcaaagtgg ttgcagccgg cacacacgag tcgtgtttat caactcaaag   2580
cacaaatact tttcctcaac ctaaaaataa ggcaattagc caaaacaac tttgcgtgta    2640
aacaacgctc aatacacgtg tcattttatt attagctatt gcttcaccgc cttagctttc   2700
tcgtgaccta gtcgtcctcg tcttttcttc ttcttcttct ataaacaat acccaaagag    2760
ctcttcttct tcacaattca gatttcaatt tctcaaaatc ttaaaaactt tctctcaatt   2820
ctctctaccg tgatcaaggt aaatttctgt gttccttatt ctctcaaaat cttcgatttt   2880
gttttcgttc gatcccaatt tcgtatatgt tctttggttt agattctgtt aatcttagat   2940
cgaagacgat tttctgggtt tgatcgttag atatcatctt aattctcgat tagggtttca   3000
tagatatcat ccgatttgtt caaataattt gagttttgtc gaataattac tcttcgattt   3060
gtgatttcta tctagatctg gtgttagttt ctagttgtg cgatcgaatt tgtcgattaa   3120
tctgagtttt tctgattaac agatggcttc atctgagaac gttatcactg agttcatgag   3180
```

```
gttcaaggtg aggatggaag gtactgttaa cggacatgag ttcgagatcg agggtgaggg      3240
tgaaggtaga ccttacgagg gacataacac cgttaagctt aaggttacaa agggtggacc      3300
tcttcctttc gcttgggata tcctttctcc tcaattccaa tacggaagca aggtaagttt      3360
gtggattctt cgtccatgtg atctttgagt ttctttagag cttgtgaggg attagtaagt      3420
aacaatgctt gagttttttg ctgctgggct tcgaaaagtt tgtcacttgt tggtttgatc      3480
cacaaggtct tcttctccat agctactaga catgttttag cttaagattc aagtttatat      3540
atgccttgtg gattaatcat tgcctgattc ttccgtgtca tctctgagtt tatttagagc      3600
ttggaagtgg tgtagtaata actaacaata ctcttgataa gttgtagcaa tgctcttgat      3660
tagtggatgt aatatgatgt tgataagata tatgaggcac agaaccaaaa gtggtgcttc      3720
cactagaccc gttttagcc taaggttcaa gtttatacct tgtagatgtt tctgtattgt       3780
ctgattcttc cctgtgatat ttgaatttct tagagctttg gaagtgatat aggaacaatg      3840
ctcttgtgtg tttgtctcta tgaagattat cgctgtcgtg tttcatccga gtgtgcggga      3900
ttttttgctg ctgggtttag cctttcttca aaaagttatt acttgttagt tttattgttt      3960
tggtcttgat aagagatgtt aggacagaca tggtgcttct tgtctatagc cactagacct      4020
atttagcat aaggttaacg aaattctctc tacataccatt gtggatttgt ttacattgcc       4080
tgatctttcc tgtgatcgct gtcatgtttc tttggaatga ttgatgttta taaatggaaa      4140
aatctttgtg caggtttacg ttaagcaccc tgctgatatc cctgattaca agaagctttc      4200
attccctgag ggattcaagt gggagagagt tatgaacttc gaggatggtg gtgttgctac      4260
tgttactcag gattcttcac ttcaggacgg atgcttcatc tacaaggtta agttcatcgg      4320
agtgaacttc ccttctgatg gacctgttat gcagaaaaag actatgggat gggaggcttc      4380
taccgagaga ctttacccta gagatggtgt tcttaagggt gagactcaca aggctcttaa      4440
gcttaaagat ggtggacact acctcgtcga gttcaagtct atctacatgg ctaagaagcc      4500
tgttcagctt cctggttact actacgttga cgctaagctt gatatcacct ctcacaacga      4560
ggactacact atcgttgagc aatacgagag aactgagggt agacatcact tgttcctctg      4620
atatcaaaat ctatttagaa atacacaata ttttgttgca ggcttgctgg agaatcgatc      4680
tgctatcata aaaattacaa aaaaattta tttgcctcaa ttattttagg attggtatta       4740
aggacgctta aattatttgt cgggtcacta cgcatcattg tgattgagaa gatcagcgat      4800
acgaaatatt cgtagtacta tcgataattt atttgaaaat tcataagaaa agcaaacgtt      4860
acatgaattg atgaaacaat acaaagacag ataaagccac gcacatttag gatattggcc      4920
gagattactg aatattgagt aagatcacgg aatttctgac aggagcatgt cttcaattca      4980
gcccaaatgg cagttgaaat actcaaaccg ccccatatgc aggagcggat cattcattgt      5040
ttgtttggtt gcctttgcca acatgggagt ccaaggttta cccagctttc ttgtacaaag      5100
tgg                                                                   5103
```

<210> SEQ ID NO 89
<211> LENGTH: 8802
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

```
ctaaattgta agcgttaata ttttgttaaa attcgcgtta aatttttgtt aaatcagctc       60
```

```
atttttaac caataggccg aaatcggcaa aatcccttat aaatcaaaag aatagaccga    120 gataggttg agtggccgct acagggcgct cccattcgcc attcaggctg cgcaactgtt    180
gggaagggcg tttcggtgcg ggcctcttcg ctattacgcc agctggcgaa aggggatgt    240 gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgggga caagtttgta caaaaaagca ggcttacttc gcctggcctc tctactgggc    420
ctgccagggc tgcgtcctaa ccggcgtctg gggtaccgtc gacaagcttc ttgcctcaat    480
tccggaggtg tttctagtgt tcaacatgac aaacaaaacc catctctttc agtatatgtc    540
tctcagttgt gcttaattca aatttcaact cagagaactt cttggcatac ttatccagat    600
tatctaatga tctcatctaa tggtaattca actttcagta tatgtctcgc agcaaactat    660
ctttacatca aatttttaac aactcaatgc acaaaatact tttcctcaac ctaaaaataa    720
ggcaattagc caaaaacaac tttgcgtgtg aacaacgcgt tacacgtccc tacacatacg    780
tgtcaattta aattggctat ttgcttccac gccttagctt tctcgtgacc gaccgagtcg    840
tcctcgtctt ttttgcttct ataaatcaaa tacccaaaga gctcttcttc ttcacaattc    900
agattccaat tttctcaaac tctaaaatca atctctcaaa tctctcaacc gtgatcaagg    960
tagatttctg agttcttatt gtatttcttc gatttgtttc gttcgatcgc aatttaggct   1020
ctgttctttg attttgatct cgttaatctc tgatcggagg caaattacat agtttcatcg   1080
ttagatctct tcttattcct cgattagggt tcgtattttt cgcagatctg tttatttcct   1140
tgttgttccc ttgtatttga tccgatttgt tgaaagaatt tgtgtgttct cgattattta   1200
cgctttgatc tgtgattttt atctagattt ggtgttagtt tcttgtttgt gcgatcgaat   1260
ttgtcgatta atctcggttt ttctgattaa cagatggctc aatctagcag aatctgccac   1320
ggtgtgcaga acccatgtgt gatcatttcc aatctctcca aatccaacca gaacaaatct   1380
cctttctcag tcagcctcaa gactcaccag cagcagcgtc gtgcttacca gatatctagc   1440
tggggattga agaagtcaaa caacgggtcc gtgattcgtc cggttaaggc agctgcaaga   1500
gggatgccag ccttgtcttt acctggatca aagagtatca cagctagggc actctttctt   1560
gctgctgctg ctgatggggt tactactttg gtgaggccat tgagaagtga cgacacagaa   1620
ggattcgctg aggggttagt tcgtttaggc tatcgtgtag gaggacacc cgatacttgg   1680 caagtcgatg gcagaccaca aggaccagca gtggctgagg ctgacgtcta ctgtagagac   1740
ggagcaacca ccgctagatt cttgccaacc ttagcagctg ctggtcacgg aacatacaga   1800
tttgatgctt caccacagat gaggagacgt cctcttttgc ccttaagcag agccttgagg   1860 gatttggtg tcgatcttag acacgaagaa gctgaaggtc atcaccctct gactgtccgt   1920
gctgctgggg ttgaaggagg agaggttact ttggatgctg gtcagtcaag tcagtatctc   1980
actgccttgt tgctccttgg tccccttaca agacaaggac tgaggataag ggttactgat   2040
ttggtgtcag caccatacgt ggagattacg cttgcaatga tgagggcttt cggagttgaa   2100
gtggcaaggg agggagatgt gttcgttgtt ccacctggtg atatcgtgc aactacgtat    2160 gctatagaac ccgacgcaag tactgcttct tacttcttcg cagctgctgc tttgactcct   2220
ggagctgaag tgactgtacc tgggttaggc acggagcac ttcaaggaga tttgggattt    2280
gtagatgtct taaggagaat gggagccgag gtgtccgtag agctgatgc aaccactgtt    2340 agaggaactg tgtgaattgcg tggccttaca gccaacatga gagacataag tgatacgatg   2400 ccgacccctcg ctgcaatagc acccttgct agtgctccag ttagaatcga ggatgttgcc    2460
```

```
aacactcgtg tcaaagaatg tgacagactt gaggcttgtg cagagaacct taggaggttg    2520
ggagtaaggg ttgcaacggg tccggactgg attgagatac accctggtcc agctactggt    2580
gctcaagtca caagctatgg tgatcacaga attgtgatgt catttgcagt gactggactt    2640
cgtgtgcctg ggatcagctt cgacgaccct ggctgtgttc gtaagacttt tcctgggttt    2700
cacgaggctt tcgcagaatt gaggcgtggc attgggagct gatgagtagt tagcttaatc    2760
acctaagatc ggcggcaata gcttcttagc gccatcccgg gttgatccta tctgtgttga    2820
aatagttgcg gtgggcaagg ctctctttca gaaagacagg cggccaaagg aacccaaggt    2880
gaggtgggct atggctctca gttccttgtg gaagcgcttg gtctaaggtg cagaggtgtt    2940
agcgggatga agcaaaagtg tccgattgta acaagatatg ttgatcctac gtaaggatat    3000
taaagtatgt attcatcact aatataatca gtgtattcca atatgtacta cgatttccaa    3060
tgtctttatt gtcgccgtat gtaatcggcg tcacaaaata atccccggtg actttctttt    3120
aatccaggat gaaataatat gttattataa tttttgcgat ttggtccgtt ataggaattg    3180
aagtgtgctt gcggtcgcca ccactcccat ttcataattt tacatgtatt tgaaaaataa    3240
aaatttatgg tattcaattt aaacacgtat acttgtaaag aatgtatatct tgaaagaaat    3300 atagtttaaa tatttattga taaaataaca agtcaggtat tatagtccaa gcaaaaacat    3360
aaatttattg atgcaagttt aaattcagaa atatttcaat aactgattat atcagctggt    3420
acattgccgt agatgaaaga ctgagtgcga tattatggtg taatacatac ggccgccaga    3480
aggtaattat ccaagatgta gcatcaagaa tccaatgttt acgggaaaaa ctatggaagt    3540
attatgtaag ctcagcaaga agcagatcaa tatgcggcac atatgcaacc tatgttcaaa    3600
aatgaagaat gtacagatac aagatcctat actgccagaa tacgaagaag aatacgtaga    3660
aattgaaaaa gaagaaccag gcgaagaaaa gaatcttgaa gacgtaagca ctgacgacaa    3720
caatgaaaag aagaagataa ggtcggtgat tgtgaaagag acatagagga cacatgtaag    3780
gtggaaaatg taagggcgga aagtaacctt atcacaaagg aatcttatcc cccactactt    3840 atcctttat attttccgt gtcattttg cccttgagtt ttcctatata aggaaccaag    3900
ttcggcattt gtgaaaacaa gaaaaaattt ggtgtaagct attttctttg aagtactgag    3960
gatacaactt cagagaaatt tgtaagtttg taatgtctcc ggagaggaga ccagttgaga    4020
ttaggccagc tacagcagct gatatggccg cggtttgtga tatcgttaac cattacattg    4080
agacgtctac agtgaacttt aggacagagc cacaaacacc acaagagtgg attgatgatc    4140
tcgagaggtt gcaagataga tacccttggt tggttgctga ggttgagggt gttgtggctg    4200
gtattgctta cgctgggccc tggaaggcta ggaacgctta cgattggaca gttgagagta    4260
ctgtttacgt gtcacatagg catcaaaggt cagttttact tcccttaatt ttctatgtac    4320
tttcataatt acttatgtta ttttcttcat gagttttaat gcaaattact atatggactc    4380
tagtgaaaac gttcagaatc ctataaacat gactactgag acgaacttga gagtagtttt    4440
gatcatacac acgtttcatg tggtacttga gagttactaa tttttgtcat cttcgtataa    4500
gtagtaaaag atactacaag aatagtttag tagaaaatac tagcggtagg tgaagatttg    4560
tcgctatgta ctattattgt ctagtaactt gagtaacaat ttcgtggtct aaatatcaaa    4620
taaaaatgga tgagtggttc accaaatcta ggcatcaaaa ctattaatgt cattgtctag    4680
atcttaggtg acaccacatt tcgaatattt attggtaatt gagatgttaa agtaccaata    4740
tttgacttaa taaactaaaa gattttggct ttatcaaatg tagacattga tgacatatcg    4800
```

```
ttgtcattat cttgagtata tacaagtcga tcaattaggt gaaagtttag tgtctcgtgg      4860
ttggtaaacg attaatacag tagtatattt tatccaaaga caaatccaa atcatttcac       4920 cagtatgaat agtattattt tatcttaaaa gctaaaatct taaaaaccaa ggtagcaccc      4980
acgttgagct agacgatcaa atcgatttct gctttgtcca atttaccaag ctatttaaag     5040
ccaaataatt gaaatatagg taggtcgtta tattaggcta agatttatct caaatgctta     5100
actaaaggaa taacaaggga ttctagttgt gtggttttat aagattggtc caatttcact     5160
taagtttgtt tattgtagaa ttttatatgt gaataatttg aattccaatt gaaaagatat     5220
tatagtaaaa gaaaaaatag tgcgaacaaa aaactttaat cccataaaaa gaaaagaaa      5280 aatgaaaagt tcttctaaca tccatatttt gcatcatatc ataaagataa gaaagataca    5340
tatcatagac gtacagataa acaaacatat catcatttgt gaaatacata gtacaataat    5400 ttgctttttaa atagagttta agtcacacac actgacacac acgataaaac gataatgtct   5460
gcaaaaacac tttaatccca ttgcctagag gacagcttct ccactttgtc tttaaggttg    5520
gttttgccgt gttgttttta tctttatata atgatctatt ttttggatta tgaaatgaat    5580
tcacacattt taattattta agaagatcca tatacaggtt tataacagta ctaagtgatg    5640
attatttttt gttttgcat agtttagttt attgggtaaa cattcattac gtgtctcttt     5700
atacgaatca cccatccaaa atttcaagta gtcttttagt tcatttatta tttcataact   5760
atttgactta ttgatttgac aagaaacaac aaaagtgttg acttattgat agattgtggg   5820
atcataaaag taattaagcg tcaaccacga cccacaacaa caaagcacat gttatacatt   5880
aatatctcgt ttacttaatt acagttttca gaatgccgtt tcatgtcttg tcactggcga   5940
tgttattatc atgttggaca atattcgact gttgtcgttt ttacattttc gtattgacta   6000
aaactaaaaa aacaaaactc tgtttcaggt tgggcctagg atccacattg tacacacatt   6060
tgcttaagtc tatggaggcg caaggtttta agtctgtggt tgctgttata ggccttccaa    6120
acgatccatc tgttaggttg catgaggctt tgggatacac agcccggggt acattgcgcg   6180
cagctggata caagcatggt ggatggcatg atgttggttt ttggcaaagg gattttgagt    6240
tgccagctcc tccaaggcca gttaggccag ttacccagat ctaatatcaa aatctatta    6300 gaaatacaca atattttgtt gcaggcttgc tggagaatcg atctgctatc ataaaaatta   6360
caaaaaaatt ttatttgcct caattatttt aggattggta ttaaggacgc ttaaattatt   6420
tgtcgggtca ctacgcatca ttgtgattga gaagatcagc gatacgaaat attcgtagta   6480
ctatcgataa tttatttgaa aattcataag aaaagcaaac gttacatgaa ttgatgaaac   6540
aatacaaaga cagatataaagc cacgcacatt taggatattg gccgagatta ctgaatattg   6600
agtaagatca cggaatttct gacaggagca tgtcttcaat tcagcccaaa tggcagttga    6660
aatactcaaa ccgccccata tgcaggagcg gatcattcat tgtttgtttg gttgcctttg   6720
ccaacatggg agtccaaggt tgcatgctac ttcgcctggc ctctctactg ggcctgccag    6780
ggctgcgtcc taaccggcgt ctggacccag cttctcttgta caaagtggtc cccggcctca   6840
tgggccttcc gctcactgcc cgcttccag tcgggaaacc tgtcgtgcca gctgcattaa    6900
catggtcata gctgtttcct tgcgtattgg gcgctctccg cttcctcgct cactgactcg   6960
ctgcgctcgg tcgttcgggt aaagcctggg gtgcctaatg agcaaaaggc cagcaaaagg   7020
ccaggaaccg taaaaaggcc gcgttgctgg cgttttttcca taggctccgc cccctgacg    7080 agcatcacaa aaatcgacgc tcaagtcaga ggtggcgaaa cccgacagga ctataaagat   7140
accaggcgtt tcccccctgga agctccctcg tgcgctctcc tgttccgacc ctgccgctta   7200
```

```
ccggatacct gtccgccttt ctcccttcgg gaagcgtggc gctttctcat agctcacgct    7260
gtaggtatct cagttcggtg taggtcgttc gctccaagct gggctgtgtg cacgaacccc    7320
ccgttcagcc cgaccgctgc gccttatccg gtaactatcg tcttgagtcc aacccggtaa    7380
gacacgactt atcgccactg gcagcagcca ctggtaacag gattagcaga gcgaggtatg    7440
taggcggtgc tacagagttc ttgaagtggt ggcctaacta cggctacact agaagaacag    7500
tatttggtat ctgcgctctg ctgaagccag ttaccttcgg aaaaagagtt ggtagctctt    7560
gatccggcaa acaaaccacc gctggtagcg gtggtttttt tgtttgcaag cagcagatta    7620
cgcgcagaaa aaaggatctc aagaagatcc tttgatcttt tctacggggt ctgacgctc     7680 agtggaacga aaactcacgt taagggattt tggtcatgag attatcaaaa aggatcttca    7740
cctagatcct tttaaattaa aaatgaagtt ttaaatcaat ctaaagtata tatgagtaaa    7800
cttggtctga cagttaccaa tgcttaatca gtgaggcacc tatctcagcg atctgtctat    7860
ttcgttcatc catagttgcc tgactccccg tcgtgtagat aactacgata cgggagggct    7920
taccatctgg ccccagtgct gcaatgatac cgcgagaacc acgctcaccg gctccagatt    7980
tatcagcaat aaaccagcca gccggaaggg ccgagcgcag aagtggtcct gcaactttat    8040
ccgcctccat ccagtctatt aattgttgcc gggaagctag agtaagtagt tcgccagtta    8100
atagtttgcg caacgttgtt gccattgcta caggcatcgt ggtgtcacgc tcgtcgtttg    8160
gtatggcttc attcagctcc ggttcccaac gatcaaggcg agttacatga tcccccatgt    8220
tgtgcaaaaa agcggttagc tccttcggtc ctccgatcgt tgtcagaagt aagttggccg    8280
cagtgttatc actcatggtt atggcagcac tgcataattc tcttactgtc atgccatccg    8340
taagatgctt ttctgtgact ggtgagtact caaccaagtc attctgagaa tagtgtatgc    8400
ggcgaccgag ttgctcttgc ccggcgtcaa tacgggataa taccgcgcca catagcagaa    8460
ctttaaaagt gctcatcatt ggaaaacgtt cttcggggcg aaaactctca aggatcttac    8520
cgctgttgag atccagttcg atgtaaccca ctcgtgcacc caactgatct tcagcatctt    8580
ttactttcac cagcgtttct gggtgagcaa aaacaggaag gcaaaatgcc gcaaaaaagg    8640
gaataagggc gacacggaaa tgttgaatac tcatactctt cctttttcaa tattattgaa    8700
gcatttatca gggttattgt ctcatgagcg gatacatatt tgaatgtatt tagaaaaata    8760
aacaaatagg ggttccgcgc acatttcccc gaaaagtgcc ac                       8802

<210> SEQ ID NO 90
<211> LENGTH: 10272
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
ttgtacaaag tggtgattcg acctgcaggc atgcaagctt ggcgtaatca tggtcatagc      60
tgtttcctgt gtgaaattgt tatccgctca caattccaca acatacga gccggaagca      120 taaagtgtaa agcctggggt gcctaatgag tgagctaact cacattaatt gcgttgcgct     180
cactgcccgc tttccagtcg ggaaacctgt cgtgccagct gcattaatga atcggccaac     240
gcgcggggag aggcggtttg cgtattgggc gctcttccgc ttcctcgctc actgactcgc     300
tgcgctcggt cgttcggctg cggcgagcgg tatcagctca ctcaaaggcg gtaatacggt     360
tatccacaga atcaggggat aacgcaggaa agaacatgtg agcaaaaggc cagcaaaagg     420
```

```
ccaggaaccg taaaaaggcc gcgttgctgg cgttttttcca taggctccgc cccctgacg      480
agcatcacaa aaatcgacgc tcaagtcaga ggtggcgaaa cccgacagga ctataaagat      540
accaggcgtt tccccctgga agctccctcg tgcgctctcc tgttccgacc ctgccgctta      600
ccggatacct gtccgccttt ctcccttcgg gaagcgtggc gctttctcat agctcacgct      660
gtaggtatct cagttcggtg taggtcgttc gctccaagct gggctgtgtg cacgaacccc      720
ccgttcagcc cgaccgctgc gccttatccg gtaactatcg tcttgagtcc aacccggtaa      780
gacacgactt atcgccactg gcagcagcca ctggtaacag gattagcaga gcgaggtatg      840
taggcggtgc tacagagttc ttgaagtggt ggcctaacta cggctacact agaaggacag      900
tatttggtat ctgcgctctg ctgaagccag ttaccttcgg aaaagagtt ggtagctctt       960
gatccggcaa acaaaccacc gctggtagcg gtggttttt tgtttgcaag cagcagatta      1020
cgcgcagaaa aaaggatct caagaagatc ctttgatctt ttctacgggg tctgacgctc      1080
agtggaacga aaactcacgt taagggattt tggtcatgag attatcaaaa aggatcttca      1140
cctagatcct tttaaattaa aaatgaagtt ttaaatcaat ctaaagtata tatgagtaaa      1200
cttggtctga cagttaccaa tgcttaatca gtgaggcacc tatctcagcg atctgtctat      1260
ttcgttcatc catagttgcc tgactccccg tcgtgtagat aactacgata cgggagggct      1320
taccatctgg ccccagtgct gcaatgatac cgcgagaccc acgctcaccg gctccagatt      1380
tatcagcaat aaaccagcca gccggaaggg ccgagcgcag aagtggtcct gcaactttat      1440
ccgcctccat ccagtctatt aattgttgcc gggaagctag agtaagtagt tcgccagtta      1500
atagtttgcg caacgttgtt gccattgcta caggcatcgt ggtgtcacgc tcgtcgtttg      1560
gtatggcttc attcagctcc ggttcccaac gatcaaggcg agttacatga tcccccatgt      1620
tgtgcaaaaa agcggttagc tccttcggtc ctccgatcgt tgtcagaagt aagttggccg      1680
cagtgttatc actcatggtt atggcagcac tgcataattc tcttactgtc atgccatccg      1740
taagatgctt ttctgtgact ggtgagtact caaccaagtc attctgagaa tagtgtatgc      1800
ggcgaccgag ttgctcttgc ccggcgtcaa tacgggataa taccgcgcca catagcagaa      1860
ctttaaaagt gctcatcatt ggaaaacgtt cttcggggcg aaaactctca aggatcttac      1920
cgctgttgag atccagttcg atgtaaccca ctcgtgcacc caactgatct tcagcatctt      1980
ttactttcac cagcgtttct gggtgagcaa aaacaggaag gcaaaatgcc gcaaaaaagg      2040
gaataagggc gacacggaaa tgttgaatac tcatactctt ccttttcaa tattattgaa       2100
gcatttatca gggttattgt ctcatgagcg gatacatatt tgaatgtatt tagaaaaata     2160
aacaaatagg ggttccgcgc acatttcccc gaaaagtgcc acctgacgtc taagaaacca     2220
ttattatcat gacattaacc tataaaaata ggcgtatcac gaggcccttt cgtctcgcgc     2280
gtttcggtga tgacggtgaa aacctctgac acatgcagct cccggagacg gtcacagctt     2340
gtctgtaagc ggatgccggg agcagacaag cccgtcaggg cgcgtcagcg ggtgttggcg     2400
ggtgtcgggg ctggcttaac tatgcggcat cagagcagat tgtactgaga gtgcaccata     2460
tgcggtgtga ataccgcac agatgcgtaa ggagaaaata ccgcatcagg cgccattcgc      2520
cattcaggct gcgcaactgt tgggaagggc gatcggtgcg ggcctcttcg ctattacgcc     2580
agctggcgaa aggggggatgt gctgcaaggc gattaagttg ggtaacgcca gggttttccc    2640
agtcacgacg ttgtaaaacg acggccagtg aattcgagct cggtacccgg ggatcctcta    2700
gagtcgaatc acaagtttgt acaaaaaagc aggctgtaag tttgtggatt cttcgtccat    2760
```

```
gtgatctttg agtttcttta gagcttgtga gggattagta agtaacaatg cttgagtttt    2820
ttgctgctgg gcttcgaaaa gtttgtcact tgttggtttg atccacaagg tcttcttctc    2880
catagctact agacatgttt tagcttaaga ttcaagttta tatatgcctt gtggattaat    2940
cattgcctga ttcttccgtg tcatctctga gtttatttag agcttggaag tggtgtagta    3000
ataactaaca atactcttga taagttgtag caatgctctt gattagtgga tgtaatatga    3060
tgttgataag atatatgagg cacagaacca aaagtggtgc ttccactaga cccgttttta    3120
gcctaaggtt caagtttata ccttgtagat gtttctgtat tgtctgattc ttccctgtga    3180
tatttgaatt tcttagagct ttggaagtga tataggaaca atgctcttgt gtgtttgtct    3240
ctatgaagat tatcgctgtc gtgtttcatc cgagtgtgcg ggattttttg ctgctgggtt    3300
tagcctttct tcaaaaagtt attacttgtt agtttttattg ttttggtctt gataagagat    3360
gttaggacag acatggtgct tcttgtctat agccactaga cctattttag cataaggtta    3420
acgaaattct ctctacatac cttgtggatt tgtttacatt gcctgatctt tcctgtgatc    3480
gctgtcatgt ttcttttggaa tgattgatgt ttataaatgg aaaaatcttt gtgcaggttt    3540
aaacgtttac gttaagcacc ctgctgatat ccctgattac aagaagcttt cattccctga    3600
gggattcaag tgggagagag ttatgaactt cgaggatggg ggtgttgcta ctgttactca    3660
ggattcttca cttcaggacg gatgcttcat ctacaaggtt aagttcatcg gagtgaactt    3720
cccttctgat ggacctgtta tgcagaaaaa gactatggga tggggaggctt ctaccgagag    3780
actttaccct agagatggtg ttcttaaggg tgagactcac aaggctctta agcttaaaga    3840
tggtggacac tacctcgtcg agttcaagtc tatctacatg gctaagaagc ctgttcagct    3900
tcctggttac tactacgttg acgctaagct tgatatcacc tctcacaacg aggactacac    3960
tatcgttgag caatacgaga gaactgaggg tagacatcac ttgttcctct gatatcaaaa    4020
tctatttaga aatacacaat atttttgttgc aggcttgctg gagaatcgat ctgctatcat    4080
aaaaattaca aaaaaatttt atttgcctca attattttag gattggtatt aaggacgctt    4140
aaattatttg tcgggtcact acgcatcatt gtgattgaga agatcagcga tacgaaatat    4200
tcgtagtact atcgataatt tatttgaaaa ttcataagaa aagcaaacgt tacatgaatt    4260
gatgaaacaa tacaaagaca gataaagcca cgcacattta ggatattggc cgagattact    4320
gaatattgag taagatcacg gaatttctga caggagcatg tcttcaattc agcccaaatg    4380
gcagttgaaa tactcaaacc gccccatatg caggagcgga tcattcattg tttgtttggt    4440
tgcctttgcc aacatgggag tccaaggttg ccttttgcag tttatctcta tgcccgggac    4500
aagtgaagac tcccgcccat ctcactaggg acaggattgg agtccatgct caacaccgtg    4560
caggatgagg atgaccaaca actttgtata caaaagttgt atccgaagta aataaaacca    4620
tcggactctc gtataagact gtcgacaagc ttcttgcctc aattccggag gtgtttctag    4680
tgttcaacat gacaaacaaa acccatctct ttcagtatat gtctctcagt tgtgcttaat    4740
tcaaatttca actcagagaa cttcttggca tacttatcca gattatctaa tgatctcatc    4800
taatggtaat tcaacttttca gtatatgtct cgcagcaaac tatctttaca tcaaattttt    4860
aacaactcaa tgcacaaaat acttttcctc aacctaaaaa taaggcaatt agccaaaaac    4920
aactttgcgt gtgaacaacg cgttacacgt ccctacacat acgtgtcaat ttataattgg    4980
ctattgcttc cacgccttag ctttctcgtg accgaccgag tcgtcctcgt ctttttttgct   5040
tctataaatc aaatacccaa agagctcttc ttcttcacaa ttcagattcc aattttctca    5100
aactctaaaa tcaatctctc aaatctctca accgtgatca aggtagattt ctgagttctt    5160
```

-continued

```
attgtatttc ttcgatttgt ttcgttcgat cgcaatttag gctctgttct ttgattttga      5220
tctcgttaat ctctgatcgg aggcaaatta catagtttca tcgttagatc tcttcttatt      5280
tctcgattag ggttcgtatt tttcgcagat ctgtttattt tcttgttgtt tccttgtatt      5340
tgatccgatt tgttgaaaga atttgtgtgt tctcgattat ttacgctttg atctgtgatt      5400
tttatctaga tttggtgtta gtttcttgtt tgtgcgatcg aatttgtcga ttaatctcgg      5460
tttttctgat taacagatgg ctcaatctag cagaatctgc cacggtgtgc agaacccatg      5520
tgtgatcatt tccaatctct ccaaatccaa ccagaacaaa tctcctttct cagtcagcct      5580
caagactcac cagcagcagc gtcgtgctta ccagatatct agctggggat tgaagaagtc      5640
aaacaacggg tccgtgattc gtccggttaa ggcagctgca agagggatgc cagccttgtc      5700
tttacctgga tcaaagagta tcacagctag ggcactcttt cttgctgctg ctgctgatgg      5760
ggttactact ttggtgaggc cattgagaag tgacgacaca gaaggattcg ctgaggggtt      5820
agttcgttta ggctatcgtg tagggaggac acccgatact tggcaagtcg atggcagacc      5880
acaaggacca gcagtggctg aggctgacgt ctactgtaga gacggagcaa ccaccgctag      5940
attcttgcca accttagcag ctgctggtca cggaacatac agatttgatg cttcaccaca      6000
gatgaggaga cgtcctcttt tgcccttaag cagagccttg agggatttgg gtgtcgatct      6060
tagacacgaa gaagctgaag gtcatcaccc tctgactgtc cgtgctgctg ggttgaagg       6120
aggagaggtt actttggatg ctggtcagtc aagtcagtat ctcactgcct tgttgctcct      6180
tggtccccct acaagacaag gactgaggat aagggttact gatttggtgt cagcaccata      6240
cgtggagatt acgcttgcaa tgatgagggc tttcggagtt gaagtggcaa gggagggaga      6300
tgtgttcgtt gttccacctg gtggatatcg tgcaactacg tatgctatag aacccgacgc      6360
aagtactgct tcttacttct tcgcagctgc tgctttgact cctggagctg aagtgactgt      6420
acctgggtta ggcacgggag cacttcaagg agatttggga tttgtagatg tcttaaggag      6480
aatgggagcc gaggtgtccg taggagctga tgcaaccact gttagaggaa ctggtgaatt      6540
gcgtggcctt acagccaaca tgagagacat aagtgatacg atgccgaccc tcgctgcaat      6600
agcacccttt gctagtgctc cagttagaat cgaggatgtt gccaacactc gtgtcaaaga      6660
atgtgacaga cttgaggctt gtgcagagaa ccttaggagg ttgggagtaa gggttgcaac      6720
gggtccggac tggattgaga tacaccctgg tccagctact ggtgctcaag tcacaagcta      6780
tggtgatcac agaattgtga tgtcatttgc agtgactgga cttcgtgtgc ctgggatcag      6840
cttcgacgac cctggctgtg ttcgtaagac ttttcctggg tttcacgagg cttttcgaga      6900
attgaggcgt ggcattggga gctgatgagt agttagctta atcacctaag atcggcggca      6960
atagcttctt agcgccatcc cgggttgatc ctatctgtgt tgaaatagtt gcggtgggca      7020
aggctctctt tcagaaagac aggcggccaa aggaacccaa ggtgaggtgg gctatggctc      7080
tcagttcctt gtggaagcgc ttggtctaag gtgcagaggt gttagcggga tgaagcaaaa      7140
gtgtccgatt gtaacaagat atgttgatcc tacgtaagga tattaaagta tgtattcatc      7200
actaatataa tcagtgtatt ccaatatgta ctacgatttc caatgtcttt attgtcgccg      7260
tatgtaatcg gcgtcacaaa ataatccccg gtgactttct tttaatccag gatgaaataa      7320
tatgttatta aattttttgc gatttggtcc gttataggaa ttgaagtgtg cttgcggtcg      7380
ccaccactcc catttcataa ttttacatgt atttgaaaaa taaaaattta tggtattcaa      7440
tttaaacacg tatacttgta aagaatgata tcttgaaaga aatatagttt aaatatttat      7500
```

```
tgataaaata acaagtcagg tattatagtc caagcaaaaa cataaattta ttgatgcaag    7560
tttaaattca gaaatatttc aataactgat tatatcagct ggtacattgc cgtagatgaa    7620
agactgagtg cgatattatg gtgtaataca tacggccgac gcataggttc atttgaagct    7680
gctattctat ttagattgaa gtttaaaccc agaaggtaat tatccaagat gtagcatcaa    7740
gaatccaatg tttacgggaa aaactatgga agtattatgt aagctcagca agaagcagat    7800
caatatgcgg cacatatgca acctatgttc aaaaatgaag aatgtacaga tacaagatcc    7860
tatactgcca gaatacgaag aagaatacgt agaaattgaa aaagaagaac caggcgaaga    7920
aaagaatctt gaagacgtaa gcactgacga caacaatgaa aagaagaaga taaggtcggt    7980
gattgtgaaa gagacataga ggacacatgt aaggtggaaa atgtaagggc ggaaagtaac    8040
cttatcacaa aggaatctta tcccccacta cttatccttt tatattttc cgtgtcattt     8100 ttgcccttga gttttcctat ataaggaacc aagttcggca tttgtgaaaa caagaaaaaa    8160
tttggtgtaa gctatttct ttgaagtact gaggatacaa cttcagagaa atttgtaagt     8220
ttgtaatgtc tccggagagg agaccagttg agattaggcc agctacagca gctgatatgg    8280
ccgcggtttg tgatatcgtt aaccattaca ttgagacgtc tacagtgaac tttaggacag    8340
agccacaaac accacaagag tggattgatg atctcgagag gttgcaagat agatacccctt   8400 ggttggttgc tgaggttgag ggtgttgtgg ctggtattgc ttacgctggg ccctggaagg    8460
ctaggaacgc ttacgattgg acagttgaga gtactgttta cgtgtcacat aggcatcaaa    8520
ggtcagtttt acttcccta attttctatg tactttcata attacttatg ttatttttctt    8580 catgagtttt aatgcaaatt actatatgga ctctagtgaa aacgttcaga atcctataaa    8640
catgactact gagacgaact tgagagtagt tttgatcata cacacgtttc atgtggtact    8700
tgagagttac taattttgt catcttcgta aagtagtaa aagatactac aagaatagtt      8760
tagtagaaaa tactagcggt aggtgaagat ttgtcgctat gtactattat tgtctagtaa    8820
cttgagtaac aatttcgtgg tctaaatatc aaataaaaat ggatgagtgg ttcaccaaat    8880
ctaggcatca aaactattaa tgtcattgtc tagatcttag gtgacaccac atttcgaata    8940
tttattggta attgagatgt taaagtacca atatttgact taataaacta aaagattttg    9000
gctttatcaa atgtagacat tgatgacata tcgttgtcat tatcttgagt atatacaagt    9060
cgatcaatta ggtgaaagtt tagtgtctcg tggttggtaa acgattaata cagtagtata    9120
ttttatccaa agacaaaatc caaatcattt caccagtatg aatagtatta ttttatctta    9180
aaagctaaaa tcttaaaaac caaggtagca cccacgttga gctagacgat caaatcgatt    9240
tctgctttgt ccaatttacc aagctatttta aagccaaata attgaaatat aggtaggtcg    9300
ttatattagg ctaagattta tctcaaatgc ttaactaaag gaataacaag ggattctagt    9360
tgtgtggttt tataagattg gtccaatttc acttaagttt gtttattgta gaattttata    9420
tgtgaataat ttgaattcca attgaaaaga tattatagta aaagaaaaaa tagtgcgaac    9480
aaaaaacttt aatcccataa aaagaaaaag aaaaatgaaa agttcttcta acatccatat    9540
tttgcatcat atcataaaga taagaaagat acatatcata gacgtacaga taaacaaaca    9600
tatcatcatt tgtgaaatac atagtacaat aatttgcttt taaatagagt ttaagtcaca    9660
cacactgaca cacacgataa aacgataatg tctgcaaaaa cactttaatc ccattgccta    9720
gaggacagct tctccacttt gtctttaagg ttggttttgc cgtgttgttt ttatctttat    9780
ataatgatct atttttttgga ttatgaaatg aattcacaca ttttaattat ttaagaagat    9840
ccatatacag gtttataaca gtactaagtg atgattattt tttgttttg catagtttag     9900
```

```
tttattgggt aaacattcat tacgtgtctc tttatacgaa tcacccatcc aaaatttcaa    9960
gtagtctttt agttcattta ttatttcata actatttgac ttattgattt gacaagaaac   10020
aacaaaagtg ttgacttatt gatagattgt gggatcataa aagtaattaa gcgtcaacca   10080
cgacccacaa caacaaagca catgttatac attaatatct cgtttactta attacagttt   10140
tcagaatgcc gtttcatgtc ttgtcactgg cgatgttatt atcatgttgg acaatattcg   10200
actgttgtcg tttttacatt ttcgtattga ctaaaactaa aaaaacaaaa ctctgtttca   10260
gacccagctt tc                                                      10272
```

<210> SEQ ID NO 91
<211> LENGTH: 9958
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

```
ttgtacaaag tggtgattcg acctgcaggc atgcaagctt ggcgtaatca tggtcatagc     60
tgtttcctgt gtgaaattgt tatccgctca caattccaca caacatacga gccggaagca    120
taaagtgtaa agcctggggt gcctaatgag tgagctaact cacattaatt gcgttgcgct    180
cactgcccgc tttccagtcg ggaaacctgt cgtgccagct gcattaatga atcggccaac    240
gcgcggggag aggcggtttg cgtattgggc gctcttccgc ttcctcgctc actgactcgc    300
tgcgctcggt cgttcggctg cggcgagcgg tatcagctca ctcaaaggcg gtaatacggt    360
tatccacaga atcaggggat aacgcaggaa agaacatgtg agcaaaaggc cagcaaaagg    420
ccaggaaccg taaaaaggcc gcgttgctgg cgtttttcca taggctccgc cccccctgacg    480 agcatcacaa aaatcgacgc tcaagtcaga ggtggcgaaa cccgacagga ctataaagat    540
accaggcgtt tcccccctgga agctcccctcg tgcgctctcc tgttccgacc ctgccgctta    600
ccggatacct gtccgccttt ctcccttcgg gaagcgtggc gctttctcat agctcacgct    660
gtaggtatct cagttcggtg taggtcgttc gctccaagct gggctgtgtg cacgaacccc    720
ccgttcagcc cgaccgctgc gccttatccg gtaactatcg tcttgagtcc aacccggtaa    780
gacacgactt atcgccactg gcagcagcca ctggtaacag gattagcaga gcgaggtatg    840
taggcggtgc tacagagttc ttgaagtggt ggcctaacta cggctacact agaaggacag    900
tatttggtat ctgcgctctg ctgaagccag ttaccttcgg aaaaagagtt ggtagctctt    960
gatccggcaa acaaaccacc gctggtagcg gtggtttttt tgtttgcaag cagcagatta   1020
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
ccgcctccat ccagtctatt aattgttgcc gggaagctag agtaagtagt tcgccagtta   1500
atagtttgcg caacgttgtt gccattgcta caggcatcgt ggtgtcacgc tcgtcgtttg   1560
gtatggcttc attcagctcc ggttcccaac gatcaaggcg agttacatga tcccccatgt   1620
```

```
tgtgcaaaaa agcggttagc tccttcggtc ctccgatcgt tgtcagaagt aagttggccg    1680
cagtgttatc actcatggtt atggcagcac tgcataattc tcttactgtc atgccatccg    1740
taagatgctt ttctgtgact ggtgagtact caaccaagtc attctgagaa tagtgtatgc    1800
ggcgaccgag ttgctcttgc ccggcgtcaa tacgggataa taccgcgcca catagcagaa    1860
ctttaaaagt gctcatcatt ggaaaacgtt cttcggggcg aaaactctca aggatcttac    1920
cgctgttgag atccagttcg atgtaaccca ctcgtgcacc caactgatct tcagcatctt    1980
ttactttcac cagcgtttct gggtgagcaa aaacaggaag gcaaaatgcc gcaaaaaagg    2040
gaataagggc gacacggaaa tgttgaatac tcatactctt cctttttcaa tattattgaa    2100
gcatttatca gggttattgt ctcatgagcg gatacatatt tgaatgtatt tagaaaaata    2160
aacaaatagg ggttccgcgc acatttcccc gaaaagtgcc acctgacgtc taagaaacca    2220
ttattatcat gacattaacc tataaaaata ggcgtatcac gaggccctt cgtctcgcgc    2280 gtttcggtga tgacggtgaa aacctctgac acatgcagct cccggagacg gtcacagctt    2340
gtctgtaagc ggatgccggg agcagacaag cccgtcaggg cgcgtcagcg ggtgttggcg    2400
ggtgtcgggc tggcttaac tatgcggcat cagagcagat tgtactgaga gtgcaccata    2460
tgcggtgtga ataccgcac agatgcgtaa ggagaaaata ccgcatcagg cgccattcgc    2520
cattcaggct gcgcaactgt tgggaagggc gatcggtgcg ggcctcttcg ctattacgcc    2580
agctggcgaa aggggggatgt gctgcaaggc gattaagttg ggtaacgcca gggttttccc    2640
agtcacgacg ttgtaaaacg acggccagtg aattcgagct cggtacccgg ggatcctcta    2700
gagtcgaatc acaagtttgt acaaaaaagc aggctgtaag tttgtggatt cttcgtccat    2760
gtgatctttg agtttctta gagcttgtga gggattagta agtaacaatg cttgagtttt    2820
ttgctgctgg gcttcgaaaa gtttgtcact tgttggttg atccacaagg tcttcttctc    2880
catagctact agacatgttt tagcttaaga ttcaagttta tatatgcctt gtggattaat    2940
cattgcctga ttcttccgtg tcatctctga gtttatttag agcttggaag tggtgtagta    3000
ataactaaca atactcttga taagttgtag caatgctctt gattagtgga tgtaatatga    3060
tgttgataag atatatgagg cacagaacca aaagtggtgc ttccactaga cccgttttta    3120
gcctaaggtt caagtttata ccttgtagat gtttctgtat tgtctgattc ttccctgtga    3180
tatttgaatt tcttagagct ttggaagtga tagggaaca atgctcttgt gtgtttgtct    3240
ctatgaagat tatcgctgtc gtgtttcatc cgagtgtgcg ggatttttg ctgctgggtt    3300 tagcctttct tcaaaaagtt attacttgtt agttttattg ttttggtctt gataagagat    3360
gttaggacag acatggtgct tcttgtctat agccactaga cctatttag cataaggtta    3420 acgaaattct ctctacatac cttgtggatt tgtttacatt gcctgatctt tcctgtgatc    3480
gctgtcatgt ttctttggaa tgattgatgt ttataaatgg aaaaatcttt gtgcaggttt    3540
aaacgtttac gttaagcacc ctgctgatat ccctgattac aagaagcttt cattccctga    3600
gggattcaag tgggagagag ttatgaactt cgaggatggt ggtgttgcta ctgttactca    3660
ggattcttca cttcaggacg gatgcttcat ctacaaggtt aagttcatcg gagtgaactt    3720
cccttctgat ggacctgtta tgcagaaaaa gactatggga tgggaggctt ctaccgagag    3780
actttaccct agagatggtg ttcttaaggg tgagactcac aaggctctta agcttaaaga    3840
tggtggacac tacctcgtcg agttcaagtc tatctcatg gctaagaagc ctgttcagct    3900
tcctggttac tactacgttg acgctaagct tgatatcacc tctcacaacg aggactacac    3960
```

```
tatcgttgag caatacgaga gaactgaggg tagacatcac ttgttcctct gatatcaaaa    4020
tctatttaga aatacacaat attttgttgc aggcttgctg gagaatcgat ctgctatcat    4080
aaaaattaca aaaaaatttt atttgcctca attattttag gattggtatt aaggacgctt    4140
aaattatttg tcgggtcact acgcatcatt gtgattgaga agatcagcga tacgaaatat    4200
tcgtagtact atcgataatt tatttgaaaa ttcataagaa aagcaaacgt tacatgaatt    4260
gatgaaacaa tacaaagaca gataaagcca cgcacattta ggatattggc cgagattact    4320
gaatattgag taagatcacg gaatttctga caggagcatg tcttcaattc agcccaaatg    4380
gcagttgaaa tactcaaacc gccccatatg caggagcgga tcattcattg tttgtttggt    4440
tgcctttgcc aacatgggag tccaaggttg ccttttgcag tttatctcta tgcccgggac    4500
aagtgaagac tcccgcccat ctcactaggg acaggattgg agtccatgct caacaccgtg    4560
caggatgagg atgaccaaca actttgtata caaaagttgt atccgaagta aataaaacca    4620
tcggactctc gtataagact gtcgacgaga ttttcaaat cagtgcgcta gacgtgacgt     4680
aagtatccga gtcagttttt attttctac taatttggtc gtttatttcg gcgtgtagga     4740
catggcaacc gggcctgaat ttcgcgggta ttctgtttct attccaactt tttcttgatc    4800
cgcagccatt aacgactttt gaatagatac gtctagggtc gagggggat ccgtcgaggg     4860 ggtccaccaa aaacgtaagc gcttacgtac atggtcgagg gggtccacca aaaacgtaag    4920
cgcttacgta catggtcgag ggggtccacc aaaaacgtaa gcgcttacgt acatggtcga    4980 ggggtccac caaaaacgta agcgcttacg tacatgctcg actagagcgt gacgctcgcg     5040
gtgacgccat ttcgcctttt cagaaatgga taaatagcct tgcttcctat tatatcttcc    5100
caaattacca atacattaca ctagcatctg aatttcataa ccaatctcga tacaccaaat    5160
cgatggctca atctagcaga atctgccacg gtgtgcagaa cccatgtgtg atcatttcca    5220
atctctccaa atccaaccag aacaaatctc cttcctcagt cagcctcaag actcaccagc    5280
agcagcgtcg tgcttaccag atatctagct ggggattgaa gaagtcaaac aacgggtccg    5340
tgattcgtcc ggttaaggca gctgcaagag ggatgccagc cttgtcttta cctggatcaa    5400
agagtatcac agctagggca ctcttttcttg ctgctgctgc tgatgggtt actactttgg    5460 tgaggccatt gagaagtgac gacacagaag gattcgctga ggggttagtt cgtttaggct    5520
atcgtgtagg gaggacaccc gatacttggc aagtcgatgg cagaccacaa ggaccagcag    5580
tggctgaggc tgacgtctac tgtagagacg gagcaaccac cgctagattc ttgccaacct    5640
tagcagctgc tggtcacgga acatacagat ttgatgcttc accacagatg aggagacgtc    5700
ctcttttgcc cttaagcaga gccttgaggg atttgggtgt cgatcttaga cacgaagaag    5760
ctgaaggtca tcaccctctg actgtccgtg ctgctgggt tgaaggagga gaggttactt     5820
tggatgctgg tcagtcaagt cagtatctca ctgccttgtt gctccttggt ccccttacaa    5880
gacaaggact gaggataagg gttactgatt tggtgtcagc accatacgtg gagattacgc    5940
ttgcaatgat gagggctttc ggagttgaag tggcaaggga gggagatgtg ttcgttgttc    6000
cacctggtgg atatcgtgca actacgtatg ctatagaacc cgacgcaagt actgcttctt    6060
acttcttcgc agctgctgct ttgactcctg gagctgaagt gactgtacct gggttaggca    6120
cgggagcact tcaaggagat ttgggatttg tagatgtctt aaggagaatg ggagccgagg    6180
tgtccgtagg agctgatgca accactgtta gaggaactgg tgaattgcgt ggccttacag    6240
ccaacatgag agacataagt gatacgatgc cgacccctcgc tgcaatagca cccttttgcta   6300 gtgctccagt tagaatcgag gatgttgcca acactcgtgt caaagaatgt gacagacttg    6360
```

```
aggcttgtgc agagaacctt aggaggttgg gagtaagggt tgcaacgggt ccggactgga    6420
ttgagataca ccctggtcca gctactggtg ctcaagtcac aagctatggt gatcacagaa    6480
ttgtgatgtc atttgcagtg actggacttc gtgtgcctgg gatcagcttc gacgaccctg    6540
gctgtgttcg taagactttt cctgggtttc acgaggcttt cgcagaattg aggcgtggca    6600
ttgggagctg atgagtagtt agcttaatca cctaagatcg gcggcaatag cttcttagcg    6660
ccatcccggg ttgatcctat ctgtgttgaa atagttgcgg tgggcaaggc tctctttcag    6720
aaagacaggc ggccaaagga acccaaggtg aggtgggcta tggctctcag ttccttgtgg    6780
aagcgcttgg tctaaggtgc agaggtgtta gcgggatgaa gcaaaagtgt ccgattgtaa    6840
caagatatgt tgatcctacg taaggatatt aaagtatgta ttcatcacta atataatcag    6900
tgtattccaa tatgtactac gatttccaat gtctttattg tcgccgtatg taatcggcgt    6960
cacaaaataa tccccggtga ctttctttta atccaggatg aaataatatg ttattataat    7020
ttttgcgatt tggtccgtta taggaattga agtgtgcttg cggtcgccac cactcccatt    7080
tcataatttt acatgtattt gaaaataaaa aatttatggt attcaattta aacacgtata    7140
cttgtaaaga atgatatctt gaaagaaata tagtttaaat attttattgat aaaataacaa    7200 gtcaggtatt atagtccaag caaaaacata aatttattga tgcaagttta aattcagaaa    7260
tatttcaata actgattata tcagctggta cattgccgta gatgaaagac tgagtgcgat    7320
attatggtgt aatacatacg gccgacgcat aggttcattt gaagctgcta ttctatttag    7380
attgaagttt aaacccagaa ggtaattatc caagatgtag catcaagaat ccaatgttta    7440
cgggaaaaac tatggaagta ttatgtaagc tcagcaagaa gcagatcaat atgcggcaca    7500
tatgcaacct atgttcaaaa atgaagaatg tacagataca agatcctata ctgccagaat    7560
acgaagaaga atacgtagaa attgaaaaag aagaaccagg cgaagaaaag aatcttgaag    7620
acgtaagcac tgacgacaac aatgaaaaga agaagataag gtcggtgatt gtgaaagaga    7680
catagaggac acatgtaagg tggaaaatgt aagggcggaa agtaaccttta tcacaaagga    7740 atcttatccc ccactactta tccttttata tttttccgtg tcattttgc ccttgagttt    7800 tcctatataa ggaaccaagt tcggcatttg tgaaaacaag aaaaaatttg gtgtaagcta    7860
ttttctttga agtactgagg atacaacttc agagaaattt gtaagtttgt aatgtctccg    7920
gagaggagac cagttgagat taggccagct acagcagctg atatggccgc ggtttgtgat    7980
atcgttaacc attacattga gacgtctaca gtgaactttta ggacagagcc acaaacacca    8040
caagagtgga ttgatgatct cgagaggttg caagatagat acccttggtt ggttgctgag    8100
gttgagggtg ttgtggctgg tattgcttac gctgggccct ggaaggctag aacgcttac    8160 gattggacag ttgagagtac tgtttacgtg tcacataggc atcaaaggtc agttttactt    8220
cccttaattt tctatgtact ttcataatta cttatgttat tttcttcatg agttttaatg    8280
caaattacta tatggactct agtgaaaacg ttcagaatcc tataaacatg actactgaga    8340
cgaacttgag agtagttttg atcatacaca cgtttcatgt ggtacttgag agttactaat    8400
ttttgtcatc ttcgtataag tagtaaaaga tactacaaga atagtttagt agaaaatact    8460
agcggtaggt gaagatttgt cgctatgtac tattattgtc tagtaacttg agtaacaatt    8520
tcgtggtcta aatatcaaat aaaaatggat gagtggttca ccaaatctag gcatcaaaac    8580
tattaatgtc attgtctaga tcttaggtga caccacattt cgaatatttta ttggtaattg    8640 agatgttaaa gtaccaatat ttgacttaat aaactaaaag attttggctt tatcaaatgt    8700
```

```
agacattgat gacatatcgt tgtcattatc ttgagtatat acaagtcgat caattaggtg    8760
aaagtttagt gtctcgtggt tggtaaacga ttaatacagt agtatatttt atccaaagac    8820
aaaatccaaa tcatttcacc agtatgaata gtattatttt atcttaaaag ctaaaatctt    8880
aaaaaccaag gtagcaccca cgttgagcta gacgatcaaa tcgatttctg ctttgtccaa    8940
tttaccaagc tatttaaagc caaataattg aaatataggt aggtcgttat attaggctaa    9000
gatttatctc aaatgcttaa ctaaaggaat aacaagggat tctagttgtg tggttttata    9060
agattggtcc aatttcactt aagtttgttt attgtagaat tttatatgtg aataatttga    9120
attccaattg aaaagatatt atagtaaaag aaaaaatagt gcgaacaaaa aactttaatc    9180
ccataaaaag aaaaagaaaa atgaaaagtt cttctaacat ccatatttg catcatatca     9240 taaagataag aaagatacat atcatagacg tacagataaa caaacatatc atcatttgtg    9300
aaatacatag tacaataatt tgcttttaaa tagagtttaa gtcacacaca ctgacacaca    9360
cgataaaacg ataatgtctg caaaaacact ttaatcccat tgcctagagg acagcttctc    9420
cactttgtct ttaaggttgg ttttgccgtg ttgttttttat ctttatataa tgatctattt    9480
tttggattat gaaatgaatt cacacatttt aattatttaa gaagatccat atacaggttt    9540
ataacagtac taagtgatga ttatttttg ttttttgcata gtttagttta ttgggtaaac    9600
attcattacg tgtctcttta tacgaatcac ccatccaaaa tttcaagtag tcttttagtt    9660
catttattat ttcataacta tttgacttat tgatttgaca agaaacaaca aaagtgttga    9720
cttattgata gattgtggga tcataaaagt aattaagcgt caaccacgac ccacaacaac    9780
aaagcacatg ttatacatta atatctcgtt tacttaatta cagttttcag aatgccgttt    9840
catgtcttgt cactggcgat gttattatca tgttggacaa tattcgactg ttgtcgtttt    9900
tacattttcg tattgactaa aactaaaaaa acaaaactct gtttcagacc cagcttttc     9958
```

<210> SEQ ID NO 92
<211> LENGTH: 10735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

```
ctaaattgta agcgttaata ttttgttaaa attcgcgtta aattttttgtt aaatcagctc      60 attttttaac caataggccg aaatcggcaa atcccttat aaatcaaaag aatagaccga      120
gatagggttg agtggccgct acagggcgct cccattcgcc attcaggctg cgcaactgtt     180
gggaagggcg tttcggtgcg ggcctcttcg ctattacgcc agctggcgaa agggggatgt     240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatg gcgcgccggg gacaagtttg tacaaaaaag caggctgcgg ccgcgaaata    420
tccttcctat tcaaagttat atatattgt ttacttttgt tttagatctg gacctgagac     480
atgtaagtac atatttgttg aatctttggg taaaaactta tgtctctggg taaaatttgc    540
tgagagattt gaccgattcc tattggctct ggattctgta gttacctaat acatgaaaaa    600
gtttcatttg gcctatgctc acttcatgct tataaacttt tcttgcaaa ttaattggat     660 tagatgctcc ttcatagatt cagatgcaat agatttgcat gaagaaaata ataggattca    720
tgatagtaaa aagattgtat ttttgtttgt tgtttatgt ttaaaagtct atatgttgac      780
```

| | |
|---|---|
| aatagagttg ctatcaactg tttcatttag gtttatgttt ttgtcaagtt gcttattcta | 840 |
| agagacattg tgattatgac ttgtcttctc taacgtagtt tagtaataaa agacgaaaga | 900 |
| aattgatatc cacaagaaag agatgtaagc tgtaacgtat caaatctcat taataactag | 960 |
| tagtattctc aacgctatcg tttatttctt tctttggttt gccactatat gccgcttctc | 1020 |
| tgctctttat cccacgtact atccattttt tttgtggtag tccatttttt tgaaacttta | 1080 |
| ataacgtaac actgaatatt aatttgttgg tttaattaac tttgagtctt tgcttttggt | 1140 |
| ttatgcagaa acatgggtgc aggtggaaga atgcaagtgt ctcctccctc caaaaagtct | 1200 |
| gaaaccgaca acatcaagcg cgtaccctgc gagacaccgc ccttcactgt cggagaactc | 1260 |
| aagaaagcaa tcccaccgca ctgtttcaaa cgctcgatcc ctcgctcttt ctcctacctc | 1320 |
| atctgggaca tcatcatagc ctcctgcttc tactacgtcg ccaccactta cttccctctc | 1380 |
| ctccctcacc ctctctccta cttcgcctgg cctctctact gggccggtac cgtcgacaag | 1440 |
| cttcttgcct caattccgga ggtgtttcta gtgttcaaca tgacaaacaa aacccatctc | 1500 |
| tttcagtata tgtctctcag ttgtgcttaa ttcaaatttc aactcagaga acttcttggc | 1560 |
| atacttatcc agattatcta atgatctcat ctaatggtaa ttcaactttc agtatatgtc | 1620 |
| tcgcagcaaa ctatctttac atcaaatttt taacaactca atgcacaaaa tactttttcct | 1680 |
| caacctaaaa ataaggcaat tagccaaaaa caactttgcg tgtgaacaac gcgttacacg | 1740 |
| tccctacaca tacgtgtcaa tttataattg gctattgctt ccacgcctta gctttctcgt | 1800 |
| gaccgaccga gtcgtcctcg tcttttttgc ttctataaat caaataccca aagagctctt | 1860 |
| cttcttcaca attcagattc caattttctc aaactctaaa atcaatctct caaatctctc | 1920 |
| aaccgtgatc aaggtagatt tctgagttct tattgtattt cttcgatttg tttcgttcga | 1980 |
| tcgcaattta ggctctgttc tttgattttg atctcgttaa tctctgatcg gaggcaaatt | 2040 |
| acatagtttc atcgttagat ctcttcttat ttctcgatta gggttcgtat ttttcgcaga | 2100 |
| tctgtttatt ttcttgttgt ttccttgtat ttgatccgat ttgttgaaag aatttgtgtg | 2160 |
| ttctcgatta tttacgcttt gatctgtgat ttttatctag atttggtgtt agtttcttgt | 2220 |
| ttgtgcgatc gaatttgtcg attaatctcg gtttttctga ttaacagatg gctcaatcta | 2280 |
| gcagaatctg ccacggtgtg cagaacccat gtgtgatcat ttccaatctc tccaaatcca | 2340 |
| accagaacaa atctcctttc tcagtcagcc tcaagactca ccagcagcag cgtcgtgctt | 2400 |
| accagatatc tagctgggga ttgaagaagt caaacaacgg gtccgtgatt cgtccggtta | 2460 |
| aggcagctgc aagagggatg ccagccttgt ctttacctgg atcaaagagt atcacagcta | 2520 |
| gggcactctt tcttgctgct gctgctgatg gggttactac tttggtgagg ccattgagaa | 2580 |
| gtgacgacac agaaggattc gctgaggggt tagttcgttt aggctatcgt gtagggagga | 2640 |
| cacccgatac ttggcaagtc gatggcagac cacaaggacc agcagtggct gaggctgacg | 2700 |
| tctactgtag agacggagca accaccgcta gattcttgcc aaccttagca gctgctggtc | 2760 |
| acggaacata cagatttgat gcttcaccac agatgaggag acgtcctctt ttgcccttaa | 2820 |
| gcagagcctt gagggatttg ggtgtcgatc ttagacacga agaagctgaa ggtcatcacc | 2880 |
| ctctgactgt ccgtgctgct ggggttgaag gaggagaggt tactttggat gctggtcagt | 2940 |
| caagtcagta tctcactgcc ttgttgctcc ttggtcccct tacaagacaa ggactgagga | 3000 |
| taagggttac tgatttggtg tcagcaccat acgtggagat tacgcttgca atgatgaggg | 3060 |
| cttttcggagt tgaagtggca agggagggag atgtgttcgt tgttccacct ggtggatatc | 3120 |
| gtgcaactac gtatgctata gaacccgacg caagtactgc ttcttacttc ttcgcagctg | 3180 |

| | | | | |
|---|---|---|---|---|
| ctgctttgac | tcctggagct | gaagtgactg | tacctgggtt | aggcacggga | gcacttcaag | 3240 |
| gagatttggg | atttgtagat | gtcttaagga | gaatgggagc | cgaggtgtcc | gtaggagctg | 3300 |
| atgcaaccac | tgttagagga | actggtgaat | tgcgtggcct | tacagccaac | atgagagaca | 3360 |
| taagtgatac | gatgccgacc | ctcgctgcaa | tagcacccct | tgctagtgct | ccagttagaa | 3420 |
| tcgaggatgt | tgccaacact | cgtgtcaaag | aatgtgacag | acttgaggct | tgtgcagaga | 3480 |
| acctaggag | gttgggagta | agggttgcaa | cgggtccgga | ctggattgag | atacaccctg | 3540 |
| gtccagctac | tggtgctcaa | gtcacaagct | atggtgatca | cagaattgtg | atgtcatttg | 3600 |
| cagtgactga | acttcgtgtg | cctgggatca | gcttcgacga | ccctggctgt | gttcgtaaga | 3660 |
| cttttcctgg | gtttcacgag | gctttcgcag | aattgaggcg | tggcattggg | agctgatgag | 3720 |
| tagttagctt | aatcacctaa | gatcggcggc | aatagcttct | tagcgccatc | ccggttgat | 3780 |
| cctatctgtg | ttgaaatagt | tgcggtgggc | aaggctctct | ttcagaaaga | caggcggcca | 3840 |
| aaggaaccca | aggtgaggtg | ggctatggct | ctcagttcct | tgtggaagcg | cttggtctaa | 3900 |
| ggtgcagagg | tgttagcggg | atgaagcaaa | agtgtccgat | tgtaacaaga | tatgttgatc | 3960 |
| ctacgtaagg | atattaaagt | atgtattcat | cactaatata | atcagtgtat | tccaatatgt | 4020 |
| actacgattt | ccaatgtctt | tattgtcgcc | gtatgtaatc | ggcgtcacaa | aataatcccc | 4080 |
| ggtgactttc | ttttaatcca | ggatgaaata | atatgttatt | ataattttg | cgatttggtc | 4140 |
| cgttatagga | attgaagtgt | gcttgcggtc | gccaccactc | ccatttcata | attttacatg | 4200 |
| tatttgaaaa | ataaaaattt | atggtattca | atttaaacac | gtatacttgt | aaagaatgat | 4260 |
| atcttgaaag | aaatatagtt | taaatattta | ttgataaaat | aacaagtcag | gtattatagt | 4320 |
| ccaagcaaaa | acataaattt | attgatgcaa | gtttaaattc | agaaatattt | caataactga | 4380 |
| ttatatcagc | tggtacattg | ccgtagatga | aagactgagt | gcgatattat | ggtgtaatac | 4440 |
| atacggccgc | cagaaggtaa | ttatccaaga | tgtagcatca | agaatccaat | gtttacggga | 4500 |
| aaaactatgg | aagtattatg | taagctcagc | aagaagcaga | tcaatatgcg | gcacatatgc | 4560 |
| aacctatgtt | caaaaatgaa | gaatgtacag | atacaagatc | ctatactgcc | agaatacgaa | 4620 |
| gaagaatacg | tagaaattga | aaagaagaa | ccaggcgaag | aaaagaatct | tgaagacgta | 4680 |
| agcactgacg | acaacaatga | aaagaagaag | ataaggtcgg | tgattgtgaa | agagacatag | 4740 |
| aggacacatg | taaggtggaa | aatgtaaggg | cggaaagtaa | ccttatcaca | aaggaatctt | 4800 |
| atcccccact | acttatcctt | ttatatttt | ccgtgtcatt | tttgcccttg | agttttccta | 4860 |
| tataaggaac | caagttcggc | atttgtgaaa | acaagaaaaa | atttggtgta | agctattttc | 4920 |
| tttgaagtac | tgaggataca | acttcagaga | aatttgtaag | tttgtaatgt | ctccggagag | 4980 |
| gagaccagtt | gagattaggc | cagctacagc | agctgatatg | gccgcggttt | gtgatatcgt | 5040 |
| taaccattac | attgagacgt | ctacagtgaa | ctttaggaca | gagccacaaa | caccacaaga | 5100 |
| gtggattgat | gatctcgaga | ggttgcaaga | tagatacctt | tggttggttg | ctgaggttga | 5160 |
| gggtgttgtg | gctggtattg | cttacgctgg | gccctggaag | gctaggaacg | cttacgattg | 5220 |
| gacagttgag | agtactgttt | acgtgtcaca | taggcatcaa | aggtcagttt | tacttcccctt | 5280 |
| aattttctat | gtactttcat | aattacttat | gttattttct | tcatgagttt | taatgcaaat | 5340 |
| tactatatgg | actctagtga | aaacgttcag | aatcctataa | acatgactac | tgagacgaac | 5400 |
| ttgagagtag | ttttgatcat | acacacgttt | catgtggtac | ttgagagtta | ctaattttg | 5460 |
| tcatcttcgt | ataagtagta | aaagatacta | caagaatagt | ttagtagaaa | atactagcgg | 5520 |

```
taggtgaaga tttgtcgcta tgtactatta ttgtctagta acttgagtaa caatttcgtg   5580
gtctaaatat caaataaaaa tggatgagtg gttcaccaaa tctaggcatc aaaactatta   5640
atgtcattgt ctagatctta ggtgacacca catttcgaat atttattggt aattgagatg   5700
ttaaagtacc aatatttgac ttaataaact aaaagatttt ggctttatca aatgtagaca   5760
ttgatgacat atcgttgtca ttatcttgag tatatacaag tcgatcaatt aggtgaaagt   5820
ttagtgtctc gtggttggta aacgattaat acagtagtat attttatcca agacaaaat   5880
ccaaatcatt tcaccagtat gaatagtatt attttatctt aaaagctaaa atcttaaaaa   5940
ccaaggtagc acccacgttg agctagacga tcaaatcgat ttctgctttg tccaatttac   6000
caagctattt aaagccaaat aattgaaata taggtaggtc gttatattag gctaagattt   6060
atctcaaatg cttaactaaa ggaataacaa gggattctag ttgtgtggtt ttataagatt   6120
ggtccaattt cacttaagtt tgtttattgt agaattttat atgtgaataa tttgaattcc   6180
aattgaaaag atattatagt aaaagaaaaa atagtgcgaa caaaaaactt taatcccata   6240
aaagaaaaa gaaaaatgaa aagttcttct aacatccata ttttgcatca tatcataaag   6300
ataagaaaga tacatatcat agacgtacag ataaacaaac atatcatcat ttgtgaaata   6360
catagtacaa taatttgctt ttaaatagag tttaagtcac acacactgac acacacgata   6420
aaacgataat gtctgcaaaa acactttaat cccattgcct agaggacagc ttctccactt   6480
tgtctttaag gttggttttg ccgtgttgtt tttatcttta tataatgatc tatttttggg   6540
attatgaaat gaattcacac attttaatta tttaagaaga tccatataca ggtttataac   6600
agtactaagt gatgattatt ttttgttttt gcatagttta gtttattggg taaacattca   6660
ttacgtgtct ctttatacga atcacccatc caaaatttca agtagtcttt tagttcattt   6720
attatttcat aactatttga cttattgatt tgacaagaaa caacaaaagt gttgacttat   6780
tgatagattg tgggatcata aaagtaatta agcgtcaacc acgacccaca caacaaagc   6840
acatgttata cattaatatc tcgtttactt aattacagtt ttcagaatgc cgtttcatgt   6900
cttgtcactg gcgatgttat tatcatgttg acaatattc gactgttgtc gttttttacat   6960
tttcgtattg actaaaacta aaaaaacaaa actctgtttc aggttgggcc taggatccac   7020
attgtacaca catttgctta agtctatgga ggcgcaaggt tttaagtctg tggttgctgt   7080
tataggcctt ccaaacgatc catctgttag gttgcatgag gctttgggat acacagcccg   7140
gggtacattg cgcgcagctg gatacaagca tggtggatgg catgatgttg gttttttggca   7200
aagggatttt gagttgccag ctcctccaag gccagttagg ccagttaccc agatctaata   7260
tcaaaatcta tttagaaata cacaatattt tgttgcaggc ttgctggaga atcgatctgc   7320
tatcataaaa attacaaaaa aattttattt gcctcaatta ttttaggatt ggtattaagg   7380
acgcttaaat tatttgtcgg gtcactacgc atcattgtga ttgagaagat cagcgatacg   7440
aaatattcgt agtactatcg ataatttatt tgaaaattca taagaaaagc aaacgttaca   7500
tgaattgatg aaacaataca aagacagata aagccacgca catttaggat attggccgag   7560
attactgaat attgagtaag atcacggaat ttctgacagg agcatgtctt caattcagcc   7620
caaatggcag ttgaaatact caaaccgccc catatgcagg agcggatcat tcattgtttg   7680
tttggttgcc tttgccaaca tgggagtcca aggttgcatg ccagggctgc gtcctaaccg   7740
gcgtctgggt catagcccac gagtgcggcc accacgcctt cagcgactac cagtggctgg   7800
acgacaccgt cggcctcatc ttccactcct tcctcctcgt cccttacttc tcctggaagt   7860
acagtcatcg acgccaccat tccaacactg gctccctcga gagagacgaa gtgtttgtcc   7920
```

```
ccaagaagaa gtcagacatc aagtggtacg gcaagtacct caacaaccct tgggacgca    7980
ccgtgatgtt aacggttcag ttcactctcg gctggccttt gtacttagcc ttcaacgtct   8040
cggggagacc ttacgacggc ggcttcgctt gccatttcca ccccaacgct cccatctaca   8100
acgaccgtga gcgtctccag atatacatct ccgacgctgg catcctcgcc gtctgctacg   8160
gtctctaccg ctacgctgct gtccaaggag ttgcctcgat ggtctgcttc tacggagttc   8220
ctcttctgat tgtcaacggg ttcttagttt tgatcactta cttgcagcac acgcatcctt   8280
ccctgcctca ctatgactcg tctgagtggg attggttgag gggagctttg gccaccgttg   8340
acagagacta cggaatcttg aacaaggtct tccacaatat cacggacacg cacgtggcgc   8400
atcacctgtt ctcgaccatg ccgcattatc acgcgatgga agctacgaag gcgataaagc   8460
cgatactggg agagtattat cagttcgatg ggacgccggt ggttaaggcg atgtggaggg   8520
aggcgaagga gtgtatctat gtggaaccgg acaggcaagg tgagaagaaa ggtgtgttct   8580
ggtacaacaa taagttatga agcaaagaag aaactgaacc tttctcatct atgattgtct   8640
ttgttttaag aagctatgtt tctgtttcaa taatctttaa ttatccattt tgttgtgttt   8700
tctgacattt tggctaaaat ggcgccaccc agctttcttg tacaaagtgg tccccttaat   8760
taactgggcc tcatgggcct tccgctcact gcccgctttc cagtcgggaa acctgtcgtg   8820
ccagctgcat taacatggtc atagctgttt ccttgcgtat tgggcgctct ccgcttcctc   8880
gctcactgac tcgctgcgct cggtcgttcg ggtaaagcct ggggtgccta atgagcaaaa   8940
ggccagcaaa aggccaggaa ccgtaaaaag gccgcgttgc tggcgttttt ccataggctc   9000
cgccccctg acgagcatca caaaaatcga cgctcaagtc agaggtggcg aaacccgaca    9060
ggactataaa gataccaggc gtttccccct ggaagctccc tcgtgcgctc tcctgttccg   9120
accctgccgc ttaccggata cctgtccgcc tttctccctt cgggaagcgt ggcgctttct   9180
catagctcac gctgtaggta tctcagttcg gtgtaggtcg ttcgctccaa gctgggctgt   9240
gtgcacgaac ccccgttca gcccgaccgc tgcgccttat ccggtaacta tcgtcttgag    9300
tccaacccgg taagacacga cttatcgcca ctggcagcag ccactggtaa caggattagc   9360
agagcgaggt atgtaggcgg tgctacagag ttcttgaagt ggtggcctaa ctacggctac   9420
actagaagaa cagtatttgg tatctgcgct ctgctgaagc cagttacctt cggaaaaaga   9480
gttggtagct cttgatccgg caaacaaacc accgctggta gcggtggttt ttttgtttgc   9540
aagcagcaga ttacgcgcag aaaaaaagga tctcaagaag atcctttgat cttttctacg   9600
gggtctgacg ctcagtggaa cgaaaactca cgttaaggga ttttggtcat gagattatca   9660
aaaaggatct tcacctagat ccttttaaat taaaatgaa gttttaaatc aatctaaagt    9720
atatatgagt aaacttggtc tgacagttac caatgcttaa tcagtgaggc acctatctca   9780
gcgatctgtc tatttcgttc atccatagtt gcctgactcc ccgtcgtgta dataactacg   9840
atacgggagg gcttaccatc tggccccagt gctgcaatga taccgcgaga accacgctca   9900
ccggctccag atttatcagc aataaaccag ccagccggaa gggccgagcg cagaagtggt   9960
cctgcaactt tatccgcctc catccagtct attaattgtt gccgggaagc tagagtaagt  10020
agttcgccag ttaatagttt gcgcaacgtt gttgccattg ctacaggcat cgtggtgtca  10080
cgctcgtcgt ttggtatggc ttcattcagc tccggttccc aacgatcaag gcgagttaca  10140
tgatccccca tgttgtgcaa aaaagcggtt agctccttcg gtcctccgat cgttgtcaga  10200
agtaagttgg ccgcagtgtt atcactcatg gttatggcag cactgcataa ttctcttact  10260
```

```
gtcatgccat ccgtaagatg cttttctgtg actggtgagt actcaaccaa gtcattctga    10320
gaatagtgta tgcggcgacc gagttgctct tgcccggcgt caatacggga taataccgcg    10380
ccacatagca gaactttaaa agtgctcatc attggaaaac gttcttcggg gcgaaaactc    10440
tcaaggatct taccgctgtt gagatccagt tcgatgtaac ccactcgtgc acccaactga    10500
tcttcagcat cttttacttt caccagcgtt tctgggtgag caaaaacagg aaggcaaaat    10560
gccgcaaaaa agggaataag ggcgacacgg aaatgttgaa tactcatact cttcctttt    10620 caatattatt gaagcattta tcagggttat tgtctcatga gcggatacat atttgaatgt    10680
atttagaaaa ataaacaaat aggggttccg cgcacatttc cccgaaaagt gccac        10735
```

<210> SEQ ID NO 93
<211> LENGTH: 10421
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa aggggggatgt    240 gctgcaaggc gattaagttg ggtaacgcca gggttttccc agtcacgacg ttgtaaaacg     300
acggccagtg agcgcgacgt aatacgactc actatagggc gaattggcgg aaggccgtca    360
aggccgcatg gcgcgccggg acaagtttg tacaaaaaag caggctgcgg ccgcgaaata    420
tccttcctat tcaaagttat atatatttgt ttacttttgt tttagatctg gacctgagac     480
atgtaagtac atatttgttg aatctttggg taaaaactta tgtctctggg taaaatttgc     540
tgagagattt gaccgattcc tattggctct ggattctgta gttacctaat acatgaaaaa     600
gtttcatttg gcctatgctc acttcatgct tataaacttt ttcttgcaaa ttaattggat     660
tagatgctcc ttcatagatt cagatgcaat agatttgcat gaagaaaata ataggattca     720
tgatagtaaa aagattgtat ttttgtttgt tgtttatgt ttaaaagtct atatgttgac     780
aatagagttg ctatcaactg tttcatttag gtttatgttt ttgtcaagtt gcttattcta     840
agagacattg tgattatgac ttgtcttctc taacgtagtt tagtaataaa agacgaaaga     900
aattgatatc cacaagaaag agatgtaagc tgtaacgtat caaatctcat taataactag     960
tagtattctc aacgctatcg tttatttctt tctttggttt gccactatat gccgcttctc    1020
tgctctttat cccacgtact atccattttt tttgtggtag tccatttttt tgaaactta    1080 ataacgtaac actgaatatt aatttgttgg tttaattaac tttgagtctt tgcttttggt    1140
ttatgcagaa acatgggtgc aggtggaaga atgcaagtgt ctcctccctc caaaaagtct    1200
gaaaccgaca acatcaagcg cgtaccctgc gagacaccgc ccttcactgt cggagaactc    1260
aagaaagcaa tcccaccgca ctgttttcaaa cgctcgatcc ctcgctcttt ctcctacctc    1320
atctgggaca tcatcatagc ctcctgcttc tactacgtcg ccaccactta cttccctctc    1380
ctccctcacc ctctctccta cttcgcctgg cctctctact gggccggtac cgtcgacgag    1440 attttttcaaa tcagtgcgct agacgtgacg taagtatccg agtcagtttt tattttttcta    1500 ctaatttggt cgtttatttc ggcgtgtagg acatggcaac cgggcctgaa tttcgcgggt    1560
```

```
attctgtttc tattccaact ttttcttgat ccgcagccat taacgacttt tgaatagata    1620
cgtctagggt cgagggggga tccgtcgagg gggtccacca aaaacgtaag cgcttacgta    1680
catggtcgag ggggtccacc aaaaacgtaa gcgcttacgt acatggtcga ggggtccac    1740 caaaaacgta agcgcttacg tacatggtcg aggggtcca ccaaaaacgt aagcgcttac    1800
gtacatgctc gactagagcg tgacgctcgc ggtgacgcca tttcgccttt tcagaaatgg    1860
ataaatagcc ttgcttccta ttatatcttc ccaaattacc aatacattac actagcatct    1920
gaatttcata accaatctcg atacaccaaa tcgatggctc aatctagcag aatctgccac    1980
ggtgtgcaga acccatgtgt gatcatttcc aatctctcca aatccaacca gaacaaatct    2040
cctttctcag tcagcctcaa gactcaccag cagcagcgtc gtgcttacca gatatctagc    2100
tggggattga agaagtcaaa caacgggtcc gtgattcgtc cggttaaggc agctgcaaga    2160
gggatgccag ccttgtcttt acctggatca aagagtatca cagctagggc actctttctt    2220
gctgctgctg ctgatggggt tactactttg gtgaggccat tgagaagtga cgacacagaa    2280
ggattcgctg aggggttagt tcgtttaggc tatcgtgtag gaggacacc cgatacttgg    2340 caagtcgatg gcagaccaca aggaccagca gtggctgagg ctgacgtcta ctgtagagac    2400
ggagcaacca ccgctagatt cttgccaacc ttagcagctg ctggtcacgg aacatacaga    2460
tttgatgctt caccacagat gaggagacgt cctcttttgc ccttaagcag agccttgagg    2520
gatttgggtg tcgatcttag acacgaagaa gctgaaggtc atcaccctct gactgtccgt    2580
gctgctgggg ttgaaggagg agaggttact ttggatgctg gtcagtcaag tcagtatctc    2640
actgccttgt tgctccttgg tccccttaca agacaaggac tgaggataag ggttactgat    2700
ttggtgtcag caccatacgt ggagattacg cttgcaatga tgagggcttt cggagttgaa    2760
gtggcaaggg agggagatgt gttcgttgtt ccacctggtg gatatcgtgc aactacgtat    2820
gctatagaac ccgacgcaag tactgcttct tacttcttcg cagctgctgc tttgactcct    2880
ggagctgaag tgactgtacc tgggttaggc acgggagcac ttcaaggaga tttgggattt    2940
gtagatgtct taaggagaat gggagccgag gtgtccgtag agctgatgc aaccactgtt    3000 agaggaactg tgaattgcg tggccttaca gccaacatga gagacataag tgatacgatg    3060 ccgacccctcg ctgcaatagc acccttgct agtgctccag ttagaatcga ggatgttgcc    3120
aacactcgtg tcaaagaatg tgacagactt gaggcttgtg cagagaacct taggaggttg    3180
ggagtaaggg ttgcaacggg tccggactgg attgagatac accctggtcc agctactggt    3240
gctcaagtca caagctatgg tgatcacaga attgtgatgt catttgcagt gactggactt    3300
cgtgtgcctg ggatcagctt cgacgaccct ggctgtgttc gtaagacttt tcctgggttt    3360
cacgaggctt tcgcagaatt gaggcgtggc attgggagct gatgagtagt tagcttaatc    3420
acctaagatc ggcggcaata gcttcttagc gccatcccgg gttgatccta tctgtgttga    3480
aatagttgcg gtgggcaagg ctctctttca gaaagacagg cggccaaagg aacccaaggt    3540
gaggtgggct atggctctca gttccttgtg gaagcgcttg gtctaaggtg cagaggtgtt    3600
agcgggatga agcaaaagtg tccgattgta acaagatatg ttgatcctac gtaaggatat    3660
taaagtatgt attcatcact aatataatca gtgtattcca atatgtacta cgatttccaa    3720
tgtctttatt gtcgccgtat gtaatcggcg tcacaaaata tccccggtg actttctttt    3780 aatccaggat gaaataatat gttattataa ttttgcgat ttggtccgtt ataggaattg    3840
aagtgtgctt gcggtcgcca ccactcccat ttcataattt tacatgtatt tgaaaaataa    3900
aaatttatgg tattcaattt aaacacgtat acttgtaaag aatgatatct tgaaagaaat    3960
```

```
atagtttaaa tatttattga taaaataaca agtcaggtat tatagtccaa gcaaaaacat    4020
aaatttattg atgcaagttt aaattcagaa atatttcaat aactgattat atcagctggt    4080
acattgccgt agatgaaaga ctgagtgcga tattatggtg taatacatac ggccgccaga    4140
aggtaattat ccaagatgta gcatcaagaa tccaatgttt acgggaaaaa ctatggaagt    4200
attatgtaag ctcagcaaga agcagatcaa tatgcggcac atatgcaacc tatgttcaaa    4260
aatgaagaat gtacagatac aagatcctat actgccagaa tacgaagaag aatacgtaga    4320
aattgaaaaa gaagaaccag gcgaagaaaa gaatcttgaa gacgtaagca ctgacgacaa    4380
caatgaaaag aagaagataa ggtcggtgat tgtgaaagag acatagagga cacatgtaag    4440
gtggaaaatg taagggcgga aagtaacctt atcacaaagg aatcttatcc cccactactt    4500 atcctttat attttccgt gtcattttg cccttgagtt ttcctatata aggaaccaag    4560
ttcggcattt gtgaaaacaa gaaaaaattt ggtgtaagct attttctttg aagtactgag    4620
gatacaactt cagagaaatt tgtaagtttg taatgtctcc ggagaggaga ccagttgaga    4680
ttaggccagc tacagcagct gatatggccg cggtttgtga tatcgttaac cattacattg    4740
agacgtctac agtgaacttt aggacagagc cacaaacacc acaagagtgg attgatgatc    4800
tcgagaggtt gcaagataga tacccttggt tggttgctga ggttgagggt gttgtggctg    4860
gtattgctta cgctgggccc tggaaggcta ggaacgctta cgattggaca gttgagagta    4920
ctgtttacgt gtcacatagg catcaaaggt cagttttact tcccttaatt ttctatgtac    4980
tttcataatt acttatgtta ttttcttcat gagttttaat gcaaattact atatggactc    5040
tagtgaaaac gttcagaatc ctataaacat gactactgag acgaacttga gagtagtttt    5100
gatcatacac acgtttcatg tggtacttga gagttactaa tttttgtcat cttcgtataa    5160
gtagtaaaag atactacaag aatagtttag tagaaaatac tagcggtagg tgaagatttg    5220
tcgctatgta ctattattgt ctagtaactt gagtaacaat ttcgtggtct aaatatcaaa    5280
taaaaatgga tgagtggttc accaaatcta ggcatcaaaa ctattaatgt cattgtctag    5340
atcttaggtg acaccacatt tcgaatattt attggtaatt gagatgttaa agtaccaata    5400
tttgacttaa taaactaaaa gattttggct ttatcaaatg tagacattga tgacatatcg    5460
ttgtcattat cttgagtata tacaagtcga tcaattaggt gaaagtttag tgtctcgtgg    5520
ttggtaaacg attaatacag tagtatattt tatccaaaga caaaatccaa atcatttcac    5580
cagtatgaat agtattattt tatcttaaaa gctaaaatct taaaaaccaa ggtagcaccc    5640
acgttgagct agacgatcaa atcgatttct gctttgtcca atttaccaag ctatttaaag    5700
ccaaataatt gaaatatagg taggtcgtta tattaggcta agatttatct caaatgctta    5760
actaaaggaa taacaaggga ttctagttgt gtggttttat aagattggtc caatttcact    5820
taagtttgtt tattgtagaa tttttatatgt gaataatttg aattccaatt gaaaagatat    5880
tatagtaaaa gaaaaaatag tgcgaacaaa aaactttaat cccataaaaa gaaaagaaa    5940 aatgaaaagt tcttctaaca tccatatttt gcatcatatc ataaagataa gaaagataca    6000
tatcatagac gtacagataa acaaacatat catcatttgt gaaatacata gtacaataat    6060
ttgcttttaa atagagttta agtcacacac actgacacac acgataaaac gataatgtct    6120
gcaaaaacac tttaatccca ttgcctagag gacagcttct ccactttgtc tttaaggttg    6180
gttttgccgt gttgttttta tctttatata atgatctatt ttttggatta tgaaatgaat    6240
tcacacattt taattattta agaagatcca tatacaggtt tataacagta ctaagtgatg    6300
```

```
attattttt   gttttgcat   agtttagttt   attgggtaaa   cattcattac   gtgtctcttt    6360
atacgaatca  cccatccaaa  atttcaagta   gtcttttagt   tcatttatta   tttcataact    6420
atttgactta  ttgatttgac  aagaaacaac   aaaagtgttg   acttattgat   agattgtggg    6480
atcataaaag  taattaagcg  tcaaccacga   cccacaacaa   caaagcacat   gttatacatt    6540
aatatctcgt  ttacttaatt  acagttttca   gaatgccgtt   tcatgtcttg   tcactggcga    6600
tgttattatc  atgttggaca  atattcgact   gttgtcgttt   ttacattttc   gtattgacta    6660
aaactaaaaa  aacaaaactc  tgtttcaggt   tgggcctagg   atccacattg   tacacacatt    6720
tgcttaagtc  tatggaggcg  caaggtttta   agtctgtggt   tgctgttata   ggccttccaa    6780
acgatccatc  tgttaggttg  catgaggctt   tgggatacac   agcccggggt   acattgcgcg    6840
cagctggata  caagcatggt  ggatggcatg   atgttggttt   ttggcaaagg   gattttgagt    6900
tgccagctcc  tccaaggcca  gttaggccag   ttacccagat   ctaatatcaa   aatctattta    6960
gaaatacaca  atattttgtt  gcaggcttgc   tggagaatcg   atctgctatc   ataaaaatta    7020
caaaaaaatt  ttatttgcct  caattatttt   aggattggta   ttaaggacgc   ttaaattatt    7080
tgtcgggtca  ctacgcatca  ttgtgattga   gaagatcagc   gatacgaaat   attcgtagta    7140
ctatcgataa  tttatttgaa  aattcataag   aaaagcaaac   gttacatgaa   ttgatgaaac    7200
aatacaaaga  cagataaagc  cacgcacatt   taggatattg   gccgagatta   ctgaatattg    7260
agtaagatca  cggaatttct  gacaggagca   tgtcttcaat   tcagcccaaa   tggcagttga    7320
aatactcaaa  ccgccccata  tgcaggagcg   gatcattcat   tgtttgtttg   gttgcctttg    7380
ccaacatggg  agtccaaggt  tgcatgccag   ggctgcgtcc   taaccggcgt   ctgggtcata    7440
gcccacgagt  gcggccacca  cgccttcagc   gactaccagt   ggctggacga   caccgtcggc    7500
ctcatcttcc  actccttcct  cctcgtccct   tacttctcct   ggaagtacag   tcatcgacgc    7560
caccattcca  acactggctc  cctcgagaga   gacgaagtgt   tgtcccaa     gaagaagtca    7620 gacatcaagt  ggtacggcaa  gtacctcaac   aaccctttgg   gacgcaccgt   gatgttaacg    7680
gttcagttca  ctctcggctg  gcctttgtac   ttagccttca   acgtctcggg   gagaccttac    7740
gacggcggct  tcgcttgcca  tttccacccc   aacgctccca   tctacaacga   ccgtgagcgt    7800
ctccagatat  acatctccga  cgctggcatc   ctcgccgtct   gctacggtct   ctaccgctac    7860
gctgctgtcc  aaggagttgc  ctcgatggtc   tgcttctacg   gagttcctct   tctgattgtc    7920
aacgggttct  tagttttgat  cacttacttg   cagcacacgc   atccttccct   gcctcactat    7980
gactcgtctg  agtgggattg  gttgagggga   gctttggcca   ccgttgacag   agactacgga    8040
atcttgaaca  aggtcttcca  caatatcacg   gacacgcacg   tggcgcatca   cctgttctcg    8100
accatgccgc  attatcacgc  gatggaagct   acgaaggcga   taaagccgat   actgggagag    8160
tattatcagt  tcgatgggac  gccggtggtt   aaggcgatgt   ggagggaggc   gaaggagtgt    8220
atctatgtgg  aaccggacag  gcaaggtgag   aagaaaggtg   tgttctggta   caacaataag    8280
ttatgaagca  aagaagaaac  tgaacctttc   tcatctatga   ttgtctttgt   tttaagaagc    8340
tatgtttctg  tttcaataat  ctttaattat   ccattttgtt   gtgttttctg   acattttggc    8400
taaaatggcg  ccacccagct  ttcttgtaca   aagtggtccc   cttaattaac   tgggcctcat    8460
gggccttccg  ctcactgccc  gctttccagt   cgggaaacct   gtcgtgccag   ctgcattaac    8520
atggtcatag  ctgttttcctt gcgtattggg   cgctctccgc   ttcctcgctc   actgactcgc    8580
tgcgctcggt  cgttcgggta  aagcctgggg   tgcctaatga   gcaaaaggcc   agcaaaaggc    8640
caggaaccgt  aaaaaggccg  cgttgctggc   gttttttccat  aggctccgcc   ccctgacga    8700
```

```
gcatcacaaa aatcgacgct caagtcagag gtggcgaaac ccgacaggac tataaagata    8760
ccaggcgttt cccctggaa gctccctcgt gcgctctcct gttccgaccc tgccgcttac    8820
cggatacctg tccgcctttc tcccttcggg aagcgtggcg ctttctcata gctcacgctg    8880
taggtatctc agttcggtgt aggtcgttcg ctccaagctg ggctgtgtgc acgaaccccc    8940
cgttcagccc gaccgctgcg ccttatccgg taactatcgt cttgagtcca acccggtaag    9000
acacgactta tcgccactgg cagcagccac tggtaacagg attagcagag cgaggtatgt    9060
aggcggtgct acagagttct tgaagtggtg gcctaactac ggctacacta agaacagt     9120 atttggtatc tgcgctctgc tgaagccagt taccttcgga aaaagagttg gtagctcttg    9180
atccggcaaa caaaccaccg ctggtagcgg tggttttttt gtttgcaagc agcagattac    9240
gcgcagaaaa aaaggatctc aagaagatcc tttgatcttt tctacggggt ctgacgctca    9300
gtggaacgaa aactcacgtt aagggatttt ggtcatgaga ttatcaaaaa ggatcttcac    9360
ctagatcctt ttaaattaaa aatgaagttt taaatcaatc taaagtatat atgagtaaac    9420
ttggtctgac agttaccaat gcttaatcag tgaggcacct atctcagcga tctgtctatt    9480
tcgttcatcc atagttgcct gactccccgt cgtgtagata actacgatac gggagggctt    9540
accatctggc cccagtgctg caatgatacc gcgagaacca cgctcaccgg ctccagattt    9600
atcagcaata aaccagccag ccggaagggc cgagcgcaga agtggtcctg caactttatc    9660
cgcctccatc cagtctatta attgttgccg ggaagctaga gtaagtagtt cgccagttaa    9720 tagtttcgc aacgttgttg ccattgctac aggcatcgtg gtgtcacgct cgtcgtttgg    9780
tatggcttca ttcagctccg gttcccaacg atcaaggcga gttacatgat cccccatgtt    9840
gtgcaaaaaa gcggttagct ccttcggtcc tccgatcgtt gtcagaagta agttggccgc    9900
agtgttatca ctcatggtta tggcagcact gcataattct cttactgtca tgccatccgt    9960
aagatgcttt tctgtgactg gtgagtactc aaccaagtca ttctgagaat agtgtatgcg    10020
gcgaccgagt tgctcttgcc cggcgtcaat acgggataat accgcgccac atagcagaac   10080
tttaaaagtg ctcatcattg gaaaacgttc ttcggggcga aaactctcaa ggatcttacc   10140
gctgttgaga tccagttcga tgtaacccac tcgtgcaccc aactgatctt cagcatcttt   10200
tactttcacc agcgtttctg ggtgagcaaa aacaggaagg caaaatgccg caaaaaaggg   10260
aataagggcg acacggaaat gttgaatact catactcttc cttttcaat attattgaag   10320 catttatcag ggttattgtc tcatgagcgg atacatattt gaatgtattt agaaaaataa   10380
acaaataggg gttccgcgca catttccccg aaaagtgcca c                       10421
```

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 94

Arg Ser Asp Asn Leu Ser Thr
1               5

<210> SEQ ID NO 95
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 95

His Ser His Ala Arg Ile Lys
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

His Arg Ser Ser Leu Arg Arg
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Ser Asp His Leu Ser Glu
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Asn Ala Asn Arg Ile Thr
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Arg Ser Asn Leu Ser Arg
1               5

<210> SEQ ID NO 100

<400> SEQUENCE: 100

000

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 101

Thr Ser Gly Asn Leu Thr Arg
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Met Ser His His Leu Arg Asp
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asp Gln Ser Asn Leu Arg Ala
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Ser Gly Asn Leu Ala Arg
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Ser Asp Asn Leu Ser Arg
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Asn Asn Ala Arg Ile Asn
1               5

<210> SEQ ID NO 107

```
<400> SEQUENCE: 107

000

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ser Asp His Leu Thr Gln
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Ser Asp Asn Leu Arg Glu
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Ser Gly Ala Leu Ala Arg
1               5

<210> SEQ ID NO 111

<400> SEQUENCE: 111

000

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Ser Asp Val Leu Ser Glu
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ser Pro Ser Ser Arg Arg Thr
```

```
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ser Asp Ser Leu Ser Arg
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Lys Asp Ala Arg Ile Thr
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Ser Asp His Leu Ser Ala
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Trp Ser Ser Ser Leu Tyr Tyr
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asn Ser Arg Asn Leu Arg Asn
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 119

Asp Gln Ser Thr Leu Arg Asn
1               5

<210> SEQ ID NO 120

<400> SEQUENCE: 120

000

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Arg Ser Asn Leu Trp Arg
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asp Arg Ser Ala Leu Ser Arg
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Ser Asp Ala Leu Ala Arg
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Ser Asp Ala Leu Ser Arg
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 125

Asp Arg Ser Asp Leu Ser Arg
1               5

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Ser Ser Ala Arg Asn Thr
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Arg Ser Ser Arg Lys Arg
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Ser Gly Asp Leu Thr Arg
1               5

<210> SEQ ID NO 133
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 133

Leu Ala His His Leu Val Gln
1               5

<210> SEQ ID NO 134

<400> SEQUENCE: 134

000

<210> SEQ ID NO 135

<400> SEQUENCE: 135

000

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Thr Ser Gly His Leu Ser Arg
1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Ser Asp Asn Leu Ser Val
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ile Arg Ser Thr Leu Arg Asp
1               5

<210> SEQ ID NO 139

<400> SEQUENCE: 139

000

<210> SEQ ID NO 140

<400> SEQUENCE: 140

000
```

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Arg Ser Ala Val Leu Ser Glu
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 150

Thr Asn Ser Asn Arg Ile Thr
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Leu Lys Gln His Leu Asn Glu
1               5

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln Arg Thr His Leu Thr Gln
1               5

<210> SEQ ID NO 159
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Ser Asp Asn Leu Ser Asn
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Asn Ser Asn Arg Ile Lys
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gln Ser Ser Asp Leu Ser Arg
1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Ser Ser Asp Leu Arg Arg
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asp Arg Ser Asn Arg Ile Lys
1               5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Arg Ser Ala Asn Leu Ala Arg
```

```
<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Arg Ser Asp Asn Leu Thr Thr
1               5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gln Ser Gly Glu Leu Ile Asn
1               5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Ser Ala Asp Leu Ser Arg
1               5

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Ser Asp Asn Leu Ser Glu
1               5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Arg Ser His Leu Ala Arg
1               5

<210> SEQ ID NO 170

<400> SEQUENCE: 170

000
```

<210> SEQ ID NO 171

<400> SEQUENCE: 171

000

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Lys Gln Tyr Leu Ile Lys
1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Glu Arg Gly Thr Leu Ala Arg
1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Arg Ser Asp His Leu Thr Thr
1               5

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Arg Ser Asp Asn Leu Thr Arg
1               5

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 189

Ala Ser Lys Thr Arg Lys Asn
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Arg Ser Asp Thr Leu Ser Glu
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gln Ser His Asn Arg Thr Lys
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gln Ser Asp His Leu Thr Gln
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Arg Ser Ser Asp Leu Ser Arg
1               5

<210> SEQ ID NO 194

<400> SEQUENCE: 194

000

<210> SEQ ID NO 195

<400> SEQUENCE: 195

000
```

<210> SEQ ID NO 196

<400> SEQUENCE: 196

000

<210> SEQ ID NO 197

<400> SEQUENCE: 197

000

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Asp Arg Ser His Leu Ser Arg
1               5

<210> SEQ ID NO 199

<400> SEQUENCE: 199

000

<210> SEQ ID NO 200

<400> SEQUENCE: 200

000

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Asp Arg Ser Ala Leu Ala Arg
1               5

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Ser Asp Asp Leu Ser Lys
1               5

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Arg Ser Asp Thr Arg Lys Thr
1               5

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Asn Asn Asp His Arg Lys Thr
1               5

<210> SEQ ID NO 208
<211> LENGTH: 10272
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208

| | | | | | |
|---|---|---|---|---|---|
| acaagtttgt | acaaaaaagc | aggctgtaag | tttgtggatt | cttcgtccat | gtgatctttg | 60 |
| agtttcttta | gagcttgtga | gggattagta | agtaacaatg | cttgagtttt | ttgctgctgg | 120 |
| gcttcgaaaa | gtttgtcact | tgttggtttg | atccacaagg | tcttcttctc | catagctact | 180 |
| agacatgttt | tagcttaaga | ttcaagttta | tatatgcctt | gtggattaat | cattgcctga | 240 |
| ttcttccgtg | tcatctctga | gtttatttag | agcttggaag | tggtgtagta | ataactaaca | 300 |
| atactcttga | taagttgtag | caatgctctt | gattagtgga | tgtaatatga | tgttgataag | 360 |
| atatatgagg | cacagaacca | aaagtggtgc | ttccactaga | cccgttttta | gcctaaggtt | 420 |
| caagtttata | ccttgtagat | gttctgtat | tgtctgattc | ttccctgtga | tatttgaatt | 480 |
| tcttagagct | ttggaagtga | tataggaaca | atgctcttgt | gtgtttgtct | ctatgaagat | 540 |
| tatcgctgtc | gtgtttcatc | cgagtgtgcg | ggatttttg | ctgctgggtt | tagcctttct | 600 |
| tcaaaaagtt | attacttgtt | agtttttattg | ttttggtctt | gataagagat | gttaggacag | 660 |
| acatggtgct | tcttgtctat | agccactaga | cctatttag | cataaggtta | acgaaattct | 720 |
| ctctacatac | cttgtggatt | tgtttacatt | gcctgatctt | tcctgtgatc | gctgtcatgt | 780 |
| ttctttggaa | tgattgatgt | ttataaatgg | aaaaatcttt | gtgcaggttt | aaacgtttac | 840 |

```
gttaagcacc ctgctgatat ccctgattac aagaagcttt cattccctga gggattcaag    900
tgggagagag ttatgaactt cgaggatggt ggtgttgcta ctgttactca ggattcttca    960
cttcaggacg gatgcttcat ctacaaggtt aagttcatcg gagtgaactt cccttctgat   1020
ggacctgtta tgcagaaaaa gactatggga tgggaggctt ctaccgagag actttaccct   1080
agagatggtg ttcttaaggg tgagactcac aaggctctta agcttaaaga tggtggacac   1140
tacctcgtcg agttcaagtc tatctacatg gctaagaagc ctgttcagct tcctggttac   1200
tactacgttg acgctaagct tgatatcacc tctcacaacg aggactacac tatcgttgag   1260
caatacgaga gaactgaggg tagacatcac ttgttcctct gatatcaaaa tctatttaga   1320
aatacacaat attttgttgc aggcttgctg gagaatcgat ctgctatcat aaaaattaca   1380
aaaaatttt atttgcctca attattttag gattggtatt aaggacgctt aaattatttg   1440
tcgggtcact acgcatcatt gtgattgaga agatcagcga tacgaaatat tcgtagtact   1500
atcgataatt tatttgaaaa ttcataagaa aagcaaacgt tacatgaatt gatgaaacaa   1560
tacaaagaca gataaagcca cgcacattta ggatattggc cgagattact gaatattgag   1620
taagatcacg gaatttctga caggagcatg tcttcaattc agcccaaatg gcagttgaaa   1680
tactcaaacc gccccatatg caggagcgga tcattcattg tttgtttggt tgcctttgcc   1740
aacatgggag tccaaggttg ccttttgcag tttatctcta tgcccgggac aagtgaagac   1800
tcccgcccat ctcactaggg acaggattgg agtccatgct caacaccgtg caggatgagg   1860
atgaccaaca actttgtata caaaagttgt atccgaagta aataaaacca tcggactctc   1920
gtataagact gtcgacaagc ttcttgcctc aattccggag gtgtttctag tgttcaacat   1980
gacaaacaaa acccatctct ttcagtatat gtctctcagt tgtgcttaat tcaaatttca   2040
actcagagaa cttcttggca tacttatcca gattatctaa tgatctcatc taatggtaat   2100
tcaacttttca gtatatgtct cgcagcaaac tatctttaca tcaaattttt aacaactcaa   2160
tgcacaaaat acttttcctc aacctaaaaa taaggcaatt agccaaaaac aactttgcgt   2220
gtgaacaacg cgttacacgt ccctacacat acgtgtcaat ttataattgg ctattgcttc   2280
cacgccttag cttttctcgtg accgaccgag tcgtcctcgt ctttttttgct tctataaatc   2340
aaatacccaa agagctcttc ttcttcacaa ttcagattcc aattttctca aactctaaaa   2400
tcaatctctc aaatctctca accgtgatca aggtagattt ctgagttctt attgtatttc   2460
ttcgatttgt ttcgttcgat cgcaatttag gctctgttct ttgattttga tctcgttaat   2520
ctctgatcgg aggcaaatta catagtttca tcgttagatc tcttcttatt tctcgattag   2580
ggttcgtatt tttcgcagat ctgtttatt tcttgttgtt tccttgtatt tgatccgatt   2640
tgttgaaaga atttgtgtgt tctcgattat ttacgctttg atctgtgatt tttatctaga   2700
tttggtgtta gtttcttgtt tgtgcgatcg aatttgtcga ttaatctcgg tttttctgat   2760
taacagatgc tcaatctag cagaatctgc acggtgtgc agaacccatg tgtgatcatt   2820
tccaatctct ccaaatccaa ccagaacaaa tctcctttct cagtcagcct caagactcac   2880
cagcagcagc gtcgtgctta ccagatatct agctggggat tgaagaagtc aaacaacggg   2940
tccgtgattc gtccggttaa ggcagctgca agagggatgc cagccttgtc tttacctgga   3000
tcaaagagta tcacagctag ggcactcttt cttgctgctg ctgctgatgg ggttactact   3060
ttggtgaggc cattgagaag tgacgacaca gaaggattcg ctgaggggtt agttcgttta   3120
ggctatcgtg tagggaggac acccgatact tggcaagtcg atggcagacc acaaggacca   3180
```

```
gcagtggctg aggctgacgt ctactgtaga gacggagcaa ccaccgctag attcttgcca    3240
accttagcag ctgctggtca cggaacatac agatttgatg cttcaccaca gatgaggaga    3300
cgtcctcttt tgcccttaag cagagccttg agggatttgg gtgtcgatct tagacacgaa    3360
gaagctgaag gtcatcaccc tctgactgtc cgtgctgctg gggttgaagg aggagaggtt    3420
actttggatg ctggtcagtc aagtcagtat ctcactgcct tgttgctcct tggtcccctt    3480
acaagacaag gactgaggat aagggttact gatttggtgt cagcaccata cgtggagatt    3540
acgcttgcaa tgatgagggc tttcggagtt gaagtggcaa gggagggaga tgtgttcgtt    3600
gttccacctg gtggatatcg tgcaactacg tatgctatag acccgacgc aagtactgct    3660 tcttacttct tcgcagctgc tgctttgact cctggagctg aagtgactgt acctgggtta    3720
ggcacgggag cacttcaagg agatttggga tttgtagatg tcttaaggag aatgggagcc    3780
gaggtgtccg taggagctga tgcaaccact gttagaggaa ctggtgaatt gcgtggcctt    3840
acagccaaca tgagagacat aagtgatacg atgccgaccc tcgctgcaat agcaccettt    3900 gctagtgctc cagttagaat cgaggatgtt gccaacactc gtgtcaaaga atgtgacaga    3960
cttgaggctt gtgcagagaa ccttaggagg ttgggagtaa gggttgcaac gggtccggac    4020
tggattgaga tacaccctgg tccagctact ggtgctcaag tcacaagcta tggtgatcac    4080
agaattgtga tgtcatttgc agtgactgga cttcgtgtgc ctgggatcag cttcgacgac    4140
cctggctgtg ttcgtaagac ttttcctggg tttcacgagg ctttcgcaga attgaggcgt    4200
ggcattggga gctgatgagt agttagctta atcacctaag atcggcggca atagcttctt    4260
agcgccatcc cgggttgatc ctatctgtgt tgaaatagtt gcggtgggca aggctctctt    4320
tcagaaagac aggcggccaa aggaacccaa ggtgaggtgg gctatggctc tcagttcctt    4380
gtggaagcgc ttggtctaag gtgcagaggt gttagcggga tgaagcaaaa gtgtccgatt    4440
gtaacaagat atgttgatcc tacgtaagga tattaaagta tgtattcatc actaatataa    4500
tcagtgtatt ccaatatgta ctacgatttc caatgtcttt attgtcgccg tatgtaatcg    4560
gcgtcacaaa ataatccccg gtgactttct tttaatccag gatgaaataa tatgttatta    4620
taatttttgc gatttggtcc gttataggaa ttgaagtgtg cttgcggtcg ccaccactcc    4680
catttcataa ttttacatgt atttgaaaaa taaaaattta tggtattcaa tttaaacacg    4740
tatacttgta aagaatgata tcttgaaaga aatatagttt aaatatttat tgataaaata    4800
acaagtcagg tattatagtc caagcaaaaa cataaattta ttgatgcaag tttaaattca    4860
gaaatatttc aataactgat tatatcagct ggtacattgc cgtagatgaa agactgagtg    4920
cgatattatg gtgtaataca tacggccgac gcataggttc atttgaagct gctattctat    4980
ttagattgaa gtttaaaccc agaaggtaat tatccaagat gtagcatcaa gaatccaatg    5040
tttacgggaa aaactatgga agtattatgt aagctcagca agaagcagat caatatgcgg    5100
cacatatgca acctatgttc aaaaatgaag aatgtacaga tacaagatcc tatactgcca    5160
gaatacgaag aagaatacgt agaaattgaa aaagaagaac caggcgaaga aaagaatctt    5220
gaagacgtaa gcactgacga caacaatgaa aagaagaaga taaggtcggt gattgtgaaa    5280
gagacataga ggacacatgt aaggtggaaa atgtaagggc ggaaagtaac cttatcacaa    5340
aggaatctta tcccccacta cttatccttt tatattttc cgtgtcattt tgcccttga    5400 gttttcctat ataaggaacc aagttcggca tttgtgaaaa caagaaaaaa tttggtgtaa    5460
gctattttct ttgaagtact gaggatacaa cttcagagaa atttgtaagt ttgtaatgtc    5520
tccggagagg agaccagttg agattaggcc agctacagca gctgatatgg ccgcggtttg    5580
```

```
tgatatcgtt aaccattaca ttgagacgtc tacagtgaac tttaggacag agccacaaac    5640
accacaagag tggattgatg atctcgagag gttgcaagat agatacccct tggttggttgc   5700 tgaggttgag ggtgttgtgg ctggtattgc ttacgctggg ccctggaagg ctaggaacgc   5760
ttacgattgg acagttgaga gtactgttta cgtgtcacat aggcatcaaa ggtcagtttt   5820
acttccctta attttctatg tactttcata attacttatg ttattttctt catgagtttt   5880
aatgcaaatt actatatgga ctctagtgaa aacgttcaga atcctataaa catgactact   5940
gagacgaact tgagagtagt tttgatcata cacacgtttc atgtggtact tgagagttac   6000 taattttttgt catcttcgta taagtagtaa aagatactac aagaatagtt tagtagaaaa   6060
tactagcggt aggtgaagat ttgtcgctat gtactattat tgtctagtaa cttgagtaac   6120
aatttcgtgg tctaaatatc aaataaaaat ggatgagtgg ttcaccaaat ctaggcatca   6180
aaactattaa tgtcattgtc tagatcttag gtgacaccac atttcgaata tttattggta   6240
attgagatgt taaagtacca atatttgact taataaacta aaagattttg ctttatcaa    6300 atgtagacat tgatgacata tcgttgtcat tatcttgagt atatacaagt cgatcaatta   6360
ggtgaaagtt tagtgtctcg tggttggtaa acgattaata cagtagtata ttttatccaa   6420
agacaaaatc caaatcattt caccagtatg aatagtatta ttttatctta aaagctaaaa   6480
tcttaaaaac caaggtagca cccacgttga gctagacgat caaatcgatt tctgctttgt   6540
ccaatttacc aagctattta aagccaaata attgaaatat aggtaggtcg ttatattagg   6600
ctaagattta tctcaaatgc ttaactaaag gaataacaag ggattctagt tgtgtggttt   6660
tataagattg gtccaatttc acttaagttt gtttattgta gaattttata tgtgaataat   6720
ttgaattcca attgaaaaga tattatagta aagaaaaaa tagtgcgaac aaaaaacttt    6780
aatcccataa aaagaaaaag aaaaatgaaa agttcttcta acatccatat tttgcatcat   6840
atcataaaga taagaaagat acatatcata gacgtacaga taaacaaaca tatcatcatt   6900
tgtgaaatac atagtacaat aatttgcttt taaatagagt ttaagtcaca cacactgaca   6960
cacacgataa aacgataatg tctgcaaaaa cactttaatc ccattgccta gaggacagct   7020
tctccacttt gtctttaagg ttggttttgc cgtgttgttt ttatctttat ataatgatct   7080
attttttgga ttatgaaatg aattcacaca ttttaattat ttaagaagat ccatatacag   7140
gtttataaca gtactaagtg atgattattt tttgttttg catagtttag tttattgggt    7200
aaacattcat tacgtgtctc tttatacgaa tcacccatcc aaaatttcaa gtagtctttt   7260
agttcattta ttatttcata actatttgac ttattgattt gacaagaaac aacaaaagtg   7320
ttgacttatt gatagattgt gggatcataa aagtaattaa gcgtcaacca cgacccacaa   7380
caacaaagca catgttatac attaatatct cgtttactta attacagttt tcagaatgcc   7440
gtttcatgtc ttgtcactgg cgatgttatt atcatgttgg acaatattcg actgttgtcg   7500
tttttacatt ttcgtattga ctaaaactaa aaaaacaaaa ctctgtttca gacccagctt   7560
tcttgtacaa agtggtgatt cgacctgcag gcatgcaagc ttggcgtaat catggtcata   7620
gctgtttcct gtgtgaaatt gttatccgct cacaattcca cacaacatac gagccggaag   7680
cataaagtgt aaagcctggg gtgcctaatg agtgagctaa ctcacattaa ttgcgttgcg   7740
ctcactgccc gctttccagt cgggaaacct gtcgtgccag ctgcattaat gaatcggcca   7800
acgcgcgggg agaggcggtt tgcgtattgg gcgctcttcc gcttcctcgc tcactgactc   7860
gctgcgctcg gtcgttcggc tgcggcgagc ggtatcagct cactcaaagg cggtaatacg   7920
```

-continued

```
gttatccaca gaatcagggg ataacgcagg aaagaacatg tgagcaaaag gccagcaaaa      7980
ggccaggaac cgtaaaaagg ccgcgttgct ggcgtttttc cataggctcc gcccccctga      8040
cgagcatcac aaaaatcgac gctcaagtca gaggtggcga acccgacag gactataaag       8100
ataccaggcg tttccccctg gaagctccct cgtgcgctct cctgttccga ccctgccgct      8160
taccggatac ctgtccgcct ttctcccttc gggaagcgtg gcgctttctc atagctcacg      8220
ctgtaggtat ctcagttcgg tgtaggtcgt tcgctccaag ctgggctgtg tgcacgaacc      8280
ccccgttcag cccgaccgct gcgccttatc cggtaactat cgtcttgagt ccaacccggt      8340
aagacacgac ttatcgccac tggcagcagc cactggtaac aggattagca gagcgaggta      8400
tgtaggcggt gctacagagt tcttgaagtg gtggcctaac tacggctaca ctagaaggac      8460
agtatttggt atctgcgctc tgctgaagcc agttaccttc ggaaaaagag ttggtagctc      8520
ttgatccggc aaacaaacca ccgctggtag cggtggtttt tttgtttgca agcagcagat      8580
tacgcgcaga aaaaaggat ctcaagaaga tcctttgatc ttttctacgg gtctgacgc        8640
tcagtggaac gaaaactcac gttaagggat tttggtcatg agattatcaa aaaggatctt     8700
cacctagatc cttttaaatt aaaaatgaag ttttaaatca atctaaagta tatatgagta      8760
aacttggtct gacagttacc aatgcttaat cagtgaggca cctatctcag cgatctgtct      8820
atttcgttca tccatagttg cctgactccc cgtcgtgtag ataactacga tacgggaggg     8880
cttaccatct ggccccagtg ctgcaatgat accgcgagac ccacgctcac cggctccaga     8940
tttatcagca ataaaccagc cagccggaag ggccgagcgc agaagtggtc ctgcaacttt      9000
atccgcctcc atccagtcta ttaattgttg ccgggaagct agagtaagta gttcgccagt      9060
taatagtttg cgcaacgttg ttgccattgc tacaggcatc gtggtgtcac gctcgtcgtt      9120
tggtatggct tcattcagct ccggttccca acgatcaagg cgagttacat gatcccccat      9180
gttgtgcaaa aaagcggtta gctccttcgg tcctccgatc gttgtcagaa gtaagttggc      9240
cgcagtgtta tcactcatgg ttatggcagc actgcataat tctcttactg tcatgccatc     9300
cgtaagatgc ttttctgtga ctggtgagta ctcaaccaag tcattctgag aatagtgtat      9360
gcggcgaccg agttgctctt gcccggcgtc aatacgggga ataccgcgc cacatagcag     9420
aactttaaaa gtgctcatca ttggaaaacg ttcttcgggg cgaaaactct caaggatctt      9480
accgctgttg agatccagtt cgatgtaacc cactcgtgca cccaactgat cttcagcatc      9540
ttttactttc accagcgttt ctgggtgagc aaaaacagga aggcaaaatg ccgcaaaaaa      9600
gggaataagg gcgacacgga aatgttgaat actcatactc ttcctttttc aatattattg     9660
aagcatttat cagggttatt gtctcatgag cggatacata tttgaatgta tttagaaaaa     9720
taaacaaata ggggttccgc gcacatttcc ccgaaaagtg ccacctgacg tctaagaaac      9780
cattattatc atgacattaa cctataaaaa taggcgtatc acgaggccct ttcgtctcgc      9840
gcgtttcggt gatgacggtg aaaacctctg acacatgcag ctcccggaga cggtcacagc      9900
ttgtctgtaa gcggatgccg ggagcagaca agcccgtcag ggcgcgtcag cgggtgttgg      9960
cgggtgtcgg ggctggctta actatgcggc atcagagcag attgtactga gagtgcacca     10020
tatgcggtgt gaaataccgc acagatgcgt aaggagaaaa taccgcatca ggcgccattc     10080
gccattcagg ctgcgcaact gttgggaagg gcgatcggtg cgggcctctt cgctattacg     10140
ccagctggcg aaagggggat gtgctgcaag gcgattaagt tgggtaacgc cagggttttc     10200
ccagtcacga cgttgtaaaa cgacggccag tgaattcgag ctcggtaccc ggggatcctc     10260
tagagtcgaa tc                                                        10272
```

<210> SEQ ID NO 209
<211> LENGTH: 8774
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 209

```
ggggacaagt ttgtacaaaa aagcaggctg cggccgcgaa atatccttcc tattcaaagt      60
tatatatatt tgtttacttt tgttttagat ctggacctga gacatgtaag tacatatttg     120
ttgaatcttt gggtaaaaac ttatgtctct gggtaaaatt tgctgagaga tttgaccgat     180
tcctattggc tctggattct gtagttacct aatacatgaa aaagtttcat ttggcctatg     240
ctcacttcat gcttataaac ttttttcttgc aaattaattg gattagatgc tccttcatag     300
attcagatgc aatagatttg catgaagaaa ataataggat tcatgatagt aaaaagattg     360
tatttttgtt tgtttgttta tgtttaaaag tctatatgtt gacaatagag ttgctatcaa     420
ctgtttcatt taggtttatg tttttgtcaa gttgcttatt ctaagagaca ttgtgattat     480
gacttgtctt ctctaacgta gtttagtaat aaaagacgaa agaaattgat atccacaaga     540
aagagatgta agctgtaacg tatcaaatct cattaataac tagtagtatt ctcaacgcta     600
tcgtttattt ctttctttgg tttgccacta tatgccgctt ctctgctctt tatcccacgt     660
actatccatt tttttgtgg tagtccattt ttttgaaact ttaataacgt aacactgaat      720
attaatttgt tggtttaatt aactttgagt ctttgctttt ggtttatgca gaaacatggg     780
tgcaggtgga agaatgcaag tgtctcctcc ctccaaaaag tctgaaaccg acaacatcaa     840
gcgcgtaccc tgcgagacac cgccttcac tgtcggagaa ctcaagaaag caatcccacc      900
gcactgtttc aaacgctcga tccctcgctc tttctcctac ctcatctggg acatcatcat     960
agcctcctgc ttctactacg tcgccaccac ttacttccct ctcctccctc accctctctc    1020
ctacttcgcc tggcctctct actgggccgg taccgtcgac tgactgactg aatctcgagg    1080
ggtgtggaag atatgaattt ttttgagaaa ctagataaga ttaatgaata tcggtgtttt    1140
ggttttttct tgtggccgtc tttgtttata ttgagatttt tcaaatcagt gcgcaagacg    1200
tgacgtaagt atccgagtca gttttttattt ttctactaat ttggtcgttt atttcggcgt    1260
gtaggacatg gcaaccgggc ctgaatttcg cgggtattct gtttctattc caacttttc    1320
ttgatccgca gccattaacg acttttgaat agatacgtct agggtcgagg ggggatccgt    1380
cgagggggtc caccaaaaac gtaagcgctt acgtacatgg tcgagggggt ccaccaaaaa    1440
cgtaagcgct tacgtacatg gtcgagggggg tccaccaaaa acgtaagcgc ttacgtacat    1500
ggtcgagggt agagcgtgac gctcgcggtg acgccatttc gccttttcag aaatggataa    1560
atagccttgc ttcctattat atcttcccaa attaccaata cattacacta gcatctgaat    1620
ttcataacca atctcgatac accaaatcgc ggatcagatc ttagtagcca tggctcaatc    1680
tagcagaatc tgccacggtg tgcagaaccc atgtgtgatc atttccaatc tctccaaatc    1740
caaccagaac aaatctccct tctcagtcag cctcaagact caccagcagc agcgtcgtgc    1800
ttaccagata tctagctggg gattgaagaa gtcaaacaac gggtccgtga ttcgtccggt    1860
taaggcagct gcaagaggga tgccagcctt gtctttacct ggatcaaaga gtatcacagc    1920
tagggcactc tttcttgctg ctgctgctga tggggttact actttggtga ggccattgag    1980
aagtgacgac acagaaggat tcgctgaggg gttagttcgt ttaggctatc gtgtagggag    2040
```

```
gacacccgat acttggcaag tcgatggcag accacaagga ccagcagtgg ctgaggctga   2100
cgtctactgt agagacggag caaccaccgc tagattcttg ccaaccttag cagctgctgg   2160
tcacggaaca tacagatttg atgcttcacc acagatgagg agacgtcctc ttttgccctt   2220
aagcagagcc ttgagggatt tgggtgtcga tcttagacac gaagaagctg aaggtcatca   2280
ccctctgact gtccgtgctg ctggggttga aggaggagag gttactttgg atgctggtca   2340
gtcaagtcag tatctcactg ccttgttgct ccttggtccc cttacaagac aaggactgag   2400
gataagggtt actgatttgg tgtcagcacc atacgtggag attacgcttg caatgatgag   2460
ggctttcgga gttgaagtgg caagggaggg agatgtgttc gttgttccac ctggtggata   2520
tcgtgcaact acgtatgcta tagaacccga cgcaagtact gcttcttact tcttcgcagc   2580
tgctgctttg actcctggag ctgaagtgac tgtacctggg ttaggcacgg agcacttca    2640 aggagatttg ggatttgtag atgtcttaag gagaatggga gccgaggtgt ccgtaggagc   2700
tgatgcaacc actgttagag gaactggtga attgcgtggc cttacagcca acatgagaga   2760
cataagtgat acgatgccga ccctcgctgc aatagcaccc tttgctagtg ctccagttag   2820
aatcgaggat gttgccaaca ctcgtgtcaa agaatgtgac agacttgagg cttgtgcaga   2880
gaaccttagg aggttgggag taagggttgc aacgggtccg gactggattg agatacaccc   2940
tggtccagct actggtgctc aagtcacaag ctatggtgat cacagaattg tgatgtcatt   3000
tgcagtgact ggacttcgtg tgcctgggat cagcttcgac gaccctggct gtgttcgtaa   3060
gacttttcct gggtttcacg aggctttcgc agaattgagg cgtggcattg ggagctgatg   3120
agtagttagc ttaatcacct aagatcggcg gcaatagctt cttagcgcca tcccgggttg   3180
atcctatctg tgttgaaata gttgcggtgg gcaaggctct ctttcagaaa gacaggcggc   3240
caaaggaacc caaggtgagg tgggctatgg ctctcagttc cttgtggaag cgcttggtct   3300
aaggtgcaga ggtgttagcg ggatgaagca aaagtgtccg attgtaacaa gatatgttga   3360
tcctacgtaa ggatattaaa gtatgtattc atcactaata taatcagtgt attccaatat   3420
gtactacgat ttccaatgtc tttattgtcg ccgtatgtaa tcggcgtcac aaaataatcc   3480
ccggtgactt tctttaatc caggatgaaa taatatgtta ttataatttt tgcgatttgg    3540
tccgttatag gaattgaagt gtgcttgcgg tcgccaccac tcccatttca taatttaca    3600 tgtatttgaa aaataaaaat ttatggtatt caatttaaac acgtatactt gtaaagaatg   3660
atatcttgaa agaaatatag tttaaatatt tattgataaa ataacaagtc aggtattata   3720
gtccaagcaa aaacataaat ttattgatgc aagtttaaat tcagaaatat ttcaataact   3780
gattatatca gctggtacat tgccgtagat gaaagactga gtgcgatatt atggtgtaat   3840
acatacggcc gccagaaggt aattatccaa gatgtagcat caagaatcca atgtttacgg   3900
gaaaaactat ggaagtatta tgtaagctca gcaagaagca gatcaatatg cggcacatat   3960
gcaacctatg ttcaaaaatg aagaatgtac agatacaaga tcctatactg ccagaatacg   4020
aagaagaata cgtagaaatt gaaaagaag aaccaggcga agaaaagaat cttgaagacg    4080
taagcactga cgacaacaat gaaaagaaga agataaggtc ggtgattgtg aaagagacat   4140
agaggacaca tgtaaggtgg aaaatgtaag ggcggaaagt aaccttatca caaaggaatc   4200
ttatccccca ctacttatcc ttttatattt ttccgtgtca ttttttgccct tgagttttcc   4260 tatataagga accaagttcg gcatttgtga aaacaagaaa aaatttggtg taagctattt   4320
tctttgaagt actgaggata caacttcaga gaaatttgta agtttgtaat gtctccggag   4380
```

```
aggagaccag ttgagattag gccagctaca gcagctgata tggccgcggt ttgtgatatc   4440
gttaaccatt acattgagac gtctacagtg aactttagga cagagccaca aacaccacaa   4500
gagtggattg atgatctcga gaggttgcaa gatagatacc cttggttggt tgctgaggtt   4560
gagggtgttg tggctggtat tgcttacgct gggccctgga aggctaggaa cgcttacgat   4620
tggacagttg agagtactgt ttacgtgtca cataggcatc aaaggttggg cctaggatcc   4680
acattgtaca cacatttgct taagtctatg gaggcgcaag gttttaagtc tgtggttgct   4740
gttataggcc ttccaaacga tccatctgtt aggttgcatg aggctttggg atacacagcc   4800
cggggtacat tgcgcgcagc tggatacaag catggtggat ggcatgatgt tggtttttgg   4860
caaagggatt ttgagttgcc agctcctcca aggccagtta ggccagttac ccagatctaa   4920
tatcaaaatc tatttagaaa tacacaatat tttgttgcag gcttgctgga gaatcgatct   4980
gctatcataa aaattacaaa aaaatttat ttgcctcaat tattttagga ttggtattaa   5040
ggacgcttaa attatttgtc gggtcactac gcatcattgt gattgagaag atcagcgata   5100
cgaaatattc gtagtactat cgataattta tttgaaaatt cataagaaaa gcaaacgtta   5160
catgaattga tgaaacaata caaagacaga taaagccacg cacatttagg atattggccg   5220
agattactga atattgagta agatcacgga atttctgaca ggagcatgtc ttcaattcag   5280
cccaaatggc agttgaaata ctcaaaccgc cccatatgca ggagcggatc attcattgtt   5340
tgtttggttg cctttgccaa catgggagtc caaggttgca tgccagggct gcgtcctaac   5400
cggcgtctgg gtcatagccc acgagtgcgg ccaccacgcc ttcagcgact accagtggct   5460
ggacgacacc gtcggcctca tcttccactc cttcctcctc gtcccttact tctcctggaa   5520
gtacagtcat cgacgccacc attccaacac tggctccctc gagagagacg aagtgtttgt   5580
ccccaagaag aagtcagaca tcaagtggta cggcaagtac ctcaacaacc ctttgggacg   5640
caccgtgatg ttaacggttc agttcactct cggctggcct ttgtacttag ccttcaacgt   5700
ctcggggaga cctacgacg gcggcttcgc ttgccatttc caccccaacg ctcccatcta   5760
caacgaccgt gagcgtctcc agatatacat ctccgacgct ggcatcctcg ccgtctgcta   5820
cggtctctac cgctacgctg ctgtccaagg agttgcctcg atggtctgct tctacggagt   5880
tcctcttctg attgtcaacg ggttcttagt tttgatcact tacttgcagc acacgcatcc   5940
ttccctgcct cactatgact cgtctgagtg ggattggttg aggggagctt tggccaccgt   6000
tgacagagac tacggaatct tgaacaaggt cttccacaat atcacggaca cgcacgtggc   6060
gcatcacctg ttctcgacca tgccgcatta tcacgcgatg gaagctacga aggcgataaa   6120
gccgatactg ggagagtatt atcagttcga tgggacgccg gtggttaagg cgatgtggag   6180
ggaggcgaag gagtgtatct atgtggaacc ggacaggcaa ggtgagaaga aggtgtgtt   6240 ctggtacaac aataagttat gaagcaaaga agaaactgaa cctttctcat ctatgattgt   6300
ctttgtttta agaagctatg tttctgtttc aataatcttt aattatccat ttgttgtgt   6360 tttctgacat tttggctaaa atggcgccac ccagctttct tgtacaaagt ggtcccctta   6420
attaactggg cctcatgggc cttccgctca ctgcccgctt ccagtcggg aaacctgtcg   6480 tgccagctgc attaacatgg tcatagctgt ttccttgcgt attgggcgct ctccgcttcc   6540
tcgctcactg actcgctgcg ctcggtcgtt cgggtaaagc ctggggtgcc taatgagcaa   6600
aaggccagca aaaggccagg aaccgtaaaa aggccgcgtt gctggcgttt ttccataggc   6660 tccgccccc tgacgagcat cacaaaaatc gacgctcaag tcagaggtgg cgaaacccga   6720
caggactata agataccag gcgttttccc ctggaagctc cctcgtgcgc tctcctgttc   6780
```

```
cgaccctgcc gcttaccgga tacctgtccg cctttctccc ttcgggaagc gtggcgcttt   6840
ctcatagctc acgctgtagg tatctcagtt cggtgtaggt cgttcgctcc aagctgggct   6900
gtgtgcacga accccccgtt cagcccgacc gctgcgcctt atccggtaac tatcgtcttg   6960
agtccaaccc ggtaagacac gacttatcgc cactggcagc agccactggt aacaggatta   7020
gcagagcgag gtatgtaggc ggtgctacag agttcttgaa gtggtggcct aactacggct   7080
acactagaag aacagtattt ggtatctgcg ctctgctgaa gccagttacc ttcggaaaaa   7140
gagttggtag ctcttgatcc ggcaaacaaa ccaccgctgg tagcggtggt ttttttgttt   7200
gcaagcagca gattacgcgc agaaaaaaag gatctcaaga agatcctttg atcttttcta   7260
cggggtctga cgctcagtgg aacgaaaact cacgttaagg gattttggtc atgagattat   7320
caaaaaggat cttcacctag atccttttaa attaaaaatg aagttttaaa tcaatctaaa   7380
gtatatatga gtaaacttgg tctgacagtt accaatgctt aatcagtgag gcacctatct   7440
cagcgatctg tctatttcgt tcatccatag ttgcctgact ccccgtcgtg tagataacta   7500
cgatacggga gggcttacca tctggcccca gtgctgcaat gataccgcga gaaccacgct   7560
caccggctcc agatttatca gcaataaacc agccagccgg aagggccgag cgcagaagtg   7620
gtcctgcaac tttatccgcc tccatccagt ctattaattg ttgccgggaa gctagagtaa   7680
gtagttcgcc agttaatagt ttgcgcaacg ttgttgccat tgctacaggc atcgtggtgt   7740
cacgctcgtc gtttggtatg gcttcattca gctccggttc ccaacgatca aggcgagtta   7800
catgatcccc catgttgtgc aaaaaagcgg ttagctcctt cggtcctccg atcgttgtca   7860
gaagtaagtt ggccgcagtg ttatcactca tggttatggc agcactgcat aattctctta   7920
ctgtcatgcc atccgtaaga tgcttttctg tgactggtga gtactcaacc aagtcattct   7980
gagaatagtg tatgcggcga ccgagttgct cttgcccggc gtcaatacgg gataataccg   8040
cgccacatag cagaacttta aaagtgctca tcattggaaa acgttcttcg gggcgaaaac   8100
tctcaaggat cttaccgctg ttgagatcca gttcgatgta acccactcgt gcacccaact   8160
gatcttcagc atcttttact ttcaccagcg tttctgggtg agcaaaaaca ggaaggcaaa   8220
atgccgcaaa aaagggaata agggcgacac ggaaatgttg aatactcata ctcttccttt   8280
ttcaatatta ttgaagcatt tatcagggtt attgtctcat gagcggatac atatttgaat   8340
gtatttagaa aaataaacaa ataggggttc cgcgcacatt tccccgaaaa gtgccaccta   8400
aattgtaagc gttaatattt tgttaaaatt cgcgttaaat ttttgttaaa tcagctcatt   8460
ttttaaccaa taggccgaaa tcggcaaaat cccttataaa tcaaaagaat agaccgagat   8520
agggttgagt ggccgctaca gggcgctccc attcgccatt caggctgcgc aactgttggg   8580
aagggcgttt cggtgcgggc ctcttcgcta ttacgccagc tggcgaaagg gggatgtgct   8640
gcaaggcgat taagttgggt aacgccaggg ttttcccagt cacgacgttg taaaacgacg   8700
gccagtgagc gcgacgtaat acgactcact atagggcgaa ttggcggaag gccgtcaagg   8760
ccgcatggcg cgcc                                                    8774
```

<210> SEQ ID NO 210
<211> LENGTH: 9491
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 210

```
gggacaagt tgtacaaaa aagcaggctg cggccgcgaa atatccttcc tattcaaagt      60
tatatatatt tgtttacttt tgttttagat ctggacctga gacatgtaag tacatatttg   120
ttgaatcttt gggtaaaaac ttatgtctct gggtaaaatt tgctgagaga tttgaccgat   180
tcctattggc tctggattct gtagttacct aatacatgaa aaagtttcat ttggcctatg   240
ctcacttcat gcttataaac ttttcttgc aaattaattg gattagatgc tccttcatag    300
attcagatgc aatagatttg catgaagaaa ataataggat tcatgatagt aaaaagattg   360
tattttgtt tgtttgttta tgtttaaaag tctatatgtt gacaatagag ttgctatcaa    420
ctgtttcatt taggtttatg tttttgtcaa gttgcttatt ctaagagaca ttgtgattat   480
gacttgtctt ctctaacgta gtttagtaat aaaagacgaa agaaattgat atccacaaga   540
aagagatgta agctgtaacg tatcaaatct cattaataac tagtagtatt ctcaacgcta   600
tcgtttattt ctttctttgg tttgccacta tatgccgctt ctctgctctt tatcccacgt   660
actatccatt tttttgtgg tagtccattt ttttgaaact ttaataacgt aacactgaat    720
attaatttgt tggtttaatt aactttgagt ctttgctttt ggtttatgca gaaacatggg   780
tgcaggtgga agaatgcaag tgtctcctcc ctccaaaaag tctgaaaccg acaacatcaa   840
gcgcgtaccc tgcgagacac cgcccttcac tgtcggagaa ctcaagaaag caatcccacc   900
gcactgtttc aaacgctcga tccctcgctc ttttctcctac ctcatctggg acatcatcat  960
agcctcctgc ttctactacg tcgccaccac ttacttccct ctcctccctc accctctctc  1020
ctacttcgcc tggcctctct actgggccgg taccgtcgac gacgacctgc aggtcaacgg  1080
atcaggatat tcttgtttaa gatgttgaac tctatggagg tttgtatgaa ctgatgatct  1140
aggaccggat aagttccctt cttcatagcg aacttattca agaatgtttt tgtgtatcat  1200
tcttgttaca ttgttattaa tgaaaaaata ttattggtca ttggactgaa cacgagtgtt  1260
aaatatggac caggcccaa ataagatcca ttgatatatg aattaaataa caagaataaa   1320
tcgagtcacc aaaccacttg cctttttaa cgagacttgt tcaccaactt gatacaaaag   1380
tcattatcct atgcaaatca ataatcatac aaaaatatcc aataacacta aaaaattaaa  1440
agaaatggat aatttcacaa tatgttatac gataaagaag ttacttttcc aagaaattca  1500
ctgattttat aagcccactt gcattagata aatggcaaaa aaaacaaaa aggaaaagaa   1560
ataaagcacg aagaattcta gaaaatacga aatacgcttc aatgcagtgg gacccacggt  1620
tcaattattg ccaattttca gctccaccgt atatttaaaa aataaaacga taatgctaaa  1680
aaaatataaa tcgtaacgat cgttaaatct caacggctgg atcttatgac gaccgttaga  1740
aattgtggtt gacgacgagt cagtaataaa cggcgtcaaa gtggttgcag ccggcacaca  1800
cgagtcgtgt ttatcaactc aaagcacaaa tactttccct caacctaaaa ataaggcaat  1860
tagccaaaaa caactttgcg tgtaaacaac gctcaataca cgtgtcattt tattattagc  1920
tattgcttca ccgccttagc tttctcgtga cctagtcgtc ctcgtctttt cttcttcttc  1980
ttctataaaa caatacccaa agagctcttc ttcttcacaa ttcagatttc aatttctcaa  2040
aatcttaaaa actttctctc aattctctct accgtgatca aggtaaattt ctgtgttcct  2100
tattctctca aaatcttcga ttttgttttc gttcgatccc aatttcgtat atgttctttg  2160
gtttagattc tgttaatctt agatcgaaga cgattttctg ggtttgatcg ttagatatca  2220
tcttaattct cgattagggt ttcatagata tcatccgatt tgttcaaata atttgagttt  2280
tgtcgaataa ttactcttcg atttgtgatt tctatctaga tctggtgtta gtttctagtt  2340
```

```
tgtgcgatcg aatttgtcga ttaatctgag tttttctgat aacagatgg  ctcaatctag    2400 cagaatctgc cacggtgtgc agaacccatg tgtgatcatt tccaatctct ccaaatccaa    2460
ccagaacaaa tctcctttct cagtcagcct caagactcac cagcagcagc gtcgtgctta    2520
ccagatatct agctggggat tgaagaagtc aaacaacggg tccgtgattc gtccggttaa    2580
ggcagctgca agagggatgc cagccttgtc tttacctgga tcaaagagta tcacagctag    2640
ggcactcttt cttgctgctg ctgctgatgg ggttactact ttggtgaggc cattgagaag    2700
tgacgacaca gaaggattcg ctgaggggtt agttcgttta ggctatcgtg tagggaggac    2760
acccgatact tggcaagtcg atggcagacc acaaggacca gcagtggctg aggctgacgt    2820
ctactgtaga gacggagcaa ccaccgctag attcttgcca accttagcag ctgctggtca    2880
cggaacatac agatttgatg cttcaccaca gatgaggaga cgtcctcttt tgcccttaag    2940
cagagccttg agggatttgg gtgtcgatct tagacacgaa gaagctgaag gtcatcaccc    3000
tctgactgtc cgtgctgctg gggttgaagg aggagaggtt actttggatg ctggtcagtc    3060
aagtcagtat ctcactgcct tgttgctcct tggtccccct acaagacaag gactgaggat    3120
aagggttact gatttggtgt cagcaccata cgtggagatt acgcttgcaa tgatgagggc    3180
tttcggagtt gaagtggcaa gggagggaga tgtgttcgtt gttccacctg gtggatatcg    3240
tgcaactacg tatgctatag aacccgacgc aagtactgct tcttacttct tcgcagctgc    3300
tgctttgact cctggagctg aagtgactgt acctgggtta ggcacgggag cacttcaagg    3360
agatttggga tttgtagatg tcttaaggag aatgggagcc gaggtgtccg taggagctga    3420
tgcaaccact gttagaggaa ctggtgaatt gcgtggcctt acagccaaca tgagagacat    3480
aagtgatacg atgccgaccc tcgctgcaat agcacccttt gctagtgctc cagttagaat    3540
cgaggatgtt gccaacactc gtgtcaaaga atgtgacaga cttgaggctt gtgcagagaa    3600
ccttaggagg ttgggagtaa gggttgcaac gggtccggac tggattgaga tacaccctgg    3660
tccagctact ggtgctcaag tcacaagcta tggtgatcac agaattgtga tgtcatttgc    3720
agtgactgga cttcgtgtgc ctgggatcag cttcgacgac cctggctgtg ttcgtaagac    3780
ttttcctggg tttcacgagg cttttcgcaga attgaggcgt ggcattggga gctgatgagt    3840
agttagctta atcacctaag atcggcggca atagcttctt agcgccatcc cgggttgatc    3900
ctatctgtgt tgaaatagtt gcggtgggca aggctctctt tcagaaagac aggcggccaa    3960
aggaacccaa ggtgaggtgg gctatggctc tcagttcctt gtggaagcgc ttggtctaag    4020
gtgcagaggt gttagcggga tgaagcaaaa gtgtccgatt gtaacaagat atgttgatcc    4080
tacgtaagga tattaaagta tgtattcatc actaatataa tcagtgtatt ccaatatgta    4140
ctacgatttc caatgtcttt attgtcgccg tatgtaatcg gcgtcacaaa ataatccccg    4200
gtgactttct tttaatccag gatgaaataa tatgttatta taattttgc  gatttggtcc    4260 gttataggaa ttgaagtgtg cttgcggtcg ccaccactcc catttcataa ttttacatgt    4320
atttgaaaaa taaaaattta tggtattcaa tttaaacacg tatacttgta aagaatgata    4380
tcttgaaaga aatatagttt aaatatttat tgataaaata acaagtcagg tattatagtc    4440
caagcaaaaa cataaattta ttgatgcaag tttaaattca gaaatatttc ataactgat   4500 tatatcagct ggtacattgc cgtagatgaa agactgagtg cgatattatg gtgtaataca    4560
tacggccgcc agaaggtaat tatccaagat gtagcatcaa gaatccaatg tttacgggaa    4620
aaactatgga agtattatgt aagctcagca agaagcagat caatatgcgg cacatatgca    4680
acctatgttc aaaaatgaag aatgtacaga tacaagatcc tatactgcca gaatacgaag    4740
```

```
aagaatacgt agaaattgaa aaagaagaac caggcgaaga aaagaatctt gaagacgtaa   4800
gcactgacga caacaatgaa aagaagaaga taaggtcggt gattgtgaaa gagacataga   4860
ggacacatgt aaggtggaaa atgtaagggc ggaaagtaac cttatcacaa aggaatctta   4920
tcccccacta cttatccttt tatattttc cgtgtcattt ttgcccttga gttttcctat    4980
ataaggaacc aagttcggca tttgtgaaaa caagaaaaaa tttggtgtaa gctattttct   5040
ttgaagtact gaggatacaa cttcagagaa atttgtaagt ttgtaatgtc tccggagagg   5100
agaccagttg agattaggcc agctacagca gctgatatgg ccgcggtttg tgatatcgtt   5160
aaccattaca ttgagacgtc tacagtgaac tttaggacag agccacaaac accacaagag   5220
tggattgatg atctcgagag gttgcaagat agataccctt ggttggttgc tgaggttgag   5280
ggtgttgtgg ctggtattgc ttacgctggg ccctggaagg ctaggaacgc ttacgattgg   5340
acagttgaga gtactgttta cgtgtcacat aggcatcaaa ggttgggcct aggatccaca   5400
ttgtacacac atttgcttaa gtctatggag gcgcaaggtt ttaagtctgt ggttgctgtt   5460
ataggccttc caaacgatcc atctgttagg ttgcatgagg ctttgggata cacagcccgg   5520
ggtacattgc gcgcagctgg atacaagcat ggtggatggc atgatgttgg tttttggcaa   5580
agggattttg agttgccagc tcctccaagg ccagttaggc cagttaccca gatctaatat   5640
caaaatctat ttagaaatac acaatatttt gttgcaggct tgctggagaa tcgatctgct   5700
atcataaaaa ttacaaaaaa attttatttg cctcaattat tttaggattg gtattaagga   5760
cgcttaaatt atttgtcggg tcactacgca tcattgtgat tgagaagatc agcgatacga   5820
aatattcgta gtactatcga taatttattt gaaaattcat aagaaaagca aacgttacat   5880
gaattgatga acaatacaa agacagataa agccacgcac attaggata ttggccgaga    5940
ttactgaata ttgagtaaga tcacggaatt tctgacagga gcatgtcttc aattcagccc   6000
aaatggcagt tgaaatactc aaaccgcccc atatgcagga gcggatcatt cattgtttgt   6060
ttggttgcct ttgccaacat gggagtccaa ggttgcatgc cagggctgcg tcctaaccgg   6120
cgtctgggtc atagcccacg agtgcggcca ccacgccttc agcgactacc agtggctgga   6180
cgacaccgtc ggcctcatct tccactcctt cctcctcgtc ccttacttct cctgaaagta   6240
cagtcatcga cgccaccatt ccaacactgg ctccctcgag agagacgaag tgtttgtccc   6300
caagaagaag tcagacatca agtggtacgg caagtacctc aacaaccctt gggacgcac    6360
cgtgatgtta acggttcagt tcactctcgg ctggcctttg tacttagcct tcaacgtctc   6420
ggggagacct tacgacggcg gcttcgcttg ccatttccac cccaacgctc ccatctacaa   6480
cgaccgtgag cgtctccaga tatacatctc cgacgctggc atcctcgccg tctgctacgg   6540
tctctaccgc tacgctgctg tccaaggagt tgcctcgatg gtctgcttct acggagttcc   6600
tcttctgatt gtcaacgggt tcttagtttt gatcacttac ttgcagcaca cgcatccttc   6660
cctgcctcac tatgactcgt ctgagtggga ttggttgagg ggagctttgg ccaccgttga   6720
cagagactac ggaatcttga acaaggtctt ccacaatatc acggacacgc acgtggcgca   6780
tcacctgttc tcgaccatgc cgcattatca cgcgatggaa gctacgaagg cgataaagcc   6840
gatactggga gagtattatc agttcgatgg gacgccggtg gttaaggcga tgtggaggga   6900
ggcgaaggag tgtatctatg tggaaccgga caggcaaggt gagaagaaag gtgtgttctg   6960
gtacaacaat aagttatgaa gcaaagaaga aactgaacct ttctcatcta tgattgtctt   7020
tgttttaaga agctatgttt ctgtttcaat aatctttaat tatccatttt gttgtgtttt   7080
```

```
ctgacatttt ggctaaaatg gcgccaccca gctttcttgt acaaagtggt ccccttaatt    7140
aactgggcct catgggcctt ccgctcactg cccgctttcc agtcgggaaa cctgtcgtgc    7200
cagctgcatt aacatggtca tagctgtttc cttgcgtatt gggcgctctc cgcttcctcg    7260
ctcactgact cgctgcgctc ggtcgttcgg gtaaagcctg gggtgcctaa tgagcaaaag    7320
gccagcaaaa ggccaggaac cgtaaaaagg ccgcgttgct ggcgtttttc cataggctcc    7380
gcccccctga cgagcatcac aaaaatcgac gctcaagtca gaggtggcga aacccgacag    7440
gactataaag ataccaggcg tttccccctg gaagctccct cgtgcgctct cctgttccga    7500
ccctgccgct taccggatac ctgtccgcct ttctcccttc gggaagcgtg gcgctttctc    7560
atagctcacg ctgtaggtat ctcagttcgg tgtaggtcgt tcgctccaag ctgggctgtg    7620
tgcacgaacc ccccgttcag cccgaccgct gcgccttatc cggtaactat cgtcttgagt    7680
ccaacccggt aagacacgac ttatcgccac tggcagcagc cactggtaac aggattagca    7740
gagcgaggta tgtaggcggt gctacagagt tcttgaagtg gtggcctaac tacggctaca    7800
ctagaagaac agtatttggt atctgcgctc tgctgaagcc agttaccttc ggaaaaagag    7860
ttggtagctc ttgatccggc aaacaaacca ccgctggtag cggtggtttt tttgtttgca    7920
agcagcagat tacgcgcaga aaaaaaggat ctcaagaaga tcctttgatc ttttctacgg    7980
ggtctgacgc tcagtggaac gaaaactcac gttaagggat tttggtcatg agattatcaa    8040
aaaggatctt cacctagatc cttttaaatt aaaaatgaag ttttaaatca atctaaagta    8100
tatatgagta aacttggtct gacagttacc aatgcttaat cagtgaggca cctatctcag    8160
cgatctgtct atttcgttca tccatagttg cctgactccc cgtcgtgtag ataactacga    8220
tacgggaggg cttaccatct ggccccagtg ctgcaatgat accgcgagaa ccacgctcac    8280
cggctccaga tttatcagca ataaaccagc cagccggaag ggccgagcgc agaagtggtc    8340
ctgcaacttt atccgcctcc atccagtcta ttaattgttg ccgggaagct agagtaagta    8400
gttcgccagt taatagtttg cgcaacgttg ttgccattgc tacaggcatc gtggtgtcac    8460
gctcgtcgtt tggtatggct tcattcagct ccggttccca acgatcaagg cgagttacat    8520
gatcccccat gttgtgcaaa aaagcggtta gctccttcgg tcctccgatc gttgtcagaa    8580
gtaagttggc cgcagtgtta tcactcatgg ttatggcagc actgcataat tctcttactg    8640
tcatgccatc cgtaagatgc ttttctgtga ctggtgagta ctcaaccaag tcattctgag    8700
aatagtgtat gcggcgaccg agttgctctt gcccggcgtc aatacgggat aataccgcgc    8760
cacatagcag aactttaaaa gtgctcatca ttggaaaacg ttcttcgggg cgaaaactct    8820
caaggatctt accgctgttg agatccagtt cgatgtaacc cactcgtgca cccaactgat    8880
cttcagcatc ttttactttc accagcgttt ctgggtgagc aaaaacagga aggcaaaatg    8940
ccgcaaaaaa gggaataagg gcgacacgga aatgttgaat actcatactc ttcctttttc    9000
aatattattg aagcatttat cagggttatt gtctcatgag cggatacata tttgaatgta    9060
tttagaaaaa taaacaaata ggggttccgc gcacatttcc ccgaaaagtg ccacctaaat    9120
tgtaagcgtt aatattttgt taaaattcgc gttaaatttt tgttaaatca gctcattttt    9180
taaccaatag gccgaaatcg gcaaaatccc ttataaatca aaagaataga ccgagatagg    9240
gttgagtggc cgctacaggg cgctcccatt cgccattcag gctgcgcaac tgttgggaag    9300
ggcgtttcgg tgcgggcctc ttcgctatta cgccagctgg cgaaaggggg atgtgctgca    9360
aggcgattaa gttgggtaac gccagggttt tcccagtcac gacgttgtaa aacgacggcc    9420
agtgagcgcg acgtaatacg actcactata gggcgaattg gcggaaggcc gtcaaggccg    9480
```
catggcgcgc c                    9491

<210> SEQ ID NO 211
<400> SEQUENCE: 211
000

<210> SEQ ID NO 212
<400> SEQUENCE: 212
000

<210> SEQ ID NO 213
<400> SEQUENCE: 213
000

<210> SEQ ID NO 214
<400> SEQUENCE: 214
000

<210> SEQ ID NO 215
<400> SEQUENCE: 215
000

<210> SEQ ID NO 216
<400> SEQUENCE: 216
000

<210> SEQ ID NO 217
<400> SEQUENCE: 217
000

<210> SEQ ID NO 218
<400> SEQUENCE: 218
000

<210> SEQ ID NO 219
<400> SEQUENCE: 219
000

<210> SEQ ID NO 220
<400> SEQUENCE: 220
000

<210> SEQ ID NO 221
<400> SEQUENCE: 221
000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256
<400> SEQUENCE: 256
000

<210> SEQ ID NO 257
<400> SEQUENCE: 257
000

<210> SEQ ID NO 258
<400> SEQUENCE: 258
000

<210> SEQ ID NO 259
<400> SEQUENCE: 259
000

<210> SEQ ID NO 260
<400> SEQUENCE: 260
000

<210> SEQ ID NO 261
<400> SEQUENCE: 261
000

<210> SEQ ID NO 262
<400> SEQUENCE: 262
000

<210> SEQ ID NO 263
<400> SEQUENCE: 263
000

<210> SEQ ID NO 264
<400> SEQUENCE: 264
000

<210> SEQ ID NO 265
<400> SEQUENCE: 265
000

<210> SEQ ID NO 266
<400> SEQUENCE: 266
000

```
<210> SEQ ID NO 267
<400> SEQUENCE: 267
000

<210> SEQ ID NO 268
<400> SEQUENCE: 268
000

<210> SEQ ID NO 269
<400> SEQUENCE: 269
000

<210> SEQ ID NO 270
<400> SEQUENCE: 270
000

<210> SEQ ID NO 271
<400> SEQUENCE: 271
000

<210> SEQ ID NO 272
<400> SEQUENCE: 272
000

<210> SEQ ID NO 273
<400> SEQUENCE: 273
000

<210> SEQ ID NO 274
<400> SEQUENCE: 274
000

<210> SEQ ID NO 275
<400> SEQUENCE: 275
000

<210> SEQ ID NO 276
<400> SEQUENCE: 276
000

<210> SEQ ID NO 277
<400> SEQUENCE: 277
000

<210> SEQ ID NO 278
```

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

```
<210> SEQ ID NO 312
<400> SEQUENCE: 312
000

<210> SEQ ID NO 313
<400> SEQUENCE: 313
000

<210> SEQ ID NO 314
<400> SEQUENCE: 314
000

<210> SEQ ID NO 315
<400> SEQUENCE: 315
000

<210> SEQ ID NO 316
<400> SEQUENCE: 316
000

<210> SEQ ID NO 317
<400> SEQUENCE: 317
000

<210> SEQ ID NO 318
<400> SEQUENCE: 318
000

<210> SEQ ID NO 319
<400> SEQUENCE: 319
000

<210> SEQ ID NO 320
<400> SEQUENCE: 320
000

<210> SEQ ID NO 321
<400> SEQUENCE: 321
000

<210> SEQ ID NO 322
<400> SEQUENCE: 322
000

<210> SEQ ID NO 323
```

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

-continued

<210> SEQ ID NO 346
<400> SEQUENCE: 346
000

<210> SEQ ID NO 347
<400> SEQUENCE: 347
000

<210> SEQ ID NO 348
<400> SEQUENCE: 348
000

<210> SEQ ID NO 349
<400> SEQUENCE: 349
000

<210> SEQ ID NO 350
<400> SEQUENCE: 350
000

<210> SEQ ID NO 351
<400> SEQUENCE: 351
000

<210> SEQ ID NO 352
<400> SEQUENCE: 352
000

<210> SEQ ID NO 353
<400> SEQUENCE: 353
000

<210> SEQ ID NO 354
<400> SEQUENCE: 354
000

<210> SEQ ID NO 355
<400> SEQUENCE: 355
000

<210> SEQ ID NO 356
<400> SEQUENCE: 356
000

<210> SEQ ID NO 357

```
<400> SEQUENCE: 357
000

<210> SEQ ID NO 358
<400> SEQUENCE: 358
000

<210> SEQ ID NO 359
<400> SEQUENCE: 359
000

<210> SEQ ID NO 360
<400> SEQUENCE: 360
000

<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
```

000

<210> SEQ ID NO 369
<400> SEQUENCE: 369
000

<210> SEQ ID NO 370
<400> SEQUENCE: 370
000

<210> SEQ ID NO 371
<400> SEQUENCE: 371
000

<210> SEQ ID NO 372
<400> SEQUENCE: 372
000

<210> SEQ ID NO 373
<400> SEQUENCE: 373
000

<210> SEQ ID NO 374
<400> SEQUENCE: 374
000

<210> SEQ ID NO 375
<400> SEQUENCE: 375
000

<210> SEQ ID NO 376
<400> SEQUENCE: 376
000

<210> SEQ ID NO 377
<400> SEQUENCE: 377
000

<210> SEQ ID NO 378
<400> SEQUENCE: 378
000

<210> SEQ ID NO 379
<400> SEQUENCE: 379
000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414
<400> SEQUENCE: 414
000

<210> SEQ ID NO 415
<400> SEQUENCE: 415
000

<210> SEQ ID NO 416
<400> SEQUENCE: 416
000

<210> SEQ ID NO 417
<400> SEQUENCE: 417
000

<210> SEQ ID NO 418
<400> SEQUENCE: 418
000

<210> SEQ ID NO 419
<400> SEQUENCE: 419
000

<210> SEQ ID NO 420
<400> SEQUENCE: 420
000

<210> SEQ ID NO 421
<400> SEQUENCE: 421
000

<210> SEQ ID NO 422
<400> SEQUENCE: 422
000

<210> SEQ ID NO 423
<400> SEQUENCE: 423
000

<210> SEQ ID NO 424
<400> SEQUENCE: 424
000

-continued

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

```
<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447
```

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 471
gacatcaagt ggtacggcaa gtacctcaac aacccgctag gacgcacggt gatgctaacc      60
gtccagttca agctcggctg ccgttgtac ttagccttca acgtctcggg aagaccttg       119

<210> SEQ ID NO 472
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 472
gacatcaagt ggtacggaaa gtacctcaac aacccgctag gacgcacggt gatgctaacc      60
gtccagttca cgctcggctg ccgttgtac ttagccttca acgtctctgg aagaccttg       119

<210> SEQ ID NO 473
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 473
gacatcaagt ggtacggcaa gtacctcaac aacccttggg gacgcaccgt gatgttaacg      60
gttcagttca ctctcggctg gccttttgtac ttagccttca acgtctcggg gagaccttg     119

<210> SEQ ID NO 474
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 474
gacatcaagt ggtacggcaa gtacctcaac aacccttggg gacgcaccgt gatgttaacg      60
gttcagttca ctctcggctg ccgttgtac ttagccttca acgtctcggg aagaccttg       119

<210> SEQ ID NO 475
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
cagacatcaa gtggtacggc                                                  20

```
<210> SEQ ID NO 476
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
acggcaagta cctcaacaac cctttggg                                              28

<210> SEQ ID NO 477
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
cgcaccgtga tgttaacggt tcagttca                                              28

<210> SEQ ID NO 478
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
cggcaagtac ctcaacaacc ctttggga                                              28

<210> SEQ ID NO 479
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
accgtgatgt taacggttca gttcactc                                              28

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
cttagccttc aacgtctcgg g                                                     21
```

FAD2 PERFORMANCE LOCI AND CORRESPONDING TARGET SITE SPECIFIC BINDING PROTEINS CAPABLE OF INDUCING TARGETED BREAKS

CROSS-REFERENCE TO RELATED APPLICATIONS

The present application is a divisional application of U.S. patent application Ser. No. 14/019,244, filed Sep. 5, 2013, which claims priority to the benefit of U.S. Provisional Patent Application No. 61/697,886, filed Sep. 7, 2012, the disclosure of which is hereby incorporated by reference in its entirety.

FIELD OF THE DISCLOSURE

The present disclosure relates generally to compositions and methods for use in recombinant plant technology (for example, for generating a transgenic plant). More specifically, the present disclosure relates to plant cells and plants including loci within their genomes that may be used for the site-specific introduction of any nucleic acid of interest.

BACKGROUND

Many plants are genetically transformed with exogenous nucleic acids (e.g., transgenes) to introduce desirable traits, for example, to improve agricultural value. Examples of improvements in agricultural value that can be achieved through genetic transformation include: improved nutritional quality, increased yield, pest or disease resistance, drought and stress tolerance, improved horticultural quality (e.g., improved pigmentation and/or growth), herbicide resistance, production of industrially useful compounds and/or materials from the plant, and/or production of pharmaceuticals. The introduction of cloned genes into plant cells and recovery of stable fertile transgenic plants can be used to make a genetic modification of a plant stable through multiple generations, and thereby allow the genetic engineering of a crop plant.

In methods for genetic transformation and transgenic plant production, exogenous DNA is typically randomly introduced into the nuclear or plastid DNA of a eukaryotic plant cell, followed by isolation of cells containing integrated exogenous DNA, and subsequent regeneration of a stably transformed plant. Transgenic plants were typically generated by *Agrobacterium*-mediated transformation technology. Successes with these techniques spurred the development of other methods to introduce a nucleic acid molecule of interest into the genome of a plant, such as PEG-mediated DNA uptake in protoplasts, microprojectile bombardment, and silicon whisker-mediated transformation.

In all of these plant transformation methods, however, the exogenous nucleic acids incorporated in the plant genome are integrated randomly in the genome of the plant cell, and in unpredictable copy number. Terada et al. (2002) *Nat Biotechnol* 20(10):1030; Terada et al. (2007) *Plant Physiol* 144(2):846; D'Halluin et al. (2008) *Plant Biotechnology J.* 6(1):93. For example, the transgenes are frequently integrated in the form of sequence repeats, either of the whole transgene or of parts thereof. Such a complex integration pattern commonly adversely impacts the expression level of the integrated nucleic acid (e.g., by destruction of transcribed RNA through post-transcriptional gene silencing mechanisms, or by inducing methylation of the integrated DNA).

Also, the location of the integration site commonly influences the level of expression of the integrated nucleic acid. Moreover, the integration of the exogenous DNA may have a disruptive effect on the region of the genome where the integration occurs, and thereby influence or disturb the normal function of that target region to produce undesirable side-effects. The combination of factors including the foregoing results in a wide variation in the level of expression of transgene or exogenous DNA (and overall agronomic quality) between different transgenic plant cell and plant lines, even those created by the same methods. Because the integration is random, these effects are not able to be controlled by the practitioner while he or she attempts to produce a new plant with desirable characteristics.

The foregoing considerations necessitate that, whenever the effects of introducing a particular exogenous nucleic acid into a plant is investigated, a large number of transgenic plant lines must be generated and analyzed in order to obtain significant results. Likewise, in the generation of a transgenic plant containing a particular integrated nucleic acid so as to provide the transgenic plant with a desired phenotype, a large population of independently created transgenic plant lines must be created to allow the selection of a plant line with optimal expression of the nucleic acid, and with minimal or no side-effects on the overall phenotype and performance of the transgenic plant. These practical considerations take on added importance in transgenic plants created by inserting multiple exogenous nucleic acids (i.e., gene stacking). In such plants, phenomena such as post-transcriptional gene silencing may be amplified.

Several methods have been developed in an effort to control transgene insertion in plants. See, e.g., Kumar and Fladung (2001) *Trends Plant Sci.* 6:155-9. These methods rely on homologous recombination-based transgene integration, which has been successfully applied both in prokaryotes and lower eukaryotes. Paszkowski et al. (1988) *EMBO J.* 7:4021-6. However, until recently in plants, the predominant mechanism for transgene integration has been based on illegitimate recombination, which involves little homology between recombining DNA strands. A major challenge in this area is therefore the detection and selective generation of rare homologous recombination events, which are masked by far more efficient integration events via illegitimate recombination. Moreover, even if the selective generation and detection of targeted homologous recombination events is achieved, the event must be targeted to a desirable location in the host genome in order to realize the maximum benefit of this strategy.

For example, an assumed benefit of targeted genetic transformation is the reduction in event-to-event variability of transgene expression, as compared to transformation events that are obtained from random integration. A further assumed benefit is a significant reduction in the number of events required to screen introduced nucleic acids, sort transformation constructs, and produce events that contribute to desirable overall characteristics in the resulting transgenic plant. A critical factor required to realize these benefits is the identification of specific locations in the genome where transgene performance is consistent, and if possible, where adverse effects on the host plant are eliminated or minimized.

Recently, methods and compositions for targeted cleavage of genomic DNA have been described. Such targeted cleavage events can be used, for example, to induce targeted mutagenesis, induce targeted deletions of cellular DNA sequences, and facilitate targeted recombination and integration at a predetermined chromosomal locus. See, for example, Urnov et al. (2010) Nature 435(7042):646-51; United States Patent Publications 20030232410; 20050208489; 20050026157; 20050064474; 20060188987; 20090263900; 20090117617; 20100047805; 20110207221; 20110301073; 2011089775; 20110239315; 20110145940; and International Publication WO 2007/014275, the disclosures of which are incorporated by reference in their entireties for all purposes. Cleavage can occur through the use of specific nucleases such as engineered zinc finger nucleases (ZFN), transcription-activator like effector nucleases (TALENs), or using the CRISPR/Cas system with an engineered crRNA/tracr RNA (single guide RNA') to guide specific cleavage. U.S. Patent Publication No. 20080182332 describes the use of non-canonical zinc finger nucleases (ZFNs) for targeted modification of plant genomes; U.S. Patent Publication No. 20090205083 describes ZFN-mediated targeted modification of a plant EPSPS locus; U.S. Patent Publication No. 20100199389 describes targeted modification of a plant Zp15 locus and U.S. Patent Publication No. 20110167521 describes targeted modification of plant genes involved in fatty acid biosynthesis. In addition, Moehle et al. (2007) Proc. Natl. Acad, Sci. USA 104(9): 3055-3060 describes using designed ZFNs for targeted gene addition at a specified locus. U.S. Patent Publication 20110041195 describes methods of making homozygous diploid organisms.

However, there remains a need for compositions and methods for modifying and/or modulating expression of FAD2 genes in plants, including generation of plants with targeted insertions of desired transgenes at the FAD2 locus.

BRIEF SUMMARY OF THE DISCLOSURE

The present disclosure describes compositions and methods for modulating expression of FAD2 genes (e.g., in plants, algae, and fungi) and the use of these loci as sites for the targeted integration of a nucleic acid sequence of interest (e.g., an exogenous nucleic acid sequence) into a host cell. In some embodiments, a host cell may contain one or more genomes with one or more FAD2 sequences (e.g., homeologues or paralogs), any or all of which may be selectively modified and/or disrupted. In specific examples, the present disclosure describes FAD2A, FAD2A', FAD2C and FAD2C' genes, as well as corresponding homeologues or paralogs, in Brassica napus (i.e., B. napus line, DH12075) and their use as loci for targeted integration of a nucleic acid sequence of interest. As described herein, though FAD2 genes are involved in fatty acid biosynthesis in the host, their modification or disruption (e.g., by integration of an exogenous nucleic acid in the FAD2 coding sequence) unexpectedly may have no or minimal adverse effects on the resultant host organism.

Also described herein is the use of one or more particular FAD2 loci in tandem with a polypeptide capable of effecting cleavage and/or integration of specific nucleic acid sequences within the FAD2 loci. Examples of the use of FAD2 loci in tandem with a polypeptide capable of effecting cleavage and/or integration of the FAD2 loci include a polypeptide selected from the group consisting of zinc finger proteins, meganucleases, TAL domains, TALENs, RNA-guided CRISPR-Cas9, recombinases, leucine zippers, CRISPr/Cas and others known to those in the art. Particular examples include a chimeric ("fusion") protein comprising a site-specific DNA binding domain polypeptide and cleavage domain polypeptide (e.g., a nuclease), such as a ZFN protein comprising a zinc-finger polypeptide and a FokI nuclease polypeptide. For example, described herein is a demonstration of the in vitro and in vivo efficacy and specificity of particular ZFNs designed to bind and induce double stranded breaks in FAD2A, FAD2A', FAD2C, FAD2C', and in combinations thereof without cleaving corresponding homeologues or paralogs. In some embodiments, particular FAD2 loci may be used with any of the foregoing polypeptides to effect site-specific integration of a nucleic acid of interest that is subsequently expressed in the host while having a minimal adverse impact on the agronomic performance of the host.

In certain aspects, described herein are polypeptides comprising a DNA-binding domain that specifically binds to a FAD2 gene. In some embodiments such a polypeptide may also comprise a nuclease (cleavage) domain or half-domain (e.g., a ZFN, a recombinase, a transposase, or a homing endonuclease, including a homing endonuclease with a modified DNA-binding domain, TAL domains, TALENs, RNA-guided CRISPR-Cas9), and/or a ligase domain, such that the polypeptide may induce a targeted double-stranded break, and/or facilitate recombination of a nucleic acid of interest at the site of the break. In particular embodiments, a DNA-binding domain that targets a FAD2 locus may be a DNA-cleaving functional domain. The foregoing polypeptides may be used in some embodiments to introduce an exogenous nucleic acid into the genome of a host organism (e.g., a plant or animal species) at one or more FAD2 loci. In certain embodiments, the DNA-binding domains comprise a zinc finger protein with one or more zinc fingers (e.g., 2, 3, 4, 5, 6, 7, 8, 9 or more zinc fingers), and can which is engineered (non-naturally occurring) to bind to any sequence within a FAD2 gene. Any of the zinc finger proteins described herein may bind to a target site within the coding sequence of the target gene or within adjacent sequences (e.g., promoter or other expression elements). In certain embodiments, the zinc finger protein binds to a target site in an FAD2 gene, for example, as shown in Table 5. The recognition helix regions of exemplary FAD2-binding zinc fingers are shown in Table 4. One or more of the component zinc finger binding domains of the zinc finger protein can be a canonical (C2H2) zinc finger or a non-canonical (e.g., C3H) zinc finger (e.g., the N-terminal and/or C-terminal zinc finger can be a non-canonical finger).

Also described herein are methods for disrupting or editing a FAD2 gene. Additionally described herein are genetically modified host organisms (e.g., transgenic plants) produced by methods according to embodiments of the invention. In particular examples, a transgenic organism produced by a method according to an embodiment of the invention may be, without limitation, algae, a fungus, a monocotyledonous plant, a dicotyledonous plant, etc.

The FAD2 genes disclosed herein may include those found in any plant, algae, or fungi that have one or more FAD2 genes.

The foregoing and other features will become more apparent from the following detailed description of several embodiments, which proceeds with reference to the accompanying figures.

BRIEF DESCRIPTION OF THE FIGURES

FIGS. 1A through 1E show a sequence alignment of FAD2 gene sequences (SEQ ID NOs:5-8), generated using AlignX®.

FIGS. 5A and 5B show ZFN targeting of FAD2 genes. FIG. 5A is a graph depicting data from ZFN targeting locus 4 of the FAD2 gene family. The locus contains two ZFN sites and two requisite control transfections. FIG. 5B shows specific sequence context (SEQ ID NOs:471-480), respectively, in order of appearance) surrounding the ZFN target site, identifying FAD2A and C containing tri-nucleotide repeats of C, T and G, leading to the observed increase in single base deletions through sequencing of the FAD2A and C loci.

SEQUENCES

Figure 2:
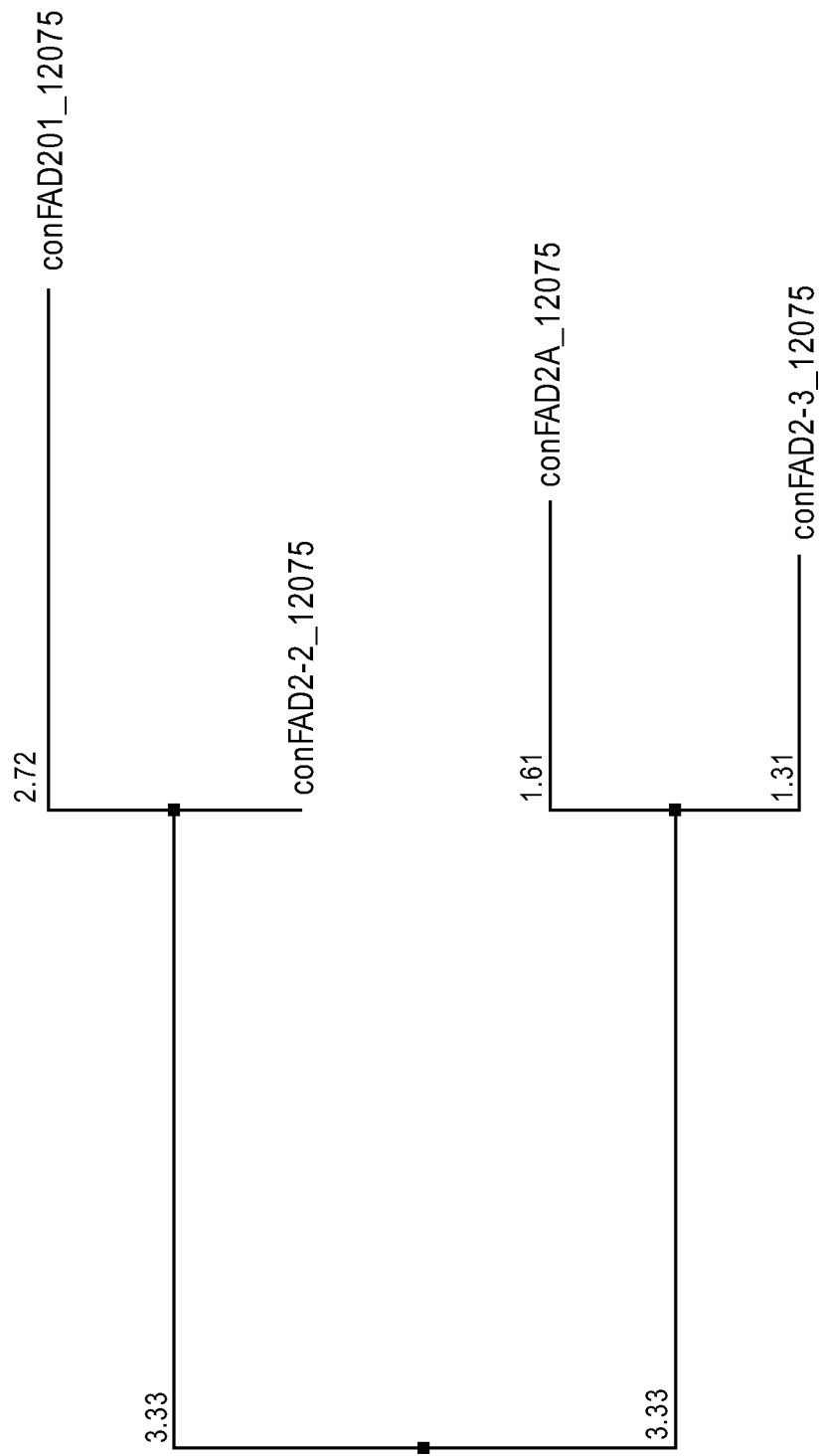
FIG. 2 is a schematic depicting a phylogenetic tree of FAD2 gene sequences generated using Jalview v 2.3 based on neighbor joining distances.

The nucleic acid sequences are shown using standard letter abbreviations for nucleotide bases, as defined in 37 C.F.R. § 1.822. Only one strand of each nucleic acid sequence is shown, but the complementary strand is understood to be included by any reference to the displayed strand.

DETAILED DESCRIPTION

I. Overview of Several Embodiments

Embodiments of the invention establish an approach for targeted integration of exogenous nucleic acids (e.g., transgenes) in a host genome without greatly adversely impacting other phenotypes of the host beyond those affected by the integrated nucleic acid. Some embodiments may be used for "stacking" multiple nucleic acids in a single host genome. Such an approach requires the development and deployment of four inter-connected technologies: targeting technologies allowing the introduction of double stranded breaks in specific genomic DNA locations (see, e.g., Puchta et al. (1993) Nucleic Acids Res. 21:5034-40; Siebert and Puchta (2002) Plant Cell 14:1121-31; D'Halluin et al. (2008) Plant Biotechnol. J. 6(1):93-102; Cai et al. (2009) Plant Mol. Biol. 69(6):699-709; Shukla et al. (2009) Nature 459(7245):437-41); Shan et al. (2103) Nature Biotechnol. 31:686-680; Le et al. (2013) Nature Biotechnol 31: 688-691; Nekrasov et al. (2013) Nature Biotechnol. 31:691-693, Ainely et al. (2013) Plant Biotechnol. J. (On Line 19 August); delivery technologies allowing the delivery of an optimized exogenous (donor) nucleic acid (Bibikova et al. (2003) Science 300(5620): 764); integration technologies involving modification of the host genes (located either in the homologous recombination or NHEJ pathways) so as to increase the HDR or NHEJ frequencies for targeted donor DNA integration; analytical tools to enrich and characterize targeted integration events; and specific desired host genomic locations ("performance loci") that are genetically well-defined and that support stable gene expression across generations without greatly adversely affecting the transformed host organism. See, also, United States Patent Publications 20030232410; 20050208489; 20050026157; 20050064474; 20060188987; 20090263900; 20090117617; 20100047805; 20110207221; 20110301073; 2011089775; 20110239315; 20110145940; 20080182332; 20090205083; 20100199389; 20110167521. For example, in plants, a performance locus is a locus where the negative impact on the agronomic or quality properties of a transgenic plant wherein a transgene has been integrated at the locus is negligible or non-existent.

Embodiments described herein take advantage of the unexpected finding that plant FAD2 genes are performance loci for the targeted integration of exogenous nucleic acids (e.g., gene(s); non-coding DNA sequences, such as an Engineered Landing Pads (ELPs) (U.S. Patent Publication No. 20080134482) and Engineered Transgene Insertion Platform (ETIP) (U.S. Patent Publication No. 20140090113); and plant transformation unit(s)). The ubiquitous nature of FAD2 loci in plants, and evidence that alteration or knock-out of FAD2 in canola, corn, sunflower, wheat, cotton, and soybean does not carry an agronomic or quality penalty, identifies FAD2 loci as a broad class of performance loci across commercially-relevant plant species.

Some embodiments utilize site-specific double-stranded DNA cleavage at a FAD2 locus, for example, resulting from the delivery and expression of a target-site specific DNA recognition and cleavage protein. In specific examples, such a FAD2-specific DNA recognition and cleavage protein may be, for example and without limitation, a ZFN; a TALEN; RNA-guided CRISPR-Cas9, a recombinase (e.g., Cre, Hin, RecA, Tre, and FLP recombinases); a meganuclease, and an engineered protein derived from any of the foregoing or their equivalents. Cleavage may also be effected using the CRISPR/Cas system with an engineered crRNA/tracr RNA (single guide RNA') to guide specific cleavage. In some embodiments, such a double-strand break may be repaired via integration of a donor nucleic acid at the cleavage site within the FAD2 performance locus, for example, by Homology Directed Repair (HDR) or Non-Homologous End Joining (NHEJ).

This disclosure exemplifies the utility of FAD2 loci as performance loci, for example, by describing the FAD2A, 2A', 2C or 2C' locus in canola (*Brassica napus*), and corresponding FAD2-specific ZFNs that may be utilized to integrate an exogenous nucleic acid at the FAD2A, 2A', 2C or 2C' locus.

Embodiments of the present invention address many unsolved problems in the art. For example, the selectivity of the targeted integration approach described herein may reduce or eliminate the necessity of repeated field trials required for elimination of unwanted transgenic events, which trials are costly due to the resources involved and the burdensome regulatory requirements in this area. Furthermore, the targeted DNA integration approaches described herein may be particularly beneficial in the process of transgene stacking.

Although the native nucleotide sequence at an endogenous FAD2 locus may be used to directly target a nucleic acid of interest, in some embodiments, a nucleic acid may first be targeted to at least one FAD2 locus of the host, such that the integration of further nucleic acid molecules of interest into the host is facilitated. In other examples, nucleotide sequences that are not homologous to native sequences of the host organism (e.g., essentially randomly generated nucleic acid sequences) that flank a DNA recognition site (e.g., zinc finger recognition sites) may be utilized.

II. Terms

As used in this application, including the claims, terms in the singular and the singular forms, "a," "an," and "the," for example, include plural referents, unless the content clearly dictates otherwise. Thus, for example, a reference to "plant," "the plant," or "a plant" also refers to a plurality of plants. Furthermore, depending on the context, use of the term, "plant," may also refer to genetically-similar or identical progeny of that plant. Similarly, the term, "nucleic acid," may refer to many copies of a nucleic acid molecule. Likewise, the term, "probe," may refer to many similar or identical probe molecules.

Numeric ranges are inclusive of the numbers defining the range, and expressly include each integer and non-integer fraction within the defined range. Unless defined otherwise, all technical and scientific terms used herein have the same meaning as commonly understood by one of ordinary skill in the art.

In order to facilitate review of the various embodiments described in this disclosure, the following explanation of specific terms is provided:

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Cross: As used herein in regard to plants, the term "cross" or "crossed" refers to the fusion of gametes via pollination to produce progeny (e.g., cells, seeds, and plants). This term encompasses both sexual crosses (i.e., the pollination of one plant by another) and selfing (i.e., self-pollination, for example, using pollen and ovule from the same plant).

Backcrossing: Backcrossing methods may be used to introduce a nucleic acid sequence into a plant. This technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a nucleic acid sequence of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred nucleic acid sequence from the non-recurrent parent.

Introgression: As used herein, the term "introgression" refers to the transmission of an allele (or modified allele comprising an exogenous nucleic acid) into a genetic background at a particular locus. In some embodiments, introgression of a specific allele at the locus may occur by transmitting the allele to at least one progeny via a sexual cross between two parents of the same species, where at least one of the parents has the specific allele form in its genome. Progeny comprising the specific allele may be repeatedly backcrossed to a line having a desired genetic background. Backcross progeny may be selected for the specific allele form, so as to produce a new variety wherein the specific allele form has been fixed in the genetic background. In some embodiments, introgression of a specific allele may occur by recombination between two donor genomes (e.g., in a fused protoplast), where at least one of the donor genomes has the specific allele form in its genome. Introgression may involve transmission of a specific allele form that may be, for example and without limitation, a disrupted or modified allele; a transgene; a PTU; and an ELP.

Germplasm: As used herein, the term "germplasm" refers to genetic material of or from an individual plant, a group of plants (e.g., a plant line, variety, and family), and a clone derived from a plant or group of plants. A germplasm may be part of an organism or cell, or it may be separate (e.g., isolated) from the organism or cell. In general, germplasm provides genetic material with a specific molecular makeup that is the basis for hereditary qualities of the plant. As used herein, "germplasm" refers to cells of a specific plant; seed; tissue of the specific plant (e.g., tissue from which new plants may be grown); and non-seed parts of the specific plant (e.g., leaf, stem, pollen, and cells). As used herein, the term "germplasm" is synonymous with "genetic material," and it may be used to refer to seed (or other plant material) from which a plant may be propagated. A "germplasm bank" may refer to an organized collection of different seed or other genetic material (wherein each genotype is uniquely identified) from which a known cultivar may be cultivated, and from which a new cultivar may be generated.

Gene: As used herein, the term "gene" (or "genetic element") may refer to a heritable genomic DNA sequence with functional significance. A gene may be a native nucleic acid, or a nucleic acid that has been integrated into the genome. The term "gene" may also be used to refer to, for example and without limitation, a cDNA and/or an mRNA encoded by a heritable genomic DNA sequence.

Nucleic acid molecule: As used herein, the term "nucleic acid molecule" may refer to a polymeric form of nucleotides (i.e., ribonucleotides, deoxyribonucleotides, and/or a modified form of either of the foregoing). A "nucleic acid molecule" as used herein is synonymous with "nucleic acid" and "polynucleotide." The term includes both sense and anti-sense strands of RNA, cDNA, genomic DNA, and synthetic forms and mixed polymers thereof. The term includes any topological conformation, including single-stranded, double-stranded, partially duplexed, triplexed, hairpinned, circular, and padlocked conformations. A nucleic acid molecule can include either or both of naturally-occurring and modified nucleotides. Such nucleotides may be linked together by naturally-occurring and/or non-naturally-occurring nucleotide linkages.

Nucleic acid molecules may be modified chemically or biochemically, or may contain derivatized nucleotide bases, as will be readily appreciated by those of skill in the art. Such modifications include, for example and without limitation: labels; methylation; substitution of one or more of the naturally-occurring nucleotides with an analog; and inter-nucleotide modifications (e.g., uncharged linkages, for example, methyl phosphonates, phosphotriesters, phosphoramidates, and carbamates; charged linkages, for example, phosphorothioates and phosphorodithioates; pendent moieties, for example, peptides; intercalators, for example, acridine and psoralen; chelators; alkylators; and modified linkages, for example, alpha anomeric nucleic acids).

Exogenous: An "exogenous" molecule is a molecule that is not native to a specified system (e.g., a germplasm, variety, elite variety, and/or plant) with respect to nucleotide sequence and/or genomic location (i.e., locus) for a polynucleotide (and with respect to amino acid sequence and/or cellular localization for a polypeptide). In embodiments, exogenous or heterologous polynucleotides or polypeptides may be molecules that have been artificially supplied to a biological system (e.g., a plant cell, a plant gene, a particular plant species or variety, and/or a plant chromosome) and are not native to that particular biological system. Thus, the designation of a nucleic acid as "exogenous" may indicate that the nucleic acid originated from a source other than a naturally-occurring source, or it may indicate that the nucleic acid has a non-natural configuration, genetic location, or arrangement of elements.

In contrast, for example, a "native" or "endogenous" nucleic acid is a nucleic acid (e.g., a gene) that does not contain a nucleic acid element other than those normally present in the chromosome or other genetic material on which the nucleic acid is normally found in nature. An endogenous gene transcript is encoded by a nucleotide sequence at its natural chromosomal locus, and is not artificially supplied to the cell.

Operably linked: A first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

Promoter: A promoter is a region of DNA that generally is located upstream (towards the 5' region) of a nucleic acid that enhances transcription of the nucleic acid. Promoters permit the proper activation or repression of the nucleic acid(s) with which they are operably linked. A promoter contains specific sequences that are recognized by transcription factors. These factors bind to the promoter DNA sequences and result in the recruitment of RNA polymerase, the enzyme that synthesizes the RNA from the coding region of the nucleic acid. Transformed: A vector "transforms" or "transduces" a cell when it transfers nucleic acid molecules into the cell. A cell is "transformed" by a nucleic acid molecule when the nucleic acid molecule becomes stably replicated by the cell, either by incorporation of the nucleic acid molecule into the cellular genome or by episomal replication. As used herein, the term "transformation" encompasses all techniques by which a nucleic acid molecule can be introduced into a cell. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Introduced: As used herein, the term "introduced," when referring to translocation of an exogenous nucleic acid into a cell, refers to the incorporation of the nucleic acid into the cell using any methodology available in the art. This term encompasses nucleic acid introduction methods including, for example and without limitation, transfection; transformation; and transduction.

Transgene: As used herein, the term "transgene" refers to an exogenous nucleic acid coding sequence of interest. For example, a transgene may encode an industrially or pharmaceutically useful compound, or an expression product that contributes to a desirable agricultural trait (e.g., herbicide resistance or pest resistance). In a further example, a transgene may be an antisense nucleic acid, wherein expression of the antisense nucleic acid inhibits expression of a target nucleic acid sequence. A transgene may comprise regulatory sequences operably linked to the transgene (e.g., a promoter). In some embodiments, a nucleic acid molecule of interest to be introduced by site-specific targeting at a FAD2 locus is a transgene. However, in other embodiments, a nucleic acid molecule of interest may be a PTU, an ELP, an ETIP, or an endogenous nucleic acid sequence (e.g., wherein additional, exogenous genomic copies of the endogenous nucleic acid sequence are desired).

Elements can also include DNA that encodes for a structural RNA, such as shRNA. Such RNA can modify exogenous or endogenous genes including, but not limited to affecting postings or conferring herbicide resistance.

Recombinant: As used herein, the term "recombinant" refers to a material (e.g., nucleic acid, gene, polynucleotide, and/or polypeptide) that has been altered by human intervention. For example, the arrangement of the parts or elements of a recombinant molecule may not be a native arrangement, and/or the primary sequence of the recombinant molecule may have been changed from its native sequence, e.g., to optimize its expression and/or activity. A material may be altered to produce a recombinant material within or removed from its natural environment or state. As one example, an open reading frame of a nucleic acid is recombinant if the nucleotide sequence of the open reading frame has been removed from it natural context and cloned into an artificial nucleic acid molecule (e.g., a vector). Protocols and reagents to produce recombinant molecules (e.g., recombinant nucleic acids) are common in the art, and their use is routine. The term "recombinant" may also refer herein to a cell or organism that comprises recombinant material (e.g., a plant and/or plant cell that comprises a recombinant nucleic acid). In some examples, a recombinant organism is a transgenic organism.

Vector: As used herein, the term "vector" refers to a polynucleotide or other molecule that is capable of transferring at least one nucleic acid segment(s) into a cell. A vector may optionally comprise components/elements that mediate vector maintenance and/or enable its intended use (e.g., sequences necessary for replication, genes imparting drug or antibiotic resistance, a multiple cloning site, and/or operably linked promoter/enhancer elements that enable the expression of a cloned gene). Vectors may be derived, for example, from plasmids, bacteriophages, or plant or animal viruses. A "cloning vector," "shuttle vector," or "subcloning vector" generally comprises operably linked elements to facilitate cloning or subcloning steps (e.g., a multiple cloning site containing multiple restriction endonuclease sites).

Expression Vector: The term "expression vector," as used herein, refers to a vector comprising operably linked polynucleotide sequences that may facilitate expression of a coding sequence in a particular host organism. For example, a bacterial expression vector may facilitate expression of a coding sequence in a bacterium. Likewise, a plant expression vector may facilitate expression of a coding sequence in a plant cell. Polynucleotide sequences that facilitate expression in prokaryotes may include, for example and without limitation, a promoter; an operator; and a ribosome binding site. Eukaryotic expression vectors (e.g., a plant expression vector) may comprise, for example, promoters; enhancers; termination signals; and polyadenylation signals (and other sequences) that are generally different from those used in prokaryotic expression vectors.

Sequence identity: The term "sequence identity" or "identity," as used herein in the context of two nucleic acid or polypeptide sequences, refers to the residues in the two sequences that are the same when aligned for maximum correspondence over a specified comparison window. A value of sequence identity may be determined by comparing two optimally aligned sequences (e.g., nucleic acid sequences and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The sequence identity is calculated as a percentage by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in Altschul et al. (1990) J. Mol. Biol. 215:403-10.

The National Center for Biotechnology Information (NCBI) Basic Local Alignment Search Tool (BLAST™; Altschul et al. (1990)) may be used to align sequences, and it is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with greater similarity to the reference sequences will show increasing percentage identity when assessed by this method.

As used herein, the term "substantially identical" may refer to nucleotide sequences that are more than 80% identical. For example, a substantially identical nucleotide sequence may be at least 85%, at least 86%; at least 87%; at least 88%; at least 89%; at least 90%; at least 91%; at least 92%; at least 93%; at least 94%; at least 95%; at least 96%; at least 97%; at least 98%; at least 99%; or at least 99.5% identical to the reference sequence.

Locus: As used herein, the term "locus" refers to a position on a genome that corresponds to a measurable characteristic (e.g., a trait). In some embodiments, a locus of particular interest is the genomic position of a FAD2 gene, where disruption of the gene reduces or eliminates expression of the mRNA transcribed from the wild-type gene. A locus may be defined by a probe that hybridizes to a unique nucleotide sequence contained within the locus either during Southern hybridization or PCR.

Marker: As used herein, a "marker" refers to a gene or nucleotide sequence that can be used to identify plants that are likely to have a particular allele and/or exhibit a particular trait or phenotype. A marker may be described as a variation at a given genomic locus. A genetic marker may be a short DNA sequence, such as a sequence surrounding a single base-pair change (single nucleotide polymorphism, or "SNP"), or a long sequence, for example, a minisatellite/simple sequence repeat ("SSR"). A "marker allele" refers to the version of the marker that is present in a particular plant. The term marker as used herein may refer to a cloned segment of plant chromosomal DNA (e.g., a segment comprising a FAD2 locus, or a modified and/or disrupted FAD2 locus), and may also or alternatively refer to a DNA molecule that is complementary to a cloned segment of plant chromosomal DNA. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome. Any and all of the above-described varieties of markers may be used in some embodiments of the present invention.

In some embodiments, the presence of a transgene or marker (which are characterized by a "target" sequence) in a germplasm may be detected through the use of a nucleic acid probe; e.g., an oligonucleotide. A probe may be a DNA molecule or an RNA molecule. An oligonucleotide probe may be prepared synthetically or by cloning. Suitable cloning vectors are well-known to those of skill in the art. RNA probes can be synthesized by means known in the art, for example, using a DNA molecule template.

An oligonucleotide probe may be labeled or unlabeled. A wide variety of techniques exist for labeling nucleic acid molecules, including, for example and without limitation, radiolabeling by nick translation; random priming; and tailing with terminal deoxytransferase, where the nucleotides employed are labeled, for example, with radioactive $^{32}$P. Other labels which may be used include, for example and without limitation, fluorophores; enzymes; enzyme substrates; enzyme cofactors; and enzyme inhibitors. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may be an exact copy of a transgene or marker to be detected. A probe may also be a nucleic acid molecule comprising, or consisting of, a nucleotide sequence that is substantially identical to a cloned segment of chromosomal DNA comprising the transgene or marker to be detected. A probe may further comprise additional nucleic acid sequences, for example, promoters; transcription signals; and/or vector sequences.

A probe may contain all or a portion of the target nucleotide sequence and additional, contiguous nucleotide sequence from the genome. This is referred to herein as a "contiguous probe." The additional, contiguous nucleotide sequence is referred to as "upstream" or "downstream" of the original target, depending on whether the contiguous nucleotide sequence from the chromosome is on the 5' or the 3' side of the original marker, as conventionally understood. A probe may also contain a nucleotide sequence that is not contiguous to that of the original target; this probe is referred to herein as a "non-contiguous probe." The sequence of the non-contiguous probe may be located sufficiently close to the sequence of the original target on the chromosome so that the non-contiguous probe is linked to the original marker or transgene.

In some embodiments, a probe is a nucleic acid molecule that is "specifically hybridizable" or "specifically complementary" to an exact copy of the target to be detected. "Specifically hybridizable" and "specifically complementary" are terms that indicate a sufficient degree of complementarity, such that stable and specific binding occurs between the nucleic acid molecule and the target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, 2$^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N Y, 1993; and Ausubel et al., Eds., *Current Protocols in Molecular Biology*, Chapter 2, Greene Publishing and Wiley-Interscience, N Y, 1995.

As used herein, "stringent conditions" encompass conditions under which hybridization will only occur if there is less than 25% mismatch between the hybridization molecule and the DNA target. "Stringent conditions" include further particular levels of stringency. Thus, as used herein, "moderate stringency" conditions are those under which molecules with more than 25% sequence mismatch will not hybridize; conditions of "medium stringency" are those under which molecules with more than 15% mismatch will not hybridize; and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6× saline-sodium citrate (SSC) buffer, 5×Denhardt's solution, 0.5% SDS, and 100 μg sheared salmon testes DNA, followed by 15-30 minute sequential washes at 65° C. in 2×SSC buffer and 0.5% SDS, followed by 1×SSC buffer and 0.5% SDS, and finally 0.2×SSC buffer and 0.5% SDS.

Linkage (dis)equilibrium: As used herein, the term "linkage equilibrium" refers to the situation where a marker and a second nucleic acid (e.g., transgene, PTU, and second marker) independently segregate; i.e., the marker and the second nucleic acid sort randomly among progeny. Nucleic acids that show linkage equilibrium are considered unlinked (whether or not they lie on the same chromosome). As used herein, the term "linkage disequilibrium" refers to the situation where a marker and a second nucleic acid segregate in a non-random manner; i.e., the nucleic acids have a recombination frequency of less than 50% (and thus by definition, are separated by less than 50 cM on the same linkage group). In some examples, nucleic acids that show linkage disequilibrium are considered linked.

Linked, tightly linked, and extremely tightly linked: As used herein, linkage between a marker and a second nucleic acid (e.g., transgene, PTU, and second marker) may refer to the phenomenon in which nucleic acids on a chromosome show a measurable probability of being passed on together to individuals in the next generation. Thus, linkage of one marker to a second nucleic acid may be measured and/or expressed as a recombination frequency. The closer two nucleic acids are to each other, the closer to "1" this probability becomes. Thus, the term "linked" may refer to one or more genes or markers that are passed together with a second nucleic acid with a probability greater than 0.5 (which is expected from independent assortment where markers/genes are located on different chromosomes). When the presence of a gene (e.g., a transgene) contributes to a phenotype in an individual, markers that are linked to the gene may be said to be linked to the phenotype. Thus, the term "linked" may refer to a relationship between a marker and a gene, or between a marker and a phenotype.

A relative genetic distance (determined by crossing over frequencies and measured in centimorgans (cM)) is generally proportional to the physical distance (measured in base pairs) that two linked markers or genes are separated from each other on a chromosome. One centimorgan is defined as the distance between two genetic markers that show a 1% recombination frequency (i.e., a crossing-over event occurs between the two markers once in every 100 cell divisions). In general, the closer one marker is to another marker or gene (whether the distance between them is measured in terms of genetic distance or physical distance,) the more tightly they are linked. Because chromosomal distance is approximately proportional to the frequency of recombination events between traits, there is an approximate physical distance that correlates with recombination frequency. This correlation is generally known or readily determinable across the major crop plants (Helentjaris and Burr (eds.) (1989) *Development and Application of Molecular Markers to Problems in Plant Genetics*. Cold Spring Harbor Laboratory, Cold Spring Harbor, N.Y.; Gresshoff (ed.) (1994) *Plant Genome Analysis*. CRC Press, Boca Raton, Fla.; Lander et al. (1987) Genomics 1:174-81; Tanksley et al. (1988) "Molecular mapping of plant chromosomes," In *Chromosome Structure and Function*. Gustafson and Appels (eds.) Plenum Press, NY, pp. 157-73) and many other organisms. For example, 1 cM corresponds to about 2.5-3.0 kb in yeast, about 140 kb in *Arabidopsis*, about 400 kb in sunflower, and about 350 kb in *Eucalyptus*.

The term "linked" may refer herein to one or more nucleic acids that show a recombination frequency of less than 50% (i.e., less than 50 cM). For example, "linked" nucleic acids may recombine with a frequency of about 45% or less, about 40% or less, about 35% or less, about 30% or less, about 25% or less, about 20% or less, about 15% or less, and about 10% or less. The physical distances between such nucleic acids on the same chromosome (nucleic acids on different chromosomes are expected to be in linkage equilibrium) that correspond to the foregoing recombination frequencies depend on the host genome, and may be easily calculated as set forth, supra.

As used herein, the term "tightly-linked" may refer to one or more nucleic acids that show a recombination frequency of about 20% or less (i.e., about 20 cM or less). For example, "tightly linked" nucleic acids may recombine with a frequency of 22% or less, about 18% or less, about 16% or less, about 14% or less, about 12% or less, about 10% or less, about 8% or less, about 6% or less, about 4% or less, and about 2% or less.

As used herein, the term "extremely tightly-linked" may refer to one or more nucleic acids that show a recombination frequency of about 10% or less (i.e., about 10 cM or less). For example, "extremely tightly linked" nucleic acids may recombine with a frequency of 11% or less, about 9% or less, about 8% or less, about 7% or less, about 6% or less, about 5% or less, about 4% or less, about 3% or less, about 2% or less, and about 1% or less.

The closer a particular nucleic acid is to a gene that encodes a polypeptide that contributes to a particular phenotype (whether measured in terms of genetic or physical distance), the more tightly-linked is the particular nucleic acid to the phenotype. In view of the foregoing, it will be appreciated that nucleic acids linked to a particular gene or phenotype include those nucleic acids that are tightly linked, and those nucleic acids that are extremely tightly linked, to the gene or phenotype. In some embodiments, the closer a particular nucleic acid is to a FAD2 locus (e.g., a modified or disrupted FAD2 locus), whether measured in terms of genetic or physical distance, the more tightly-linked is the particular nucleic acid to any trait/phenotype conferred by an exogenous nucleic acid integrated at the FAD2 locus (or to a wild-type FAD2 phenotype in the case of an unmodified locus). Thus, genetic markers that are linked, tightly linked, and/or extremely tightly linked to a FAD2 locus comprising an integrated exogenous nucleic acid may be useful in an MAS program to identify organisms (e.g., plants and plant varieties) comprising the integrated nucleic acid, to identify organisms comprising a phenotype conferred by the integrated nucleic acid, and to breed such an integrated nucleic acid and/or a phenotype conferred by the integrated nucleic acid into other compatible organisms.

Marker-assisted breeding: As used herein, the term "marker-assisted breeding" may refer to an approach to breeding plants directly for one or more trait(s) (e.g., a polygenic trait). In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships between traits of interest and easily detectable traits available for use in plant breeding. In some embodiments of the invention, marker-assisted breeding comprises identifying one or more genetic markers (e.g., SNP, isozyme, and/or SSR markers) that are linked to a FAD2 locus wherein an exogenous nucleic acid contributing to a trait of interest has been integrated, and following the trait of interest in a segregating, breeding population by following the segregation of the one or more genetic markers. In some examples, the segregation of the one or more genetic markers may be determined utilizing a probe for the one or more genetic markers by assaying a genetic sample from a progeny plant for the presence of the one or more genetic markers.

Marker-assisted breeding provides a time- and cost-efficient process for improvement of plant varieties.

Trait or phenotype: The terms "trait" and "phenotype" are used interchangeably herein. For the purposes of the present disclosure, traits of particular interest include agronomically important traits, as may be expressed, for example, in a crop plant, and the production of transgene expression products from a targeted integration event. The term "molecular phenotype" may refer to a phenotype that is detectable at the level of a population of (one or more) molecules. In some examples, the molecular phenotype may only be detectable at the molecular level. The detectable molecules of the phenotype may be nucleic acids (e.g., genomic DNA or RNA); proteins; and/or metabolites. For example, a molecular phenotype may be an expression profile for one or more gene products (e.g., at a specific stage of plant development, or in response to an environmental condition or stress).

Quantitative Trait Locus: Traits that are continuously varying due to genetic (additive, dominant, and epistatic) and environmental influences are commonly referred to as "quantitative traits." Quantitative traits may be distinguished from "qualitative," or "discrete," traits on the basis of two factors; environmental influences on gene expression that produce a continuous distribution of phenotypes, and the complex segregation pattern produced by multigenic inheritance. The identification of one or more regions of the genome linked to the expression of a quantitative trait defines such regions as Quantitative Trait Loci ("QTL").

Plant: As used herein, the term "plant" may refer to a whole plant, a cell or tissue culture derived from a plant, and/or any part of any of the foregoing. Thus, the term "plant" encompasses, for example and without limitation, whole plants; plant components and/or organs (e.g., leaves, stems, and roots); plant tissue; seed; and a plant cell. A plant cell may be, for example and without limitation, a cell in and/or of a plant, a cell isolated from a plant, and a cell obtained through culturing of a cell isolated from a plant.

A "transgenic plant" is a plant comprising within at least one of its cells an exogenous polynucleotide. The term "transgenic" is used herein to refer to any cell, cell line, callus, tissue, plant part, or plant, the genotype of which has been altered by the presence of a exogenous nucleic acid. Thus, this term encompasses transgenic organisms and cells that have been initially altered to comprise the exogenous polynucleotide, and those organisms and cells created by crosses or asexual propagation of the initial transgenic organism or cell. The term "transgenic," as used herein, does not encompass genome (chromosomal or extra-chromosomal) alternations introduced by conventional plant breeding methods (e.g., crosses of only non-transgenic organisms) or by naturally-occurring events (e.g., random cross-fertilization, non-recombinant viral infection, non-recombinant bacterial transformation, non-recombinant transposition, and spontaneous mutation).

A plant "line," "variety," or "strain" is a group of individual plants having the same parentage. Plants of a line generally are inbred to some degree, and are generally homozygous and homogeneous at most genetic loci (e.g., a FAD2 locus). A "subline" may refer to an inbred subset of descendents from a common progenitor that are genetically distinct from other similarly inbred subsets descended from the same progenitor. In some embodiments, a "subline" may be produced by inbreeding seed from an individual transgenic plant selected at the F3 to F5 generation until the residual segregating loci are homozygous across most or all loci.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197, WO 02/099084 and U.S. Publication No. 20110301073.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and −cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 2008/0131962 and 2011/0201055, incorporated herein by reference in their entireties.

Means for generating a double strand DNA break: As used herein, the term "means for generating a double strand DNA break" is intended to invoke the special claiming provisions authorized by Congress in 35 U.S.C. § 112, sixth paragraph. Specifically, a "means for generating a double strand DNA break" refers to a molecular structure that is capable of cleaving both strands of a double-stranded DNA molecule. Such structures include polypeptide domains comprised within many known nuclease proteins, for example, the FoId nuclease domain, the catalytic domain is selected from the group consisting of proteins MmeI, Colicin-E7 (CEA7_ECOLX), Colicin-E9, APFL, EndA, Endo I (END1_EC0L1), Human Endo G (NUCG_HUMAN), Bovine Endo G (NUCG_BOVIN), R.HinPll, 1-Basl, 1-Bmol, 1-Hmul, 1-Tevl, 1-Tevll, 1-Tevlll, 1-Twol, R.Mspl, R.Mval, NucA, NucM, Vvn, Vvn CLS, Staphylococcal nuclease (NUC_STAAU), Staphylococcal nuclease (NUC_STAHY), Micrococcal nuclease (NUC_SHIFL), Endonuclease yncB, Endodeoxyribonuclease I (ENRN BPT7), Metnase, Nb.BsrDI, BsrDI A, Nt.BspD6l (R.BspD6l large subunit), ss.BspD6l (R.BspD6l small subunit), R.PIel, Mlyl, Alwl, Mval269l, Bsrl, Bsml, Nb.BtsCI, Nt.BtsCI, Rl.Btsl, R2.Btsl, BbvCI subunit 1, BbvCI subunit 2, BpulOI alpha subunit, BpulOI beta subunit, Bmrl, Bfil, 1-Crel, hExol (EX01JHUMAN), Yeast Exol (EX01_YEAST), E. coli Exol, Human TREX2, Mouse TREX1, Human TREX1, Bovine TREX1, Rat TREX1, Human DNA2, Yeast DNA2 (DNA2_YEAST).

Means for repairing a double strand DNA break: As used herein, the term "means for repairing a double strand DNA break" is also intended to invoke the special claiming provisions authorized by Congress in 35 U.S.C. § 112, sixth paragraph. Specifically, a "means for repairing a double strand DNA break" refers to a molecular structure that is capable of facilitating/catalyzing the joining of the ends of double-stranded DNA molecules, for example, by joining ends generated by cleaving a single double-stranded DNA molecule, or by joining one end generated by cleaving a single double-stranded DNA molecule with the end of an exogenous double-stranded DNA molecule. Such structures include polypeptide domains comprised within many known ligase proteins, for example, Cre recombinase. In some examples, the same molecular structure may serve as both a means for generating a double strand DNA break and a means for repairing a double strand DNA break, where the same structure facilitates both the cleavage and repair of double-stranded DNA molecules (e.g., Hin recombinase).

The induction of the site specific double stranded breaks in the genome induces the host plant cell DNA repair pathway which resolves the double stranded break through homology-directed repair (HDR) or non-homologous end-joining (NHEJ) repair. In plants, the scientific literature reports that precise gene or donor DNA integration into native genomic or at pre-engineered locations have involved incoming donor DNA construct(s) that comprise varying amounts of sequence homologous to the sequences flanking the targeted double stranded break. The integration of such donors into the specific target locus presumably has relied on the HDR pathway. Exclusively relying on the HDR approach for gene targeting in plants can have limitations due to reports that the HDR repair pathway is not the dominate DNA repair pathway when compared to NHEJ. The published plant scientific literature utilizing target specific DNA breaks (ZFN, TALeNs, or Engineered Meganucleases, etc.) the NHEJ pathway has been reported as the method to introduce specific point mutations (insertions, or deletions) into the geneome. Here we report that site specific double stranded breaks (induced by ZFN, TALeNs, etc.) in the presents of various donor DNA design with homology regions of 0 to <10 bp can be specifically inserted at targeted break via the NHEJ repair pathway in plants. A variety of different DNA donor designs with zero homology to small 1-10 bp of ranging from linear to circular, single stranded to double stranded can be targeted to specific locations using the NHEJ pathway. NHEJ based donor DNA plant genome targeting can be based on "sticky end capture", where the targeted double stranded break in the genome generated by FokI (or other Type II endonuclease domains) and the corresponding sticky ends are on the NHEJ donor DNA designs. The sticky ends donor DNA can be delivered directly to the cell as linear donor DNA with predefined overhangs. An alternative approach is to produce the donor DNA sticky ends in vivo by co-delivering the host target ZFN and a circular DNA donor molecule that contains at least one ZFN recognition site that is identical to the target recognition site. Expression of at least one ZFN cuts the host genomic DNA (native or pre-engineered) and the circular donor DNA to produce sticky ends that are resolved using the hosts NHEJ repair pathway.

It is possible to have one or more ZFN cuts sites on the donor molecule (a single ZFN cut site to linearize the entire donor molecule, 2 of the same ZFN sites to release a smaller donor DNA fragment or 2 different ZFN sites to release a fragment from the donor and a corresponding fragment from the host genomic DNA (DNA replacement).

Thus, the donor polynucleotide can be DNA or RNA, single-stranded and/or double-stranded and can be introduced into a cell in linear or circular form. See, e.g., U.S. Patent Publication Nos. 20100047805 and 20110207221. In certain, embodiments of the present invention may also include linear exogenous (donor) nucleic acid(s), compositions comprising these nucleic acids and methods of making and using these linear donor molecules. In certain embodiments, the linear donor molecule stably persists in the cell into which it is introduced. In other embodiments, the linear donor molecule is modified to resist exonucleolytic cleavage, for example by placing one or more phosphorothioate phosphodiester bonds between one or more base pairs on the ends of the donor molecule. The linear exogenous nucleic acid may also include single stranded specific DNA.

III. FAD2 Performance Loci

The loci designated FAD2 (fatty acid desaturase 2) are included in QTLs involved in the inheritance of the complex multigenic trait of fatty acid content in plants. FAD2 encodes the enzyme responsible for the desaturation of oleic acid (18:1) to linoleic acid (C18:2). Tanhuanpaa et al. (1998) Mol. Breed. 4:543-50; Schierholt et al. (2001) Crop Sci. 41:1444-9.

Within the plant oil biosynthetic pathway the fatty acid desaturases (FADs) play a key role in plant lipid biosynthesis and their activity significantly influences the fatty acid composition. FADs are abundant in plants, and expression analysis suggested that FAD mRNAs are produced in overabundance. Furthermore, FAD genes are expressed in various, tissues, and cell types, as well as subcellular compartments including the plastid and endoplasmic reticulum.

The fatty acid composition of plants, and the performance of oils produced therefrom in many applications, is determined by the relative concentrations of the major fatty acid constituents; oleic, linoleic, and linolenic (C18:3). The concentrations of these fatty acids are predominantly regulated by the function of the enzymes FAD2 and FAD3. Oleic acid is converted to linoleic acid and linolenic acid in plants according to the scheme:

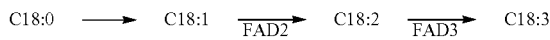

FAD2 genes have been identified in major plant and algal species including but not limited to maize, soybean, cotton, Arabidopsis, wheat, forage grasses, rice, sunflower and Brassica, and modification of FAD2 expression leads to altered fatty acid profiles in such organisms. Furthermore, plants comprising modified FAD2 genes have been commercialized, and disruption of a FAD2 gene has been shown to be able to improve the nutritional and functional properties of oil produced by a host plant without an agronomic penalty to the host plant. For example, canola and sunflower varieties that have been commercialized under the Nexera® brand (Dow AgroSciences, LLC) are characterized by a higher oleic acid, lower linoleic aced, and lower linolenic acid (and lower saturated fatty acid) composition, when compared to wild-type canola and sunflower profiles.

The dominant canola species grown in Europe, North America, and Australia is Brassica napus, a polyploid Brassica species considered to have arisen from the hybridization of B. oleracea (having a diploid C genome) and B. rapa (having a diploid A genome). Cytogenetic investigation revealed the AA and CC genomes show a degree of relatedness as being partially homologous to one another. Both the A and C genomes contain a high percentage of homeologous or paralogous genes. Thus, it is thought that the AA and CC genomes are derived from a common ancestor genome. Prakash and Hinata (1980) Opera Botanica 55:1-57. Although the genomes of both progenitor species are technically classified as diploids, these genomes contain a high percentage of regions that are duplicative of one another. Song et al. (1991) Theor. Appl. Genet. 82:296-304. A detailed organelle and nuclear RFLP analysis revealed that the AA genome of B. rapa contributed ten chromosomes to B. napus, while B. oleracea contributed nine chromosomes from its CC genome as the maternal donor. Song et al. (1992) Genome 35:992-1001. Through the number of genome duplications in both ancestral genomes, as well as the high percentage of similarity between the A, B and C genomes, there have arisen several copies of FAD2 and FAD3 genes. As a practical matter, this fact makes breeding canola with modified and/or disrupted copies of these genes in order to produce a particular fatty acid profile particularly challenging.

The known functional gene copies of FAD2 in canola are located on linkage group N4 of the A genome. Scheffler et al. (1997) TAG 94(5):583-91; Schierholt et al. (2000) TAG 101(5-6):897-901. More recently, a high oleic trait in canola has been associated with a modified and disrupted FAD2 gene that is located on the A genome. U.S. Patent Publication No. US 2006/0248611 A1; Hu et al. (2006) "Identification and Mapping of FAD2 and FAD3 Mutations and Development of Allele-specific Markers for High Oleic and Low Linolenic Acid Contents in Canola (Brassica napus L.)," Plant & Animal Genomes XIV Conference, Jan. 14-18, 2006, San Diego, Calif. An inactivating FAD2 allele contributes to the control of oleic acid content by reducing the desaturation of oleic acid to linoleic acid. This high oleic acid and fad2 trait was identified in a B. napus variety (DMS100) that has a characteristic oleic acid content of about 77%. See, U.S. Pat. No. 9,029,629. Additionally, FAD2 genes were recently located on the A5 chromosome and were alleged to be responsible for high C18:1 content. See, Yang et al., "Brassica napus genome" Theor Appl Genet (2012 125:715-729. Further, genetic markers have been developed to assist the introgression of the FAD2 and high oleic acid trait into canola.

FAD2 loci may be modified and/or disrupted in a plant without detrimentally affecting the value of the plant, and for many purposes, with an actual increase in its value, including alteration of FAD2 expression, alteration of oil content/ratios and/or integration and expression of desired transgenes. Furthermore, according to the ubiquitous nature of FAD loci in plants, FAD2 loci may be modified and/or disrupted without detriment for at least some purposes in many species, including, for example and without limitation: canola; soybean; maize; wheat; forage grasses; brassica sp.; rice, tomatoes, barley; oats; sorghum; cotton; and sunflower, as well as fungi and algae. Embodiments of the invention include FAD2 loci, and the use thereof as performance loci for integration of exogenous nucleic acids. In examples, a FAD2 locus exhibits at least one of several features that have been found to be desirable within the context of its use as a performance locus, including, for example and without limitation: that there is an approximately consistent level of expression during the life cycle of the host organism; and surprisingly, that integration of donor DNA at a FAD2 locus does not induce a quality or fitness penalty on the host.

In some embodiments of the present invention, at least one FAD2 locus (e.g., a FAD2A, FAD2A', FAD2C and/or FAD2C' locus) is used as a target site for the site-specific integration of an exogenous nucleic acid (e.g., a nucleic acid comprising a nucleotide sequence encoding a polypeptide of interest). In particular embodiments, integration of the exogenous nucleic acid results in a modified locus. For example, integration of the exogenous nucleic acid may modify the locus so as to produce a disrupted (i.e., inactivated) FAD2 gene.

In some embodiments, a FAD2 locus may comprise a nucleotide sequence that is specifically hybridizable to the complement of a nucleotide sequence selected from the group consisting of SEQ ID NOs: 22-26, SEQ ID NOs: 28-33 and SEQ ID NOs: 35-38. For example, a FAD2 locus may comprise a nucleotide sequence selected from the group consisting of SEQ ID NOs: 22-26, SEQ ID NOs: 28-33 and SEQ ID NOs: 35-38. In some embodiments, a FAD2 locus may comprise a nucleotide sequence that is substantially identical to a nucleotide sequence selected from the group consisting of SEQ ID NOs: 22-26, SEQ ID NOs: 28-33 and SEQ ID NOs: 35-38. For example, in some embodiments, a FAD2 locus is a FAD2 homologue (e.g., an ortholog or a paralog) that comprises a nucleotide sequence that is at least about 85% identical to a nucleotide sequence selected from the group consisting of SEQ ID NOs: 22-26, SEQ ID NOs: 28-33 and SEQ ID NOs: 35-38. A FAD2 homologue may comprise a nucleotide sequence that is, for example and without limitation: at least 80%; at least 85%; at least about 90%; at least about 91%; at least about 92%; at least about 93%; at least about 94%; at least about 95%; at least about 96%; at least about 97%; at least about 98%; at least about 99%; at least about 99.5%; 99.6%, 99.7%, 99.8% and/or at least about 99.9% identical to a nucleotide sequence selected from the group consisting of SEQ ID NOs: 22-26, SEQ ID NOs: 28-33 and SEQ ID NOs: 35-38. Such a FAD2 homologue may be readily identified and isolated from any complete or partial genome readily available to those of skill in the art for a variety of organisms.

IV. Targeted Integration of a Nucleic Acid at a FAD2 Locus

Site-specific integration of an exogenous nucleic acid at a FAD2 locus may be accomplished by any technique known to those of skill in the art. In some embodiments, integration of an exogenous nucleic acid at a FAD2 locus comprises contacting a cell (e.g., an isolated cell or a cell in a tissue or organism) with a nucleic acid molecule comprising the exogenous nucleic acid. In examples, such a nucleic acid molecule may comprise nucleotide sequences flanking the exogenous nucleic acid that facilitate homologous recombination between the nucleic acid molecule and at least one FAD2 locus. In particular examples, the nucleotide sequences flanking the exogenous nucleic acid that facilitate homologous recombination may be complementary to endogenous nucleotides of the FAD2 locus. In particular examples, the nucleotide sequences flanking the exogenous nucleic acid that facilitate homologous recombination may be complementary to previously integrated exogenous nucleotides. In some embodiments, a plurality of exogenous nucleic acids may be integrated at one FAD2 locus, such as in gene stacking.

Integration of a nucleic acid at a FAD2 locus may be facilitated (e.g., catalyzed) in some embodiments by endogenous cellular machinery of a host cell, such as, for example and without limitation, endogenous DNA and endogenous recombinase enzymes. In some embodiments, integration of a nucleic acid at a FAD2 locus may be facilitated by one or more factors (e.g., polypeptides) that are provided to a host cell. For example, nuclease(s), recombinase(s), and/or ligase polypeptides may be provided (either independently or as part of a chimeric polypeptide) by contacting the polypeptides with the host cell, or by expressing the polypeptides within the host cell. Accordingly, in some examples, a nucleic acid comprising a nucleotide sequence encoding at least one nuclease, recombinase, and/or ligase polypeptide may be introduced into the host cell, either concurrently or sequentially with a nucleic acid to be integrated site-specifically at a FAD2 locus, wherein the at least one nuclease, recombinase, and/or ligase polypeptide is expressed from the nucleotide sequence in the host cell.

A. DNA-Binding Polypeptides

In some embodiments, site-specific integration may be accomplished by utilizing factors that are capable of recognizing and binding to particular nucleotide sequences, for example, in the genome of a host organism. For instance, many proteins comprise polypeptide domains that are capable of recognizing and binding to DNA in a site-specific manner. A DNA sequence that is recognized by a DNA-binding polypeptide may be referred to as a "target" sequence. Polypeptide domains that are capable of recognizing and binding to DNA in a site-specific manner generally fold correctly and function independently to bind DNA in a site-specific manner, even when expressed in a polypeptide other than the protein from which the domain was originally isolated. Similarly, target sequences for recognition and binding by DNA-binding polypeptides are generally able to be recognized and bound by such polypeptides, even when present in large DNA structures (e.g., a chromosome), particularly when the site where the target sequence is located is one known to be accessible to soluble cellular proteins (e.g., a gene).

While DNA-binding polypeptides identified from proteins that exist in nature typically bind to a discrete nucleotide sequence or motif (e.g., a consensus recognition sequence), methods exist and are known in the art for modifying many such DNA-binding polypeptides to recognize a different nucleotide sequence or motif. DNA-binding polypeptides include, for example and without limitation: zinc finger DNA-binding domains; leucine zippers; UPA DNA-binding domains; GAL4; TAL; LexA; a Tet repressor; LacR; and a steroid hormone receptor.

In some examples, a DNA-binding polypeptide is a zinc finger. Individual zinc finger motifs can be designed to target and bind specifically to any of a large range of DNA sites. Canonical Cys2His2 (as well as non-canonical Cys3His) zinc finger polypeptides bind DNA by inserting an α-helix into the major groove of the target DNA double helix. Recognition of DNA by a zinc finger is modular; each finger contacts primarily three consecutive base pairs in the target, and a few key residues in the polypeptide mediate recognition. By including multiple zinc finger DNA-binding domains in a targeting endonuclease, the DNA-binding specificity of the targeting endonuclease may be further increased (and hence the specificity of any gene regulatory effects conferred thereby may also be increased). See, e.g., Urnov et al. (2005) Nature 435:646-51. Thus, one or more zinc finger DNA-binding polypeptides may be engineered and utilized such that a targeting endonuclease introduced into a host cell interacts with a DNA sequence that is unique within the genome of the host cell.

Preferably, the zinc finger protein is non-naturally occurring in that it is engineered to bind to a target site of choice. See, for example, See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599, 692; 6,503,717; 6,689,558; 7,030,215; 6,794,136; 7,067, 317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some examples, a DNA-binding polypeptide is a DNA-binding domain from GAL4. GAL4 is a modular transactivator in *Saccharomyces cerevisiae*, but it also operates as a transactivator in many other organisms. See, e.g., Sadowski et al. (1988) Nature 335:563-4. In this regulatory system, the expression of genes encoding enzymes of the galactose metabolic pathway in *S. cerevisiae* is stringently regulated by the available carbon source. Johnston (1987) Microbiol. Rev. 51:458-76. Transcriptional control of these metabolic enzymes is mediated by the interaction between the positive regulatory protein, GAL4, and a 17 bp symmetrical DNA sequence to which GAL4 specifically binds (the UAS).

Native GAL4 includes 881 amino acid residues, with a molecular weight of 99 kDa. GAL4 comprises functionally autonomous domains, the combined activities of which account for activity of GAL4 in vivo. Ma and Ptashne (1987) Cell 48:847-53); Brent and Ptashne (1985) Cell 43(3 Pt 2):729-36. The N-terminal 65 amino acids of GAL4 comprise the GAL4 DNA-binding domain. Keegan et al. (1986) Science 231:699-704; Johnston (1987) Nature 328:353-5. Sequence-specific binding requires the presence of a divalent cation coordinated by 6 Cys residues present in the DNA binding domain. The coordinated cation-containing domain interacts with and recognizes a conserved CCG triplet at each end of the 17 bp UAS via direct contacts with the major groove of the DNA helix. Marmorstein et al. (1992) Nature 356:408-14. The DNA-binding function of the protein positions C-terminal transcriptional activating domains in the vicinity of the promoter, such that the activating domains can direct transcription.

Additional DNA-binding polypeptides that may be utilized in certain embodiments include, for example and without limitation, a binding sequence from a AVRBS3-inducible gene; a consensus binding sequence from a AVRBS3-inducible gene or synthetic binding sequence engineered therefrom (e.g., UPA DNA-binding domain); TAL; LexA (see, e.g., Brent & Ptashne (1985), supra); LacR (see, e.g., Labow et al. (1990) Mol. Cell. Biol. 10:3343-56; Baim et al. (1991) Proc. Natl. Acad. Sci. USA 88(12):5072-6); a steroid hormone receptor (Ellliston et al. (1990) J. Biol. Chem. 265:11517-121); the Tet repressor (U.S. Pat. No. 6,271,341) and a mutated Tet repressor that binds to a tet operator sequence in the presence, but not the absence, of tetracycline (Tc); the DNA-binding domain of NF-κB; and components of the regulatory system described in Wang et al. (1994) Proc. Natl. Acad. Sci. USA 91(17):8180-4, which utilizes a fusion of GAL4, a hormone receptor, and VP16.

In certain embodiments, the DNA-binding domain of one or more of the nucleases used in the methods and compositions described herein comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) Science 318:648-651). These proteins contain a DNA binding domain and a transcriptional activation domain. One of the most well characterized TAL-effectors is AvrBs3 from *Xanthomonas* campestgris pv. Vesicatoria (see Bonas et al (1989) Mol Gen Genet 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) J Plant Physiol 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) Appl and Envir Micro 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. Nos. 8,420,782 and 8,440,431 and U.S. Patent Publication No. 20110301073.

In other embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In particular embodiments, a DNA-binding polypeptide specifically recognizes and binds to a target nucleotide sequence comprised within a genomic nucleic acid of a host organism. Any number of discrete instances of the target nucleotide sequence may be found in the host genome in some examples. The target nucleotide sequence may be rare within the genome of the organism (e.g., fewer than about 10, about 9, about 8, about 7, about 6, about 5, about 4, about 3, about 2, or about 1 copy(ies) of the target sequence may exist in the genome). For example, the target nucleotide sequence may be located at a unique site within the genome of the organism. Target nucleotide sequences may be, for example and without limitation, randomly dispersed throughout the genome with respect to one another; located in different linkage groups in the genome; located in the same linkage group; located on different chromosomes; located on the same chromosome; located in the genome at sites that are expressed under similar conditions in the organism (e.g., under the control of the same, or substantially functionally identical, regulatory factors); and located closely to one another in the genome (e.g., target sequences may be comprised within nucleic acids integrated as concatemers at genomic loci).

B. Targeting Endonucleases

In particular embodiments, a DNA-binding polypeptide that specifically recognizes and binds to a target nucleotide sequence may be comprised within a chimeric polypeptide, so as to confer specific binding to the target sequence upon the chimeric polypeptide. In examples, such a chimeric polypeptide may comprise, for example and without limitation, nuclease, recombinase, and/or ligase polypeptides, as these polypeptides are described above. Chimeric polypeptides comprising a DNA-binding polypeptide and a nuclease, recombinase, and/or ligase polypeptide may also comprise other functional polypeptide motifs and/or domains, such as for example and without limitation: a spacer sequence positioned between the functional polypeptides in the chimeric protein; a leader peptide; a peptide that targets the fusion protein to an organelle (e.g., the nucleus); polypeptides that are cleaved by a cellular enzyme; peptide tags (e.g., Myc, His, etc.); and other amino acid sequences that do not interfere with the function of the chimeric polypeptide.

Functional polypeptides (e.g., DNA-binding polypeptides and nuclease polypeptides) in a chimeric polypeptide may be operatively linked. In some embodiments, functional polypeptides of a chimeric polypeptide may be operatively linked by their expression from a single polynucleotide encoding at least the functional polypeptides ligated to each other in-frame, so as to create a chimeric gene encoding a chimeric protein. In alternative embodiments, the functional polypeptides of a chimeric polypeptide may be operatively linked by other means, such as by cross-linkage of independently expressed polypeptides.

In some embodiments, a DNA-binding polypeptide that specifically recognizes and binds to a target nucleotide sequence may be comprised within a natural isolated protein (or mutant thereof), wherein the natural isolated protein or mutant thereof also comprises a nuclease polypeptide (and may also comprise a recombinase and/or ligase polypeptide). Examples of such isolated proteins include TALENs, recombinases (e.g., Cre, Hin, Tre, and FLP recombinase), RNA-guided CRISPR-Cas9, and meganucleases.

As used herein, the term "targeting endonuclease" refers to natural or engineered isolated proteins and mutants thereof that comprise a DNA-binding polypeptide and a nuclease polypeptide, as well as to chimeric polypeptides comprising a DNA-binding polypeptide and a nuclease. Any targeting endonuclease comprising a DNA-binding polypeptide that specifically recognizes and binds to a target nucleotide sequence comprised within a FAD2 locus (e.g., either because the target sequence is comprised within the native sequence at the locus, or because the target sequence has been introduced into the locus, for example, by recombination) may be utilized in certain embodiments.

Some examples of chimeric polypeptides that may be useful in particular embodiments of the invention include, without limitation, combinations of the following polypeptides: zinc finger DNA-binding polypeptides; a FokI nuclease polypeptide; TALE domains; leucine zippers; transcription factor DNA-binding motifs; and DNA recognition and/or cleavage domains isolated from, for example and without limitation, a TALEN, a recombinase (e.g., Cre, Hin, RecA, Tre, and FLP recombinases), RNA-guided CRISPR-Cas9, a meganuclease; and others known to those in the art. Particular examples include a chimeric protein comprising a site-specific DNA binding polypeptide and a nuclease polypeptide. Chimeric polypeptides may be engineered by methods known to those of skill in the art to alter the recognition sequence of a DNA-binding polypeptide comprised within the chimeric polypeptide, so as to target the chimeric polypeptide to a particular nucleotide sequence of interest.

In certain embodiments, the chimeric polypeptide comprises a DNA-binding domain (e.g., zinc finger, TAL-effector domain, etc.) and a nuclease (cleavage) domain. The cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding, for example, such that one or more exogenous sequences (donors/trangseses) are integrated at or near the binding (target) sites. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Publication No. 20070134796, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E)

residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

C. Zinc Finger Nucleases

In specific embodiments, a chimeric polypeptide is a custom-designed zinc finger nuclease (ZFN) that may be designed to deliver a targeted site-specific double-strand DNA break into which an exogenous nucleic acid, or donor DNA, may be integrated (See co-owned US Patent publication 20100257638, incorporated by reference herein). ZFNs are chimeric polypeptides containing a non-specific cleavage domain from a restriction endonuclease (for example, FokI) and a zinc finger DNA-binding domain polypeptide. See, e.g., Huang et al. (1996) J. Protein Chem. 15:481-9; Kim et al. (1997a) Proc. Natl. Acad. Sci. USA 94:3616-20; Kim et al. (1996) Proc. Natl. Acad. Sci. USA 93:1156-60; Kim et al. (1994) Proc Natl. Acad. Sci. USA 91:883-7; Kim et al. (1997b) Proc. Natl. Acad. Sci. USA 94:12875-9; Kim et al. (1997c) Gene 203:43-9; Kim et al. (1998) Biol. Chem. 379:489-95; Nahon and Raveh (1998) Nucleic Acids Res. 26:1233-9; Smith et al. (1999) Nucleic Acids Res. 27:674-81. In some embodiments, the ZFNs comprise non-canonical zinc finger DNA binding domains (see co-owned US Patent publication 20080182332, incorporated by reference herein). The FokI restriction endonuclease must dimerize via the nuclease domain in order to cleave DNA and introduce a double-strand break. Consequently, ZFNs containing a nuclease domain from such an endonuclease also require dimerization of the nuclease domain in order to cleave target DNA. Mani et al. (2005) Biochem. Biophys. Res. Commun. 334:1191-7; Smith et al. (2000) Nucleic Acids Res. 28:3361-9. Dimerization of the ZFN can be facilitated by two adjacent, oppositely oriented DNA-binding sites. Id.

The flexibility and specificity of the ZFN system provides a level of control previously unachievable by known recombinase-mediated gene editing strategies. As one example, ZFNs can be easily engineered, for example, to recognize specific nucleic acid sequences. Wu et al. (2007) Cell. Mol. Life Sci. 64:2933-44 (See, US Patent Publications 20090205083, 20110189775, 20110167521 and 20100199389, incorporated by reference in their entireties herein). Randomization of the codons for zinc finger recognition residues allows the selection of new fingers that have high affinity for arbitrarily chosen DNA sequences. Furthermore, zinc fingers are natural DNA-binding molecules, and engineered zinc fingers have been shown to act on their designed targets in living cells. Thus, nucleases based on zinc fingers are targetable to specific but arbitrary recognition sites.

In particular examples, a method for the site-specific integration of an exogenous nucleic acid into at least one FAD2 performance locus of a host comprises introducing into a cell of the host a ZFN, wherein the ZFN recognizes and binds to a target nucleotide sequence, wherein the target nucleotide sequence is comprised within at least one FAD2 locus of the host. In certain examples, the target nucleotide sequence is not comprised within the genome of the host at any other position than the at least one FAD2 locus. For example, a DNA-binding polypeptide of the ZFN may be engineered to recognize and bind to a target nucleotide sequence identified within the at least one FAD2 locus (e.g., by sequencing the FAD2 locus). A method for the site-specific integration of an exogenous nucleic acid into at least one FAD2 performance locus of a host that comprises introducing into a cell of the host a ZFN may also comprise introducing into the cell an exogenous nucleic acid, wherein recombination of the exogenous nucleic acid into a nucleic acid of the host comprising the at least one FAD2 locus is facilitated by site-specific recognition and binding of the ZFN to the target sequence (and subsequent cleavage of the nucleic acid comprising the FAD2 locus).

V. Exogenous Nucleic Acids for Integration at a FAD2 Locus

Embodiments of the invention may include one or more nucleic acids selected from the group consisting of: an exogenous nucleic acid for site-specific integration in at least one FAD2 locus, for example and without limitation, a PTU, ELP, ETIP or an ORF; a nucleic acid comprising a nucleotide sequence encoding a targeting endonuclease; and a vector comprising at least one of either or both of the foregoing. Thus, particular nucleic acids for use in some embodiments include nucleotide sequences encoding a polypeptide, structural nucleotide sequences, and/or DNA-binding polypeptide recognition and binding sites.

A. Exogenous Nucleic Acid Molecules for Site-Specific Integration

As noted above, integration of an exogenous sequence (also called a "donor sequence" or "donor" or "transgene") is provided, for example for expression of a polypeptide, correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted integration of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See, e.g., U.S. Patent Publication Nos. 20100047805, 20110281361, 20110207221 and U.S. Publication No. 20130326645. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally integrated so that its expression is driven by the endogenous promoter at the integration site, namely the promoter that drives expression of the endogenous gene into which the donor is integrated (e.g., FAD2). However, it will be apparent that the donor may comprise a promoter and/or enhancer, for example a constitutive promoter or an inducible or tissue specific promoter.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Exogenous nucleic acids that may be integrated in a site-specific manner into at least one FAD2 locus, so as to modify the FAD2 locus, in embodiments include, for example and without limitation, nucleic acids comprising a nucleotide sequence encoding a polypeptide of interest; nucleic acids comprising an agronomic gene; nucleic acids comprising a nucleotide sequence encoding an RNAi molecule; or nucleic acids that disrupt the FAD2 gene.

In some embodiments, an exogenous nucleic acid is integrated at a FAD2 locus, so as to modify the FAD2 locus, wherein the nucleic acid comprises an agronomic gene or nucleotide sequence encoding a polypeptide of interest, such that the agronomic gene or nucleotide sequence is expressed in the host from the FAD2 locus. In some examples, the polypeptide of interest (e.g., a foreign protein) is expressed from a nucleotide sequence encoding the polypeptide of interest in commercial quantities. In such examples, the polypeptide of interest may be extracted from the host cell, tissue, or biomass. In some embodiments, the host is a plant, and plant material provided for commercial production of a polypeptide of interest may be a plant, plant part, plant tissue, or plant cell. In some examples, the plant part may be plant seed. Protein extraction from a plant biomass may be accomplished by known methods which are discussed, for example, in Heney and Orr (1981) Anal. Biochem. 114:92-6.

Likewise, agronomic genes may be expressed in transformed plant cells, plants, and/or their progeny. For example, a plant may be genetically engineered via methods of particular embodiments to express various phenotypes of agronomic interest from at least one FAD2 locus.

In some embodiments, nucleic acids comprising an agronomic gene or nucleotide sequence encoding a polypeptide of interest may include, for example and without limitation: a gene that confers resistance to a pests or disease (See, e.g., Jones et al. (1994) Science 266:789 (cloning of the tomato Cf-9 gene for resistance to *Cladosporium fulvum*); Martin et al. (1993) Science 262:1432; Mindrinos et al. (1994) Cell 78:1089 (RSP2 gene for resistance to *Pseudomonas syringae*); PCT International Patent Publication No. WO 96/30517 (resistance to soybean cyst nematode); PCT International Patent Publication No. WO 93/19181); a gene that encodes a *Bacillus thuringiensis* protein, a derivative thereof, or a synthetic polypeptide modeled thereon (See, e.g., Geiser et al. (1986) Gene 48:109 (cloning and nucleotide sequence of a Bt δ-endotoxin gene; moreover, DNA molecules encoding δ-endotoxin genes can be purchased from American Type Culture Collection (Manassas, Va.), for example, under ATCC Accession Nos. 40098; 67136; 31995; and 31998)); a gene that encodes a lectin (See, e.g., Van Damme et al. (1994) Plant Molec. Biol. 24:25 (nucleotide sequences of several *Clivia miniata* mannose-binding lectin genes)); a gene that encodes a vitamin-binding protein, e.g., avidin (See PCT International Patent Publication No. US93/06487 (use of avidin and avidin homologues as larvicides against insect pests)); a gene that encodes an enzyme inhibitor, e.g., a protease, proteinase inhibitor, or amylase inhibitor (See, e.g., Abe et al. (1987) J. Biol. Chem. 262:16793 (nucleotide sequence of rice cysteine proteinase inhibitor); Huub et al. (1993) Plant Molec. Biol. 21:985 (nucleotide sequence of cDNA encoding tobacco proteinase inhibitor I); Sumitani et al. (1993) Biosci. Biotech. Biochem. 57:1243 (nucleotide sequence of *Streptomyces nitrosporeus* alpha-amylase inhibitor) and U.S. Pat. No. 5,494,813); a gene encoding an insect-specific hormone or pheromone, e.g., an ecdysteroid or juvenile hormone, a variant thereof, a mimetic based thereon, or an antagonist or agonist thereof (See, e.g., Hammock et al. (1990) Nature 344:458 (baculovirus expression of cloned juvenile hormone esterase, an inactivator of juvenile hormone)); a gene encoding an insect-specific peptide or neuropeptide that, upon expression, disrupts the physiology of the affected pest (See, e.g., Regan (1994) J. Biol. Chem. 269:9 (expression cloning yields DNA coding for insect diuretic hormone receptor); Pratt et al. (1989) Biochem. Biophys. Res. Comm. 163:1243 (an allostatin in *Diploptera puntata*); and U.S. Pat. No. 5,266,317 (genes encoding insect-specific, paralytic neurotoxins)); a gene encoding an insect-specific venom produced in nature by a snake, a wasp, or other organism (See, e.g., Pang et al. (1992) Gene 116:165 (heterologous expression in plants of a gene coding for a scorpion insectotoxic peptide)); a gene encoding an enzyme responsible for a hyperaccumulation of a monoterpene, a sesquiterpene, a steroid, hydroxamic acid, a phenylpropanoid derivative or other molecule with insecticidal activity; a gene encoding an enzyme involved in the modification, including the post-translational modification, of a biologically active molecule, e.g., a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, or a glucanase, whether natural or synthetic (See, e.g., PCT International Patent Publication No. WO 93/02197 (nucleotide sequence of a callase gene); moreover, DNA molecules containing chitinase-encoding sequences can be obtained, for example, from the ATCC, under Accession Nos. 39637 and 67152; Kramer et al. (1993) Insect Biochem. Molec. Biol. 23:691 (nucleotide sequence of a cDNA encoding tobacco hornworm chitinase); and Kawalleck et al. (1993) Plant Molec. Biol. 21:673 (nucleotide sequence of the parsley ubi4-2 polyubiquitin gene)); a gene encoding a molecule that stimulates signal transduction (See, e.g., Botella et al. (1994) Plant Molec. Biol. 24:757 (nucleotide sequences for mung bean calmodulin cDNA clones); and Griess et al. (1994) Plant Physiol. 104:1467 (nucleotide sequence of a maize calmodulin cDNA clone)); a gene that encodes a hydrophobic moment peptide (See, e.g., PCT International Patent Publication No. WO 95/16776 (peptide derivatives of Tachyplesin which inhibit fungal plant pathogens); and PCT International Patent Publication No. WO 95/18855 (synthetic antimicrobial peptides that confer disease resistance)); a gene that encodes a membrane permease, a channel former, or a channel blocker (See, e.g., Jaynes et al. (1993) Plant Sci 89:43 (heterologous expression of a cecropin-β lytic peptide analog to render transgenic tobacco plants resistant to *Pseudomonas solanacearum*)); a gene that encodes a viral-invasive protein or complex toxin derived therefrom (See, e.g., Beachy et al. (1990) Ann. rev. Phytopathol. 28:451); a gene that encodes an insect-specific antibody or immunotoxin derived therefrom (See, e.g., Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments)); a gene encoding a virus-specific antibody (See, e.g., Tavladoraki et al. (1993) Nature 366:469 (transgenic plants expressing recombinant antibody genes are protected from virus attack)); a gene encoding a developmental-arrestive protein produced in nature by a pathogen or a parasite (See, e.g., Lamb et al. (1992) Bio/Technology 10:1436 (fungal endo α-1,4-D-polygalacturonases facilitate fungal colonization and plant nutrient release by solubilizing plant cell wall homo-α-1,4-D-galacturonase); Toubart et al. (1992) Plant J. 2:367 (cloning and characterization of a gene which encodes a bean endopolygalacturonase-inhibiting protein)); a gene encoding a developmental-arrestive protein produced in nature by a plant (See, e.g., Logemann et al. (1992) Bio/Technology 10:305 (transgenic plants expressing the barley ribosome-inactivating gene have an increased resistance to fungal disease)).

In some embodiments, nucleic acids comprising an agronomic gene or nucleotide sequence encoding a polypeptide of interest may also and/or alternatively include, for example and without limitation: genes that confer resistance to an herbicide, such as an herbicide that inhibits the growing point or meristem, for example, an imidazolinone or a sulfonylurea (exemplary genes in this category encode mutant ALS and AHAS enzymes, as described, for example, by Lee et al. (1988) EMBO J. 7:1241, and Mild et al. (1990) Theor. Appl. Genet. 80:449, respectively); glyphosate resistance as conferred by, e.g., mutant 5-enolpyruvylshikimate-3-phosphate synthase (EPSPs) genes (via the introduction of recombinant nucleic acids and/or various forms of in vivo mutagenesis of native EPSPs genes (including but not limited to CP4, DMMG, and DGT-28); aroA genes and glyphosate acetyl transferase (GAT) genes, respectively); other phosphono compounds, such as glufosinate phosphinothricin acetyl transferase (PAT) genes from *Streptomyces* species, including *Streptomyces hygroscopicus* and *Streptomyces viridichromogenes*); and pyridinoxy or phenoxy proprionic acids and cyclohexones (ACCase inhibitor-encoding genes). See, e.g., U.S. Pat. Nos. 4,940,835 and 6,248,876 (nucleotide sequences of forms of EPSPs which can confer glyphosate resistance to a plant). A DNA molecule encoding a mutant aroA gene can be obtained under ATCC accession number 39256. See also U.S. Pat. No. 4,769,061 (nucleotide sequence of a mutant aroA gene). European patent publication No. 0 333 033 and U.S. Pat. No. 4,975,374 disclose nucleotide sequences of glutamine synthetase genes, which may confer resistance to herbicides such as L-phosphinothricin. Nucleotide sequences of exemplary PAT genes are provided in European publication No. 0 242 246, and DeGreef et al. (1989) Bio/Technology 7:61 (production of transgenic plants that express chimeric bar genes coding for PAT activity). Exemplary of genes conferring resistance to phenoxy proprionic acids and cyclohexones, such as sethoxydim and haloxyfop, include the Accl-S1, Accl-S2 and Accl-S3 genes described by Marshall et al. (1992) Theor. Appl. Genet. 83:435. GAT genes capable of conferring glyphosate resistance are described, for example, in WO 2005012515. Genes conferring resistance to 2,4-D, phenoxyproprionic acid and pyridyloxy auxin herbicides are described, for example, in WO 2005107437 and WO 2007053482.

Nucleic acids comprising an agronomic gene or nucleotide sequence encoding a polypeptide of interest may also include, for example and without limitation: a gene conferring resistance to an herbicide that inhibits photosynthesis, such as a triazine (psbA and gs+ genes) or a benzonitrile (nitrilase gene). See, e.g., Przibila et al. (1991) Plant Cell 3:169 (transformation of *Chlamydomonas* with plasmids encoding mutant psbA genes). Nucleotide sequences for nitrilase genes are disclosed in U.S. Pat. No. 4,810,648, and DNA molecules containing these genes are available under ATCC Accession Nos. 53435; 67441; and 67442. See also Hayes et al. (1992) Biochem. J. 285:173 (cloning and expression of DNA coding for a glutathione S-transferase).

In some embodiments, nucleic acids comprising an agronomic gene or nucleotide sequence encoding a polypeptide of interest may also and/or alternatively include, genes that confer or contribute to a value-added trait, for example and without limitation: modified fatty acid metabolism, e.g., by transforming a plant with an antisense gene of stearyl-ACP desaturase to increase stearic acid content of the plant (See, e.g., Knultzon et al. (1992) Proc. Natl. Acad. Sci. U.S.A. 89:2624); decreased phytate content, e.g., introduction of a phytase-encoding gene may enhance breakdown of phytate, adding more free phosphate to the transformed plant (See, e.g., Van Hartingsveldt et al. (1993) Gene 127:87 (nucleotide sequence of an *Aspergillus niger* phytase gene); a gene may be introduced to reduce phytate content—in maize, for example, this may be accomplished by cloning and then reintroducing DNA associated with the single allele which may be responsible for maize mutants characterized by low levels of phytic acid (See Raboy et al. (1990) Maydica 35:383)); and modified carbohydrate composition effected, e.g., by transforming plants with a gene encoding an enzyme that alters the branching pattern of starch (See, e.g., Shiroza et al. (1988) J. Bacteol. 170:810 (nucleotide sequence of *Streptococcus* mutant fructosyltransferase gene); Steinmetz et al. (1985) Mol. Gen. Genet. 20:220 (levansucrase gene); Pen et al. (1992) Bio/Technology 10:292 (α-amylase); Elliot et al. (1993) Plant Molec. Biol. 21:515 (nucleotide sequences of tomato invertase genes); Sogaard et al. (1993) J. Biol. Chem. 268:22480 (barley α-amylase gene); and Fisher et al. (1993) Plant Physiol. 102:1045 (maize endosperm starch branching enzyme II)).

In some embodiments, an exogenous nucleic acid is integrated at a FAD2 locus, so as to modify the FAD2 locus, wherein the nucleic acid comprises a PTU or ELP, such that, for example, the subsequent site-specific integration of a second exogenous nucleic acid at the site of the PTU or ELP is facilitated. See, also, U.S. Publication No. 20130326645.

Targeting endonuclease-mediated integration of a nucleic acid molecule of interest into a plant genome via targeted integration requires delivery of targeting endonucleases or targeting endonuclease-encoding nucleic acid molecules, followed by expression of a functional targeting endonuclease protein in the host. An exogenous nucleic acid is preferably also be present in the host cell at the same time as the targeting endonuclease is delivered or expressed therein, such that functional targeting endonuclease protein induces double-stranded breaks at the target site(s) in the at least one FAD2 locus, which are then repaired, for example via homology-driven integration of the exogenous nucleic acid into the locus. One skilled in the art may envision that expression of a functional targeting endonuclease protein may be achieved by several methods, including, but not limited to, transgenesis of a targeting endonuclease-encoding construct, and transient expression of a targeting endonuclease-encoding construct. In both these cases, expression of a functional targeting endonuclease protein and delivery of an exogenous nucleic acid in the host cell may be simultaneously achieved in order to drive targeted integration at a FAD2 locus.

A particular advantage obtained in embodiments utilizing ZFNs as targeting endonucleases, is that the requirement for dimerization of cleavage domains of chimeric zinc finger nucleases imparts a high level of sequence, and hence cleavage, specificity. Since each set of three fingers binds nine consecutive base pairs, two chimeric nucleases effectively demand an 18 bp target if each zinc finger domain has perfect specificity. Any given sequence of this length is predicted to be unique within a single genome (assuming approximately $10^9$ bp). Bibikova et al. (2001) Mol. Cell. Biol. 21(1):289-97; Wu et al. (2007), supra. Furthermore, additional fingers can provide enhanced specificity, Beerli et al. (1998) Proc. Natl. Acad. Sci. USA 95:14628-33; Kim and Pabo (1998) Proc. Natl. Acad. Sci. USA 95:2812-7; Liu et al. (1997) Proc. Natl. Acad. Sci. USA 94:5525-30, so the number of zinc fingers in each DNA-binding domain may be increased to provide even further specificity. For example, specificity may be further increased by using a pair of 4-, 5-, 6- or more finger ZFNs that recognize a 24 bp sequence. Urnov et al. (2005) Nature 435:646-51. Thus, ZFNs may be used such that a recognition sequence is introduced into the host plant genome is unique within the genome.

B. Nucleic Acid Molecules Comprising a Nucleotide Sequence Encoding a Targeting Endonuclease In some embodiments, a nucleotide sequence encoding a targeting endonuclease may be engineered by manipulation (e.g., ligation) of native nucleotide sequences encoding polypeptides comprised within the targeting endonuclease. For example, the nucleotide sequence of a gene encoding a protein comprising a DNA-binding polypeptide may be inspected to identify the nucleotide sequence of the gene that corresponds to the DNA-binding polypeptide, and that nucleotide sequence may be used as an element of a nucleotide sequence encoding a targeting endonuclease comprising the DNA-binding polypeptide. Alternatively, the amino acid sequence of a targeting endonuclease may be used to deduce a nucleotide sequence encoding the targeting endonuclease, for example, according to the degeneracy of the genetic code.

In exemplary nucleic acid molecules comprising a nucleotide sequence encoding a targeting endonuclease, the last codon of a first polynucleotide sequence encoding a nuclease polypeptide, and the first codon of a second polynucleotide sequence encoding a DNA-binding polypeptide, may be separated by any number of nucleotide triplets, e.g., without coding for an intron or a "STOP." Likewise, the last codon of a nucleotide sequence encoding a first polynucleotide sequence encoding a DNA-binding polypeptide, and the first codon of a second polynucleotide sequence encoding a nuclease polypeptide, may be separated by any number of nucleotide triplets. In these and further embodiments, the last codon of the last (i.e., most 3' in the nucleic acid sequence) of a first polynucleotide sequence encoding a nuclease polypeptide, and a second polynucleotide sequence encoding a DNA-binding polypeptide, may be fused in phase-register with the first codon of a further polynucleotide coding sequence directly contiguous thereto, or separated therefrom by no more than a short peptide sequence, such as that encoded by a synthetic nucleotide linker (e.g., a nucleotide linker that may have been used to achieve the fusion). Examples of such further polynucleotide sequences include, for example and without limitation, tags, targeting peptides, and enzymatic cleavage sites. Likewise, the first codon of the most 5' (in the nucleic acid sequence) of the first and second polynucleotide sequences may be fused in phase-register with the last codon of a further polynucleotide coding sequence directly contiguous thereto, or separated therefrom by no more than a short peptide sequence.

A sequence separating polynucleotide sequences encoding functional polypeptides in a targeting endonuclease (e.g., a DNA-binding polypeptide and a nuclease polypeptide) may, for example, include any sequence, such that the amino acid sequence encoded is not likely to significantly alter the translation of the targeting endonuclease. Due to the autonomous nature of known nuclease polypeptides and known DNA-binding polypeptides, intervening sequences will not in examples interfere with the respective functions of these structures.

C. Vectors and Expression Constructs

In some embodiments, at least one nucleic acid molecule(s) comprising at least one exogenous polynucleotide sequence encoding a polypeptide of interest, and/or a targeting endonuclease, may be introduced into a cell, tissue, or organism for expression therein. For example, a nucleic acid molecule comprising a polynucleotide sequence encoding a targeting endonuclease that specifically recognizes a nucleotide sequence comprised within at least one FAD2 locus may be introduced into a cell for expression of the targeting endonuclease, and a nucleic acid molecule comprising a polynucleotide sequence encoding a polypeptide of interest may be introduced into the cell, such that the polynucleotide sequence encoding the polypeptide of interest is integrated into the at least one FAD2 locus, e.g., by homologous recombination following introduction of a double strand break at the locus by the expressed targeting endonuclease, and the polypeptide of interest is expressed from the integrated polynucleotide sequence.

In some embodiments, a nucleic acid molecule such as one of the foregoing may, for example, be a vector system including, for example and without limitation, a linear plasmid, or a closed circular plasmid. In particular examples, the vector may be an expression vector. Nucleic acid sequences according to particular embodiments may, for example, be integrated into a vector, such that the nucleic acid sequence is operably linked to one or more regulatory sequences. Many vectors are available for this purpose, and selection of the particular vector may depend, for example, on the size of the nucleic acid to be inserted into the vector, the particular host cell to be transformed with the vector, and/or the amount of any encoded polypeptide that is desired to be expressed. A vector typically contains various components, the identity of which depend on a function of the vector (e.g., amplification of DNA or expression of DNA), and the particular host cell(s) with which the vector is compatible.

In some embodiments, a regulatory sequence operably linked to one or more coding sequence(s) may be a promoter sequence that functions in a host cell, such as a bacterial cell, algal cell, fungal cell, or plant cell, wherein the nucleic acid molecule is to be amplified or expressed. Some embodiments may include a plant transformation vector that comprises a nucleotide sequence comprising at least one regulatory sequence operably linked to one or more nucleotide sequence(s) encoding a polypeptide of interest or a targeting endonuclease, wherein the one or more nucleotide sequence(s) may be expressed, under the control of the regulatory sequence(s), in a plant cell, tissue, or organism to produce the polypeptide of interest or the targeting endonuclease.

Promoters suitable for use in nucleic acid molecules according to some embodiments include those that are inducible, tissue-specific, viral, synthetic, or constitutive, all of which are well known in the art. Non-limiting examples of promoters that may be useful in embodiments of the invention are provided by: U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); U.S. Pat. No. 5,447,858 (soybean heat shock promoter); and U.S. Pat. No. 7,151,204 (maize chloroplast aldolase promoter).

Additional exemplary promoters include the nopaline synthase (NOS) promoter (Ebert et al. (1987) Proc. Natl. Acad. Sci. USA 84(16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313: 810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV35S (U.S. Pat. Nos. 5,322,938, 5,352,605, 5,359,142, and 5,530, 196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982) J. Mol. Appl. Genet. 1:561-73; Bevan et al. (1983) Nature 304:184-7).

In particular embodiments, nucleic acid molecules may comprise a tissue-specific promoter. A tissue-specific promoter is a nucleotide sequence that directs a higher level of transcription of an operably linked nucleotide sequence in the tissue for which the promoter is specific, relative to the other tissues of the organism. Examples of tissue-specific promoters include, without limitation: tapetum-specific promoters; anther-specific promoters; pollen-specific promoters (See, e.g., U.S. Pat. No. 7,141,424, and International PCT Publication No. WO 99/042587); ovule-specific promoters; (See, e.g., U.S. Patent Publication No. 2001/047525 A1); fruit-specific promoters (See, e.g., U.S. Pat. Nos. 4,943,674, and 5,753,475); and seed-specific promoters (See, e.g., U.S. Pat. Nos. 5,420,034, and 5,608,152). In some embodiments, a developmental stage-specific promoter (e.g., a promoter active at a later stage in development) may be used.

Additional regulatory sequences that may in some embodiments be operably linked to a nucleic acid molecule include 5' UTRs located between a promoter sequence and a coding sequence that function as a translation leader sequence. The translation leader sequence is present in the fully-processed mRNA, and it may affect processing of the primary transcript, and/or RNA stability. Examples of translation leader sequences include maize and *petunia* heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5' UTRs are provided by: GmHsp (U.S. Pat. No. 5,659,122); PhDnaK (U.S. Pat. No. 5,362,865); AtAntl; TEV (Carrington and Freed (1990) J. Virol. 64:1590-7); and AGRtunos (GenBank Accession No. V00087; and Bevan et al. (1983), supra).

Additional regulatory sequences that may in some embodiments be operably linked to a nucleic acid molecule also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al. (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank Accession No. E01312).

Additional information regarding regulatory sequences that may be useful in particular embodiments is described, for example, in Goeddel (1990) "Gene Expression Technology," Methods Enzymol. 185, Academic Press, San Diego, Calif.

A recombinant nucleic acid molecule or vector may comprise a selectable marker that confers a selectable phenotype on a transformed cell, such as a plant cell. Selectable markers may also be used to select for cells or organisms that comprise a nucleic acid molecule comprising the selectable marker. A marker may encode biocide resistance, antibiotic resistance (e.g., kanamycin, Geneticin (G418), bleomycin, and hygromycin), or herbicide resistance (e.g., glyphosate). Examples of selectable markers include, but are not limited to: a neo gene that confers kanamycin resistance and can be selected for using, e.g., kanamycin and G418; a bar gene that confers bialaphos resistance; a mutant EPSP synthase gene that confers glyphosate resistance; a nitrilase gene that confers resistance to bromoxynil; a mutant acetolactate synthase gene (ALS) that confers imidazolinone or sulfonylurea resistance; and a methotrexate-resistant DHFR gene. Multiple selectable markers are available that confer resistance to chemical agents including, for example and without limitation, ampicillin; bleomycin; chloramphenicol; gentamycin; hygromycin; kanamycin; lincomycin; methotrexate; phosphinothricin; puromycin; spectinomycin; rifampicin; streptomycin; and tetracycline. Examples of such selectable markers are illustrated in, e.g., U.S. Pat. Nos. 5,550,318; 5,633,435; 5,780,708 and 6,118,047.

A nucleic acid molecule or vector may also or alternatively include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18*th Stadler Genetics Symposium*, P. Gustafson and R. Appels, eds., Plenum, NY (pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); a xylE gene that encodes a catechol dioxygenase that converts chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone, which in turn condenses to melanin (Katz et al. (1983) J. Gen. Microbiol. 129:2703-14); and an α-galactosidase.

All of the nucleotide sequences that encode, for example, a particular polypeptide of interest or a particular targeting endonuclease, will be immediately recognizable by those of skill in the art. The degeneracy of the genetic code provides a finite number of coding sequences for a particular amino acid sequence. The selection of a particular sequence to encode a polypeptide according to embodiments of the invention is within the discretion of the practitioner. Different coding sequences may be desirable in different applications.

In some embodiments, it may be desirable to modify the nucleotides of a nucleic acid, for example, to enhance expression of a polynucleotide sequence comprised within the nucleic acid in a particular host. The genetic code is redundant with 64 possible codons, but most organisms preferentially use a subset of these codons. The codons that are utilized most often in a species are called optimal codons, and those not utilized very often are classified as rare or low-usage codons. Zhang et al. (1991) Gene 105: 61-72. Codons may be substituted to reflect the preferred codon usage of a particular host in a process sometimes referred to as "codon optimization." Optimized coding sequences containing codons preferred by a particular prokaryotic or eukaryotic host may be prepared, for example, to increase the rate of translation or to produce recombinant RNA transcripts having desirable properties (e.g., a longer half-life, as compared with transcripts produced from a non-optimized sequence).

Nucleic acids may be introduced into a host cell in embodiments of the invention by any method known to those of skill in the art, including, for example and without limitation: by transformation of protoplasts (See, e.g., U.S. Pat. No. 5,508,184); by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by *Agrobacterium*-mediated transformation (See, e.g., U.S. Pat. Nos. 5,563,055, 5,591,616, 5,693,512, 5,824,877, 5,981,840, and 6,384,301); and by acceleration of DNA-coated particles (See, e.g., U.S. Pat. Nos. 5,015,580, 5,550,318, 5,538,880, 6,160,208, 6,399,861, and 6,403,865). Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences of the invention in the genome of the transgenic plant.

The most widely-utilized method for introducing an expression vector into plants is based on the natural transformation system of *Agrobacterium*. *A. tumefaciens* and *A. rhizogenes* are plant pathogenic soil bacteria that genetically transform plant cells. The $T_i$ and $R_i$ plasmids of *A. tumefaciens* and *A. rhizogenes*, respectively, carry genes responsible for genetic transformation of the plant. The $T_i$ (tumor-inducing)-plasmids contain a large segment, known as T-DNA, which is transferred to transformed plants. Another segment of the $T_i$ plasmid, the vir region, is responsible for T-DNA transfer. The T-DNA region is bordered by left-hand and right-hand borders that are each composed of terminal repeated nucleotide sequences. In some modified binary vectors, the tumor-inducing genes have been deleted, and the functions of the vir region are utilized to transfer foreign DNA bordered by the T-DNA border sequences. The T-region may also contain, for example, a selectable marker for efficient recovery of transgenic plants and cells, and a multiple cloning site for inserting sequences for transfer such as a nucleic acid encoding a fusion protein of the invention.

Thus, in some embodiments, a plant transformation vector is derived from a $T_i$ plasmid of *A. tumefaciens* (See, e.g., U.S. Pat. Nos. 4,536,475, 4,693,977, 4,886,937, and 5,501,967; and European Patent EP 0 122 791) or a $R_i$ plasmid of *A. rhizogenes*. Additional plant transformation vectors include, for example and without limitation, those described by Herrera-Estrella et al. (1983) Nature 303:209-13; Bevan et al. (1983), supra; Klee et al. (1985) Bio/Technol. 3:637-42; and in European Patent EP 0 120 516, and those derived from any of the foregoing. Other bacteria, such as *Sinorhizobium*, *Rhizobium*, and *Mesorhizobium*, that naturally interact with plants can be modified to mediate gene transfer to a number of diverse plants. These plant-associated symbiotic bacteria can be made competent for gene transfer by acquisition of both a disarmed $T_i$ plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a nucleic acid molecule of interest (for example, a nucleotide sequence encoding a polypeptide comprising at least one fusion protein of the invention) in a regenerating plant, a variety of assays may be performed. Such assays include, for example: molecular biological assays, such as Southern and Northern blotting, PCR, and nucleic acid sequencing; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Integration events may be analyzed, for example, by PCR amplification using, e.g., oligonucleotide primers that are specific for a nucleotide sequence of interest. PCR genotyping is understood to include, but not be limited to, polymerase-chain reaction (PCR) amplification of genomic DNA derived from isolated host plant tissue predicted to contain a nucleic acid molecule of interest integrated into the genome, followed by standard cloning and sequence analysis of PCR amplification products. Methods of PCR genotyping have been well described (see, e.g., Rios, G. et al. (2002) Plant J. 32:243-53), and may be applied to genomic DNA derived from any plant species or tissue type, including cell cultures.

A transgenic plant formed using *Agrobacterium*-dependent transformation methods typically contains a single to multiple copies of recombinant DNA. The single recombinant DNA sequence is referred to as a "transgenic event" or "integration event." Such transgenic plants are heterozygous for the inserted DNA sequence. In some embodiments, a transgenic plant homozygous with respect to a transgene may be obtained by sexually mating (selfing) an independent segregant transgenic plant that contains a single exogenous gene sequence to itself, for example, an $F_0$ plant, to produce $F_1$ seed. One fourth of the $F_1$ seed produced will be homozygous with respect to the transgene. Germinating $F_1$ seed results in plants that can be tested for heterozygosity, typically using a SNP assay or a thermal amplification assay that allows for the distinction between heterozygotes and homozygotes (i.e., a zygosity assay).

In addition to direct transformation of a plant or plant cell with a nucleic acid molecule in some embodiments, transgenic plants may be prepared in particular embodiments by crossing a first plant having at least one transgenic event with a second plant lacking such an event. For example, a nucleic acid comprising at least one modified FAD2 locus, wherein an exogenous nucleic acid has been integrated in a site-specific manner, may be introduced into a first plant line that is amenable to transformation, to produce a transgenic plant, which transgenic plant may be crossed with a second plant line to introgress the at least one modified FAD2 locus (and therefore the exogenous nucleic acid) into the second plant line.

To confirm the presence of a nucleic acid molecule of interest in regenerating plants, a variety of assays may be performed. Such assays include, for example: molecular biological assays, such as Southern and Northern blotting and PCR; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Targeted integration events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two are feasible. Thus, PCR genotyping strategies may include (but are not limited to) amplification of specific sequences in the plant genome, amplification of multiple specific sequences in the plant genome, amplification of non-specific sequences in the plant genome, or combinations thereof. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule of interest, for example, at a sequence corresponding to a coding region within the nucleic acid molecule of interest, or other parts of the nucleic acid molecule of interest. These primers may be used in conjunction with the primers described above. Oligonucleotide primers may be synthesized according to a desired sequence, and are commercially available (e.g., from Integrated DNA Technologies, Inc., Coralville, Iowa). Amplification may be followed by cloning and sequencing, or by direct sequence analysis of amplification products. One skilled in the art might envision alternative methods for analysis of amplification products generated during PCR genotyping. In one embodiment, oligonucleotide primers specific for the gene target are employed in PCR amplifications.

VI. Transgenic Plants and Plant Materials Comprising a Nucleic Acid Integrated at a FAD2 Performance Locus In some embodiments, a transgenic plant is provided, wherein the plant comprises a plant cell comprising at least one modified (e.g., disrupted and/or targeted integration of an exogenous sequence) FAD2 locus. In particular embodiments, such a plant may be produced by transformation of a plant tissue or plant cell, and regeneration of a whole plant. In further embodiments, such a plant may be obtained through introduction of an exogenous nucleic acid at the at least one FAD2 locus in a site-specific manner, or through introgression of the modified FAD2 locus into a germplasm. Plant materials comprising such a plant cell are also provided. Such a plant material may be obtained from a plant comprising the plant cell.

A transgenic plant or plant material comprising a plant cell comprising at least one modified FAD2 locus may in some embodiments exhibit one or more of the following characteristics: expression of a targeting endonuclease in a cell of the plant; expression of a polypeptide of interest in a cell of the plant (or in a plastid therein); expression of a targeting endonuclease in the nucleus of a cell of the plant; localization of a targeting endonuclease in a cell of the plant; integration at a FAD2 locus in the genome of a cell of the plant; integration of a nucleotide sequence encoding a polypeptide of interest or an agronomic gene at a FAD2 locus in the genome of a cell of the plant; and/or the presence of an RNA transcript corresponding to a coding sequence integrated at a FAD2 locus in the genome of a cell of the plant. Such a plant may additionally have one or more desirable traits, including, for example and without limitation, those resulting from the expression of an endogenous or transgenic nucleotide sequence, the expression of which is regulated by a polypeptide of interest or an agronomic gene integrated at a FAD2 locus in the genome of a cell of the plant; resistance to insects, other pests, and disease-causing agents; tolerances to herbicides; enhanced stability, yield, or shelf-life; environmental tolerances; pharmaceutical production; industrial product production; and nutritional enhancements.

A transgenic plant according to the invention may be any plant capable of being transformed with a nucleic acid that is subsequently integrated in at least one FAD2 locus according to methods described herein. Accordingly, the plant may be a dicot or monocot. Non-limiting examples of dicotyledonous plants usable in the present methods include *Arabidopsis*, alfalfa, beans, broccoli, cabbage, canola, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tobacco, tomato, and watermelon. Non-limiting examples of monocotyledonous plants usable in the present methods include corn, barley, onion, rice, sorghum, wheat, rye, millet, sugarcane, oat, triticale, switchgrass, and turfgrass. Transgenic plants according to the invention may be used or cultivated in any manner.

Some embodiments also provide commodity products produced from transgenic plants of the invention. Commodity products include, for example and without limitation: food products, meals, oils, or crushed or whole grains or seeds of a plant comprising one or more nucleotide sequences integrated in at least one FAD2 locus. The detection of one or more such nucleotide sequences in one or more commodity or commodity products is de facto evidence that the commodity or commodity product was at least in part produced from a transgenic plant produced according to an embodiment of the invention. In some embodiments, a transgenic plant or seed comprising a plant cell comprising at least one modified FAD2 locus may comprise at least one other transgenic event in its genome, including without limitation: a transgenic event from which is transcribed an RNAi molecule; a gene encoding an insecticidal protein (e.g., a *Bacillus thuringiensis* insecticidal protein); an herbicide tolerance gene (e.g., a gene providing tolerance to glyphosate); and a gene contributing to a desirable phenotype in the transgenic plant (e.g., increased yield, altered fatty acid metabolism, or restoration of cytoplasmic male sterility).

A transgenic plant comprising a plant cell comprising at least one modified FAD2 locus may have one or more desirable traits. Such traits can include, for example: resistance to insects, other pests, and disease-causing agents; tolerances to herbicides; enhanced stability, yield, or shelf-life; environmental tolerances; pharmaceutical production; industrial product production; and nutritional enhancements. The desirable traits may be conferred by one or more nucleic acid molecules integrated by targeted recombination at the FAD2 locus that are expressed in the plant exhibiting the desirable traits. Thus, in some embodiments, the desired trait can be due to the presence of a transgene(s) in the plant, which is introduced into the genome of the plant at the site of at least one modified FAD2 locus. In an additional embodiment, the desirable trait can be obtained through conventional breeding, which trait may be conferred by one or more nucleic acid molecules integrated by targeted recombination at the at least one modified FAD2 locus.

Transgenic plants according to the invention may be used or cultivated in any manner, wherein presence of at least one modified FAD2 locus is desirable. Accordingly, a plant may be engineered to, inter alia, have one or more desired traits, by being transformed with nucleic acid molecules that are subsequently integrated in a site-specific manner in at least one FAD2 locus according to the invention, and cropped and cultivated by any method known to those of skill in the art.

VII. Marker-Assisted Breeding of Transgenic Plants Comprising a Nucleic Acid Integrated at a FAD2 Performance Locus Molecular markers that are linked (e.g., tightly-linked) to fad2 in *Brasicca* spp. are provided. For example, DNA segments containing sequences involved in the HO trait (fad2) are identified. These segments are located around and between markers that are linked (e.g., tightly-linked) to the mutant alleles in a genomic linkage group. Thus, nucleic acid molecules comprising a mutant FAD2 gene having an inactivating mutation are also provided. The segments identified, and the markers thereof, are included in the present subject matter, in part, by their position in linkage groups in the *B. napus* genome. For example, FAD2 and molecular markers linked thereto may be located in linkage groups N5 and Ni.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention. The following examples are provided to illustrate certain particular features and/or embodiments. The examples should not be construed to limit the disclosure to the particular features or embodiments exemplified.

EXAMPLES

Example 1: Identification of FAD2 Target Sequences from a Bacterial Artificial Chromosome Library BAC Library Construction A Bacterial Artificial Chromosome (BAC) library was sourced from a commercial vendor (Amplicon Express, Pullman, Wash.). The BAC library included 110,592 BAC clones containing high molecular weight genomic DNA (gDNA) fragments isolated from *Brassica napus* L. var. DH10275. The gDNA was digested with either the BamHI or HindIII restriction enzyme. Isolated gDNA fragments of about 135 Kbp were ligated into the pCC1BAC vector (Epicentre, Madison, Wis.) and transformed into *Escherichia coli* str. DH10B (Invitrogen). The BAC library was made up of an even number of BAC clones that were constructed using the two different restriction enzymes. As such, the Hind III constructed BAC library was contained in 144 individual 384-well plates. Likewise, the BamHI constructed BAC library was contained in 144 individual 384-well plates. A total of 110,592 BAC clones were isolated and arrayed into 288 individual 384-well plates. Each of the 288 individual 384 well plates were provided by the vendor as a single DNA extraction for rapid PCR based screening. The resulting BAC library covers approximately 15 Gbp of gDNA, which corresponds to a 12-fold genome coverage of *Brassica napus* L. var. DH10275genome (estimate of the *Brassica napus* L. genome is ca. 1.132 Gbp as described in Johnston et al. (2005) Annals of Botany 95:229-235).

Sequence Analysis of FAD2 Coding Sequences Isolated from the Bac Library

The constructed BAC library was used to isolate FAD2 gene coding sequences. Sequencing experiments were conducted to identify the specific gene sequences of four FAD2 gene paralogs from *Brassica napus* L. var. DH10275.

The FAD2 gene sequence was initially identified within the model species *Arabidopsis thaliana*. The gene sequence is listed in Genbank as Locus Tag: At3g12120. Comparative genomic relationships between the model plant species *Arabidopsis thaliana* and the diploid *Brassica rapa*, one of the progenitors of the tetraploid *Brassica napus*, have been previously described. (Schranz et al. (2006) Trends in Plant Science 11(11):535-542). With specific relation to the FAD2 gene the comparative analysis predicted that 3-4 copies of the gene may occur within the diploid *Brassica* genome. Additional genetic mapping studies were completed by Scheffler et al. (1997) Theoretical and Applied Genetics 94; 583-591. The results of these genetic mapping studies indicated that four copies of the FAD2 gene were present in *Brassica napus*.

Sequencing analysis of the BAC library which was constructed from *B. napus* L. var. DH12075 resulted in the isolation of four BAC sequences (SEQ ID NO:1, SEQ ID NO:2, SEQ ID NO:3, and SEQ ID NO:4) from which the coding sequences for the FAD2A (SEQ ID NO:5), FAD2-1 (SEQ ID NO:6), FAD2-2 (SEQ ID NO:7), and FAD2-3 (SEQ ID NO:8) genes were determined. The FAD2A, FAD2-1, FAD2-2, and FAD2-3 gene sequences were identified and genetically mapped. Sequence analysis of the four FAD2 genes was conducted using a sequence alignment program and a neighbor-joining tree using percentage of identity. The sequence alignment was made via the AlignX® program from the Vector NTI Advance 11.0 computer program (Life Technologies, Carlsbad, Calif.) and is shown in FIG. 1. AlignX® uses a modified Clustal W algorithm to generate multiple sequence alignments of either protein or nucleic acid sequences for similarity comparisons and for annotation.

The neighbour-joining tree was created with Jalview v2.3® software and is shown in FIG. 2. (Waterhouse et al. (2009) Bioinformatics 25 (9) 1189-1191). As shown in FIG. 2, the analysis of the isolated sequences indicated that the FAD2A and FAD2-3 sequences shared high levels of sequence similarity and that, likewise, FAD2-1 and FAD2-2 shared high levels of sequence similarity. The four sequences can be categorized in two clades, wherein FAD2A and FAD2-3 comprise a first clade, and FAD2-1 and FAD2-2 comprise a second clade.

Next, the newly isolated FAD2 sequences from *Brassica napus* were used to BLAST genomic libraries isolated from a *Brassica rapa* genomic BAC library and *Brassica oleracea* shotgun genomic sequence reads. Both, *Brassica rapa* and *Brassica oleracea* are diploid progenitors of *Brassica napus* which is an amphidiploid species (AC genome, n=19). *Brassica napus* derived from a recent hybridization event between *Brassica rapa* (A sub-genome, n=10) and *Brassica oleracea* (C sub-genome, n=9). The diploid progenitor sequences were compared to the four different FAD2 coding sequences isolated from *Brassica napus* using a BLASTn analysis. This sequence analysis identified specific, annotated gene sequences from *Brassica rapa* and *Brassica oleracea* which shared the highest sequence similarity to the newly discovered *Brassica napus* FAD2 sequences. Table 1 lists the newly identified FAD2 coding sequence and the corresponding progenitor reference sequence accession number and source organism.

TABLE 1

FAD2 sequences from *Brassica napus* and the corresponding progenitor organism and related FAD sequence accession number.

| Isolated gene sequence | Progenitor organism and sequence accession number | |
| --- | --- | --- |
| FAD2A | B. rapa | Genbank Accession No: KBrB063G23 (A05) |
| FAD2-3 | B. oleracea | Genbank Accession No: GSS23580801 |
| FAD2-1 | B. rapa | Genbank Accession No: KBrB130I19 |
| FAD2-2 | B. oleracea | Genbank Accession No: GSS 17735412 |

The FAD2 genes exist in the *Brassica napus* genome as two copies of each gene per sub-genome. One copy of each gene is located on the A sub-genome, and likewise one copy of each gene is located on the C sub-genome. New naming conventions are described to indicate which sub-genome that each gene is located on. The high levels of sequence similarity between the four different FAD2 coding sequences isolated from the *Brassica napus* BAC genomic DNA library and the progenitor sequence data suggest that FAD2-3 is a duplicate of the FAD2 sequence from the C sub-genome and could be relabeled as FAD2C; FAD2-1 is a duplicate of the FAD2 sequence from the A sub-genome and could therefore be labeled as FAD2A'; and finally, FAD2-2 is a second copy that was duplicated from the FAD2 sequence of the C sub-genome and could be labeled as FAD2C'.

PCR Based Screening

A cohort of PCR primers were design to screen the aforementioned BAC library. The primers were designed as either universal primers, which would amplify all members of the gene family, or as gene specific primers for targeted allele amplification. The PCR primers were designed to be 20 bp long (+/−1 bp) and contain a G/C content of 50% (+/−8%). Table 2 lists the primers which were designed and synthesized. The clones of the BAC library were pooled and screened via the Polymerase Chain Reaction (PCR).

TABLE 2

PCR primer sequences designed for BAC for FAD2 library screening gene identification.

| Primer Name | SEQ ID NO: | Sequence |
|---|---|---|
| D_UnivF2_F1 | SEQ ID NO: 9 | ATGGGTGCAGGTGGAAGAATG |
| D_UnivF2_F2 | SEQ ID NO: 10 | AGCGTCTCCAGATATACATC |
| D_UnivF2_R1 | SEQ ID NO: 11 | ATGTATATCTGGAGACGCTC |
| D_UnivF2_R2 | SEQ ID NO: 12 | TAGATACACTCCTTCGCCTC |
| D_SpecificF2_F3 | SEQ ID NO: 13 | TCTTTCTCCTACCTCATCTG |
| D_SpecificF2_R3 | SEQ ID NO: 14 | TTCGTAGCTTCCATCGCGTG |
| D_UnivF2_F4 | SEQ ID NO: 15 | GACGCCACCATTCCAACAC |
| D_UnivF2_R4 | SEQ ID NO: 16 | ACTTGCCGTACCACTTGATG |

Two different sets of conditions were used for the polymerase chain reactions (PCR). The first series of PCR reactions contained: 1×PCR buffer (containing dNTPs); 1.5 mM MgCl$_2$; 200 µM of 0.25 U Immolase® DNA polymerase (Bioline, London, UK); 250 nM of each primer; and, about 5-10 ng template DNA. A second series of PCR reactions were developed for the amplification of genomic DNA and contained: 5-10 ng of genomic DNA, 1×PCR buffer, 2 mM dNTPs, 0.4 µM forward and reverse primer, and 0.25 U Immolase® DNA polymerase (Bioline, London, UK). Amplifications were pooled into a final volume of 13 µL and amplified using an MJ PTC200® thermocycler (BioRad, Hercules, Calif.) or an ABI 9700 Gene Amp System® (Life Technologies, Carlsbad, Calif.). PCR based screening of specific plates was conducted using a 4 dimension screening approach based on the screening system described by Bryan et al (Scottish Crops Research Institute annual report: 2001-2002) with the above described PCR conditions. Following PCR based screening of pooled BAC libraries; the amplified PCR product was sequenced using a direct Sanger sequencing method. The amplified products were purified with ethanol, sodium acetate and EDTA following the BigDye® v3.1 protocol (Applied Biosystems) and electrophoresis was performed on an ABI3730xl® automated capillary electrophoresis platform.

Following PCR based screening and conformational Sanger sequencing, a collection of plates were identified that contained the various different FAD2 gene family members. A total of four unique FAD2 paralogous gene sequences were identified (Table 2). A total of two plates per each FAD2 paralogous gene sequence were chosen to undergo plate screening to identify the specific well and clone within the plate that contained the FAD2 gene (Table 3). The specific wells were identified for both of the plates and an individual clone was selected for each of the FAD2 gene family members.

TABLE 3

Identification of the BAC clone plates that provided positive reaction with the detailed PCR primer combinations, along with two plate identities that were taken forward for clone identification within the plate

| Gene Name | Primer Sets | Positive Plate Pools | Chosen Plates | Well Id |
|---|---|---|---|---|
| FAD2A | F4 + R1, F1 + R1, F1 + R4, F3 + R3 | 8, 27, 30, 83, 109, 147, 180, 199, 209, 251, 288 | Plate 199 Plate 27 | L23 D20 |
| FAD2-1 | F1 + R4, F4 + R1, F1 + R1, F2 + R2 | 12, 89, 123, 148, 269 | Plate 123 Plate 148 | N17 B15 |
| FAD2-2 | F4 + R1, F1 + R1, F1 + R4, F2 + R2 | 24, 44, 46, 47, 80, 91, 104, 110, 119, 121, 124, 248 | Plate 44 Plate 121 | H03 A17 |
| FAD2-3 | F1 + R4, F4 + R1, F1 + R1, F3 + R3 | 8, 62, 113, 205, 276 | Plate 62 Plate 205 | I16 K11 |

The single BAC clone, for each identified FAD gene family member, was further analysed via sequencing. The DNA was isolated for the BAC clone and was prepared for sequencing using a Large Construct Kit® (Qiagen, Valencia, Calif.) following the manufacturer's instructions. The extracted BAC DNA was prepared for sequencing using GS-FLX Titanium Technology® (Roche, Indianapolis, Ind.) following manufacturer's instructions. Sequencing reactions were performed using a physically sectored GS-FLX TI Pico-titer Plate® with the BACs pooled in pairs for optimal data output. The BACs were combined in pairs where the FAD2 gene was paired with a FAD3 gene. All generated sequence data was assembled by Newbler v2.0.01.14® (454 Life Sciences, Branford, Conn.). The assembled contigs were manually assessed for the presence of the corresponding FAD gene using Sequencher v3.7® (GeneCodes, Ann Arbor, Mich.).

After the full genomic sequence of all four FAD2 genes had been identified and fully characterized, zinc finger nucleases were designed to bind to the sequences for each specific gene family member.

Example 2: Design of Zinc Finger Binding Domains Specific to FAD2 Genes

Novel zinc finger proteins directed against DNA sequences encoding various functional sequences of the FAD2 gene locus were designed essentially as previously described. See, e.g., Urnov et al. (2005) Nature 435:646-651. Exemplary target sequence and recognition helices are shown in Table 4 (recognition helix regions designs) and Table 5 (target sites). In Table 5, nucleotides in the target site that are contacted by the ZFP recognition helices are indicated in uppercase letters; non-contacted nucleotides indicated in lowercase.

Zinc Finger Nuclease (ZFN) target sites were designed to bind five target sites of FAD2A. The FAD2A zinc finger designs were incorporated into zinc finger expression vectors encoding a protein having at least one finger with a CCHC structure. See, U.S. Patent Publication No. 2008/0182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al., (1998) Proc. Natl. Acad. Sci. USA 95:10564-10569) via a four amino acid ZC linker and an opaque-2 nuclear localization signal derived from *Zea mays* to form FAD2A zinc-finger nucleases (ZFNs). Expression of the fusion proteins was driven by a relatively strong constitutive promoter such as a promoter derived from the Cassava Vein Mosaic Virus (CsVMV) promoter and flanked by the *Agrobacterium tumefaciens* ORF23 3'UnTranslated Region (AtuORF23 3'UTR v1). The self-hydrolyzing 2A encoding nucleotide sequence from Thosea asigna virus (Szymczak et al., 2004) was added between the two Zinc Finger Nuclease fusion proteins that were cloned into the construct. Exemplary vectors or plasmids are described in Table 5, below.

The optimal FAD2 zinc finger nucleases were verified for cleavage activity using a budding yeast based system previously shown to identify active nucleases. See, e.g., U.S. Patent Publication No. 20090111119; Doyon et al. (2008) *Nat Biotechnol.* 26:702-708; Geurts et al. (2009) *Science* 325:433. Zinc fingers for the various functional domains were selected for in-vivo use. Of the numerous ZFNs that were designed, produced and tested to bind to the putative FAD genomic polynucleotide target sites, eleven ZFNs were identified as having in vivo activity at high levels, and selected for further experimentation. These ZFNs were characterized as being capable of efficiently binding and cleaving the unique FAD2 genomic polynucleotide target sites in planta.

TABLE 4

FAD2 Zinc Finger Designs

| ZFP | F1 | F2 | F3 | F4 | F5 | F6 |
|-----|-----|-----|-----|-----|-----|-----|
| 24800 | RSDNLST (SEQ ID NO: 94) | HSHARIK SEQ ID NO: 95 | HRSSLRR SEQ ID NO: 96 | RSDHLSE SEQ ID NO: 97 | QNANRIT SEQ ID NO: 98 | N/A |
| 24801 | DRSNLSR SEQ ID NO: 99 | HRSSLRR SEQ ID NO: 96 | TSGNLTR SEQ ID NO: 101 | MSHHLRD SEQ ID NO: 102 | DQSNLRA SEQ ID NO: 103 | N/A |
| 24794 | QSGNLAR SEQ ID NO: 104 | RSDNLSR SEQ ID NO: 105 | DNNARIN SEQ ID NO: 106 | DRSNLSR SEQ ID NO: 99 | RSDHLTQ SEQ ID NO: 108 | N/A |
| 24795 | RSDNLRE SEQ ID NO: 109 | QSGALAR SEQ ID NO: 110 | QSGNLAR SEQ ID NO: 104 | RSDVLSE SEQ ID NO: 112 | SPSSRRT SEQ ID NO: 113 | N/A |
| 24810 | RSDSLSR SEQ ID NO: 114 | RKDARIT SEQ ID NO: 115 | RSDHLSA SEQ ID NO: 116 | WSSSLYY SEQ ID NO: 117 | NSRNLRN SEQ ID NO: 118 | N/A |
| 24811 | DQSTLRN SEQ ID NO: 119 | DRSNLSR SEQ ID NO: 99 | DRSNLWR SEQ ID NO: 121 | DRSALSR SEQ ID NO: 122 | RSDALAR SEQ ID NO: 123 | N/A |
| 24814 | RSDALSR SEQ ID NO: 124 | DRSDLSR SEQ ID NO: 125 | RSDHLTQ SEQ ID NO: 108 | QSGALAR SEQ ID NO: 110 | QSGNLAR SEQ ID NO: 104 | N/A |
| 24815 | DRSNLSR SEQ ID NO: 99 | DSSARNT SEQ ID NO: 130 | DRSSRKR SEQ ID NO: 131 | QSGDLTR SEQ ID NO: 132 | LAHHLVQ SEQ ID NO: 133 | N/A |
| 24818 | RSDNLST SEQ ID NO: 94 | HSHARIK SEQ ID NO: 95 | TSGHLSR SEQ ID NO: 136 | RSDNLSV SEQ ID NO: 137 | IRSTLRD SEQ ID NO: 138 | N/A |
| 24819 | TSGHLSR SEQ ID NO: 136 | DRSNLSR SEQ ID NO: 99 | HRSSLRR SEQ ID NO: 96 | TSGNLTR SEQ ID NO: 101 | MSHHLRD SEQ ID NO: 102 | N/A |
| 24796 | RSDALSR SEQ ID NO: 124 | DRSDLSR SEQ ID NO: 125 | RSDHLTQ SEQ ID NO: 108 | QSGALAR SEQ ID NO: 110 | QSGNLAR SEQ ID NO: 104 | N/A |
| 24797 | RSAVLSE SEQ ID NO: 149 | TNSNRIT SEQ ID NO: 150 | LKQHLNE SEQ ID NO: 151 | QSGALAR SEQ ID NO: 110 | QSGNLAR SEQ ID NO: 104 | N/A |
| 24836 | DRSNLSR SEQ ID NO: 99 | QSGDLTR SEQ ID NO: 132 | QSGALAR SEQ ID NO: 110 | DRSNLSR SEQ ID NO: 99 | QRTHLTQ SEQ ID NO: 158 | N/A |
| 24837 | RSDNLSN SEQ ID NO: 159 | TNSNRIK SEQ ID NO: 160 | QSSDLSR SEQ ID NO: 161 | QSSDLRR SEQ ID NO: 162 | DRSNRIK SEQ ID NO: 163 | N/A |

TABLE 4 -continued

FAD2 Zinc Finger Designs

| ZFP | F1 | F2 | F3 | F4 | F5 | F6 |
|---|---|---|---|---|---|---|
| 24844 | RSANLAR SEQ ID NO: 164 | RSDNLTT SEQ ID NO: 165 | QSGELIN SEQ ID NO: 166 | RSADLSR SEQ ID NO: 167 | RSDNLSE SEQ ID NO: 168 | DRSHLAR SEQ ID NO: 169 |
| 24845 | DRSHLAR SEQ ID NO: 169 | RSDNLSE SEQ ID NO: 168 | SKQYLIK SEQ ID NO: 172 | ERGTLAR SEQ ID NO: 173 | RSDHLTT SEQ ID NO: 174 | N/A |
| 24820 | QSGALAR SEQ ID NO: 110 | QSGNLAR SEQ ID NO: 104 | DRSHLAR SEQ ID NO: 169 | DRSDLSR SEQ ID NO: 125 | RSDNLTR SEQ ID NO: 179 | N/A |
| 24821 | DRSHLAR SEQ ID NO: 169 | RSDNLSE SEQ ID NO: 168 | SKQYLIK SEQ ID NO: 172 | ERGTLAR SEQ ID NO: 173 | RSDHLTT SEQ ID NO: 174 | N/A |
| 24828 | DRSDLSR SEQ ID NO: 125 | RSDNLTR SEQ ID NO: 179 | QRTHLTQ SEQ ID NO: 158 | RSDNLSE SEQ ID NO: 168 | ASKTRKN SEQ ID NO: 189 | N/A |
| 24829 | RSDTLSE SEQ ID NO: 190 | QSHNRTK SEQ ID NO: 191 | QSDHLTQ SEQ ID NO: 192 | RSSDLSR SEQ ID NO: 193 | QSSDLSR SEQ ID NO: 161 | RSDHLTQ SEQ ID NO: 108 |
| 24832 | RSDSLSR SEQ ID NO: 114 | RKDARIT SEQ ID NO: 115 | DRSHLSR SEQ ID NO: 198 | QSGNLAR SEQ ID NO: 104 | QSSDLSR SEQ ID NO: 161 | DRSALAR SEQ ID NO: 201 |
| 24833 | RSDDLSK SEQ ID NO: 202 | RSDTRKT SEQ ID NO: 203 | DRSNLSR SEQ ID NO: 99 | DRSNLWR SEQ ID NO: 121 | RSDSLSR SEQ ID NO: 114 | NNDHRKT SEQ ID NO: 207 |

TABLE 5

Target Sites of FAD2 Zinc Fingers

| ZFP | Plasmid No. | Target Site (5' to 3') | ZFP target/ binding site present in SEQ ID Nos. |
|---|---|---|---|
| 24800 | pDAB104001 | ccCAAAGGGTTGTTGAGgtacttgccgt | SEQ ID NO: 17 |
| 24801 | pDAB104001 | cgCACCGTGATGTTAACggttcagttca | SEQ ID NO: 18 |
| 24794 | pDAB104002 | taAGGGACGAGGAGGAAggagtggaaga | SEQ ID NO: 19 |
| 24795 | pDAB104002 | ttCTCCTGGAAGTACAGtcatcgacgcc | SEQ ID NO: 20 |
| 24810 | pDAB104003 | gtCGCTGAAGGcGTGGTGgccgcactcg | SEQ ID NO: 21 |
| 24811 | pDAB104003 | caGTGGCTgGACGACACCgtcggcctca | SEQ ID NO: 22 |
| 24814 | pDAB104004 | gaGAAGTAAGGGACGAGgaggaaggagt | SEQ ID NO: 23 |
| 24815 | pDAB104004 | gaAGTACAGTCATCGACgccaccattcc | SEQ ID NO: 24 |
| 24818 | pDAB104005 | tcCCAAAGGGTtGTTGAGgtacttgccg | SEQ ID NO: 25 |
| 24819 | pDAB104005 | acCGTGATGTTAACGGTtcagttcactc | SEQ ID NO: 26 |
| 24796 | pDAB104006 | gaGAAGTAAGGGACGAGgaggaaggagt | SEQ ID NO: 23 |
| 24797 | pDAB104006 | tgGAAGTAcAGTCATCGAcgccaccatt | SEQ ID NO: 28 |
| 24836 | pDAB104007 | gtAGAGACcGTAGCAGACggcgaggatg | SEQ ID NO: 29 |
| 24837 | pDAB104007 | gcTACGCTGCTgTCCAAGgagttgcctc | SEQ ID NO: 30 |
| 24844 | pDAB104008 | gaGGCCAGGCGAAGTAGGAGagagggtg | SEQ ID NO: 31 |

TABLE 5 -continued

Target Sites of FAD2 Zinc Fingers

| ZFP | Plasmid No. | Target Site (5' to 3') | ZFP target/ binding site present in SEQ ID Nos. |
|---|---|---|---|
| 24845 | pDAB104008 | acTGGGCCTGCCAGGGCtgcgtcctaac | SEQ ID NO: 32 |
| 24820 | pDAB104009 | gaGAGGCCaGGCGAAGTAggagagaggg | SEQ ID NO: 33 |
| 24821 | pDAB104009 | acTGGGCCTGCCAGGGCtgcgtcctaac | SEQ ID NO: 32 |
| 24828 | pDAB104010 | agGCCCAGtAGAGAGGCCaggcgaagta | SEQ ID NO: 35 |
| 24829 | pDAB104010 | ccAGGGCTGCGTCCTAACCGgcgtctgg | SEQ ID NO: 36 |
| 24832 | pDAB104011 | taGTCGCTGAAGGCGTGGTGgccgcact | SEQ ID NO: 37 |
| 24833 | pDAB104011 | agTGGCTGGACGACaCCGTCGgcctcat | SEQ ID NO: 38 |

Example 3: Evaluation of Zinc Finger Nuclease Cleavage of FAD2 Genes

Construct Assembly

Plasmid vectors containing ZFN expression constructs of the exemplary zinc finger nucleases, which were identified using the yeast assay, as described in Example 2, were designed and completed using skills and techniques commonly known in the art. Each zinc finger-encoding sequence was fused to a sequence encoding an opaque-2 nuclear localization signal (Maddaloni et al. (1989) *Nuc. Acids Res.* 17(18):7532), that was positioned upstream of the zinc finger nuclease.

Next, the opaque-2 nuclear localization signal::zinc finger nuclease fusion sequence was paired with the complementary opaque-2 nuclear localization signal::zinc finger nuclease fusion sequence. As such, each construct included a single open reading frame comprised of two opaque-2 nuclear localization signal::zinc finger nuclease fusion sequences separated by the 2A sequence from *Thosea asigna* virus (Mattion et al. (1996) *J. Virol.* 70:8124-8127). Expression of the fusion proteins was driven by a relatively strong constitutive promoter such as a promoter derived from the Cassava Vein Mosaic Virus (CsVMV) promoter and flanked by the *Agrobacterium tumefaciens* ORF23 3'UnTranslated Region (AtuORF23 3'UTR).

The vectors were assembled using the IN-FUSION™ Advantage Technology (Clontech, Mountain View, Calif.). Restriction endonucleases were obtained from New England BioLabs (NEB; Ipswich, Mass.) and T4 DNA Ligase (Invitrogen) was used for DNA ligation. Plasmid preparations were performed using NUCLEOSPIN® Plasmid Kit (Macherey-Nagel Inc., Bethlehem, Pa.) or the Plasmid Midi Kit (Qiagen) following the instructions of the suppliers. DNA fragments were isolated using QIAquick Gel Extraction Kit™ (Qiagen) after agarose Tris-acetate gel electrophoresis. Colonies of all assembled plasmids were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.). Before delivery to *B. napus* protoplasts, Plasmid DNA was prepared from cultures of *E. coli* using the Pure Yield Plasmid Maxiprep System® (Promega Corporation, Madison, Wis.) or Plasmid Maxi Kit® (Qiagen, Valencia, Calif.) following the instructions of the suppliers.

The resulting eleven plasmid constructs; pDAB104008 (containing the ZFN24845 and ZFN24844 construct), pDAB104009 (containing the ZFN24820 and ZFN24821 construct), pDAB104010 (containing the ZFN24828 and ZFN24829 construct) (FIG. 3), pDAB104003 (containing the ZFN24810 and ZFN24811 construct), pDAB104011 (containing the ZFN24832 and ZFN24833 construct), pDAB104002 (containing the ZFN24794 and ZFN24795 construct), pDAB104006 (containing the ZFN24796 and ZFN24797 construct), pDAB104004 (containing the ZFN24814 and ZFN24815 construct), pDAB104001 (containing the ZFN24800 and ZFN24801 construct), pDAB104005 (containing the ZFN24818 and ZFN24819 construct), and pDAB104007 (containing the ZFN24836 and ZFN24837 construct) were confirmed via restriction enzyme digestion and via DNA sequencing. Table 6 lists the different constructs and the specific FAD2A sequence which each ZFN was designed to cleave and bind.

Table 6: lists the Zinc Finger protein binding motif and the corresponding construct number. Each Zinc Finger was designed to bind and cleave the FAD2A which is described in the table

| ZFN Design | Construct No. | Locus ID. | Target Cut Site in FAD2A Sequence |
|---|---|---|---|
| 24844-2A-24845 | pDAB104008 | FAD2_ZFN_Locus1_F2A | 263-265 |
| 24820-2A-24821 | pDAB104009 | FAD2_ZFN_Locus1_F2B | 265 |
| 24828-2A-24829 | pDAB104010 | FAD2_ZFN_Locus1_F2C | 275 |
| 24810-2A-24811 | pDAB104003 | FAD2_ZFN_Locus2_F1D | 343-345 |
| 24832-2A-24833 | pDAB104011 | FAD2_ZFN_Locus2_F1E | 345-346 |
| 24794-2A-24795 | pDAB104002 | FAD2_ZFN_Locus3_F2F | 402 |
| 24796-2A-24797 | pDAB104006 | FAD2_ZFN_Locus3_F2G | 408 |
| 24814-2A-24815 | pDAB104004 | FAD2_ZFN_Locus3_F2H | 408-410 |
| 24800-2A-24801 | pDAB104001 | FAD2_ZFN_Locus4_F1J | 531 |

| ZFN Design | Construct No. | Locus ID. | Target Cut Site in FAD2A Sequence |
|---|---|---|---|
| 24818-2A-24819 | pDAB104005 | FAD2_ZFN_Locus4_F1K | 532-534 |
| 24836-2A-24837 | pDAB104007 | FAD2_ZFN_Locus5_F1L | 724 |

Preparation of DNA for Transfection

Plasmid DNA of the above described vectors was sterilized by precipitation and washing in 100% (v/v) ethanol and dried in a laminar flow hood. The DNA pellet was suspended in 30 µl of sterile double-distilled water at a final concentration of 0.7 µg/µl for transfection into protoplast cells as described below. The preparation of the plasmid DNA was undertaken to result in supercoiled plasmid DNA for transient transfection and linearized plasmid DNA for stable transfection. The addition of carrier DNA (e.g. fish-sperm DNA) to the transforming plasmid was not required for the transient transfection of protoplast cells. For transient studies about 30 µg of plasmid DNA per $10^6$ protoplasts was used per transformation.

Transfection

Transfection of *Brassica napus* L. var. DH10275 was completed as described in Spangenberg et al., (1986) Plant Physiology 66: 1-8, the media formulations are described in Spangenberg G. and Protrykus I. (1995) Polyethylene Glycol-Mediated Direct Gene Transfer in Tobacco Protoplasts. In: *Gene Transfer to Plants*. (Protrykus I. and Spangenberg G. Eds.) Springer-Verlag, Berlin. *Brassica napus* seeds were surface sterilized in 70% ethanol. The seeds were immersed in 12 mL of the 70% ethanol solution and mixed by gently rocking the cocktail for 10 minutes. The 70% ethanol solution was removed by decanting the solution and exchanged with a seed sterilization solution consisting of 1% w/v calcium hypochlorite and 0.1% v/v Tween-20. The seeds were immersed in the seed sterilization solution and mixed by gently rocking the cocktail for 25 minutes. The seed sterilization solution was decanted and the sterilized seeds were rinsed three times in 50 mL of sterile water. Finally, the seeds were transferred to a sterile 80 mm Whatman filter paper Disc® (Fisher-Scientific, St. Louis, Mo.) that had been laid within a Petri dish and the seeds were lightly saturated with sterile water. The Petri dish was sealed with Parafilm® (Fisher-Scientific, St. Louis, Mo.) and the plates were incubated at 25° C. under complete darkness for one to two days. After signs of seedling emergence were observed from the seeds, the seedlings were transferred to Petri dish containing solidified GEM medium to encourage further seed germination. The seedlings were incubated on the GEM medium at 25° C. for four to five days.

A volume of liquid PS medium (about 10 mL) was decanted into a sterile Petri dish. Using sterile forceps and a scalpel, an aerial portion of the four to five day old seedling in the 4-leaf stage of growth and development, was removed and discarded. Hypocotyl segments in lengths of 20-40 mm were determined to produce the highest population of small, cytoplasmic-rich protoplasts. The hypocotyl segments were aseptically excised and transferred to liquid PS medium. The excised hypocotyl segments were grouped together and cut transversely into 5-10 mm segments. Next, the hypocotyl segments were transferred to fresh PS medium and incubated at room temperature for 1 hour. The plasmolysed hypocotyls were transferred to a Petri dish containing enzyme solution. Care was taken to immerse all of the hypocotyl segments into the solution. The Petri dishes were sealed with Parafilm® and incubated overnight for sixteen to eighteen hours at 20-22° C. with gentle rocking.

Protoplast cells were released from the hypocotyl segments. The overnight hypocotyl digests were gently agitated to release protoplasts into the enzyme solution. The Petri dish was angled slightly to aid the transfer of the digesting suspension of enzyme solution and plant debris. Using a 10 mL pipette the digesting suspension was transferred to a sterilized protoplast filtration (a filter of 100 micron mesh) unit to further separate the protoplasts from the plant debris. The filtration unit was tapped gently to release the excess liquid that had been caught in the sieve. The protoplast suspension, about 8 to 9 mL, was gently mixed and distributed into 14 mL sterile plastic round-bottomed centrifuge tubes. Each suspension was overlaid with 1.5 mL of W5 solution. The W5 solution was carefully dispensed over the protoplast suspension at an angle and dispensed drop-by-drop with minimal agitation. The addition of the W5 solution to the protoplast suspension resulted in the production of a protoplast rich interface. This interface was collected using a pipette. Next, the collected protoplasts were transferred into a new 14 mL centrifuge tube, and gently mixed. The yield or obtained protoplasts were determined using a haemocytometer to determine the number of protoplasts per milliliter. The method was repeated, wherein leaf tissue was digested to produce mesophyll protoplasts.

Next, W5 solution was added to a volume of 10 mL and the protoplasts were pelleted at 70 g, before removing the W5 solution. The remaining protoplast suspension was resuspended by gentle shaking. Each tube containing the protoplast suspension was filled with 5 mL of W5 solution and incubated at room temperature from one to four hours. The protoplast suspensions were pelleted at 70 g, and all of the W5 solution was removed. Next, 300 µL of transformation buffer was added to each of the pelleted protoplast suspensions which contained the isolated protoplasts. To each of the tubes, 10 µg of plasmid DNA was added to the protoplast suspensions. The plasmid DNA included the zinc finger nuclease constructs described above (e.g., pDAB104010). Next, 300 µL of pre-warmed PEG 4000 solution was added to the protoplast suspension and the tubes were gently tapped. The protoplast suspensions and transformation mixture was allowed to incubate at room temperature for fifteen minutes without any agitation. An additional 10 mL of W5 solution was added to each tube in sequential aliquots of 1 mL, 1 mL, 1 mL, 2 mL, 2 mL, and 3 mL with gentle inversion of the tubes between each addition of W5 solution. The protoplasts were pelleted by spinning in a centrifuge at 70 g. All of the W5 solution was removed leaving a pure protoplast suspension.

Next, 0.5 mL of K3 medium was added to the pelleted protoplast cells and the cells were resuspended. The resuspended protoplast cells were placed in the center of a Petri dish and 5 mL of K3 and 0.6 mL Sea Plaque™ agarose (Cambrex, East Rutherford, N.J.) in a 1:1 concentration. The Petri dishes were shaken in a single gentle swirling motion and left to incubate for 20-30 minutes at room temperature. The Petri dishes were sealed with Parafilm® and the protoplasts were cultured for twenty-four hours in complete darkness. After the incubation in darkness, the Petri dishes were cultured for six days in dim light (5 µMol m$^{-2}$ s$^{-1}$ of Osram L36 W/21 Lumilux white tubes). After the culture step, a sterile spatula was used to divide the agarose containing the protoplasts into quadrants. The separated quadrants were placed into a 250 mL plastic culture vessel containing 20 mL of A medium and incubated on a rotary shaker at 80 rpm and 1.25 cm throw at 24° C. in continuous dim light for 14 days and then analyzed to determine the level of activity of each Zinc Finger Nuclease construct.

Genomic DNA Isolation from Canola Protoplasts

Transfected protoplasts were supplied in individual 1.5 or 2.0 mL microfuge tubes. The cells were pelleted at the base of the tube in a buffer solution. DNA extraction was carried out by snap freezing the cells in liquid nitrogen followed by freeze drying the cells, for about 48 hours in a Labconco Freezone 4.5® (Labconco, Kansas City, Mo.) at −40° C. and about $133 \times 10^{-3}$ mBar pressure. The lyophilized cells were subjected to DNA extraction using the DNeasy® (QIAGEN, Carlsbad, Calif.) plant kit following manufactures instructions, with the exception that tissue disruption was not required and the protoplast cells were added directly to the lysis buffer.

Testing of FAD2A ZFN's for Genomic DNA Sequence Cleavage in Canola Protoplasts

The design of the ZFN target sites in the FAD2A gene locus were clustered, so that multiple pairs of ZFN were designed to overlapping target sites. The clustering of ZFN target sites enabled PCR primers to be designed that would amplify the surrounding genomic sequence from all FAD2A gene family members within a 100 bp window as to encompass all of the overlapping ZFN target sites. As such, the Illumina short read sequence technology could be used to assess the integrity of the target ZFN site of the transfected protoplasts. In addition, the PCR primers designs are needed to include specific nucleotide bases that would attribute sequence reads to the specific gene member of the FAD2A family. Therefore, all of the PCR primers would be required to bind 5-10 nucleotides away from any ZFN target cut site as non-homologous end joining (NHEJ) activity is known to cause small deletions that could remove a priming site, inhibit amplification and therefore distort the assessment of NHEJ activity.

Primers were designed to bind to all of the ZFN target loci for the FAD2A gene families (Table 7) and were empirically tested for amplification of all gene family members through Sanger based sequencing of PCR amplification products. In several instances primers could not be developed that would distinguish all gene family members (Table 8), however in all instances the target gene sequences of FAD2A, could be distinguished. Following PCR primer design custom DNA barcode sequences were incorporated into the PCR primers that were used to distinguish the different ZFN target loci and identify specific sequence reads to a transfection and ZFN (Tables 7 and 8).

TABLE 7

Primer sequences designed for FAD2 ZFN activity assessment of activity.

| Locus ID | SEQ ID NO: | Illumina Adaptor Primer Sequence Barcode Locus Primer |
|---|---|---|
| FAD2_ZFN_Locus1_F2A | SEQ ID NO: 39 | ACACTCTTTCCCTACACGACGCTCTTCCGATCT<u>ACGTA</u>CCCTCTCYCYTA CYTCGCC |
| FAD2_ZFN_Locus1_F2B | SEQ ID NO: 40 | ACACTCTTTCCCTACACGACGCTCTTCCGATCT<u>CGTAC</u>CCCTCTCYCYTA CYTCGCC |
| FAD2_ZFN_Locus1_F2C | SEQ ID NO: 41 | ACACTCTTTCCCTACACGACGCTCTTCCGATCT<u>GTACG</u>CCCTCTCYCYTA CYTCGCC |
| FAD2_ZFN_Locus2_F1D | SEQ ID NO: 42 | ACACTCTTTCCCTACACGACGCTCTTCCGATCT<u>TACGT</u>GTCATAGCCCA CGAGTGCGGC |
| FAD2_ZFN_Locus2_F1E | SEQ ID NO: 43 | ACACTCTTTCCCTACACGACGCTCTTCCGATCT<u>CTGAC</u>GTCATAGCCCA CGAGTGCGGC |
| FAD2_ZFN_Locus3_F2F | SEQ ID NO: 44 | ACACTCTTTCCCTACACGACGCTCTTCCGATCT<u>TGACT</u>GTCGGCCTCAT CTTCCACTCC |
| FAD2_ZFN_Locus3_F2G | SEQ ID NO: 45 | ACACTCTTTCCCTACACGACGCTCTTCCGATCT<u>GACTG</u>GTCGGCCTCAT CTTCCACTCC |
| FAD2_ZFN_Locus3_F2H | SEQ ID NO: 46 | ACACTCTTTCCCTACACGACGCTCTTCCGATCT<u>ACTGA</u>GTCGGCCTCAT CTTCCACTCC |
| FAD2_ZFN_Locus4_F1J | SEQ ID NO: 47 | ACACTCTTTCCCTACACGACGCTCTTCCGATCT<u>GCTAG</u>CAGACATCAAG TGGTACGGC |
| FAD2_ZFN_Locus4_F1K | SEQ ID NO: 48 | ACACTCTTTCCCTACACGACGCTCTTCCGATCT<u>CTAGC</u>CAGACATCAAG TGGTACGGC |

TABLE 7 -continued

Primer sequences designed for FAD2 ZFN activity assessment of activity.

| Locus ID | SEQ ID NO: | Illumina Adaptor Primer Sequence Barcode Locus Primer |
|---|---|---|
| FAD2_ZFN_Locus5_F1L | SEQ ID NO: 49 | ACACTCTTTCCCTACACGACGCTCTTCCGATCTTAGCTATCTCCGACGC TGGCATCCTC |
| FAD2_ZFN_Locus1_R1A | SEQ ID NO: 50 | CGGTCTCGGCATTCCTGCTGAACCGCTCTTCCGATCTACGTACTGGTAG TCGCTGAAGGCGT |
| FAD2_ZFN_Locus1_R1B | SEQ ID NO: 51 | CGGTCTCGGCATTCCTGCTGAACCGCTCTTCCGATCTCGTACCTGGTAG TCGCTGAAGGCGT |
| FAD2_ZFN_Locus1_R1C | SEQ ID NO: 52 | CGGTCTCGGCATTCCTGCTGAACCGCTCTTCCGATCTGTACGCTGGTAG TCGCTGAAGGCGT |
| FAD2_ZFN_Locus2_R1D | SEQ ID NO: 53 | CGGTCTCGGCATTCCTGCTGAACCGCTCTTCCGATCTTACGTGGACGAG GAGGAAGGAGTGGA |
| FAD2_ZFN_Locus2_R1E | SEQ ID NO: 54 | CGGTCTCGGCATTCCTGCTGAACCGCTCTTCCGATCTCTGACGGACGA GGAGGAAGGAGTGGA |
| FAD2_ZFN_Locus3_R1F | SEQ ID NO: 55 | CGGTCTCGGCATTCCTGCTGAACCGCTCTTCCGATCTTGACTAGTGTTG GAATGGTGGCGTCG |
| FAD2_ZFN_Locus3_R1G | SEQ ID NO: 56 | CGGTCTCGGCATTCCTGCTGAACCGCTCTTCCGATCTGACTGAGTGTTG GAATGGTGGCGTCG |
| FAD2_ZFN_Locus3_R1H | SEQ ID NO: 57 | CGGTCTCGGCATTCCTGCTGAACCGCTCTTCCGATCTACTGAAGTGTTG GAATGGTGGCGTCG |
| FAD2_ZFN_Locus4_R1J | SEQ ID NO: 58 | CGGTCTCGGCATTCCTGCTGAACCGCTCTTCCGATCTGCTAGCCCGAGA CGTTGAAGGCTAAG |
| FAD2_ZFN_Locus4_R1K | SEQ ID NO: 59 | CGGTCTCGGCATTCCTGCTGAACCGCTCTTCCGATCTCTAGCCCCGAGA CGTTGAAGGCTAAG |
| FAD2_ZFN_Locus5_R1L | SEQ ID NO: 60 | CGGTCTCGGCATTCCTGCTGAACCGCTCTTCCGATCTTAGCTGAAGGAT GCGTGTGCTGCAAG |

Primers include custom barcodes, along with both requisite Illumina adaptor sequences for construction of Illumina library for sequencing-by-synthesis analysis. Purchased primer was the sum of all three columns presented.

Amplification performance of the designed PCR primers on the FAD2 gene families are shown in Table 8. An "X" indicates gene copy detection specificity, a "+" indicates that at the specific locus in question the sequence reads designed by the two primers were unable to be distinguished.

TABLE 8

Results of cleavage at the FAD2A and FAD2C locus

| ZFN Locus | FAD2A | FAD2C | FAD2A' | FAD2C' |
|---|---|---|---|---|
| Locus 1 | X | X | X | X |
| Locus 2 | X | X | X | X |
| Locus 3 | + | + | X | X |
| Locus 4 | X | X | X | X |
| Locus 5 | X | X | X | X |

Following DNA extraction of canola protoplasts transfected with the ZFN(s), PCR amplification of the target ZFN loci was performed to generate the requisite loci specific DNA molecules in the correct format for Illumina based sequencing by synthesis technology. Each assay was optimised to work on 25 ng starting DNA (about 12,500 cell equivalents of the Brassica napus genome). Multiple reactions were performed, per sample to provide the coverage required to assess NHEJ efficiency and specificity at the appropriate level, about sixteen PCR reactions equivalent to 200,000 copies of the Brassica napus genome taken from individual protoplasts. PCR amplification master-mixes were made for all samples to be tested with the same assay and one reaction, performed in triplicate, was assayed using a quantitative PCR method that was used to determine the optimal number of cycles to perform on the target tissue, to ensure that PCR amplification had not become reagent limited and was still in an exponential amplification stage. The experimentation with the necessary negative control reactions, was performed in 96 well format using a MX3000P Thermocycler® (Stratagene, LaJolla, Calif.). From the output gathered from the quantitative PCR platform, the relative increase in fluorescence was plotted from cycle-to-cycle and the cycle number was determined per assay that would deliver sufficient amplification, while not allowing the reaction to become reagent limited, in an attempt to reduce over cycling and the amplification of common transcripts or molecules. The unused master mix, remained on ice until the quantitative PCR analysis was concluded and the cycle number determined and was then aliquoted into the desired number of reaction tubes (about 16 per ZFN assay) and the PCR reaction was performed.

Following amplification, samples for a single ZFN locus were pooled together and 200 µL of pooled product per ZFN was cleaned using the MinElute PCR purification Kit® (Qiagen) following manufacturer's instructions. To enable the sample to be sequenced using the Illumina short read technology additional paired end primers were required to be attached by amplification onto the generated fragments. This was achieved by PCR amplification using primers that would be, in part complementary to the sequence added in the first round of amplification, but also contain the paired end sequence required. The optimal number of PCR cycles to perform, that would add the paired end sequences without over amplifying common fragments to the template was again determined using a sample pass through a quantitative PCR cycle analysis, as described previously.

Following PCR amplification, the generated product was cleaned using a MinElute Column® (Qiagen) following manufacturer's instructions and was resolved on a 2.5% agarose gel. DNA fragments visualised using Syber® Safe (Life Technologies, Carlsbad, Calif.) as bands of the correct size were gel extracted to remove any residual PCR generated primer-dimer or other spurious fragments, the DNA was extracted from the gel slice using a MinElute gel extraction Kit® (Qiagen) following manufacturer's instructions. After completion of the gel extraction an additional clean up of the DNA was performed using AMPure magnetic Beads® (Beckman-Coulter, Brea, Calif.) with a DNA to bead ratio of 1:1.7. The DNA was then assessed for concentration using a quantitative PCR based library quantification kit for Illumina sequencing (KAPA) with a 1/40,000 and a 1/80,000 dilution and with the reaction being performed in triplicate. Based on the quantitative PCR results the DNA was diluted to a standard concentration of 2 nM and all libraries were combined for DNA sequencing. The samples were prepared for sequencing using a cBot cluster generation Kit® (Illumina, San Diego, Calif.) and were sequenced on an Illumina GA2x® with 100 bp paired-end sequencing reads following manufacturer's instructions.

Method of Data Analysis for Detection of Non-Homologous End Joining at Target Zinc Finger Sites Following completion of the sequencing reaction and primary data calling performed using the Illumina bioinformatic pipeline for base calling, full analysis was performed to identify deleted bases at the target ZFN site in each instance. A custom PERL script was designed to extract and sort barcodes from DNA sequences computationally following a list of input sequences. The barcode had to match the reference sequence at a Phred score of greater than 30 to be accepted, to reduce misattributing sequence reads. After the sequence reads had been binned into the different barcode groups that had been used, a quality filter was passed across all sequences. The quality filter was a second custom developed PERL script. Sequence reads were excluded if there were more than three bases called as "N", or if the median Phred score was less than 20, or if there were 3 consecutive bases with a Phred score of less than 20, or if the sequence read was shorter than 40 bp in length. The remaining sequences were merged where both of the paired sequence reads were available using the NextGENe® (SoftGenetics, State College, Pa.) package. The remaining merged sequence reads were then reduced to a collection of unique sequence reads using a third custom PERL script with a count of the number of redundant sequences that had been identified recorded on the end of the remaining sequence identifier. The unique sequence reads were then aligned to the FAD2 reference sequence using the NextGENe® software that created a gapped FASTA aligned file.

Using the gapped FASTA file a conversion of the gapped base position number to the input reference was performed using a fourth custom PERL script. This enabled bases that discriminate the different gene family members (either homoeologous or paralogous sequence variation between the different gene family members) to be identified in the assembled data. Once the conversion of base numbering had been performed it was possible to generate haplotype reports for each unique sequence reads and assign the reads to specific gene family members. Once the reads had been grouped by gene a 10 bp window was identified and assessed that surrounded the ZFN target site. The number of sequences with deletions was recorded per gene along with the number of missing bases.

Figure 4:
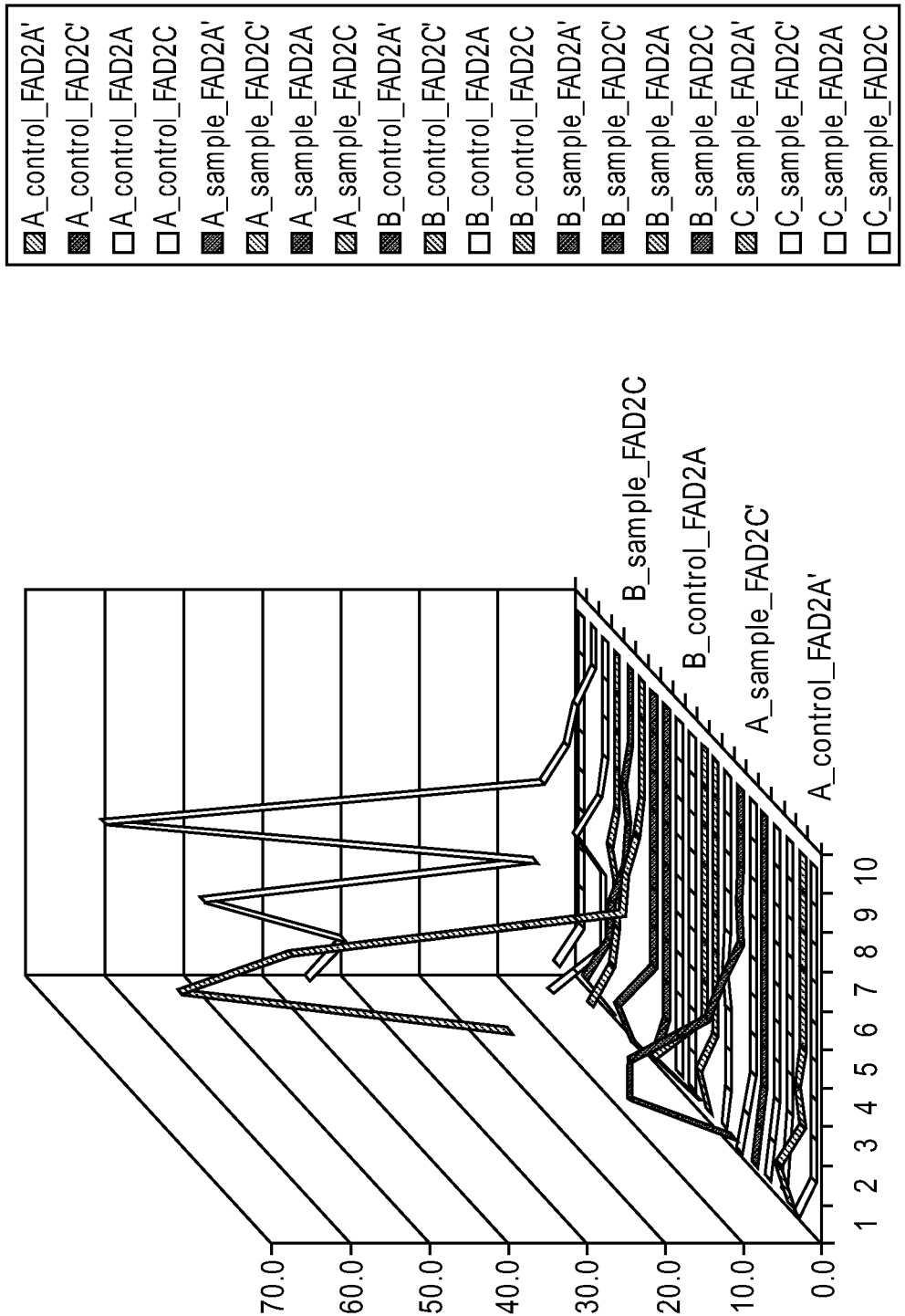
FIG. 4 is an example multiple line graph showing number of sequence reads per 10,000 sequence reads with deletions at the target ZFN site. The X axis on the graph denotes number of bases deleted, the Y axis denotes number of sequence reads and the Z axis denotes colour-coded sample identity as described to the right of the graph. Specific example shown is for locus 1 of the FAD2 gene family that contains 3 target ZFN sites, A, B and C with the four gene family members and two control transfections assessed as control samples A and B. The lines listed from top to bottom (A-control_FADA' at the top of the legend to C_sample_FAD2C at the bottom of the legend) are shown on the graph from closest to the labeled X-axis (A_control_FADA') to farthest from the labeled X-axis (C_sample_FAD2C).
Figure 5A:
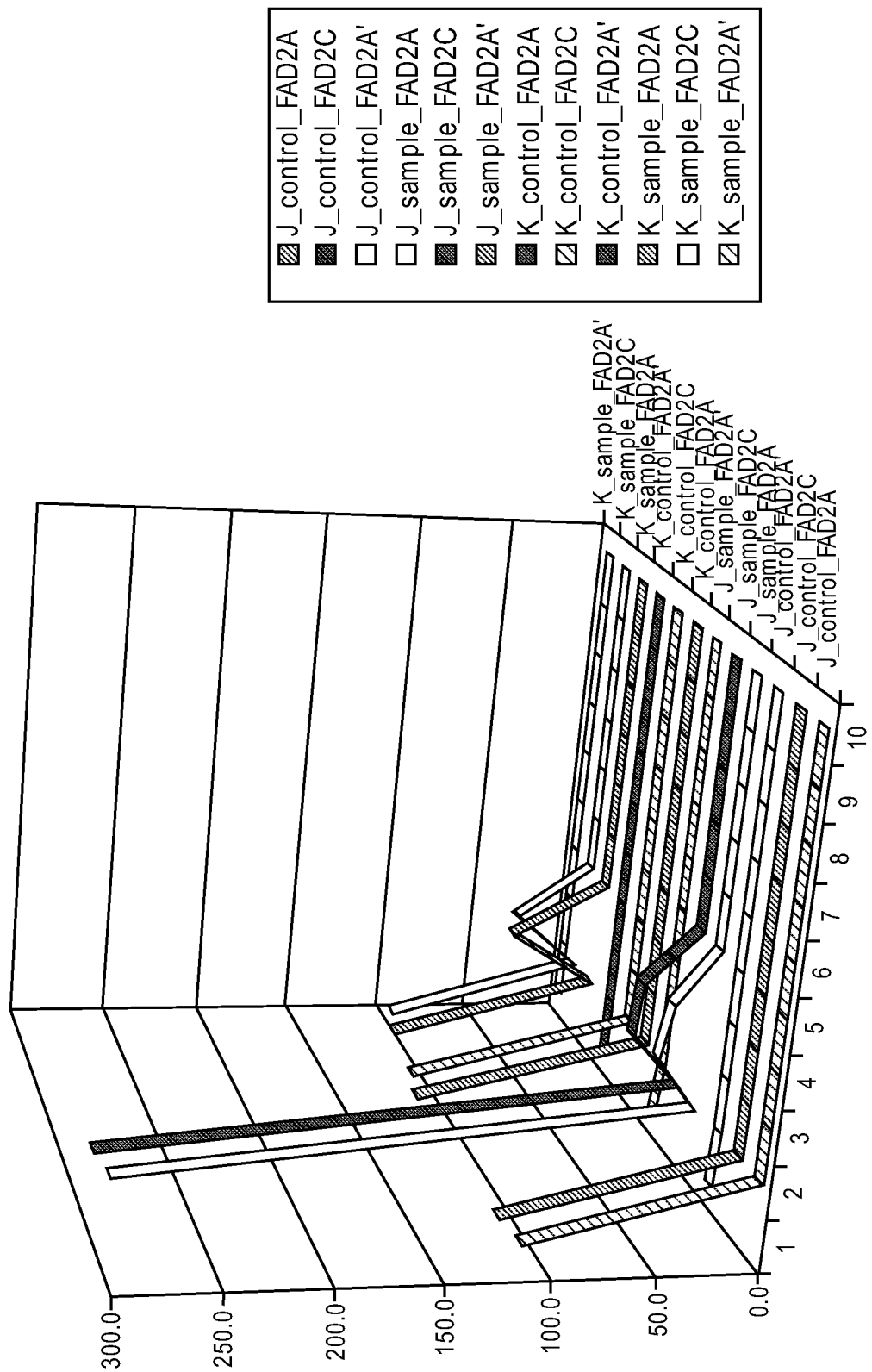
Figure 5B:
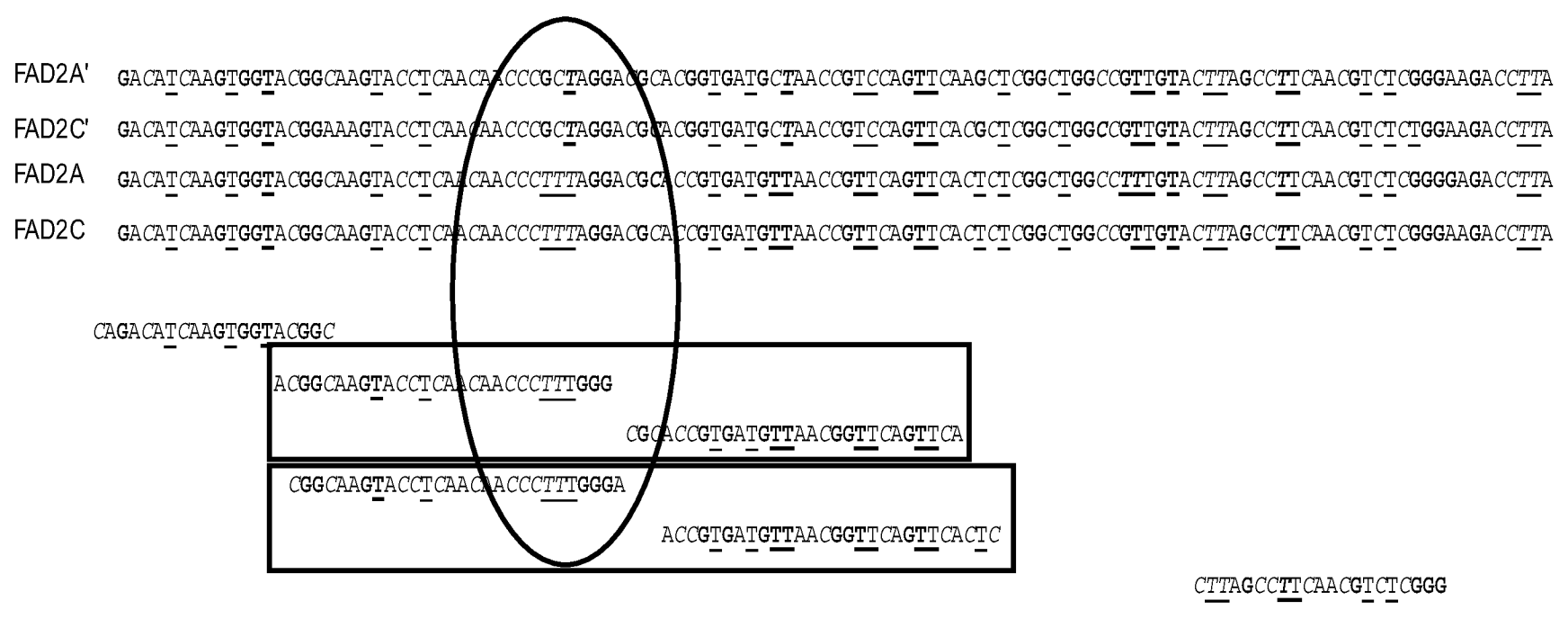

The data was then graphically displayed as a multiple line graph, with the number of sequences with 1 through 10 bases deleted at the target ZFN site per 10,000 sequence reads (FIG. 4). This analysis was performed for all ZFN transfections along with control transfections. In several instances, repeats in the native DNA sequence lead to an increase in sequencing error in the target ZFN site, such an error can be commonly seen as an increase in the prevalence of single base deletions that were reported in all samples, both transfected with ZFN or controls (FIG. 5).

From these results highest level of ZFN activity at a FAD2 target site, as determined by the greater activity of NHEJ, was identified at locus E. The ZFNs which were encoded on plasmid pDAB104010 (i.e., ZFN24828 and 24829) were selected for in planta targeting of an Engineered Transgene Integration Platform (ETIP) given its characteristics of significant genomic DNA cleavage activity and minimal non-target activity.

Example 4: DNA Constructs for Engineered Transgene Integration Platform (ETIP) Canola Plant Lines The plasmid vector constructs described below were built using methods and techniques commonly known by one with skill in the art. The application of specific reagents and techniques described within this paragraph are readily known by those with skill in the art, and could be readily interchanged with other reagents and techniques to achieve the desired purpose of building plasmid vector constructs. The restriction endonucleases were obtained from New England BioLabs (NEB; Ipswich, Mass.). Ligations were completed with T4 DNA Ligase (Invitrogen, Carlsbad, Calif.). Gateway reactions were performed using GATEWAY® LR CLONASE® enzyme mix (Invitrogen) for assembling one entry vector into a single destination vector. IN-FUSION™ reactions were performed using IN-FUSION™ Advantage Technology (Clontech, Mountain View, Calif.) for assembling one entry vector into a single destination vector Plasmid preparations were performed using NUCLEOSPIN® Plasmid Kit (Macherey-Nagel Inc., Bethlehem, Pa.) or the Plasmid Midi Kit® (Qiagen) following the instructions of the suppliers. DNA fragments were isolated using QIAquick Gel Extraction Kit™ (Qiagen) after agarose Tris-acetate gel electrophoresis. Colonies of all assembled plasmids were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.).

Figure 6:
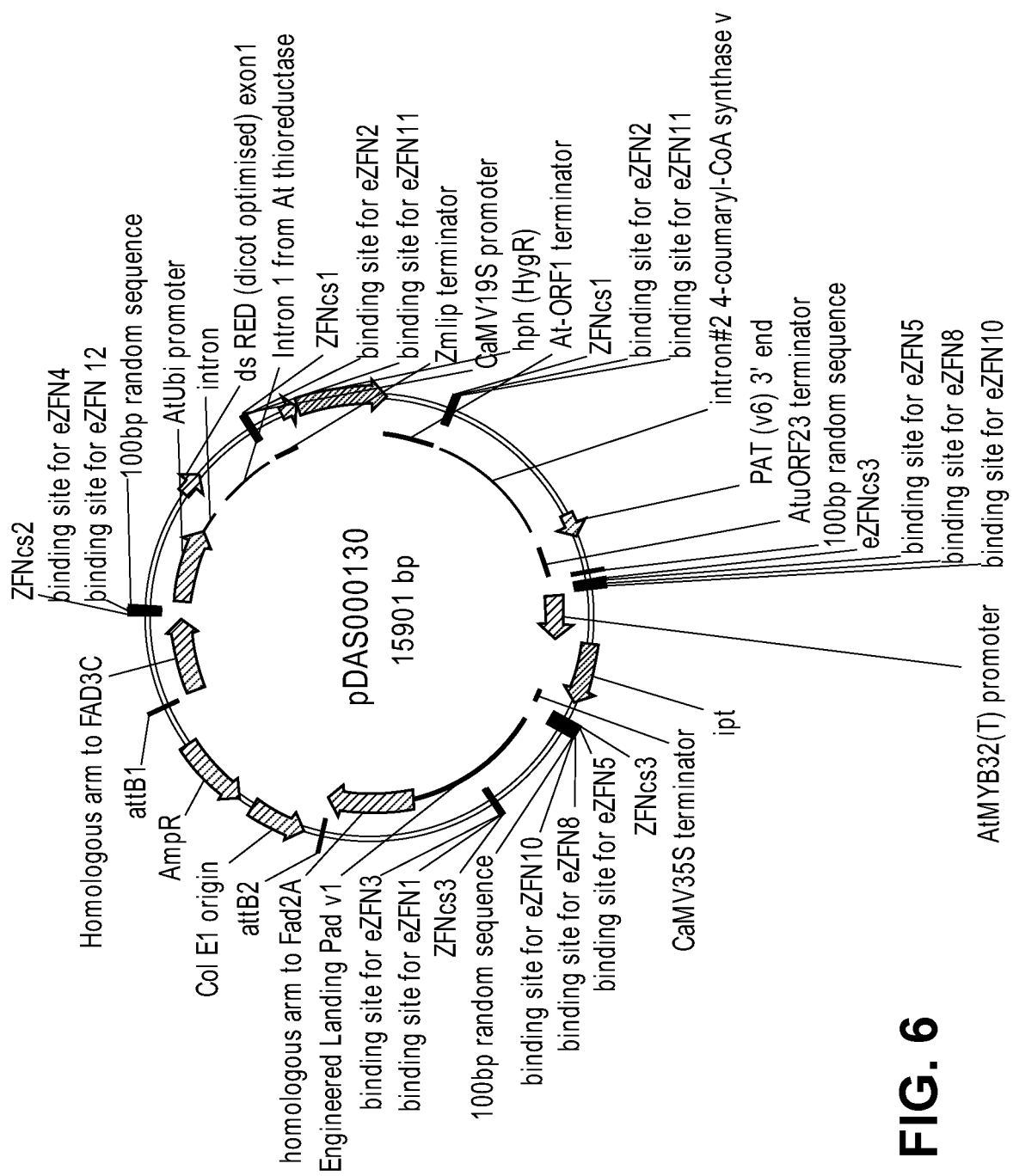
FIG. 6 shows a plasmid map of pDAS000130.

Direct-Delivery Vectors for Precision Integration of ETIP in the FAD2A Locus of Canola Standard cloning methods were used in the construction of the ETIP-containing vectors pDAS000130 (FIG. 6, T-strand insert as SEQ ID NO:61), for specific integration into the FAD2A gene of B. napus. This construct has been designed to be delivered into canola protoplasts with the Zinc Finger Nuclease construct pDAB104010. The Zinc Finger Nuclease Construct will cleave the FAD2A locus and then the pDAS000130 construct will integrate within the canola genome via a homology directed or non homologous end joining repair mechanism. The ETIP includes four expression cassettes (two incomplete) separated by additional ZFN recognition sequences and an Engineered Landing Pad (ELP) containing another ZFN recognition sequences. The additional ZFN recognition sequences are unique and have been designed to be targeted for the introduction of polynucleotide sequences within the ETIP and ELP transgene insertions. Similarly, the ZFN recognition sequences can be utilized for excision of polynucleotide sequences. The first gene expression cassette was an incomplete dsRED expression cassette and contained the promoter, 5' untranslated region and intron from the *Arabidopsis thaliana* Polyubiquitin 10 (AtUbi promoter) gene (Callis, et al., (1990) *J Biol. Chem.*, 265: 12486-12493) followed by 210 bp of a dsRed gene from the reef coral Discosoma sp. (Clontech, Mountain View, Calif.) codon-optimised for expression in dicot plants (ds RED (dicot optimized)exon 1) followed by an intron from the *Arabidopsis thaliana* thioreductase-like gene (Intron 1 from At thioreductase: Accession No: NC_00374) and the 3' untranslated region comprising the transcriptional terminator and polyadenylation site of the *Zea mays* Viviparous-1 (Vp1) gene (Zmlip terminator: Paek et al., (1998) Molecules and Cells, 8(3): 336-342). The second expression cassette contained the 19S promoter including 5' UTR from cauliflower mosaic virus (CaMV 19S: Cook and Penon (1990) *Plant Molecular Biology* 14(3): 391-405) followed by the hph gene from *E. coli*, codon-optimised for expression in dicots (hph(HygR): Kaster et al., (1983) Nucleic Acids Research 11(19): 6895-6911) and the 3'UTR comprising the transcriptional terminator and polyadenylation site of open reading frame 1 of *A. tumefaciens* pTi15955 (At-ORF1 terminator: Barker et al., (1983) Plant Molecular Biology 2(6): 335-50). The third expression cassette was an incomplete PAT expression cassette and contained the first intron from *Arabidopsis* 4-coumaryl-CoA synthase (intron #2 4-coumaryl-CoA synthase v: Accession No: At3g21320/NC003074) followed by the last 256 bp of a synthetic, plant-optimized version of phosphinothricin acetyl transferase gene, isolated from *Streptomyces viridochromogenes*, which encodes a protein that confers resistance to inhibitors of glutamine synthetase comprising phosphinothricin, glufosinate, and bialaphos (PAT(v6) 3' end: Wohlleben et al., (1988) Gene 70(1): 25-37). This cassette was terminated with the 3' UTR comprising the transcriptional terminator and polyadenylation sites of open reading frame 23 of *A. tumefaciens* pTi15955 (AtuORF23 terminator: Barker et al., (1983) Plant Molecular Biology 2(6): 335-50). The fourth Expression Cassette was the ipt gene cassette and contained a 588 bp truncated version of the promoter and 5' UTR from the *Arabidopsis* DNA-binding protein MYB32 gene (U26933) (AtMYB32(T) promoter: Li et al., (1999) Plant Physiology 121: 313) followed by the isopentyl transferase (ipt) gene from *A. tumefaciens* and the 35s terminator comprising the transcriptional terminator and polyadenylation sites from cauliflower mosaic virus (CaMV 35S terminator: Chenault et al., (1993) Plant Physiology 101 (4): 1395-1396). For delivery to FAD2A, each end of the ETIP sequence was flanked by 1 kb of FAD2A genomic sequence from either side of the location of the double-stranded break induced by delivery of the ZFN encoded in pDAB104010 to the FAD2A gene of *B. napus*.

The ETIP sequence was synthesized by a commercial gene synthesis vendor (GeneArt, Life Technologies). The 1 kb segments of FAD2A genome sequence were amplified from genomic DNA purified from leaf tissue of *B. napus* DH12075 using a Qiagen DNeasy plant mini Kit® (Qiagen, Hilden) following instructions supplied by the manufacturer. The 1 kb FAD2A sequences were ligated into the ETIP vector using T4 ligase (NEB, Ipswich, Mass.). Colonies of all assembled plasmids were initially screened by restriction digestion of miniprep DNA. Restriction endonucleases were obtained from New England BioLabs (NEB, Ipswich, Mass.) and Promega (Promega Corporation, WI). Plasmid preparations were performed using the QIAprep Spin Miniprep Kit® (Qiagen) or the Pure Yield Plasmid Maxiprep System® (Promega Corporation, WI) following the instructions of the suppliers. Plasmid DNA of selected clones was sequenced using ABI Sanger Sequencing and Big Dye Terminator v3.1 cycle sequencing Protocol® (Applied Biosystems, Life Technologies). Sequence data were assembled and analyzed using the SEQUENCHER™ software (Gene Codes Corp., Ann Arbor, Mich.).

Control Vectors

Figure 7:
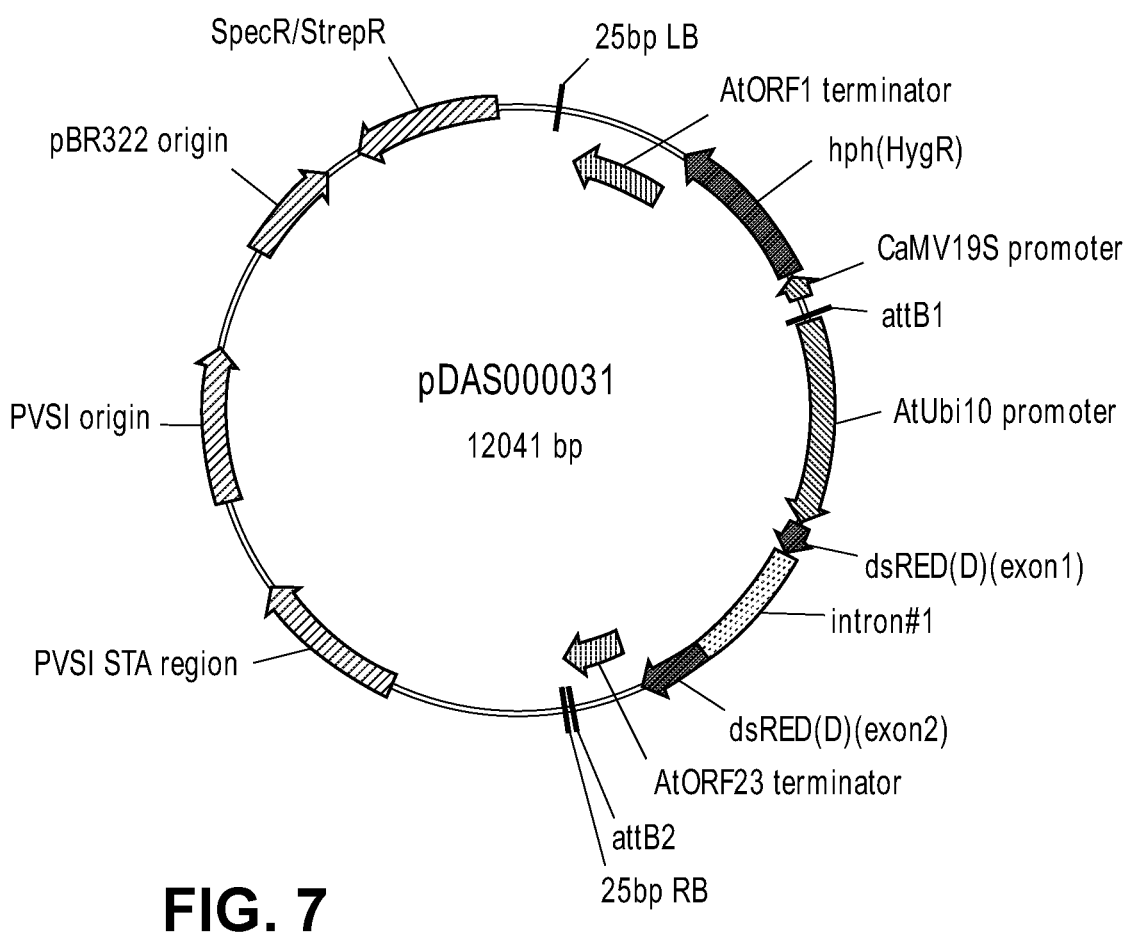
FIG. 7 shows a plasmid map of pDAS000031.

A control vector was used to develop a Fluorescence Activated Cell Sorting (FACS) cell based sorting method. Standard cloning methods were used in the construction of a control vector, pDAS000031 (FIG. 7: T-strand insert as SEQ ID NO:62) including two gene expression cassettes. The first gene expression cassette contained the Cauliflower mosaic virus 19s promoter (CaMV 19S promoter; Shillito, et al., (1985) *Bio/Technology* 3; 1099-1103):: hygromycin resistance gene (hph(HygR); U.S. Pat. No. 4,727,028):: and the *Agrobacterium tumefaciens* Open Reading Frame 1 3'UnTranslated Region (AtORF1 terminator; Huang et al., (1990) *J Bacteriol.* 1990 172:1814-1822). The second gene expression cassette contained the *Arabidopsis thaliana* Ubiquitin 10 promoter (AtUbi10 promoter; Callis, et al., (1990) *J Biol. Chem.*, 265: 12486-12493):: dsRED (dsRED (D); U.S. Pat. No. 6,852,849) and an intron from *Arabidopsis* (intron #1; GenBank: AB025639.1) *Agrobacterium tumefaciens* Open Reading Frame 23 3'UnTranslated Region (AtORF23 terminator; U.S. Pat. No. 5,428,147) as an in-frame fusion with a trans orientation (e.g., head to head orientation). The plasmid vector was assembled using the IN-FUSION™ Advantage Technology (Clontech, Mountain View, Calif.).

Example 5: Generation of ETIP Canola Plant Lines

Transformation of *Brassica napus*

The FAD2A site specific integration deploys the use of the ETIP construct (pDAS000130), accompanying Zinc Finger Nuclease (pDAB104010), and the DS-Red control construct (pDAS000031) described in Example 4. The binary vectors were transformed into *Agrobacterium tumefaciens* strain GV3101: PM90. Transformation of *Brassica napus* protoplast cells was completed using the transfection protocol described in Example 3 with some modification.

The modifications to the protocol included the use of sodium alginate instead of Sea Plaque™ agarose. The transfection experiments in which both the Zinc Finger Nuclease construct, pDAB104010, and the ETIP construct, pDAS000130, were co-delivered into *Brassica napus* protoplast cells were completed at DNA concentrations comprising a 5:1 and a 12:1 molar ratio, wherein pDAS000130 had a concentration of 27.8 µg of plasmid DNA and pDAB104010 had a concentration of 2.2 µg of plasmid DNA. The control plasmid constructs were transformed at concentrations of 30 µg of plasmid DNA.

Additional modifications to the protocol included the propagation of whole plants from the transformed protoplast cells in medium containing 1.5 mg/mL of hygromycin. The propagation of whole plants required that the A medium was replaced every two weeks and the growth of the protoplast-derived colonies was monitored. After the protoplast-derived colonies had grown to approximately 2-3 mm in diameter, the colonies were transferred into individual wells of a 12-well Costar® plate (Fisher Scientific, St. Louis, Mo.) containing solidified MS morpho medium. The plates were incubated for one to two weeks at 24° C. under continuous dim light until the calli had proliferated to a size of 8-10 mm in diameter.

After the protoplast cells had reached a diameter of 1-2 cm, the protoplast cells were transferred to individual 250 mL culture vessels containing MS morpho medium. The vessels were incubated at 24° C. under 16 h light (20 µMol $m^{-2}$ $s^{-1}$ of Osram L36 W/21 Lumilux white tubes) and 8 h dark conditions. Within one to two weeks, multiple shoots were visible. The shoots were transferred into 250 mL culture vessels containing MS medium after they reached a length of 3-4 cm. The 250 mL culture vessels were incubated at 24° C. under 16 h light (20 µMol $m^{-2}$ $s^{-1}$ of Osram L36 W/21 Lumilux white tubes) and 8 h dark conditions. The shoots were maintained in the culture vessels until they developed into plantlets at which time they were transferred to a greenhouse to grow to maturity.

Example 6: Molecular Confirmation of Integration of T-DNAs Containing ETIPS in Canola Genomic DNA was extracted from leaf tissue of all putative transgenic plants using a DNeasy Plant Mini Kit™ (Qiagen) following the manufacturer's instructions, with the exception that tissue was eluted in 80 µl of AE buffer. Thirty milligrams of young leaf tissue from regenerated plants was snap frozen in liquid nitrogen before being ground to a powder.

Molecular characterization of the FAD2A locus was performed using three independent assays. Assays were designed and optimized using the following controls; characterized transgenic events comprising a single randomly integrated transgene, characterized transgenic event with five randomly integrated transgenes, wildtype canola c.v. DH12075 plants and non-template control reactions. The results from the three following molecular analyses are considered together in order to provide evidence for integration of the ETIP at FAD2A via HDR.

Identifying Transgene Integration by Real-Time Polymerase Chain Reaction

Figure 8:
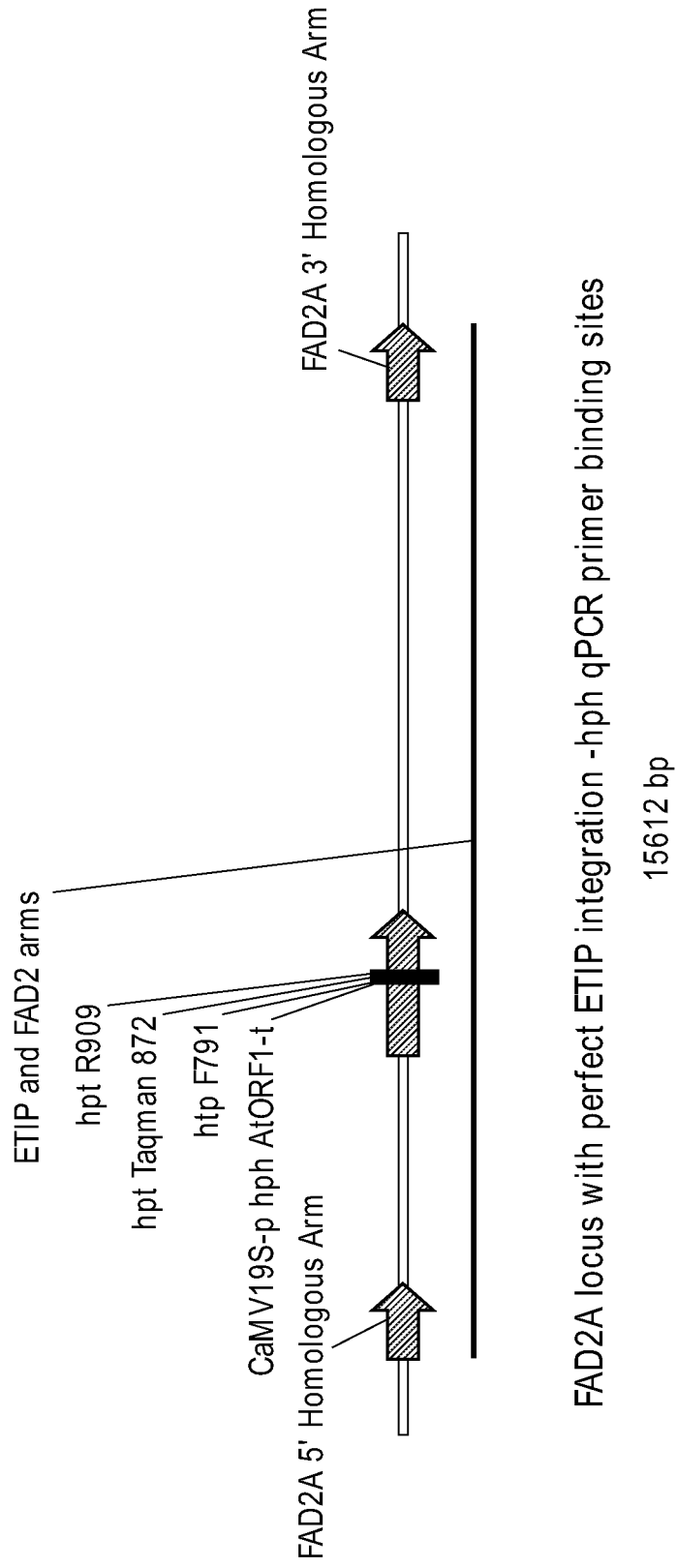
FIG. 8 is a schematic showing binding sites of transgene target primers and probe for transgene copy number estimation assay.

Four replicates of each plant were analyzed using primers specific to the hph (also described as hpt) target gene (SEQ ID NO:63, hpt F791 5' CTTACATGCTTAGGATCG-GACTTG 3'; SEQ ID NO:64, hpt R909 5' AGTTCCAG-CACCAGATCTAACG 3'; SEQ ID NO:65, hpt Taqman 872 5' CCCTGAGCCCAAGCAGCATCATCG 3' FAM) (FIG. 8) and reference gene encoding High Mobility Group protein I/Y (HMG I/Y) (SEQ ID NO:66, F 5' CGGA-GAGGGCGTGGAAGG 3'; SEQ ID NO:67, R 5' TTC-GATTTGCTACAGCGTCAAC 3; SEQ ID NO:68, Probe 5' AGGCACCATCGCAGGCTTCGCT 3' HEX). The reactions were amplified using the following conditions: 95° C. for 10 minutes followed by 40 cycles of 95° C. for 30 seconds, 60° C. for 1 minute, with amplification data being captured at the end of each annealing step. Copy number was calculated using the ΔCq method, where ΔCq=Cq(target gene)−Cq(reference gene). Livak, K. J. and T. D. Schmittgen, *Analysis of relative gene expression data using real-time quantitative PCR and the 2(−Delta Delta C(T)) Method.* Methods, 2001. 25(4): p. 402-8. Plants with amplification of hph and HMG I/Y and a copy number of 0.5 or more were considered transgenic, while plants with a copy number of ≥0.5 and ≤1.2 were scored as putatively single copy. Amplification was performed on a BioRad CFX96 Touch™ Real-Time PCR Detection System with FastStart Universal Probe Master (ROX), (Roche, Basel, Switzerland).

Detection of Disrupted FAD2A ZFN Site

Figure 9:
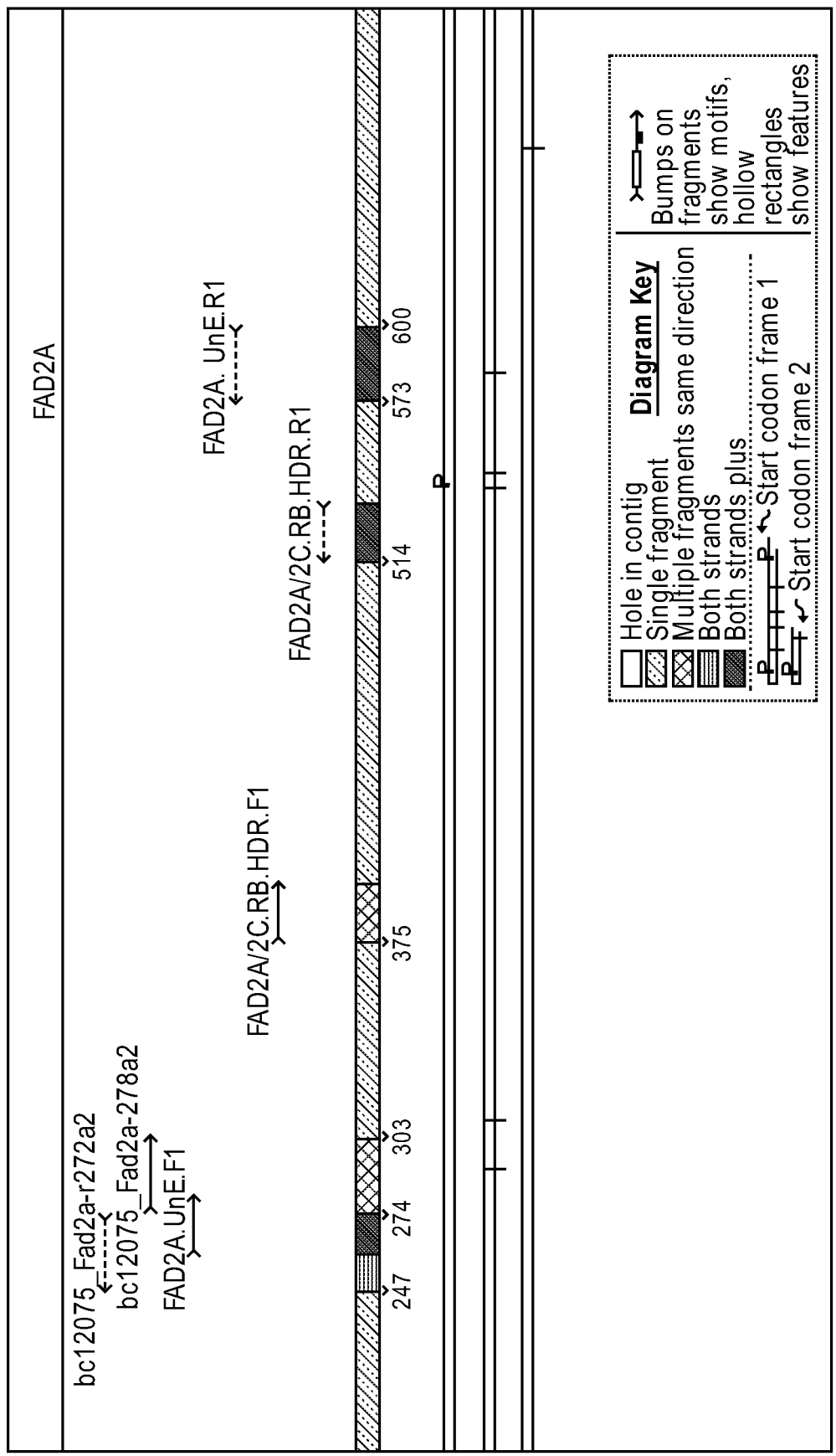
FIG. 9 shows a Sequencher file showing FAD2A ZFN DNA recognition domain (bc12075_Fad2A-r272a2 and bc12075_Fad2A-278a2), and binding sites of ZFN specific primers (FAD2A.UnE.F1 and FAD2A.UnE.R1) and endogenous primers (FAD2A/2C.RB.UnE.F1 and FAD2A/2C.R-B.UnE.R1).
Figure 10:
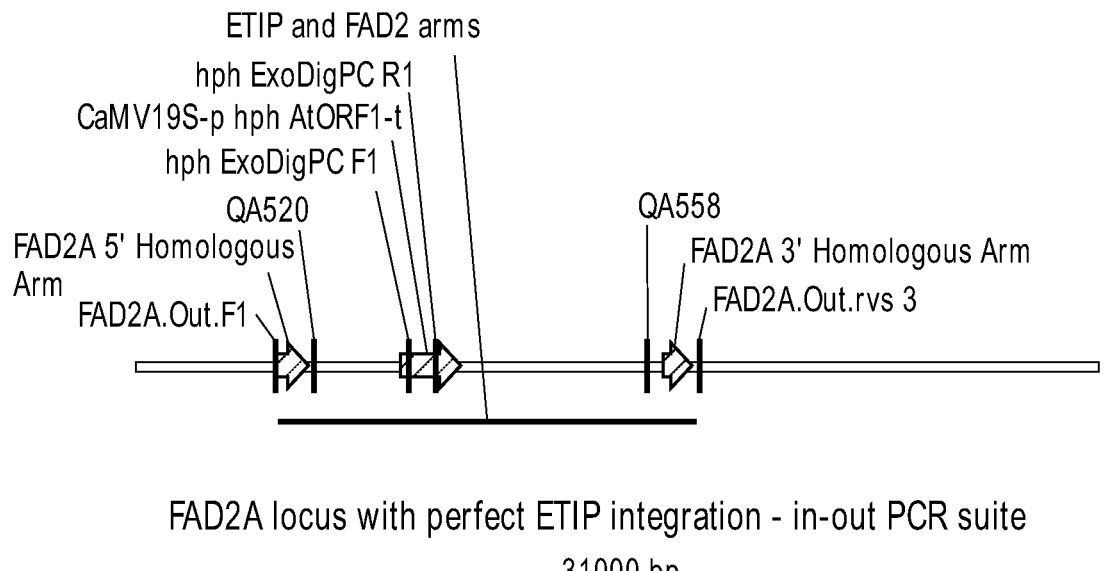
FIG. 10 shows a schematic showing binding sites of endogenous and transgene target primers used in the detection of transgene integration at FAD2A via perfect HDR.

Each plant was analysed for presence or absence of amplification of endogenous target in the disrupted locus test, which is a dominant assay. The assay is a SYBR® Green I qPCR assay and in singleplex, but with each reaction run simultaneously on the same PCR plate, targets an endogenous locus (FAD2A/2C.RB.UnE.F1, SEQ ID NO:69, 5' CTTCCACTCCTTCCTCCTCGT*C 3' and FAD2A/2C.RB.UnE.R1, 5' SEQ ID NO:70, GCGTCCCAAAGGGTTGTTGA*G 3') and the ZFN locus (locus at which the ZFN pDAB104010 binds and cuts the genome) (FAD2A.UnE.F1, SEQ ID NO:71, 5' TCTCTACTGGGCCTGCCAGGG*C 3' and FAD2A.UnE.R1, SEQ ID NO:72, 5' CCCCGAGACGTTGAAGGCTAAGTACAA*A 3') (FIG. 9). Both primer pairs were amplified using the following conditions: 98° C. for 30 seconds followed by 35 cycles of (98° C. for 10 seconds, 65° C. for 20 seconds, 72° C. for 90 seconds) then followed by 95° C. for 10 seconds then a melt analysis from 50° C. to 95° C. with 0.5° C. increments for 0.05 seconds and a plate read at each increment. The reaction conditions are listed in Table 9.

TABLE 9

Single reaction reagent components and concentrations for PCR amplification

| Reaction Components | Volume (µl) |
|---|---|
| 10 mM dNTP | 0.40 |
| 5X Phusion HF Buffer | 4.00 |
| Phusion Hot Start II High-Fidelity DNA Polymerase (2 U/µl) (Thermo Scientific) | 0.25 |
| Forward Primer 10 µM | 0.40 |

TABLE 9-continued

Single reaction reagent components and
concentrations for PCR amplification

| Reaction Components | Volume (μl) |
|---|---|
| Reverse Primer 10 μM | 0.40 |
| 1:10000 dilution of SYBR Green I dye (Invitrogen) | 1.00 |
| Molecular Biology Grade H$_2$O | 11.55 |
| Genomic DNA template (~20 ng/μl) | 2.00 |
| Total Volume | 20.00 |

Plants that had amplification of the endogenous target but no amplification of the ZFN target, were scored as positive for the disrupted locus test and were considered to have a disrupted ZFN locus. This assay was considered to be positive when the ZFN binding site on both alleles at the FAD2A locus have been disrupted.

PCR Detection of Transgene Integration at FAD2A Via Homology Directed Repair

Figure 3:
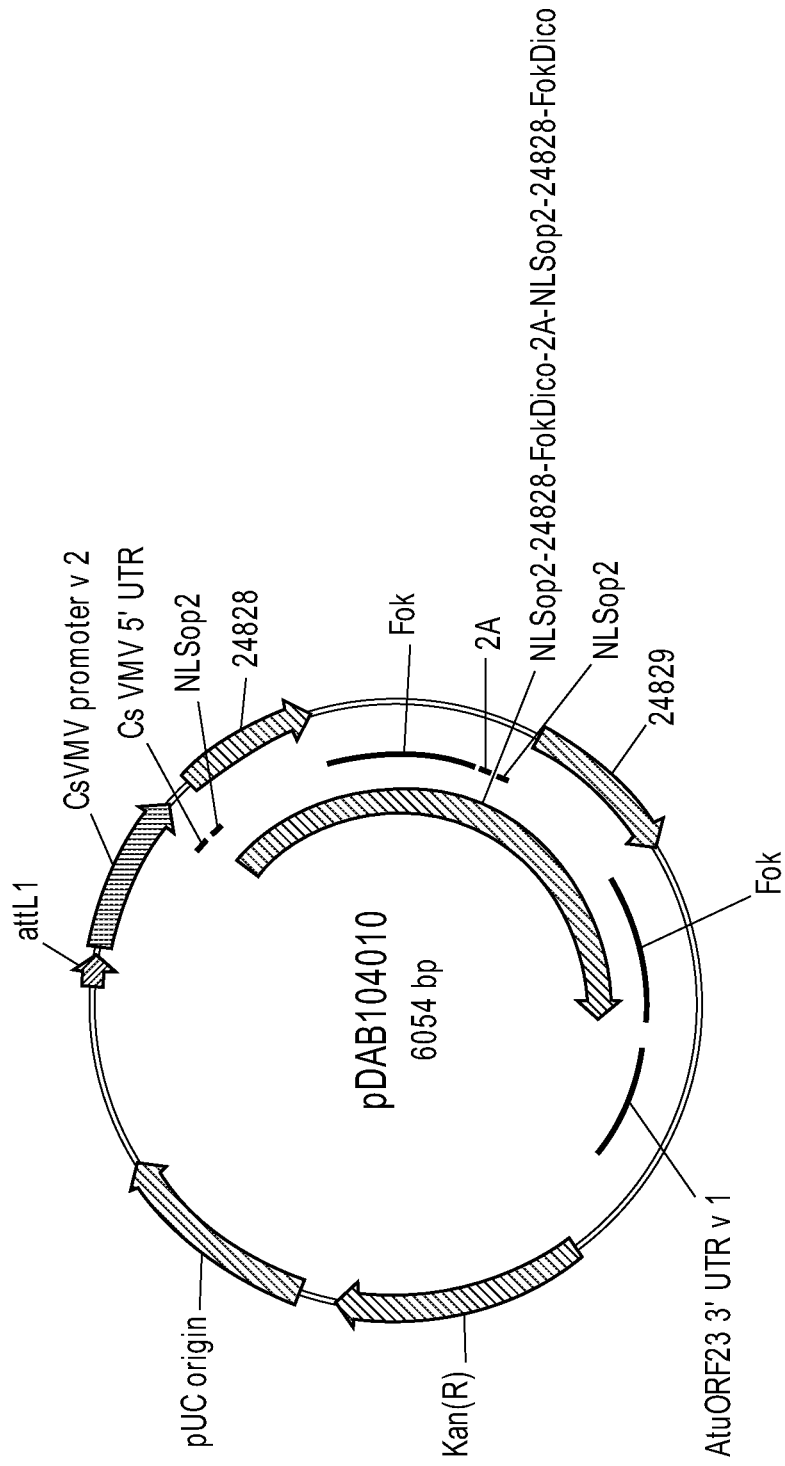
FIG. 3 shows a plasmid map of pDAB104010 which that is a representative Zinc Finger Nuclease expression cassette. The lay-out of this construct was similar for the other ZFN expression cassettes, wherein the Zinc Finger domains, 24828 and 24829, were exchanged with alternative Zinc Finger domains that are described above.

Each putative plant transformant was analysed using endpoint with PCR primers designed to amplify the transgene target hph (hph_ExoDigPC_F1, SEQ ID NO:73, 5' TTGCGCTGACGGATTCTACAAGGA 3' and hph_ExoDigPC_R1, SEQ ID NO:74, 5' TCCATCAGTCCAAACAGCAGCAGA 3'), the FAD2A endogenous locus (FAD2A.Out.F1, SEQ ID NO:75, 5' CATAGCAGTCTCACGTCCTGGT*C 3' and FAD2A.Out.Rvs3, SEQ ID NO:76, 5' GGAAGCTAAGCCATTACACTGTTCA*G 3'), the region spanning the 5' end of any transgene integrated into the FAD2A locus via HDR, upstream of the transgene into the FAD2 A locus (FAD2A.Out.F1, SEQ ID NO:77, 5' CATAGCAGTCTCACGTCCTGGT*C 3' and QA520, SEQ ID NO:78, 5' CCTGATCCGTTGACCTGCAG 3') and the region spanning the 3' end of any transgene integrated into the FAD2A locus via HDR, downstream of the transgene into the FAD2 A locus (QA558, SEQ ID NO:79, 5' GTGTGAGGTGGCTAGGCATC 3' and FAD2A.Out.Rvs3, SEQ ID NO:80, 5' GGAAGCTAAGCCATTACACTGTTCA*G 3') (FIG. 3). All primer pairs were amplified using the following conditions 98° C. for 30 seconds followed by 35 cycles of (98° C. for 10 seconds, 65° C. for 20 seconds, 72° C. for 90 seconds). Reaction reagent conditions are as described in Table 10.

TABLE 10

Single reaction reagent components and
concentrations for PCR amplification

| Reaction Components | Volume (μl) |
|---|---|
| 5x Phusion HF Buffer | 6.00 |
| 10 mM dNTPs | 0.60 |
| Forward Primer 10 μM | 0.60 |
| Reverse Primer 10 μM | 0.60 |
| Phusion Hot Start II High-Fidelity DNA Polymerase (2 U/μl) (Thermo Scientific) | 0.25 |
| Molecular Biology Grade H$_2$O | 19.95 |
| Genomic DNA template (~20 ng/μl) | 2.00 |
| Total Volume | 30.0 |

Amplification of the 5' transgene-genome flanking target and/or amplification of the 3' transgene-genome flanking target indicated a putative insertion event. It must be noted that due to the approximately 1,000 bp FAD2A homology arms in the pDAS000130 cassette (comprising polynucleotide sequences with 100% sequence identity to the FAD2A regions immediately upstream and downstream of the ZFN cut site), the PCR reactions were subject to false positive PCR product amplification due to PCR chimerism arising from amplification of off-target ETIP integration events. Amplification of the hph target confirmed transgene integration had occurred. Amplification of the FAD2A target suggests that the FAD2A locus is intact or contains only a partial insertion. Due to the size of the ETIP (11,462 bp for the ETIP cassettes or 13,472 bp including the FAD2A homologous arms and the ETIP cassettes) it is expected that the FAD2A primers would not amplify a product when an intact ETIP is integrated into the FAD2A locus.

Southern Detection of FAD2A Editing

Figure 11:
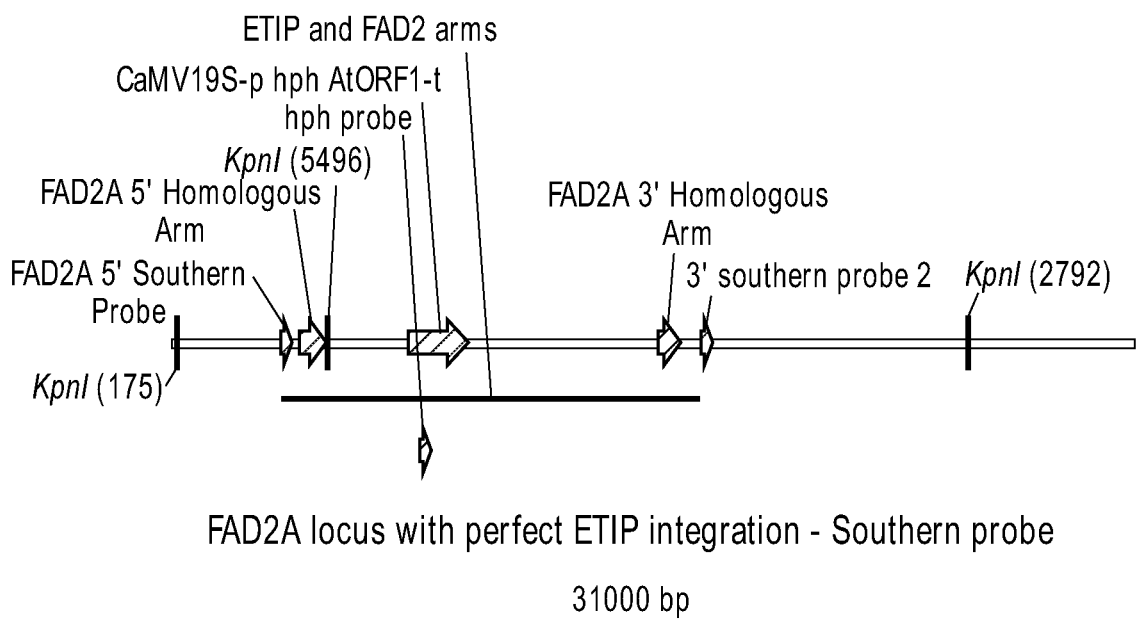
FIG. 11 is a schematic showing where Kpn1 restriction endonuclease sites would occur in a perfectly edited FAD2A locus, and where FAD2a 5', hph and FAD2A 3' Southern probes bind.

Plants that had amplification of either a 5' genome-transgene flanking target product and/or amplification of a 3' transgene-genome flanking target, or no amplification of the ZFN locus target, or both, were subject to Southern analysis for detection of transgene integration at the FAD2A locus. Genomic DNA was purified from 5 g of leaf tissue using a modified CTAB method (Maguire, T. L., G. G. Collins, and M. Sedgley *A modified CTAB DNA extraction procedure for plants belonging to the family proteaceae.* Plant Molecular Biology Reporter, 1994. 12(2): p. 106-109). Next, 12 μg of genomic DNA was digested with Kpn1-HF (New England BioLabs) and digestion fragments were separated by electrophoresis on a 0.8% agarose gel before transfer to membrane using a standard Southern blotting protocol. Primers to FAD2A 5' target region (F, SEQ ID NO:81, 5' AGAGAG-GAGACAGAGAGAGAGT 3' and R, SEQ ID NO:82, 5' AGACAGCATCAAGATTTCACACA 3'), FAD2A 3' target region (F, SEQ ID NO:83, 5' CAACGGCGAGCGTAATCTTAG 3' and R, SEQ ID NO:84, 5' GTTCCCTGGAATTGCTGATAGG 3') and hph (F, SEQ ID NO:85, 5' TGTTG-GTGGAAGAGGATACG 3' and R, SEQ ID NO:86, 5' ATCAGCAGCAGCGATAGC 3') were used to generate probes to detect the presence of the ETIP within the FAD2A locus using the DIG Easy Hyb System® (Roche, South San Francisco, Calif.) following the manufacturer's instructions (FIG. 11). Hybridization was performed at 42° C. for FAD2A 5' region, 45° C. for FAD2A 3' region and 42° C. for detection of hph.

Figure 12:
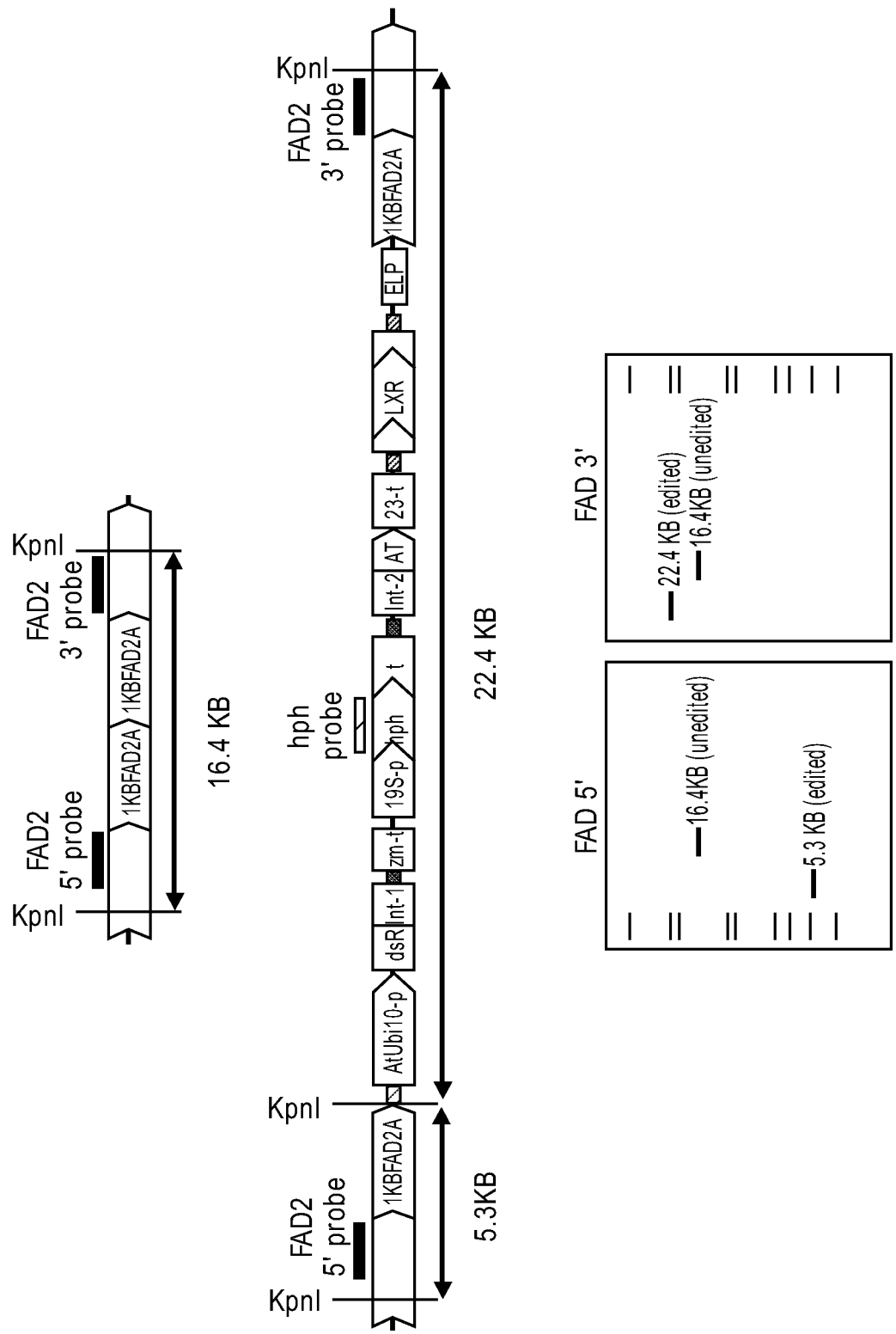
FIG. 12 shows the location and size of Kpn1 fragments, FAD2A 5', hph, FAD2A 3' probes and expected outcomes of Southern analysis for plants that have integration of ETIP at FAD2A locus via HDR.

Membrane-bound genomic DNA was probed in a specific order; firstly FAD2A 5' sequences were probed, then the FAD2A 3' sequences were probe, and finally the hph sequences were probed (FIG. 12). The rational for this is as follows. The first probe (FAD2A 5') is the diagnostic probe, and if the ETIP has integrated into FAD2A via perfect HDR, a 5,321 bp fragment will be visible on the membrane. The resulting band size is easily differentiated during electroporation and will sit close to the 5,148 bp fragments in the DIG labeled Roche DNA Molecular Weight Marker III® (Roche, Indianapolis, Ind.). The second probe of the membrane is with the FAD2A 3' probe and an edited plant will have a 22,433 bp fragment whereas an unedited plant will have a 16,468 bp fragment. The same 22,433 bp fragment identified with the FAD2A 3' probe should also be bound by and identified with the hph probe. These fragments are difficult to differentiate on a gel as they are extremely large and it may be difficult to determine any difference between a fragment occurring above or below the largest, 21,226 bp fragment in the DIG labeled Roche DNA Molecular Weight Marker III®. As such, these probes provide evidence that may strengthen the identification of ETIP integration into FAD2A via homology directed repair (HDR), by visualization of a 5 kb fragment using the FAD2A 5' probe. The restriction enzyme, Kpn1 was the only suitable restriction endonuclease for use in this assay, as Kpn1 sites occurred in a single locus of the cut the ETIP cassette in a single locus, and was present in two sites of the FAD2A ZFN locus. One site was located upstream and the second site located downstream of the FAD2A homology arms. In addition, Kpn1 is not methylation sensitive, and is available as a recombinant enzyme with increased fidelity (New England Biolabs).

Results of Molecular and Southern Analysis

Figure 13:
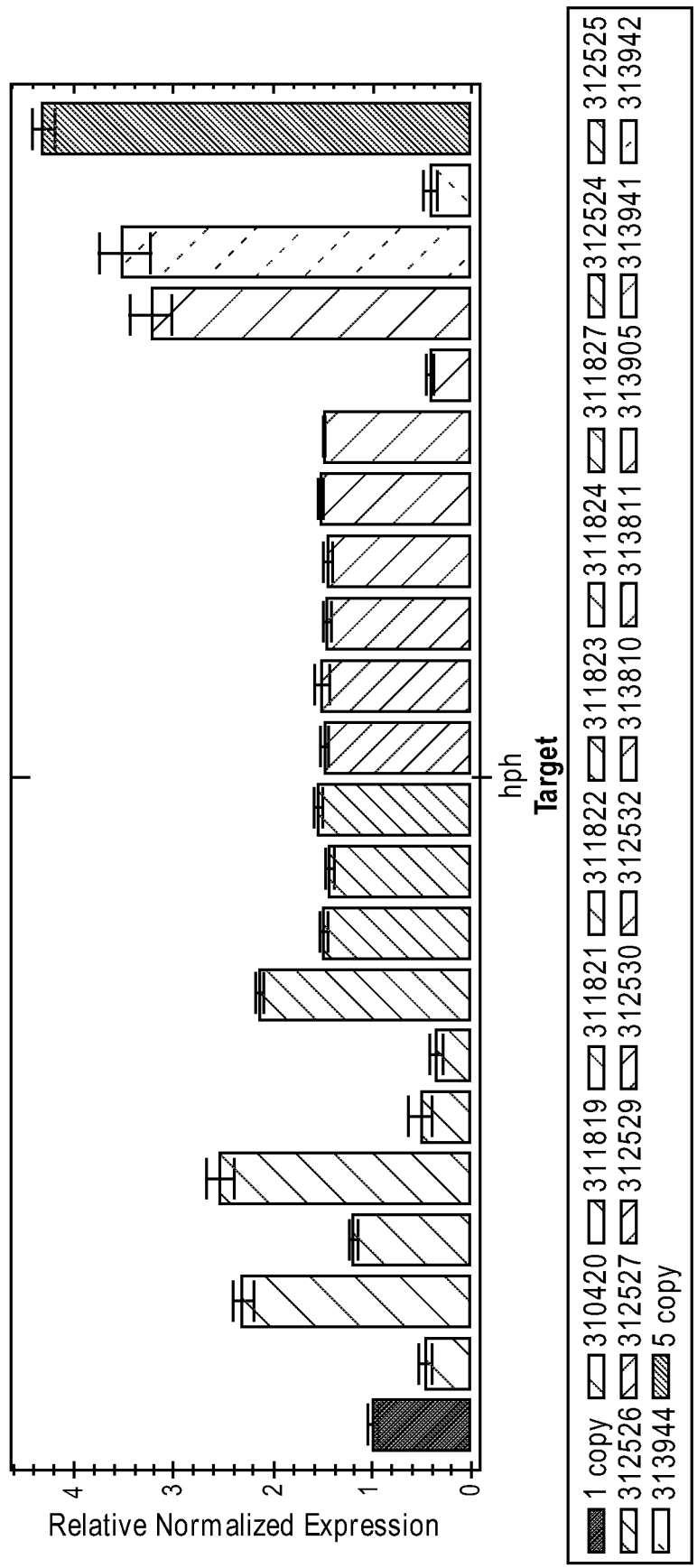
FIG. 13 shows representative data output from copy number estimation qPCR. The left hand column represents data obtained from a known $T_0$ transgenic plant with a single random transgene insert and is used as the calibrator sample to which all other samples are 'normalized' against. The right hand column is a known $T_0$ transgenic plant with 5 transgene integrations. The insert copy numbers for both plants was determined using Southern analysis. The remaining columns provide copy number estimates for the putative transgenic plants. The columns are labeled as; 1 copy control, 310420, 311819, 311821, 311822, 311823, 311824, 311827, 312524, 312525, 312526, 312527, 312529, 312530, 312532, 313810, 313811, 313905, 313941, 313942, 313944, and 5 copy control. The columns can be used to determine the estimated copy number for each transgenic plant. When using the software to estimate copy numbers, wildtype plants, non-transformed control plants, and plasmid only controls do not result in a copy number as they do not possess a Cq for both the hph and HMG I/Y target.

Following transfection, culturing, and selection the transgenic plants were transferred to soil. From this process, 139 plants survived and had tissue sampled for gDNA extraction and analysis. All 139 plants were analyzed for copy number estimation. Of these 139 plants, 56 were positive for the ETIP and 11 of the 56 positive plants had a putative single copy integration (FIG. 13) (Table 11). Of the 56 plants that were positive for ETIP integration, amplification of the FAD2A 5'-genome-transgene flanking sequence occurred in 7 plants. Amplification of the FAD2A 3'-transgene-genome flanking sequence did not occur in any of the 56 plants that were positive for ETIP integration. Additionally, of the 56 plants that were positive for transgene integration, 11 plants were positive for the disrupted locus qPCR test. Fourteen plants that were positive for amplification of the FAD2A 5' genome-transgene flanking sequence and/or positive for the disrupted locus qPCR test were subject to Southern analysis, with the 3 probes described above. Of the 14 plants advanced for Southern analysis, all of the plants showed partial integration within the FAD2A locus, but none of these plants showed evidence of a complete full-length integration of the ETIP at the FAD2A locus via HDR when probed with the FAD2A 5' probe, FAD2A 3' and hph probes. No bands that appeared to be i) larger than WT and ii) identical to bands observed for those samples when probed with FAD2A 3' probe (Table 11).

TABLE 11

Overview of outcomes from analysis of ETIP integration.

| | |
|---|---|
| No. of plants surviving in soil | 139 |
| No. of plants sampled | 139 |
| No. of plants for which qPCR copy number analysis was completed | 139 |
| No. of plants positive for ETIP integration | 56 |
| No. of plants comprising a putative single copy insert | 11 |
| No. of ETIP/FAD2 in-out 5' reactions | 7 (from 56) |
| No. of ETIP/FAD2 in-out 3' reactions | 0 (from 56) |
| No. of locus disrupted qPCR tests | 9 (from 56) |
| ETIP on-target (Southern) | 0 (from 14) |

Results of ETIP Transgenic Canola Transformed with pDAS000130 and pDAB104010.

The transgenic *Brassica napus* events which are produced via transformation of pDAS000130 and pDAB104010 result in the integration of a single copy, full length T-strand insertion of the ETIP polynucleotide sequence from pDAS000130 within the FAD2A locus. Three to four events are fully characterized and confirmed to contain the integrated ETIP. The confirmation is completed using an in-out PCR amplification method, and further validated via Southern blot. The selected $T_0$ events are grown to the $T_1$ stage of development. The $T_1$ plants are re-screened to determine the zygosity of the integrated T-strand. Screened events are categorized as homozygous, hemizygous, or null.

The homozygous events are used to produce protoplasts via the previously described method. The protoplasts are subsequently co-transformed with at least one zinc finger nuclease that is designed to target a binding site which is incorporated within the ETIP sequence and a donor plasmid which shares homology with specific regions of the ETIP wherein the donor is integrated within the ETIP via an HDR mechanism. Likewise, the protoplasts are subsequently co-transformed with at least one zinc finger nuclease that is designed to target a binding site which is incorporated within the ETIP sequence and a donor plasmid which does not share homology with specific regions of the ETIP, wherein the donor is integrated within the ETIP via an non-homologous end joining mechanism. The ZFN(s) cleave(s) the ETIP locus and the donor plasmid is integrated within the genome of *Brassica napus* cells via homology directed repair or non-homologous end joining.

As a result of the integration of the donor plasmid, the partial DS-red transgene is repaired to a full length DS-red transgene. The expression of the now fully operational DS-red transgene is used to sort protoplast cells with a FACS method. Putative transgenic plants are sorted using the FACS method described in Example 7 and the isolated protoplasts are regenerated into mature plants. The integration of the donor plasmid is confirmed within the ETIP-targeted plants using molecular confirmation methods. As such, the ETIP locus serves as a site-specific locus for gene targeted integration of a donor polynucleotide sequence.

Example 7: FACs Based Sorting of Protoplast Cells

*Brassica napus* protoplasts that were transfected with the DS-Red control construct, pDAS000031, were sorted via FACS-mediated cell sorting using a BD Biosciences Influx-Cell Sorter™ (San Jose, Calif.). The protoplast cells were isolated and transfected as described in Example 3. After the cells had been transfected with pDAS000031, the cells were sorted using the FACS sorter with the conditions described in Table 12.

TABLE 12

Conditions used for sorting protoplast cells transfected with pDAS000031.

| Parameters | |
|---|---|
| Drop frequency | 6.1 KHz |
| Nozzle diameter | 200 μm |
| Sheath pressure | 4 psi |
| Recovery media | W5 media |
| Culture conditions | Bead type culture using sea-plaque agarose and sodium alginate |
| Sort criteria | Sorting based on chlorophyll autofluorescence, reporter gene expression (Ds-Red) |
| Sort recovery (%) | 50-75 |
| Viability post sorting (%) | >95 |

The protoplasts which expressed the DS-red transgene were sorted and isolated. The FACS isolated protoplasts were counted using the sorter. About $1 \times 10^5$ to $1.8 \times 10^5$ of cells were placed in a well of a 24-well micro titer plate on the first day after the FACS isolation. The cells were transferred to a bead culture for 5 to 20 days. Similar conditions were tested, wherein about $1 \times 10^4$ of cells were placed in a well of a 2 or 4-well micro titer plate on the second day after the FACS isolation. The various conditions that were tested resulted in the recovery of cells at a viability or 95-98% of the total isolated protoplast cells. The FACS sorted protoplast cells were transferred to a bead culture for 3-20 days. The FACS sorted protoplast cells were regenerated into plants on media which contained 1.5 mg/mL of hygromycin using the above described protocol. The putative transgenic plants were confirmed to contain an intact T-strand insert from pDAS000031 via molecular conformation protocols.

The FACS sorting method is directly applicable to screen any fluorescent transgene sequence and is used to isolate a proportion of Brassica napus protoplast cells that are targeted with a fluorescent transgene via homology mediated repair within a specific site in the ETIP region within a genomic locus.

Example 8: Targeted Integration and Disruption of Brassica napus Omega-3 Fatty Acid Desaturase (FAD2) Via Homology Directed Repair Selection of Zinc Finger Binding Domains Specific to FAD2A The transcribed regions for homoeologous FAD2 genes were identified and characterized, zinc finger nucleases that were designed to bind and cleave these sites for NHEJ-mediated targeting of a donor sequence. Zinc finger proteins (ZFPs) directed against DNA sequences from homeologues of FAD2 sequences were designed and tested as described above. From the ZFNs showing on-target activity, one zinc finger proteins were selected that cut the FAD2 target at high efficiency: ZFP 24828-2A-24829 recognizes SEQ ID NO:35 5'-agGCCCAGtAGAGAGGCCaggcgaagta-3' and SEQ ID NO:36 5'-ccAGGGCTGCGTCCTAACCGgcgtctgg-3'. This ZFN was shown to specifically bind and cleave the FAD2A genomic locus.

Design and Construction of "Donor" Vectors for HDR-Directed DNA Repair

Figure 14:
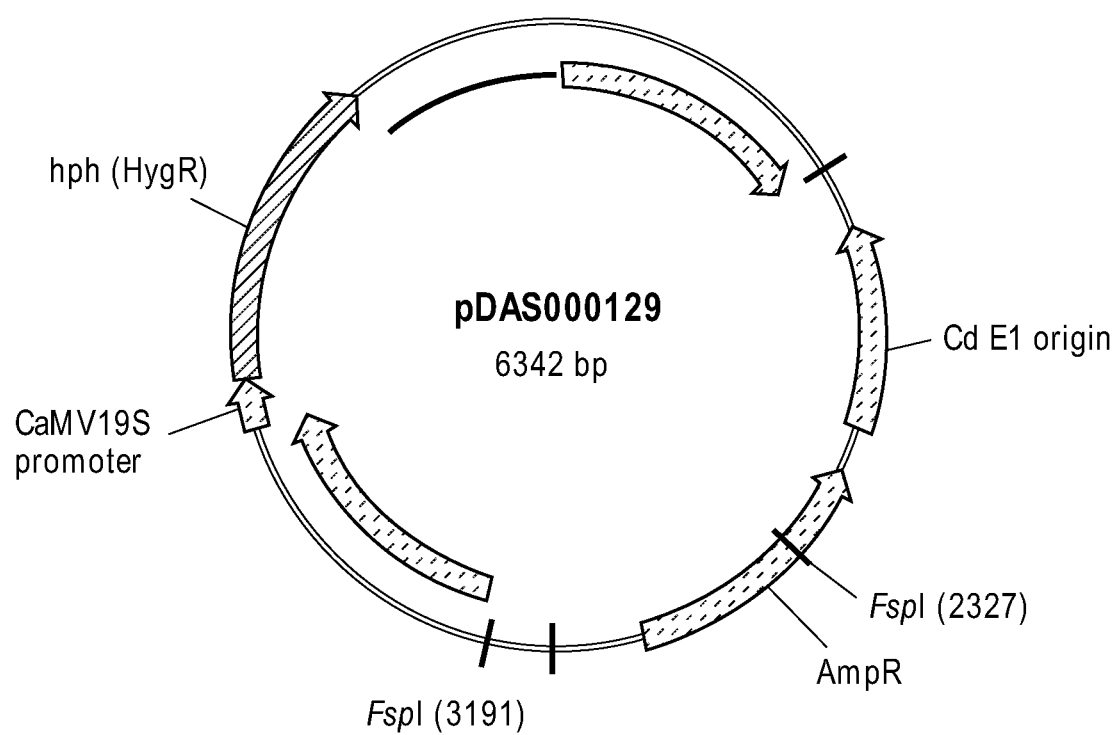
FIG. 14 shows a plasmid map of pDAS000129.

For integration of a donor sequence via HDR, a single vector was constructed. The vector encoded a hygromycin (hph or hpt) resistance gene expression cassette. The hygromycin resistance gene expression cassette included the 19S promoter including a 5' UTR from cauliflower mosaic virus (CaMV) (Cook and Penon Plant Molecular Biology 1990 14(3), 391-405) followed by the hygromycin phosphotransferase (hph) gene (Kaster et al Nucleic Acids Research 1983 11 (19), 6895-6911). The hph gene was codon-optimised for expression in dicotyledonous plants and was flanked by a 3'UTR comprising the transcriptional terminator and polyadenylation site of Open Reading Frame 1 (ORF1) of A. tumefaciens pTi15955 (Barker et al, Plant Molecular Biology 1983, 2(6), 335-50). The cassettes were synthesized by a commercial gene synthesis vendor (GeneArt, Life Technologies, Regensberg, Germany). Flanking FAD2A sequences were added upstream and downstream of the gene expression cassette. The hygromycin resistance cassette was cloned into specific restriction enzyme sites of each vector resulting in a "donor" vectors: pDAS000129 (hygromycin-resistant gene-splicing donor: SEQ ID NO:87 FIG. 14).

Colonies of the assembled plasmids were initially screened by restriction endonuclease digestion of DNA purified from overnight cultures of E. coli. Restriction endonucleases were obtained from NEW ENGLAND BIOLABS™ (NEB, Ipswich, Mass.) and PROMEGA™ (Promega Corporation, WI). Plasmid preparations were performed using the QIAPREP SPIN MINIPREP KIT™ (Qiagen, Hilden, Germany) or the PURE YIELD PLASMID MAXIPREP SYSTEM™ (Promega Corporation, WI) following the instructions of the suppliers. After the restriction fragments were confirmed by agarose gel electrophoresis of resulting fragments, plasmid DNA of selected clones were sequenced using ABI Sanger Sequencing and BIG DYE TERMINATOR V3.1™ cycle sequencing protocol (Applied Biosystems, Life Technologies). Sequence data were assembled and analyzed using the SEQUENCHER™ software (Gene Codes, Ann Arbor, Mich.).

Transformation of Brassica napus

PEG-Mediated Protoplast Transfection and Regeneration of ETIP Targeted to FAD2a and FAD2a ZFN (Precision Events)

Mesophyll derived protoplasts were isolated from three weeks old sterile shoot cultures of Brassica napus (DH10275). The corresponding seeds were germinated. The seeds were surface-sterilized using 70% ethanol for 1 minute by gentle shaking followed by 3-4 rinses in sterile double-distilled water and subsequently sterilized using 20% bleach and 10 μl of Tween 20™; the seeds were treated with the bleach on a shaker (table top rotary shaker approximately 100 RPM) for 15 minutes followed by 3-4 rinses in sterile double-distilled water, seeds were carefully transferred to a sterile filter paper to remove the excess moisture and plated on seed germination medium (½ strength MS/B5 Vitamins+1% sucrose+0.8% Agar; pH 5.8 and 50-60 ml of the media was poured per Petri dish (15×100 mm) that was placed with a slight angle using a support); approximately 50 seeds were placed in each plate. The plates were incubated upright at 22° C. in 16 h/d light (20 μmol m$^{-2}$ s$^{-1}$) for 6 days. Hypocotyl segments of 0.5 cm size were dissected from the six day old seedlings and cultured on shoot induction medium (MS/B5 Vitamins+3% sucrose+500 mg/L MES+BAP (13 μm)+Zeatin (5 μm)+Silver Nitrate (5 mg/L)+0.8% Agar (pH 5.8) and poured in 100×20 mm sterile Petri dish) approximately 20 explants were placed on each plate. Shoot meristems that appeared after 3-4 weeks were transferred to shoot elongation medium (MS/B5 Vitamins+2% sucrose+500 mg/L MES+BAP (2 μm)+GA-3 (0.1 μm)+0.8% Agar (pH 5.8) and poured in 250 ml culture vessels) and the cultures were maintained in this medium for 4 weeks with one round of sub-culturing in between. Shoots of 2-3 cm height were then transferred to root initiation media (½ strength MS/B5 Vitamins+1% sucrose+500 mg/L MES+IBA (2.5 μm)+0.6% Agar (pH 5.8) and poured in 700 ml culture vessels) for root development. Rooted shoots were sub-cultured in fresh root initiation media at 3-4 weeks intervals as stem cuttings for two-three rounds before use. The cultures were maintained throughout at 22° C. in 16 h/d light (30 μmol m$^{-2}$ s$^{-1}$).

Protoplast Isolation and Purification

In vitro grown DH12075 Brassica napus plants were used as the explant source for isolating mesophyll protoplasts. The 3rd to 4$^{th}$ upper fully expanded leaves from 3 to 4 weeks old plantlets were cut into small strips (0.5 to 1 mm) with a sharp scalpel for protoplast isolation. Enzymatic digestion was carried out by treating 250-500 mg of leaf material with 25 ml of digestion buffer (1.2% (w/v) Cellulase "Onozuka" R10® and 0.2% (w/v) Macerozyme® R10 dissolved in K4 media (Spangenberg et al. 1998)). The Petri dish containing the leaf material and digestion buffer was sealed with Parafilm™ and incubated at room temperature for 12 to 15 h in darkness. After overnight incubation the digests were filtered through a BD® cell strainer (mesh size 70 μm). Protoplasts suspension (5-6 ml) were collected in a 14 ml round bottomed tube that was over layered with 1 ml of washing solution W5 buffer (154 mM NaCl, 125 mM CaCl$_2$, 5 mM KCl and 5 mM glucose; pH 5.8 Mcnczel et al. 1981) and centrifuged at 400 RPM for 10 min. After centrifugation, protoplasts that floated in the interphase were withdrawn and washed by centrifugation using 10 ml of W5 buffer at 400 RPM for 10 min. After the final wash, isolated protoplasts were resuspended at a density of $1 \times 10^6$ protoplasts per mL of W5 buffer and incubated for 1 hour before transfections.

Assessment of Protoplasts Yield and Viability

Protoplasts yield was assessed using a haemocytometer following Sambrook and Russel, 2006 and the viability was tested using Evans blue stain (400 mg/L dissolved in 0.5 M of Mannitol) following Huang et al. 1996 with few modifications.

PEG 4000 Mediated Stable DNA Delivery

Plasmid DNA of the ETIP-containing vector pDAS000129 and the ZFN vector (pDAB104010) targeting the FAD2 A locus was isolated from cultures of E. coli using the Pure Yield Plasmid Maxiprep System™ (Promega Corporation, WI) or Plasmid Maxi Kit™ (Qiagen, Hilden) following the instructions of the suppliers. The plasmid DNA was dissolved at a density of 0.7 μg per μL of sterile double-distilled water. A total of thirty micrograms (30 μg) of the plasmid DNA (5:1 molar of pDAS000129 and pDAB104010) was applied to one million protoplasts (viability ≥95) suspended in 100 μl of transformation buffer (15 mM $MgCl_2$, 0.1% (w/v) morpholinoethanesulphonic acid (MES) and 0.5 M mannitol; pH 5.8) followed by 150 μl of PEG solution (40% (w/v) PEG 4000 in 0.4 M Mannitol and 0.1 M Ca $(NO_3)_2$ (pH 6-7) Spangenberg and Potrykus (1995). Control transformations included a total of thirty micrograms (30 μg) of plasmid DNA of either pDAS000129 or pDAB104010. After 10-15 minutes of incubation at room temperature, 5 ml of W5 buffer was added in a drop wise manner and the protoplasts were gently mixed and another 5 ml of W5 buffer was added as slow stream to the protoplasts suspension. Protoplasts were mixed gently and centrifuged at 400 RPM for 10 min and the W5 supernatant was removed carefully leaving behind the protoplasts in the form of a pellet. Transfected protoplasts were then incubated in 1 ml of W5 buffer at room temperature until they were embedded in bead type cultures. Protoplasts samples co-transfected with the construct pDAS000129 and pDAB104010 exhibited a cell viability ranging between 60-80% immediately after transfection. The transfected protoplasts were embedded following either sea plaque agarose or sodium alginate method.

Culturing of Mesophyll Derived Protoplasts to Recover Viable Microcalli

Before embedding the transfected protoplasts were centrifuged at 400 RPM for 10 min and the W5 buffer was carefully removed. The protoplasts were then resuspended in 0.5 ml of K3 media (Spangenberg et al. 1998). Exactly 0.5 ml of the transfected protoplast suspension (ca. $5 \times 10^5$ protoplasts) was placed in a 6 cm Petri dish and to this 4.5 ml of pre-warmed (melted in a microwave oven and incubated in a water bath at 40-45° C.) 1:1 mix of K3:H medium (Spangenberg et al. 1998) containing 0.6% Sea Plaque™ agarose was added. The agarose and the protoplasts suspension was mixed gently and allowed to set. After solidification (after 20-30 min.), seal the dishes were sealed with Parafilm® and the protoplasts were cultured for 24 h in darkness at 24° C., followed by 6 days in continuous dim light (5-10 μmol $m^{-2}$ $s^{-1}$), where first and multiple cell divisions occur. After 6 days the protoplasts embedded in agarose was cut into four quadrants and placed in 100 ml of A medium (Spangenberg et al. 1998) in a 700 ml culture vessel. The liquid A medium, was supplemented with 1.5 mg/l hygromycin. The cultures were incubated on a rotary shaker with 80-100 RPM at 24° C. in continuous dim light. Resistant colonies appear after 5-6 weeks and 3-4 weeks post protoplast plating in the case of sea-plaque agarose and sodium alginate method respectively. Microcalli of size between 2-3 mm diameter were transferred onto B1 medium (MS/MS Vitamins+3.5% Sucrose+500 mg/L MES+BAP (5 μm)+NAA (5 μm)+2, 4-D (5 μm)+1.5 mg/L Hygromycin+0.7% Agarose Type I (pH 6.0) and poured in 100×20 mm sterile Petri dish) by gently breaking the agarose beads. The microcalli thus obtained was resuspended in sufficient quantity of liquid A (50 ml of liquid A was used for one ml of the settled cell volume (SCV: This was measured after transferring all the released microcalli to a sterile 50 or 15 ml falcon tube and allowed to settle down for 5 min)). After mixing the microcalli uniformly, 0.5 ml of the microcalli suspended in the liquid A media was transferred to B1 plates and using 1-2 ml of additional liquid A media the microcalli was distributed uniformly in the B1 media and the excess liquid A media was carefully removed from each plate. The plates were sealed using a micropore tape which enhanced the embryo maturation.

Sodium-Alginate Method

Before embedding the transfected protoplasts were centrifuged at 400 RPM for 10 min and the W5 buffer was carefully removed. The protoplasts were then resuspended in 1.0 ml of 0.5 M Mannitol and incubated in ice. To this equal volume of 1.0% sodium alginate was added and mixed gently. The protoplasts suspension was incubated in ice until it was embedded. Bead forming solution (0.4 M Mannitol+50 mM $CaCl_2$ (pH 5.8)) was transferred to a sterile six well plate (3-4 ml per well) using a serological pipette. Exactly 1.0 ml of the protoplasts suspension was added in a drop wise manner using a 1 ml pipette into the bead forming solution and each transfected sample (ca. $5 \times 10^5$ protoplasts) was embedded per well. The protoplasts suspension was incubated for 1-2 hours at room temperature to form sodium alginate beads. After the incubation period the bead forming solution was carefully removed and replaced with 4-5 ml of 1:2 mixture of K3+H:A media (Spangenberg et al. 1998) supplemented with 1.5 mg/L of Hygromycin. The protoplasts were cultured for 3-4 weeks in darkness at 22° C. in a shaker (50 RPM). After 3-4 weeks the resistant microcalli (0.5-1.0 mm) were released by treating with depolymerisation buffer (0.3 M Mannitol+20 mM Sodium Citrate (pH 5.8)). After removing the liquid media 3-4 ml of depolymerisation buffer (was added to each well containing the bead-type cultures and incubated at room temperature for 2 hours. Using a sterile forceps the beads were gently mixed and to enhance the efficient release of the microcalli. Using a sterile 1.0 ml pipette gently mix gelling agent released in the depolymerisation buffer was removed. The microcalli was washed twice using 5 ml of liquid A media and the microcalli was resuspended in sufficient quantity of liquid A (50 ml of liquid A was used for one ml of the settled cell volume (SCV: This was measured after transferring all the released microcalli to a sterile 50 or 15 ml falcon tube and allowed to settle down for 5 min)). After mixing the microcalli uniformly, 0.5 ml of the microcalli suspended in the liquid A media was transferred to B1 media (MS/MS Vitamins+3.5% Sucrose+500 mg/L MES+BAP (5 μm)+NAA (5 μm)+2, 4-D (5 μm)+1.5 mg/L Hygromycin+0.7% Agarose Type I (pH 6.0) and poured in 100×20 mm sterile Petri dish) and using 1-2 ml of additional liquid A media the microcalli was distributed uniformly in the B1 media and the excess liquid A media was carefully removed from each plate. The plates were sealed using a micropore tape which enhanced the embryo maturation. The cultures were maintained at 22° C. in 16 h/d light (30 µmol m$^{-2}$ s$^{-1}$).

Isolation of Genomic DNA from Mesophyll Protoplasts

Transfected protoplasts were transferred from the 3 cm PETRI™ dish to a 2 mL microfuge tube. The cells were pelleted by centrifugation at 70 g and the supernatant was removed. To maximize the recovery of transfected protoplasts, the PETRI™ dish was rinsed three times with 1 mL of wash buffer. Each rinse was performed by swirling the wash buffer in the PETRI™ dish for 1 minute, followed by transfer of the liquid to the same 2 mL microfuge tube. At the end of each rinse, the cells were pelleted by centrifugation at 70 g and the supernatant was removed. The pelleted protoplasts were snap frozen in liquid nitrogen before freeze drying for 24 h in a LABCONCO FREEZONE 4.5® (Labconco, Kansas City, Mo.) at −40° C. and 133×10$^{-3}$ mBar pressure. The lyophilized cells were subjected to DNA extraction using the DNEASY® PLANT DNA EXTRACTION MINI KIT (Qiagen) following the manufacturer's instructions, with the exception that tissue disruption was not required and the protoplast cells were added directly to the lysis buffer.

Isolation of Genomic DNA from Callus Tissue

Individual calli was snap frozen in liquid nitrogen before freeze drying for 24 h in a LABCONCO FREEZONE 4.5® (Labconco, Kansas City, Mo.) at −40° C. and 133×10$^{-3}$ mBar pressure. The lyophilized calli was subjected to DNA extraction using the DNEASY® PLANT DNA EXTRACTION MAXI kit (Qiagen, Hilden, Germany) following the manufacturer's instructions.

Detection of Gene Addition to FAD2A by Homology Directed Repair in Proliferated Callus Genomic DNA was extracted from protoplast pools (one million protoplast per pool) to which donor DNA encoding a functional HGH reporter cassette (pDAS000129), ZFN DNA (pDAB104010) or a mixture of donor and ZFN DNA had been delivered twenty-four hours earlier. Quantities of DNA delivered for transformation are described above. PCR products were cloned into plasmid vectors. The genomic editing occurs independently in each cell giving rise to a variety of different insertion events, by cloning into a plasmid vector, each genomic edit can be sequenced without ambiguity. Several clones were sequenced on an ABI3730XL® automated capillary electrophoresis platform. Analysis of gene sequences was done using SEQUENCHER SOFTWARE V5.0™ (GeneCodes, Ann Arbor, Mich.).

Figure 15:
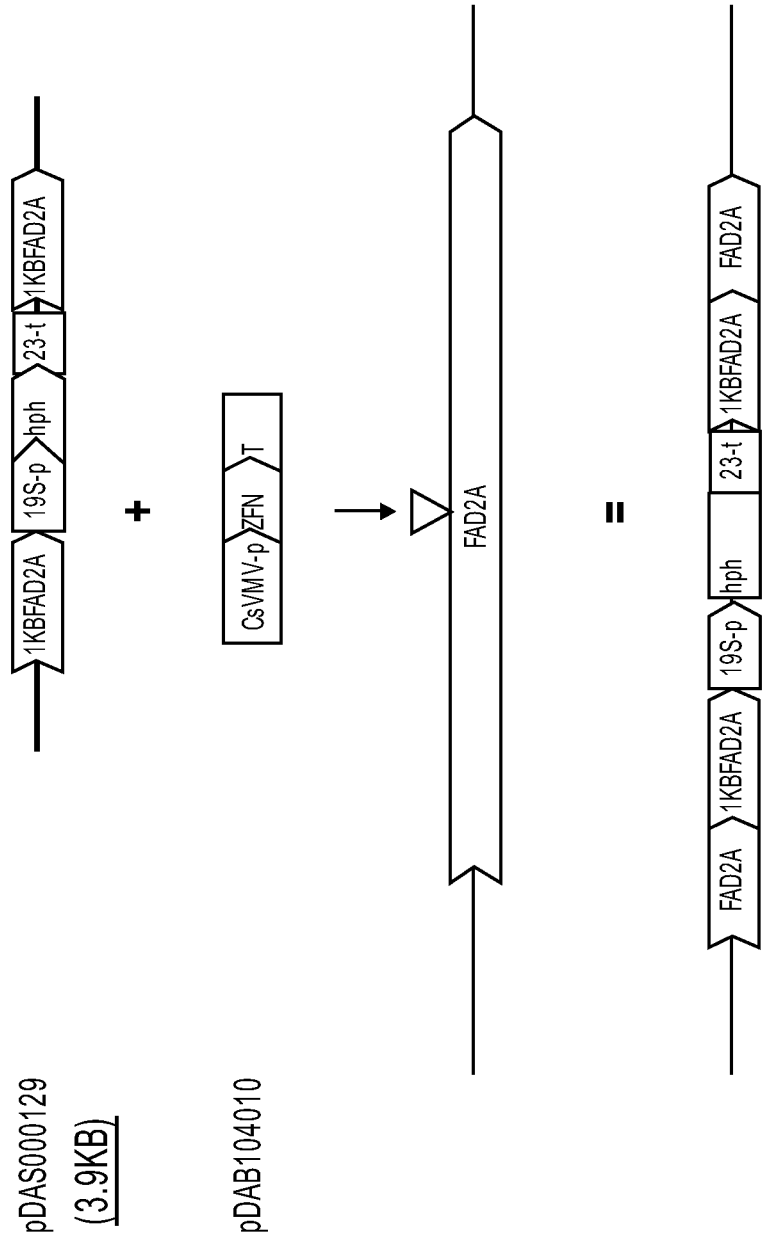
FIG. 15 shows a schematic for integration of pDAS000129 into the FAD2A locus.

Evidence of gene addition to the FAD2A locus by homologous directed repair was provided by amplification of both the 5' and 3' FAD2A cassette and junctions from genomic DNA extracted from protoplasts using the primers described in Table 13. No amplification was observed from protoplasts to which ZFN plasmid or donor plasmid alone had been delivered. All junction sequences were indicative of insertion of the hgh cassette at the FAD2A locus via an HDR-mediated repair pathway. Deletions of varying lengths from either or both the genome and the cassette were observed as well as the addition of sequences derived from the vector backbones (either from the donor or ZFN) being inserted between the genome and the cassette (FIG. 15).

TABLE 13

List of constructs used for donor integration within the FAD2A locus

| Treatments | Constructs | Hph Assay | In-out PCR (LB) | In-out PCR (RB) |
|---|---|---|---|---|
| ZFN | pDAB104010 (No Hyg) | NO | NO | NO |
| ZFN | pDAB104010 (1.5 mg/L Hyg) | NO | NO | NO |
| DNR | pDAS000129 (No Hyg) | YES | NO | NO |
| DNR | pDAS000129 (1.5 mg/L Hyg) | YES | NO | NO |
| DNR + ZFN2c | pDAS000129 + pDAB104010 (No Hyg) | YES | NO | NO |
| DNR + ZFN2c | pDAS000129 + pDAB104010 (1.5 mg/L Hyg) | YES | YES | YES |
| DsRed Ctrl | pDAS00097 (2 mg/L PPT) | NO | NO | NO |
| negative control | untrasfected DH12075 | NO | NO | NO |
| negative control | water | NO | v | NO |

Example 9: Targeted Integration and Disruption of *Brassica napus* Omega-3 Fatty Acid Desaturase (FAD2) Via Non Homologous End Joining Selection of Zinc Finger Binding Domains Specific to FAD2A The transcribed regions for homoeologous FAD2 genes were identified and characterized, zinc finger nucleases that were designed to bind and cleave these sites for NHEJ-mediated targeting of a donor sequence. Zinc finger proteins (ZFPs) directed against DNA sequences from homoeologues of FAD2 sequences were designed and tested as described above. From the ZFNs showing on-target activity, one zinc finger proteins were selected that cut the FAD2A target at high efficiency: ZFP 24828-2A-24829 recognizes SEQ ID NO:35 5'-agGCCCAGtAGAGAGGCCaggcgaagta-3' and SEQ ID NO:36 5'-ccAGGGCTGCGTCCTAACCG-gcgtctgg-3'. This ZFN was shown to specifically bind and cleave the FAD2A genomic locus. The plasmid construct, pDAB104010 that is previously described above was constructed and is used for transformation experiments.

Figure 16:
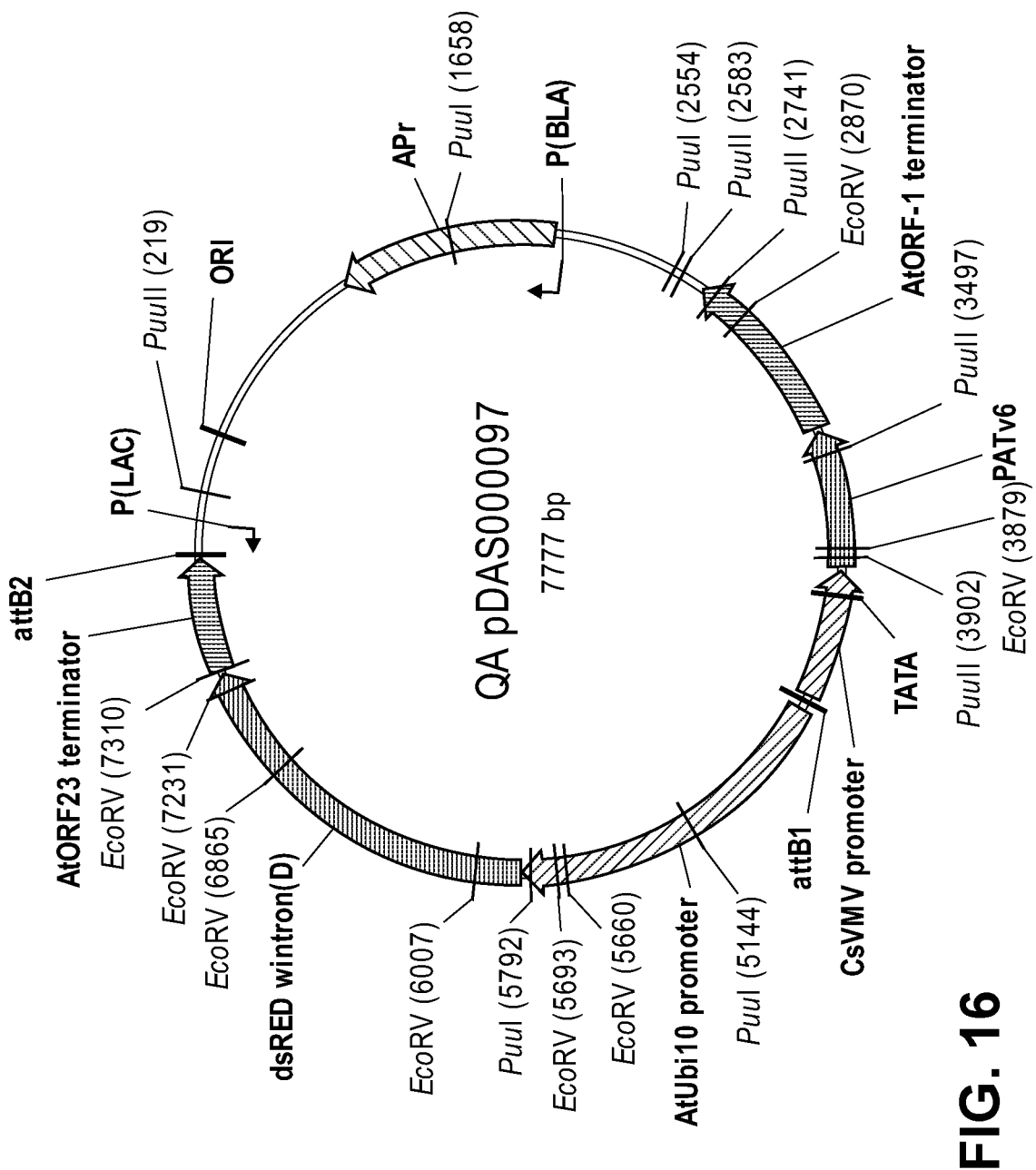
FIG. 16 shows plasmid map pDAS000097.

Design and Construction of Expression Vectors Encoding Zinc Finger Nucleases and Donor Vectors Specific to FAD2A For integration of a donor sequence via NHEJ, a single donor vector was constructed. The vector encoded a dsRED reporter gene expression cassette. The WED reporter gene expression cassette included the *Arabidopsis thalinana* Ubiquitin 10 promoter (Callis, et al., 1990, J. Biol. Chem., 265:12486-12493) followed by the dsRED gene (Dietrich et al. (2002) Biotechniques 2(2):286-293). The WED gene was codon-optimised for expression in dicotyledonous plants and was flanked by a 3'UTR comprising the transcriptional terminator and polyadenylation site of Open Reading Frame 23 (ORF23) of *A. tumefaciens* pTi15955 (Barker et al, Plant Molecular Biology 1983, 2(6), 335-50). The selectable marker cassette included the CsVMV promoter fused to the pat transgene. The pat transgene was terminated with Open Reading Frame 1 (ORF1) of *A. tumefaciens* pTi15955 (Barker et al, Plant Molecular Biology 1983, 2(6), 335-50). The dsRED resistance cassette was cloned into specific restriction enzyme sites of each vector resulting in "donor" vector: pDAS000097 (SEQ ID NO:88, FIG. 16). The pDAS00097 donor is designed to be delivered as linear DNA or circular DNA into the plant cell and integrated within the FAD2A locus upon cleavage of the FAD2A genomic locus by the ZFN pDAB104010. The linear DNA mediated integration is the result of integrating a linearized pDAS000097 plasmid into the plant cell during transformation. The plasmid can be linearized by cleavage at a unique restriction enzyme site. The circular DNA mediated integration is the result of integrating a circularized pDAS000097 plasmid into the plant cell during the transformation. pDAS000097 is modified to contain a zinc finger binding site that can be cleaved by the ZFP 24828-2A-24829 zinc finger nuclease. The circular plasmid, pDAS000097, is cleaved in the plant cell by the pDAB104010 encoded zinc finger nuclease, and the dsRED gene cassette is integrated into the FAD2A genomic locus.

Colonies of the assembled plasmids were initially screened by restriction endonuclease digestion of DNA purified from overnight cultures of E. coli. Restriction endonucleases were obtained from NEW ENGLAND BIOLABS™ (NEB, Ipswich, Mass.) and PROMEGA™ (Promega Corporation, WI). Plasmid preparations were performed using the QIAPREP SPIN MINIPREP KIT™ (Qiagen, Hilden, Germany) or the PURE YIELD PLASMID MAXIPREP SYSTEM™ (Promega Corporation, WI) following the instructions of the suppliers. After the restriction fragments were confirmed by agarose gel electrophoresis of resulting fragments, plasmid DNA of selected clones were sequenced using ABI Sanger Sequencing and BIG DYE TERMINATOR V3.1™ cycle sequencing protocol (Applied Biosystems, Life Technologies). Sequence data were assembled and analyzed using the SEQUENCHER™ software (Gene Codes, Ann Arbor, Mich.).

Transformation of Brassica napus

Mesophyll derived protoplasts are isolated and prepared from Brassica napus (DH10275) plants as described above. The protoplasts are transformed with purified plasmid DNA. Aliquots of donor and ZFN plasmid DNA are prepared in three molar ratios: 1:1 (30 of each plasmid), 5:1 (donor plasmid to ZFN plasmid to a total of 30 µg of plasmid DNA) and 10:1 (donor plasmid to ZFN plasmid to a total of 30 µg of plasmid DNA). Additionally, donor-only and ZFN-only aliquots (30 µg) are prepared as controls. The amounts of DNA delivered to the B. napus protoplasts via a PEG4000 mediated transformation are summarized in Table 14. The transformed protoplast cells are cultured as previously described, wherein the selection medium is glufosinate selection medium, and putative transformants are assayed via qPCR analysis for transgene insertions.

TABLE 14

Quantities of ZFN and donor DNA delivered to protoplasts

| | Molar Ratio of plasmid DNA | Total quantity of DNA (µg) delivered to 1 million protoplasts |
|---|---|---|
| Splicing | Donor plasmid only | 30 |
| | ZFN plasmid only (pDAB104010) | 30 |
| | 1:1 Donor:ZFN | 60 |
| | 5:1 Donor:ZFN | 30 |
| | 10:1 Donor:ZFN | 30 |
| Editing | Donor plasmid only | 30 |
| | 1:1 ZFN plasmids (pDAB104010) | 30 |
| | 1:1:1 Donor:ZFN:ZFN | 90 |
| | 5:1:1 Donor:ZFN:ZFN | 30 |
| | 10:1:1 Donor:ZFN:ZFN | 30 |

Detection of Gene Addition to FAD2A by Non-Homologous End Joining in Protoplasts Genomic DNA is extracted from protoplast pools (one million protoplast per pool) to which donor DNA encoding a functional dsRFP reporter cassette (pDAS000097), ZFN DNA (pDAB104010) or a mixture of donor and ZFN DNA are delivered twenty-four hours earlier. Quantities of DNA delivered for transformation are described above. PCR products are cloned into plasmid vectors. The genomic editing occurs independently in each cell giving rise to a variety of different insertion events, by cloning into a plasmid vector, each genomic edit can be sequenced without ambiguity. Several clones are sequenced on an ABI3730XL® automated capillary electrophoresis platform. Analysis of gene sequences is done using SEQUENCHER SOFTWARE V5.0™ (GeneCodes, Ann Arbor, Mich.).

Evidence of gene addition to the FAD2A locus by editing or splicing is provided by amplification of both the 5' and 3' FAD2A-cassette junctions from genomic DNA extracted from protoplasts. No amplification is observed from protoplasts to which ZFN plasmid or donor plasmid alone had been delivered. All junction sequences are indicative of insertion of the dsRED cassette at the FAD2A locus via an NHEJ-mediated repair pathway. Deletions of varying lengths from either or both the genome and the cassette are observed as well as the addition of sequences derived from the vector backbones (either from the donor or ZFN) being inserted between the genome and the cassette.

Detection of Gene Addition to FAD2A by Non-Homologous End Joining in Callus Tissue Regenerated from Protoplasts Further evidence of splicing and editing of the FAD2A locus was obtained from callus tissue regenerated from protoplasts on selection to which donor DNA encoding a dsRED cassette (pDAS000097), ZFN DNA only (pDAB104010) or donor and ZFN DNA are delivered. DNA is extracted from approximately 80 calli for each ratio.

Integration of the (MED cassette into the B. napus genome is confirmed by TAQMAN™ qPCR using primer and probes specific to the donor insert and the genomic flanking sequences. Relative quantification is calculated according to the $2^{-\Delta\Delta ct}$ method (Livak and Schmittgen, 2001), which provided an estimation of the number of copies of dsRED cassette inserted into the genome. Evidence of NHEJ-mediated splicing and editing of FAD2A is obtained by conducting PCR assays with one primer specific to FAD2A and a second primer specific to either the promoter or terminator of the dsRED cassette. PCR products are gel-purified using QIAQUICK MINIELUTE PCR PURIFICATION KIT™ (Qiagen) and sequenced using a direct Sanger sequencing method. The sequencing products are purified with ethanol, sodium acetate and EDTA following the BIGDYE® v3.1 protocol (Applied Biosystems) and sequenced and analysed as above.

The numbers of calli containing the donor cassette in each experiment are determined. Evidence of donor gene addition to the FAD2A locus by editing and/or splicing is provided by PCR amplification across the ZFN cut sites and both the 5' and 3' FAD2A-dsRED cassette junctions. PCR amplification of the genomic DNA isolated from callus tissue recovered from control protoplasts which are transformed with only the (MED plasmid (pDAS000097) or only the ZFN plasmid (pDAB104010) do not result in the production of PCR amplification products.

The PCR amplicons produced from the amplification of the 5' and 3' FAD2A-dsRED cassette junctions are purified from the agarose gel and sequenced to confirm specificity of the integration within the FAD2A genomic locus. The results of the sequencing analysis of the PCR products indicate that each isolated callus which is generated from an individually transformed protoplast only produce a single PCR amplification product and do not contain cells of mixed genotypes.
Detection of Gene Addition to FAD2A by Non-Homologous End Joining in Plants DNA is extracted from plants that are regenerated from protoplasts and transferred to potting medium. The majority of plants recovered are estimated to contain only 1-2 copies of the dsRED cassette encoded in the donor DNA. Plants are analyzed with the same suite of assays described for callus tissue as well as with assays to determine if the cassette had inserted in the FAD2A locus.

The frequency of on-target splicing, where the dsRED cassette is inserted into FAD2A locus is determined using the PCR assays described above. The amplicon bands obtained are sequenced to determine the flanking sequences. Additionally, plants are screened for off-target insertions to determine the frequency of integration of dsRED at sites other than FAD2A.

Figure 17:
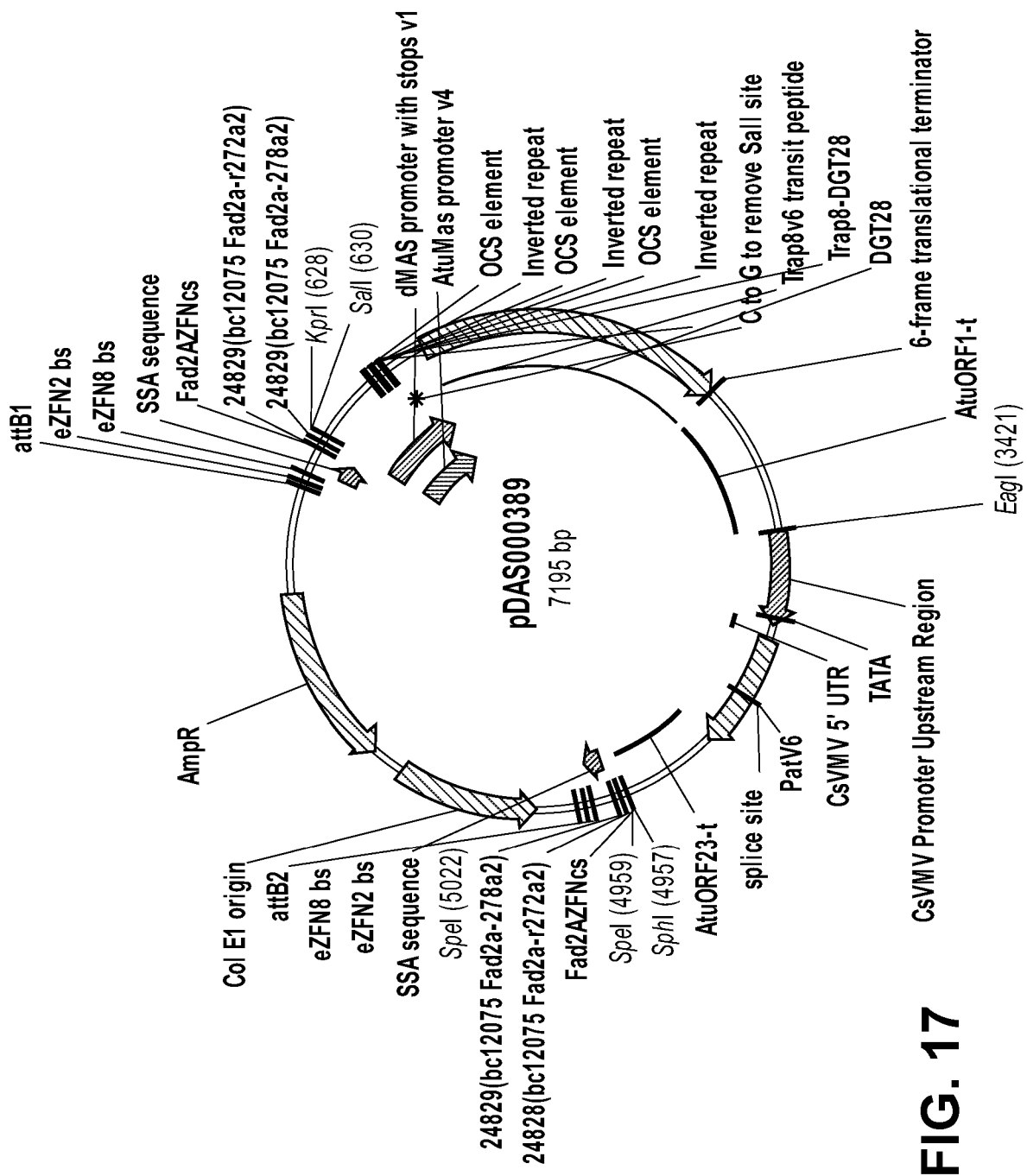
FIG. 17 shows a plasmid map of pDAS000389.
Figure 18:
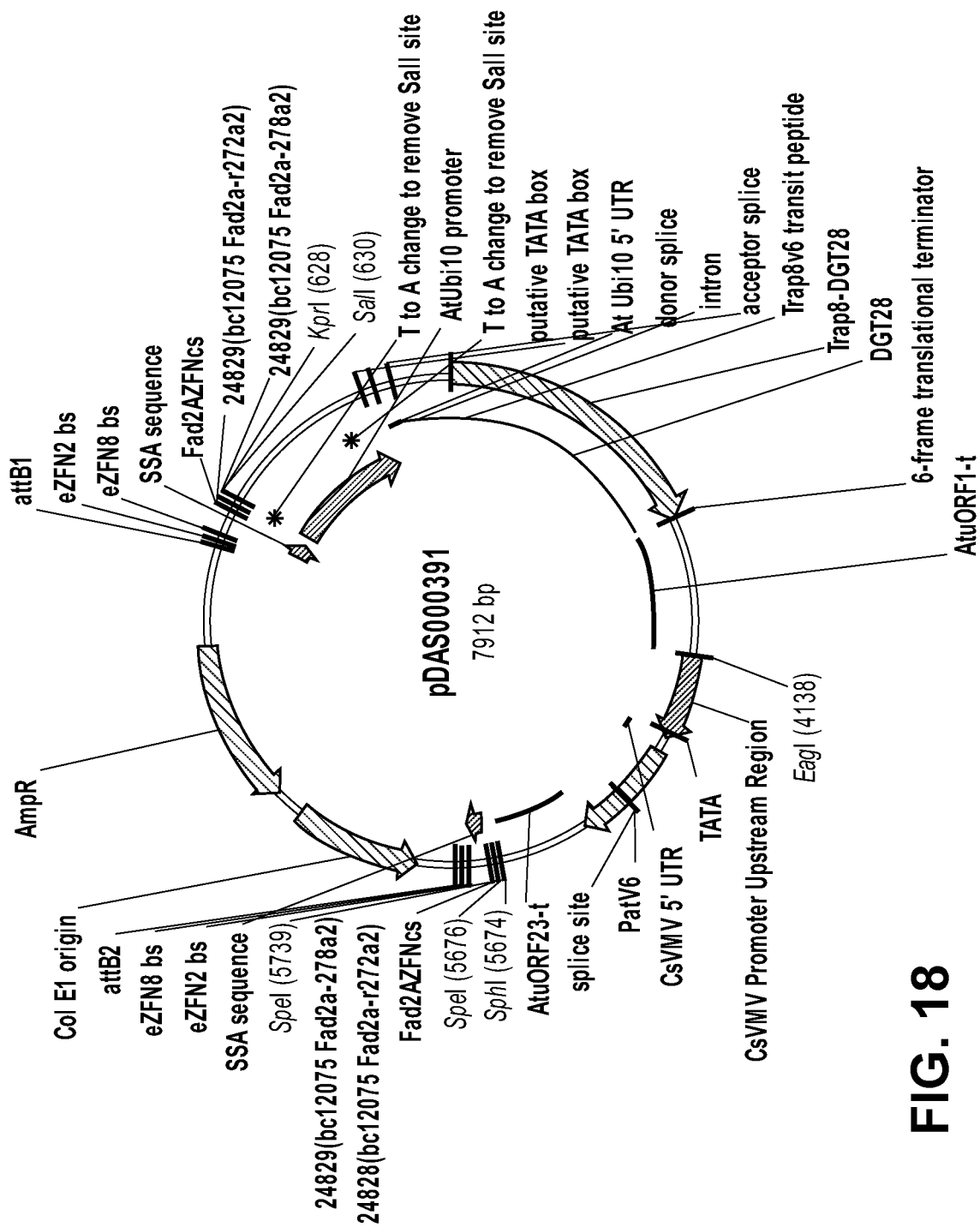
FIG. 18 shows a plasmid map of pDAS000391.
Figure 19:
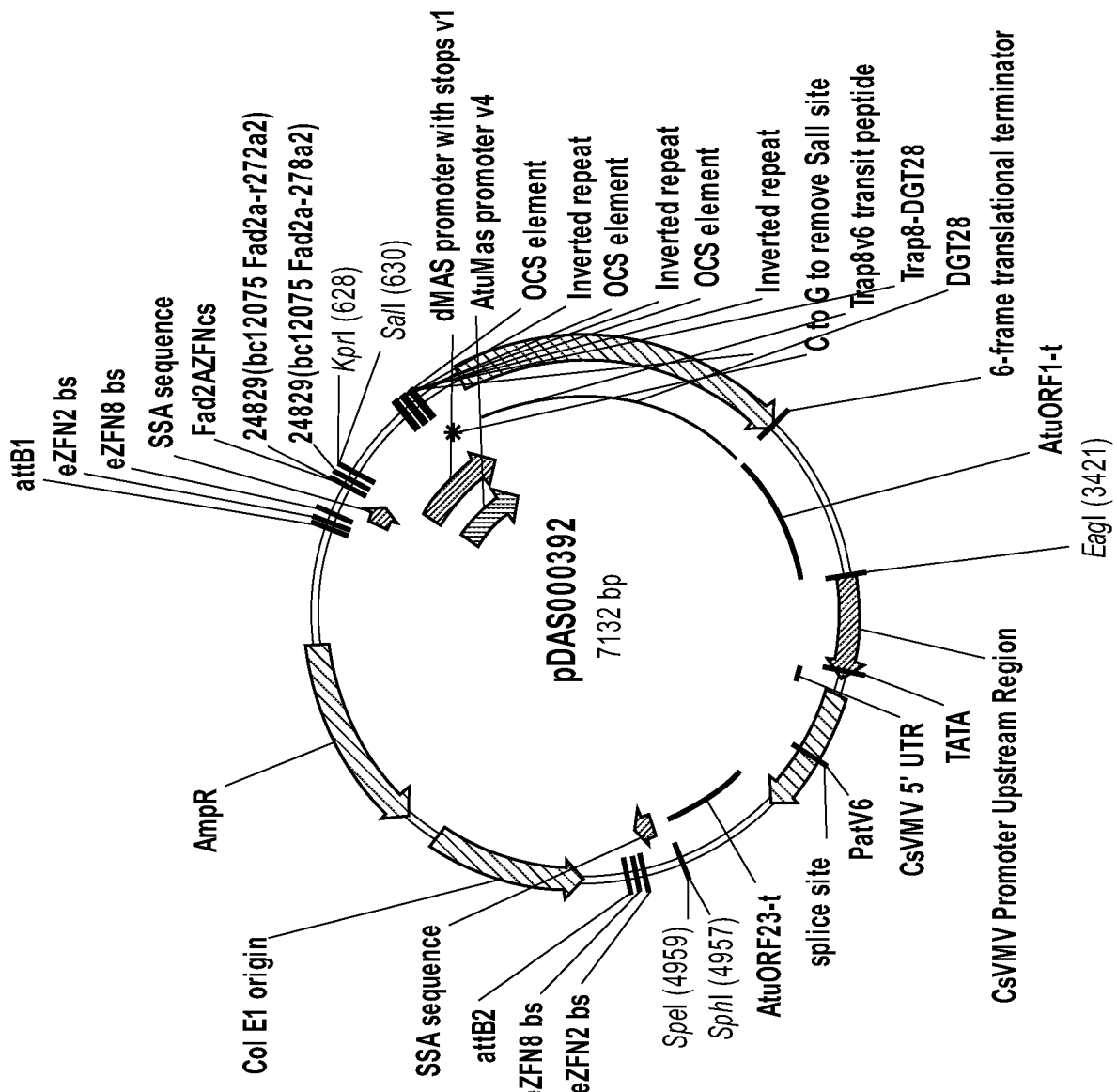
FIG. 19 shows a plasmid map of pDAS000392.
Figure 20:
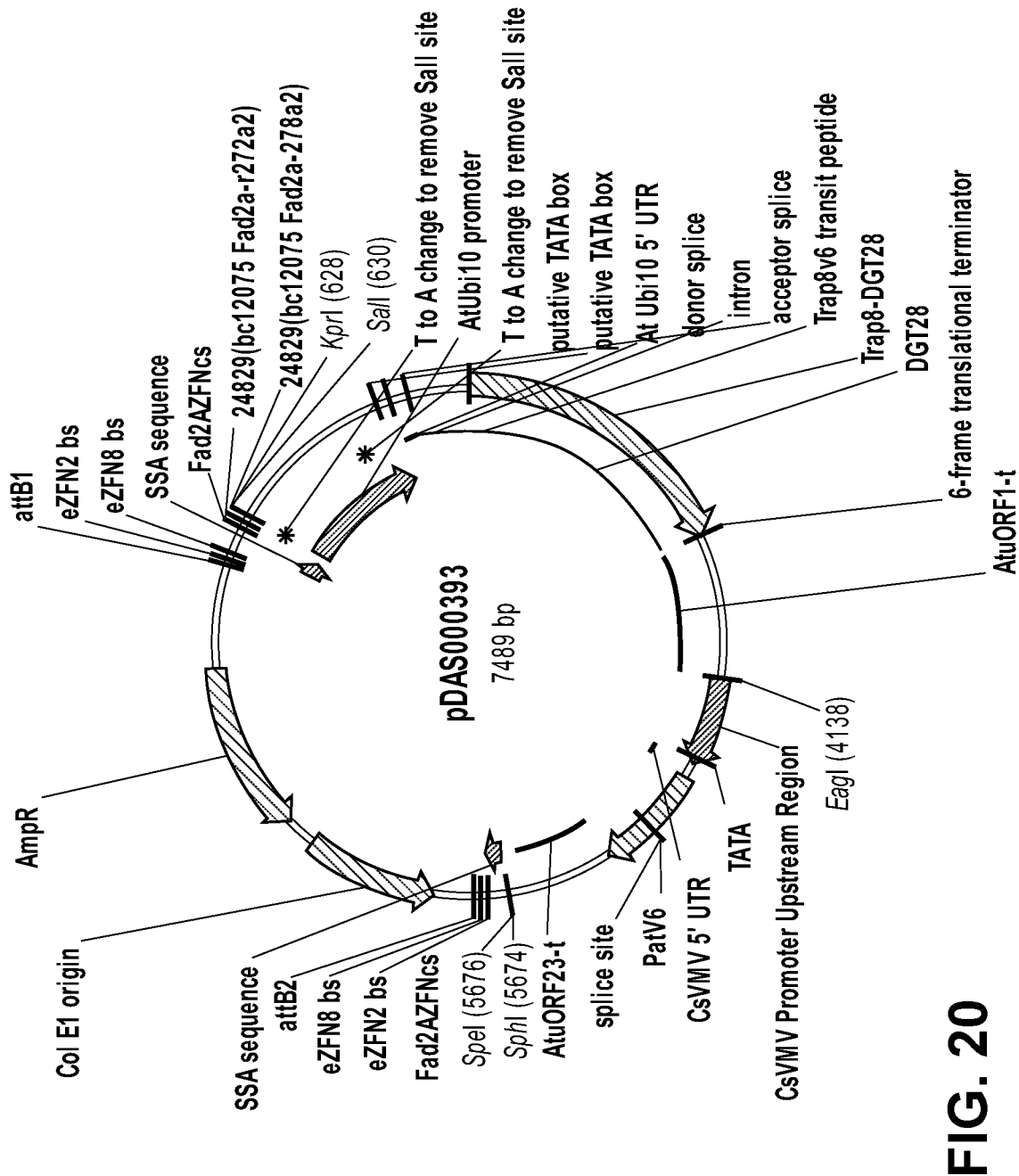
FIG. 20 shows a plasmid map of pDAS000393.
Figure 21:
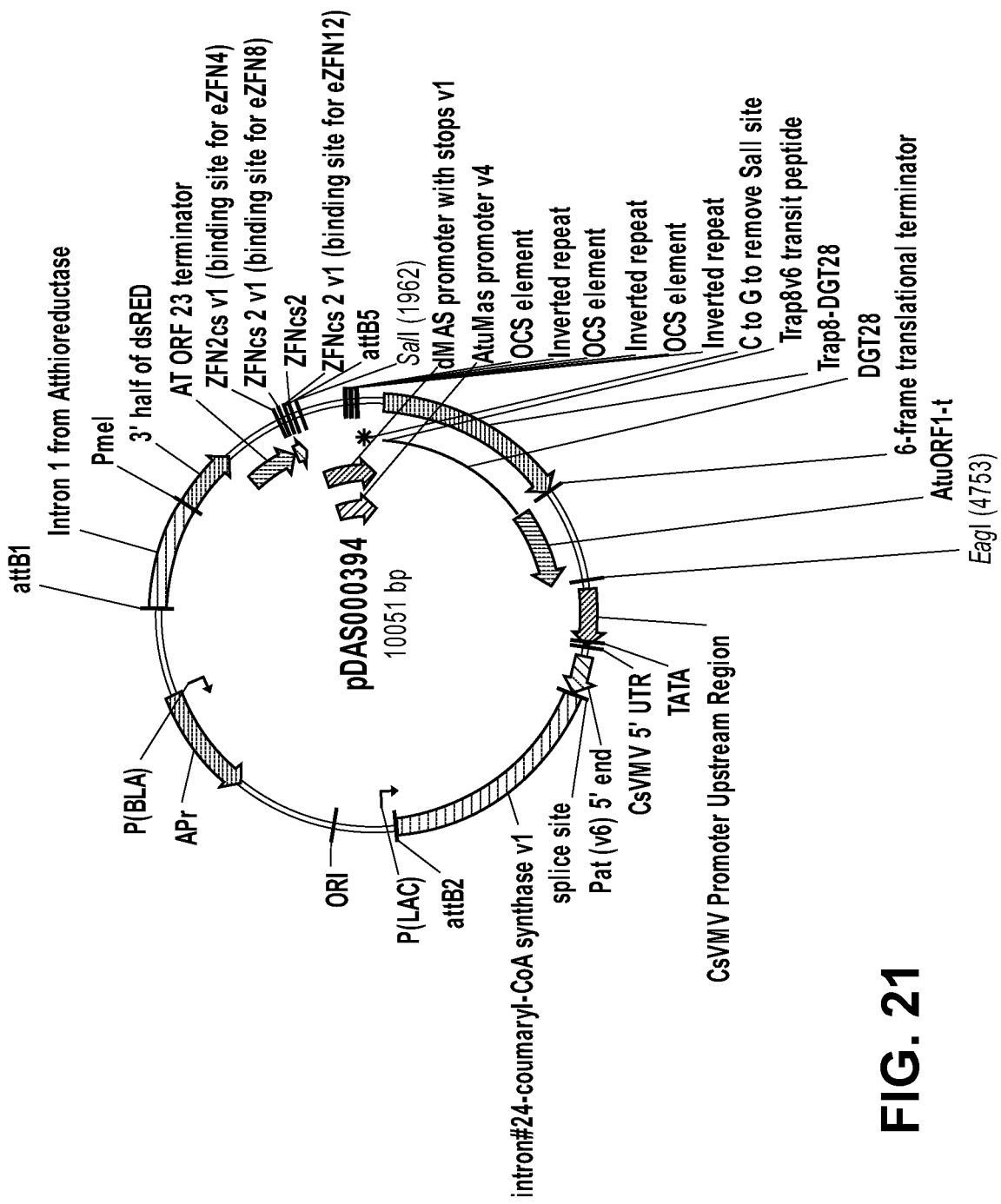
FIG. 21 shows a plasmid map of pDAS000394.
Figure 22:
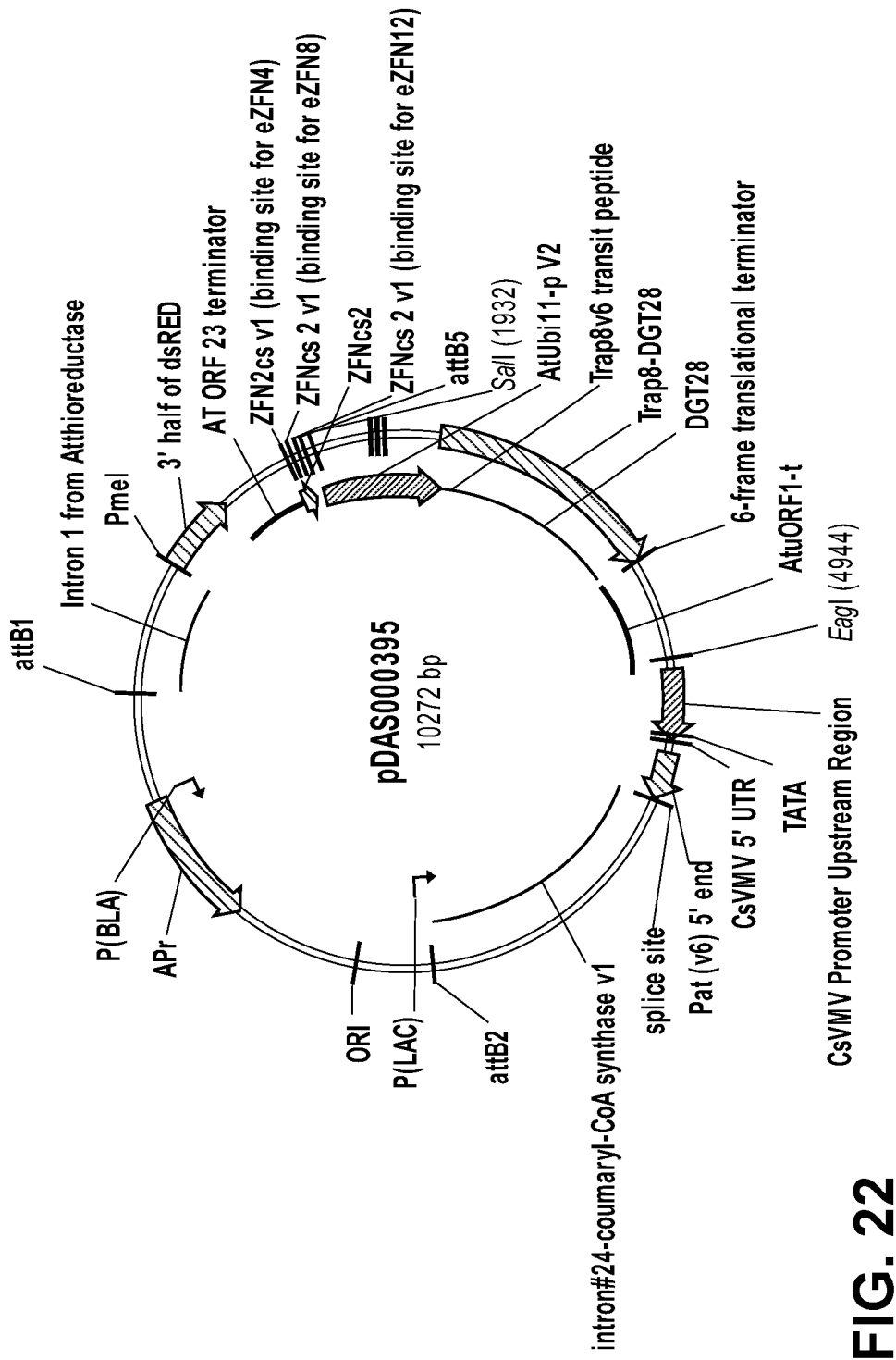
FIG. 22 shows a plasmid map of pDAS000395.
Figure 23:
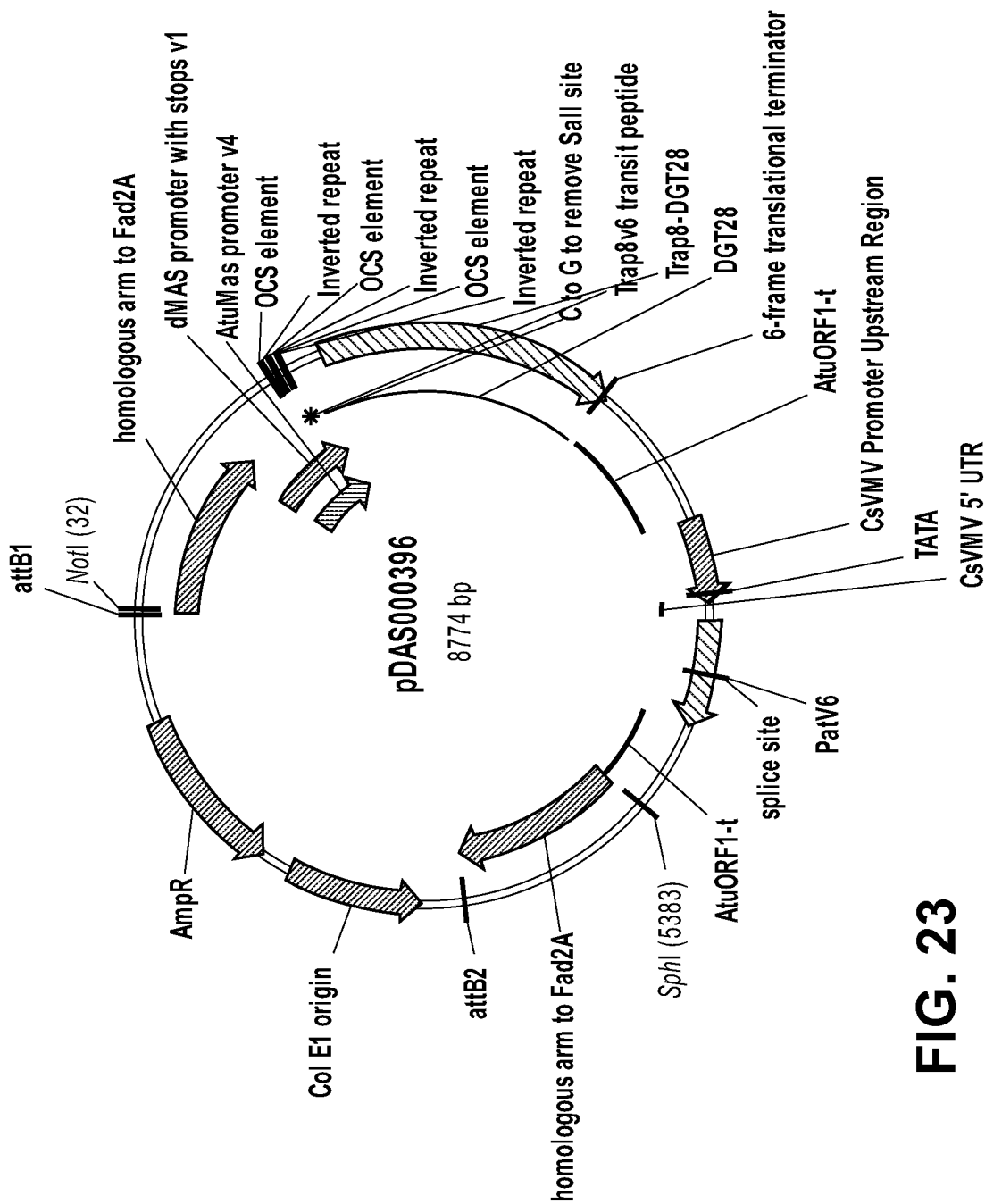
FIG. 23 shows a plasmid map of pDAS000396.
Figure 24:
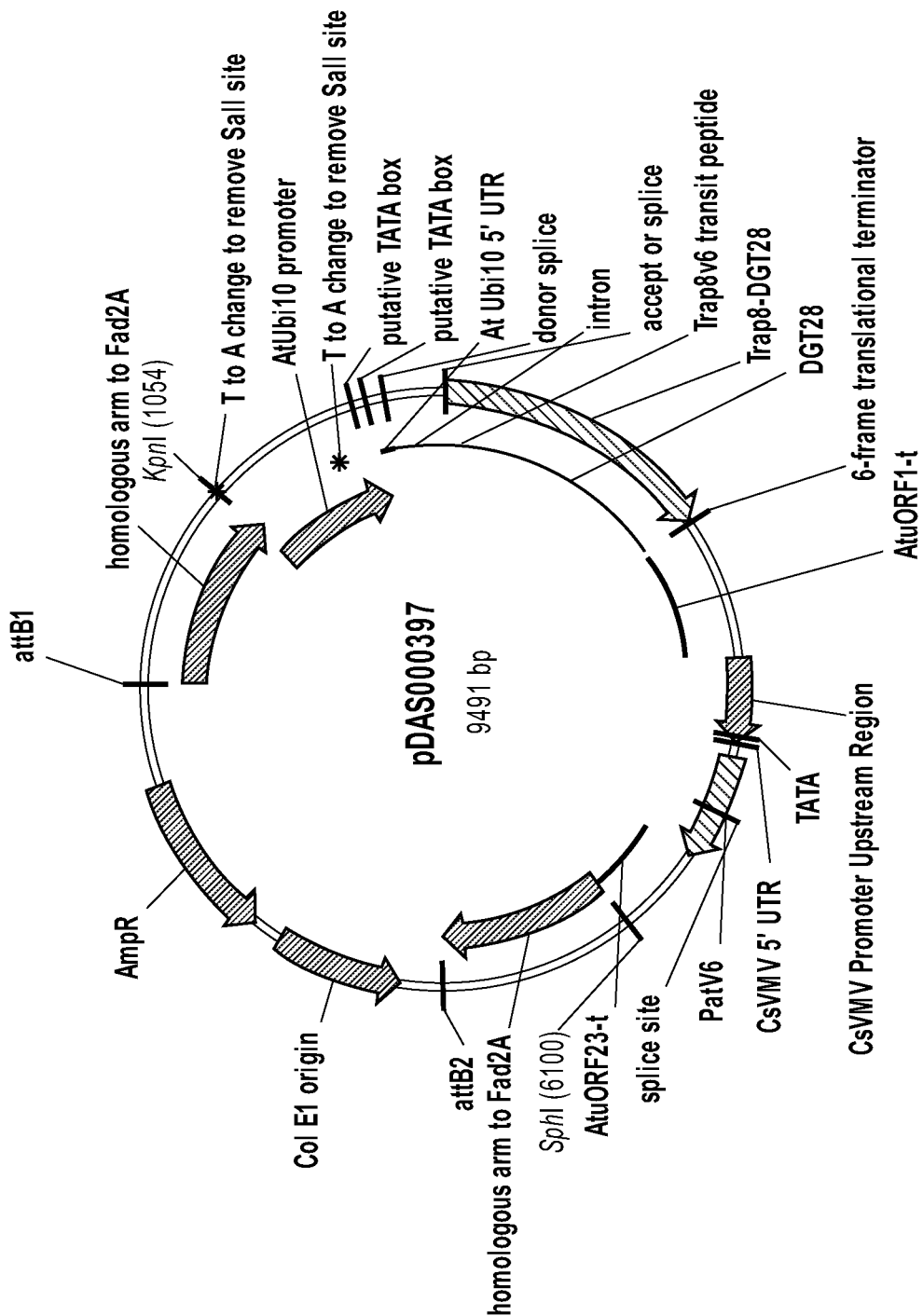
FIG. 24 shows a plasmid map of pDAS000397.

Example 10: Targeted Integration of Brassica napus Omega-3 Fatty Acid Desaturase (FAD2) with an Agronomically Important Gene Constructs containing the DGT-28 transgene (International Patent Publication No. WO/2013/116700, herein incorporated by reference) that confers resistance to the herbicide glyphosate are designed and built for integration within the FAD2A genomic loci of Brassica napus. Exemplary donor constructs include pDAS000389 (FIG. 17, SEQ ID NO:89) for NHEJ integration within FAD2A locus, pDAS000391 (FIG. 18, SEQ ID NO:90) for NHEJ integration within FAD2A locus, pDAS000392 (FIG. 19, SEQ ID NO:91) for NHEJ integration within FAD2A locus, pDAS000393 (FIG. 20, SEQ ID NO:92) for NHEJ integration within FAD2A locus, pDAS000394 (FIG. 21, SEQ ID NO:93) for HDR integration within the ETIP site of the FAD2A locus, pDAS000395 (FIG. 22, SEQ ID NO:208) for HDR integration within the ETIP site of the FAD2A locus, pDAS000396 (FIG. 23, SEQ ID NO:209) for HDR integration within FAD2A locus, and pDAS000397 (FIG. 24, SEQ ID NO:210) for HDR integration within FAD2A locus. The constructs and associated zinc finger nuclease constructs (e.g., pDAB104010) are transformed into Brassica napus cells as previously described above. Transformants are identified and confirmed via molecular confirmation assays as previously described. The FAD2A chromosomal integrants, comprising an integrated dgt-28 transgene are isolated. The integration of the dgt-28 transgene within the FAD2A locus is exemplified via NHEJ mediated integration and HDR mediated integration. The integration within the FAD2A locus can be directed into the FAD2A endogenous sequence or into the previouslt described ETIP (pDAS000130) that is stably integrated within the FAD2A locus. The integration within the FAD2A locus via an NHEJ mediated mechanism can be made using linearized donor or circular donor DNA designs. Transformed DGT-28 Brassica napus events are obtained and tested for robust expression of the DGT-28 and the subsequent resistance to the herbicide glyphosate.

While certain exemplary embodiments have been described herein, those of ordinary skill in the art will recognize and appreciate that many additions, deletions, and modifications to the exemplary embodiments may be made without departing from the scope of the following claims. In addition, features from one embodiment may be combined with features of another embodiment.

What may be claimed is:

1. A method of cleaving a FAD2 loci in a *Brassica* spp plant cell, the method comprising: introducing a nuclease comprising a DNA-binding domain and a cleavage domain or cleavage half-domain into the cell, wherein the DNA-binding domain binds to a target site within any of SEQ ID Nos:17-26, 28-33 or 35-38 in the FAD2 loci and the nuclease cleaves the FAD2 loci.

2. The method according to claim 1, further comprising integrating a nucleic acid of interest into the cleaved FAD2 loci.

3. The method according to claim 1, wherein the FAD2 loci is a FAD2A, FAD2A', FAD2C and/or FAD2C' gene.

4. The method according to claim 1, wherein the DNA-binding domain is selected from the group consisting of a meganuclease DNA-binding domain, a leucine zipper DNA-binding domain, a transcription activator-like (TAL) DNA-binding domain, a RNA-guided CRISPR-Cas9, a recombinase, a zinc finger protein DNA-binding domain, and chimeric combinations of any of the foregoing.

5. The method according to claim 1, wherein the cleavage domain or cleavage half-domain is selected from the group consisting of a cleavage half-domain from a type IIS restriction endonuclease, a cleavage half-domain from FokI endonuclease, a cleavage half-domain from StsI endonuclease, and a homing endonuclease.

6. The method according to claim 1, wherein the nuclease is a zinc finger nuclease.

7. The method according to claim 6, wherein the zinc finger nuclease comprises five or six zinc finger domains ordered finger 1 to finger 5 or finger 1 to finger 6, each zinc finger domain comprising a recognition helix region, wherein the zinc finger protein comprises the recognition helix regions ordered and shown in a single row of Table 4.

8. The method according to claim 1, wherein the cleaving is specific for some but not all copies FAD2A, FAD2A', FAD2C and/or FAD2C'.

9. The method according to claim 1, wherein the plant cell is a monocot plant cell or a dicot plant cell.

10. The method according to claim 1, wherein the plant cell is from *Brassica rapa*; *Brassica juencea*; *Brassica oleracea*; or *Brassica nigra*.

11. The method according to claim 1, wherein the cleavage is a double strand break.

12. The method according to claim 2, wherein the nucleic acid of interest encodes a protein.

13. The method according to claim 12, wherein the nucleic acid sequence of interest is selected from the group consisting of insecticidal resistance genes, herbicide tolerance genes, nitrogen use efficiency genes, water use efficiency genes, nutritional quality genes, DNA binding genes, and selectable marker genes.

14. The method according to claim 2, wherein the nucleic acid of interest comprises a DNA-binding domain binding site.

15. The method according to claim 1, wherein the nuclease is introduced into the cell as a polynucleotide encoding the nuclease.

* * * * *